(12) United States Patent
Strovel et al.

(10) Patent No.: US 10,508,106 B2
(45) Date of Patent: Dec. 17, 2019

(54) BICYCLIC BET BROMODOMAIN INHIBITORS AND USES THEREOF

(71) Applicants: ConverGene LLC, Cambridge, MD (US); The United States of America, as represented by the Secretary, Department of Health and Human Services, Bethesda, MD (US)

(72) Inventors: Jeffrey William Strovel, Laurel, MA (US); Makoto Yoshioka, Gaithersburg, MD (US); David J. Maloney, Point of Rocks, MD (US); Shyh Ming Yang, Doylestown, PA (US); Ajit Jadhav, Chantilly, VA (US); Daniel Jason Urban, Poolesville, MD (US)

(73) Assignees: ConverGene LLC, Cambridge, MD (US); The United States of America, As Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/779,353

(22) PCT Filed: Nov. 23, 2016

(86) PCT No.: PCT/US2016/063485
§ 371 (c)(1),
(2) Date: May 25, 2018

(87) PCT Pub. No.: WO2017/091661
PCT Pub. Date: Jun. 1, 2017

(65) Prior Publication Data
US 2018/0305344 A1    Oct. 25, 2018

Related U.S. Application Data

(60) Provisional application No. 62/259,894, filed on Nov. 25, 2015.

(51) Int. Cl.
| | | |
|---|---|---|
| *C07D 413/04* | (2006.01) | |
| *C07D 413/14* | (2006.01) | |
| *C07D 401/04* | (2006.01) | |
| *C07D 239/84* | (2006.01) | |
| *C07D 471/04* | (2006.01) | |
| *C07D 471/10* | (2006.01) | |
| *A61P 39/00* | (2006.01) | |
| *C07D 239/95* | (2006.01) | |
| *C07D 401/14* | (2006.01) | |
| *C07D 403/04* | (2006.01) | |
| *C07D 417/14* | (2006.01) | |

(52) U.S. Cl.
CPC .......... *C07D 413/04* (2013.01); *A61P 39/00* (2018.01); *C07D 239/84* (2013.01); *C07D 239/95* (2013.01); *C07D 401/04* (2013.01); *C07D 401/14* (2013.01); *C07D 403/04* (2013.01); *C07D 413/14* (2013.01); *C07D 417/14* (2013.01); *C07D 471/04* (2013.01); *C07D 471/10* (2013.01)

(58) Field of Classification Search
CPC .............................. C07D 239/48; A61K 45/06
See application file for complete search history.

(56) References Cited

U.S. PATENT DOCUMENTS

| | | | |
|---|---|---|---|
| 3,755,332 A | 8/1973 | Wasley et al. | |
| 8,557,984 B2 * | 10/2013 | Bouillot | C07D 471/04 544/126 |
| 2017/0226065 A1 * | 8/2017 | Shonbrunn | C07D 239/48 |

FOREIGN PATENT DOCUMENTS

| | | |
|---|---|---|
| EP | 0393926 | 10/1990 |
| EP | 1430030 | 5/2005 |
| EP | 1854789 | 11/2007 |
| EP | 2072502 | 6/2009 |
| EP | 2221301 | 8/2010 |
| EP | 1012166 | 10/2013 |
| EP | 2650286 | 10/2013 |
| EP | 1865958 | 7/2015 |
| EP | 3056207 | 8/2016 |
| WO | 1993/03030 | 2/1993 |
| WO | 2006/121767 | 11/2006 |
| WO | 2008/054599 | 5/2008 |

(Continued)

OTHER PUBLICATIONS

Vankayalapati et al. CAS: 161: 559305, 2014.*

(Continued)

*Primary Examiner* — Rei Tsang Shiao
(74) *Attorney, Agent, or Firm* — Fish & Richardson P.C.

(57) ABSTRACT

The present invention relates to compounds that bind to and otherwise modulate the activity of bromodomain-containing proteins, to processes for preparing these compounds, to pharmaceutical compositions containing these compounds, and to methods of using these compounds for treating a wide variety of conditions and disorders.

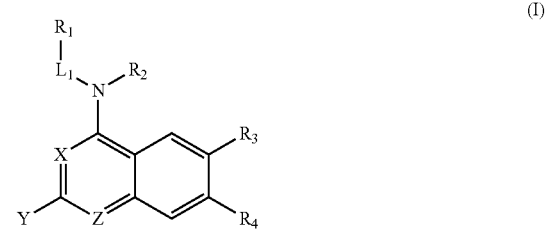

(I)

2 Claims, No Drawings

(56) References Cited

FOREIGN PATENT DOCUMENTS

| WO | 2008/117079 | | 10/2008 |
|---|---|---|---|
| WO | 2008/141843 | | 11/2008 |
| WO | 2011/054846 | | 5/2011 |
| WO | 2011/140442 | | 11/2011 |
| WO | 2012/040499 | | 3/2012 |
| WO | 2012/125913 | | 9/2012 |
| WO | 2012/143416 | | 10/2012 |
| WO | 2013/003586 | | 1/2013 |
| WO | 2014/089546 | | 6/2014 |
| WO | WO2014/159837 | * | 10/2014 |
| WO | WO2014159837 | * | 10/2014 |
| WO | 2015/015318 | | 2/2015 |
| WO | 2016/120808 | | 8/2016 |

OTHER PUBLICATIONS

Klaus et al. CAS: 164:296632, 2016.*
Schoenbrunn et al. CAS: 164: 290388, 2016.*
Stern et al. CAS: 163: 609542, 2015.*
Bradner et al. CAS: 162:638659, 2015.*
Liu et al. CAS: 162:190394, 2015.*
Abel et al., "Epigenetic targets of HDAC inhibition in neurodegenerative and psychiatric disorders.", Curr. Opin. Pharmacol. 8(1): 57-64, 2008.
Chung et al., "Progress in the discovery of small-molecule inhibitors of bromodomain—histone interactions.", J. Biomol. Screen. (10): 1170-85, 2011.
Delmore et al., "BET bromodomain inhibition as a therapeutic strategy to target c-Myc.", Cell. 146(6): 904-1, 2011.
Denis et al., "An emerging role for bromodomain-containing proteins in chromatin regulation and transcriptional control of adipogenesis.", FEBS Lett. 584(15): 3260-8, 2010.
Denis, "Bromodomain coactivators in cancer, obesity, type 2 diabetes, and inflammation.", Discov. Med. (55): 489-99, 2010.
Filippakopoulos et al., "Selective inhibition of BET bromodomains.", Nature 468(7327): 1067-73, 2010.
Florence et al., "You bet-cha: a novel family of transcriptional regulators.", Front. Biosci. 6: D1008-18, 2001.
McPhillips et al., "Interaction of bovine papillomavirus E2 protein with Brd4 stabilizes its association with chromatin.", J Virol. 79(14): 8920-32, 2005.
Furdas et al., "Inhibition of bromodomain-mediated protein—protein interactions as a novel therapeutic strategy", Med. Chem. Commun. 25 3(2): 123-134, 2012.
Mertz et al., "Targeting MYC dependence in cancer by inhibiting BET bromodomains.", Proc. Natl. Acad. Sci. USA. 108(40): 16669-74, 2011.
Puissant et al., "Targeting MYCN in neuroblastoma by BET bromodomain inhibition.", Cancer Discov. 3(3) 308-23, 2013.
Sanchez et al., "The role of human bromodomains in chromatin biology and gene transcription.", Curr. Opin. Drug Discov. Devel. (5): 659-65, 2009.
Tamkun et al., "brahma: A regulator of *Drosophila* homeotic genes structurally related to the yeast transcriptional activator SNF2SWI2", Cell., 68(3): 561-72, 1992.
Wu et al., "The double bromodomain-containing chromatin adaptor Brd4 and transcriptional regulation.", J. Biol Chem. 282(18): 13141-5, 2007.
You et al., "Kaposi's sarcoma-associated herpesvirus latency-associated nuclear antigen interacts with bromodomain protein Brd4 on host mitotic chromosomes.", J. Virol. 80(18): 8909-19, 2006.
Yuan et al., "Enhanced homology searching through genome reading frame predetermination.", Bioinformatics.20(9): 1416-27, 2004.
Zuber et al., "RNAi screen identifies Brd4 as a therapeutic target in acute myeloid leukaemia.", Nature 478(7370): 524-8, 2011.
Gao et al., "Identification of Essential Residues Involved in the Allosteric Modulation of the Human A3 Adenosine Receptor," Molecular Pharmacology 63(5):1021-1031 (May 1, 2003) XP055334146.
Yang S.H., et al., "Synthesis, in vitro and in vivo evaluation of 3-arylisoquinolinamines as potent antitumor agents," Bioorganic & Medicinal Chemistry Letters, 20(17):5277-5281 (Sep. 1, 2010) XP027207974.
Marvania et al., "The synthesis and biological evaluation of new DNA-directed alkylating agents, phenyl N-mustard-4-anilinoquinoline conjugates containing a urea linker," European Journal of Medicinal Chemistry, 83:695-708 (Aug. 1, 2014) XP055334281.
Moyer, et al., "The synthesis and identification of 4,6-diaminoquinoline derivatives as potent immunostimulants," Bioorganic & Medicinal Chemistry Letters, 2(12):1589-1594 (Jan. 1, 1992) XP002907109.
Abouzid et al., "Design, synthesis and in vitro antitumor activity of 4-aminoquinoline and 4-aminoquinazoline derivatives targeting EGFR tyrosine kinase," Bioorganic & Medicinal Chemistry 16(16):7543-7551 (Aug. 15, 2008) XP023904496.
Stuhlmiller et al. "Inhibition of lapatinib-induced kinome reprogramming in ERBB2-positive breast cancer by targeting BET family bromodomains," Cell Reports 11(3):390-404 (Apr. 1, 2015) XP055334508.
ISA/EP, International Search Report for PCT/US2016/063485 (dated Jan. 24, 2017).

* cited by examiner

BICYCLIC BET BROMODOMAIN INHIBITORS AND USES THEREOF

CROSS-REFERENCE TO RELATED APPLICATIONS

This application is a § 371 National Stage Application of and claims priority to PCT/US2016/063485, filed Nov. 23, 2016, which, in turn, claims the benefit of priority under 35 U.S.C. § 119(e) to provisional U.S. Patent Application No. 62/259,894 filed Nov. 25, 2015, the entire contents of each of which are hereby incorporated by reference.

STATEMENT REGARDING FEDERALLY SPONSORED RESEARCH OR DEVELOPMENT

This invention was created in the performance of a Cooperative Research and Development Agreement with the National Institutes of Health (NIH), an Agency of the Department of Health and Human Services. The Government of the United States has certain rights in this invention.

THE NAMES OF THE PARTIES TO A JOINT RESEARCH AGREEMENT

This invention is the subject of a joint research agreement between ConverGene, LLC and the National Institutes of Health (NIH), an Agency of the Department of Health and Human Services.

FIELD OF THE INVENTION

The present invention relates to compounds that inhibit bromodomain-containing proteins from binding acetylated proteins, to processes for preparing these compounds, to pharmaceutical compositions containing these compounds, and to methods of using these compounds for treating a wide variety of medical conditions, diseases or disorders.

BACKGROUND OF THE INVENTION

Epigenetic chromatin remodeling is a central mechanism for the regulation of gene expression. Pharmacological modulation of epigenetic change represents a new mode of therapeutic interventions for cancer and inflammation. Emerging evidence suggests that such epigenetic modulations may also provide therapeutic means for treatment of obesity, as well as metabolic, cardiovascular, neurodegenerative, psychiatric and infectious diseases.

The eukaryotic genome is organized into a basic packaging unit called a nucleosome, which is comprised of approximately 147 base pairs of double-stranded DNA helix wound around a histone octamer, which, in turn, consists of two subunits each of H2A, H2B, H3, and H4 proteins. Nucleosomes are further packaged into chromatin structures, which can exist in a relatively loose state of euchromatin or in a tightly packed heterochromatin structure. Transition from heterochromatin to euchromatin allows transcription of genes, although not all of the genes in euchromatin structure are transcribed. This transition from heterochromatin to euchromatin is controlled by post-translational modifications of histone proteins, including acetylation of lysine residues in H3/H4 proteins. Histone acetylation is catalyzed by histone acetyltransferases (HATs), resulting in open euchromatin structures that allow transcription of genes including tumor suppressor genes. Conversely, histone deacetylation leads to suppression of such genes and this activity is catalyzed by histone deacetylases (HDACs). Inhibition of histone deacetylases is a mode of cancer treatment and vorinostat (Zolinza®), a histone deacetylase inhibitor, has been shown to be an effective drug for cutaneous T-cell lymphoma in humans.

Histone acetylation also is modulated by bromodomain-containing proteins. A bromodomain is an approximately 110 amino acid-long evolutionarily conserved bundle of four alpha-helices that binds to acetyllysine residues of acetylated proteins. These domains are present in a number of chromatin-associated proteins including HATs. Bromodomains were first identified as a novel structural motif in the brahma protein, a regulator of Drosophila homeotic genes, but are also found in proteins in humans and yeast either as single-copy or contiguously repeated domains, and are thought to confer specificity for the complex pattern of epigenetic modifications known as the histone code (Cell. 1992 Feb. 7; 68(3):561-72; J. Biomol. Screen. 2011 December; 16(10):1170-85). The human genome encodes approximately 50 bromodomain-containing proteins (Bioinformatics. 2004 Jun. 12; 20(9):1416-27), some of which may be involved in etiology of cancer, inflammation, obesity, metabolic, cardiovascular, neurodegenerative, psychiatric and infectious diseases (Med. Chem. Commun. 2012 Jan. 4 3(2):123-134; Curr. Opin. Drug Discov. Devel. 2009 September; 12(5):659-65; Discov. Med. 2010 December; 10(55):489-99; FEBS Lett. 2010 Aug. 4; 584(15):3260-8; J. Virol. 2006 September; 80(18):8909-19; J Virol. 2005 July; 79(14):8920-32; Curr. Opin. Pharmacol. 2008 February; 8(1):57-64). Thus, inhibition and/or modulation of bromodomain-containing proteins may present a new mode of pharmacological intervention for such diseases.

Of approximately 50 bromodomain-containing proteins encoded by the human genome, BET proteins represent a small protein family that includes BRD2, BRD3, BRD4 and BRDT. BET proteins contain two tandem bromodomains followed by an extraterminal (ET) domain for protein-protein interaction in the carboxy-terminal region (J. Biol Chem. 2007 May 4; 282(18):13141-5). BET proteins bind to acetylated nucleosomes and are thought to function by opening chromatin structure and/or by facilitating transcriptional initiation (Front. Biosci. 2001 Aug. 1; 6:D1008-18).

Previously, inhibition of BRD4, either by a BRD4-specific RNAi or by a small-molecule BET inhibitor (JQ1), was unequivocally shown to induce suppression of MYC oncogene (Nature 2011 Aug. 3; 478(7370):524-8). This indirect suppression of MYC gene expression as a secondary effect of BRD4 inhibition comprises the central mechanism of action exerted by a BET inhibitor.

Inhibition of BET proteins was shown to be an effective mode of intervention in rodent models of human NUT midline carcinoma, multiple myeloma, Burkitt's lymphoma and acute myeloid leukemia by suppressing the expression of MYC gene (Nature 2010 Dec. 23; 468(7327):1067-73; Cell. 2011 Sep. 16; 146(6):904-1; Proc. Natl. Acad. Sci. USA. 2011 Oct. 4; 108(40):16669-74), as well as MYCN gene (Cancer Discov. 2013 March: 3(3) 308-23). MYC and homologous genes are some of the most overexpressed genes in human cancers; however, there has not been a pharmaceutical compound that directly antagonizes the activity of proteins encoded by the MYC gene and homologous genes to date partly due to the lack of effective drug binding sites. Thus, there exists a need for a means of indirect suppression of the expression of the MYC and homologous genes by inhibiting bromodomains of BET proteins which provide an effective mode of treatment for various diseases, disorders or medical conditions, including various cancers.

SUMMARY OF THE INVENTION

The present invention includes compounds which bind to bromodomain-containing proteins and subsequently modulate the binding of acetylated proteins to bromodomain-containing proteins. In one aspect, the invention provides compounds of Formula I,

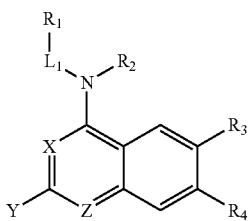

Formula I wherein each of $R_1$, $R_2$, $R_3$, $R_4$, $L_1$, X, Y, and Z is as defined and described in embodiments herein, and pharmaceutically acceptable salts, solvates, polymorphs, isomers and prodrugs thereof.

DETAILED DESCRIPTION OF THE INVENTION

According to one aspect of the invention, a compound having the structure of Formula I, including pharmaceutically acceptable salts, polymorphs, and isomers thereof:

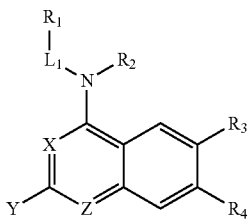

Formula I wherein:

X is CH or N;

Z is CH or N; with the proviso that when X is CH, Z is not also CH;

Y is selected from the group consisting of hydrogen (H), Cl, $C_{1-6}$ alkyl, $C_{3-10}$ cycloalkyl, 4-10 membered heterocycloalkyl, $OR_5$, $NR_6R_7$, —$C(O)R_{11}$, —$C(O)OR_{11}$, —$C(O)NR_{11}R_{12}$, $C_{6-10}$ aryl and 5-10 membered heteroaryl, wherein said 4-10 membered heterocycloalkyl and 5-10 membered heteroaryl include one or more nitrogen (N), oxygen (O) or sulfur (S) atoms; wherein said $C_{1-6}$ alkyl, $C_{3-10}$ cycloalkyl, 4-10 membered heterocycloalkyl, $C_{6-10}$ aryl and 5-10 membered heteroaryl may each optionally be substituted by one or more $R_8$;

$L_1$ is —$(CR_9R_{10})_n$—, C(O) or $S(O)_2$;

n is 0, 1, 2, or 3;

$R_1$ is selected from the group consisting of $C_{6-10}$ aryl and 5-10 membered heteroaryl, wherein said 5-10 membered heteroaryl includes one or more N, O or S atoms; wherein each of said $C_{6-10}$ aryl and 5-10 membered heteroaryl may optionally be substituted with one or more $R_8$;

$R_2$ is H, $C_{1-6}$ alkyl, —$C(O)R_{11}$, —$CH_2C(O)OR_{11}$, —$C(O)NR_{11}R_{12}$, $S(O)_2NR_{11}R_{12}$ or —$C(O)OR_{11}$, wherein said $C_{1-6}$ alkyl is optionally substituted with one or more $R_8$;

or optionally, $R_1$ and $R_2$, together with the included nitrogen atom and $L_1$, may form a 4-, 5-, 6- or 7-membered heterocyclic or heteroaryl ring system, wherein said heterocyclic or heteroaryl ring system may include one or more additional N, O or S atoms; and wherein said heterocyclic or heteroaryl ring system may optionally be substituted with one or more $R_8$;

$R_3$ and $R_4$ are independently selected from the group consisting of H, $C_{1-6}$ alkyl, —$OR_{11}$, halogen, —CN, —$CF_3$, —$NO_2$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}S(O)_2R_{12}$, —$NR_{11}C(O)NR_{12}R_{13}$, $S(O)_2NR_{11}R_{12}$, $C_{6-10}$ aryl, 5-10 membered heteroaryl, $C_{3-10}$ cycloalkyl and 4-10 membered heterocycloalkyl, wherein each of said 4-10 membered heterocycloalkyl and 5-10 membered heteroaryl include one or more N, O or S atoms; wherein said $C_{1-6}$ alkyl, $C_{6-10}$ aryl, 5-10 membered heteroaryl, $C_{3-10}$ cycloalkyl or 4-10 membered heterocycloalkyl are each optionally substituted with one or more $R_8$;

$R_5$ is $C_{1-6}$ alkyl, $C_{3-10}$ cycloalkyl, 4-10 membered heterocycloalkyl, $C_{5-10}$ aryl or 5-10 membered heteroaryl, wherein each of said $C_{1-6}$ alkyl, $C_{3-10}$ cycloalkyl, 4-10 membered heterocycloalkyl, $C_{3-10}$ aryl or 5-10 membered heteroaryl is optionally substituted with one or more $R_8$;

$R_6$ and $R_7$ are independently selected for each occurrence from the group consisting of H, $C_{1-6}$ alkyl, $C_{6-10}$ aryl, 5-10 membered heteroaryl, $C_{3-10}$ cycloalkyl and 4-10 membered heterocycloalkyl, wherein said 4-10 membered heterocycloalkyl or 5-10 membered heteroaryl include one or more N, O or S atoms; wherein each of said $C_{1-6}$ alkyl, $C_{6-10}$ aryl, 5-10 membered heteroaryl, $C_{3-10}$ cycloalkyl, and 4-10 membered heterocycloalkyl may optionally be substituted with one or more $R_8$;

or optionally, $R_6$ and $R_7$, together with the included nitrogen, may form a 4-, 5-, 6- or 7-membered heterocyclic or heteroaryl ring system, wherein said heterocyclic or heteroaryl ring system is a mono- or bicyclic ring optionally having an additional from one to four heteroatoms selected from N, O and S; wherein said heterocyclic or heteroaryl ring system may optionally be substituted with one or more $R_8$;

$R_8$ is selected independently for each occurrence from the group consisting of H, OH, SH, halogen, —CN, —$CF_3$, —$NO_2$, —$OR_{11}$, —$SR_{11}$, —$C(O)R_{11}$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}S(O)_2R_{12}$, —$NR_{11}C(O)NR_{12}R_{13}$, —$(CH_2)_m$—$R_{16}$, —$(CH_2)_q$—$R_{17}$, —$S(O)R_{11}$, —$S(O)_2R_{11}$, $C_{1-6}$ alkyl, $C_{6-10}$ aryl, 5-10 membered heteroaryl, $C_{3-10}$ cycloalkyl and 4-10 membered heterocycloalkyl, wherein said $C_{1-6}$ alkyl, $C_{6-10}$ aryl, 5-10 membered heteroaryl, $C_{3-10}$ cycloalkyl and 4-10 membered heterocycloalkyl are each optionally substituted with one or more $R_{14}$;

m is 1, 2, 3 or 4;

q is 2, 3 or 4;

$R_9$ and $R_{10}$ are independently chosen for each occurrence from H or $C_{1-6}$ alkyl, wherein said $C_{1-6}$ alkyl may optionally be substituted with one or more $R_8$;

or optionally, $R_9$ and $R_{10}$, together with the included carbon, may form a 3-, 4-, 5-, or 6-membered carbocyclic ring system;

$R_{11}$, $R_{12}$, and $R_{13}$ are independently chosen for each occurrence from the group consisting of H, $C_{1-6}$ alkyl, $C_{3-10}$ cycloalkyl, 4-10 membered heterocycloalkyl, $C_{6-10}$ aryl and 5-10 membered heteroaryl, wherein each of said $C_{1-6}$ alkyl, $C_{3-10}$ cycloalkyl, 4-10 membered heterocycloalkyl, $C_{6-10}$ aryl and 5-10 membered heteroaryl may optionally be substituted with one or more $R_{14}$;

or optionally, $R_{11}$ and $R_{12}$, or $R_{12}$ and $R_{13}$, together with the included nitrogen, may form a 4-, 5-, 6- or 7-membered heterocyclic or heteroaryl ring system, wherein said heterocyclic or heteroaryl ring system is a mono- or bicyclic ring optionally having an additional from one to four heteroatoms selected from N, O and S; wherein said heterocyclic or heteroaryl ring system may optionally be substituted with one or more $R_8$;

$R_{14}$ is selected independently for each occurrence from the group consisting of H, OH, $OR_{18}$, SH, $SR_{18}$, halogen, CN, $CF_3$, $NO_2$, $C(O)R_{18}$, $C(O)OR_{18}$, $OC(O)NR_{18}R_{19}$, $C(O)NR_{18}R_{19}$, $NR_{18}R_{19}$, $NR_{18}C(O)R_{19}$, $NR_{18}C(O)OR_{19}$, $NR_{18}S(O)_2R_{19}$, $NR_{18}C(O)NR_{19}R_{20}$, $S(O)R_{18}$, $S(O)_2R_{18}$, $C_{1-6}$ alkyl, $C_{3-10}$ cycloalkyl, 4-10 membered heterocycloalkyl, $C_{6-10}$ aryl and 5-10 membered heteroaryl, wherein said $C_{1-6}$ alkyl, $C_{3-10}$ cycloalkyl, 4-10 membered heterocycloalkyl, $C_{6-10}$ aryl and 5-10 membered heteroaryl groups may be optionally substituted with one or more of $R_{15}$;

$R_{15}$ is selected independently for each occurrence from the group consisting of H, —$CH_3$, —$CH_2CH_3$, n-propyl, isopropyl, —$OCH_3$, halogen, —CN, —$CF_3$, —$NH_2$, —$N(CH_3)_2$, —$CO_2H$, —$C(O)NH_2$, —$C(O)NH(CH_3)$, and —$C(O)N(CH_3)_2$;

each $R_{16}$ is independently —$CO_2H$ or —$C(O)NR_6R_7$;

each $R_{17}$ is independently —OH or —$NR_6R_7$; and each $R_{18}$, $R_{19}$, and $R_{20}$ are independently selected for each occurrence from the group consisting of H, $C_{1-6}$ alkyl, $C_{3-10}$ cycloalkyl, 4-10 membered heterocycloalkyl, $C_{6-10}$ aryl and 5-10 membered heteroaryl.

In some embodiments:

X is CH or N;

Z is CH or N; with the proviso that when X is CH, Z is not also CH;

Y is selected from the group consisting of hydrogen (H), Cl, alkyl, cycloalkyl, heterocycloalkyl, $OR_5$, $NR_6R_7$, aryl and heteroaryl, wherein said heterocycloalkyl and heteroaryl include one or more nitrogen (N), oxygen (O) or sulfur (S) atoms; wherein said alkyl, cycloalkyl, heterocycloalkyl, aryl and heteroaryl may each optionally be substituted by one or more $R_8$;

$L_1$ is —$(CR_9R_{10})_n$—, C(O) or $S(O)_2$;

n is 0, 1, 2, or 3;

$R_1$ is selected from the group consisting of aryl and heteroaryl, wherein said heteroaryl includes one or more N, O or S atoms; wherein each of said aryl and heteroaryl may optionally be substituted with one or more $R_8$;

$R_2$ is H, alkyl, —$C(O)R_{11}$, —$CH_2C(O)OR_{11}$, —$C(O)NR_{11}R_{12}$, $S(O)_2NR_{11}R_{12}$ or —$C(O)OR_{11}$, wherein said alkyl is optionally substituted with one or more $R_8$;

optionally, $R_1$ and $R_2$, together with the included nitrogen atom and $L_1$, may form a 4-, 5-, 6- or 7-membered heterocyclic ring system, wherein said heterocyclic ring system may include one or more additional N, O or S atoms; and wherein said heterocyclic ring system may optionally be substituted with one or more $R_8$;

$R_3$ and $R_4$ are independently selected for each occurrence from the group consisting of H, alkyl, —$OR_{11}$, halogen, —CN, —$CF_3$, —$NO_2$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}S(O)_2R_{12}$, —$NR_{11}C(O)NR_{12}R_{13}$, $S(O)_2NR_{11}R_{12}$, aryl, heteroaryl, cycloalkyl and heterocycloalkyl, wherein each of said heterocycloalkyl and heteroaryl include one or more N, O or S atoms; wherein said alkyl, aryl, heteroaryl, cycloalkyl or heterocycloalkyl are each optionally substituted with one or more $R_8$;

$R_5$ is alkyl, cycloalkyl, heterocycloalkyl, aryl or heteroaryl, wherein each of said alkyl, cycloalkyl, heterocycloalkyl, aryl or heteroaryl is optionally substituted with one or more $R_8$;

$R_6$ and $R_7$ are independently selected for each occurrence from the group consisting of H, alkyl, aryl, heteroaryl, cycloalkyl and heterocycloalkyl, wherein said heterocycloalkyl or heteroaryl include one or more N, O or S atoms; wherein each of said alkyl, aryl, heteroaryl, cycloalkyl, and heterocycloalkyl may optionally be substituted with one or more $R_8$;

optionally, $R_6$ and $R_7$, together with the included nitrogen, may form a 4-, 5-, 6- or 7-membered heterocyclic ring system, wherein said heterocyclic ring system is a mono- or bicyclic ring optionally having an additional from one to four heteroatoms selected from N, O and S; wherein said cyclic ring system may optionally be substituted with one or more $R_8$;

$R_8$ is selected independently for each occurrence from the group consisting of H, OH, SH, halogen, —CN, —$CF_3$, —$NO_2$, —$OR_{11}$, —$SR_{11}$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}S(O)_2R_{12}$, —$NR_{11}C(O)NR_{12}R_{13}$, —$(CH_2)_m$—$R_{16}$, —$(CH_2)_q$—$R_{17}$, alkyl, aryl, heteroaryl, cycloalkyl and heterocycloalkyl, wherein said alkyl, aryl, heteroaryl, cycloalkyl and heterocycloalkyl are each optionally substituted with one or more $R_{14}$;

m is 1, 2, 3 or 4;

q is 2, 3 or 4;

$R_9$ and $R_{10}$ are independently chosen for each occurrence from H or alkyl, wherein said alkyl may optionally be substituted with one or more $R_8$;

optionally, $R_9$ and $R_{10}$, together with the included carbon, may form a 3-, 4-, 5-, or 6-membered carbocyclic ring system;

$R_{11}$, $R_{12}$, and $R_{13}$ are independently chosen for each occurrence from the group consisting of H, alkyl, cycloalkyl, heterocycloalkyl, aryl and heteroaryl, wherein each of said alkyl, cycloalkyl, heterocycloalkyl, aryl and heteroaryl may optionally be substituted with one or more $R_{14}$;

optionally, $R_{11}$ and $R_{12}$, or $R_{12}$ and $R_{13}$, together with the included nitrogen, may form a 4-, 5-, 6- or 7-membered heterocyclic ring system, wherein said heterocyclic ring system is a mono- or bicyclic ring optionally having an additional from one to four heteroatoms selected from N, O and S; wherein said cyclic ring system may optionally be substituted with one or more $R_{14}$;

$R_{14}$ is selected independently for each occurrence from the group consisting of H, OH, $OR_{18}$, SH, $SR_{18}$, halogen, CN, $CF_3$, $NO_2$, $C(O)R_{18}$, $C(O)OR_{18}$, $OC(O)NR_{18}R_{19}$, $C(O)NR_{18}R_{19}$, $NR_{18}R_{19}$, $NR_{18}C(O)R_{19}$, $NR_{18}C(O)OR_{19}$, $NR_{18}S(O)_2R_{19}$, $NR_{18}C(O)NR_{19}R_{20}$, $S(O)R_{18}$, $S(O)_2R_{18}$, alkyl, cycloalkyl, heterocycloalkyl, aryl and heteroaryl, wherein said alkyl, cycloalkyl, heterocycloalkyl, aryl and heteroaryl groups may optionally be further substituted with one or more of $R_{15}$;

$R_{15}$ is selected independently for each occurrence from the group consisting of H, —$CH_3$, —$CH_2CH_3$, n-propyl, isopropyl, —$OCH_3$, halogen, —CN, —$CF_3$, —$NH_2$, —$N(CH_3)_2$, —$CO_2H$, —$C(O)NH_2$, —$C(O)NH(CH_3)$, and —$C(O)N(CH_3)_2$;

each $R_{16}$ is independently —$CO_2H$ or —$C(O)NR_6R_7$;

each $R_{17}$ is independently —OH or —$NR_6R_7$; and each $R_{18}$, $R_{19}$, and $R_{20}$ are independently selected for each occurrence from the group consisting of H, alkyl, cycloalkyl, heterocycloalkyl, aryl and heteroaryl.

In some embodiments:

X is CH or N;

Z is CH or N, with the proviso that when X is CH, Z is not also CH;

Y is selected from the group consisting of hydrogen (H), Cl, alkyl, cycloalkyl, heterocycloalkyl, $OR_5$, $NR_6R_7$, aryl and heteroaryl, wherein said heterocycloalkyl and heteroaryl include one or more nitrogen (N), oxygen (O) or sulfur (S) atoms; wherein said alkyl, cycloalkyl, heterocycloalkyl, aryl and heteroaryl may each optionally be substituted by one or more $R_8$;

$L_1$ is —$(CR_9R_{10})_n$—, C(O) or $S(O)_2$;

n is 0, 1, 2, or 3;

$R_1$ is selected from the group consisting of aryl and heteroaryl, wherein said heteroaryl includes one or more N, O or S atoms; wherein each of said aryl and heteroaryl may optionally be substituted with one or more $R_8$;

$R_2$ is H, alkyl, —$C(O)R_{11}$, —$CH_2C(O)OR_{11}$, —$C(O)NR_{11}R_{12}$, $S(O)_2NR_{11}R_{12}$ or —$C(O)OR_{11}$, wherein said alkyl is optionally substituted with one or more $R_8$;

optionally, $R_1$ and $R_2$, together with the included nitrogen atom and $L_1$, may form a 4-, 5-, 6- or 7-membered heterocyclic ring system, wherein said heterocyclic ring system may include one or more additional N, O or S atoms; and wherein said heterocyclic ring system may optionally be substituted with one or more $R_8$;

$R_3$ and $R_4$ are independently selected for each occurrence from the group consisting of H, alkyl, —$OR_{11}$, halogen, —CN, —$CF_3$, —$NO_2$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, $NR_{11}S(O)_2R_{12}$, —$NR_{11}C(O)NR_{12}R_{13}$, $S(O)_2NR_{11}R_{12}$, aryl, heteroaryl, cycloalkyl and heterocycloalkyl, wherein each of said heterocycloalkyl and heteroaryl include one or more N, O or S atoms; wherein said alkyl, aryl, heteroaryl, cycloalkyl or heterocycloalkyl are each optionally substituted with one or more $R_8$;

$R_5$ is alkyl, cycloalkyl, heterocycloalkyl, aryl or heteroaryl, wherein each of said alkyl, cycloalkyl, heterocycloalkyl, aryl or heteroaryl is optionally substituted with one or more $R_8$;

$R_6$ and $R_7$ are independently selected for each occurrence from the group consisting of H, alkyl, aryl, heteroaryl, cycloalkyl and heterocycloalkyl, wherein said heterocycloalkyl or heteroaryl include one or more N, O or S atoms; wherein each of said alkyl, aryl, heteroaryl, cycloalkyl, and heterocycloalkyl may optionally be substituted with one or more $R_8$;

optionally, $R_6$ and $R_7$, together with the included nitrogen, may form a 4-, 5-, 6- or 7-membered heterocyclic ring system, wherein said heterocyclic ring system is a mono- or bicyclic ring optionally having an additional from one to four heteroatoms selected from N, O and S; wherein said cyclic ring system may optionally be substituted with one or more $R_8$;

$R_8$ is selected independently for each occurrence from the group consisting of H, OH, SH, halogen, —CN, —$CF_3$, —$NO_2$, —$OR_{11}$, —$SR_{11}$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}C(O)OR_{12}$, —$NR_{11}C$ $(O)OR_{12}$, —$NR_{11}S(O)_2R_{12}$, —$NR_{11}C(O)NR_{12}R_{13}$, —$(CH_2)_m$—$R_{16}$, —$(CH_2)_q$—$R_{17}$, alkyl, aryl, heteroaryl, cycloalkyl and heterocycloalkyl, wherein said alkyl, aryl, heteroaryl, cycloalkyl and heterocycloalkyl are each optionally substituted with one or more $R_{14}$;

m is 1, 2, 3 or 4;

q is 2, 3 or 4;

$R_9$ and $R_{10}$ are independently chosen for each occurrence from H or alkyl, wherein said alkyl may optionally be substituted with one or more $R_8$;

optionally, $R_9$ and $R_{10}$, together with the included carbon, may form a 3-, 4-, 5-, or 6-membered carbocyclic ring system;

$R_{11}$, $R_{12}$, and $R_{13}$ are independently chosen for each occurrence from the group consisting of H, alkyl, cycloalkyl, heterocycloalkyl, aryl and heteroaryl, wherein each of said alkyl, cycloalkyl, heterocycloalkyl, aryl and heteroaryl may optionally be substituted with one or more $R_{14}$;

optionally, $R_{11}$ and $R_{12}$, or $R_{12}$ and $R_{13}$, together with the included atoms, may form a 4-, 5-, 6- or 7-membered heterocyclic ring system, wherein said heterocyclic ring system is a mono- or bicyclic ring optionally having an additional from one to four heteroatoms selected from N, O and S; wherein said cyclic ring system may optionally be substituted with one or more $R_8$;

$R_{14}$ is selected independently for each occurrence from the group consisting of H, OH, $OR_{11}$, SH, $SR_{11}$, halogen, CN, $CF_3$, $NO_2$, $C(O)OR_{11}$, $OC(O)NR_{11}R_{12}$, $C(O)NR_{11}R_{12}$, $NR_{11}R_{12}$, $NR_{11}C(O)R_{12}$, $NR_{11}C(O)OR_{12}$, $NR_{11}S(O)_2R_{12}$, $NR_{11}C(O)NR_{12}R_{13}$, alkyl, cycloalkyl, heterocycloalkyl, aryl and heteroaryl, wherein said alkyl, cycloalkyl, heterocycloalkyl, aryl and heteroaryl groups may optionally be further substituted with one or more of $R_{15}$;

$R_{15}$ is selected independently for each occurrence from the group consisting of H, —$CH_3$, —$CH_2CH_3$, n-propyl, isopropyl, —$OCH_3$, halogen, —CN, —$CF_3$, —$NH_2$, —$N(CH_3)_2$, —$CO_2H$, —$C(O)NH_2$, —$C(O)NH(CH_3)$, and —$C(O)N(CH_3)_2$;

$R_{16}$ is —$CO_2H$ or —$C(O)NR_6R_7$; and $R_{17}$ is —OH or —$NR_6R_7$.

In some embodiments, $R_8$ is selected independently for each occurrence from the group consisting of H, OH, SH, halogen, —CN, —$CF_3$, —$NO_2$, —$OR_{11}$, —$SR_{11}$, —$C(O)R_{11}$, —$C(O)OR_{11}$, —$OC(O)NR_{11}R_{12}$, —$C(O)NR_{11}R_{12}$, —$NR_{11}R_{12}$, —$NR_{11}C(O)R_{12}$, —$NR_{11}C(O)OR_{12}$, —$NR_{11}S(O)_2R_{12}$, —$NR_{11}C(O)NR_{12}R_{13}$, —$(CH_2)_m$—$R_{16}$, —$(CH_2)_q$—$R_{17}$, —$S(O)R_{11}$, —$S(O)_2R_{11}$, $C_{1-6}$ alkyl, $C_{6-10}$ aryl, 5-10 membered heteroaryl, $C_{3-10}$ cycloalkyl and 4-10 membered heterocycloalkyl, wherein said $C_{1-6}$ alkyl, $C_{6-10}$ aryl, 5-10 membered heteroaryl, $C_{3-10}$ cycloalkyl and 4-10 membered heterocycloalkyl are each optionally substituted with one or more $R_{14}$;

provided that when $R_8$ is attached to a nitrogen atom (e.g., a nitrogen atom of $R_1$, $R_2$, or a heterocycloalkyl group formed by $R_1$ and $R_2$, together with the included nitrogen atom and $L_1$) $R_8$ is selected from $R_{21}$, wherein $R_{21}$ is $C_{1-6}$ alkyl, $C_{3-6}$ cycloalkyl, 4-7 membered heterocycloalkyl, 5-6 membered heteroaryl, phenyl, —$C(O)R_{11}$, —$C(O)OR_{11}$, —$C(O)NR_{11}R_{12}$, or —$S(O)_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with one or more $R_{14}$.

In some embodiments, the $C_{1-6}$ alkyl, $C_{3-6}$ cycloalkyl, 4-7 membered heterocycloalkyl, 5-6 membered heteroaryl, and phenyl of $R_{21}$ are each optionally substituted with 1, 2, or 3 independently selected $R_{14}$.

In some embodiments, $R_{21}$ is $C_{1-6}$ alkyl, $C_{3-6}$ cycloalkyl, —C(O)R$_{11}$, —C(O)OR$_{11}$, —C(O)NR$_{11}$R$_{12}$, or —S(O)$_2$R$_{11}$, wherein said $C_{1-6}$ alkyl may optionally be substituted with NR$_{11}$R$_{12}$.

In some embodiments, $R_{21}$ is $C_{1-6}$ alkyl, —C(O)R$_{11}$, —C(O)OR$_{11}$, —C(O)NR$_{11}$R$_{12}$, or —S(O)$_2$R$_{11}$, wherein said $C_{1-6}$ alkyl may optionally be substituted with NR$_{11}$R$_{12}$.

In some embodiments, $R_{21}$ is C(O)CH$_3$, S(O)$_2$CH$_3$, CH$_2$CH$_2$N(CH$_3$)$_2$, or C(O)NH(cyclopropyl).

In some embodiments, $R_{21}$ is C(O)CH$_3$ or S(O)$_2$CH$_3$.

In some embodiments, $R_8$ is selected independently for each occurrence from the group consisting of H, OH, SH, halogen, —CN, —CF$_3$, —NO$_2$, —OR$_{11}$, —SR$_{11}$, —C(O)R$_{11}$, —C(O)OR$_{11}$, —OC(O)NR$_{11}$R$_{12}$, —C(O)NR$_{11}$R$_{12}$, —NR$_{11}$R$_{12}$, —NR$_{11}$C(O)R$_{12}$, —NR$_{11}$C(O)OR$_{12}$, —NR$_{11}$S(O)$_2$R$_{12}$, —NR$_{11}$C(O)NR$_{12}$R$_{13}$, —(CH$_2$)$_m$—R$_{16}$, —(CH$_2$)$_q$—R$_{17}$, —S(O)R$_{11}$, —S(O)$_2$R$_{11}$, $C_{1-6}$ alkyl, $C_{6-10}$ aryl, 5-10 membered heteroaryl, $C_{3-10}$ cycloalkyl and 4-10 membered heterocycloalkyl, wherein said $C_{1-6}$ alkyl, $C_{6-10}$ aryl, 5-10 membered heteroaryl, $C_{3-10}$ cycloalkyl and 4-10 membered heterocycloalkyl are each optionally substituted with one or more R$_{14}$;

provided that when R$_8$ is attached to a carbon atom (e.g., a carbon atom of R$_1$, R$_2$, or a heterocycloalkyl group formed by R$_1$ and R$_2$, together with the included nitrogen atom and L$_1$) R$_8$ is selected from R$_{8a}$, wherein R$_{8a}$ is $C_{1-6}$ alkyl, $C_{3-6}$ cycloalkyl, phenyl, or a 5-6 membered heteroaryl, wherein said $C_{1-6}$ alkyl, phenyl, and heteroaryl may optionally be substituted by 1, 2, or 3 independently selected R$_{14}$.

In some embodiments, R$_{8a}$ is benzyl, phenyl, or a 5-6 membered heteroaryl, wherein said phenyl and heteroaryl may optionally be substituted by 1, 2, or 3 independently selected R$_{14}$.

In some embodiments, R$_{8a}$ is phenyl or a 5-6 membered heteroaryl, wherein said phenyl and heteroaryl may optionally be substituted by 1, 2, or 3 independently selected R$_{14}$.

In some embodiments, R$_{8a}$ is phenyl or thienyl, wherein said phenyl may optionally be substituted with 1, 2 or 3 substituents independently selected from the group consisting of F, Cl, Br, Me, Et, cycropropyl, OMe, OEt, CF$_3$, CN, NH$_2$, —NHC(O)—$C_{1-4}$alkyl, and —NHC(O)—$C_{1-4}$ alkenyl; and said thienyl may optionally be substituted with 1 or 2 substituents independently selected from the group consisting of F, Cl, Br, Me, Et, cycropropyl, OMe, OEt, CF$_3$, CN, NH$_2$, —NHC(O)—$C_{1-4}$alkyl, and —NHC(O)—$C_{1-4}$ alkenyl.

In some embodiments, the compound is a compound of Formula I, or a pharmaceutically acceptable salt thereof.

In some embodiments, L$_1$ is —(CH$_2$)—, —(CH(CH$_3$))—, —(C(CH$_3$)$_2$)— —CH(CH$_2$OH)— or

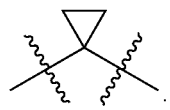 [SMILES: *C1(*)CC1]

In some embodiments, L$_1$ is —(CH$_2$)—, —(CH(CH$_3$))—, —(C(CH$_3$)$_2$)— or

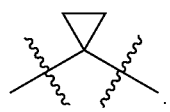 [SMILES: *C1(*)CC1]

In some embodiments, L$_1$ is —(CH$_2$)— or —(CH(CH$_3$))—.

In some embodiments, L$_1$ is —(CH$_2$)—.

In some embodiments, R$_1$ is aryl or heteroaryl, wherein said aryl or heteroaryl is optionally substituted with one or more R$_8$.

In some embodiments, R$_1$ is $C_{6-10}$ aryl or 5-10 membered heteroaryl, wherein said $C_{6-10}$ aryl or 5-10 membered heteroaryl is optionally substituted with one or more R$_8$.

In some embodiments, R$_1$ is aryl or heteroaryl, wherein said aryl or heteroaryl may each optionally be substituted with one or two substitutents selected from the group consisting of F, Cl, Br, CH$_3$ and —OCH$_3$.

In some embodiments, R$_1$ is $C_{6-10}$ aryl or 5-6 membered heteroaryl, wherein said $C_{6-10}$ aryl or 5-10 membered heteroaryl is optionally substituted with 1, 2, 3, or 4 independently selected R$_8$.

In some embodiments, R$_1$ is phenyl or 5-6 membered heteroaryl, wherein said phenyl or 5-6 membered heteroaryl may each optionally be substituted with one or two substitutents selected from the group consisting of F, Cl, Br, CH$_3$ and —OCH$_3$.

In some embodiments, R$_1$ is phenyl, thienyl, or pyridyl, wherein said phenyl, thienyl, or pyridyl may each optionally be substituted with one or two substitutents selected from the group consisting of F, Cl, Br, CH$_3$ and —OCH$_3$ In some embodiments, R$_1$ is phenyl which is optionally substituted with one or two substitutents selected from the group consisting of F, Cl, Br, CH$_3$ and —OCH$_3$.

In some embodiments, L$_1$R$_1$ is CH$_2$-phenyl, wherein said phenyl is optionally substituted with one or two substitutents selected from the group consisting of F, Cl, Br, CH$_3$ and —OCH$_3$.

In some embodiments, L$_1$R$_1$ is CH$_2$-pyridyl wherein said pyridyl is optionally substituted with one or two substitutents selected from the group consisting of F, Cl, Br, CH$_3$ and —OCH$_3$.

In some embodiments, L$_1$R$_1$ is CH$_2$-thienyl, wherein said thienyl is optionally substituted with one or two substitutents selected from the group consisting of F, Cl, Br, and CH$_3$.

In some embodiments, L$_1$R$_1$ is CH$_2$—CH$_2$-phenyl, wherein said phenyl is optionally substituted with one or two substitutents selected from the group consisting of F, Cl, Br, CH$_3$ and —OCH$_3$.

In some embodiments, L$_1$R$_1$ is -1,1-cyclopropyl-phenyl, wherein said phenyl is optionally substituted with one or two substitutents selected from the group consisting of F, Cl, Br, CH$_3$ and —OCH$_3$.

In some embodiments, R$_2$ is H, CH$_3$, or cyclopropyl.

In some embodiments, R$_2$ is H or CH$_3$.

In some embodiments, R$_2$ is H.

In some embodiments, R$_1$ and R$_2$, together with the included nitrogen atom and L$_1$, form a 4-6 membered heterocycloalkyl group having one or two heteroatoms independently selected from nitrogen and oxygen, wherein said heterocycloalkyl group is optionally substituted by one or two independently selected R$_8$ groups.

In some embodiments, R$_1$ and R$_2$, together with the included nitrogen atom and L$_1$, form an azetidinyl, pyrrolodinyl, piperidinyl, piperazinyl, or morpholinyl ring, wherein said azetidinyl, pyrrolodinyl, piperidinyl, piperazinyl, or morpholinyl ring is optionally substituted by one or two independently selected R$_8$ groups.

In some embodiments, R$_1$ and R$_2$, together with the included nitrogen atom and L$_1$, form a heterocycloalkyl group selected from the group consisting of:

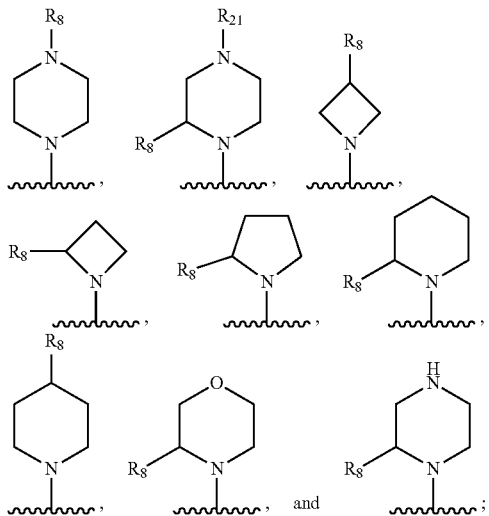

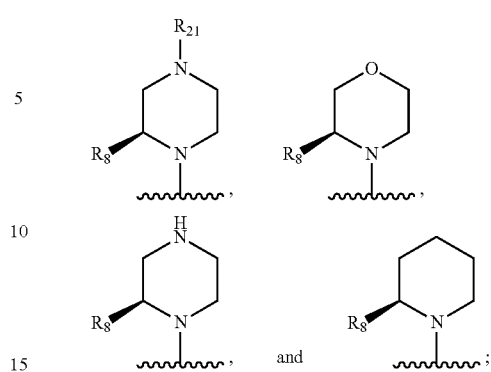

wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$.

In some embodiments, $R_{21}$ is $C_{1-6}$ alkyl, —C(O)$R_{11}$, —C(O)O$R_{11}$, —C(O)N$R_{11}R_{12}$, or —S(O)$_2R_{11}$, wherein said $C_{1-6}$ alkyl may optionally be substituted with N$R_{11}R_{12}$.

In some embodiments, $R_{21}$ is C(O)CH$_3$, S(O)$_2$CH$_3$, CH$_2$CH$_2$N(CH$_3$)$_2$, or C(O)NH(cyclopropyl).

In some embodiments, $R_{21}$ is C(O)CH$_3$ or S(O)$_2$CH$_3$.

In some embodiments, $R_1$ and $R_2$, together with the included nitrogen atom and $L_1$, form a heterocycloalkyl group selected from the group consisting of:

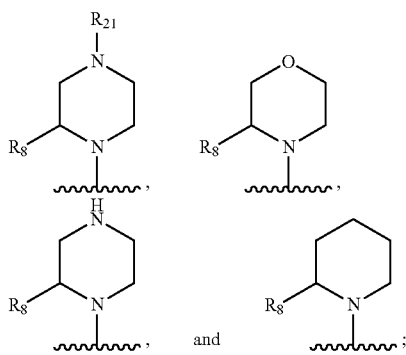

wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$.

In some embodiments, $R_1$ and $R_2$, together with the included nitrogen atom and $L_1$, form a heterocycloalkyl group selected from the group consisting of:

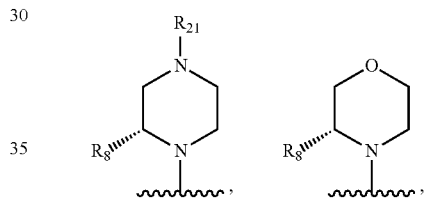

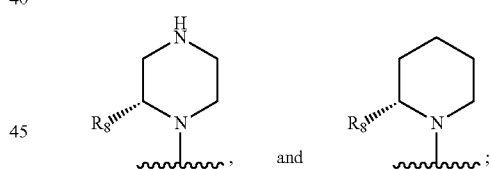

wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$.

In some embodiments, $R_{21}$ is $C_{1-6}$ alkyl, $C_{3-6}$ cycloalkyl, —C(O)$R_{11}$, —C(O)O$R_{11}$, —C(O)N$R_{11}R_{12}$, or —S(O)$_2R_{11}$, wherein said $C_{1-6}$ alkyl may optionally be substituted with N$R_{11}R_{12}$.

In some embodiments, $R_{21}$ is C(O)CH$_3$, S(O)$_2$CH$_3$, CH$_2$CH$_2$N(CH$_3$)$_2$, or C(O)NH(cyclopropyl).

In some embodiments, $R_{21}$ is C(O)CH$_3$ or S(O)$_2$CH$_3$.

In some embodiments, $R_1$ and $R_2$, together with the included nitrogen atom and $L_1$, form a heterocycloalkyl group selected from the group consisting of:

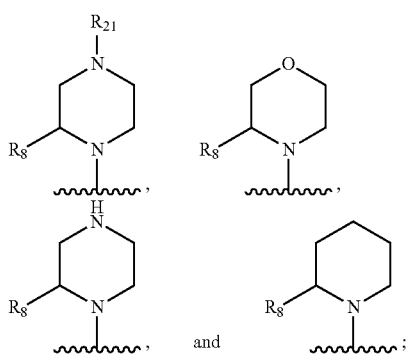

wherein R$_8$ is phenyl; and wherein R$_{21}$ is C$_{1-6}$ alkyl, C$_{3-6}$ cycloalkyl, 4-7 membered heterocycloalkyl, 5-6 membered heteroaryl, phenyl, —C(O)R$_{11}$, —C(O)OR$_{11}$, —C(O)NR$_{11}$R$_{12}$, or —S(O)$_2$R$_{11}$, wherein said C$_{1-6}$ alkyl, C$_{3-6}$ cycloalkyl, 4-7 membered heterocycloalkyl, 5-6 membered heteroaryl, and phenyl are each optionally substituted with 1, 2, or 3 independently selected R$_{14}$.

In some embodiments, R$_1$ and R$_2$, together with the included nitrogen atom and L$_1$, form a heterocycloalkyl group selected from the group consisting of:

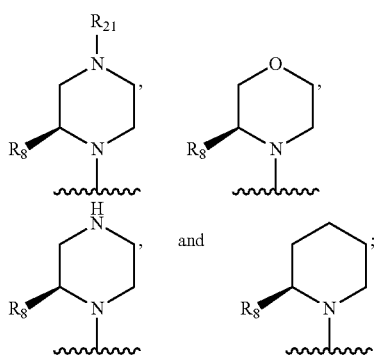

wherein R$_8$ is phenyl; and wherein R$_{21}$ is C$_{1-6}$ alkyl, C$_{3-6}$ cycloalkyl, 4-7 membered heterocycloalkyl, 5-6 membered heteroaryl, phenyl, —C(O)R$_{11}$, —C(O)OR$_{11}$, —C(O)NR$_{11}$R$_{12}$, or —S(O)$_2$R$_{11}$, wherein said C$_{1-6}$ alkyl, C$_{3-6}$ cycloalkyl, 4-7 membered heterocycloalkyl, 5-6 membered heteroaryl, and phenyl are each optionally substituted with 1, 2, or 3 independently selected R$_{14}$.

In some embodiments, R$_1$ and R$_2$, together with the included nitrogen atom and L$_1$, form a heterocycloalkyl group selected from the group consisting of:

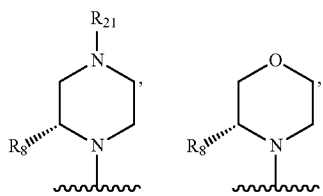

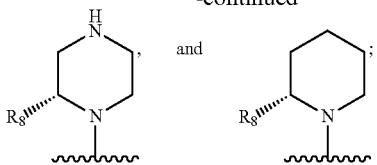

wherein R$_8$ is phenyl; and wherein R$_{21}$ is C$_{1-6}$ alkyl, C$_{3-6}$ cycloalkyl, 4-7 membered heterocycloalkyl, 5-6 membered heteroaryl, phenyl, —C(O)R$_{11}$, —C(O)OR$_{11}$, —C(O)NR$_{11}$R$_{12}$, or —S(O)$_2$R$_{11}$, wherein said C$_{1-6}$ alkyl, C$_{3-6}$ cycloalkyl, 4-7 membered heterocycloalkyl, 5-6 membered heteroaryl, and phenyl are each optionally substituted with 1, 2, or 3 independently selected R$_{14}$.

In some embodiments, R$_{21}$ is C$_{1-6}$ alkyl, C$_{3-6}$ cycloalkyl, —C(O)R$_{11}$, —C(O)OR$_{11}$, —C(O)NR$_{11}$R$_{12}$, or —S(O)$_2$R$_{11}$, wherein said C$_{1-6}$ alkyl may optionally be substituted with NR$_{11}$R$_{12}$.

In some embodiments, R$_{21}$ is C(O)CH$_3$, S(O)$_2$CH$_3$, CH$_2$CH$_2$N(CH$_3$)$_2$, or C(O)NH(cyclopropyl).

In some embodiments, R$_{21}$ is C(O)CH$_3$ or S(O)$_2$CH$_3$.

In some embodiments, R$_1$ and R$_2$, together with the included nitrogen atom and L$_1$, form a heterocycloalkyl group selected from the group consisting of:

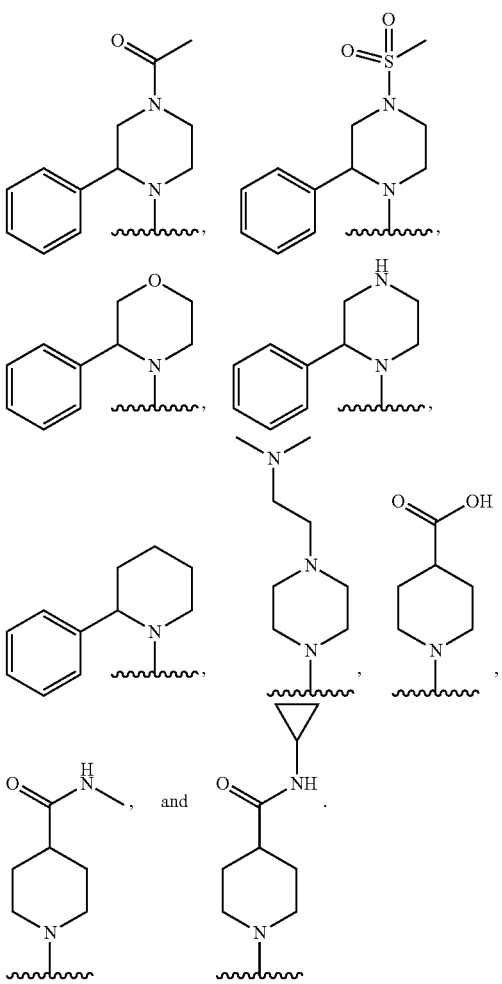

In some embodiments, $R_1$ and $R_2$, together with the included nitrogen atom and $L_1$, form a heterocycloalkyl group selected from the group consisting of:

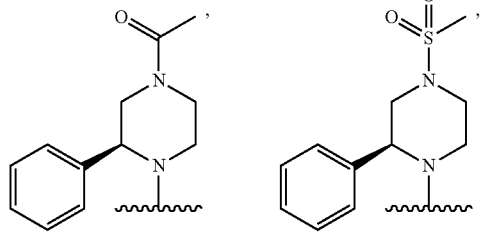

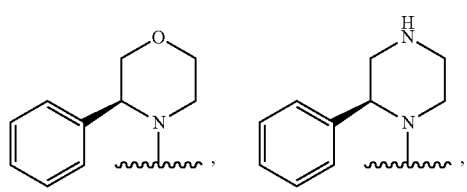

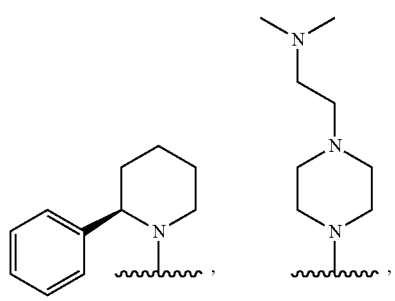

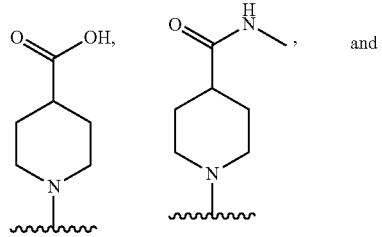

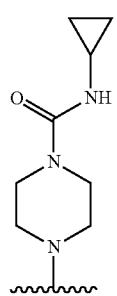

In some embodiments, $R_1$ and $R_2$, together with the included nitrogen atom and $L_1$, form a heterocycloalkyl group selected from the group consisting of:

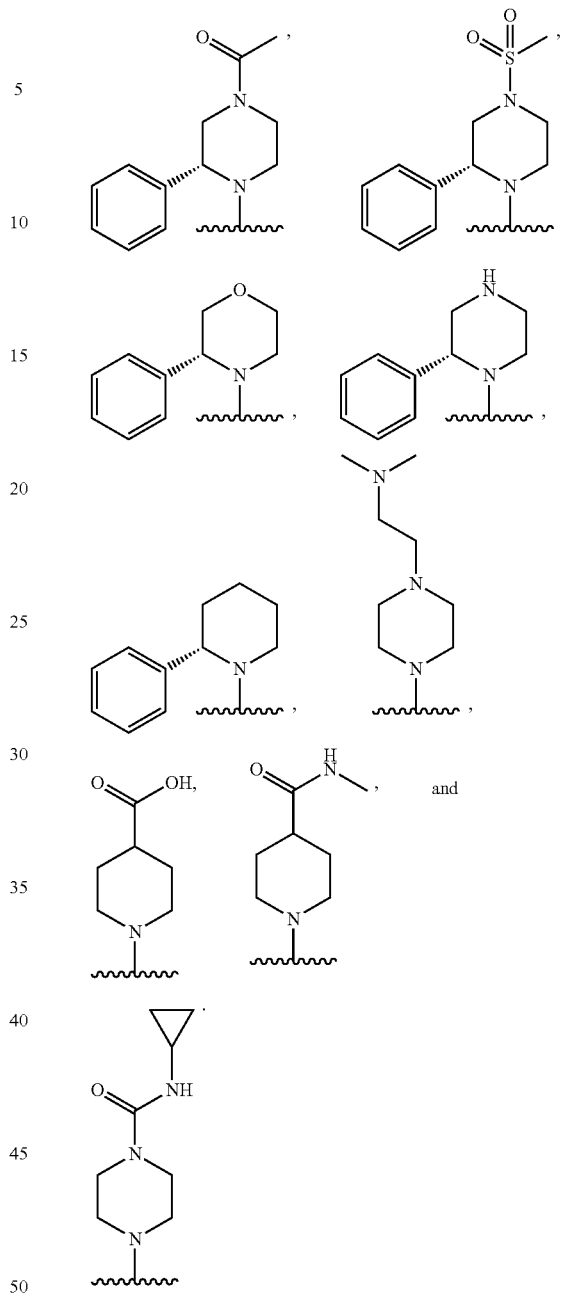

In some embodiments, $R_1$ and $R_2$, together with the included nitrogen atom and $L_1$, form a heterocycloalkyl group selected from the group consisting of:

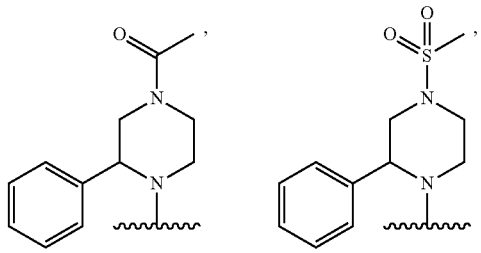

-continued

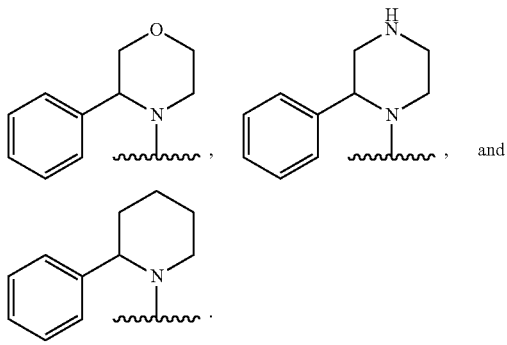

In some embodiments, $R_1$ and $R_2$, together with the included nitrogen atom and $L_1$, form a heterocycloalkyl group selected from the group consisting of:

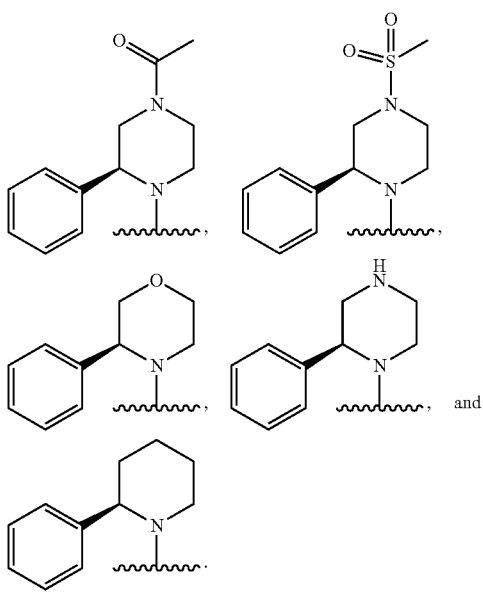

In some embodiments, $R_1$ and $R_2$, together with the included nitrogen atom and $L_1$, form a heterocycloalkyl group selected from the group consisting of:

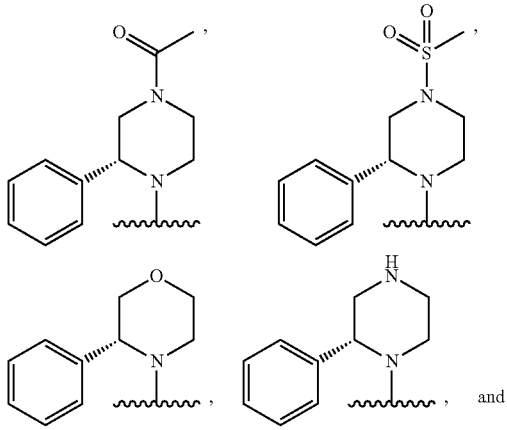

-continued

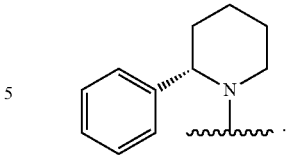

In some embodiments, $R_3$ and $R_4$ are independently selected for each occurrence from the group consisting of aryl and heteroaryl, wherein said aryl and heteroaryl may each optionally be substituted with one or more $R_8$.

In some embodiments, $R_3$ and $R_4$ are each independently from the group consisting of $C_{6-10}$ aryl and 5-10 membered heteroaryl, wherein said $C_{6-10}$ aryl and 5-10 membered heteroaryl may each optionally be substituted with one or more $R_8$.

In some embodiments, $R_3$ and $R_4$ are each independently from the group consisting of $C_{6-10}$ aryl and 5-10 membered heteroaryl, wherein said $C_{6-10}$ aryl and 5-10 membered heteroaryl may each optionally be substituted with 1, 2, 3, or 4 independently selected $R_8$.

In some embodiments, $R_3$ and $R_4$ are each independently selected from the group consisting of phenyl and 5-6 membered heteroaryl, wherein said phenyl and 5-6 membered heteroaryl may each optionally be substituted with 1, 2, 3, or 4 independently selected $R_8$.

In some embodiments, $R_3$ is isoxazolyl, pyrazolyl, 2-oxopyridinyl, 2-hydroxypyridinyl, each of which is optionally substituted by one or two methyl groups.

In some embodiments, $R_3$ and $R_4$ are each independently selected from the group consisting of H,

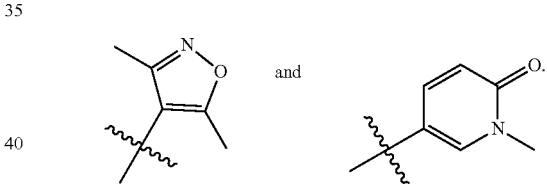

In some embodiments, $R_3$ is selected from the group consisting of

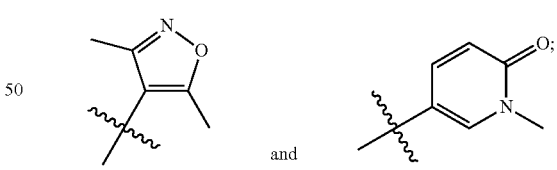

and $R_4$ is H.

In some embodiments, X is CH.
In some embodiments, X is N.
In some embodiments, Z is CH.
In some embodiments, Z is N.
In some embodiments, X is CH and Z is N.
In some embodiments, both X and Z are N.
In some embodiments, X is N; and Z is CH.
In some embodiments, Y is selected from the group consisting of $NR_6R_7$, —$C(O)R_{11}$, —$C(O)NR_{11}R_{12}$, heterocycloalkyl, and heteroaryl, wherein said heterocycloalkyl and heteroaryl is optionally be substituted with one or more $R_8$.

In some embodiments, Y is selected from the group consisting of $NR_6R_7$, —$C(O)R_{11}$, —$C(O)NR_{11}R_{12}$, 4-10 membered heterocycloalkyl, and 5-10 membered heteroaryl, wherein said heterocycloalkyl and heteroaryl is optionally be substituted with 1, 2, 3, or 4 independently selected $R_8$.

In some embodiments, Y is $NR_6R_7$.

In some embodiments, Y is —$C(O)R_{11}$.

In some embodiments, Y is —$C(O)NR_{11}R_{12}$.

In some embodiments, Y is 4-6 membered heterocycloalkyl, wherein said 4-6 membered heterocycloalkyl may optionally be substituted with one or more $R_8$.

In some embodiments, Y is 4-6 membered heterocycloalkyl, wherein said 4-6 membered heterocycloalkyl may optionally be substituted with 1 or 2 $R_8$ groups independently selected from the group consisting of $C_{1-6}$ alkyl, 5-6 membered heterocycloalkyl, phenyl, $OR_{11}$, —$C(O)R_{11}$, —$C(O)OR_{11}$, —$C(O)NR_{11}R_{12}$, $S(O)_2R_{11}$, wherein said $C_{1-6}$ alkyl, 5-6 membered heterocycloalkyl, and phenyl are each optionally substituted with 1 or 2 independently selected $R_{14}$ groups;

each $R_{11}$ of $OR_{11}$, —$C(O)R_{11}$, —$C(O)OR_{11}$, —$C(O)NR_{11}R_{12}$, $S(O)_2R_{11}$ is independently selected from the group consisting of H, $C_{1-6}$ alkyl, $C_{3-6}$ cycloalkyl, 4-6 membered heterocycloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1 or 2 independently selected $R_{14}$;

each $R_{12}$ of —$C(O)NR_{11}R_{12}$ is independently selected from the group consisting of H and $C_{1-6}$ alkyl; and each $R_{14}$ attached to $R_8$ or $R_{11}$ is independently selected from the group consisting of halogen, $C_{1-6}$ alkyl, phenyl, 5-6 membered heterocycloalkyl, 5-6 membered heteroaryl, $OR_{18}$, $NR_{18}R_{19}$, $C(O)R_{18}$, $C(O)NR_{18}R_{19}$, and $S(O)_2R_{18}$, wherein said phenyl, 5-6 membered heterocycloalkyl, and 5-6 membered heteroaryl may optionally be substituted with 1 or 2 methyl groups.

In some embodiments, Y is 4-6 membered heterocycloalkyl, wherein said 4-6 membered heterocycloalkyl may optionally be substituted with 1 or 2 $R_8$ groups independently selected from the group consisting of $C_{1-3}$ alkyl, 5-6 membered heterocycloalkyl, phenyl, —$C(O)R_{11}$, —$C(O)NHR_{11}$, $S(O)_2CH_3$, wherein said $C_{1-6}$ alkyl, 5-6 membered heterocycloalkyl, and phenyl are each optionally substituted with 1 or 2 independently selected $R_{14}$;

wherein each $R_{11}$ of —$C(O)R_{11}$ and —$C(O)NHR_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1 or 2 independently selected $R_{14}$; and wherein each $R_{14}$ attached to $R_8$ or $R_{11}$ is independently selected from the group consisting of chloro, methyl, OH, $N(CH_3)_2$, $C(O)CH_3$, $C(O)NH_2$, $C(O)NHCH_3$, 1-methyl-1H-imidazolyl, 1,3-dimethyl-1H-pyrazolyl, and 1-methylazetidinyl.

In some embodiments, Y is 5-6 membered heteroaryl, wherein said 5-6 membered heteroaryl may optionally be substituted with one or more $R_8$.

In some embodiments, Y is 5-6 membered heteroaryl, wherein said 5-6 membered heteroaryl may optionally be substituted with 1 or 2 independently selected $R_8$ groups independently selected from the group consisting of $C_{1-6}$ alkyl, 5-6 membered heterocycloalkyl, phenyl, $OR_{11}$, —$C(O)R_{11}$, —$C(O)OR_{11}$, —$C(O)NR_{11}R_{12}$, $S(O)_2R_{11}$, wherein said $C_{1-6}$ alkyl, 5-6 membered heterocycloalkyl, and phenyl are each optionally substituted with 1 or 2 independently selected $R_{14}$ groups;

each $R_{11}$ of $OR_{11}$, —$C(O)R_{11}$, —$C(O)OR_{11}$, —$C(O)NR_{11}R_{12}$, $S(O)_2R_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1 or 2 independently selected $R_{14}$;

each $R_{12}$ of —$C(O)NR_{11}R_{12}$ is independently selected from the group consisting of H and $C_{1-6}$ alkyl; and each $R_{14}$ attached to $R_8$ or $R_{11}$ is independently selected from the group consisting of halogen, $C_{1-6}$ alkyl, phenyl, 5-6 membered heterocycloalkyl, 5-6 membered heteroaryl, $OR_{18}$, $NR_{18}R_{19}$, $C(O)R_{18}$, $C(O)NR_{18}R_{19}$, and $S(O)_2R_{18}$, wherein said phenyl, 5-6 membered heterocycloalkyl, and 5-6 membered heteroaryl may optionally be substituted with 1 or 2 methyl groups.

In some embodiments, Y is 5-6 membered heteroaryl, wherein said 5-6 membered heteroaryl may optionally be substituted with one or more $R_8$ groups independently selected from the group consisting of $C_{1-3}$ alkyl, 5-6 membered heterocycloalkyl, phenyl, —$C(O)R_{11}$, —$C(O)NHR_{11}$, $S(O)_2CH_3$, wherein said $C_{1-6}$ alkyl, 5-6 membered heterocycloalkyl, and phenyl are each optionally substituted with 1 or 2 independently selected $R_{14}$;

wherein each $R_{11}$ of —$C(O)R_{11}$ and —$C(O)NHR_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1 or 2 independently selected $R_{14}$; and wherein each $R_{14}$ attached to $R_8$ or $R_{11}$ is independently selected from the group consisting of chloro, methyl, OH, $N(CH_3)_2$, $C(O)CH_3$, $C(O)NH_2$, $C(O)NHCH_3$, 1-methyl-1H-imidazolyl, 1,3-dimethyl-1H-pyrazolyl, and 1-methylazetidinyl.

In some embodiments, Y is H, chloro, methyl, methoxy, $NHR_7$, —$C(O)R_{11}$, —$C(O)NHR_{11}$, pyridinyl, piperazinyl, pyrazolyl, piperidinyl, thienyl, isoxazolyl, 1,2,3,6-tetrahydropyridinyl, diazepanyl, 1,1-dioxidothiomorpholinyl, 4,5,6,7-tetrahydropyrazolo[4,3-c]pyridinyl, 7-azaspiro[3.5]nonanyl, 1,8-diazaspiro[4.5]decan-2-onyl, and 4,5,6,7-tetrahydroimidazo[4,5-c]pyridinyl, wherein said pyridinyl, piperazinyl, pyrazolyl, piperidinyl, thienyl, isoxazolyl, 1,2,3,6-tetrahydropyridinyl, diazepanyl, 1,1-dioxidothiomorpholinyl, 4,5,6,7-tetrahydropyrazolo[4,3-c]pyridinyl, 7-azaspiro[3.5]nonanyl, 1,8-diazaspiro[4.5]decan-2-onyl, 4,5,6,7-tetrahydroimidazo[4,5-c]pyridinyl may optionally be substituted with 1 or 2 $R_8$ groups independently selected from the group consisting of $C_{1-3}$ alkyl, 5-6 membered heterocycloalkyl, phenyl, —$C(O)R_{11}$, —$C(O)NHR_{11}$, and $S(O)_2CH_3$, wherein said $C_{1-6}$ alkyl, 5-6 membered heterocycloalkyl, and phenyl are each optionally substituted with 1 or 2 independently selected $R_{14}$;

wherein each $R_{11}$ of —$C(O)R_{11}$ and —$C(O)NHR_{11}$ is independently selected from the group consisting of H, $C_{1-6}$ alkyl, $C_{3-6}$ cycloalkyl, 4-6 membered heterocyloalkyl, and 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1 or 2 independently selected $R_{14}$; and wherein each $R_{14}$ attached to $R_8$ or $R_{11}$ is independently selected from the group consisting of chloro, methyl, OH, N(CH$_3$)$_2$, C(O)CH$_3$, C(O)NH$_2$, C(O)NHCH$_3$, 1-methyl-1H-imidazolyl, 1,3-dimethyl-1H-pyrazolyl, and 1-methylazetidinyl.

In some embodiments, Y is H, —C(O)R$_{11}$, —C(O)NHR$_{11}$, piperazinyl, pyrazolyl, piperidinyl, or thienyl, wherein said piperazinyl, pyrazolyl, piperidinyl, thienyl, may optionally be substituted with 1 or 2 independently selected R$_8$ groups independently selected from the group consisting of C$_{1-3}$ alkyl, 5-6 membered heterocycloalkyl, phenyl, —C(O)R$_{11}$, —C(O)NHR$_{11}$, and S(O)$_2$CH$_3$, wherein said C$_{1-6}$ alkyl, 5-6 membered heterocycloalkyl, and phenyl are each optionally substituted with 1 or 2 independently selected R$_{14}$;

wherein each R$_{11}$ of —C(O)R$_{11}$ and —C(O)NHR$_{11}$ is independently selected from the group consisting of H, C$_{1-6}$ alkyl, C$_{3-6}$ cycloalkyl, 4-6 membered heterocyloalkyl, 5-6 membered heteroaryl, wherein said C$_{1-6}$ alkyl, C$_{3-6}$ cycloalkyl, 4-6 membered heterocycloalkyl, and 5-6 membered heteroaryl may optionally be substituted with 1 or 2 independently selected R$_{14}$; and wherein each R$_{14}$ attached to R$_8$ or R$_{11}$ is independently selected from the group consisting of chloro, methyl, OH, N(CH$_3$)$_2$, C(O)CH$_3$, C(O)NH$_2$, C(O)NHCH$_3$, 1-methyl-1H-imidazolyl, 1,3-dimethyl-1H-pyrazolyl, and 1-methylazetidinyl.

In some embodiments, Y is selected from the group consisting of:

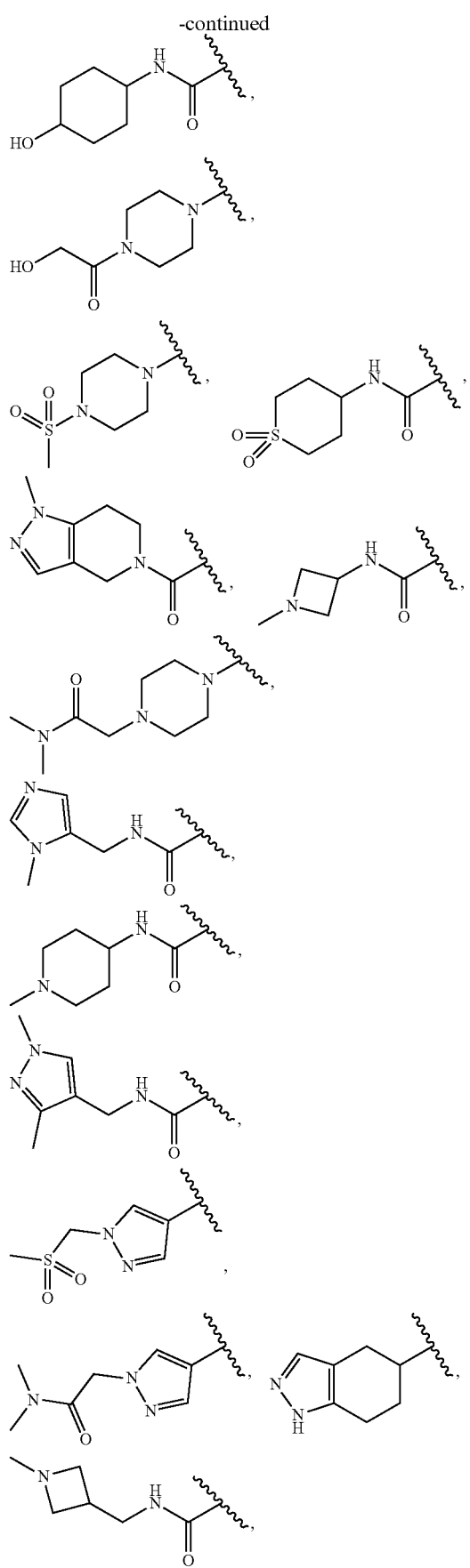

-continued

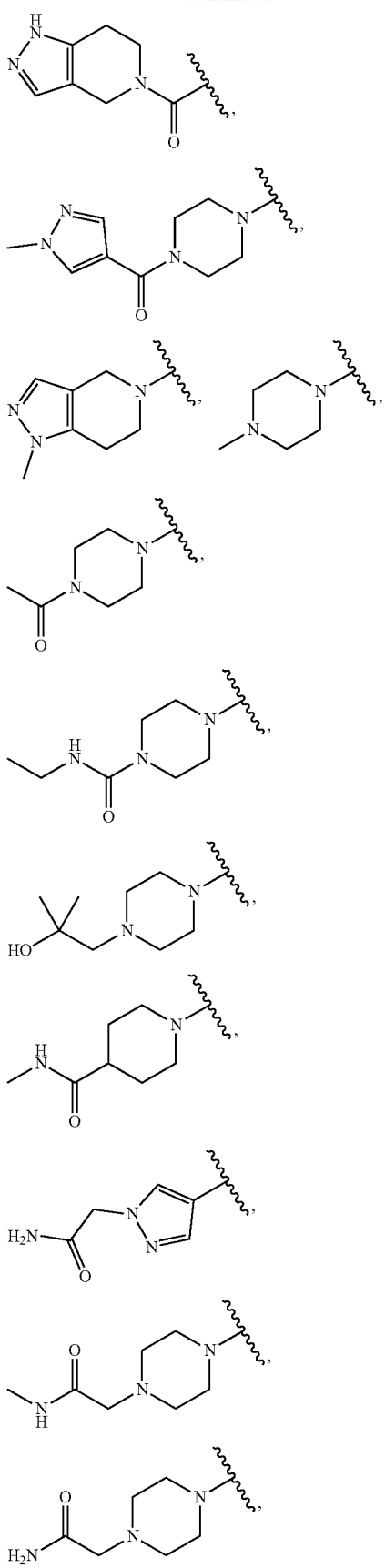

-continued

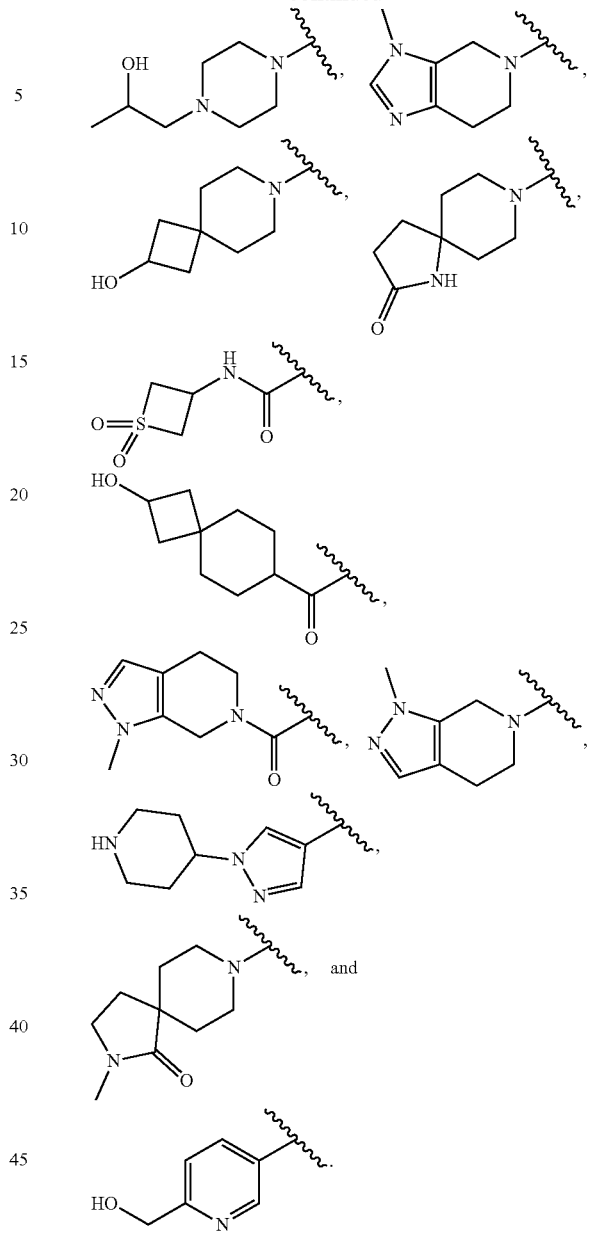

In some embodiments, the invention provides a compound of Formula I wherein:

X is CH or N;

Z is CH or N, with the proviso that when X is CH, Z is not also CH;

Y is selected from heterocycloalkyl, heteroaryl or $NR_6R_7$, wherein said heterocycloalkyl or heteroaryl is optionally substituted with one or more $R_8$;

$L_1$ is —$CH_2$— or —$CH(CH_3)$—;

$R_1$ is aryl or heteroaryl, wherein said aryl or heteroaryl may each optionally be substituted with one or two substituents selected from the group consisting of F, Cl, Br, $CH_3$ and —$OCH_3$;

$R_2$ is H or $CH_3$;

$R_3$ and $R_4$ are independently selected for each occurrence from H, aryl or heteroaryl, wherein said aryl or heteroaryl may each optionally be substituted with one or more $R_8$.

In some embodiments, the invention provides a compound of Formula I wherein:

X is CH or N;

Z is CH or N, with the proviso that when X is CH, Z is not also CH;

Y is —C(O)NR$_{11}$R$_{12}$, 4-7 membered heterocycloalkyl, 5-6 membered heteroaryl or NR$_6$R$_7$, wherein said 4-7 membered heterocycloalkyl and 5-6 membered heteroaryl are each optionally substituted with 1 or 2 independently selected R$_8$;

L$_1$ is —CH$_2$— or —CH(CH$_3$)—;

R$_1$ is phenyl or 5-6 membered heteroaryl, wherein said phenyl or 5-6 membered heteroaryl may each optionally be substituted with one or two substituents selected from the group consisting of F, Cl, Br, CH$_3$ and OCH$_3$;

R$_2$ is H or CH$_3$;

R$_3$ is a 5-6 membered heteroaryl which is substituted with 1 or 2 methyl groups; and R$_4$ is H.

In some embodiments, the invention provides a compound of Formula I wherein:

X is CH or N;

Z is CH or N, with the proviso that when X is CH, Z is not CH;

Y is —C(O)NR$_{11}$R$_{12}$ or a heterocycloalkyl or heteroaryl selected from:

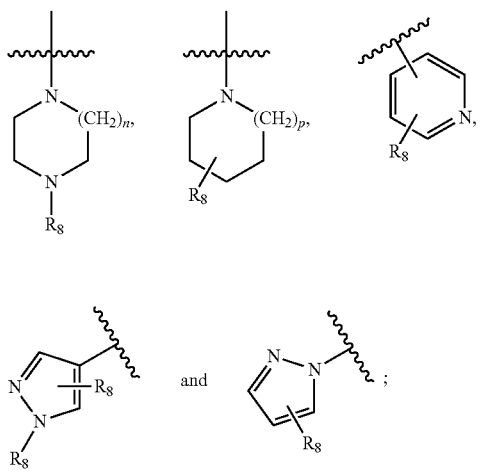

wherein:
n is 1 or 2;
p is 0, 1 or 2;
R$_8$ is H, C$_1$-C$_6$ alkyl, or —(CH$_2$)$_m$—R$_{16}$ or —(CH$_2$)$_q$—R$_{17}$;
m is 1, 2, 3 or 4;
q is 2, 3 or 4;
R$_{16}$ is —CO$_2$H or —C(O)NR$_6$R$_7$; and
R$_{17}$ is OH or NR$_6$R$_7$.

In some embodiments, the invention provides a compound of Formula I wherein:

X is CH or N;

Z is CH or N, with the proviso that when X is CH, Z is not CH;

Y is a heterocycloalkyl or heteroaryl selected from:

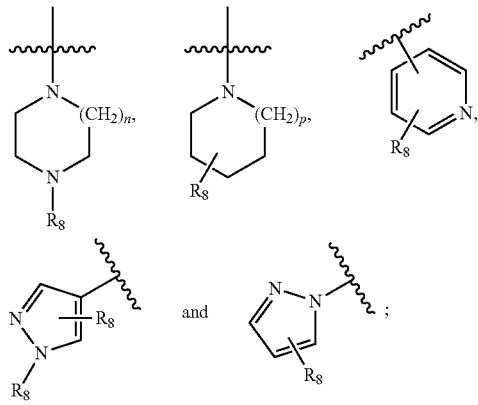

wherein:
n is 1 or 2;
p is 0, 1 or 2;
R$_8$ is H, C$_1$-C$_6$ alkyl, or —(CH$_2$)$_m$—R$_{16}$ or —(CH$_2$)$_q$—R$_{17}$;
m is 1, 2, 3 or 4;
q is 2, 3 or 4;
R$_{16}$ is —CO$_2$H or —C(O)NR$_6$R$_7$; and
R$_{17}$ is OH or NR$_6$R$_7$.

In some embodiments, the invention provides a compound of Formula I wherein:

X is CH or N;

Z is CH or N, with the proviso that when X is CH, Z is not also CH;

L$_1$ is —CH$_2$— or —CH(CH$_3$)—;

Y is —C(O)NR$_{11}$R$_{12}$ or a heterocycloalkyl or heteroaryl selected from:

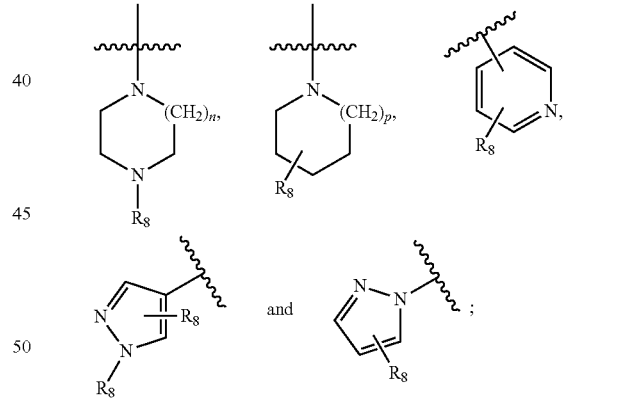

wherein:
n is 1 or 2;
p is 0, 1 or 2;
R$_8$ is H, C$_1$-C$_6$ alkyl, or —(CH$_2$)$_m$—R$_{16}$ or —(CH$_2$)$_q$—R$_{17}$;
m is 1, 2, 3 or 4;
q is 2, 3 or 4;
R$_{16}$ is —CO$_2$H or —C(O)NR$_6$R$_7$;
R$_{17}$ is OH or NR$_6$R$_7$.
R$_1$ is C$_{6-10}$ aryl or 5-10 membered heteroaryl, wherein said C$_{6-10}$ aryl or 5-10 membered heteroaryl may each optionally be substituted with one or two substituents selected from the group consisting of F, Cl, Br, CH$_3$ and —OCH$_3$;

$R_2$ is H or $CH_3$; and $R_3$ and $R_4$ are independently selected for each occurrence from H, $C_{6-10}$ aryl or 5-10 membered heteroaryl, wherein said $C_{6-10}$ aryl or 5-10 membered heteroaryl may each optionally be substituted with one or more $R_8$.

In some embodiments, the invention provides a compound of Formula I wherein:

X is CH or N;

Z is CH or N, with the proviso that when X is CH, Z is not also CH;

$L_1$ is —$CH_2$— or —$CH(CH_3)$—;

Y is a heterocycloalkyl or heteroaryl selected from:

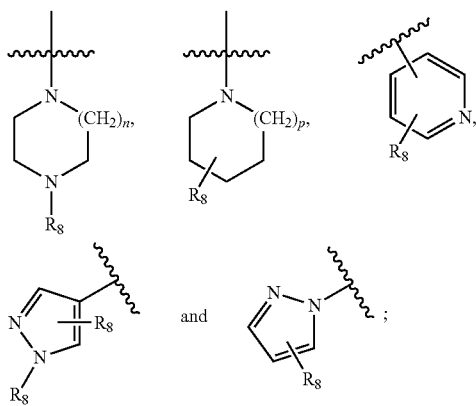

wherein:

n is 1 or 2;

p is 0, 1 or 2;

$R_8$ is H, $C_1$-$C_6$ alkyl, or —$(CH_2)_m$—$R_{16}$ or —$(CH_2)_q$—$R_{17}$;

m is 1, 2, 3 or 4;

q is 2, 3 or 4;

$R_{16}$ is —$CO_2H$ or —$C(O)NR_6R_7$;

$R_{17}$ is OH or $NR_6R_7$.

$R_1$ is aryl or heteroaryl, wherein said aryl or heteroaryl may each optionally be substituted with one or two substituents selected from the group consisting of F, Cl, Br, $CH_3$ and —$OCH_3$;

$R_2$ is H or $CH_3$; and $R_3$ and $R_4$ are independently selected for each occurrence from H, aryl or heteroaryl, wherein said aryl or heteroaryl may each optionally be substituted with one or more $R_8$.

In some embodiments, the invention provides a compound of Formula I wherein:

X is N;

Z is N;

$L_1$ is —$CH_2$— or —$CH(CH_3)$—;

Y is —$C(O)NR_{11}R_{12}$ or a heterocycloalkyl or heteroaryl selected from:

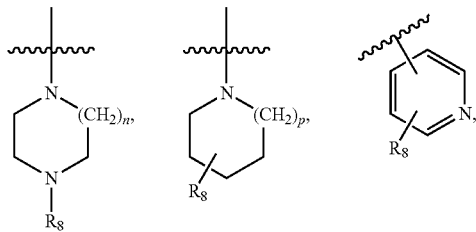

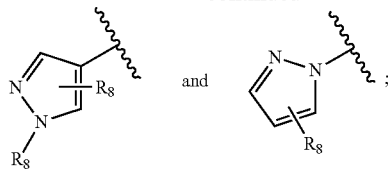

wherein:

n is 1 or 2;

p is 0, 1 or 2;

$R_8$ is H, $C_{1-6}$ alkyl, —$(CH_2)_m$—$R_{16}$ or —$(CH_2)_q$—$R_{17}$;

m is 1, 2, 3 or 4;

q is 2, 3 or 4;

$R_{16}$ is —$CO_2H$ or —$C(O)NR_6R_7$;

$R_{17}$ is OH or $NR_6R_7$;

$R_1$ is $C_{6-10}$ aryl or 5-10 membered heteroaryl, wherein said $C_{6-10}$ aryl or 5-10 membered heteroaryl may each optionally be substituted with one or two substituents selected from the group consisting of F, Cl, Br, $CH_3$ and —$OCH_3$;

$R_2$ is H or $CH_3$; and $R_3$ and $R_4$ are independently selected for each occurrence from H, $C_{6-10}$ aryl or 5-10 membered heteroaryl, wherein said $C_{6-10}$ aryl or 5-10 membered heteroaryl may each optionally be substituted with one or more $R_8$.

In some embodiments, the invention provides a compound of Formula I wherein:

X is N;

Z is N;

$L_1$ is —$CH_2$— or —$CH(CH_3)$—;

Y is a heterocycloalkyl or heteroaryl selected from:

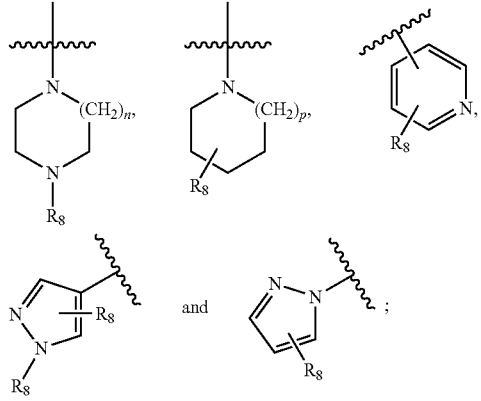

wherein:

n is 1 or 2;

p is 0, 1 or 2;

$R_8$ is H, $C_1$-$C_6$ alkyl, —$(CH_2)_m$—$R_{16}$ or —$(CH_2)_q$—$R_{17}$;

m is 1, 2, 3 or 4;

q is 2, 3 or 4;

$R_{16}$ is —$CO_2H$ or —$C(O)NR_6R_7$;

$R_{17}$ is OH or $NR_6R_7$;

$R_1$ is aryl or heteroaryl, wherein said aryl or heteroaryl may each optionally be substituted with one or two substituents selected from the group consisting of F, Cl, Br, $CH_3$ and —$OCH_3$;

$R_2$ is H or $CH_3$; and $R_3$ and $R_4$ are independently selected for each occurrence from H, aryl or heteroaryl, wherein said aryl or heteroaryl may each optionally be substituted with one or more $R_8$.

In some embodiments:

X is CH or N;

Z is CH or N; with the proviso that when X is CH, Z is not also CH;

Y is selected from the group consisting of H, Cl, $C_{1-6}$ alkyl, $OR_5$, $NR_6R_7$, —$C(O)R_{11}$, —$C(O)OR_{11}$, —$C(O)NR_{11}R_{12}$, $C_{3-10}$ cycloalkyl, 4-10 membered heterocycloalkyl, $C_{6-10}$ aryl, and 5-10 membered heteroaryl, wherein said $C_{3-10}$ cycloalkyl, 4-10 membered heterocycloalkyl, $C_{6-10}$ aryl, and 5-10 membered heteroaryl, may optionally be substituted with 1, 2, 3, or 4 independently selected $R_8$;

$R_1$ and $R_2$, together with the included nitrogen atom and $L_1$, form a 4-, 5-, 6- or 7-membered heterocycloalkyl group which is optionally substituted with 1 or 2 independently selected $R_8$;

$R_3$ is selected from the group consisting of H, 5-6 membered heterocycloalkyl, and 5-6 membered heteroaryl, wherein said 5-6 membered heterocycloalkyl, and 5-6 membered heteroaryl, may optionally be substituted with 1, 2, 3, or 4 independently selected $R_8$;

$R_4$ is selected from the group consisting of H and 5-6 membered heteroaryl, wherein said 5-6 membered heteroaryl may optionally be substituted with 1, 2, 3, or 4 independently selected $R_8$;

$R_5$ is selected from the group consisting of $C_{1-6}$ alkyl and phenyl, wherein said phenyl may optionally be substituted with 1, 2, 3, or 4 independently selected $R_8$;

each $R_6$ is independently selected from the group consisting of H and $C_{1-6}$ alkyl;

each $R_7$ is independently selected from the group consisting of H, $C_{1-6}$ alkyl, and 4-10 membered heterocycloalkyl, wherein said $C_{1-6}$ alkyl and 4-10 membered heterocycloalkyl may optionally be substituted by 1, 2, 3, or 4 independently selected $R_8$;

each $R_8$ is independently selected from the group consisting of halogen, $C_{1-6}$ alkyl, $C_{3-6}$ cycloalkyl, 4-10 membered heterocycloalkyl, 5-10 membered heteroaryl, phenyl, CN, $OR_{11}$, —$C(O)R_{11}$, —$C(O)OR_{11}$, —$C(O)NR_{11}R_{12}$, $NR_{11}R_{12}$, and $S(O)_2R_{11}$, wherein said $C_{1-6}$ alkyl, 4-10 membered heterocycloalkyl, and 5-10 membered heteroaryl may optionally be substituted by 1, 2, 3, or 4 independently selected $R_{14}$;

each $R_{11}$ is independently selected from the group consisting of H, $C_{1-6}$ alkyl, $C_{3-6}$ cycloalkyl, 4-10 membered heterocycloalkyl, and 5-10 membered heteroaryl, wherein said $C_{1-6}$ alkyl, $C_{3-6}$ cycloalkyl, 4-10 membered heterocycloalkyl and 5-10 membered heteroaryl may optionally be substituted with 1, 2, 3, or 4 independently selected $R_{14}$;

each $R_{12}$ is independently selected from the group consisting of H and $C_{1-6}$ alkyl;

each $R_{14}$ is independently selected from the group consisting of H, halogen, $C_{1-6}$ alkyl, CN, $OR_{18}$, $NR_{18}R_{19}$, $C(O)R_{18}$, $C(O)OR_{18}$, $C(O)NR_{18}R_{19}$, $S(O)_2R_{18}$, $C_{3-6}$ cycloalkyl, 4-10 membered heterocycloalkyl, 5-10 membered heteroaryl, and phenyl, wherein said $C_{3-6}$ cycloalkyl, 4-10 membered heterocycloalkyl, 5-10 membered heteroaryl, and phenyl may optionally be substituted with 1, 2, 3, or 5 independently selected $R_{15}$;

each $R_{15}$ is independently selected from the group consisting of —$CH_3$, halogen, and CN;

each $R_{18}$ is independently selected from the group consisting of H and $C_{1-6}$ alkyl; and each $R_{19}$ is independently selected from the group consisting of H and $C_{1-6}$ alkyl.

In some embodiments:

X is CH or N;

Z is CH or N; with the proviso that when X is CH, Z is not also CH;

Y is selected from the group consisting of H, Cl, $C_{1-6}$ alkyl, $NR_6R_7$, —$C(O)R_{11}$, —$C(O)OR_{11}$, —$C(O)NR_{11}R_{12}$, 4-10 membered heterocycloalkyl, phenyl, and 5-10 membered heteroaryl, wherein said cycloalkyl, heterocycloalkyl, aryl and heteroaryl may optionally be substituted with one or more $R_8$;

$R_1$ and $R_2$, together with the included nitrogen atom and $L_1$, form a 4-, 5-, 6- or 7-membered heterocycloalkyl group which is optionally substituted with one or more $R_8$;

$R_3$ is selected from the group consisting of H, 5-6 membered heterocycloalkyl, and 5-6 membered heteroaryl, wherein said 5-6 membered heterocycloalkyl, and 5-6 membered heteroaryl may optionally be substituted with 1, 2, 3, or 4 independently selected $R_8$;

$R_4$ is H;

each $R_6$ is independently selected from the group consisting of H and $C_{1-6}$ alkyl;

each $R_7$ is an independently selected $C_{1-6}$ alkyl group, each of which may optionally be substituted by 1, 2, 3, or 4 independently selected $R_8$;

each $R_8$ is independently selected from the group consisting of $C_{1-6}$ alkyl, $C_{3-6}$ cycloalkyl, 4-10 membered heterocycloalkyl, phenyl, $OR_{11}$, —$C(O)R_{11}$, —$C(O)OR_{11}$, —$C(O)NR_{11}R_{12}$, $S(O)_2R_{11}$, wherein said $C_{1-6}$ alkyl, 4-10 membered heterocycloalkyl, phenyl, are each optionally substituted with 1, 2, 3, or 4 independently selected $R_{14}$;

each $R_{11}$ is independently selected from the group consisting of H, $C_{1-6}$ alkyl, $C_{3-6}$ cycloalkyl, 4-10 membered heterocyloalkyl, and 5-10 membered heteroaryl, wherein said $C_{1-6}$ alkyl, $C_{3-6}$ cycloalkyl, 4-10 membered heterocyloalkyl, 5-10 membered heteroaryl, may optionally be substituted with one or more $R_{14}$;

each $R_{12}$ is independently selected from the group consisting of H and $C_{1-6}$ alkyl;

each $R_{14}$ is independently selected from the group consisting of halogen, $C_{1-6}$ alkyl, phenyl, 4-10 membered heterocycloalkyl, 5-10 membered heteroaryl, $OR_{18}$, $NR_{18}R_{19}$, $C(O)R_{18}$, $C(O)NR_{18}R_{19}$, and $S(O)_2R_{18}$, wherein said phenyl, 4-10 membered heterocycloalkyl, 5-10 membered heteroaryl, may optionally be substituted with one or more $R_{15}$;

each $R_{15}$ is $CH_3$ or CN;

each $R_{18}$ is independently selected from the group consisting of H and $C_{1-6}$ alkyl; and each $R_{19}$ is independently selected from the group consisting of H and $C_{1-6}$ alkyl.

In some embodiments:

X is CH or N;

Z is CH or N; with the proviso that when X is CH, Z is not also CH;

Y is selected from the group consisting of H, Cl, $NR_6R_7$, —$C(O)R_{11}$, —$C(O)NR_{11}R_{12}$, 4-10 membered heterocycloalkyl, and 5-10 membered heteroaryl, wherein said 4-10 heterocycloalkyl and 5-10 heteroaryl may optionally be substituted with 1, 2, 3, or 4 independently selected $R_8$;

$R_1$ and $R_2$, together with the included nitrogen atom and $L_1$, form a 4-, 5-, 6- or 7-membered heterocycloalkyl group which is optionally substituted with 1, 2, 3, or 4 independently selected $R_8$;

$R_3$ is selected from the group consisting of H, 5-6 membered heterocycloalkyl, and 5-6 membered heteroaryl, wherein said 5-6 membered heterocycloalkyl and 5-6 membered heteroaryl may optionally be substituted with 1, 2, 3, or 4 independently selected $R_8$;

$R_4$ is H;

each $R_6$ is independently selected from the group consisting of H and $C_{1-6}$ alkyl;

each $R_7$ is an independently selected $C_{1-6}$ alkyl group, each of which may optionally be substituted by 1, 2, 3, or 4 independently selected $R_8$;

each $R_8$ is independently selected from the group consisting of $C_{1-6}$ alkyl, $C_{3-6}$ cycloalkyl, 4-6 membered heterocycloalkyl, phenyl, $OR_{11}$, —C(O)$R_{11}$, —C(O)O$R_{11}$, —C(O)N$R_{11}R_{12}$, S(O)$_2R_{11}$, wherein said $C_{1-6}$ alkyl, 4-6 membered heterocycloalkyl, and phenyl are each optionally substituted with 1, 2, 3, or 4 independently selected $R_{14}$;

each $R_{11}$ is independently selected from the group consisting of H, $C_{1-6}$ alkyl, $C_{3-6}$ cycloalkyl, 4-10 membered heterocyloalkyl, and 5-10 membered heteroaryl, wherein said $C_{1-6}$ alkyl, $C_{3-6}$ cycloalkyl, 4-10 membered heterocyloalkyl, and 5-10 membered heteroaryl may optionally be substituted with 1, 2, 3, or 4 independently selected $R_{14}$;

each $R_{12}$ is independently selected from the group consisting of H and $C_{1-6}$ alkyl;

each $R_{14}$ is independently selected from the group consisting of halogen, $C_{1-6}$ alkyl, phenyl, 4-6 membered heterocycloalkyl, 5-6 membered heteroaryl, $OR_{18}$, $NR_{18}R_{19}$, C(O)$R_{18}$, C(O)N$R_{18}R_{19}$, and S(O)$_2R_{18}$, wherein said phenyl, 4-6 membered heterocycloalkyl, and 5-6 membered heteroaryl may optionally be substituted with 1, 2, 3, or 4 independently selected $R_{15}$;

each $R_{15}$ is $CH_3$ or CN;

each $R_{18}$ is independently selected from the group consisting of H and $C_{1-6}$ alkyl; and each $R_{19}$ is independently selected from the group consisting of H and $C_{1-6}$ alkyl.

In some embodiments:

X is CH or N;

Z is CH or N; with the proviso that when X is CH, Z is not also CH;

Y is selected from the group consisting of H, $NR_6R_7$, —C(O)$R_{11}$, —C(O)N$R_{11}R_{12}$, 4-10 membered heterocycloalkyl, and 5-10 membered heteroaryl, wherein said 4-10 membered heterocycloalkyl and 5-6 membered heteroaryl may optionally be substituted with 1, 2, 3, or 4 independently selected $R_8$;

$R_1$ and $R_2$, together with the included nitrogen atom and $L_1$, form a heterocycloalkyl group selected from the group consisting of:

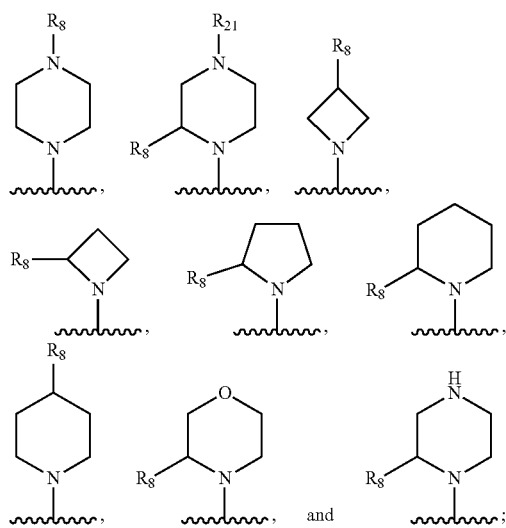

$R_3$ is selected from the group consisting of H, 5-6 membered heterocycloalkyl, and 5-6 membered heteroaryl, wherein said 5-6 membered heterocycloalkyl and 5-6 membered heteroaryl may optionally be substituted with 1, 2, 3, or 4 independently selected $R_8$;

$R_4$ is H;

each $R_6$ is independently selected from the group consisting of H and $C_{1-6}$ alkyl;

each $R_7$ is an independently selected $C_{1-6}$ alkyl group, each of which may optionally be substituted by 1, 2, 3, or 4 independently selected $R_8$;

each $R_8$ is independently selected from the group consisting of $C_{1-6}$ alkyl, $C_{3-6}$ cycloalkyl, 5-6 membered heterocycloalkyl, phenyl, $OR_{11}$, —C(O)$R_{11}$, —C(O)O$R_{11}$, —C(O)N$R_{11}R_{12}$, S(O)$_2R_{11}$, wherein said $C_{1-6}$ alkyl, 5-6 membered heterocycloalkyl, and phenyl are each optionally substituted with 1, 2, 3, or 4 independently selected $R_{14}$;

each $R_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1, 2, 3, or 4 independently selected $R_{14}$;

each $R_{12}$ is independently selected from the group consisting of H and $C_{1-6}$ alkyl;

each $R_{14}$ is independently selected from the group consisting of halogen, $C_{1-6}$ alkyl, phenyl, 4-6 membered heterocycloalkyl, 5-6 membered heteroaryl, $OR_{18}$, $NR_{18}R_{19}$, C(O)$R_{18}$, C(O)N$R_{18}R_{19}$, and S(O)$_2R_{18}$, wherein said phenyl, 4-6 membered heterocycloalkyl, and 5-6 membered heteroaryl may optionally be substituted with 1, 2, 3, or 4 independently selected $R_{15}$;

each $R_{15}$ is $CH_3$ or CN;

each $R_{18}$ is independently selected from the group consisting of H and $C_{1-6}$ alkyl;

each $R_{19}$ is independently selected from the group consisting of H and $C_{1-6}$ alkyl; and wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$.

In some embodiments:

X is CH or N;

Z is CH or N; with the proviso that when X is CH, Z is not also CH;

Y is selected from the group consisting of H, $NR_6R_7$, —C(O)$R_{11}$, —C(O)N$R_{11}R_{12}$, 4-10 membered heterocycloalkyl, and 5-10 membered heteroaryl, wherein said heterocycloalkyl and heteroaryl may optionally be substituted with 1, 2, 3, or 4 independently selected $R_8$;

$R_1$ and $R_2$, together with the included nitrogen atom and $L_1$, form a heterocycloalkyl group selected from the group consisting of:

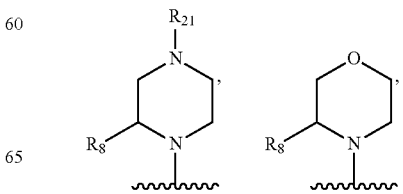

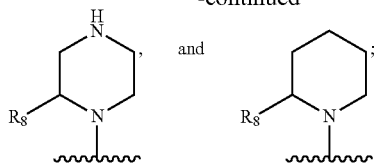

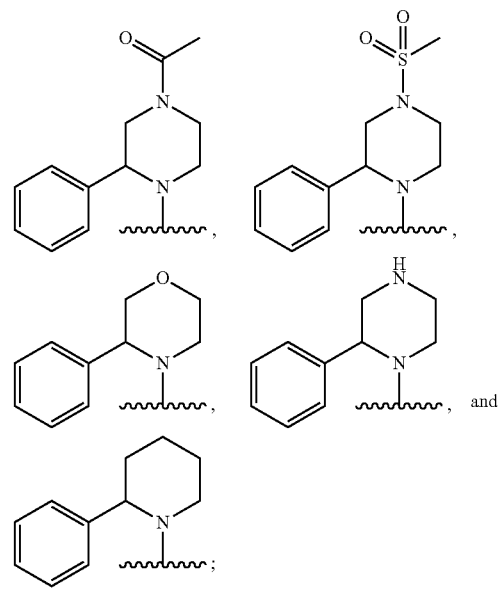

$R_3$ is selected from the group consisting of H, 5-6 membered heterocycloalkyl, and 5-6 membered heteroaryl, wherein said 5-6 membered heterocycloalkyl and 5-6 membered heteroaryl may optionally be substituted with 1, 2, 3, or 4 independently selected $R_8$;

$R_4$ is H;

each $R_6$ is independently selected from the group consisting of H and $C_{1-6}$ alkyl;

each $R_7$ is an independently selected $C_{1-6}$ alkyl group, each of which may optionally be substituted by 1, 2, 3, or 4 independently selected $R_8$;

each $R_8$ is independently selected from the group consisting of $C_{1-6}$ alkyl, $C_{3-6}$ cycloalkyl, 5-6 membered heterocycloalkyl, phenyl, $OR_{11}$, —$C(O)R_{11}$, —$C(O)OR_{11}$, —$C(O)NR_{11}R_{12}$, $S(O)_2R_{11}$, wherein said $C_{1-6}$ alkyl, 5-6 membered heterocycloalkyl, and phenyl are each optionally substituted with 1, 2, 3, or 4 independently selected $R_{14}$;

each $R_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1, 2, 3, or 4 independently selected $R_{14}$;

each $R_{12}$ is independently selected from the group consisting of H and $C_{1-6}$ alkyl;

each $R_{14}$ is independently selected from the group consisting of halogen, $C_{1-6}$ alkyl, phenyl, 5-6 membered heterocycloalkyl, 5-6 membered heteroaryl, $OR_{18}$, $NR_{18}R_{19}$, $C(O)R_{18}$, $C(O)NR_{18}R_{19}$, and $S(O)_2R_{18}$, wherein said phenyl, 5-6 membered heterocycloalkyl, and 5-6 membered heteroaryl may optionally be substituted with 1, 2, 3, or 4 independently selected $R_{15}$;

each $R_{15}$ is $CH_3$ or CN;

each $R_{18}$ is independently selected from the group consisting of H and $C_{1-6}$ alkyl;

each $R_{19}$ is independently selected from the group consisting of H and $C_{1-6}$ alkyl; and $R_{21}$ is selected from the group consisting of $C(O)CH_3$, $S(O)_2CH_3$, $CH_2CH_2N(CH_3)_2$, and $C(O)NH(cyclopropyl)$.

In some embodiments:

X is CH or N;

Z is CH or N; with the proviso that when X is CH, Z is not also CH;

Y is selected from the group consisting of H, $NR_6R_7$, —$C(O)R_{11}$, —$C(O)NR_{11}R_{12}$, 4-10 membered heterocycloalkyl, and 5-10 membered heteroaryl, wherein said 4-10 membered heterocycloalkyl and 5-10 membered heteroaryl may optionally be substituted with 1, 2, 3, or 4 independently selected $R_8$;

$R_1$ and $R_2$, together with the included nitrogen atom and $L_1$, form a heterocycloalkyl group selected from the group consisting of:

$R_3$ is selected from the group consisting of H, 5-6 membered heterocycloalkyl, and 5-6 membered heteroaryl, wherein said 5-6 membered heterocycloalkyl and 5-6 membered heteroaryl may optionally be substituted with 1, 2, 3, or 4 independently selected $R_8$;

$R_4$ is H;

each $R_6$ is independently selected from the group consisting of H and $C_{1-6}$ alkyl;

each $R_7$ is an independently selected $C_{1-6}$ alkyl group, each of which may optionally be substituted by 1, 2, 3, or 4 independently selected $R_8$;

each $R_8$ is independently selected from the group consisting of $C_{1-6}$ alkyl, $C_{3-6}$ cycloalkyl, 5-6 membered heterocycloalkyl, phenyl, $OR_{11}$, —$C(O)R_{11}$, —$C(O)OR_{11}$, —$C(O)NR_{11}R_{12}$, $S(O)_2R_{11}$, wherein said $C_{1-6}$ alkyl, 5-6 membered heterocycloalkyl, and phenyl are each optionally substituted with 1, 2, 3, or 4 independently selected $R_{14}$;

each $R_{11}$ is independently selected from the group consisting of H, $C_{1-6}$ alkyl, $C_{3-6}$ cycloalkyl, 4-6 membered heterocyloalkyl, 5-6 membered heteroaryl, wherein said $C_{1-6}$ alkyl, $C_{3-6}$ cycloalkyl, 4-6 membered heterocycloalkyl, and 5-6 membered heteroaryl may optionally be substituted with 1, 2, 3, or 4 independently selected $R_{14}$;

each $R_{12}$ is independently selected from the group consisting of H and $C_{1-6}$ alkyl;

each $R_{14}$ is independently selected from the group consisting of halogen, $C_{1-6}$ alkyl, phenyl, 5-6 membered heterocycloalkyl, 5-6 membered heteroaryl, $OR_{18}$, $NR_{18}R_{19}$, $C(O)R_{18}$, $C(O)NR_{18}R_{19}$, and $S(O)_2R_{18}$, wherein said phenyl, 5-6 membered heterocycloalkyl, and 5-6 membered heteroaryl may optionally be substituted with 1, 2, 3, or 4 independently selected $R_{15}$;

each $R_{15}$ is $CH_3$ or CN;

each $R_{18}$ is independently selected from the group consisting of H and $C_{1-6}$ alkyl; and each $R_{19}$ is independently selected from the group consisting of H and $C_{1-6}$ alkyl.

In some embodiments:

X is CH or N;

Z is CH or N; with the proviso that when X is CH, Z is not also CH;

Y is selected from the group consisting of H, NHR$_7$, —C(O)R$_{11}$, —C(O)NHR$_{11}$, piperazinyl, pyrazolyl, piperidinyl, and thienyl, wherein said piperazinyl, pyrazolyl, piperidinyl, and thienyl may be optionally substituted with 1 or 2 independently selected R$_8$;

R$_1$ and R$_2$, together with the included nitrogen atom and L$_1$, form a heterocycloalkyl group selected from the group consisting of:

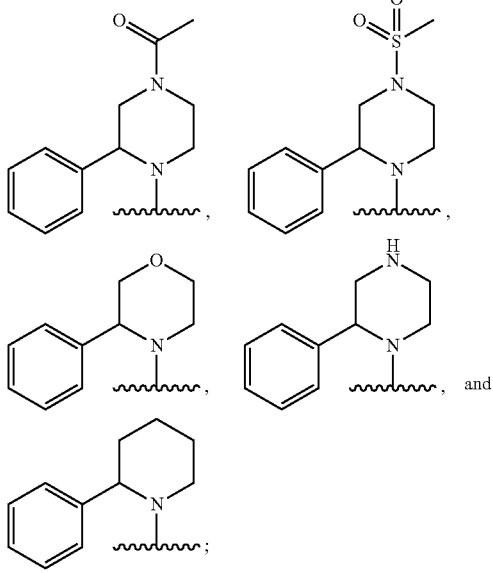

R$_3$ is isoxazolyl, pyrazolyl, 2-oxopyridinyl, 2-hydroxypyridinyl, each of which is optionally substituted by one or two methyl groups;

R$_4$ is H;

each R$_6$ is independently selected from the group consisting of H and C$_{1-6}$ alkyl;

each R$_7$ is an independently selected C$_{1-6}$ alkyl group, each of which may optionally be substituted by 1 or 2 independently selected R$_8$;

each R$_8$ is independently selected from the group consisting of C$_{1-6}$ alkyl, C$_{3-6}$ cycloalkyl, 5-6 membered heterocycloalkyl, phenyl, OR$_{11}$, —C(O)R$_{11}$, —C(O)OR$_{11}$, —C(O)NR$_{11}$R$_{12}$, S(O)$_2$R$_{11}$, wherein said C$_{1-6}$ alkyl, 5-6 membered heterocycloalkyl, and phenyl are each optionally substituted with 1 or 2 independently selected R$_{14}$;

each R$_{11}$ is independently selected from the group consisting of H, C$_{1-6}$ alkyl, C$_{3-6}$ cycloalkyl, 4-6 membered heterocyloalkyl, 5-6 membered heteroaryl, wherein said C$_{1-6}$ alkyl, C$_{3-6}$ cycloalkyl, 4-6 membered heterocycloalkyl, and 5-6 membered heteroaryl may optionally be substituted with 1 or 2 independently selected R$_{14}$;

each R$_{12}$ is independently selected from the group consisting of H and C$_{1-6}$ alkyl;

each R$_{14}$ is independently selected from the group consisting of halogen, C$_{1-6}$ alkyl, phenyl, 5-6 membered heterocycloalkyl, 5-6 membered heteroaryl, OR$_{18}$, NR$_{18}$R$_{19}$, C(O)R$_{18}$, C(O)NR$_{18}$R$_{19}$, and S(O)$_2$R$_{18}$, wherein said phenyl, 5-6 membered heterocycloalkyl, and 5-6 membered heteroaryl may optionally be substituted with 1 or 2 independently selected R$_{15}$;

each R$_{15}$ is CH$_3$ or CN;

each R$_{18}$ is independently selected from the group consisting of H and C$_{1-6}$ alkyl; and each R$_{19}$ is independently selected from the group consisting of H and C$_{1-6}$ alkyl.

In some embodiments:

X is CH or N;

Z is CH or N; with the proviso that when X is CH, Z is not also CH;

Y is selected from the group consisting of H, NHR$_7$, —C(O)R$_{11}$, —C(O)NHR$_{11}$, piperazinyl, pyrazolyl, piperidinyl, and thienyl, wherein said piperazinyl, pyrazolyl, piperidinyl, and thienyl may be optionally substituted with 1 or 2 independently selected R$_8$;

R$_1$ and R$_2$, together with the included nitrogen atom and L$_1$, form a heterocycloalkyl group selected from the group consisting of:

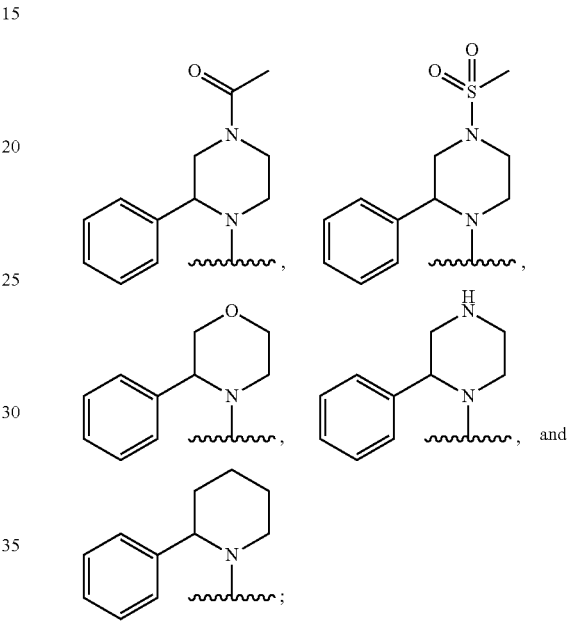

R$_3$ is isoxazolyl, pyrazolyl, 2-oxopyridinyl, 2-hydroxypyridinyl, each of which is optionally substituted by one or two methyl groups;

R$_4$ is H;

each R$_6$ is independently selected from the group consisting of H and C$_{1-3}$ alkyl;

each R$_7$ is an independently selected C$_{1-3}$ alkyl group, each of which may optionally be substituted by 1 or 2 independently selected R$_8$;

each R$_8$ is independently selected from the group consisting of C$_{1-6}$ alkyl, C$_{3-6}$ cycloalkyl, 5-6 membered heterocycloalkyl, phenyl, —C(O)R$_{11}$, —C(O)NHR$_{11}$, S(O)$_2$CH$_3$, wherein said C$_{1-6}$ alkyl, 5-6 membered heterocycloalkyl, and phenyl are each optionally substituted with 1 or 2 independently selected R$_{14}$;

each R$_{11}$ is independently selected from the group consisting of H, C$_{1-6}$ alkyl, C$_{3-6}$ cycloalkyl, 4-6 membered heterocyloalkyl, 5-6 membered heteroaryl, wherein said C$_{1-6}$ alkyl, C$_{3-6}$ cycloalkyl, 4-6 membered heterocycloalkyl, and 5-6 membered heteroaryl may optionally be substituted with 1 or 2 independently selected R$_{14}$; and each R$_{14}$ is independently selected from the group consisting of chloro, methyl, OH, N(CH$_3$)$_2$, C(O)CH$_3$, C(O)NH$_2$, C(O)NHCH$_3$, 1-methyl-1H-imidazolyl, 1,3-dimethyl-1H-pyrazolyl, and 1-methylazetidinyl.

In some embodiments, R$_1$ and R$_2$, together with the included nitrogen atom and L$_1$, form a heterocycloalkyl group selected from the group consisting of:

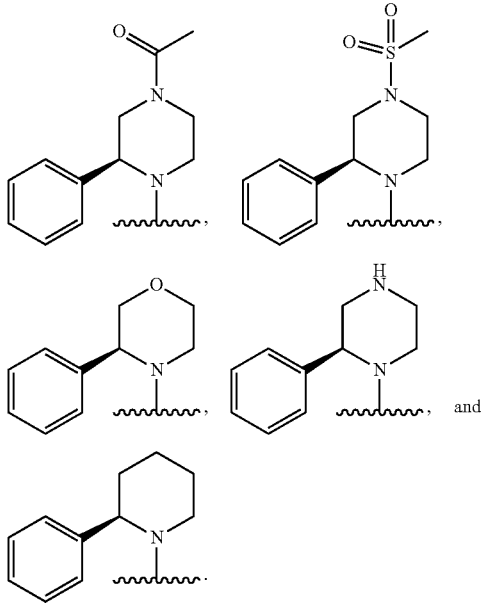

In some embodiments, $R_1$ and $R_2$, together with the included nitrogen atom and $L_1$, form a heterocycloalkyl group selected from the group consisting of:

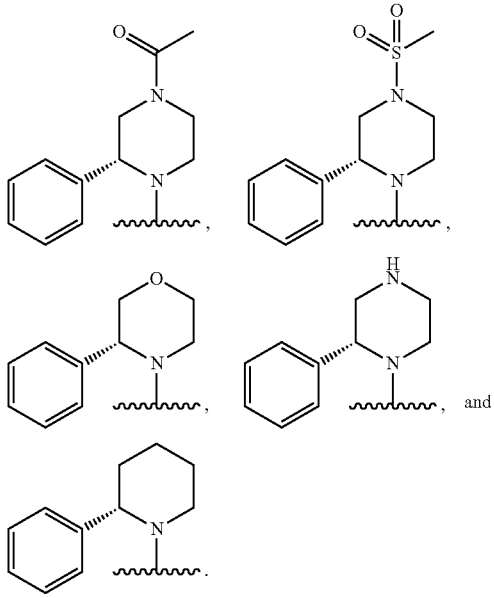

In some embodiments, the invention provides compounds of Formula I wherein $R_3$ and $R_4$ are selected independently for each occurrence from the group consisting of:

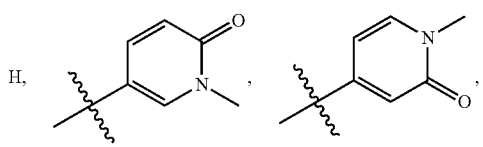

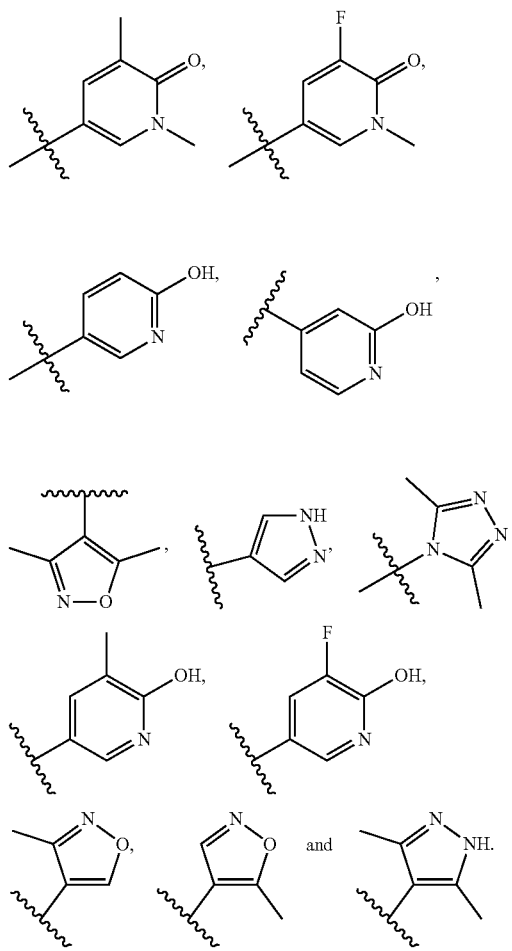

In some embodiments, the compound is a compound of Formula II:

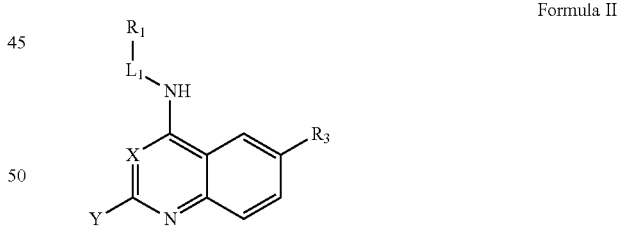

or a pharmaceutically acceptable salt thereof.

In some embodiments, $R_3$ is

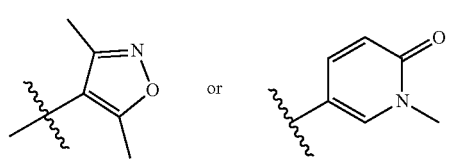

In some embodiments, the compound is a compound of Formula III:

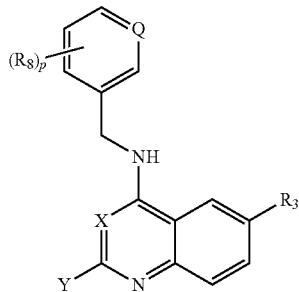

Formula III or a pharmaceutically acceptable salt thereof, wherein p is an integer from 0 to 4 and Q is CH or N.

In some embodiments, $R_3$ is

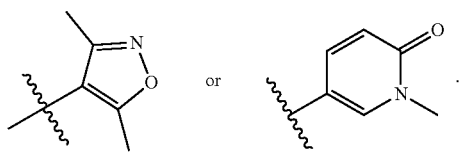

In some embodiments, p is an integer from 0 to 2.

In some embodiments, p is 0.

In some embodiments, p is 1.

In some embodiments, p is 2.

In some embodiments, the compound is a compound of Formula IV:

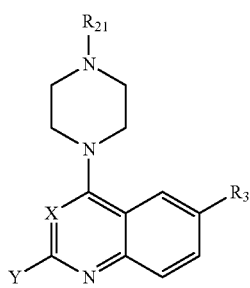

Formula IV or a pharmaceutically acceptable salt thereof, wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$.

In some embodiments, $R_{21}$ is $C_{1-6}$ alkyl, $C_{3-6}$ cycloalkyl, —C(O)O$R_{11}$, —C(O)O$R_{11}$, —C(O)N$R_{11}R_{12}$, or —S(O)$_2$$R_{11}$, wherein said $C_{1-6}$ alkyl may optionally be substituted with N$R_{11}R_{12}$.

In some embodiments, $R_{21}$ is C(O)CH$_3$, S(O)$_2$CH$_3$, CH$_2$CH$_2$N(CH$_3$)$_2$, or C(O)NH(cyclopropyl).

In some embodiments, $R_{21}$ is C(O)CH$_3$ or S(O)$_2$CH$_3$.

In some embodiments, $R_3$ is

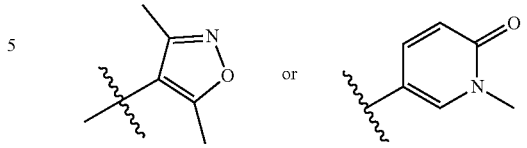

In some embodiments, the compound is a compound of Formula V:

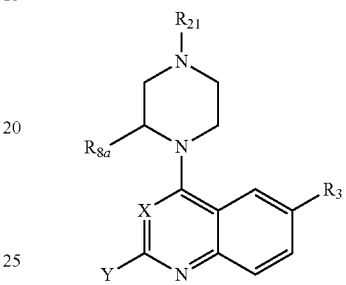

Formula V or a pharmaceutically acceptable salt thereof, wherein $R_{21}$ is $C_{1-6}$ alkyl, $C_{3-6}$ cycloalkyl, 4-7 membered heterocycloalkyl, 5-6 membered heteroaryl, phenyl, —C(O)$R_{11}$, —C(O)O$R_{11}$, —C(O)N$R_{11}R_{12}$, or —S(O)$_2R_{11}$, wherein said $C_{1-6}$ alkyl, $C_{3-6}$ cycloalkyl, 4-7 membered heterocycloalkyl, 5-6 membered heteroaryl, and phenyl are each optionally substituted with 1, 2, or 3 independently selected $R_{14}$; and $R_{8a}$ is $C_{1-6}$ alkyl, $C_{3-6}$ cycloalkyl, phenyl or a 5-6 membered heteroaryl, wherein said $C_{1-6}$ alkyl, phenyl, and heteroaryl may optionally be substituted by 1, 2, or 3 independently selected $R_{14}$.

In some embodiments, $R_{8a}$ is benzyl, phenyl, or a 5-6 membered heteroaryl, wherein said phenyl and heteroaryl may optionally be substituted by 1, 2, or 3 independently selected $R_{14}$.

In some embodiments, $R_{8a}$ is phenyl or a 5-6 membered heteroaryl, wherein said phenyl and heteroaryl may optionally be substituted by 1, 2, or 3 independently selected $R_{14}$.

In some embodiments, $R_{8a}$ is phenyl or thienyl, wherein said phenyl may optionally be substituted with 1, 2 or 3 substituents independently selected from the group consisting of F, Cl, Br, Me, Et, cycropropyl, OMe, OEt, CF$_3$, CN, NH$_2$, —NHC(O)—$C_{1-4}$alkyl, and —NHC(O)—$C_{1-4}$ alkenyl; and said thienyl may optionally be substituted with 1 or 2 substituents independently selected from the group consisting of F, Cl, Br, Me, Et, cycropropyl, OMe, OEt, CF$_3$, CN, NH$_2$, —NHC(O)—$C_{1-4}$alkyl, and —NHC(O)—$C_{1-4}$ alkenyl.

In some embodiments, $R_{21}$ is $C_{1-6}$ alkyl, $C_{3-6}$ cycloalkyl, —C(O)O$R_{11}$, —C(O)O$R_{11}$, —C(O)N$R_{11}R_{12}$, or —S(O)$_2$$R_{11}$, wherein said $C_{1-6}$ alkyl may optionally be substituted with N$R_{11}R_{12}$.

In some embodiments, $R_{21}$ is C(O)CH$_3$, S(O)$_2$CH$_3$, CH$_2$CH$_2$N(CH$_3$)$_2$, or C(O)NH(cyclopropyl).

In some embodiments, $R_{21}$ is C(O)CH$_3$ or S(O)$_2$CH$_3$.

In some embodiments, R$_3$ is

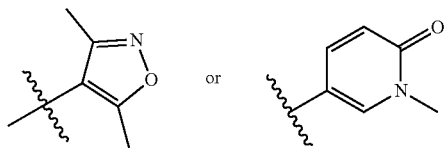

In some embodiments, the compound of Formula V, or a pharmaceutically acceptable salt thereof, is a compound of Formula Va:

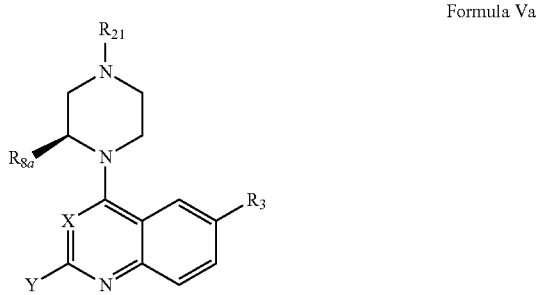

Formula Va or a pharmaceutically acceptable salt thereof.

In some embodiments, the compound of Formula V, or a pharmaceutically acceptable salt thereof, is a compound of Formula Vb:

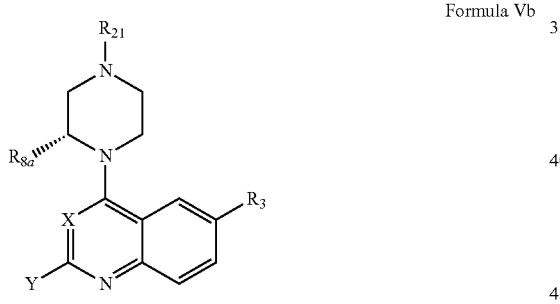

Formula Vb or a pharmaceutically acceptable salt thereof.

In some embodiments, the compound is a compound of Formula VI:

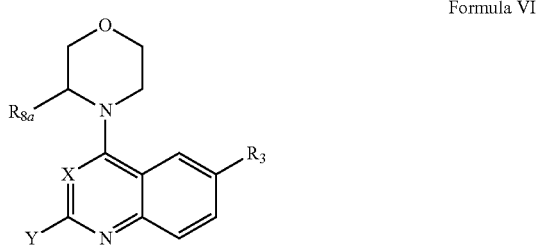

Formula VI or a pharmaceutically acceptable salt thereof, wherein R$_{8a}$ is C$_{1-6}$ alkyl, C$_{3-6}$ cycloalkyl, phenyl or a 5-6 membered heteroaryl, wherein said C$_{1-6}$ alkyl, phenyl, and heteroaryl may optionally be substituted by 1, 2, or 3 independently selected R$_{14}$.

In some embodiments, R$_{8a}$ is benzyl, phenyl, or a 5-6 membered heteroaryl, wherein said phenyl, and heteroaryl may optionally be substituted by 1, 2, or 3 independently selected R$_{14}$.

In some embodiments, R$_{8a}$ is phenyl or a 5-6 membered heteroaryl, wherein said phenyl and heteroaryl may optionally be substituted by 1, 2, or 3 independently selected R$_{14}$.

In some embodiments, R$_{8a}$ is phenyl or thienyl, wherein said phenyl may optionally be substituted with 1, 2 or 3 substituents independently selected from the group consisting of F, Cl, Br, Me, Et, cycropropyl, OMe, OEt, CF$_3$, CN, NH$_2$, —NHC(O)—C$_{1-4}$alkyl, and —NHC(O)—C$_{1-4}$ alkenyl; and said thienyl may optionally be substituted with 1 or 2 substituents independently selected from the group consisting of F, Cl, Br, Me, Et, cycropropyl, OMe, OEt, CF$_3$, CN, NH$_2$, —NHC(O)—C$_{1-4}$alkyl, and —NHC(O)-C$_{1-4}$alkenyl.

In some embodiments, R$_3$ is

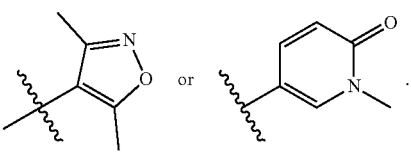

In some embodiments, the compound of Formula VI, or a pharmaceutically acceptable salt thereof, is a compound of Formula VIa:

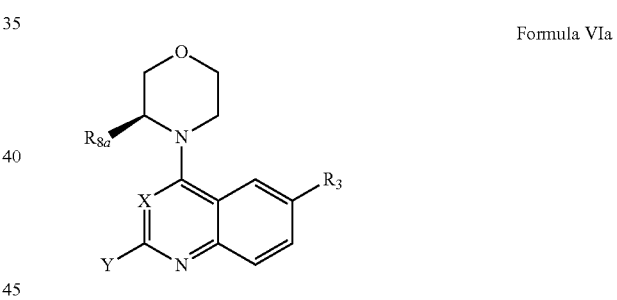

Formula VIa or a pharmaceutically acceptable salt thereof,

In some embodiments, the compound of Formula VI, or a pharmaceutically acceptable salt thereof, is a compound of Formula VIb:

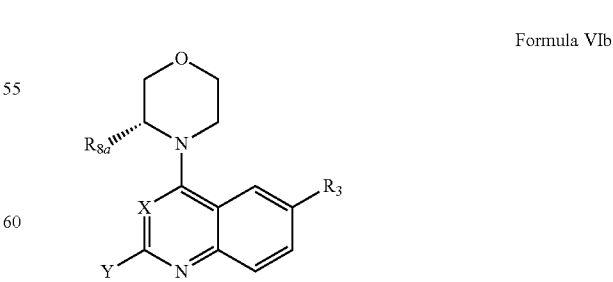

Formula VIb or a pharmaceutically acceptable salt thereof,

In some embodiments, the compound is a compound of Formula VII:

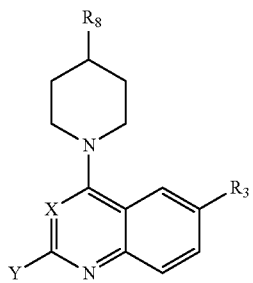

Formula VII or a pharmaceutically acceptable salt thereof.

In some embodiments, the R₈ group attached to the piperidinyl ring formed by R₁ and R₂, together with the included nitrogen atom and L₁, is R₈ₐ, wherein R₈ₐ is phenyl or a 5-6 membered heteroaryl, wherein said phenyl and heteroaryl may optionally be substituted by 1, 2, or 3 independently selected R₁₄.

In some embodiments, R₈ₐ is phenyl or thienyl, wherein said phenyl may optionally be substituted with 1, 2 or 3 substituents independently selected from the group consisting of F, Cl, Br, Me, Et, cycropropyl, OMe, OEt, CF₃, CN, NH₂, —NHC(O)—C₁₋₄alkyl, and —NHC(O)—C₁₋₄ alkenyl; and said thienyl may optionally be substituted with 1 or 2 substituents independently selected from the group consisting of F, Cl, Br, Me, Et, cycropropyl, OMe, OEt, CF₃, CN, NH₂, —NHC(O)—C₁₋₄alkyl, and —NHC(O)—C₁₋₄ alkenyl.

In some embodiments, R₃ is

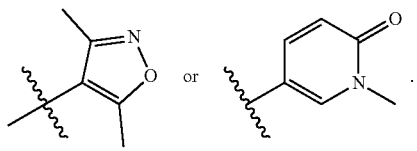

In some embodiments, the compound is a compound of Formula VIII:

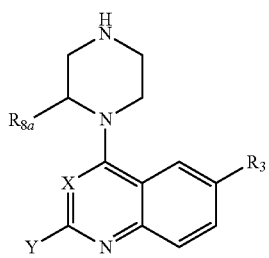

Formula VIII or a pharmaceutically acceptable salt thereof, wherein R₈ₐ is C₁₋₆ alkyl, C₃₋₆ cycloalkyl, phenyl, or a 5-6 membered heteroaryl, wherein said phenyl and heteroaryl may optionally be substituted by 1, 2, or 3 independently selected R₁₄.

In some embodiments, R₈ₐ is phenyl or thienyl, wherein said phenyl may optionally be substituted with 1, 2 or 3 substituents independently selected from the group consisting of F, Cl, Br, Me, Et, cycropropyl, OMe, OEt, CF₃, CN, NH₂, —NHC(O)—C₁₋₄alkyl, and —NHC(O)—C₁₋₄ alkenyl; and said thienyl may optionally be substituted with 1 or 2 substituents independently selected from the group consisting of F, Cl, Br, Me, Et, cycropropyl, OMe, OEt, CF₃, CN, NH₂, —NHC(O)—C₁₋₄alkyl, and —NHC(O)—C₁₋₄ alkenyl.

In some embodiments, R₃ is

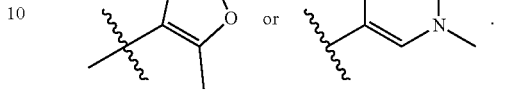

In some embodiments, the compound of Formula VIII, or a pharmaceutically acceptable salt thereof, is a compound of Formula VIIIa:

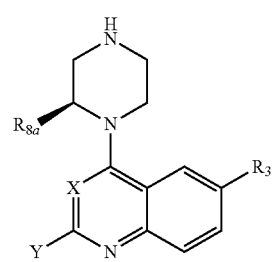

Formula VIIIa or a pharmaceutically acceptable salt thereof,

In some embodiments, the compound of Formula VIII, or a pharmaceutically acceptable salt thereof, is a compound of Formula VIIIb:

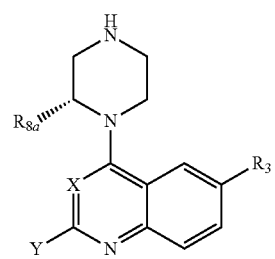

Formula VIIIb or a pharmaceutically acceptable salt thereof,

In some embodiments, the compound is selected from the group consisting of:
2-chloro-N-(3-chlorobenzyl)-6-(3,5-dimethylisoxazol-4-yl) quinazolin-4-amine;
N-(3-chlorobenzyl)-6-(3,5-dimethylisoxazol-4-yl)quinazolin-4-amine;
N-(3-chlorobenzyl)-6-(3,5-dimethylisoxazol-4-yl)quinolin-4-amine;
N-(3-chlorobenzyl)-6-(3,5-dimethylisoxazol-4-yl)-2-methylquinolin-4-amine;
N4-(3-chlorobenzyl)-6-(3,5-dimethylisoxazol-4-yl)-N2-methylquinazoline-2,4-diamine;
N-(3-chlorobenzyl)-6-(3,5-dimethylisoxazol-4-yl)-2-(4-methylpiperazin-1-yl)quinazolin-4-amine;
N4-(3-chlorobenzyl)-6-(3,5-dimethylisoxazol-4-yl)-N2-(1-methylpiperidin-4-yl)quinazoline-2,4-diamine;
N-(3-chlorobenzyl)-6-(3,5-dimethylisoxazol-4-yl)-2-methoxyquinazolin-4-amine;

N-(3-chlorobenzyl)-6-(3,5-dimethylisoxazol-4-yl)-2-methylquinazolin-4-amine;
N4-(3-chlorobenzyl)-6-(3,5-dimethylisoxazol-4-yl)-N2-(2-morpholinoethyl)quinazoline-2,4-diamine;
N4-(3-chlorobenzyl)-6-(3,5-dimethylisoxazol-4-yl)-N2-(2-(4-methylpiperazin-1-yl)ethyl)quinazoline-2,4-diamine;
N-(3-chlorobenzyl)-2-(4-(2-(dimethylamino)ethyl)piperazin-1-yl)-6-(3,5-dimethylisoxazol-4-yl)quinazolin-4-amine;
3-((4-((3-chlorobenzyl)amino)-6-(3,5-dimethylisoxazol-4-yl)quinazolin-2-yl)amino)propan-1-ol;
N-(3-chlorobenzyl)-2,6-bis(3,5-dimethylisoxazol-4-yl)quinolin-4-amine;
6-bromo-N-(3-chlorobenzyl)-2-(3,5-dimethylisoxazol-4-yl)quinolin-4-amine;
N-(3-chlorobenzyl)-2-(4-(3-(dimethylamino)propyl)piperazin-1-yl)-6-(3,5-dimethylisoxazol-4-yl)quinazolin-4-amine;
(4-(4-((3-chlorobenzyl)amino)-6-(3,5-dimethylisoxazol-4-yl)quinazolin-2-yl)piperazin-1-yl)(cyclopropyl)methanone;
(4-(4-((3-chlorobenzyl)amino)-6-(3,5-dimethylisoxazol-4-yl)quinazolin-2-yl)piperazin-1-yl)(1-methyl-1H-pyrazol-4-yl)methanone;
6-bromo-N-(3-chlorobenzyl)-2-(4-(2-(dimethylamino)ethyl)piperazin-1-yl)quinazolin-4-amine;
2-(4-(4-((3-chlorobenzyl)amino)-6-(3,5-dimethylisoxazol-4-yl)quinazolin-2-yl)piperazin-1-yl)ethanol;
N-(3-chlorobenzyl)-6-(3,5-dimethylisoxazol-4-yl)-2-(4-isopentylpiperazin-1-yl)quinazolin-4-amine;
N4-(3-chlorobenzyl)-N2-(2-(dimethylamino)ethyl)-6-(3,5-dimethylisoxazol-4-yl)-N2-methylquinazoline-2,4-diamine;
(1-(4-((3-chlorobenzyl)amino)-6-(3,5-dimethylisoxazol-4-yl)quinazolin-2-yl)piperidin-4-yl)methanol;
(1-(4-((3-chlorobenzyl)amino)-6-(3,5-dimethylisoxazol-4-yl)quinazolin-2-yl)piperidin-3-yl)methanol;
(1-(4-((3-chlorobenzyl)amino)-6-(3,5-dimethylisoxazol-4-yl)quinazolin-2-yl)piperidin-2-yl)methanol;
N-(3-chlorobenzyl)-2-(4-(2-(dimethylamino)ethyl)piperazin-1-yl)-6-(3,5-dimethylisoxazol-4-yl)quinolin-4-amine
N-(3-chlorobenzyl)-4-(4-(2-(dimethylamino)ethyl)piperazin-1-yl)-6-(3,5-dimethylisoxazol-4-yl)quinolin-2-amine;
N-(3-chlorobenzyl)-6-(3,5-dimethylisoxazol-4-yl)-2-(1-(2-morpholinoethyl)-1H-pyrazol-4-yl)quinazolin-4-amine;
(4-(4-((3-chlorobenzyl)amino)-6-(3,5-dimethylisoxazol-4-yl)quinazolin-2-yl)piperazin-1-yl)(pyridin-4-yl)methanone;
2-(1-(4-((3-chlorobenzyl)amino)-6-(3,5-dimethylisoxazol-4-yl)quinazolin-2-yl)piperidin-4-yl)ethanol;
N-(3-chlorobenzyl)-6-(3,5-dimethylisoxazol-4-yl)-2-(1,2,3,6-tetrahydropyridin-4-yl)quinazolin-4-amine;
N-(3-chlorobenzyl)-2-(4-(2-(dimethylamino)ethyl)-1,4-diazepan-1-yl)-6-(3,5-dimethylisoxazol-4-yl)quinazolin-4-amine;
2-(4-(4-((3-chlorobenzyl)amino)-6-(3,5-dimethylisoxazol-4-yl)quinazolin-2-yl)-1,4-diazepan-1-yl)ethanol;
N-(3-chlorobenzyl)-2-(4-(2-(dimethylamino)ethyl)piperidin-1-yl)-6-(3,5-dimethylisoxazol-4-yl)quinazolin-4-amine;
(4-(4-((3-chlorobenzyl)amino)-6-(3,5-dimethylisoxazol-4-yl)quinazolin-2-yl)piperazin-1-yl)(pyridin-3-yl)methanone;
1-(4-(4-((3-chlorobenzyl)amino)-6-(3,5-dimethylisoxazol-4-yl)quinazolin-2-yl)piperazin-1-yl)-2-hydroxyethanone;
1-(4-(4-((3-chlorobenzyl)amino)-6-(3,5-dimethylisoxazol-4-yl)quinazolin-2-yl)piperazin-1-yl)-2-(dimethylamino)ethanone;
2-chloro-N-(3-chlorobenzyl)-7-(3,5-dimethylisoxazol-4-yl)quinazolin-4-amine;
N-(3-chlorobenzyl)-2-(4-(2-(dimethylamino)ethyl)piperazin-1-yl)-7-(3,5-dimethylisoxazol-4-yl)quinazolin-4-amine;
2-(4-(4-((3-chlorobenzyl)amino)-7-(3,5-dimethylisoxazol-4-yl)quinazolin-2-yl)piperazin-1-yl)ethanol;
N-(3-chlorobenzyl)-2-(4-((dimethylamino)methyl)piperidin-1-yl)-6-(3,5-dimethylisoxazol-4-yl)quinazolin-4-amine;
2-(1-(4-((3-chlorobenzyl)amino)-6-(3,5-dimethylisoxazol-4-yl)quinazolin-2-yl)-1H-pyrazol-4-yl)ethanol;
N-(3-chlorobenzyl)-3-(4-(2-(dimethylamino)ethyl)piperazin-1-yl)-7-(3,5-dimethylisoxazol-4-yl)isoquinolin-1-amine;
2-(4-(1-((3-chlorobenzyl)amino)-7-(3,5-dimethylisoxazol-4-yl)isoquinolin-3-yl)piperazin-1-yl)ethanol;
1-(4-(4-((3-chlorobenzyl)amino)-6-(3,5-dimethylisoxazol-4-yl)quinazolin-2-yl)piperazin-1-yl)propan-2-ol;
(R)-1-(4-(4-((3-chlorobenzyl)amino)-6-(3,5-dimethylisoxazol-4-yl)quinazolin-2-yl)piperazin-1-yl)propan-2-ol;
(S)-1-(4-(4-((3-chlorobenzyl)amino)-6-(3,5-dimethylisoxazol-4-yl)quinazolin-2-yl)piperazin-1-yl)propan-2-ol;
2-(4-(4-((3-chlorobenzyl)amino)-6-(3,5-dimethylisoxazol-4-yl)quinazolin-2-yl)-1H-pyrazol-1-yl)ethanol;
N-(3-chlorobenzyl)-6-(3,5-dimethylisoxazol-4-yl)-2-(1-methyl-1H-pyrazol-4-yl)quinazolin-4-amine;
2-(4-(4-((3-chlorobenzyl)amino)-6-(3,5-dimethylisoxazol-4-yl)quinazolin-2-yl)-1H-pyrazol-1-yl)acetamide;
2-(4-(4-((3-chlorobenzyl)amino)-7-(3,5-dimethylisoxazol-4-yl)quinazolin-2-yl)-1H-pyrazol-1-yl)acetamide;
2-(4-(4-((3-chlorobenzyl)amino)-6-(3,5-dimethylisoxazol-4-yl)quinazolin-2-yl)piperazin-1-yl)-N,N-dimethylacetamide;
2-(4-(4-((3-chlorobenzyl)amino)-6-(3,5-dimethylisoxazol-4-yl)quinazolin-2-yl)piperazin-1-yl)-N-methylacetamide;
2-(4-(4-((3-chlorobenzyl)amino)-6-(3,5-dimethylisoxazol-4-yl)quinazolin-2-yl)piperazin-1-yl)acetamide;
2-amino-1-(4-(4-((3-chlorobenzyl)amino)-6-(3,5-dimethylisoxazol-4-yl)quinazolin-2-yl)piperazin-1-yl)ethanone;
1-(4-(4-((3-chlorobenzyl)amino)-6-(3,5-dimethylisoxazol-4-yl)quinazolin-2-yl)-1H-pyrazol-1-yl)-2-methylpropan-2-ol;
3-(4-(4-((3-chlorobenzyl)amino)-6-(3,5-dimethylisoxazol-4-yl)quinazolin-2-yl)-1H-pyrazol-1-yl)propanenitrile;
N-(3-chlorobenzyl)-6-(3,5-dimethylisoxazol-4-yl)-2-(1-(2-methoxyethyl)-1H-pyrazol-4-yl)quinazolin-4-amine;
2-(4-(4-((3-chlorobenzyl)amino)-6-(3,5-dimethylisoxazol-4-yl)quinazolin-2-yl)-1H-pyrazol-1-yl)acetonitrile;
N-(3-chlorobenzyl)-2-(1-(2-(dimethylamino)ethyl)-1H-pyrazol-4-yl)-6-(3,5-dimethylisoxazol-4-yl)quinazolin-4-amine;
N-(3-chlorobenzyl)-6-(3,5-dimethylisoxazol-4-yl)-2-(1-(oxetan-3-yl)-1H-pyrazol-4-yl)quinazolin-4-amine;
2-(4-(4-((3-chlorobenzyl)amino)-6-(3,5-dimethylisoxazol-4-yl)quinazolin-2-yl)-1H-pyrazol-1-yl)-2-methylpropan-1-ol;
(5-(4-((3-chlorobenzyl)amino)-6-(3,5-dimethylisoxazol-4-yl)quinazolin-2-yl)pyridin-2-yl)methanol;
N-(3-chlorobenzyl)-2-(4-(2-(dimethylamino)ethyl)piperazin-1-yl)-6-(1H-pyrazol-4-yl)quinazolin-4-amine;
N-(3-chlorobenzyl)-6-(3,5-dimethyl-1H-pyrazol-4-yl)-2-(4-(2-(dimethylamino)ethyl)piperazin-1-yl)quinazolin-4-amine;

5-(4-((3-chlorobenzyl)amino)-2-(4-(2-(dimethylamino) ethyl)piperazin-1-yl)quinazolin-6-yl)-1-methylpyridin-2 (1H)-one;
5-(4-((3-chlorobenzyl)amino)-2-(4-(2-(dimethylamino) ethyl)piperazin-1-yl)quinazolin-6-yl)pyridin-2-ol;
2,6-bis(3,5-dimethylisoxazol-4-yl)-N-(thiophen-2-ylmethyl)quinazolin-4-amine;
N-(3-chlorobenzyl)-2,6-bis(3,5-dimethylisoxazol-4-yl)quinazolin-4-amine;
2-(4-(2-(dimethylamino)ethyl)piperazin-1-yl)-6-(3,5-dimethylisoxazol-4-yl)-N-(thiophen-2-ylmethyl)quinazolin-4-amine;
2-(4-(2-(dimethylamino)ethyl)piperazin-1-yl)-6-(3,5-dimethylisoxazol-4-yl)-N-(2-methoxybenzyl)quinazolin-4-amine;
2-(4-(2-(dimethylamino)ethyl)piperazin-1-yl)-6-(3,5-dimethylisoxazol-4-yl)-N-(3-methoxybenzyl)quinazolin-4-amine;
N-(2-chlorobenzyl)-2-(4-(2-(dimethylamino)ethyl)piperazin-1-yl)-6-(3,5-dimethylisoxazol-4-yl)quinazolin-4-amine;
N-(3-bromobenzyl)-2-(4-(2-(dimethylamino)ethyl)piperazin-1-yl)-6-(3,5-dimethylisoxazol-4-yl)quinazolin-4-amine;
2-(4-(2-(dimethylamino)ethyl)piperazin-1-yl)-6-(3,5-dimethylisoxazol-4-yl)-N-(2-fluorobenzyl)quinazolin-4-amine;
2-(4-(2-(dimethylamino)ethyl)piperazin-1-yl)-6-(3,5-dimethylisoxazol-4-yl)-N-(3-fluorobenzyl)quinazolin-4-amine;
N-(3-chlorobenzyl)-2-(4-(2-(dimethylamino)ethyl)piperazin-1-yl)-6-(5-methylisoxazol-4-yl)quinazolin-4-amine;
2-(4-(2-(dimethylamino)ethyl)piperazin-1-yl)-6-(3,5-dimethylisoxazol-4-yl)-N-(furan-2-ylmethyl)quinazolin-4-amine;
2-(4-(2-(dimethylamino)ethyl)piperazin-1-yl)-6-(3,5-dimethylisoxazol-4-yl)-N-(pyridin-3-ylmethyl)quinazolin-4-amine;
N-((5-chloropyridin-3-yl)methyl)-2-(4-(2-(dimethylamino)ethyl)piperazin-1-yl)-6-(3,5-dimethylisoxazol-4-yl)quinazolin-4-amine;
N-((4-chloropyridin-2-yl)methyl)-2-(4-(2-(dimethylamino)ethyl)piperazin-1-yl)-6-(3,5-dimethylisoxazol-4-yl)quinazolin-4-amine;
2-(4-(2-(dimethylamino)ethyl)piperazin-1-yl)-6-(3,5-dimethylisoxazol-4-yl)-N-((5-fluoropyridin-3-yl)methyl)quinazolin-4-amine;
2-(4-(2-(dimethylamino)ethyl)piperazin-1-yl)-6-(3,5-dimethylisoxazol-4-yl)-N-((4-methylpyridin-3-yl)methyl)quinazolin-4-amine;
N-(3-chlorobenzyl)-2-(4-(2-(dimethylamino)ethyl)piperazin-1-yl)-6-(3,5-dimethylisoxazol-4-yl)-N-methylquinazolin-4-amine;
5-(4-((3-chlorobenzyl)amino)-2-(4-(2-(dimethylamino) ethyl)piperazin-1-yl)quinazolin-6-yl)-3-fluoropyridin-2-ol;
2-(4-(2-(dimethylamino)ethyl)piperazin-1-yl)-6-(3,5-dimethylisoxazol-4-yl)-N-((4-methylthiophen-2-yl)methyl)quinazolin-4-amine;
2-(4-(2-(dimethylamino)ethyl)piperazin-1-yl)-6-(3,5-dimethylisoxazol-4-yl)-N-((5-methylthiophen-2-yl)methyl)quinazolin-4-amine;
2-(4-(2-(dimethylamino)ethyl)piperazin-1-yl)-6-(3,5-dimethylisoxazol-4-yl)-N-(1-(thiophen-2-yl)ethyl)quinazolin-4-amine;
N-(1-(3-chlorophenyl)ethyl)-2-(4-(2-(dimethylamino)ethyl) piperazin-1-yl)-6-(3,5-dimethylisoxazol-4-yl)quinazolin-4-amine;
5-(4-((3-chlorobenzyl)amino)-2-(4-(2-(dimethylamino) ethyl)piperazin-1-yl)quinazolin-6-yl)-3-methylpyridin-2-ol;
N-benzyl-2-(4-(2-(dimethylamino)ethyl)piperazin-1-yl)-6-(3,5-dimethylisoxazol-4-yl)quinazolin-4-amine;
N-(3-chlorobenzyl)-2-(4-(2-(dimethylamino)ethyl)piperazin-1-yl)-6-(3-methylisoxazol-4-yl)quinazolin-4-amine;
N-((5-chlorothiophen-2-yl)methyl)-2-(4-(2-(dimethylamino)ethyl)piperazin-1-yl)-6-(3,5-dimethylisoxazol-4-yl)quinazolin-4-amine;
N-(4-chlorobenzyl)-2-(4-(2-(dimethylamino)ethyl)piperazin-1-yl)-6-(3,5-dimethylisoxazol-4-yl)quinazolin-4-amine;
4-(4-((3-chlorobenzyl)amino)-2-(4-(2-(dimethylamino) ethyl)piperazin-1-yl)quinazolin-6-yl)pyridin-2-ol;
2-(4-(4-((3-chlorobenzyl)amino)-6-(3,5-dimethylisoxazol-4-yl)quinazolin-2-yl)-1H-pyrazol-1-yl)-N-methylacetamide;
2-(4-(4-((3-chlorobenzyl)amino)-6-(3,5-dimethylisoxazol-4-yl)quinazolin-2-yl)-1H-pyrazol-1-yl)-N,N-dimethylacetamide;
2-(4-(2-(dimethylamino)ethyl)piperazin-1-yl)-6-(3,5-dimethylisoxazol-4-yl)-N-(4-fluorobenzyl)quinazolin-4-amine;
5-(2-chloro-4-((3-chlorobenzyl)amino)quinazolin-6-yl)-1-methylpyridin-2(1H)-one;
2-(4-(4-((3-chlorobenzyl)amino)-6-(1-methyl-6-oxo-1,6-dihydropyridin-3-yl)quinazolin-2-yl)-1H-pyrazol-1-yl)acetamide;
2-(4-(4-((3-chlorobenzyl)amino)-6-(1-methyl-6-oxo-1,6-dihydropyridin-3-yl)quinazolin-2-yl)-1H-pyrazol-1-yl)-N-methylacetamide;
5-(4-((3-chlorobenzyl)amino)-2-(1-(2-hydroxy-2-methylpropyl)-1H-pyrazol-4-yl)quinazolin-6-yl)-1-methylpyridin-2(1H)-one;
3-(4-(4-((3-chlorobenzyl)amino)-6-(1-methyl-6-oxo-1,6-dihydropyridin-3-yl)quinazolin-2-yl)-1H-pyrazol-1-yl)propanenitrile;
5-(4-((3-chlorobenzyl)amino)-2-(1-(1-hydroxy-2-methylpropan-2-yl)-1H-pyrazol-4-yl)quinazolin-6-yl)-1-methylpyridin-2(1H)-one;
5-(4-((3-chlorobenzyl)amino)-2-(4-(2-hydroxyacetyl)piperazin-1-yl)quinazolin-6-yl)-1-methylpyridin-2(1H)-one;
5-(2-(4-(2-aminoacetyl)piperazin-1-yl)-4-((3-chlorobenzyl) amino)quinazolin-6-yl)-1-methylpyridin-2(1H)-one;
2-(4-(4-((3-chlorobenzyl)amino)-6-(1-methyl-6-oxo-1,6-dihydropyridin-3-yl)quinazolin-2-yl)piperazin-1-yl)acetamide;
2-(4-(4-((3-chlorobenzyl)amino)-6-(1-methyl-6-oxo-1,6-dihydropyridin-3-yl)quinazolin-2-yl)piperazin-1-yl)-N-methylacetamide;
2-(4-(4-((3-chlorobenzyl)amino)-6-(1-methyl-6-oxo-1,6-dihydropyridin-3-yl)quinazolin-2-yl)piperazin-1-yl)-N,N-dimethylacetamide;
(S)-5-(4-((3-chlorobenzyl)amino)-2-(4-(2-hydroxypropyl) piperazin-1-yl)quinazolin-6-yl)-1-methylpyridin-2(1H)-one;
2-chloro-N-((5-chloropyridin-3-yl)methyl)-6-(3,5-dimethylisoxazol-4-yl)quinazolin-4-amine;
5-(2-chloro-4-(((5-chloropyridin-3-yl)methyl)amino)quinazolin-6-yl)-1-methylpyridin-2(1H)-one;
5-(4-((3-chlorobenzyl)amino)-2-(1-(2-hydroxyethyl)-1H-pyrazol-4-yl)quinazolin-6-yl)-1-methylpyridin-2(1H)-one;

2-(4-(2-(dimethylamino)ethyl)piperazin-1-yl)-6-(3,5-dimethylisoxazol-4-yl)-N-((5-methylpyridin-3-yl)methyl)quinazolin-4-amine;

4-(4-((3-chlorobenzyl)amino)-2-(4-(2-(dimethylamino)ethyl)piperazin-1-yl)quinazolin-6-yl)-1-methylpyridin-2(1H)-one;

2-(4-(4-(((5-chloropyridin-3-yl)methyl)amino)-6-(3,5-dimethylisoxazol-4-yl)quinazolin-2-yl)piperazin-1-yl)acetamide;

2-(4-(4-(((5-chloropyridin-3-yl)methyl)amino)-6-(3,5-dimethylisoxazol-4-yl)quinazolin-2-yl)piperazin-1-yl)-N-methylacetamide;

2-(4-(4-(((5-chloropyridin-3-yl)methyl)amino)-6-(3,5-dimethylisoxazol-4-yl)quinazolin-2-yl)piperazin-1-yl)-N,N-dimethylacetamide;

2-(4-(4-(((5-chloropyridin-3-yl)methyl)amino)-6-(3,5-dimethylisoxazol-4-yl)quinazolin-2-yl)piperazin-1-yl)ethanol;

5-(4-((3-chlorobenzyl)amino)-2-(4-(2-hydroxyethyl)piperazin-1-yl)quinazolin-6-yl)-1-methylpyridin-2(1H)-one;

5-(4-((3-chlorobenzyl)amino)-2-(4-(1-methyl-1H-pyrazole-4-carbonyl)piperazin-1-yl)quinazolin-6-yl)-1-methylpyridin-2(1H)-one;

5-(4-((3-chlorobenzyl)amino)-2-(4-(3-(dimethylamino)propyl)piperazin-1-yl)quinazolin-6-yl)-1-methylpyridin-2(1H)-one;

5-(4-(((5-chloropyridin-3-yl)methyl)amino)-2-(4-(2-(dimethylamino)ethyl)piperazin-1-yl)quinazolin-6-yl)-1-methylpyridin-2(1H)-one;

5-(4-(((5-chloropyridin-3-yl)methyl)amino)-2-(4-(3-(dimethylamino)propyl)piperazin-1-yl)quinazolin-6-yl)-1-methylpyridin-2(1H)-one;

5-(4-(((5-chloropyridin-3-yl)methyl)amino)-2-(4-(2-hydroxyethyl)piperazin-1-yl)quinazolin-6-yl)-1-methylpyridin-2(1H)-one;

2-(4-(4-(((5-chloropyridin-3-yl)methyl)amino)-6-(1-methyl-6-oxo-1,6-dihydropyridin-3-yl)quinazolin-2-yl)piperazin-1-yl)acetamide;

2-(4-(4-(((5-chloropyridin-3-yl)methyl)amino)-6-(1-methyl-6-oxo-1,6-dihydropyridin-3-yl)quinazolin-2-yl)piperazin-1-yl)-N-methylacetamide;

2-(4-(4-(((5-chloropyridin-3-yl)methyl)amino)-6-(1-methyl-6-oxo-1,6-dihydropyridin-3-yl)quinazolin-2-yl)piperazin-1-yl)-N,N-dimethylacetamide;

N-((5-chloropyridin-3-yl)methyl)-2-(4-(3-(dimethylamino)propyl)piperazin-1-yl)-6-(3,5-dimethylisoxazol-4-yl)quinazolin-4-amine;

2-amino-1-(4-(4-(((5-chloropyridin-3-yl)methyl)amino)-6-(3,5-dimethylisoxazol-4-yl)quinazolin-2-yl)piperazin-1-yl)ethanone;

1-(4-(4-(((5-chloropyridin-3-yl)methyl)amino)-6-(3,5-dimethylisoxazol-4-yl)quinazolin-2-yl)piperazin-1-yl)-2-hydroxyethanone; and 5-(2-(4-(2-aminoacetyl)piperazin-1-yl)-4-(((5-chloropyridin-3-yl)methyl)amino)quinazolin-6-yl)-1-methylpyridin-2(1H)-one;

5-(4-((3-chlorobenzyl)amino)-2-(4-(2-hydroxy-2-methylpropyl)piperazin-1-yl)quinazolin-6-yl)-1-methylpyridin-2(1H)-one;

5-(4-(((5-chloropyridin-3-yl)methyl)amino)-2-(4-(2-hydroxy-2-methylpropyl)piperazin-1-yl)quinazolin-6-yl)-1-methylpyridin-2(1H)-one;

1-(4-(4-(((5-chloropyridin-3-yl)methyl)amino)-6-(3,5-dimethylisoxazol-4-yl)quinazolin-2-yl)piperazin-1-yl)-2-methylpropan-2-ol;

1-(4-(4-((3-chlorobenzyl)amino)-6-(3,5-dimethylisoxazol-4-yl)quinazolin-2-yl)piperazin-1-yl)-2-methylpropan-2-ol;

2-(4-(4-(((5-chloropyridin-3-yl)methyl)amino)-6-(3,5-dimethylisoxazol-4-yl)quinazolin-2-yl)-1H-pyrazol-1-yl)-2-methylpropan-1-ol;

1-(4-(4-(((5-chloropyridin-3-yl)methyl)amino)-6-(3,5-dimethylisoxazol-4-yl)quinazolin-2-yl)-1H-pyrazol-1-yl)-2-methylpropan-2-ol;

2-(4-(4-(((5-chloropyridin-3-yl)methyl)amino)-6-(3,5-dimethylisoxazol-4-yl)quinazolin-2-yl)-1H-pyrazol-1-yl)-N,N-dimethylacetamide;

2-(4-(4-(((5-chloropyridin-3-yl)methyl)amino)-6-(3,5-dimethylisoxazol-4-yl)quinazolin-2-yl)-1H-pyrazol-1-yl)-N-methylacetamide;

2-(4-(4-(((5-chloropyridin-3-yl)methyl)amino)-6-(3,5-dimethylisoxazol-4-yl)quinazolin-2-yl)-1H-pyrazol-1-yl)acetamide;

5-(4-(((5-chloropyridin-3-yl)methyl)amino)-2-(1-(2-hydroxyethyl)-1H-pyrazol-4-yl)quinazolin-6-yl)-1-methylpyridin-2(1H)-one;

2-(4-(4-(((5-chloropyridin-3-yl)methyl)amino)-6-(3,5-dimethylisoxazol-4-yl)quinazolin-2-yl)-1H-pyrazol-1-yl)ethanol;

2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)acetamide;

2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)-N,N-dimethylacetamide;

2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)-N-methylacetamide;

5-(4-(((5-chloropyridin-3-yl)methyl)amino)-2-(1-(2-hydroxy-2-methylpropyl)-1H-pyrazol-4-yl)quinazolin-6-yl)-1-methylpyridin-2(1H)-one;

5-(4-(((5-chloropyridin-3-yl)methyl)amino)-2-(1-(1-hydroxy-2-methylpropan-2-yl)-1H-pyrazol-4-yl)quinazolin-6-yl)-1-methylpyridin-2(1H)-one;

2-(4-(4-((4-chlorophenyl)amino)-6-(3,5-dimethylisoxazol-4-yl)quinazolin-2-yl)-1H-pyrazol-1-yl)ethanol;

6-bromo-2-chloro-N-(4-chlorophenyl)quinazolin-4-amine;

N-((5-chloropyridin-3-yl)methyl)-6-(3,5-dimethylisoxazol-4-yl)-2-(4-(methylsulfonyl)piperazin-1-yl)quinazolin-4-amine;

N-(3-chlorobenzyl)-6-(3,5-dimethylisoxazol-4-yl)-2-(4-(methylsulfonyl)piperidin-1-yl)quinazolin-4-amine;

N-((5-chloropyridin-3-yl)methyl)-6-(3,5-dimethylisoxazol-4-yl)-2-(4-(methylsulfonyl)piperidin-1-yl)quinazolin-4-amine;

N-(3-chlorobenzyl)-6-(3,5-dimethylisoxazol-4-yl)-2-(4-(methylsulfonyl)piperazin-1-yl)quinazolin-4-amine;

1-(4-((3-chlorobenzyl)amino)-6-(3,5-dimethylisoxazol-4-yl)quinazolin-2-yl)-4-methylpiperidine-4-carbonitrile;

1-(4-(((5-chloropyridin-3-yl)methyl)amino)-6-(3,5-dimethylisoxazol-4-yl)quinazolin-2-yl)-4-methylpiperidine-4-carbonitrile;

N-(4-chlorophenyl)-6-(3,5-dimethylisoxazol-4-yl)quinazolin-4-amine;

5-(4-((4-chlorophenyl)amino)quinazolin-6-yl)-1-methylpyridin-2(1H)-one;

N-(4-chlorophenethyl)-2-(4-(2-(dimethylamino)ethyl)piperazin-1-yl)-6-(3,5-dimethylisoxazol-4-yl)quinazolin-4-amine;

2-(4-(4-(3-benzylazetidin-1-yl)-6-(3,5-dimethylisoxazol-4-yl)quinazolin-2-yl)piperazin-1-yl)-N,N-dimethylethanamine;

N-(4-chlorophenyl)-2-(4-(2-(dimethylamino)ethyl)piperazin-1-yl)-6-(3,5-dimethylisoxazol-4-yl)quinazolin-4-amine;
4-((3-chlorobenzyl)amino)-6-(3,5-dimethylisoxazol-4-yl)quinazoline-2-carboxylic acid;
2-(4-(4-((1-(3-chlorophenyl)cyclopropyl)amino)-6-(3,5-dimethylisoxazol-4-yl)quinazolin-2-yl)-1H-pyrazol-1-yl)ethanol;
(4-((3-chlorobenzyl)amino)-6-(3,5-dimethylisoxazol-4-yl)quinazolin-2-yl)(4-(2-(dimethylamino)ethyl)piperazin-1-yl)methanone;
2-(4-(4-((3-chlorobenzyl)amino)-6-(3,5-dimethylisoxazol-4-yl)quinazolin-2-yl)-1H-pyrazol-1-yl)acetic acid;
N4-(3-chlorobenzyl)-N2-(4-chlorobenzyl)-6-(3,5-dimethylisoxazol-4-yl)quinazoline-2,4-diamine;
N-(4-chlorobenzyl)-4-((3-chlorobenzyl)amino)-6-(3,5-dimethylisoxazol-4-yl)quinazoline-2-carboxamide;
N-(3-chlorobenzyl)-2-(4-chlorophenoxy)-6-(3,5-dimethylisoxazol-4-yl)quinazolin-4-amine;
N-(1-(3-chlorophenyl)cyclopropyl)-2-(4-(2-(dimethylamino)ethyl)piperazin-1-yl)-6-(3,5-dimethylisoxazol-4-yl)quinazolin-4-amine;
4-((3-chlorobenzyl)amino)-6-(3,5-dimethylisoxazol-4-yl)-N-(pyridin-4-ylmethyl)quinazoline-2-carboxamide;
4-((3-chlorobenzyl)amino)-6-(3,5-dimethylisoxazol-4-yl)-N-(1-methylpiperidin-4-yl)quinazoline-2-carboxamide;
(S)-2-((2-(4-(2-(dimethylamino)ethyl)piperazin-1-yl)-6-(3,5-dimethylisoxazol-4-yl)quinazolin-4-yl)amino)-2-phenylethanol;
2-(4-(6-(3,5-dimethylisoxazol-4-yl)-4-(2-phenylpyrrolidin-1-yl)quinazolin-2-yl)piperazin-1-yl)-N,N-dimethylethanamine;
2-(4-(6-(3,5-dimethylisoxazol-4-yl)-4-(2-phenylpiperidin-1-yl)quinazolin-2-yl)piperazin-1-yl)-N,N-dimethylethanamine;
2-(4-(6-(3,5-dimethylisoxazol-4-yl)-4-(3-phenylmorpholino)quinazolin-2-yl)piperazin-1-yl)-N,N-dimethylethanamine;
N-((1H-imidazol-2-yl)methyl)-4-((3-chlorobenzyl)amino)-6-(3,5-dimethylisoxazol-4-yl)quinazoline-2-carboxamide;
N2-((1H-imidazol-2-yl)methyl)-N4-(3-chlorobenzyl)-6-(3,5-dimethylisoxazol-4-yl)quinazoline-2,4-diamine;
2-(4-(6-(3,5-dimethylisoxazol-4-yl)-4-(2-phenylazetidin-1-yl)quinazolin-2-yl)piperazin-1-yl)-N,N-dimethylethanamine;
N-(1-(3-chlorophenyl)cyclopropyl)-6-(3,5-dimethylisoxazol-4-yl)-2-(4-(methylsulfonyl)piperazin-1-yl)quinazolin-4-amine;
2-(4-(4-((1-(3-chlorophenyl)cyclopropyl)amino)-6-(3,5-dimethylisoxazol-4-yl)quinazolin-2-yl)-1H-pyrazol-1-yl)-N-methylacetamide;
1-(4-(4-((1-(3-chlorophenyl)cyclopropyl)amino)-6-(3,5-dimethylisoxazol-4-yl)quinazolin-2-yl)-1H-pyrazol-1-yl)-2-methylpropan-2-ol;
4-((3-chlorobenzyl)amino)-6-(3,5-dimethylisoxazol-4-yl)-N-((1-methyl-1H-imidazol-5-yl)methyl)quinazoline-2-carboxamide;
1-(4-(4-((3-chlorobenzyl)amino)-6-(3,5-dimethylisoxazol-4-yl)quinazolin-2-yl)piperazin-1-yl)ethanone;
1-(4-(4-((1-(3-chlorophenyl)cyclopropyl)amino)-6-(3,5-dimethylisoxazol-4-yl)quinazolin-2-yl)piperazin-1-yl)ethanone;
4-((3-chlorobenzyl)amino)-6-(3,5-dimethylisoxazol-4-yl)-N-((1-methyl-1H-pyrazol-4-yl)methyl)quinazoline-2-carboxamide;
4-((3-chlorobenzyl)amino)-6-(3,5-dimethylisoxazol-4-yl)-N-((4-methylpyridin-3-yl)methyl)quinazoline-2-carboxamide;
4-((3-chlorobenzyl)amino)-N-((4-chloropyridin-2-yl)methyl)-6-(3,5-dimethylisoxazol-4-yl)quinazoline-2-carboxamide;
4-((3-chlorobenzyl)amino)-6-(3,5-dimethylisoxazol-4-yl)-N-(pyridin-3-ylmethyl)quinazoline-2-carboxamide;
4-((3-chlorobenzyl)amino)-N-((1,5-dimethyl-1H-pyrazol-4-yl)methyl)-6-(3,5-dimethylisoxazol-4-yl)quinazoline-2-carboxamide;
4-((3-chlorobenzyl)amino)-N-((5-chloropyridin-3-yl)methyl)-6-(3,5-dimethylisoxazol-4-yl)quinazoline-2-carboxamide;
4-((3-chlorobenzyl)amino)-6-(3,5-dimethylisoxazol-4-yl)-N-((5-fluoropyridin-3-yl)methyl)quinazoline-2-carboxamide;
4-((3-chlorobenzyl)amino)-6-(3,5-dimethylisoxazol-4-yl)-N-((5-methylpyridin-3-yl)methyl)quinazoline-2-carboxamide;
4-((3-chlorobenzyl)amino)-6-(3,5-dimethylisoxazol-4-yl)-N-((1,3,5-trimethyl-1H-pyrazol-4-yl)methyl)quinazoline-2-carboxamide;
1-(4-(4-(((5-chloropyridin-3-yl)methyl)amino)-6-(3,5-dimethylisoxazol-4-yl)quinazolin-2-yl)piperazin-1-yl)ethanone;
4-((3-chlorobenzyl)amino)-6-(3,5-dimethylisoxazol-4-yl)-N-((2-methylthiazol-4-yl)methyl)quinazoline-2-carboxamide;
4-((3-chlorobenzyl)amino)-6-(3,5-dimethylisoxazol-4-yl)-N-((6-methylpyridin-3-yl)methyl)quinazoline-2-carboxamide;
4-((3-chlorobenzyl)amino)-6-(3,5-dimethylisoxazol-4-yl)-N-(1-methylazetidin-3-yl)quinazoline-2-carboxamide;
N-(1-acetylpiperidin-4-yl)-4-((3-chlorobenzyl)amino)-6-(3,5-dimethylisoxazol-4-yl)quinazoline-2-carboxamide;
4-((3-chlorobenzyl)amino)-6-(3,5-dimethylisoxazol-4-yl)-N-((1-methylazetidin-3-yl)methyl)quinazoline-2-carboxamide;
4-((3-chlorobenzyl)amino)-6-(3,5-dimethylisoxazol-4-yl)-N-(1-(methylsulfonyl)piperidin-4-yl)quinazoline-2-carboxamide;
4-((3-chlorobenzyl)amino)-N-((2-chloropyridin-4-yl)methyl)-6-(3,5-dimethylisoxazol-4-yl)quinazoline-2-carboxamide;
4-((3-chlorobenzyl)amino)-N-((6-chloropyridin-3-yl)methyl)-6-(3,5-dimethylisoxazol-4-yl)quinazoline-2-carboxamide;
4-((3-chlorobenzyl)amino)-6-(3,5-dimethylisoxazol-4-yl)-N-(1,1-dioxidotetrahydro-2H-thiopyran-4-yl)quinazoline-2-carboxamide;
4-((3-chlorobenzyl)amino)-N-((1,3-dimethyl-1H-pyrazol-4-yl)methyl)-6-(3,5-dimethylisoxazol-4-yl)quinazoline-2-carboxamide;
4-(((5-chloropyridin-3-yl)methyl)amino)-N-((2-chloropyridin-4-yl)methyl)-6-(3,5-dimethylisoxazol-4-yl)quinazoline-2-carboxamide;
4-(((5-chloropyridin-3-yl)methyl)amino)-6-(3,5-dimethylisoxazol-4-yl)-N-(pyridin-4-ylmethyl)quinazoline-2-carboxamide;
4-((3-chlorobenzyl)amino)-N-((3-chloropyridin-4-yl)methyl)-6-(3,5-dimethylisoxazol-4-yl)quinazoline-2-carboxamide;
4-(((5-chloropyridin-3-yl)methyl)amino)-6-(3,5-dimethylisoxazol-4-yl)-N-(1-methylpiperidin-4-yl)quinazoline-2-carboxamide;

N-(3-chlorobenzyl)-6-(3,5-dimethylisoxazol-4-yl)-2-(1-(methylsulfonyl)-1,2,3,6-tetrahydropyridin-4-yl)quinazolin-4-amine;

4-((3-chlorobenzyl)amino)-6-(3,5-dimethylisoxazol-4-yl)-N-methyl-N-(1-methylpiperidin-4-yl)quinazoline-2-carboxamide;

4-((3-chlorobenzyl)amino)-6-(3,5-dimethylisoxazol-4-yl)-N-((2-methylthiazol-5-yl)methyl)quinazoline-2-carboxamide;

4-((3-chlorobenzyl)amino)-6-(3,5-dimethylisoxazol-4-yl)-N-((5-methylthiazol-2-yl)methyl)quinazoline-2-carboxamide;

4-((3-chlorobenzyl)amino)-6-(3,5-dimethylisoxazol-4-yl)-N-((4-methylthiazol-2-yl)methyl)quinazoline-2-carboxamide;

4-((3-chlorobenzyl)amino)-6-(3,5-dimethylisoxazol-4-yl)-N-((3-fluoropyridin-4-yl)methyl)quinazoline-2-carboxamide;

4-((3-chlorobenzyl)amino)-6-(3,5-dimethylisoxazol-4-yl)-N-((5-methyloxazol-2-yl)methyl)quinazoline-2-carboxamide;

4-((3-chlorobenzyl)amino)-6-(3,5-dimethylisoxazol-4-yl)-N-((3-methylpyridin-4-yl)methyl)quinazoline-2-carboxamide;

4-((3-chlorobenzyl)amino)-6-(3,5-dimethylisoxazol-4-yl)-N-(2-methylpyridin-4-yl)quinazoline-2-carboxamide;

4-((3-chlorobenzyl)amino)-6-(3,5-dimethylisoxazol-4-yl)-N-(6-methylpyridin-3-yl)quinazoline-2-carboxamide;

4-((3-chlorobenzyl)amino)-6-(3,5-dimethylisoxazol-4-yl)-N-(4-methylpyridin-3-yl)quinazoline-2-carboxamide;

4-((3-chlorobenzyl)amino)-6-(3,5-dimethylisoxazol-4-yl)-N-(5-fluoropyridin-3-yl)quinazoline-2-carboxamide;

4-((3-chlorobenzyl)amino)-N-(6-chloropyridin-3-yl)-6-(3,5-dimethylisoxazol-4-yl)quinazoline-2-carboxamide;

4-((3-chlorobenzyl)amino)-6-(3,5-dimethylisoxazol-4-yl)-N-(3-fluoropyridin-4-yl)quinazoline-2-carboxamide;

4-((3-chlorobenzyl)amino)-6-(3,5-dimethylisoxazol-4-yl)-N-(2,6-dimethylpyridin-4-yl)quinazoline-2-carboxamide;

4-((3-chlorobenzyl)amino)-6-(3,5-dimethylisoxazol-4-yl)-N-(1-methyl-1H-pyrazol-4-yl)quinazoline-2-carboxamide;

4-((3-chlorobenzyl)amino)-6-(3,5-dimethylisoxazol-4-yl)-N-(tetrahydro-2H-pyran-4-yl)quinazoline-2-carboxamide;

4-((3-chlorobenzyl)amino)-6-(1-methyl-6-oxo-1,6-dihydropyridin-3-yl)-N-(1-methylpiperidin-4-yl)quinoline-2-carboxamide;

4-((3-chlorobenzyl)amino)-6-(3,5-dimethylisoxazol-4-yl)-N-(1-methylpiperidin-4-yl)quinoline-2-carboxamide;

4-(((5-chloropyridin-3-yl)methyl)amino)-6-(3,5-dimethylisoxazol-4-yl)-N-(tetrahydro-2H-pyran-4-yl)quinazoline-2-carboxamide;

4-((3-chlorobenzyl)amino)-N-((1,3-dimethyl-1H-pyrazol-4-yl)methyl)-6-(3,5-dimethylisoxazol-4-yl)quinoline-2-carboxamide;

4-((3-chlorobenzyl)amino)-6-(3,5-dimethylisoxazol-4-yl)-N-((1-methylazetidin-3-yl)methyl)quinoline-2-carboxamide;

4-(((5-chloropyridin-3-yl)methyl)amino)-6-(3,5-dimethylisoxazol-4-yl)-N-((1-methyl-1H-imidazol-5-yl)methyl)quinazoline-2-carboxamide;

4-(((5-chloropyridin-3-yl)methyl)amino)-6-(3,5-dimethylisoxazol-4-yl)-N-((1-methylazetidin-3-yl)methyl)quinazoline-2-carboxamide;

4-((3-chlorobenzyl)amino)-6-(3,5-dimethylisoxazol-4-yl)-N-(1-methylazetidin-3-yl)quinoline-2-carboxamide;

4-((3-chlorobenzyl)amino)-6-(3,5-dimethylisoxazol-4-yl)-N-(1,1-dioxidotetrahydro-2H-thiopyran-4-yl)quinoline-2-carboxamide;

4-((3-chlorobenzyl)amino)-6-(3,5-dimethylisoxazol-4-yl)-N-(tetrahydro-2H-pyran-4-yl)quinoline-2-carboxamide;

4-(((5-chloropyridin-3-yl)methyl)amino)-6-(3,5-dimethylisoxazol-4-yl)-N-(1-methylazetidin-3-yl)quinazoline-2-carboxamide;

4-(((5-chloropyridin-3-yl)methyl)amino)-N-((1,3-dimethyl-1H-pyrazol-4-yl)methyl)-6-(3,5-dimethylisoxazol-4-yl)quinazoline-2-carboxamide;

4-(((5-chloropyridin-3-yl)methyl)amino)-6-(3,5-dimethylisoxazol-4-yl)-N-(1,1-dioxidotetrahydro-2H-thiopyran-4-yl)quinazoline-2-carboxamide;

4-((1-(3-chlorophenyl)cyclopropyl)amino)-6-(3,5-dimethylisoxazol-4-yl)-N-((1-methylazetidin-3-yl)methyl)quinazoline-2-carboxamide;

4-(4-(((5-chloropyridin-3-yl)methyl)amino)-6-(3,5-dimethylisoxazol-4-yl)quinazolin-2-yl)thiomorpholine 1,1-dioxide;

4-((1-(3-chlorophenyl)cyclopropyl)amino)-6-(3,5-dimethylisoxazol-4-yl)-N-(1-methylazetidin-3-yl)quinazoline-2-carboxamide;

4-(4-((3-chlorobenzyl)amino)-6-(3,5-dimethylisoxazol-4-yl)quinazolin-2-yl)thiomorpholine 1,1-dioxide;

4-(4-((3-chlorobenzyl)amino)-6-(3,5-dimethylisoxazol-4-yl)quinazolin-2-yl)-N,N-dimethylpiperazine-1-carboxamide;

4-((1-(3-chlorophenyl)cyclopropyl)amino)-N-((1,3-dimethyl-1H-pyrazol-4-yl)methyl)-6-(3,5-dimethylisoxazol-4-yl)quinazoline-2-carboxamide;

4-((1-(3-chlorophenyl)cyclopropyl)amino)-6-(3,5-dimethylisoxazol-4-yl)-N-(1,1-dioxidotetrahydro-2H-thiopyran-4-yl)quinazoline-2-carboxamide;

4-((1-(3-chlorophenyl)cyclopropyl)amino)-6-(3,5-dimethylisoxazol-4-yl)-N-(tetrahydro-2H-pyran-4-yl)quinazoline-2-carboxamide;

4-(4-(((5-chloropyridin-3-yl)methyl)amino)-6-(3,5-dimethylisoxazol-4-yl)quinazolin-2-yl)-N,N-dimethylpiperazine-1-carboxamide;

4-((3-chlorobenzyl)amino)-6-(3,5-dimethylisoxazol-4-yl)-N-((2-methylpyridin-4-yl)methyl)quinazoline-2-carboxamide;

4-((3-chlorobenzyl)amino)-6-(3,5-dimethylisoxazol-4-yl)-N-((trans)-4-hydroxycyclohexyl)quinazoline-2-carboxamide;

4-((3-chlorobenzyl)amino)-6-(3,5-dimethylisoxazol-4-yl)-N-((1-methyl-1H-imidazol-2-yl)methyl)quinazoline-2-carboxamide;

4-((3-chlorobenzyl)amino)-N-(4,4-difluorocyclohexyl)-6-(3,5-dimethylisoxazol-4-yl)quinazoline-2-carboxamide;

4-((3-chlorobenzyl)amino)-6-(3,5-dimethylisoxazol-4-yl)-N-((trans)-3-hydroxycyclobutyl)quinazoline-2-carboxamide;

1-(2-(4-(2-(dimethylamino)ethyl)piperazin-1-yl)-6-(3,5-dimethylisoxazol-4-yl)quinazolin-4-yl)piperidine-4-carboxylic acid;

1-(6-(3,5-dimethylisoxazol-4-yl)-2-(1-(2-hydroxyethyl)-1H-pyrazol-4-yl)quinazolin-4-yl)piperidine-4-carboxylic acid;

4-((3-chlorobenzyl)amino)-N-((3,3-difluorocyclobutyl)methyl)-6-(3,5-dimethylisoxazol-4-yl)quinazoline-2-carboxamide;

4-((3-chlorobenzyl)amino)-N-((3,5-dimethyl-1H-pyrazol-4-yl)methyl)-6-(3,5-dimethylisoxazol-4-yl)quinazoline-2-carboxamide;

4-((3-chlorobenzyl)amino)-6-(3,5-dimethylisoxazol-4-yl)-N-((4-methylthiazol-5-yl)methyl)quinazoline-2-carboxamide;
4-((3-chlorobenzyl)amino)-6-(3,5-dimethylisoxazol-4-yl)-N-((3,5-dimethylisoxazol-4-yl)methyl)quinazoline-2-carboxamide;
4-((3-chlorobenzyl)amino)-6-(3,5-dimethylisoxazol-4-yl)-N-((2,4-dimethylthiazol-5-yl)methyl)quinazoline-2-carboxamide;
1-(6-(3,5-dimethylisoxazol-4-yl)quinazolin-4-yl)piperidine-4-carboxylic acid;
(S)-1-(4-(6-(3,5-dimethylisoxazol-4-yl)-4-(3-phenylmorpholino)quinazolin-2-yl)-1H-pyrazol-1-yl)-2-methylpropan-2-ol;
(R)-1-(4-(6-(3,5-dimethylisoxazol-4-yl)-4-(3-phenylmorpholino)quinazolin-2-yl)-1H-pyrazol-1-yl)-2-methylpropan-2-ol;
4-(6-(3,5-dimethylisoxazol-4-yl)quinazolin-4-yl)-3-phenylmorpholine;
(S)-2-(4-(6-(3,5-dimethylisoxazol-4-yl)-4-(3-phenylmorpholino)quinazolin-2-yl)piperazin-1-yl)-N,N-dimethylethanamine;
(R)-2-(4-(6-(3,5-dimethylisoxazol-4-yl)-4-(3-phenylmorpholino)quinazolin-2-yl)piperazin-1-yl)-N,N-dimethylethanamine;
1-(2-(4-(2-(dimethylamino)ethyl)piperazin-1-yl)-6-(3,5-dimethylisoxazol-4-yl)quinazolin-4-yl)-N-methylpiperidine-4-carboxamide;
(R)-4-(6-(3,5-dimethylisoxazol-4-yl)-2-(4-(methylsulfonyl)piperazin-1-yl)quinazolin-4-yl)-3-phenylmorpholine;
(S)-4-(6-(3,5-dimethylisoxazol-4-yl)-2-(4-(methylsulfonyl)piperazin-1-yl)quinazolin-4-yl)-3-phenylmorpholine;
1-(6-(3,5-dimethylisoxazol-4-yl)quinazolin-4-yl)-N-methylpiperidine-4-carboxamide;
4-((3-chlorobenzyl)amino)-6-(3,5-dimethylisoxazol-4-yl)-N-(1,1-dioxidothietan-3-yl)quinazoline-2-carboxamide;
(S)-2-(4-(6-(3,5-dimethylisoxazol-4-yl)-4-(3-phenylmorpholino)quinazolin-2-yl)-1H-pyrazol-1-yl)-N-methylacetamide;
6-(3,5-dimethylisoxazol-4-yl)-N-((trans)-4-hydroxycyclohexyl)-4-((S)-3-phenylmorpholino)quinazoline-2-carboxamide;
4-((3-chlorobenzyl)amino)-6-(3,5-dimethylisoxazol-4-yl)-N-((trans)-4-hydroxycyclohexyl)quinoline-2-carboxamide;
(S)-6-(3,5-dimethylisoxazol-4-yl)-N-(1,1-dioxidotetrahydro-2H-thiopyran-4-yl)-4-(3-phenylmorpholino)quinazoline-2-carboxamide;
(S)-(6-(3,5-dimethylisoxazol-4-yl)-4-(3-phenylmorpholino)quinazolin-2-yl)(1-methyl-1,4,6,7-tetrahydro-5H-pyrazolo[4,3-c]pyridin-5-yl)methanone;
(S)-6-(3,5-dimethylisoxazol-4-yl)-N-(1-methylazetidin-3-yl)-4-(3-phenylmorpholino)quinazoline-2-carboxamide;
N-(3-chlorobenzyl)-6-(3,5-dimethylisoxazol-4-yl)-2-(1-methyl-1,4,6,7-tetrahydro-5H-pyrazolo[4,3-c]pyridin-5-yl)quinazolin-4-amine;
(S)-6-(3,5-dimethylisoxazol-4-yl)-N-((1-methyl-1H-imidazol-5-yl)methyl)-4-(3-phenylmorpholino)quinazoline-2-carboxamide;
(S)-6-(3,5-dimethylisoxazol-4-yl)-N-(1-methylpiperidin-4-yl)-4-(3-phenylmorpholino)quinazoline-2-carboxamide;
(S)—N-((1,3-dimethyl-1H-pyrazol-4-yl)methyl)-6-(3,5-dimethylisoxazol-4-yl)-4-(3-phenylmorpholino)quinazoline-2-carboxamide;
(S)-4-(6-(3,5-dimethylisoxazol-4-yl)-2-(1,4,6,7-tetrahydro-5H-pyrazolo[4,3-c]pyridin-5-yl)quinazolin-4-yl)-3-phenylmorpholine;
(S)-6-(3,5-dimethylisoxazol-4-yl)-N-((1-methylazetidin-3-yl)methyl)-4-(3-phenylmorpholino)quinazoline-2-carboxamide;
(4-(((5-chloropyridin-3-yl)methyl)amino)-6-(3,5-dimethylisoxazol-4-yl)quinazolin-2-yl)(1,4,6,7-tetrahydro-5H-pyrazolo[4,3-c]pyridin-5-yl)methanone;
(S)-(6-(3,5-dimethylisoxazol-4-yl)-4-(3-phenylmorpholino)quinazolin-2-yl)(1,4,6,7-tetrahydro-5H-pyrazolo[4,3-c]pyridin-5-yl)methanone;
(4-((1-(3-chlorophenyl)cyclopropyl)amino)-6-(3,5-dimethylisoxazol-4-yl)quinazolin-2-yl)(1,4,6,7-tetrahydro-5H-pyrazolo[4,3-c]pyridin-5-yl)methanone;
(4-((3-chlorobenzyl)amino)-6-(3,5-dimethylisoxazol-4-yl)quinazolin-2-yl)(1,4,6,7-tetrahydro-5H-pyrazolo[4,3-c]pyridin-5-yl)methanone;
(4-((3-chlorobenzyl)amino)-6-(3,5-dimethylisoxazol-4-yl)quinolin-2-yl)(1,4,6,7-tetrahydro-5H-pyrazolo[4,3-c]pyridin-5-yl)methanone;
(S)-4-(6-(3,5-dimethylisoxazol-4-yl)-2-(1-methyl-1,4,6,7-tetrahydro-5H-pyrazolo[4,3-c]pyridin-5-yl)quinazolin-4-yl)-3-phenylmorpholine;
N-(3-chlorobenzyl)-6-(3,5-dimethylisoxazol-4-yl)-2-(1,4,6,7-tetrahydro-5H-pyrazolo[4,3-c]pyridin-5-yl)quinazolin-4-amine;
(S)-1-(4-(6-(3,5-dimethylisoxazol-4-yl)-4-(2-phenylpiperazin-1-yl)quinazolin-2-yl)-1H-pyrazol-1-yl)-2-methylpropan-2-ol;
(S)-5-(2-(1-(2-hydroxy-2-methylpropyl)-1H-pyrazol-4-yl)-4-(3-phenylmorpholino)quinazolin-6-yl)-1-methylpyridin-2(1H)-one;
(S)-4-(6-(3,5-dimethylisoxazol-4-yl)-2-(4-methylpiperazin-1-yl)quinazolin-4-yl)-3-phenylmorpholine;
(S)-1-(4-(6-(3,5-dimethylisoxazol-4-yl)-4-(3-phenylmorpholino)quinazolin-2-yl)piperazin-1-yl)ethan-1-one;
(S)-1-(4-(6-(3,5-dimethylisoxazol-4-yl)-4-(3-phenylmorpholino)quinazolin-2-yl)piperazin-1-yl)-2-methylpropan-2-ol;
(S)-1-(4-(6-(3,5-dimethylisoxazol-4-yl)-4-(3-phenylmorpholino)quinazolin-2-yl)-N-methylpiperidine-4-carboxamide;
(S)-2-(4-(6-(3,5-dimethylisoxazol-4-yl)-4-(3-phenylmorpholino)quinazolin-2-yl)-1H-pyrazol-1-yl)acetamide;
(S)-1-(4-(6-(3,5-dimethylisoxazol-4-yl)-4-(3-phenylmorpholino)quinazolin-2-yl)-N-methylpiperidine-4-carboxamide;
(S)-4-(6-(3,5-dimethylisoxazol-4-yl)-4-(3-phenylmorpholino)quinazolin-2-yl)-N-ethylpiperazine-1-carboxamide;
(S)-(4-(6-(3,5-dimethylisoxazol-4-yl)-4-(3-phenylmorpholino)quinazolin-2-yl)piperazin-1-yl)(1-methyl-1H-pyrazol-4-yl)methanone;
(S)-2-(4-(6-(3,5-dimethylisoxazol-4-yl)-4-(3-phenylmorpholino)quinazolin-2-yl)-1H-pyrazol-1-yl)-N,N-dimethylacetamide;
(S)-4-(6-(3,5-dimethylisoxazol-4-yl)-2-(1-((methylsulfonyl)methyl)-1H-pyrazol-4-yl)quinazolin-4-yl)-3-phenylmorpholine;
(S)-2-(4-(6-(3,5-dimethylisoxazol-4-yl)-4-(3-phenylmorpholino)quinazolin-2-yl)piperazin-1-yl)-N,N-dimethylacetamide;
(S)-2-(4-(6-(3,5-dimethylisoxazol-4-yl)-4-(3-phenylmorpholino)quinazolin-2-yl)-1H-pyrazol-1-yl)-2-methylpropan-1-ol;
(S)-1-(4-(6-(3,5-dimethylisoxazol-4-yl)-4-(3-phenylmorpholino)quinazolin-2-yl)piperazin-1-yl)-2-hydroxyethan-1-one;

(S)-2-(4-(6-(3,5-dimethylisoxazol-4-yl)-4-(3-phenylmor-
    pholino)quinazolin-2-yl)-1H-pyrazol-1-yl)ethan-1-ol;
(S)-2-(4-(6-(3,5-dimethylisoxazol-4-yl)-4-(3-phenylmor-
    pholino)quinazolin-2-yl)piperazin-1-yl)acetamide;
(S)-1-(4-(6-(3,5-dimethylisoxazol-4-yl)-4-((S)-3-phenyl-
    morpholino)quinazolin-2-yl)piperazin-1-yl)propan-2-ol;
(S)-1-(4-(6-(3,5-dimethylisoxazol-4-yl)-2-(1-(2-hydroxy-2-
    methylpropyl)-1H-pyrazol-4-yl)quinazolin-4-yl)-3-phe-
    nylpiperazin-1-yl)ethan-1-one;
(S)-1-(4-(6-(3,5-dimethylisoxazol-4-yl)-4-(4-(methylsulfo-
    nyl)-2-phenylpiperazin-1-yl)quinazolin-2-yl)-1H-pyra-
    zol-1-yl)-2-methylpropan-2-ol;
(S)-4-(6-(3,5-dimethylisoxazol-4-yl)-2-(3-methyl-3,4,6,7-
    tetrahydro-5H-imidazo[4,5-c]pyridin-5-yl)quinazolin-4-
    yl)-3-phenylmorpholine;
1-(4-(4-((3-chlorobenzyl)(cyclopropyl)amino)-6-(3,5-dim-
    ethylisoxazol-4-yl)quinazolin-2-yl)-1H-pyrazol-1-yl)-2-
    methylpropan-2-ol;
(S)-7-(6-(3,5-dimethylisoxazol-4-yl)-4-(3-phenylmor-
    pholino)quinazolin-2-yl)-7-azaspiro[3.5]nonan-2-ol;
(S)-8-(6-(3,5-dimethylisoxazol-4-yl)-4-(3-phenylmor-
    pholino)quinazolin-2-yl)-1,8-diazaspiro[4.5]decan-2-
    one;
(S)-6-(3,5-dimethylisoxazol-4-yl)-N-(1,1-dioxidothietan-3-
    yl)-4-(3-phenylmorpholino)quinazoline-2-carboxamide;
(S)-(6-(3,5-dimethylisoxazol-4-yl)-4-(3-phenylmorpholino)
    quinazolin-2-yl)(2-hydroxy-7-azaspiro[3.5]nonan-7-yl)
    methanone;
(S)-(6-(3,5-dimethylisoxazol-4-yl)-4-(3-phenylmorpholino)
    quinazolin-2-yl)(1-methyl-1,4,5,7-tetrahydro-6H-pyra-
    zolo[3,4-c]pyridin-6-yl)methanone;
(S)-4-(6-(3,5-dimethylisoxazol-4-yl)-2-(1-methyl-1,4,5,7-
    tetrahydro-6H-pyrazolo[3,4-c]pyridin-6-yl)quinazolin-4-
    yl)-3-phenylmorpholine;
tert-butyl (S)-4-(4-(6-(3,5-dimethylisoxazol-4-yl)-4-(3-phe-
    nylmorpholino)quinazolin-2-yl)-1H-pyrazol-1-yl)piperi-
    dine-1-carboxylate;
(S)-8-(6-(3,5-dimethylisoxazol-4-yl)-4-(3-phenylmor-
    pholino)quinazolin-2-yl)-2-methyl-2,8-diazaspiro[4.5]
    decan-1-one;
(S)-(5-(6-(3,5-dimethylisoxazol-4-yl)-4-(3-phenylmor-
    pholino)quinazolin-2-yl)pyridin-2-yl)methanol;
(S)—N-cyclopropyl-4-(6-(3,5-dimethylisoxazol-4-yl)-2-(1-
    (2-hydroxy-2-methylpropyl)-1H-pyrazol-4-yl)quinazo-
    lin-4-yl)-3-phenylpiperazine-1-carboxamide;
(S)-(5-(6-(3,5-dimethylisoxazol-4-yl)-4-(3-phenylmor-
    pholino)quinazolin-2-yl)thiophen-2-yl)methanol;
(S)-1-(3-(4-(6-(3,5-dimethylisoxazol-4-yl)-4-(3-phenylmor-
    pholino)quinazolin-2-yl)-1H-pyrazol-1-yl)azetidin-1-yl)
    ethan-1-one;
(S)-4-(2-(1-(azetidin-3-yl)-1H-pyrazol-4-yl)-6-(3,5-dimeth-
    ylisoxazol-4-yl)quinazolin-4-yl)-3-phenylmorpholine;
(S)-(4-(6-(3,5-dimethylisoxazol-4-yl)-4-(3-phenylmor-
    pholino)quinazolin-2-yl)thiophen-2-yl)methanol;
(S)-1-(4-(4-(6-(3,5-dimethylisoxazol-4-yl)-4-(3-phenylmor-
    pholino)quinazolin-2-yl)-1H-pyrazol-1-yl)piperidin-1-yl)
    ethan-1-one;
(S)-4-(6-(3,5-dimethylisoxazol-4-yl)-2-(1-methyl-1,4,6,7-
    tetrahydro-5H-imidazo[4,5-c]pyridin-5-yl)quinazolin-4-
    yl)-3-phenylmorpholine;
(S)-8-(6-(3,5-dimethylisoxazol-4-yl)-4-(3-phenylmor-
    pholino)quinazolin-2-yl)-2,8-diazaspiro[4.5]decan-1-
    one;
(S)-8-(6-(3,5-dimethylisoxazol-4-yl)-4-(3-phenylmor-
    pholino)quinazolin-2-yl)-1-methyl-1,8-diazaspiro[4.5]
    decan-2-one;
(S)—N-((3,5-dimethyl-1H-pyrazol-4-yl)methyl)-6-(3,5-di-
    methylisoxazol-4-yl)-4-(3-phenylmorpholino)quinazo-
    line-2-carboxamide;
1-(6-(3,5-dimethylisoxazol-4-yl)-2-(1-(2-hydroxy-2-meth-
    ylpropyl)-1H-pyrazol-4-yl)quinazolin-4-yl)-N-methylpi-
    peridine-4-carboxamide;
(S)-4-(6-(3,5-dimethylisoxazol-4-yl)-2-(1-(tetrahydro-2H-
    pyran-4-yl)-1H-pyrazol-4-yl)quinazolin-4-yl)-3-phenyl-
    morpholine;
(S)-4-(6-(3,5-dimethylisoxazol-4-yl)-2-(1-methyl-1H-pyra-
    zol-4-yl)quinazolin-4-yl)-3-phenylmorpholine;
(S)-3-(4-(6-(3,5-dimethylisoxazol-4-yl)-4-(3-phenylmor-
    pholino)quinazolin-2-yl)-1H-pyrazol-1-yl)propanenitrile;
(S)-8-(4-(4-acetyl-2-phenylpiperazin-1-yl)-6-(3,5-dimethyl-
    isoxazol-4-yl)quinazolin-2-yl)-1-methyl-1,8-diazaspiro
    [4.5]decan-2-one;
(S)-8-(6-(3,5-dimethylisoxazol-4-yl)-4-(4-(methylsulfo-
    nyl)-2-phenylpiperazin-1-yl)quinazolin-2-yl)-1-methyl-
    1,8-diazaspiro[4.5]decan-2-one;
(S)-5-(2-(1-(2-hydroxy-2-methylpropyl)-1H-pyrazol-4-yl)-
    4-(2-phenylpiperazin-1-yl)quinazolin-6-yl)-1-methyl-
    pyridin-2(1H)-one;
1-(4-(6-(3,5-dimethylisoxazol-4-yl)-4-morpholinoquinazo-
    lin-2-yl)-1H-pyrazol-1-yl)-2-methylpropan-2-ol;
(S)-5-(4-(4-acetyl-2-phenylpiperazin-1-yl)-2-(1-(2-hy-
    droxy-2-methylpropyl)-1H-pyrazol-4-yl)quinazolin-6-
    yl)-1-methylpyridin-2(1H)-one;
or a pharmaceutically acceptable salt thereof.

In some embodiments, the compound is selected from the group of compounds provided in Table 1, or a pharmaceutically acceptable salt thereof. In some embodiments, the pharmaceutically acceptable salt of a compound provided herein (e.g., a compound of Formula I) is a trifluoroacetic acid salt.

Certain of the compounds described herein contain one or more chiral centers (e.g., including the compound species of the examples unless otherwise indicated by the chemical name), or may otherwise be capable of existing as multiple stereoisomers. The scope of the present disclosure includes mixtures of stereoisomers as well as purified enantiomers or enantiomerically and/or diastereomerically enriched mixtures. In some embodiments, the compounds provided herein are present as the (S)-enantiomer. In some embodiments, the compounds provided herein are present as the (R)-enantiomer. Also included within the scope of the present disclosure are the individual stereoisomers of the compounds represented by Formula I, as well as any wholly or partially equilibrated mixtures thereof. The present disclosure also includes the individual stereoisomers of the compounds represented by the formulas above as mixtures with isomers thereof in which one or more chiral centers are inverted.

In some embodiments, compounds of the present invention are provided as pharmaceutically acceptable salts which include non-toxic salts of the compounds set forth herein. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt.

The salts provided may be in some cases hydrates or solvates. The present invention includes a salt or solvate of the compounds herein described, including combinations thereof such as a solvate of a salt. The compounds of the present disclosure may exist in solvated, for example hydrated or ethanol complexed, as well as un-solvated forms, and the present invention encompasses all such forms. The salts of the present disclosure can be pharmaceutically acceptable salts.

The compounds or their pharmaceutically acceptable salts as provided herein may crystallize in more than one form, a characteristic known as polymorphism, and such polymorphic forms ("polymorphs") are within the scope of the present disclosure. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Although it is possible to administer the compounds of the present disclosure in the form of a bulk active chemical, it is preferred to administer the compound in the form of a pharmaceutical composition or formulation. Thus, pharmaceutical compositions are provided that include one or more compounds of Formula I and/or pharmaceutically acceptable salts thereof and one or more pharmaceutically acceptable carriers, diluents, or excipients.

Further embodiments of the invention provide a process for the preparation of a pharmaceutical composition including admixing one or more compounds of Formula I and/or pharmaceutically acceptable salts thereof with one or more pharmaceutically acceptable carriers, diluents or excipients.

In some embodiments, compounds which bind to and otherwise modulate acetylated protein binding to bromodomain-containing proteins are provided. Such compounds include at least one compound selected from Formula I as provided herein. Exemplary compounds include, but are not limited to, those compounds set forth previously by name.

In some embodiments, compounds for use in the treatment or prevention of a disease or condition mediated by inhibiting bromodomain-containing proteins from binding acetylated proteins are provided. In some embodiments, compounds for use in the treatment of a disease or condition mediated by inhibiting bromodomain-containing proteins from binding acetylated proteins are provided.

In some embodiments, compounds for use in the treatment or prevention of a disease or condition mediated by inhibiting acetylated proteins from binding bromodomain-containing proteins are provided. In some embodiments, compounds for use in the treatment of a disease or condition mediated by inhibiting acetylated proteins from binding bromodomain-containing proteins are provided.

In some embodiments, a method for the treatment or prevention of a disease is provided that includes the step of administering a compound as provided herein to inhibit the activity of bromodomain-containing proteins.

In some embodiments, a method for the treatment or prevention of a disease is provided that includes the step of administering a compound as provided herein to inhibit the activity of bromodomain-containing proteins by inhibiting binding to acetylated proteins. In some embodiments, the method is a method of treating a disease which includes the step of administering a compound as provided herein to inhibit the activity of bromodomain-containing proteins by inhibiting binding to acetylated proteins.

In some embodiments, the use of a compound or salt thereof, for the preparation of a pharmaceutical composition for the treatment or prevention of a disease or condition mediated by inhibiting bromodomain-containing proteins by inhibiting binding to acetylated proteins is provided. In some embodiments, the use of a compound or salt thereof, for the preparation of a pharmaceutical composition for the treatment of a disease or condition mediated by inhibiting bromodomain-containing proteins by inhibiting binding to acetylated proteins is provided. In some embodiments, the acetylated protein is an acetylated histone.

In some embodiments, the acetylated protein is an acetylated histone involved in the regulation or dysregulation of gene expression.

The compounds of the present invention, their pharmaceutically acceptable salts and their pharmaceutical compositions can be used for treating or preventing a wide variety of conditions or disorders. In some embodiments, the compounds of the present invention their pharmaceutically acceptable salts and their pharmaceutical compositions can be used for treating a wide variety of conditions or disorders.

In some embodiments, the disease or condition subject to prevention or treatment includes human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, neuroendocrine tumors, Merkel cell carcinoma, prostate cancer, ovarian cancer, chordoma, osteoarthritis, rheumatoid arthritis (e.g, juvenile rheumatoid arthritis), Alzheimer's disease, and HIV infection. In some embodiments, the disease or condition subject to treatment includes human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, neuroendocrine tumors, Merkel cell carcinoma, prostate cancer, ovarian cancer, chordoma, osteoarthritis, rheumatoid arthritis (e.g, juvenile rheumatoid arthritis), Alzheimer's disease, and HIV infection.

In some embodiments, the disease or condition subject to prevention or treatment includes human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, neuroendocrine tumors, Merkel cell carcinoma, prostate cancer, osteoarthritis, rheumatoid arthritis (e.g, juvenile rheumatoid arthritis), Alzheimer's disease, and HIV infection. In some embodiments, the disease or condition subject to treatment includes human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, neuroendocrine tumors, Merkel cell carcinoma, prostate cancer, osteoarthritis, rheumatoid arthritis (e.g, juvenile rheumatoid arthritis), Alzheimer's disease, and HIV infection.

In some embodiments, the disease or condition subject to prevention or treatment includes Hodgkin Lymphoma, non-Hodgkin lymphoma, acute myeloid leukemia, chronic myeloid leukemia, and acute lymphocytic leukemia. In some embodiments, the disease to be treated is selected from Hodgkin Lymphoma, non-Hodgkin lymphoma, acute myeloid leukemia, chronic myeloid leukemia, and acute lymphocytic leukemia.

In some embodiments, a method for the treatment or prevention of a disease or condition mediated by bromodomain-containing proteins is provided and includes the step of administering a compound as provided herein. In some embodiments, a method for the treatment of a disease or condition mediated by bromodomain-containing proteins is provided and includes the step of administering a compound as provided herein. Any of the methods or uses provided herein may include administering to a subject a therapeutically effective amount of a compound as provided herein, including a salt or polymorph thereof, or a pharmaceutical composition that includes such compounds, salts, or polymorphs.

The manner in which the compounds or their pharmaceutical composition set forth herein may be administered can vary. In some embodiments, the compounds can be administered orally. Preferred pharmaceutical compositions may be formulated for oral administration in the form of tablets, capsules, caplets, syrups, solutions, and suspensions. Such oral formulations can be provided in modified release dosage forms such as time-release tablet and capsule formulations. Pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

Pharmaceutical compositions may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation); by powder injection; or by buccal, sublingual, or intranasal absorption. Pharmaceutical compositions may be formulated in unit dose form, or in multiple or subunit doses.

The administration of the pharmaceutical compositions described herein can be intermittent, or at a gradual, continuous, constant or controlled rate. The pharmaceutical compositions may be administered to a warm-blooded animal, for example, a mammal such as a human being. In addition, the time of day and the number of times per day that the pharmaceutical composition is administered can vary.

The compounds as provided herein may also be used for the preparation of a medicament for the treatment or prevention of a disease or condition characterized by bromodomain-containing proteins binding acetylated proteins and altering normal gene expression. In some embodiments, the compounds as provided herein may be used for the preparation of a medicament for the treatment of a disease or condition characterized by bromodomain-containing proteins binding acetylated proteins and altering normal gene expression. Methods for treating, preventing, delaying the onset of, or slowing the progression of disorders mediated by acetylated proteins involved in the regulation or dysregulation of gene expression, in mammals in need of such treatment are also provided. The methods involve administering to a subject a therapeutically effective amount of a compound as provided herein, including a salt thereof, or a pharmaceutical composition that includes such compounds.

In some embodiments, the methods for treating, preventing, delaying the onset of, or slowing the progression of disorders mediated by acetylated proteins involved in the regulation or dysregulation of gene expression, in mammals in need of such treatment include the administration of at least one compound as provided herein including, but not limited to, the compounds provided according to Formula I.

The compounds alone or in a pharmaceutical composition as provided herein may be used in the treatment of a variety of disorders and conditions and, as such, may be used in combination with a variety of other suitable therapeutic agents useful in the treatment or prophylaxis of those disorders or conditions. Thus, in some embodiments, the present disclosure includes the administration of the compound of the present disclosure in combination with other therapeutic compounds. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present disclosure with other treatment agents may be in combination by administration concomitantly in: (1) a unitary pharmaceutical composition including two or more compounds; or (2) separate pharmaceutical compositions each including one of the compounds. Alternatively, the combination may be administered separately in a sequential manner wherein one treatment agent is administered first and the other second. Such sequential administration may be close in time or remote in time.

In some embodiments, the present disclosure includes combination therapy comprising administering to the subject a therapeutically or prophylactically effective amount of the compound of the present disclosure and one or more other therapy including chemotherapy, radiation therapy, gene therapy, or immunotherapy.

The compounds of the present disclosure can be used to mediate the prevention or treatment of various conditions or disorders mediated by inhibiting bromodomain-containing proteins from binding acetylated proteins. In some embodiments, the compounds of the present disclosure can be used to mediate the treatment of various conditions or disorders mediated by inhibiting bromodomain-containing proteins from binding acetylated proteins. The compounds and their pharmaceutical compositions are particularly useful in the treatment or prevention of various types of cancer, inflammation, obesity, metabolic, cardiovascular, neurodegenerative, psychiatric and infectious diseases. In some embodiments, the compounds and their pharmaceutical compositions are particularly useful in the treatment of various types of cancer, inflammation, obesity, metabolic, cardiovascular, neurodegenerative, psychiatric and infectious diseases.

In some embodiments, the compounds and their pharmaceutical compositions are particularly useful in the treatment or prevention of systemic or tissue inflammation, inflammatory responses to infection or hypoxia, cellular activation and proliferation, lipid metabolism, fibrosis and viral infections. In some embodiments, the compounds and their pharmaceutical compositions are particularly useful in the treatment of systemic or tissue inflammation, inflammatory responses to infection or hypoxia, cellular activation and proliferation, lipid metabolism, fibrosis and viral infections.

In some embodiments, the compounds and their pharmaceutical compositions are particularly useful in the treatment or prevention of a variety of chronic autoimmune and inflammatory conditions such as Graves' Opthalomapthy, Graves' Disease, Guillain-Barr syndrome, rheumatoid arthritis (e.g. juvenile rheumatoid arthritis), osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs. In some embodiments, the compounds and their pharmaceutical compositions are particularly useful in the treatment of a variety of chronic autoimmune and inflammatory conditions provided herein. In some embodiments, the compounds and their pharmaceutical compositions are particularly useful in the treatment or prevention of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs. In some embodiments, the compounds and their pharmaceutical compositions are particularly useful in the treatment of a wide variety of acute inflammatory conditions provided herein.

In some embodiments, the compounds and their pharmaceutical compositions are particularly useful in the treatment or prevention of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In some embodiments, the compounds and their pharmaceutical compositions are particularly useful in the treatment of diseases or conditions which involve inflammatory responses to infections with bacteria, viruses, fungi, parasites or their toxins, provided herein.

In some embodiments, the compounds and their pharmaceutical compositions are particularly useful in the treatment or prevention of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism. In some embodiments, the compounds and their pharmaceutical compositions are particularly useful in the treatment of conditions associated with ischaemia-reperfusion injury provided herein.

In some embodiments, the compounds and their pharmaceutical compositions are particularly useful in the treatment or prevention of disorders of lipid metabolism via the regulation of APO-A1 such as hypercholesterolemia, atherosclerosis and Alzheimer's disease. In some embodiments, the compounds and their pharmaceutical compositions are particularly useful in the treatment of disorders of lipid metabolism provided herein, via the regulation of APO-A1.

In some embodiments, the compounds and their pharmaceutical compositions are particularly useful in the treatment or prevention of fibrotic conditions such as idiopathic pulmonary fibrosis, renal fibrosis, post-operative stricture, keloid formation, scleroderma, cardiac fibrosis, cystic fibrosis lung inflammation, and liver fibrosis. In some embodiments, the compounds and their pharmaceutical compositions are particularly useful in the treatment or prevention of fibrotic conditions such as idiopathic pulmonary fibrosis, renal fibrosis, post-operative stricture, keloid formation, scleroderma, and cardiac fibrosis. In some embodiments, the compounds and their pharmaceutical compositions are particularly useful in the treatment or prevention of fibrotic conditions such as cystic fibrosis lung inflammation, idiopathic pulmonary fibrosis, and liver fibrosis. In some embodiments, the compounds and their pharmaceutical compositions are particularly useful in the treatment of fibrotic conditions provided herein.

In some embodiments, the compounds and their pharmaceutical compositions are particularly useful in the treatment or prevention of Rubinstein-Taybi syndrome. In some embodiments, the compounds and their pharmaceutical compositions are particularly useful in the treatment of Rubinstein-Taybi syndrome.

In some embodiments, the compounds and their pharmaceutical compositions are particularly useful in the treatment or prevention of a disease selected from juvenile rheumatoid arthritis, cystic fibrosis lung inflammation, idiopathic pulmonary fibrosis, liver fibrosis, Guillain-Barr syndrome, and Rubinstein-Taybi syndrome. In some embodiments, the compounds and their pharmaceutical compositions are particularly useful in the treatment of a disease selected from juvenile rheumatoid arthritis, cystic fibrosis lung inflammation, idiopathic pulmonary fibrosis, liver fibrosis, Guillain-Barr syndrome, and Rubinstein-Taybi syndrome.

In some embodiments, the compounds and their pharmaceutical compositions are particularly useful in the treatment or prevention of viral infections such as herpes virus, human papilloma virus, adenovirus and poxvirus and other DNA viruses. In some embodiments, the compounds and their pharmaceutical compositions are particularly useful in the treatment of viral infections provided herein.

In some embodiments, the compounds and their pharmaceutical compositions are particularly useful in the treatment or prevention of diseases associated with systemic inflammatory response syndrome including sepsis, burns, pancreatitis, major trauma, haemorrhage and ischaemia. In some embodiments, the compounds and their pharmaceutical compositions are particularly useful in the treatment of diseases associated with systemic inflammatory response syndrome provided herein.

In some embodiments, the compounds and their pharmaceutical compositions are particularly useful in the treatment or prevention of SIRS, the onset of shock, multi-organ dysfunction syndrome, which includes the onset of acute lung injury, ARDS, acute renal, hepatic, cardiac and gastro-intestinal injury and mortality. In some embodiments, the compounds and their pharmaceutical compositions are particularly useful in the treatment of SIRS, the onset of shock, and multi-organ dysfunction syndrome.

In some embodiments, the compounds and their pharmaceutical compositions are particularly useful in the treatment or prevention of sepsis, sepsis syndrome, septic shock and endotoxaemia, acute or chronic pancreatitis, herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus and for the treatment of Human papilloma virus infections of skin or cervical epithelia. In some embodiments, the compounds and their pharmaceutical compositions are particularly useful in the treatment of sepsis, sepsis syndrome, septic shock and endotoxaemia, acute or chronic pancreatitis, herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus and for the treatment of Human papilloma virus infections of skin or cervical epithelia.

In some embodiments, the compounds and their pharmaceutical compositions are particularly useful in the treatment or prevention of various forms of cancer, leukemias and lymphomas including acute myeloid leukemia, NPM1c mutant leukemia, Burkitt's lymphoma, multiple myeloma, T-cell lymphoblastic leukemia and other hematological cancers that involve translocations of mixed-lineage leukemia gene (MLL); solid tumors such as hepatocellular carcinoma, glioblastoma, medulloblastoma, neuroblastoma, NUT midline carcinoma, sarcoma, breast cancer, colorectal cancer, lung cancer, pancreatic cancer, ovarian cancer, chordoma, neuroendocrine tumors including those involving the pancreas and thymus (PanNETS and NETs), and Merkel cell carcinoma (MCC) and prostate cancer; osteoarthritis and rheumatoid arthritis (e.g. juvenile rheumatoid arthritis); Alzheimer's disease; and HIV infection. In some embodiments, the compounds and their pharmaceutical compositions are particularly useful in the treatment of various forms of cancer, leukemias and lymphomas including acute myeloid leukemia, NPM1c mutant leukemia, Burkitt's lymphoma, multiple myeloma, T-cell lymphoblastic leukemia and other hematological cancers that involve translocations of mixed-lineage leukemia gene (MLL); solid tumors such as hepatocellular carcinoma, glioblastoma, medulloblastoma, neuroblastoma, NUT midline carcinoma, sarcoma, breast cancer, colorectal cancer, lung cancer, pancreatic cancer, ovarian cancer, chordoma, neuroendocrine tumors including those involving the pancreas and thymus (PanNETS and NETs), and Merkel cell carcinoma (MCC) and prostate cancer; osteoarthritis and rheumatoid arthritis (e.g, juvenile rheumatoid arthritis); Alzheimer's disease; and HIV infection. In some embodiments, the disease is selected from human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, ovarian cancer, chordoma, neuroendocrine tumors, Merkel cell carcinoma, prostate cancer, osteoarthritis, rheumatoid arthritis, Alzheimer's disease, and HIV infection. In some embodiments, the disease is selected from human NUT midline carcinoma, multiple myeloma, Burkitt's lymphoma, myeloid leukemia, NPM1c mutant leukemia, T-cell lymphoblastic leukemia, hepatocellular carcinoma, glioblastoma, neuroblastoma, sarcoma, breast cancer, colorectal cancer, lung cancer, pancreatic cancer, neuroendocrine tumors, Merkel cell carcinoma, prostate cancer, osteoarthritis, rheumatoid arthritis, Alzheimer's disease, and HIV infection.

It is contemplated and therefore within the scope of the present invention that any feature that is described above can be combined with any other feature that is described above.

It is also contemplated and therefore within the scope of the present invention that negative provisos can be added to exclude any compound or remove any feature.

Definitions

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well. Thus, for example, $C_{1-6}$ alkyl represents a straight or branched chain hydrocarbon containing one to six carbon atoms. Additional examples include $C_{1-4}$, $C_{1-3}$, and the like.

As used herein the term "alkyl" refers to a straight or branched chain hydrocarbon, which may be optionally substituted, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl. In some embodiments, the alkyl group contains from 1 to 6 carbon atoms, from 1 to 4 carbon atoms, from 1 to 3 carbon atoms, or 1 to 2 carbon atoms.

As used herein, the term "alkene" refers to an unsaturated hydrocarbon that includes one or more carbon-carbon double bonds. The term "lower alkene" refers to an alkene that includes from five to twenty carbon atoms, such as from two to ten carbon atoms, while the term "upper alkene" refers to an alkene that includes more than twenty carbon atoms, such as from twenty-one to one hundred carbon atoms. The term "substituted alkene" refers to an alkene that has one or more of its hydrogen atoms replaced by one or more substituent groups, such as halogen. In some embodiments, the alkene group contains 2 to 6, 2 to 4, or 2 to 3 carbon atoms.

As used herein, the term "alkyne" refers to an unsaturated hydrocarbon that includes one or more carbon-carbon triple bonds. The term "lower alkyne" refers to an alkyne that includes from five to twenty carbon atoms, such as from two to ten carbon atoms, while the term "upper alkyne" refers to an alkyne that includes more than twenty carbon atoms, such as from twenty-one to one hundred carbon atoms. The term "substituted alkyne" refers to an alkyne that has one or more of its hydrogen atoms replaced by one or more substituent groups, such as halogen. In some embodiments, the alkynyl moiety contains 2 to 6, 2 to 4, or 2 to 3 carbon atoms.

As used herein, the term "cycloalkyl" refers to a fully saturated optionally substituted monocyclic, bicyclic, spirocyclic, or bridged hydrocarbon ring, with multiple degrees of substitution being allowed. Preferably, the ring is three to twelve-membered, more preferably, from five- to six-membered. Exemplary "cycloalkyl" groups as used herein include, but are not limited to, cyclopropyl, cyclobutyl, cyclopentyl, cyclohexyl, and cycloheptyl. Ring-forming carbon atoms of a cycloalkyl group can be optionally substituted by oxo or sulfido (e.g., C(O) or C(S)). In some embodiments, the cycloalkyl is a $C_{3-10}$ monocyclic or bicyclic cyclocalkyl. In some embodiments, the cycloalkyl is a $C_{3-10}$ monocyclic cyclocalkyl.

As used herein, the term "alkoxy" refers to a group —$OR^a$, where $R^a$ is "alkyl" as defined herein. Example alkoxy groups include methoxy, ethoxy, propoxy (e.g., n-propoxy and isopropoxy), tert-butoxy, and the like. In some embodiments, the alkoxy group has 1 to 6, 1 to 4, or 1 to 3 carbon atoms.

As used herein, the term "heterocycloalkyl" or "heterocycle" or "heterocyclyl" refers to an optionally substituted mono- or polycyclic ring system, optionally containing one or more degrees of unsaturation, and also containing one or more heteroatoms, which may be optionally substituted, with multiple degrees of substitution being allowed. Exemplary heteroatoms include nitrogen, oxygen, or sulfur atoms, including N-oxides, sulfur oxides, and dioxides. Preferably, the ring is three to twelve-membered, preferably five or six-membered and is either fully saturated or has one or more degrees of unsaturation. Such rings may be optionally fused to one or more of another heterocyclic ring(s) or cycloalkyl ring(s). Examples of "heterocyclic" groups as used herein include, but are not limited to, tetrahydrofuran, pyran, tetrahydropyran, 1,4-dioxane, 1,3-dioxane, piperidine, pyrrolidine, morpholine, tetrahydrothiopyran, and tetrahydrothiophene. In some embodiments, the heterocycloalkyl is a mono or bicyclic ring system, which may be spirocyclic, having 4-10 ring members, wherein 1 or 2 ring members of the monocyclic ring system or 1, 2, 3, or 4 ring members of the bicyclic ring system are independently selected from nitrogen, oxygen, and sulfur.

As used herein, the term "aryl" refers to a single benzene ring or fused benzene ring system which may be optionally substituted, with multiple degrees of substitution being allowed. Examples of "aryl" groups as used include, but are not limited to, phenyl, benzyl, 2-naphthyl, 1-naphthyl, anthracene, and phenanthrene. Preferable aryl rings have five- to ten-members. The term "aryl" also includes a fused benzene ring system, namely where a cyclic hydrocarbon or heterocycle (e.g., a cyclohexane or dioxane ring) or heteroaryl (e.g., pyridine) is fused with an aromatic ring (aryl, such as a benzene ring). In some embodiments, aryl groups have from 6 to 10 carbon atoms.

As used herein, the term "heteroaryl" refers to a monocyclic five to seven membered aromatic ring, a fused bicyclic aromatic ring system comprising two of such aromatic rings, which may be optionally substituted, with multiple degrees of substitution being allowed, or to a fused bicyclic ring system namely where a cycloalkyl or heterocycle (e.g., a cyclohexane or dioxane ring) is fused with a heteroaryl ring. Preferably, heteroaryl rings contain five- to ten-members. These heteroaryl rings contain one or more nitrogen, sulfur, and/or oxygen atoms. In certain embodiments, the heteroaryl rings contain one to three nitrogen, one to three oxygen, or one or two sulfur atoms. N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinoxaline, benzofuran, benzoxazole, benzothiophene, indole, indazole, benzimidazole, imidazopyridine, pyrazolopyridine, and pyrazolopyrimidine. In some embodiments, the heteroaryl is a mono or bicyclic ring system having 5-10 ring members, wherein 1, 2, or 3 ring members of the monocyclic ring system or 1, 2, 3, or 4 ring members of the bicyclic ring system are independently selected from nitrogen, oxygen, and sulfur.

As used herein the term "halogen" refers to fluorine, chlorine, bromine, or iodine.

As used herein the term "haloalkyl" refers to a substituted or unsubstituted alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$. In some embodiments, the haloalkyl group has 1 to 6, 1 to 4, or 1 to 3 carbon atoms.

As used herein, the term "sulfhydryl" refers to refers to a —SH group.

As used herein, the term "thioalkoxy" refers to a group —$SR^a$, where $R^a$ is "alkyl" as defined herein. In some embodiments, the thioalkoxy group has 1 to 6, 1 to 4, or 1 to 3 carbon atoms.

As used herein, the term "carboxyamido" refers to —NH—C(O)—W, wherein W is hydrogen or an unsubstituted or substituted alkyl, alkene, alkyne, cycloalkyl, aryl, or heterocycle group.

As used herein, the term "amine" is given its ordinary meaning and includes primary (e.g., —$NH_2$), secondary (e.g. —NHR) and tertiary amines (e.g. —NRR).

As used herein, the term "amido" refers to a group of the formula —C(O)NR'R", wherein R' and R" are substituted or unsubstituted alkyl, cycloalkyl or heterocycle, or R' and R" can form cycloalkyl or heterocycle.

As used herein, the term "sulfamido" refers to the group —$SO_2$NR'R", wherein R' and R" are as defined in the definition of "amido".

As used herein, "optionally substituted", groups may be substituted or unsubstituted. The substituent (or substitution) group may include, without limitation, one or more substituents independently selected from the following groups or designated subsets thereof: lower ($C_1$-$C_6$) alkyl, lower alkenyl, lower alkynyl, lower aryl, heteroaryl, alicyclic, heterocyclic, arylalkyl, heteroarylalkyl, lower alkoxy, lower aryloxy, amino, alkylamino, dialkylamino, diarylalkylamino, alkylthio, arylthio, heteroarylthio, oxo, oxa, carbonyl (—C(O)), carboxyesters (—C(O)OR), carboxamido (—C(O)$NH_2$), carboxy, acyloxy, —H, halo, —CN, —$NO_2$, —$N_3$, —SH, —OH, —C(O)$CH_3$, perhaloalkyl, perhaloalkoxy, perhaloacyl, guanidine, pyridinyl, thiophene, furanyl, indole, indazole, esters, amides, phosphonates, phosphonic add, phosphates, phosphoramides, sulfonates, sulfones, sulfates, sulphonamides, carbamates, ureas, thioureas and thioamides, thioalkyls. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). In some embodiments, a group may optionally be substituted by 1, 2, 3, 4, or 5 independently selected groups (e.g., the aryl and heteroaryl groups of $R_1$ may optionally be substituted by 1, 2, 3, 4, or 5 independently selected $R_8$ groups), In some embodiments, a group may optionally be substituted by 1, 2, 3 independently selected groups (e.g., the aryl and heteroaryl groups of $R_1$ may optionally be substituted by 1, 2, or 3 independently selected $R_8$ groups). In some embodiments, a group may optionally be substituted by 1 or 2 independently selected groups (e.g., the aryl and heteroaryl groups of $R_1$ may optionally be substituted by 1 or 2 independently selected $R_8$ groups). In some embodiments, a group may optionally be substituted by 1 group (e.g., the aryl and heteroaryl groups of $R_1$ may optionally be substituted by 1 $R_8$ group).

As used herein, the term "pharmaceutically acceptable" refers to carrier(s), diluent(s), excipient(s) or salt forms of the compounds of the present disclosure that are compatible with the other ingredients of the formulation of the pharmaceutical composition.

As used herein, the term "pharmaceutical composition" refers to a compound of the present disclosure optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutic amount", and "effective dose" refer to an amount of the compound of the present disclosure sufficient to elicit the desired pharmacological or therapeutic effects, thus resulting in an effective prevention or treatment of a disorder. Treatment of a disorder may be manifested by delaying or preventing the onset or progression of the disorder, as well as the onset or progression of symptoms associated with the disorder. Treatment of a disorder may also be manifested by a decrease or elimination of symptoms, reversal of the progression of the disorder, as well as any other contribution to the well-being of the patient. The effective dose can vary, depending upon factors such as the condition of the patient, the severity of the symptoms of the disorder, and the manner in which the pharmaceutical composition is administered.

The term "prodrug" as used herein is intended to encompass a class of analogs of compounds of the present invention wherein a metabolically labile moiety is attached to said compound of the invention through an available NH, C(O)H, COOH, C(O)NH$_2$, OH or SH functionality. The prodrug-forming moieties are removed by metabolic processes and release the active compounds having the free NH, C(O)H, COOH, C(O)NH$_2$, OH or SH group in vivo. Prodrugs are useful for adjusting such pharmacokinetic properties of the compounds as solubility and/or hydrophobicity, absorption in the gastrointestinal tract, bioavailability, tissue penetration, and rate of clearance. Design and preparation of various forms of prodrugs is known to those skilled in the art, and is described in, for example:

a) The Practice of Medicinal Chemistry, Camille G. Wermuth et al., Ch. 31 (Academic Press, 1996).
b) Design of Prodrugs, edited by H. Bundgaard, (Elsevier, 1985); 33.
c) A Textbook of Drug Design and Development, P. Krogsgaard-Larson and H. Bundgaard, eds. Ch. 5, pp. 113-191 (Harwood Academic Publishers, 1991); and
d) Hydrolysis in Drug and Prodrug Metabolism, Bernard Testa and Joachim M. Mayer, (Wiley-VCH, 2003).

Said references are incorporated herein by reference for the description of prodrugs.

General Methods for Preparation of Compounds

The present invention also provides a method for the synthesis of compounds of the present disclosure. The present invention further provides a method for the synthesis of compounds useful as intermediates in the preparation of compounds of the present disclosure. The compounds can be prepared according to the methods described below using readily available starting materials and reagents. In these reactions, variants may be employed which are themselves known to those of ordinary skill in this art but are not described in detail here. Those skilled in the art of organic synthesis will appreciate that there exist multiple means of producing compounds of the present disclosure. Illustrative synthetic methods, including those directed to specific, selected compounds noted in Table 2, are as set forth herein.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures.

One skilled in the art of organic synthesis understands that vulnerable moieties such as C(O)OH, C(O) and C(O)H, NH, C(O)NH$_2$, OH and SH moieties may be protected and deprotected, as necessary. Protecting groups for C(O)OH moieties include, but are not limited to, allyl, benzoylmethyl, benzyl, benzyloxymethyl, tert-butyl, ethyl, methyl, 2,2,2-trichloroethyl, and the like. Protecting groups for C(O) and C(O)H moieties include, but are not limited to, 1,3-dioxylketal, diethylketal, dimethylketal, 1,3-dithianylketal, O-methyloxime, O-phenyloxime and the like. Protecting groups for NH moieties include, but are not limited to, acetyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio) ethoxycarbonyl and the like.

A discussion of protecting groups is provided in T. H. Greene and P. G. M. Wuts, Protective Groups in Organic Synthesis, 3rd Ed., John Wiley & Sons, New York (1999).

EXAMPLES

General Synthetic Protocols

The invention will now be further described with reference to the following illustrative examples in which, unless stated otherwise, (i) all air or moisture sensitive reactions were performed under positive pressure of nitrogen with oven-dried glassware; (ii) chemical reagents and anhydrous solvents were obtained from commercial sources and used as is; (iii) temperatures are given in degrees Celsius (° C.); operations are carried out at room temperature (RT) or ambient temperature, that is, in a range of 18-25° C.; (iv) organic solutions were dried over anhydrous sodium or magnesium sulfate unless otherwise stated; evaporation of organic solvent was carried out using a rotary evaporator under reduced pressure; (v) column chromatography means flash chromatography on silica gel; thin layer chromatography (TLC) was carried out on silica gel plates; (vi) in general, the course of reactions was followed by TLC or liquid chromatography/mass spectroscopy (LC/MS) and reaction times are given for illustration only; (vii) preparative purification was performed on a Waters semi-preparative HPLC with a Phenomenex Luna C18 (5 micron, 30×75 mm) column at a flow rate of 45 mL/min, the mobile phase consisted of acetonitrile and water (each containing 0.1% trifluoroacetic acid); a gradient of 10% to 50% acetonitrile over 8 minutes was used during the purification; fraction collection was triggered by UV detection (220 nm); (viii) analytical analysis for purity was determined by two different methods denoted as Final QC Methods 1 and 2; Method 1: analysis was performed on an Agilent 1290 Infinity Series HPLC; UHPLC Long Gradient Equivalent 4% to 100% acetonitrile (0.05% trifluoroacetic acid) in water over 3 minutes, run time of 4.5 minutes with a flow rate of 0.8 mL/min; a Phenomenex Luna C18 column (3 micron, 3×75 mm) was used at a temperature of 50° C.; Method 2: analysis was performed on an Agilent 1260 with a 7 minute gradient of 4% to 100% acetonitrile (containing 0.025% trifluoroacetic acid) in water (containing 0.05% trifluoroacetic acid) over 8 minute run time at a flow rate of 1 mL/min; a Phenomenex Luna C18 column (3 micron, 3×75 mm) was used at a temperature of 50° C.; purity determination was performed using an Agilent Diode Array Detector for both Method 1 and Method 2; mass determination was performed using an Agilent 6130 mass spectrometer with electrospray ionization in the positive mode; all of the analogs for assay have purity greater than 95% based on both analytical methods; (ix) high resolution mass spectrometry was recorded on Agilent 6210 Time-of-Flight LC/MS system; (x) final products have satisfactory proton nuclear magnetic resonance (NMR) spectra and/or mass spectra data; (xi) when given, NMR data is in the form of delta values for major diagnostic protons, given in part per million (ppm) relative to tetramethylsilane (TMS) as an internal standard, and were obtained on Varian 400 (100) and 600 MHz spectrometers in the solvent indicated; (xii) chemical symbols have their usual meanings; (xiii) in the event that the nomenclature assigned to a given compound does not correspond to the compound structure depicted herein, the structure will control; (xiv) solvent ratio is given in volume:volume (v/v) terms; (xv) yields are given for illustration only and are not necessarily those which can be obtained by diligent process development; preparations were repeated if more material was required.

Representative Synthetic Schemes

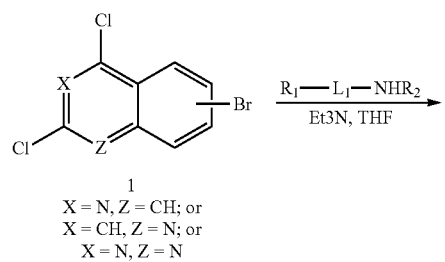

Scheme 1

1
X = N, Z = CH; or
X = CH, Z = N; or
X = N, Z = N

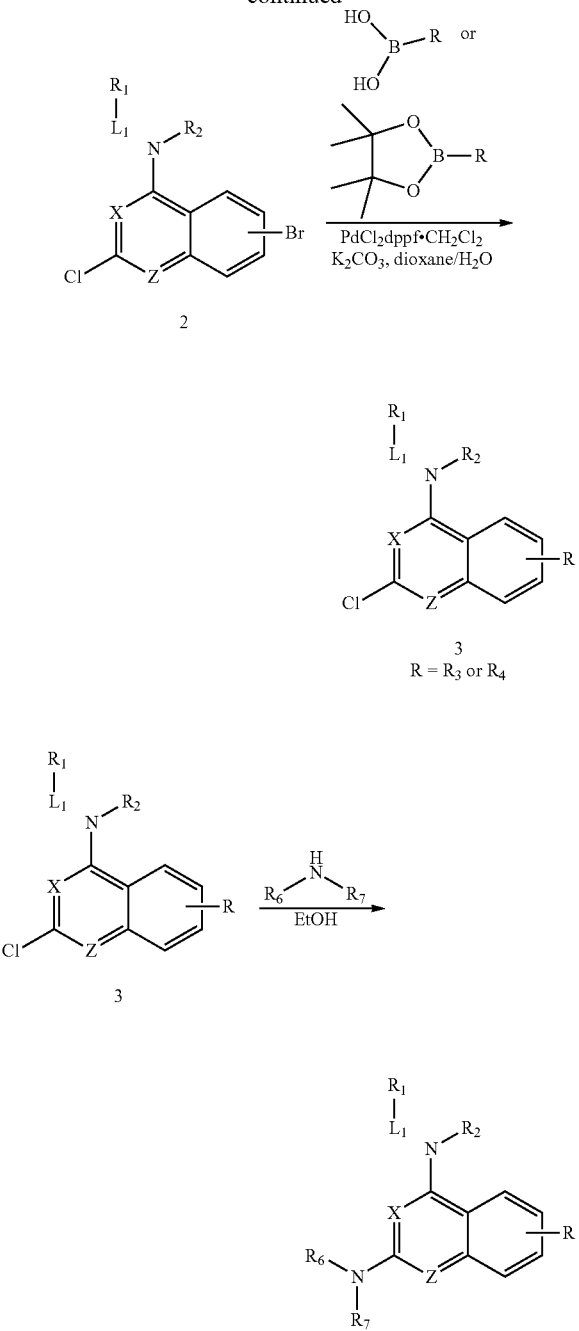

2

3
R = $R_3$ or $R_4$

3

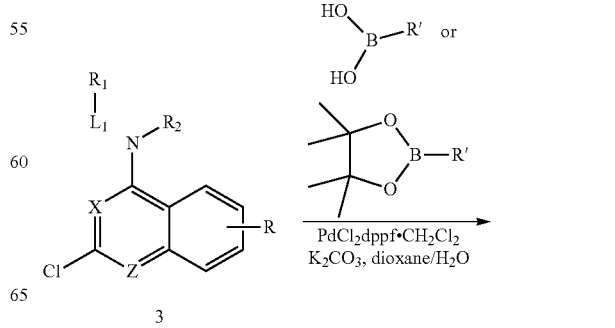

3

-continued

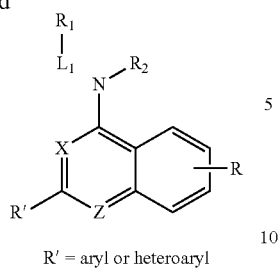

R' = aryl or heteroaryl

Compounds of Formula I wherein Y is $NR_6R_7$, aryl or heteroaryl may be prepared according to Scheme 1. A dichloride 1 may be allowed to react with an amine, $R_1$-$L_1$-NH—$R_2$, in ethanolic solution, to provide an intermediate compound 2. Coupling of 2 may be performed with a boronic acid or boronate ester in the presence of a palladium catalyst to provide a compound 3. Treatment of 3 with an amine R6R7NH in ethanolic solution will provide an amine of Formula I wherein Y is $NR_6R_7$, while coupling of 3 may be performed with a aryl or heteroaryl boronic acid or boronate ester in the presence of a palladium catalyst to provide a compound of Formula I wherein Y is aryl or heteroaryl.

Scheme 2

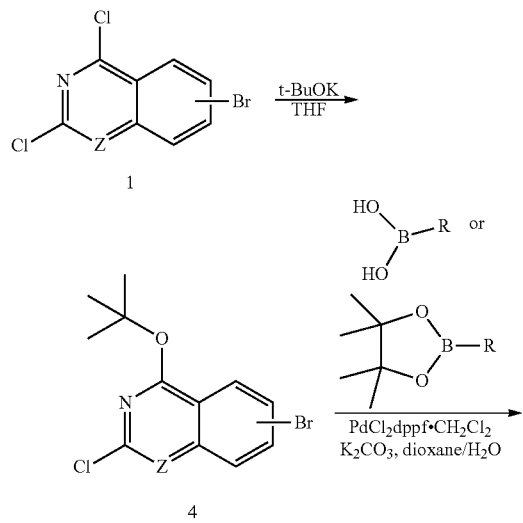

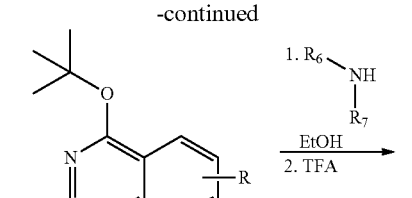

R = $R_3$ or $R_4$

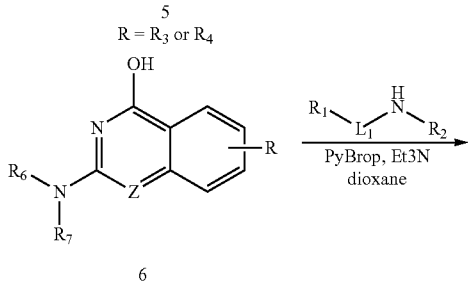

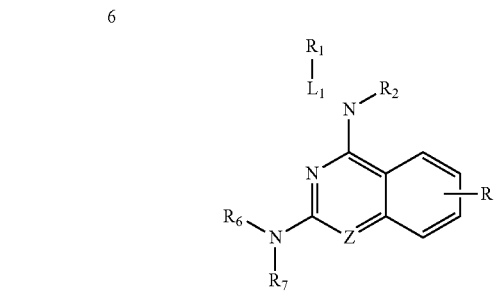

In the alternative, compounds of Formula I wherein X and Z are N and Y is $NR_6R_7$ may be prepared according to Scheme 2. A dichloride 1 may be allowed to react with potassium tert-butoxide to give a t-butyl ether 4. Coupling of 4 may be performed with a boronic acid or boronate ester in the presence of a palladium catalyst to provide a compound 5. Treatment of 5 with an amine in ethanolic solution, followed by deprotection in the presence of trifluoroacetic acid, will provide an amine 6, which may be coupled with an amine, $R_1$-$L_1$-NH—$R_2$, in the presence of a suitable activating agent, such as PyBrOP, to give a compound of Formula I.

Compounds of the present invention prepared according to Scheme 1 or Scheme 2 are presented in Table 1, and further details of their preparation are subsequently provided in the following Synthetic Procedures.

TABLE 1

| Example # | Structure | Compound Name |
|---|---|---|
| 1 | 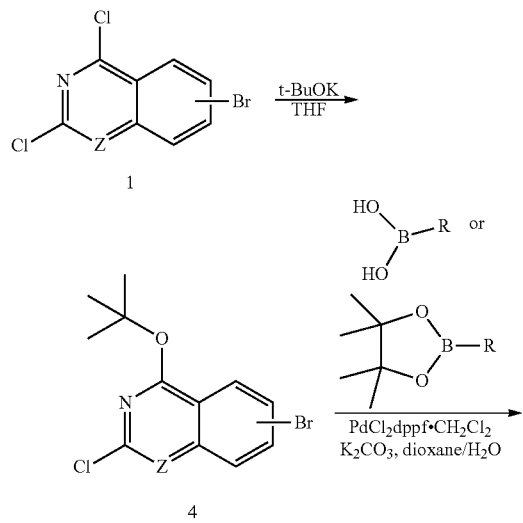 | 2-chloro-N-(3-chlorobenzyl)-6-(3,5-dimethylisoxazol-4-yl)quinazolin-4-amine |

TABLE 1-continued

| Example # | Structure | Compound Name |
|---|---|---|
| 2 | 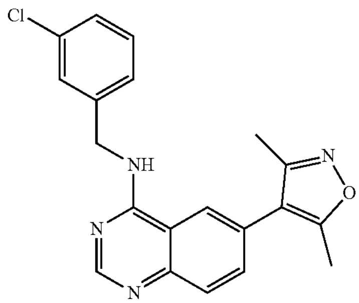 | N-(3-chlorobenzyl)-6-(3,5-dimethylisoxazol-4-yl)quinazolin-4-amine |
| 3 | 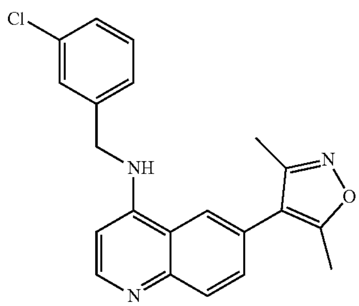 [SMILES: Cc1noc(C)c1-c1ccc2nccc(NCc3cccc(Cl)c3)c2c1] | N-(3-chlorobenzyl)-6-(3,5-dimethylisoxazol-4-yl)quinolin-4-amine |
| 4 | 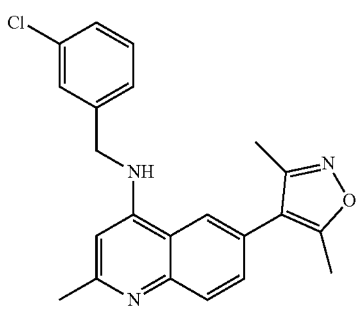 [SMILES: Cc1cc(NCc2cccc(Cl)c2)c2cc(-c3c(C)noc3C)ccc2n1] | N-(3-chlorobenzyl)-6-(3,5-dimethylisoxazol-4-yl)-2-methylquinolin-4-amine |
| 5 | 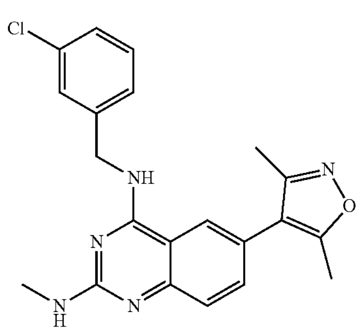 [SMILES: CNc1nc(NCc2cccc(Cl)c2)c2cc(-c3c(C)noc3C)ccc2n1] | N4-(3-chlorobenzyl)-6-(3,5-dimethylisoxazol-4-yl)-N2-methylquinazoline-2,4-diamine, 2TFA |

TABLE 1-continued

| Example # | Structure | Compound Name |
|---|---|---|
| 6 | 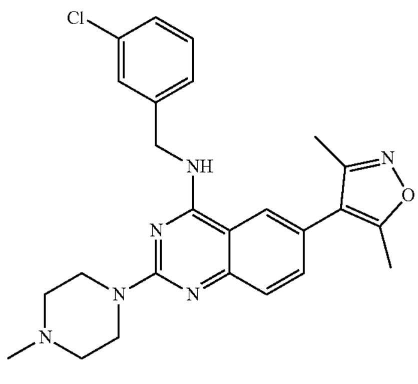 [SMILES: Cc1noc(C)c1-c1ccc2nc(N3CCN(C)CC3)nc(NCc3cccc(Cl)c3)c2c1] | N-(3-chlorobenzyl)-6-(3,5-dimethylisoxazol-4-yl)-2-(4-methylpiperazin-1-yl)quinazolin-4-amine, 2TFA |
| 7 | 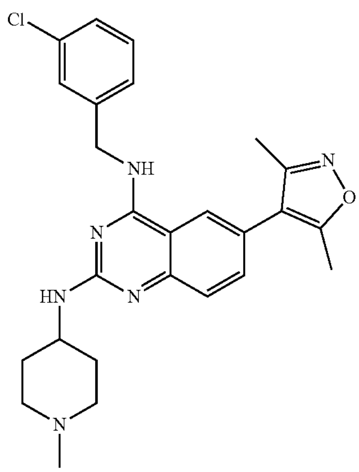 [SMILES: Cc1noc(C)c1-c1ccc2nc(NC3CCN(C)CC3)nc(NCc3cccc(Cl)c3)c2c1] | N4-(3-chlorobenzyl)-6-(3,5-dimethylisoxazol-4-yl)-N2-(1-methylpiperidin-4-yl)quinazoline-2,4-diamine, 2TFA |
| 8 | 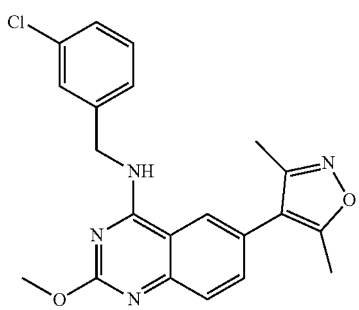 [SMILES: COc1nc(NCc2cccc(Cl)c2)c2cc(-c3c(C)noc3C)ccc2n1] | N-(3-chlorobenzyl)-6-(3,5-dimethylisoxazol-4-yl)-2-methoxyquinazolin-4-amine |
| 9 | 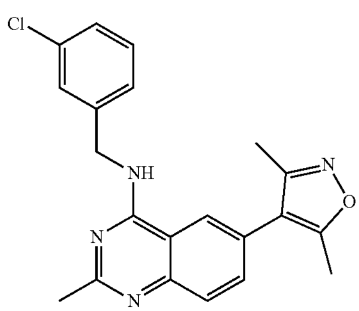 | N-(3-chlorobenzyl)-6-(3,5-dimethylisoxazol-4-yl)-2-methylquinazolin-4-amine |

TABLE 1-continued

| Example # | Structure | Compound Name |
|---|---|---|
| 10 | 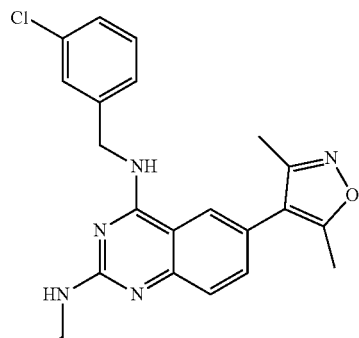 | N4-(3-chlorobenzyl)-6-(3,5-dimethylisoxazol-4-yl)-N2-(2-morpholinoethyl)quinazoline-2,4-diamine, 2TFA |
| 11 | 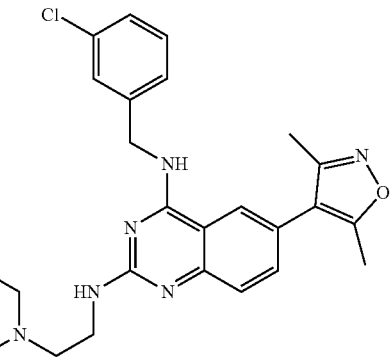 | N4-(3-chlorobenzyl)-6-(3,5-dimethylisoxazol-4-yl)-N2-(2-(4-methylpiperazin-1-yl)ethyl)quinazoline-2,4-diamine, 2TFA |
| 12 | 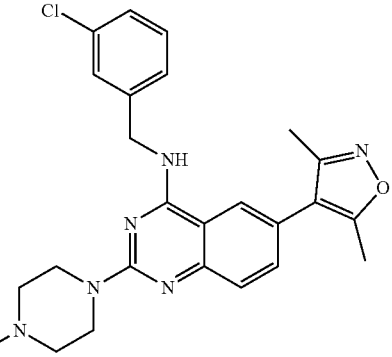 | N-(3-chlorobenzyl)-2-(4-(2-(dimethylamino)ethyl)piperazin-1-yl)-6-(3,5-dimethylisoxazol-4-yl)quinazolin-4-amine, 2TFA |
| 13 | 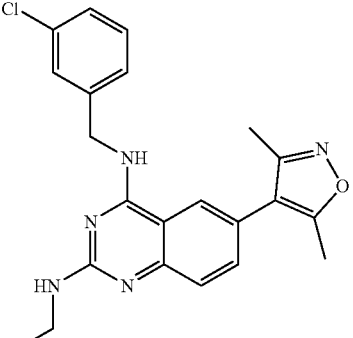 | 3-((4-((3-chlorobenzyl)amino)-6-(3,5-dimethylisoxazol-4-yl)quinazolin-2-yl)amino)propan-1-ol, 2TFA |

TABLE 1-continued

| Example # | Structure | Compound Name |
|---|---|---|
| 14 | 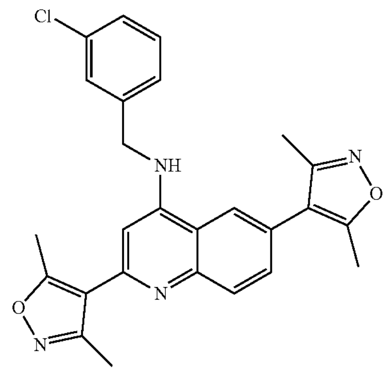 [SMILES: Cc1noc(C)c1-c1ccc2nc(-c3c(C)noc3C)cc(NCc3cccc(Cl)c3)c2c1] | N-(3-chlorobenzyl)-2,6-bis(3,5-dimethylisoxazol-4-yl)quinolin-4-amine, 2TFA |
| 15 | 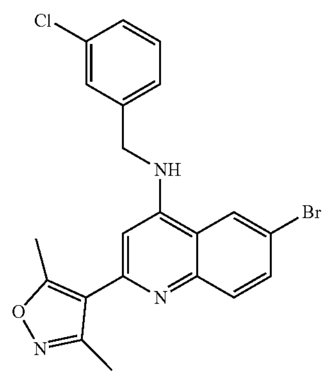 [SMILES: Cc1noc(C)c1-c1cc(NCc2cccc(Cl)c2)c2cc(Br)ccc2n1] | 6-bromo-N-(3-chlorobenzyl)-2-(3,5-dimethylisoxazol-4-yl)quinolin-4-amine, 2TFA |
| 16 | 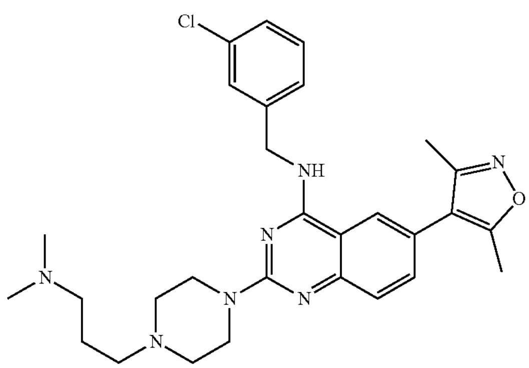 [SMILES: Cc1noc(C)c1-c1ccc2nc(N3CCN(CCCN(C)C)CC3)nc(NCc3cccc(Cl)c3)c2c1] | N-(3-chlorobenzyl)-2-(4-(3-(dimethylamino)propyl)piperazin-1-yl)-6-(3,5-dimethylisoxazol-4-yl)quinazolin-4-amine, 2TFA |
| 17 | 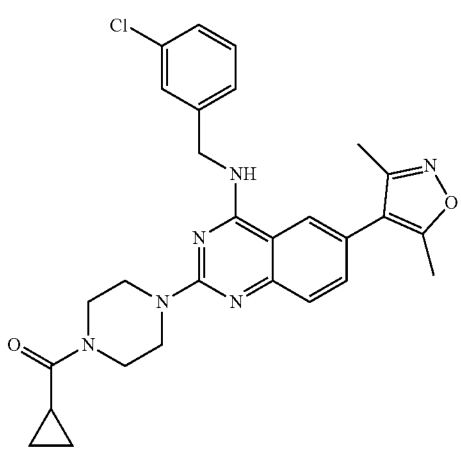 [SMILES: Cc1noc(C)c1-c1ccc2nc(N3CCN(C(=O)C4CC4)CC3)nc(NCc3cccc(Cl)c3)c2c1] | (4-(4-((3-chlorobenzyl)amino)-6-(3,5-dimethylisoxazol-4-yl)quinazolin-2-yl)piperazin-1-yl)(cyclopropyl)methanone, 2TFA |

TABLE 1-continued

| Example # | Structure | Compound Name |
|---|---|---|
| 18 | 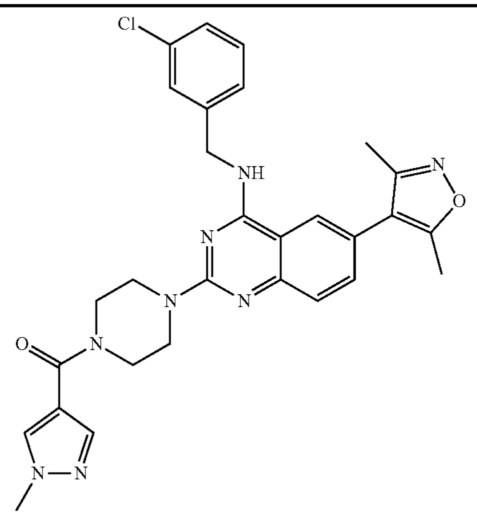 | (4-(4-((3-chlorobenzyl)amino)-6-(3,5-dimethylisoxazol-4-yl)quinazolin-2-yl)piperazin-1-yl)(1-methyl-1H-pyrazol-4-yl)methanone, 2TFA |
| 19 | 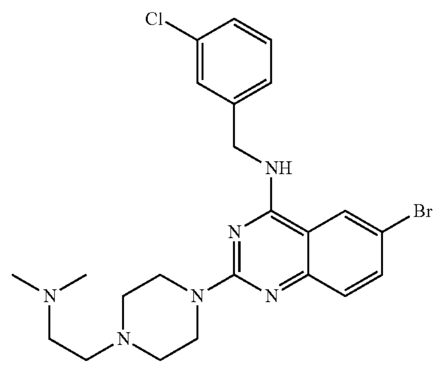 [SMILES: CN(C)CCN1CCN(c2nc(NCc3cccc(Cl)c3)c3cc(Br)ccc3n2)CC1] | 6-bromo-N-(3-chlorobenzyl)-2-(4-(2-(dimethylamino)ethyl)piperazin-1-yl)quinazolin-4-amine, 2TFA |
| 20 | 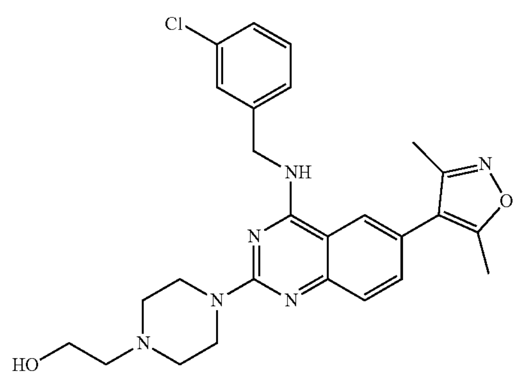 [SMILES: Cc1noc(C)c1-c1ccc2nc(N3CCN(CCO)CC3)nc(NCc3cccc(Cl)c3)c2c1] | 2-(4-(4-((3-chlorobenzyl)amino)-6-(3,5-dimethylisoxazol-4-yl)quinazolin-2-yl)piperazin-1-yl)ethanol, 2TFA |
| 21 | 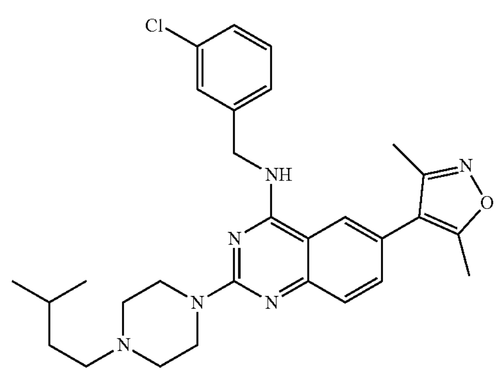 | N-(3-chlorobenzyl)-6-(3,5-dimethylisoxazol-4-yl)-2-(4-isopentylpiperazin-1-yl)quinazolin-4-amine, 2TFA |

TABLE 1-continued

| Example # | Structure | Compound Name |
|---|---|---|
| 22 | 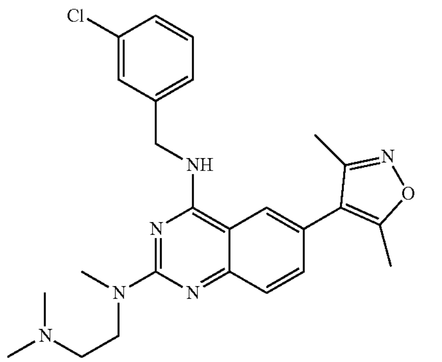 [SMILES: Cc1noc(C)c1-c1ccc2nc(N(C)CCN(C)C)nc(NCc3cccc(Cl)c3)c2c1] | N4-(3-chlorobenzyl)-N2-(2-(dimethylamino)ethyl)-6-(3,5-dimethylisoxazol-4-yl)-N2-methylquinazoline-2,4-diamine, 2TFA |
| 23 | 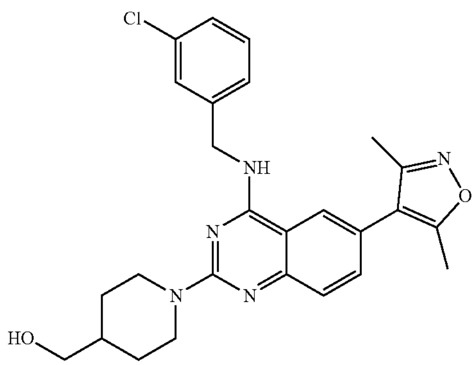 [SMILES: Cc1noc(C)c1-c1ccc2nc(N3CCC(CO)CC3)nc(NCc3cccc(Cl)c3)c2c1] | (1-(4-((3-chlorobenzyl)amino)-6-(3,5-dimethylisoxazol-4-yl)quinazolin-2-yl)piperidin-4-yl)methanol, 2TFA |
| 24 | 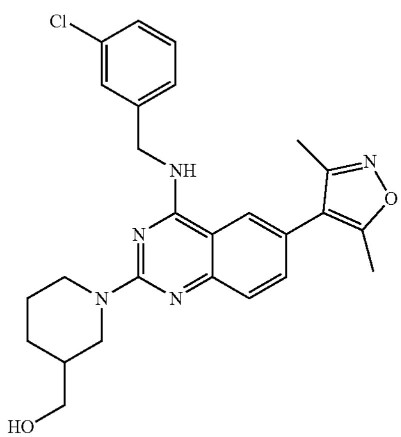 [SMILES: Cc1noc(C)c1-c1ccc2nc(N3CCCC(CO)C3)nc(NCc3cccc(Cl)c3)c2c1] | (1-(4-((3-chlorobenzyl)amino)-6-(3,5-dimethylisoxazol-4-yl)quinazolin-2-yl)piperidin-3-yl)methanol, 2TFA |
| 25 | 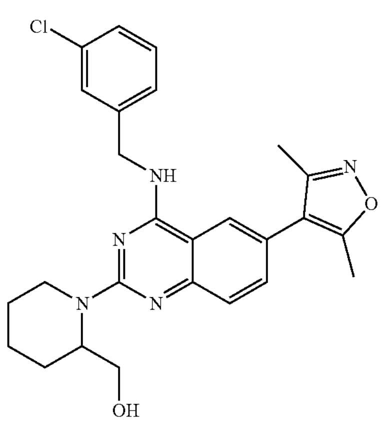 [SMILES: Cc1noc(C)c1-c1ccc2nc(N3CCCCC3CO)nc(NCc3cccc(Cl)c3)c2c1] | (1-(4-((3-chlorobenzyl)amino)-6-(3,5-dimethylisoxazol-4-yl)quinazolin-2-yl)piperidin-2-yl)methanol, 2TFA |

TABLE 1-continued

| Example # | Structure | Compound Name |
|---|---|---|
| 26 | 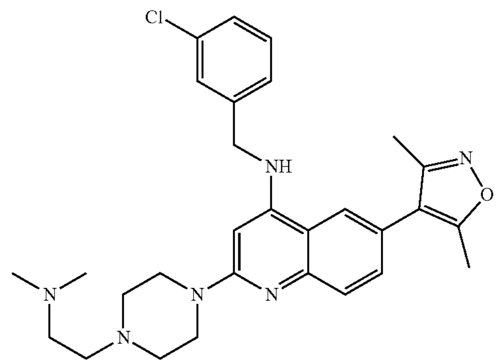 [SMILES: Cc1noc(C)c1-c1ccc2nc(N3CCN(CCN(C)C)CC3)cc(NCc3cccc(Cl)c3)c2c1] | N-(3-chlorobenzyl)-2-(4-(2-(dimethylamino)ethyl)piperazin-1-yl)-6-(3,5-dimethylisoxazol-4-yl)quinolin-4-amine, 2TFA |
| 27 | 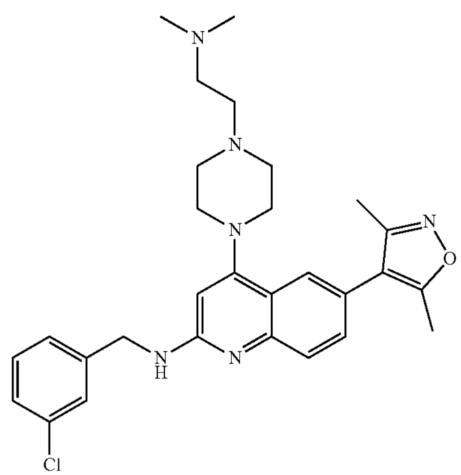 [SMILES: Cc1noc(C)c1-c1ccc2nc(NCc3cccc(Cl)c3)cc(N3CCN(CCN(C)C)CC3)c2c1] | N-(3-chlorobenzyl)-4-(4-(2-(dimethylamino)ethyl)piperazin-1-yl)-6-(3,5-dimethylisoxazol-4-yl)quinolin-2-amine, 2TFA |
| 28 | 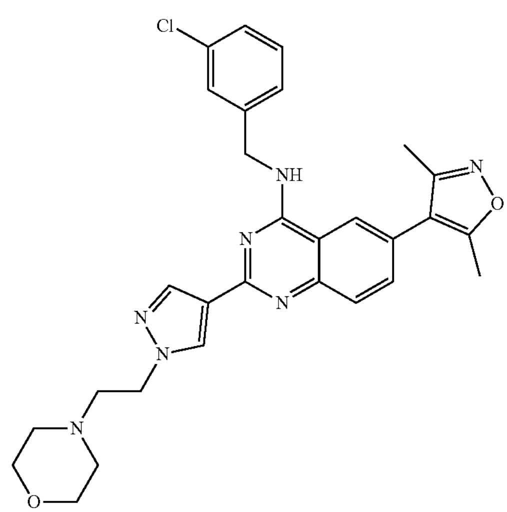 [SMILES: Cc1noc(C)c1-c1ccc2nc(-c3cnn(CCN4CCOCC4)c3)nc(NCc3cccc(Cl)c3)c2c1] | N-(3-chlorobenzyl)-6-(3,5-dimethylisoxazol-4-yl)-2-(1-(2-morpholinoethyl)-1H-pyrazol-4-yl)quinazolin-4-amine, 2TFA |

TABLE 1-continued

| Example # | Structure | Compound Name |
|---|---|---|
| 29 | 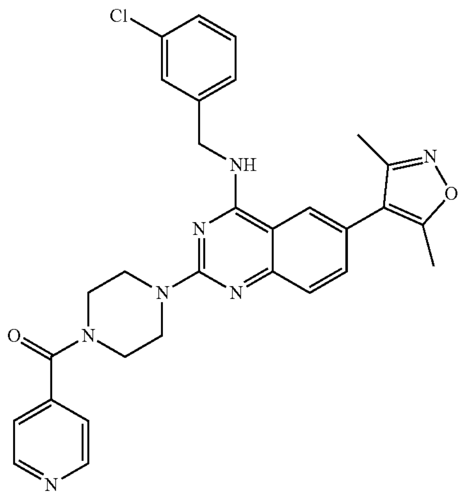 [SMILES: Cc1noc(C)c1-c1ccc2nc(N3CCN(C(=O)c4ccncc4)CC3)nc(NCc3cccc(Cl)c3)c2c1] | (4-(4-((3-chlorobenzyl)amino)-6-(3,5-dimethylisoxazol-4-yl)quinazolin-2-yl)piperazin-1-yl)(pyridin-4-yl)methanone, 2TFA |
| 30 | 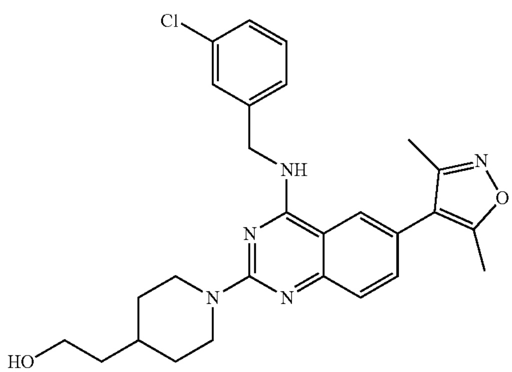 [SMILES: Cc1noc(C)c1-c1ccc2nc(N3CCC(CCO)CC3)nc(NCc3cccc(Cl)c3)c2c1] | 2-(1-(4-((3-chlorobenzyl)amino)-6-(3,5-dimethylisoxazol-4-yl)quinazolin-2-yl)piperidin-4-yl)ethanol, 2TFA |
| 31 | 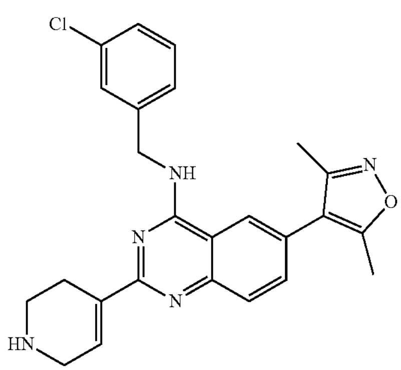 [SMILES: Cc1noc(C)c1-c1ccc2nc(C3=CCNCC3)nc(NCc3cccc(Cl)c3)c2c1] | N-(3-chlorobenzyl)-6-(3,5-dimethylisoxazol-4-yl)-2-(1,2,3,6-tetrahydropyridin-4-yl)quinazolin-4-amine, 2TFA |

TABLE 1-continued
| Example # | Structure | Compound Name |
|---|---|---|
| 32 | 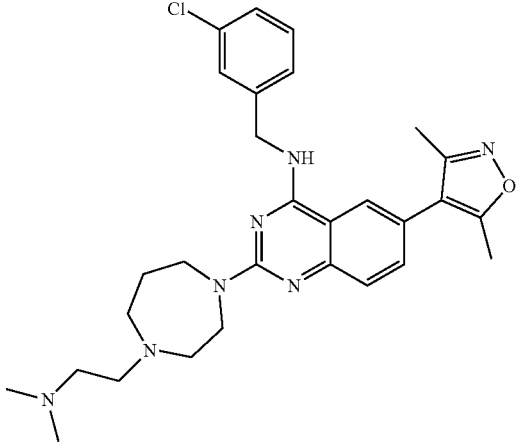 [SMILES: Cc1noc(C)c1-c1ccc2nc(N3CCCN(CCN(C)C)CC3)nc(NCc3cccc(Cl)c3)c2c1] | N-(3-chlorobenzyl)-2-(4-(2-(dimethylamino)ethyl)-1,4-diazepan-1-yl)-6-(3,5-dimethylisoxazol-4-yl)quinazolin-4-amine, 2TFA |
| 33 | 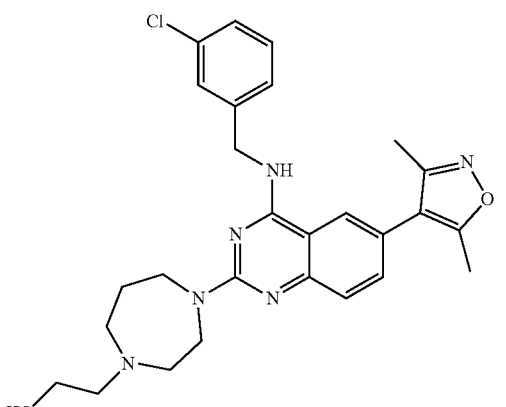 | 2-(4-(4-((3-chlorobenzyl)amino)-6-(3,5-dimethylisoxazol-4-yl)quinazolin-2-yl)-1,4-diazepan-1-yl)ethanol, 2TFA |
| 34 | 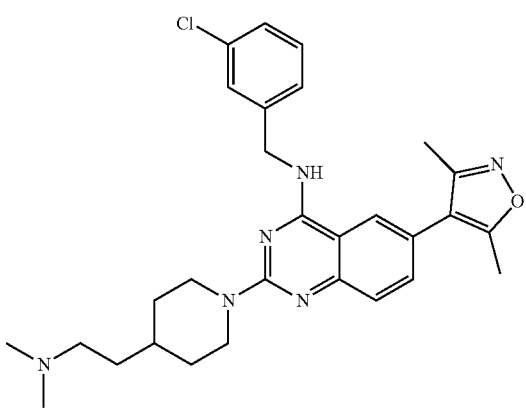 | N-(3-chlorobenzyl)-2-(4-(2-(dimethylamino)ethyl)piperidin-1-yl)-6-(3,5-dimethylisoxazol-4-yl)quinazolin-4-amine, 2TFA |

TABLE 1-continued

| Example # | Structure | Compound Name |
|---|---|---|
| 35 | 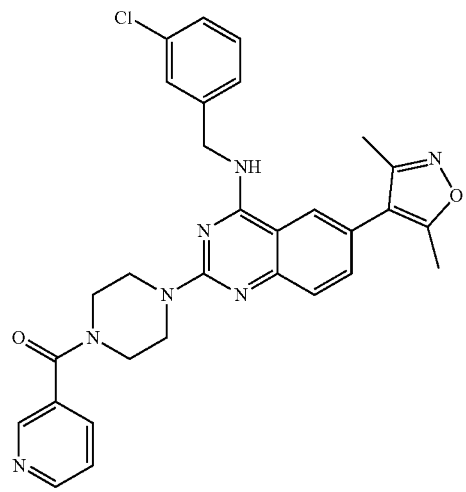 [SMILES: Cc1noc(C)c1-c1ccc2nc(N3CCN(C(=O)c4cccnc4)CC3)nc(NCc3cccc(Cl)c3)c2c1] | (4-(4-((3-chlorobenzyl)amino)-6-(3,5-dimethylisoxazol-4-yl)quinazolin-2-yl)piperazin-1-yl)(pyridin-3-yl)methanone, 2TFA |
| 36 | 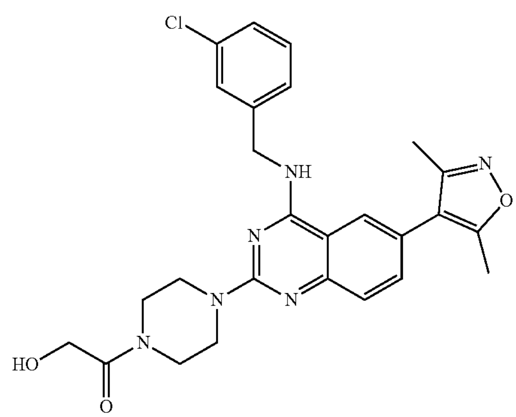 [SMILES: Cc1noc(C)c1-c1ccc2nc(N3CCN(C(=O)CO)CC3)nc(NCc3cccc(Cl)c3)c2c1] | 1-(4-(4-((3-chlorobenzyl)amino)-6-(3,5-dimethylisoxazol-4-yl)quinazolin-2-yl)piperazin-1-yl)-2-hydroxyethanone, 2TFA |
| 37 | 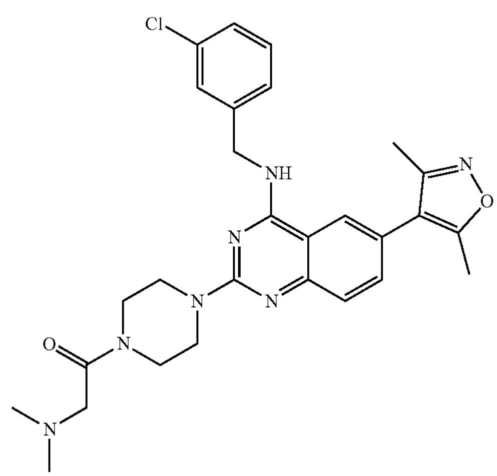 [SMILES: Cc1noc(C)c1-c1ccc2nc(N3CCN(C(=O)CN(C)C)CC3)nc(NCc3cccc(Cl)c3)c2c1] | 1-(4-(4-((3-chlorobenzyl)amino)-6-(3,5-dimethylisoxazol-4-yl)quinazolin-2-yl)piperazin-1-yl)-2-(dimethylamino)ethanone, 2TFA |

TABLE 1-continued

| Example # | Structure | Compound Name |
|---|---|---|
| 38 | 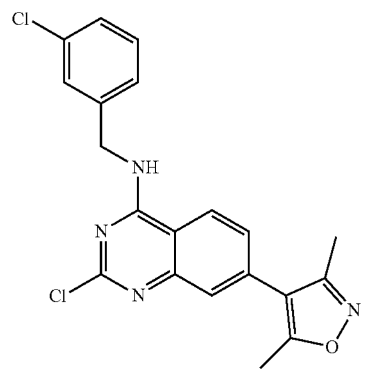 [SMILES: Cc1noc(C)c1-c1ccc2c(NCc3cccc(Cl)c3)nc(Cl)nc2c1] | 2-chloro-N-(3-chlorobenzyl)-7-(3,5-dimethylisoxazol-4-yl)quinazolin-4-amine, 2TFA |
| 39 | 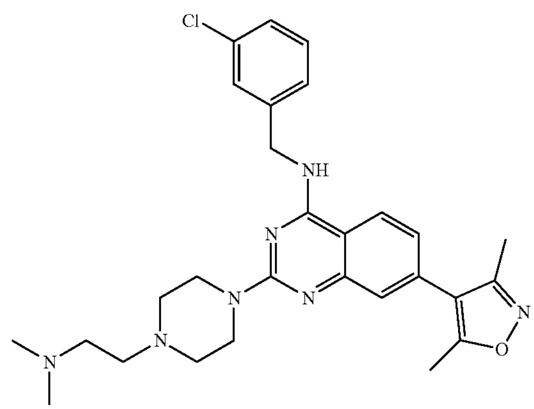 [SMILES: Cc1noc(C)c1-c1ccc2c(NCc3cccc(Cl)c3)nc(N3CCN(CCN(C)C)CC3)nc2c1] | N-(3-chlorobenzyl)-2-(4-(2-(dimethylamino)ethyl)piperazin-1-yl)-7-(3,5-dimethylisoxazol-4-yl)quinazolin-4-amine, 2TFA |
| 40 | 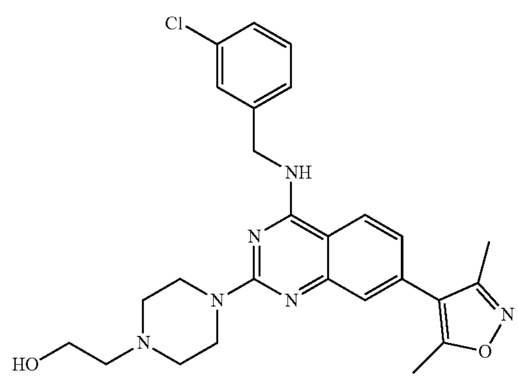 [SMILES: Cc1noc(C)c1-c1ccc2c(NCc3cccc(Cl)c3)nc(N3CCN(CCO)CC3)nc2c1] | 2-(4-(4-((3-chlorobenzyl)amino)-7-(3,5-dimethylisoxazol-4-yl)quinazolin-2-yl)piperazin-1-yl)ethanol, 2TFA |
| 41 | 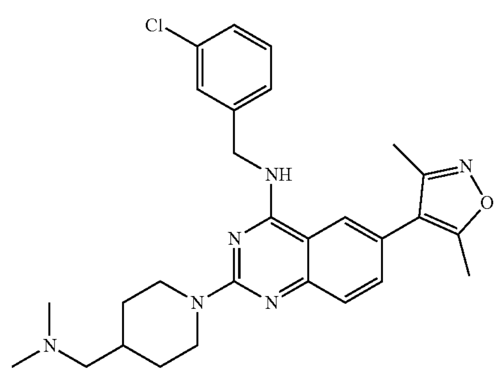 [SMILES: Cc1noc(C)c1-c1ccc2nc(N3CCC(CN(C)C)CC3)nc(NCc3cccc(Cl)c3)c2c1] | N-(3-chlorobenzyl)-2-(4-((dimethylamino)methyl)piperidin-1-yl)-6-(3,5-dimethylisoxazol-4-yl)quinazolin-4-amine, 2TFA |

TABLE 1-continued

| Example # | Structure | Compound Name |
|---|---|---|
| 42 | 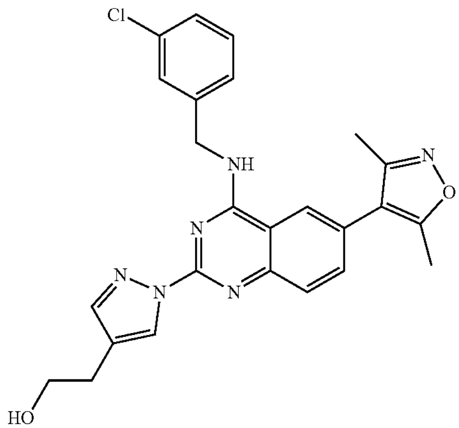 [SMILES: Cc1noc(C)c1-c1ccc2nc(-n3cc(CCO)cn3)nc(NCc3cccc(Cl)c3)c2c1] | 2-(1-(4-((3-chlorobenzyl)amino)-6-(3,5-dimethylisoxazol-4-yl)quinazolin-2-yl)-1H-pyrazol-4-yl)ethanol, 2TFA |
| 43 | 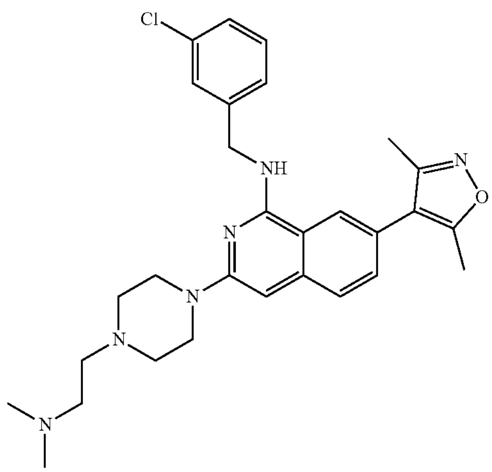 [SMILES: Cc1noc(C)c1-c1ccc2cc(N3CCN(CCN(C)C)CC3)nc(NCc3cccc(Cl)c3)c2c1] | N-(3-chlorobenzyl)-3-(4-(2-(dimethylamino)ethyl)piperazin-1-yl)-7-(3,5-dimethylisoxazol-4-yl)isoquinolin-1-amine, 2TFA |
| 44 | 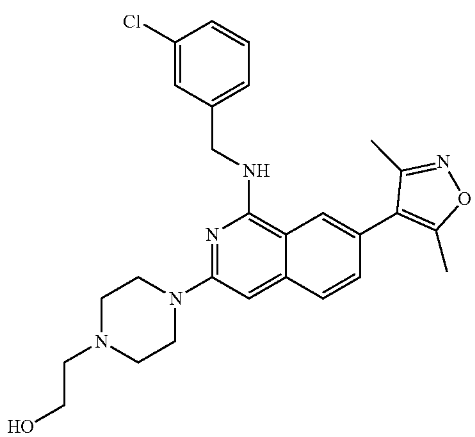 [SMILES: Cc1noc(C)c1-c1ccc2cc(N3CCN(CCO)CC3)nc(NCc3cccc(Cl)c3)c2c1] | 2-(4-(1-((3-chlorobenzyl)amino)-7-(3,5-dimethylisoxazol-4-yl)isoquinolin-3-yl)piperazin-1-yl)ethanol, 2TFA |

TABLE 1-continued

| Example # | Structure | Compound Name |
|---|---|---|
| 45 | 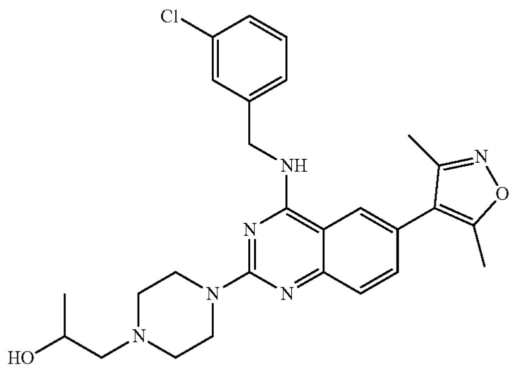 [SMILES: Cc1noc(C)c1-c1ccc2nc(N3CCN(CC(C)O)CC3)nc(NCc3cccc(Cl)c3)c2c1] | 1-(4-(4-((3-chlorobenzyl)amino)-6-(3,5-dimethylisoxazol-4-yl)quinazolin-2-yl)piperazin-1-yl)propan-2-ol, 2TFA |
| 46 | 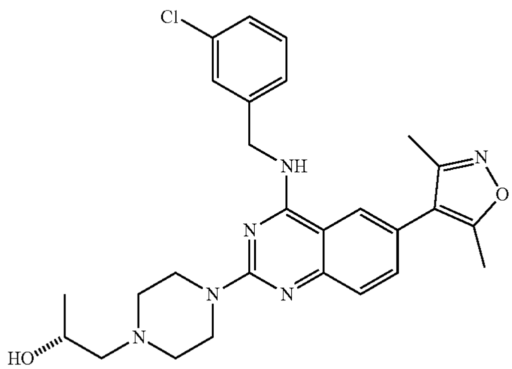 [SMILES: Cc1noc(C)c1-c1ccc2nc(N3CCN(C[C@@H](C)O)CC3)nc(NCc3cccc(Cl)c3)c2c1] | (R)-1-(4-(4-((3-chlorobenzyl)amino)-6-(3,5-dimethylisoxazol-4-yl)quinazolin-2-yl)piperazin-1-yl)propan-2-ol, 2TFA |
| 47 | 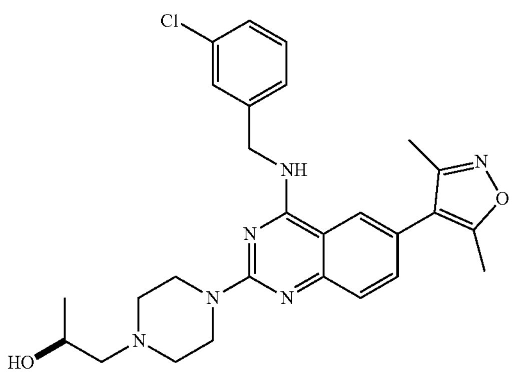 [SMILES: Cc1noc(C)c1-c1ccc2nc(N3CCN(C[C@H](C)O)CC3)nc(NCc3cccc(Cl)c3)c2c1] | (S)-1-(4-(4-((3-chlorobenzyl)amino)-6-(3,5-dimethylisoxazol-4-yl)quinazolin-2-yl)piperazin-1-yl)propan-2-ol, 2TFA |
| 48 | 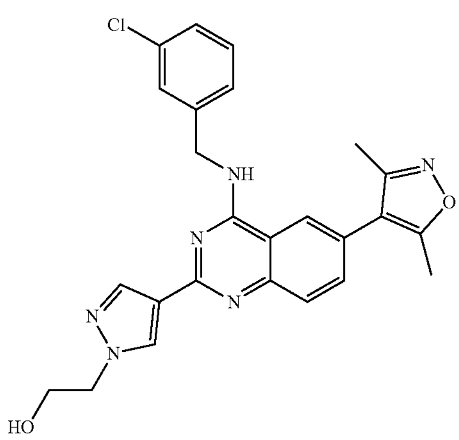 | 2-(4-(4-((3-chlorobenzyl)amino)-6-(3,5-dimethylisoxazol-4-yl)quinazolin-2-yl)-1H-pyrazol-1-yl)ethanol, 2TFA |

TABLE 1-continued

| Example # | Structure | Compound Name |
|---|---|---|
| 49 | 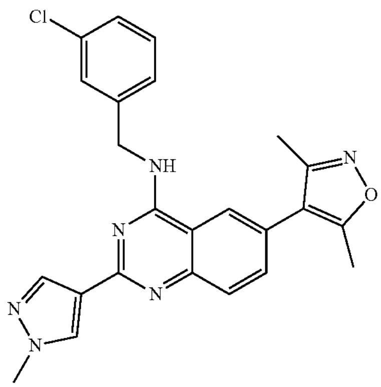 [SMILES: Cc1noc(C)c1-c1ccc2nc(-c3cnn(C)c3)nc(NCc3cccc(Cl)c3)c2c1] | N-(3-chlorobenzyl)-6-(3,5-dimethylisoxazol-4-yl)-2-(1-methyl-1H-pyrazol-4-yl)quinazolin-4-amine, 2TFA |
| 50 | 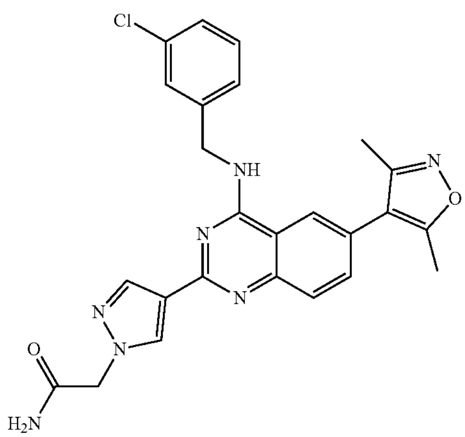 | 2-(4-(4-((3-chlorobenzyl)amino)-6-(3,5-dimethylisoxazol-4-yl)quinazolin-2-yl)-1H-pyrazol-1-yl)acetamide, 2TFA |
| 51 | 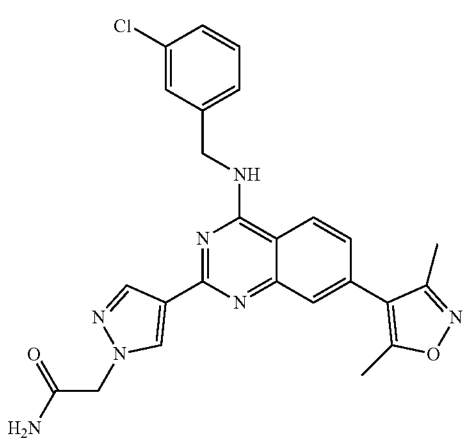 [SMILES: Cc1noc(C)c1-c1ccc2c(NCc3cccc(Cl)c3)nc(-c3cnn(CC(N)=O)c3)nc2c1] | 2-(4-(4-((3-chlorobenzyl)amino)-7-(3,5-dimethylisoxazol-4-yl)quinazolin-2-yl)-1H-pyrazol-1-yl)acetamide, 2TFA |

TABLE 1-continued

| Example # | Structure | Compound Name |
|---|---|---|
| 52 | 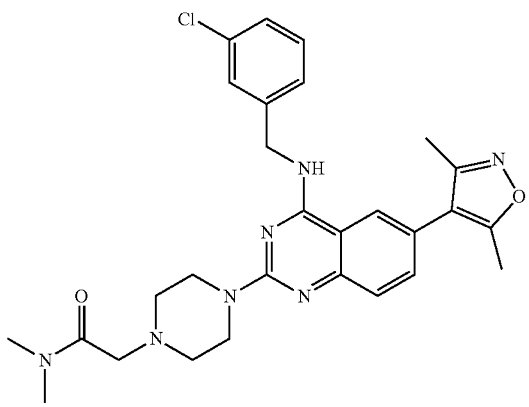 [SMILES: Cc1noc(C)c1-c1ccc2nc(N3CCN(CC(=O)N(C)C)CC3)nc(NCc3cccc(Cl)c3)c2c1] | 2-(4-(4-((3-chlorobenzyl)amino)-6-(3,5-dimethylisoxazol-4-yl)quinazolin-2-yl)piperazin-1-yl)-N,N-dimethylacetamide, 2TFA |
| 53 | 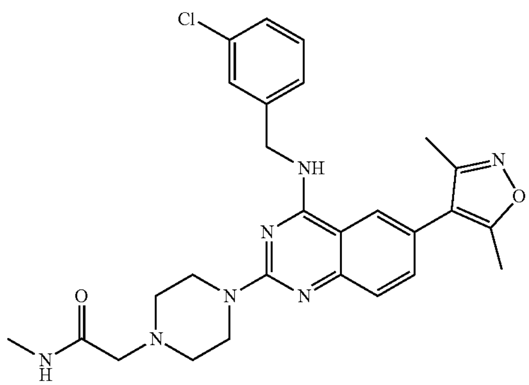 [SMILES: CNC(=O)CN1CCN(c2nc(NCc3cccc(Cl)c3)c3cc(-c4c(C)noc4C)ccc3n2)CC1] | 2-(4-(4-((3-chlorobenzyl)amino)-6-(3,5-dimethylisoxazol-4-yl)quinazolin-2-yl)piperazin-1-yl)-N-methylacetamide, 2TFA |
| 54 | 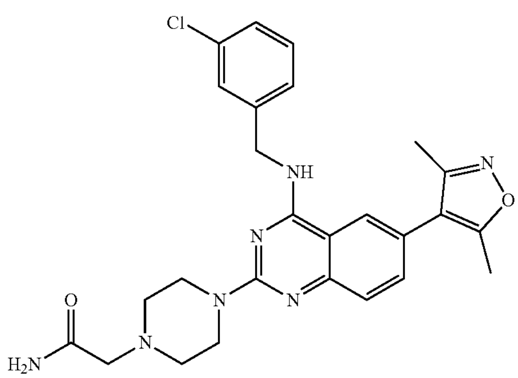 [SMILES: Cc1noc(C)c1-c1ccc2nc(N3CCN(CC(N)=O)CC3)nc(NCc3cccc(Cl)c3)c2c1] | 2-(4-(4-((3-chlorobenzyl)amino)-6-(3,5-dimethylisoxazol-4-yl)quinazolin-2-yl)piperazin-1-yl)acetamide, 2TFA |
| 55 | 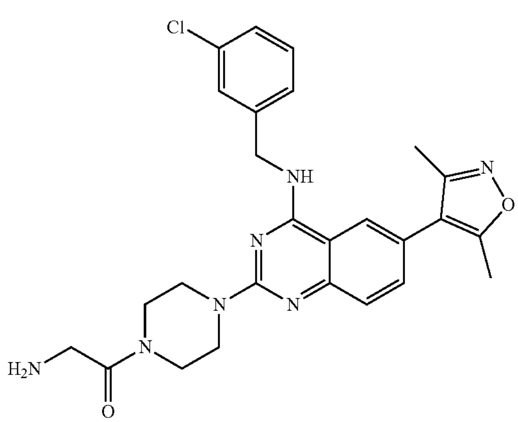 [SMILES: Cc1noc(C)c1-c1ccc2nc(N3CCN(C(=O)CN)CC3)nc(NCc3cccc(Cl)c3)c2c1] | 2-amino-1-(4-(4-((3-chlorobenzyl)amino)-6-(3,5-dimethylisoxazol-4-yl)quinazolin-2-yl)piperazin-1-yl)ethanone, 2TFA |

TABLE 1-continued

| Example # | Structure | Compound Name |
|---|---|---|
| 56 | 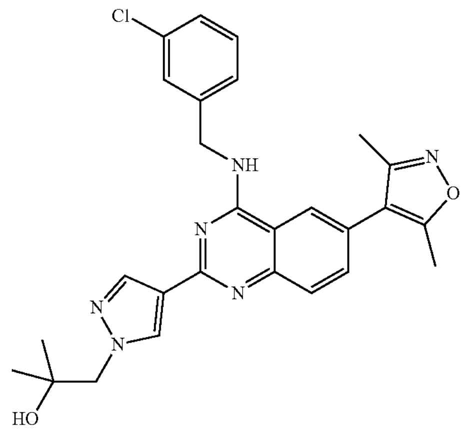 [SMILES: Cc1noc(C)c1-c1ccc2nc(-c3cnn(CC(C)(C)O)c3)nc(NCc3cccc(Cl)c3)c2c1] | 1-(4-(4-((3-chlorobenzyl)amino)-6-(3,5-dimethylisoxazol-4-yl)quinazolin-2-yl)-1H-pyrazol-1-yl)-2-methylpropan-2-ol, 2TFA |
| 57 | 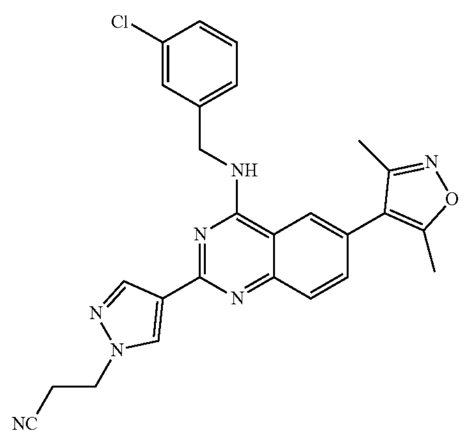 [SMILES: Cc1noc(C)c1-c1ccc2nc(-c3cnn(CCC#N)c3)nc(NCc3cccc(Cl)c3)c2c1] | 3-(4-(4-((3-chlorobenzyl)amino)-6-(3,5-dimethylisoxazol-4-yl)quinazolin-2-yl)-1H-pyrazol-1-yl)propanenitrile, 2TFA |
| 58 | 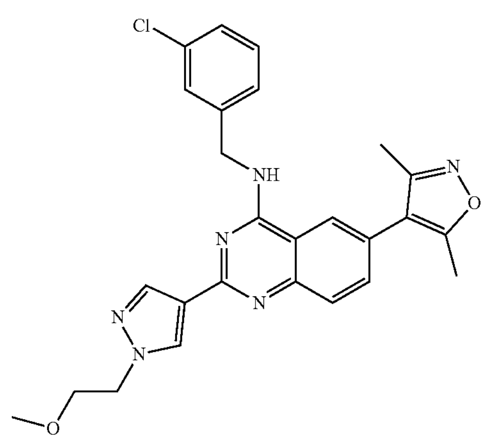 [SMILES: COCCn1cc(-c2nc(NCc3cccc(Cl)c3)c3cc(-c4c(C)noc4C)ccc3n2)cn1] | N-(3-chlorobenzyl)-6-(3,5-dimethylisoxazol-4-yl)-2-(1-(2-methoxyethyl)-1H-pyrazol-4-yl)quinazolin-4-amine, 2TFA |

TABLE 1-continued

| Example # | Structure | Compound Name |
|---|---|---|
| 59 | 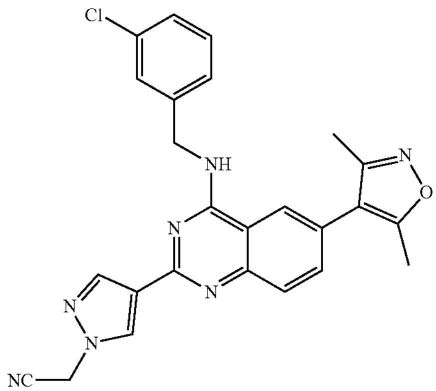 [SMILES: Cc1noc(C)c1-c1ccc2nc(-c3cnn(CC#N)c3)nc(NCc3cccc(Cl)c3)c2c1] | 2-(4-(4-((3-chlorobenzyl)amino)-6-(3,5-dimethylisoxazol-4-yl)quinazolin-2-yl)-1H-pyrazol-1-yl)acetonitrile, 2TFA |
| 60 | 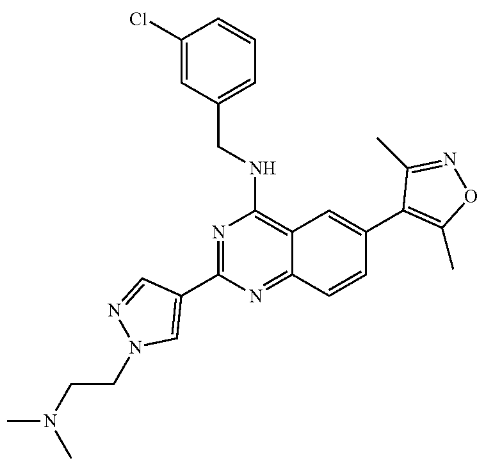 [SMILES: Cc1noc(C)c1-c1ccc2nc(-c3cnn(CCN(C)C)c3)nc(NCc3cccc(Cl)c3)c2c1] | N-(3-chlorobenzyl)-2-(1-(2-(dimethylamino)ethyl)-1H-pyrazol-4-yl)-6-(3,5-dimethylisoxazol-4-yl)quinazolin-4-amine, 2TFA |
| 61 | 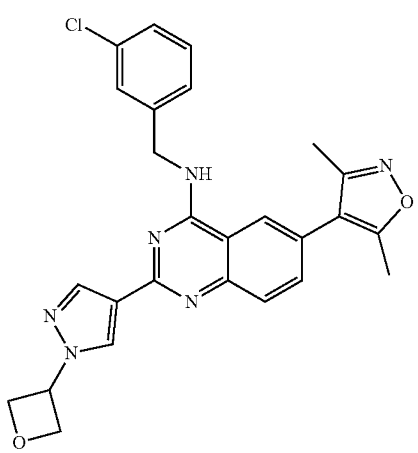 [SMILES: Cc1noc(C)c1-c1ccc2nc(-c3cnn(C4COC4)c3)nc(NCc3cccc(Cl)c3)c2c1] | N-(3-chlorobenzyl)-6-(3,5-dimethylisoxazol-4-yl)-2-(1-(oxetan-3-yl)-1H-pyrazol-4-yl)quinazolin-4-amine, 2TFA |

TABLE 1-continued

| Example # | Structure | Compound Name |
|---|---|---|
| 62 | 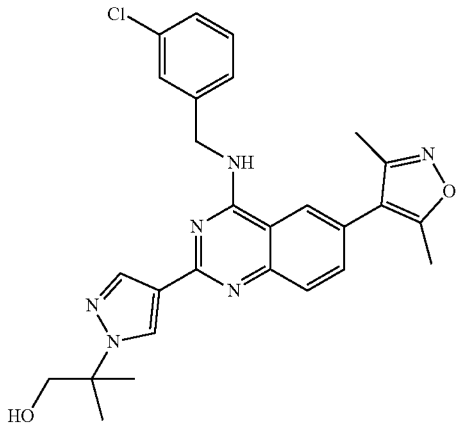 [SMILES: Cc1noc(C)c1-c1ccc2nc(-c3cnn(C(C)(C)CO)c3)nc(NCc3cccc(Cl)c3)c2c1] | 2-(4-(4-((3-chlorobenzyl)amino)-6-(3,5-dimethylisoxazol-4-yl)quinazolin-2-yl)-1H-pyrazol-1-yl)-2-methylpropan-1-ol |
| 63 | 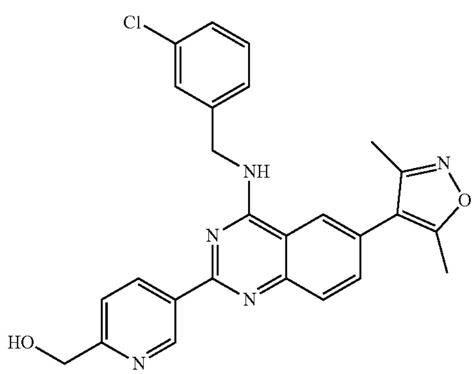 [SMILES: Cc1noc(C)c1-c1ccc2nc(-c3ccc(CO)nc3)nc(NCc3cccc(Cl)c3)c2c1] | (5-(4-((3-chlorobenzyl)amino)-6-(3,5-dimethylisoxazol-4-yl)quinazolin-2-yl)pyridin-2-yl)methanol, 2TFA |
| 64 | 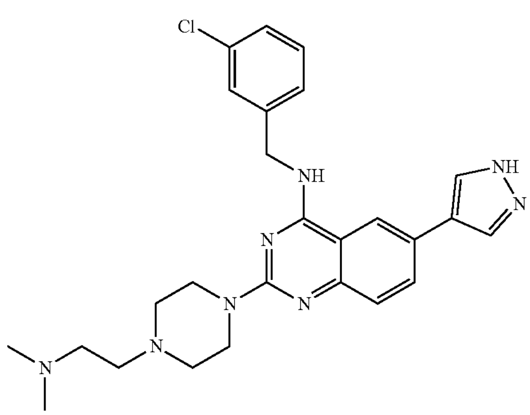 [SMILES: CN(C)CCN1CCN(c2nc(NCc3cccc(Cl)c3)c3cc(-c4cn[nH]c4)ccc3n2)CC1] | N-(3-chlorobenzyl)-2-(4-(2-(dimethylamino)ethyl)piperazin-1-yl)-6-(1H-pyrazol-4-yl)quinazolin-4-amine, 2TFA |

TABLE 1-continued

| Example # | Structure | Compound Name |
|---|---|---|
| 65 | 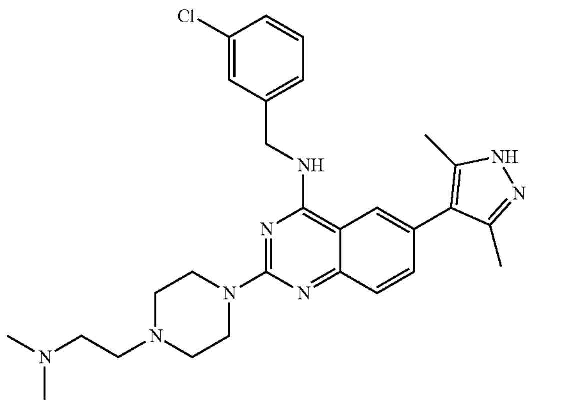 [SMILES: Cc1n[nH]c(C)c1-c1ccc2nc(N3CCN(CCN(C)C)CC3)nc(NCc3cccc(Cl)c3)c2c1] | N-(3-chlorobenzyl)-6-(3,5-dimethyl-1H-pyrazol-4-yl)-2-(4-(2-(dimethylamino)ethyl)piperazin-1-yl)quinazolin-4-amine, 2TFA |
| 66 | 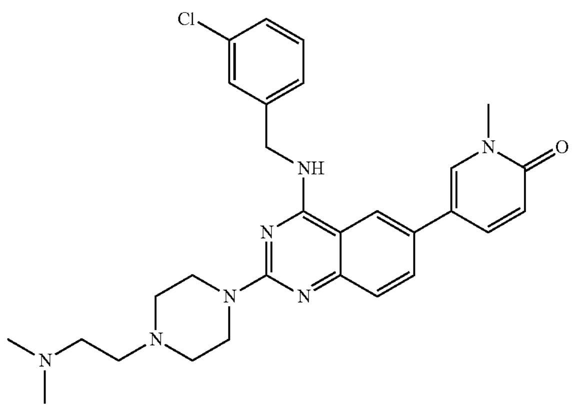 [SMILES: CN(C)CCN1CCN(c2nc(NCc3cccc(Cl)c3)c3cc(-c4ccc(=O)n(C)c4)ccc3n2)CC1] | 5-(4-((3-chlorobenzyl)amino)-2-(4-(2-(dimethylamino)ethyl)piperazin-1-yl)quinazolin-6-yl)-1-methylpyridin-2(1H)-one, 2TFA |
| 67 | 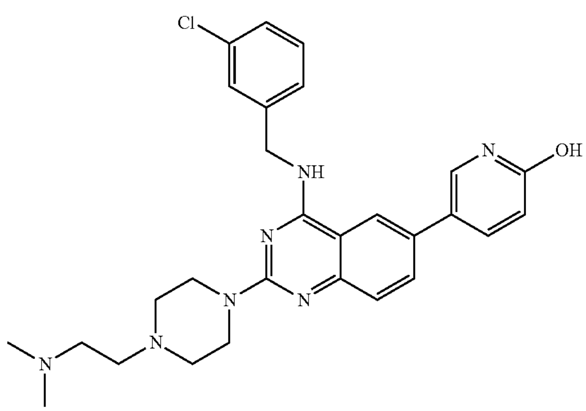 [SMILES: CN(C)CCN1CCN(c2nc(NCc3cccc(Cl)c3)c3cc(-c4ccc(O)nc4)ccc3n2)CC1] | 5-(4-((3-chlorobenzyl)amino)-2-(4-(2-(dimethylamino)ethyl)piperazin-1-yl)quinazolin-6-yl)pyridin-2-ol, 2TFA |
| 68 | 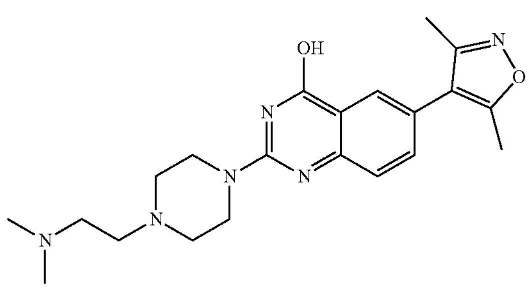 [SMILES: Cc1noc(C)c1-c1ccc2nc(N3CCN(CCN(C)C)CC3)nc(O)c2c1] | 2-(4-(2-(dimethylamino)ethyl)piperazin-1-yl)-6-(3,5-dimethylisoxazol-4-yl)quinazolin-4-ol, 2HCl |

TABLE 1-continued

| Example # | Structure | Compound Name |
|---|---|---|
| 69 | 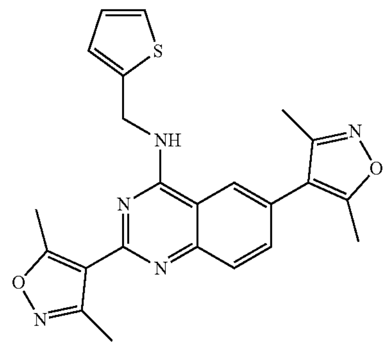 [SMILES: Cc1noc(C)c1-c1ccc2nc(-c3c(C)noc3C)nc(NCc3cccs3)c2c1] | 2,6-bis(3,5-dimethylisoxazol-4-yl)-N-(thiophen-2-ylmethyl)quinazolin-4-amine, 2TFA |
| 70 | 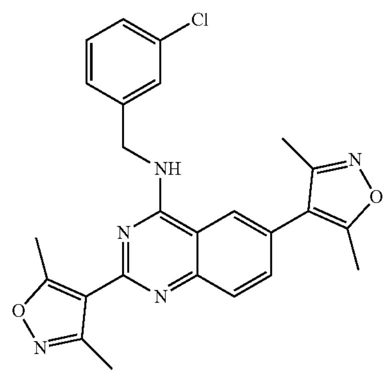 [SMILES: Cc1noc(C)c1-c1ccc2nc(-c3c(C)noc3C)nc(NCc3cccc(Cl)c3)c2c1] | N-(3-chlorobenzyl)-2,6-bis(3,5-dimethylisoxazol-4-yl)quinazolin-4-amine, 2TFA |
| 71 | 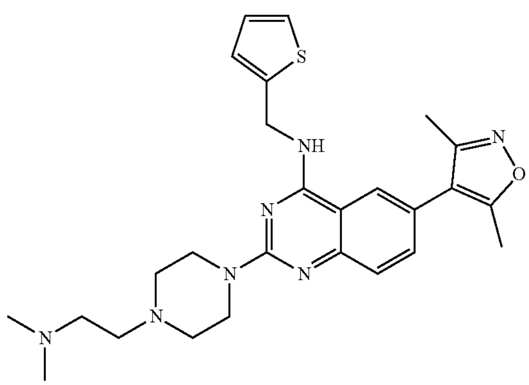 | 2-(4-(2-(dimethylamino)ethyl)piperazin-1-yl)-6-(3,5-dimethylisoxazol-4-yl)-N-(thiophen-2-ylmethyl)quinazolin-4-amine, 2TFA |
| 72 | 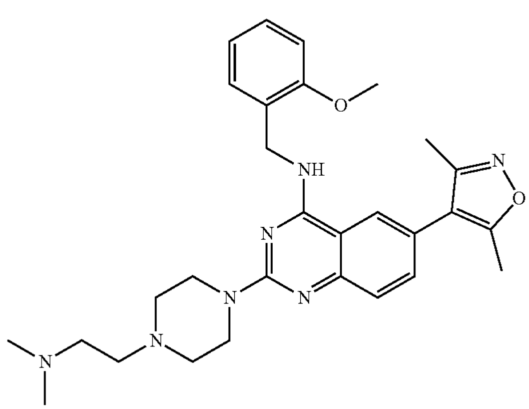 [SMILES: COc1ccccc1CNc1nc(N2CCN(CCN(C)C)CC2)nc2ccc(-c3c(C)noc3C)cc12] | 2-(4-(2-(dimethylamino)ethyl)piperazin-1-yl)-6-(3,5-dimethylisoxazol-4-yl)-N-(2-methoxybenzyl)quinazolin-4-amine, 2TFA |

TABLE 1-continued

| Example # | Structure | Compound Name |
|---|---|---|
| 73 | 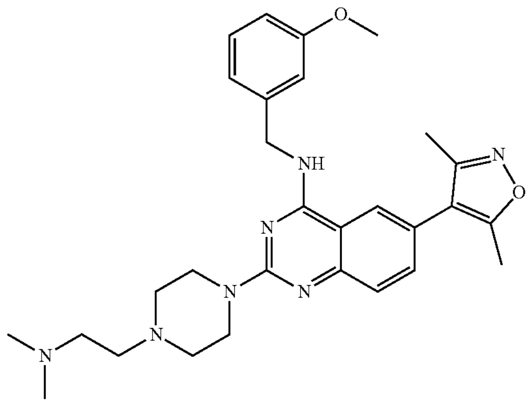 [SMILES: COc1cccc(CNc2nc(N3CCN(CCN(C)C)CC3)nc3ccc(-c4c(C)noc4C)cc23)c1] | 2-(4-(2-(dimethylamino)ethyl)piperazin-1-yl)-6-(3,5-dimethylisoxazol-4-yl)-N-(3-methoxybenzyl)quinazolin-4-amine, 2TFA |
| 74 | 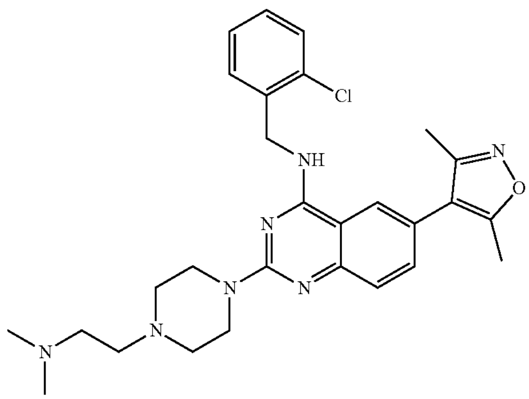 [SMILES: Cc1noc(C)c1-c1ccc2nc(N3CCN(CCN(C)C)CC3)nc(NCc3ccccc3F)c2c1] | N-(2-chlorobenzyl)-2-(4-(2-(dimethylamino)ethyl)piperazin-1-yl)-6-(3,5-dimethylisoxazol-4-yl)quinazolin-4-amine, 2TFA |
| 75 | 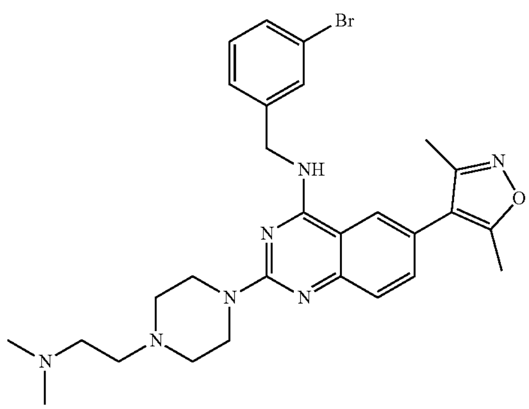 | N-(3-bromobenzyl)-2-(4-(2-(dimethylamino)ethyl)piperazin-1-yl)-6-(3,5-dimethylisoxazol-4-yl)quinazolin-4-amine, 2TFA |
| 76 | 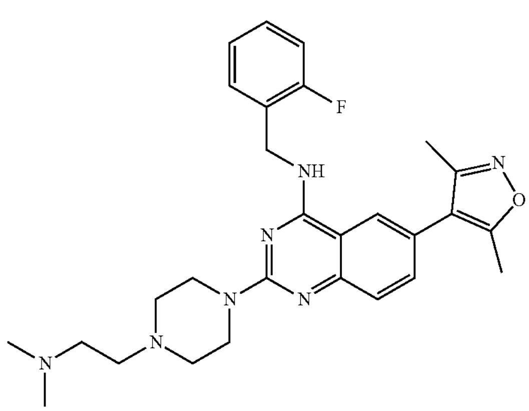 | 2-(4-(2-(dimethylamino)ethyl)piperazin-1-yl)-6-(3,5-dimethylisoxazol-4-yl)-N-(2-fluorobenzyl)quinazolin-4-amine, 2TFA |

TABLE 1-continued

| Example # | Structure | Compound Name |
|---|---|---|
| 77 | 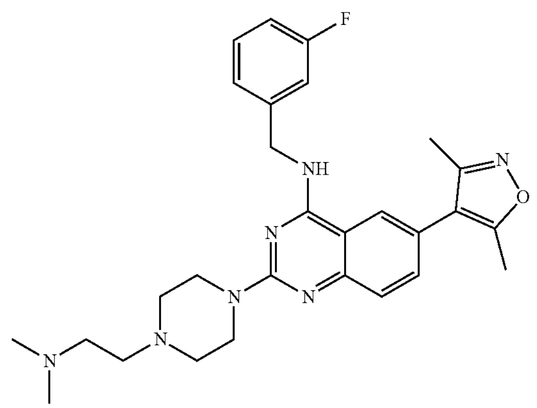 [SMILES: Cc1noc(C)c1-c1ccc2nc(N3CCN(CCN(C)C)CC3)nc(NCc3cccc(F)c3)c2c1] | 2-(4-(2-(dimethylamino)ethyl)piperazin-1-yl)-6-(3,5-dimethylisoxazol-4-yl)-N-(3-fluorobenzyl)quinazolin-4-amine, 2TFA |
| 78 | 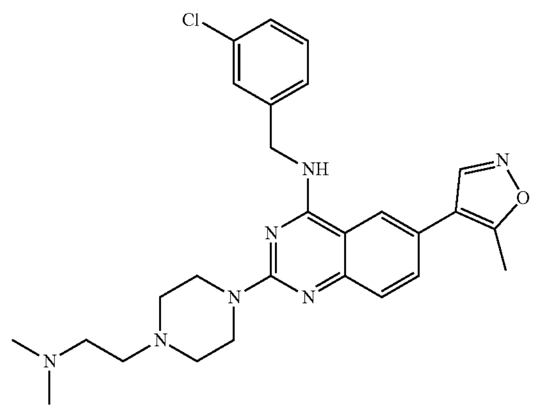 [SMILES: Cc1oncc1-c1ccc2nc(N3CCN(CCN(C)C)CC3)nc(NCc3cccc(Cl)c3)c2c1] | N-(3-chlorobenzyl)-2-(4-(2-(dimethylamino)ethyl)piperazin-1-yl)-6-(5-methylisoxazol-4-yl)quinazolin-4-amine, 2TFA |
| 79 | 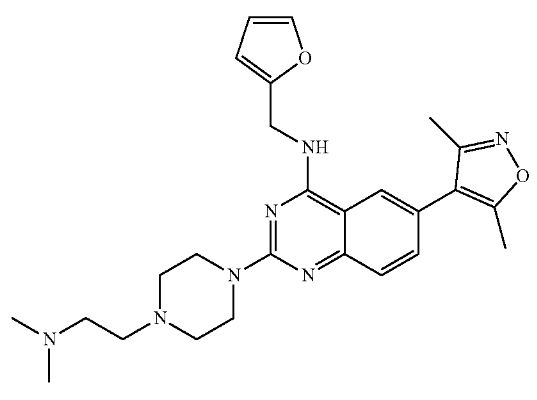 [SMILES: Cc1noc(C)c1-c1ccc2nc(N3CCN(CCN(C)C)CC3)nc(NCc3ccco3)c2c1] | 2-(4-(2-(dimethylamino)ethyl)piperazin-1-yl)-6-(3,5-dimethylisoxazol-4-yl)-N-(furan-2-ylmethyl)quinazolin-4-amine, 2TFA |
| 80 | 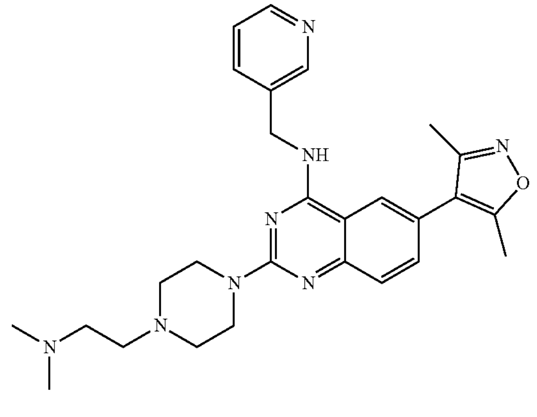 [SMILES: Cc1noc(C)c1-c1ccc2nc(N3CCN(CCN(C)C)CC3)nc(NCc3cccnc3)c2c1] | 2-(4-(2-(dimethylamino)ethyl)piperazin-1-yl)-6-(3,5-dimethylisoxazol-4-yl)-N-(pyridin-3-ylmethyl)quinazolin-4-amine, 2TFA |

TABLE 1-continued

| Example # | Structure | Compound Name |
|---|---|---|
| 81 | 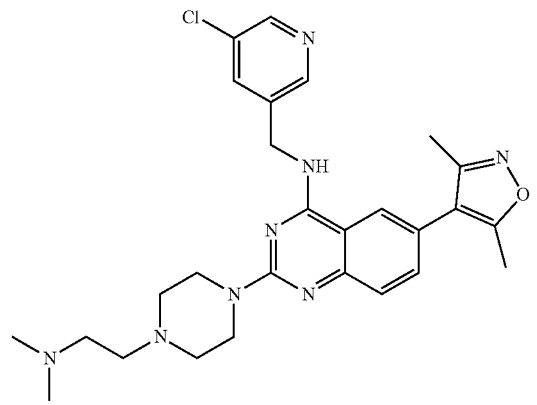 | N-((5-chloropyridin-3-yl)methyl)-2-(4-(2-(dimethylamino)ethyl)piperazin-1-yl)-6-(3,5-dimethylisoxazol-4-yl)quinazolin-4-amine, 2TFA |
| 82 | 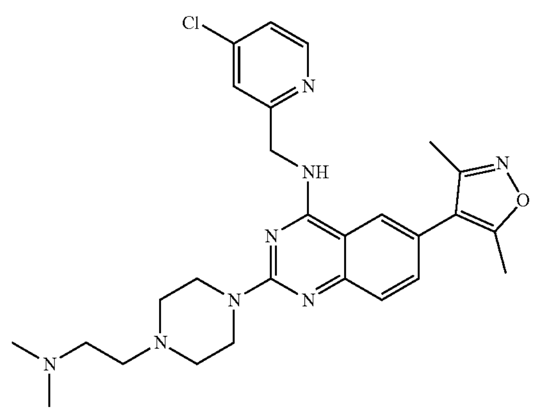 [SMILES: Cc1noc(C)c1-c1ccc2nc(N3CCN(CCN(C)C)CC3)nc(NCc3cc(Cl)ccn3)c2c1] | N-((4-chloropyridin-2-yl)methyl)-2-(4-(2-(dimethylamino)ethyl)piperazin-1-yl)-6-(3,5-dimethylisoxazol-4-yl)quinazolin-4-amine, 2TFA |
| 83 | 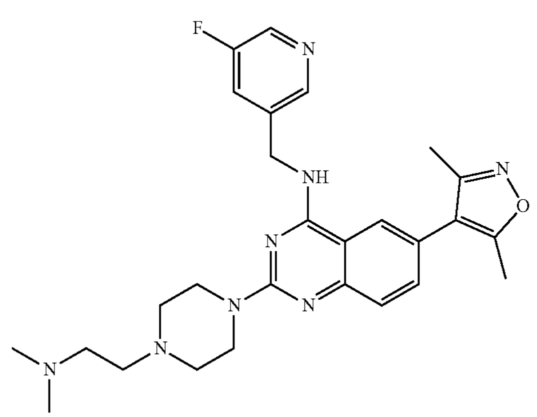 [SMILES: Cc1noc(C)c1-c1ccc2nc(N3CCN(CCN(C)C)CC3)nc(NCc3cncc(F)c3)c2c1] | 2-(4-(2-(dimethylamino)ethyl)piperazin-1-yl)-6-(3,5-dimethylisoxazol-4-yl)-N-((5-fluoropyridin-3-yl)methyl)quinazolin-4-amine, 2TFA |

TABLE 1-continued

| Example # | Structure | Compound Name |
|---|---|---|
| 84 | 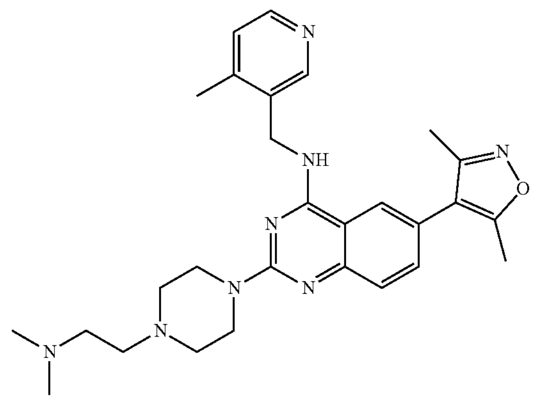 [SMILES: Cc1ccncc1CNc1nc(N2CCN(CCN(C)C)CC2)nc2ccc(-c3c(C)noc3C)cc12] | 2-(4-(2-(dimethylamino)ethyl)piperazin-1-yl)-6-(3,5-dimethylisoxazol-4-yl)-N-((4-methylpyridin-3-yl)methyl)quinazolin-4-amine, 2TFA |
| 85 | 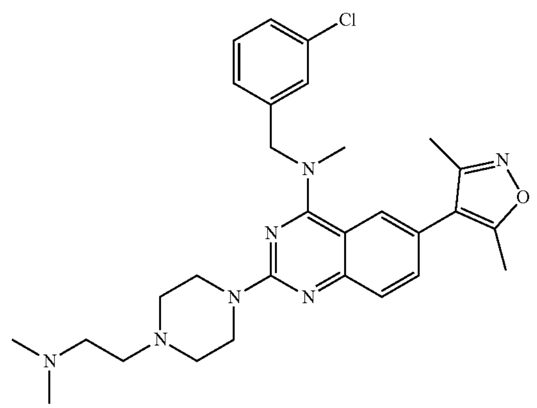 [SMILES: Cc1noc(C)c1-c1ccc2nc(N3CCN(CCN(C)C)CC3)nc(N(C)Cc3cccc(Cl)c3)c2c1] | N-(3-chlorobenzyl)-2-(4-(2-(dimethylamino)ethyl)piperazin-1-yl)-6-(3,5-dimethylisoxazol-4-yl)-N-methylquinazolin-4-amine, 2TFA |
| 86 | 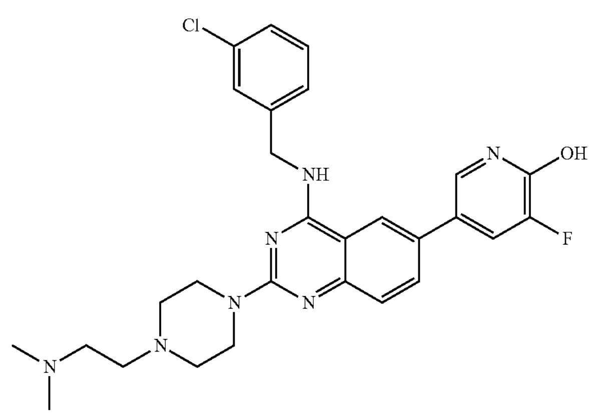 [SMILES: CN(C)CCN1CCN(c2nc(NCc3cccc(Cl)c3)c3cc(-c4cnc(O)c(F)c4)ccc3n2)CC1] | 5-(4-((3-chlorobenzyl)amino)-2-(4-(2-(dimethylamino)ethyl)piperazin-1-yl)quinazolin-6-yl)-3-fluoropyridin-2-ol, 2TFA |

TABLE 1-continued

| Example # | Structure | Compound Name |
|---|---|---|
| 87 | 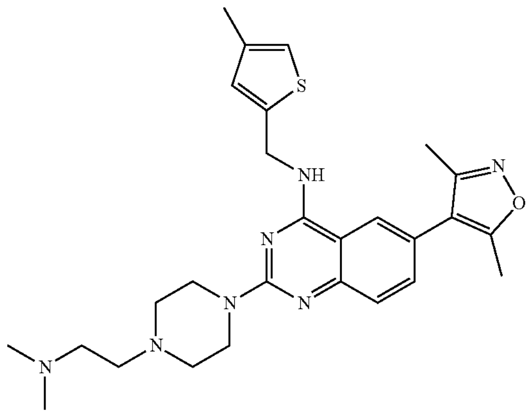 [SMILES: Cc1csc(CNc2nc(N3CCN(CCN(C)C)CC3)nc3ccc(-c4c(C)noc4C)cc23)c1] | 2-(4-(2-(dimethylamino)ethyl)piperazin-1-yl)-6-(3,5-dimethylisoxazol-4-yl)-N-((4-methylthiophen-2-yl)methyl)quinazolin-4-amine, 2TFA |
| 88 | 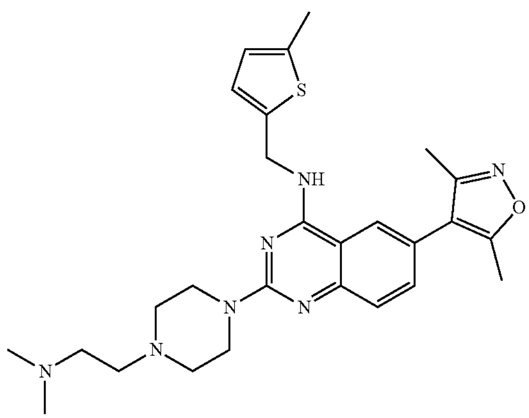 [SMILES: Cc1ccc(CNc2nc(N3CCN(CCN(C)C)CC3)nc3ccc(-c4c(C)noc4C)cc23)s1] | 2-(4-(2-(dimethylamino)ethyl)piperazin-1-yl)-6-(3,5-dimethylisoxazol-4-yl)-N-((5-methylthiophen-2-yl)methyl)quinazolin-4-amine, 2TFA |
| 89 | 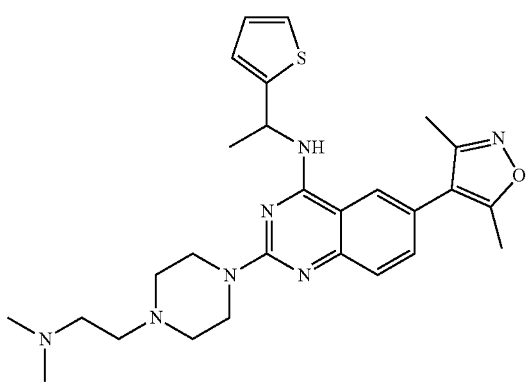 [SMILES: Cc1noc(C)c1-c1ccc2nc(N3CCN(CCN(C)C)CC3)nc(NC(C)c3cccs3)c2c1] | 2-(4-(2-(dimethylamino)ethyl)piperazin-1-yl)-6-(3,5-dimethylisoxazol-4-yl)-N-(1-(thiophen-2-yl)ethyl)quinazolin-4-amine, 2TFA |

TABLE 1-continued

| Example # | Structure | Compound Name |
|---|---|---|
| 90 | 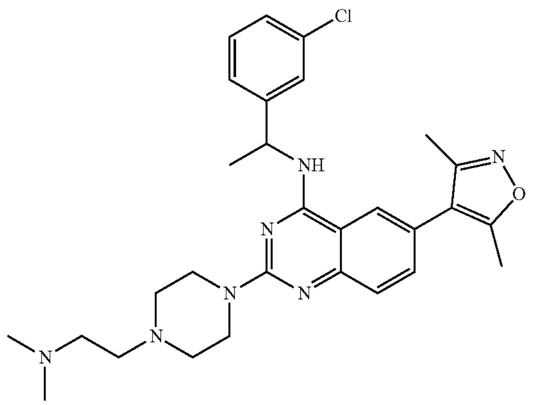 [SMILES: Cc1noc(C)c1-c1ccc2nc(N3CCN(CCN(C)C)CC3)nc(NC(C)c3cccc(Cl)c3)c2c1] | N-(1-(3-chlorophenyl)ethyl)-2-(4-(2-(dimethylamino)ethyl)piperazin-1-yl)-6-(3,5-dimethylisoxazol-4-yl)quinazolin-4-amine, 2TFA |
| 91 | 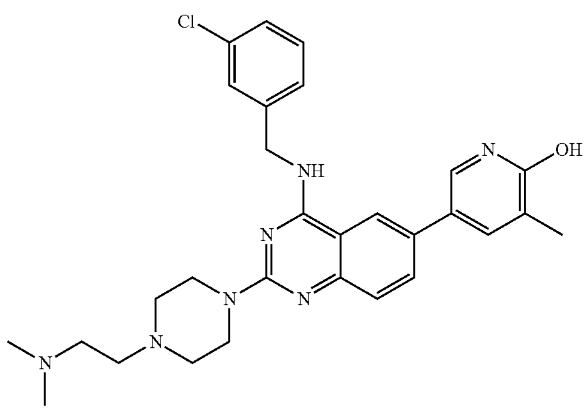 | 5-(4-((3-chlorobenzyl)amino)-2-(4-(2-(dimethylamino)ethyl)piperazin-1-yl)quinazolin-6-yl)-3-methylpyridin-2-ol, 2TFA |
| 92 | 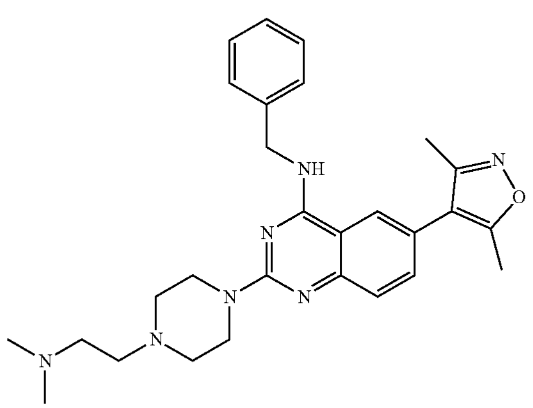 [SMILES: Cc1noc(C)c1-c1ccc2nc(N3CCN(CCN(C)C)CC3)nc(NCc3ccccc3)c2c1] | N-benzyl-2-(4-(2-(dimethylamino)ethyl)piperazin-1-yl)-6-(3,5-dimethylisoxazol-4-yl)quinazolin-4-amine, 2TFA |

TABLE 1-continued

| Example # | Structure | Compound Name |
|---|---|---|
| 93 | 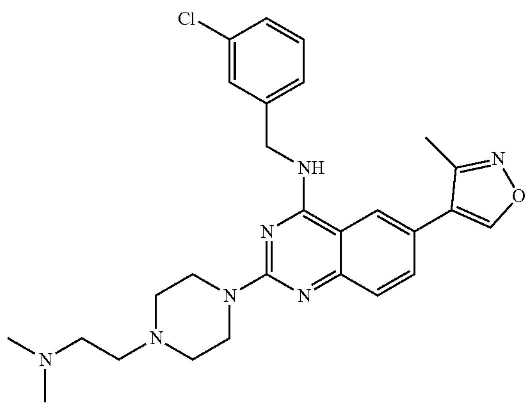 [SMILES: Cc1nocc1-c1ccc2nc(N3CCN(CCN(C)C)CC3)nc(NCc3cccc(Cl)c3)c2c1] | N-(3-chlorobenzyl)-2-(4-(2-(dimethylamino)ethyl)piperazin-1-yl)-6-(3-methylisoxazol-4-yl)quinazolin-4-amine, 2TFA |
| 94 | 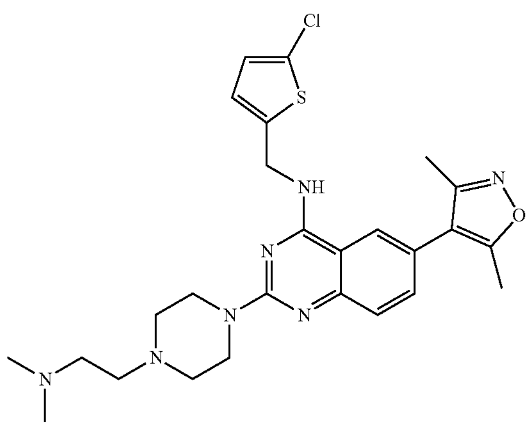 [SMILES: Cc1noc(C)c1-c1ccc2nc(N3CCN(CCN(C)C)CC3)nc(NCc3ccc(Cl)s3)c2c1] | N-((5-chlorothiophen-2-yl)methyl)-2-(4-(2-(dimethylamino)ethyl)piperazin-1-yl)-6-(3,5-dimethylisoxazol-4-yl)quinazolin-4-amine, 2TFA |
| 95 | 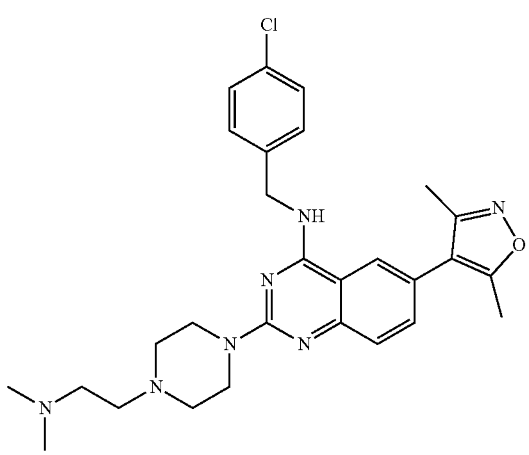 [SMILES: Cc1noc(C)c1-c1ccc2nc(N3CCN(CCN(C)C)CC3)nc(NCc3ccc(Cl)cc3)c2c1] | N-(4-chlorobenzyl)-2-(4-(2-(dimethylamino)ethyl)piperazin-1-yl)-6-(3,5-dimethylisoxazol-4-yl)quinazolin-4-amine, 2TFA |

TABLE 1-continued

| Example # | Structure | Compound Name |
|---|---|---|
| 96 | 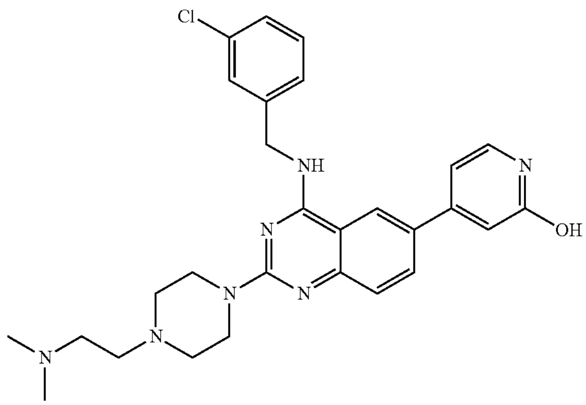 [SMILES: CN(C)CCN1CCN(c2nc(NCc3cccc(Cl)c3)c3cc(-c4ccnc(O)c4)ccc3n2)CC1] | 4-(4-((3-chlorobenzyl)amino)-2-(4-(2-(dimethylamino)ethyl)piperazin-1-yl)quinazolin-6-yl)pyridin-2-ol, 2TFA |
| 97 | 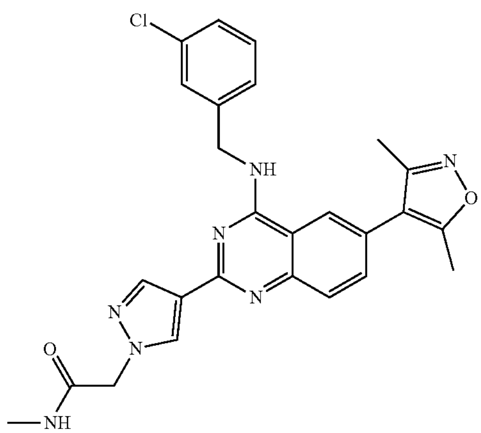 [SMILES: CNC(=O)Cn1cc(-c2nc(NCc3cccc(Cl)c3)c3cc(-c4c(C)noc4C)ccc3n2)cn1] | 2-(4-(4-((3-chlorobenzyl)amino)-6-(3,5-dimethylisoxazol-4-yl)quinazolin-2-yl)-1H-pyrazol-1-yl)-N-methylacetamide, 2TFA |
| 98 | 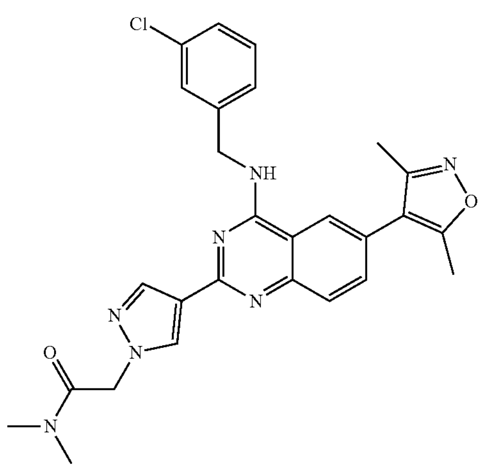 [SMILES: Cc1noc(C)c1-c1ccc2nc(-c3cnn(CC(=O)N(C)C)c3)nc(NCc3cccc(Cl)c3)c2c1] | 2-(4-(4-((3-chlorobenzyl)amino)-6-(3,5-dimethylisoxazol-4-yl)quinazolin-2-yl)-1H-pyrazol-1-yl)-N,N-dimethylacetamide, 2TFA |

TABLE 1-continued
| Example # | Structure | Compound Name |
|---|---|---|
| 99 | 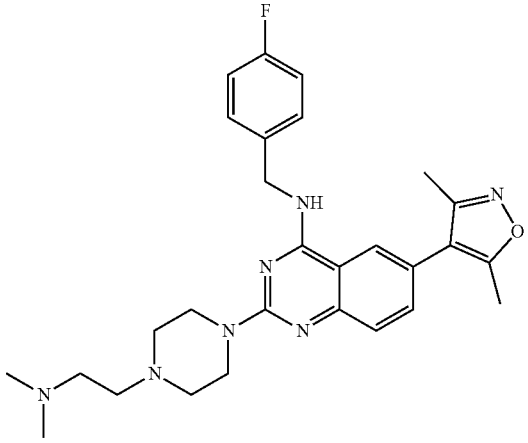 | 2-(4-(2-(dimethylamino)ethyl)piperazin-1-yl)-6-(3,5-dimethylisoxazol-4-yl)-N-(4-fluorobenzyl)quinazolin-4-amine, 2TFA |
| 100 | 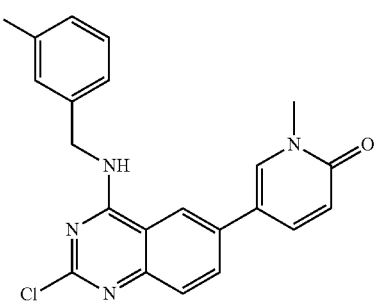 | 5-(2-chloro-4-((3-chlorobenzyl)amino)quinazolin-6-yl)-1-methylpyridin-2(1H)-one, 2TFA |
| 101 | 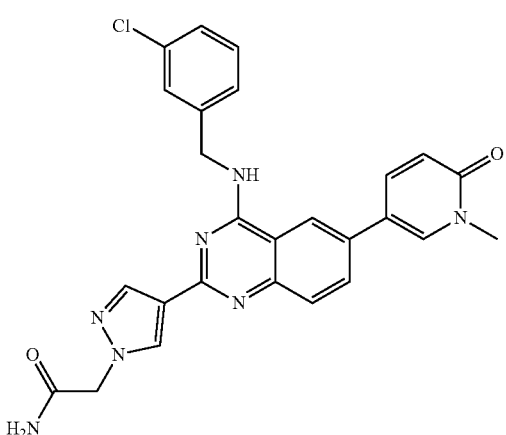 | 2-(4-(4-((3-chlorobenzyl)amino)-6-(1-methyl-6-oxo-1,6-dihydropyridin-3-yl)quinazolin-2-yl)-1H-pyrazol-1-yl)acetamide, 2TFA |

TABLE 1-continued

| Example # | Structure | Compound Name |
|---|---|---|
| 102 | 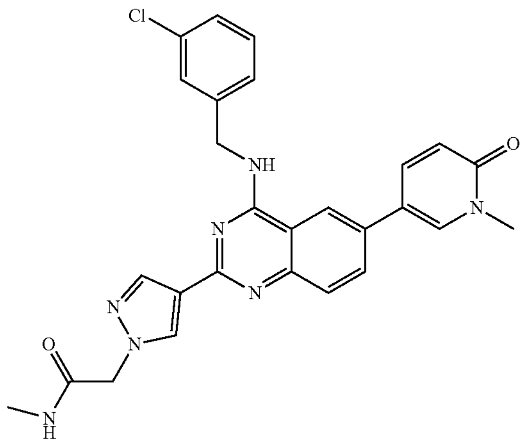 | 2-(4-(4-((3-chlorobenzyl)amino)-6-(1-methyl-6-oxo-1,6-dihydropyridin-3-yl)quinazolin-2-yl)-1H-pyrazol-1-yl)-N-methylacetamide, 2TFA |
| 103 | 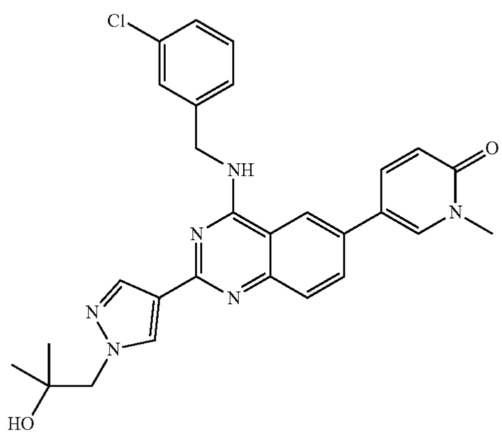 [SMILES: Cn1cc(-c2ccc3nc(-c4cnn(CC(C)(C)O)c4)nc(NCc4cccc(Cl)c4)c3c2)ccc1=O] | 5-(4-((3-chlorobenzyl)amino)-2-(1-(2-hydroxy-2-methylpropyl)-1H-pyrazol-4-yl)quinazolin-6-yl)-1-methylpyridin-2(1H)-one, 2TFA |
| 104 | 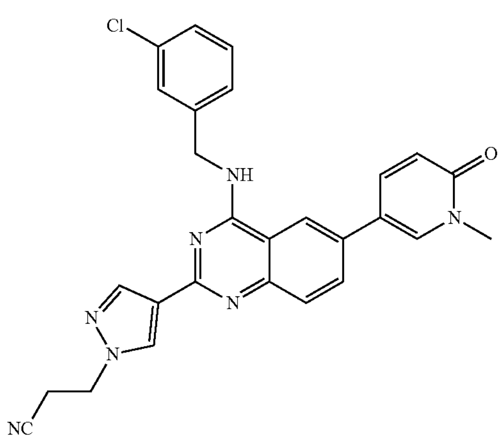 [SMILES: Cn1cc(-c2ccc3nc(-c4cnn(CCC#N)c4)nc(NCc4cccc(Cl)c4)c3c2)ccc1=O] | 3-(4-(4-((3-chlorobenzyl)amino)-6-(1-methyl-6-oxo-1,6-dihydropyridin-3-yl)quinazolin-2-yl)-1H-pyrazol-1-yl)propanenitrile, 2TFA |

TABLE 1-continued

| Example # | Structure | Compound Name |
|---|---|---|
| 105 | 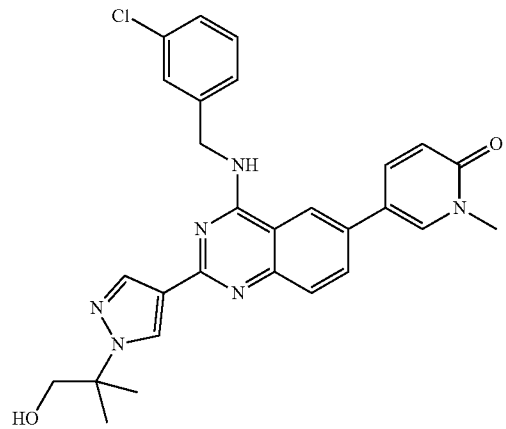 [SMILES: Cn1cc(-c2ccc3nc(-c4cnn(C(C)(C)CO)c4)nc(NCc4cccc(Cl)c4)c3c2)ccc1=O] | 5-(4-((3-chlorobenzyl)amino)-2-(1-(1-hydroxy-2-methylpropan-2-yl)-1H-pyrazol-4-yl)quinazolin-6-yl)-1-methylpyridin-2(1H)-one, 2TFA |
| 106 | 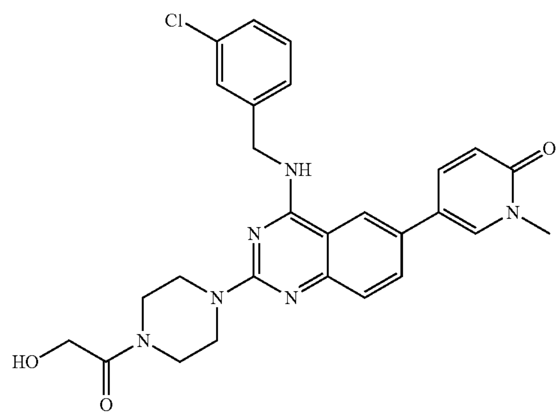 [SMILES: Cn1cc(-c2ccc3nc(N4CCN(C(=O)CO)CC4)nc(NCc4cccc(Cl)c4)c3c2)ccc1=O] | 5-(4-((3-chlorobenzyl)amino)-2-(4-(2-hydroxyacetyl)piperazin-1-yl)quinazolin-6-yl)-1-methylpyridin-2(1H)-one, 2TFA |
| 107 | 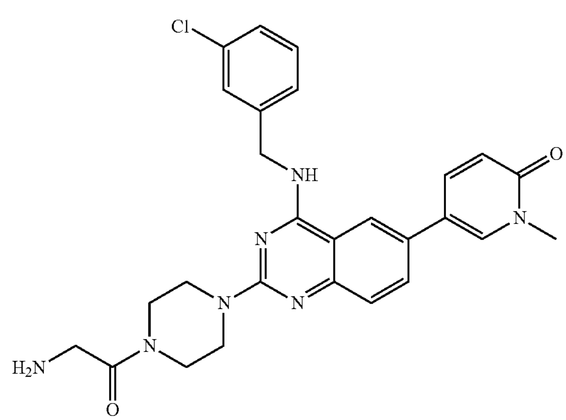 [SMILES: Cn1cc(-c2ccc3nc(N4CCN(C(=O)CN)CC4)nc(NCc4cccc(Cl)c4)c3c2)ccc1=O] | 5-(2-(4-(2-aminoacetyl)piperazin-1-yl)-4-((3-chlorobenzyl)amino)quinazolin-6-yl)-1-methylpyridin-2(1H)-one, 2TFA |

TABLE 1-continued

| Example # | Structure | Compound Name |
|---|---|---|
| 108 | 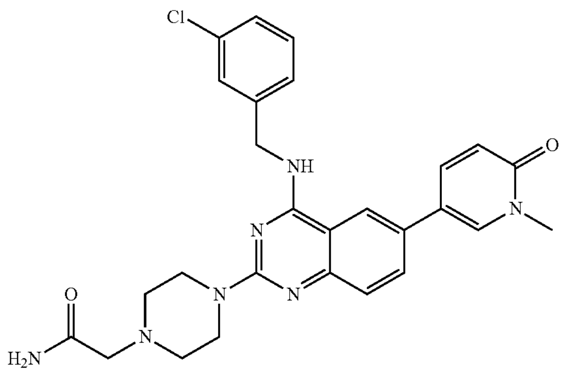 [SMILES: Cn1cc(-c2ccc3nc(N4CCN(CC(N)=O)CC4)nc(NCc4cccc(Cl)c4)c3c2)ccc1=O] | 2-(4-(4-((3-chlorobenzyl)amino)-6-(1-methyl-6-oxo-1,6-dihydropyridin-3-yl)quinazolin-2-yl)piperazin-1-yl)acetamide, 2TFA |
| 109 | 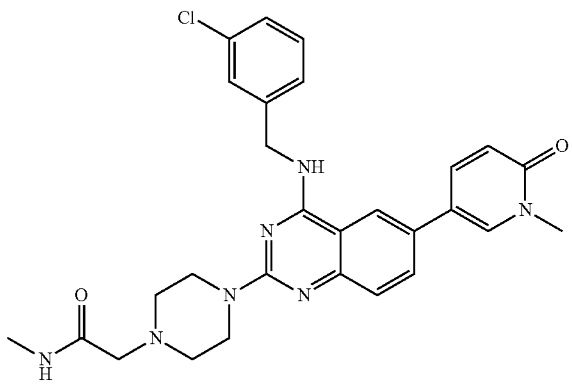 | 2-(4-(4-((3-chlorobenzyl)amino)-6-(1-methyl-6-oxo-1,6-dihydropyridin-3-yl)quinazolin-2-yl)piperazin-1-yl)-N-methylacetamide, 2TFA |
| 110 | 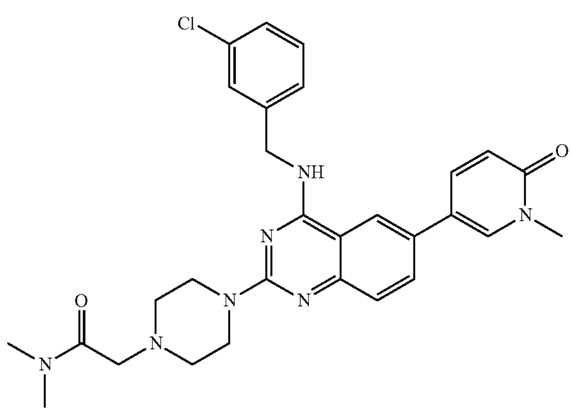 | 2-(4-(4-((3-chlorobenzyl)amino)-6-(1-methyl-6-oxo-1,6-dihydropyridin-3-yl)quinazolin-2-yl)piperazin-1-yl)-N,N-dimethylacetamide, 2TFA |
| 111 | 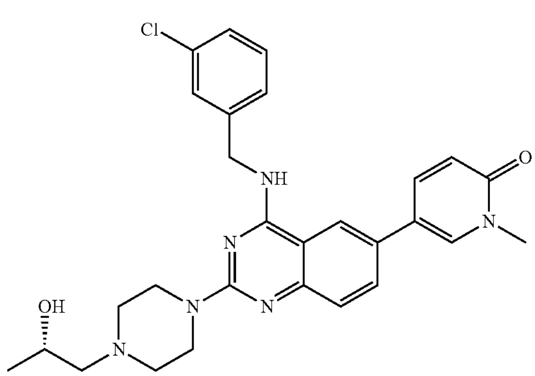 [SMILES: C[C@H](O)CN1CCN(c2nc(NCc3cccc(Cl)c3)c3cc(-c4ccc(=O)n(C)c4)ccc3n2)CC1] | (S)-5-(4-((3-chlorobenzyl)amino)-2-(4-(2-hydroxypropyl)piperazin-1-yl)quinazolin-6-yl)-1-methylpyridin-2(1H)-one, 2TFA |

TABLE 1-continued

| Example # | Structure | Compound Name |
|---|---|---|
| 112 | 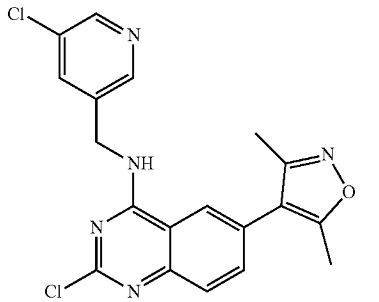 [SMILES: Cc1noc(C)c1-c1ccc2nc(Cl)nc(NCc3cncc(Cl)c3)c2c1] | 2-chloro-N-((5-chloropyridin-3-yl)methyl)-6-(3,5-dimethylisoxazol-4-yl)quinazolin-4-amine |
| 113 | 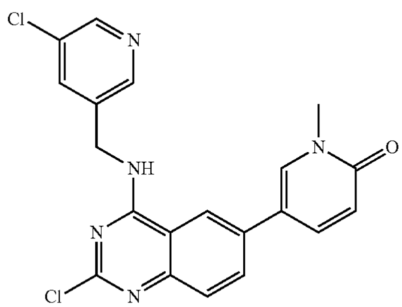 [SMILES: Cn1cc(-c2ccc3nc(Cl)nc(NCc4cncc(Cl)c4)c3c2)ccc1=O] | 5-(2-chloro-4-(((5-chloropyridin-3-yl)methyl)amino)quinazolin-6-yl)-1-methylpyridin-2(1H)-one |
| 114 | 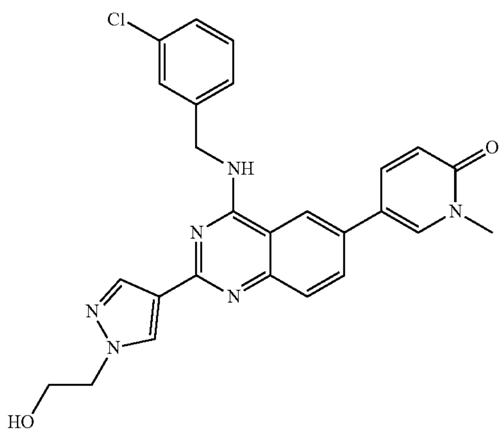 | 5-(4-((3-chlorobenzyl)amino)-2-(1-(2-hydroxyethyl)-1H-pyrazol-4-yl)quinazolin-6-yl)-1-methylpyridin-2(1H)-one |
| 115 | 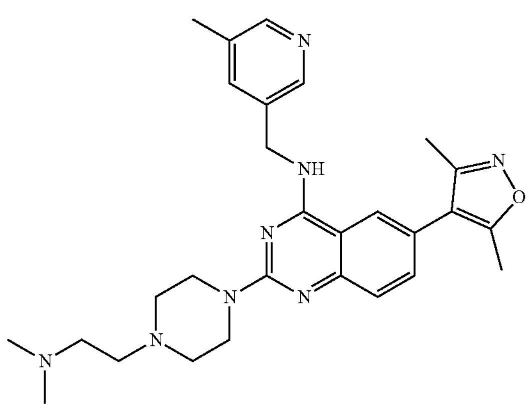 [SMILES: Cc1cncc(CNc2nc(N3CCN(CCN(C)C)CC3)nc3ccc(-c4c(C)noc4C)cc23)c1] | 2-(4-(2-(dimethylamino)ethyl)piperazin-1-yl)-6-(3,5-dimethylisoxazol-4-yl)-N-((5-methylpyridin-3-yl)methyl)quinazolin-4-amine, 2TFA |

TABLE 1-continued

| Example # | Structure | Compound Name |
|---|---|---|
| 116 | 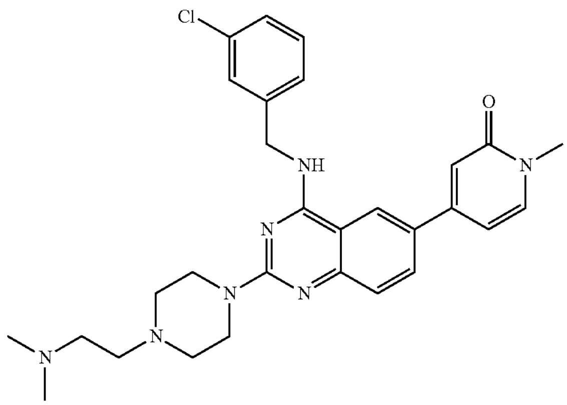 | 4-(4-((3-chlorobenzyl)amino)-2-(4-(2-(dimethylamino)ethyl)piperazin-1-yl)quinazolin-6-yl)-1-methylpyridin-2(1H)-one, 2TFA |
| 117 | 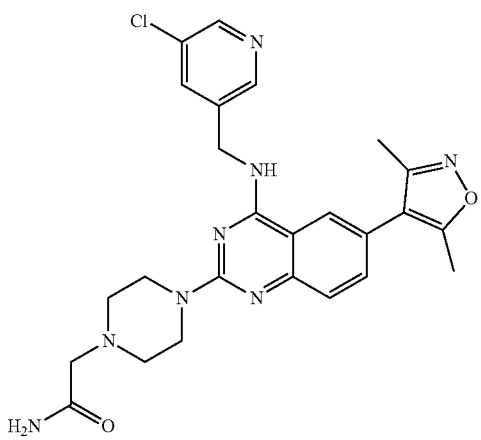 [SMILES: Cc1noc(C)c1-c1ccc2nc(N3CCN(CC(N)=O)CC3)nc(NCc3cncc(Cl)c3)c2c1] | 2-(4-(4-(((5-chloropyridin-3-yl)methyl)amino)-6-(3,5-dimethylisoxazol-4-yl)quinazolin-2-yl)piperazin-1-yl)acetamide, 2TFA |
| 118 | 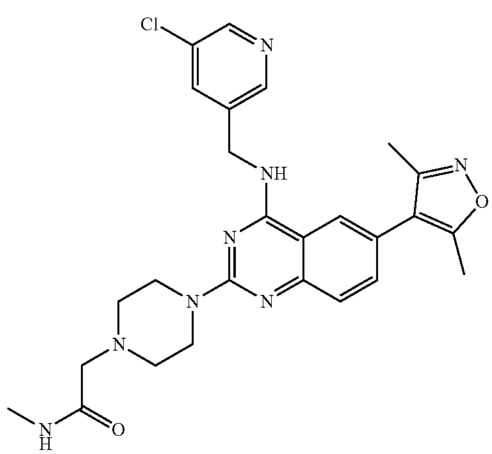 [SMILES: CNC(=O)CN1CCN(c2nc(NCc3cncc(Cl)c3)c3cc(-c4c(C)noc4C)ccc3n2)CC1] | 2-(4-(4-(((5-chloropyridin-3-yl)methyl)amino)-6-(3,5-dimethylisoxazol-4-yl)quinazolin-2-yl)piperazin-1-yl)-N-methylacetamide, 2TFA |

TABLE 1-continued

| Example # | Structure | Compound Name |
|---|---|---|
| 119 | 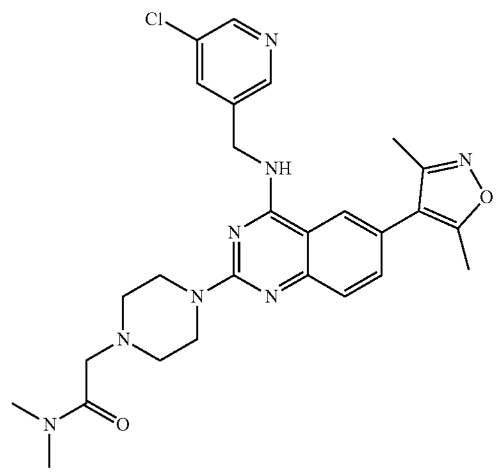 [SMILES: Cc1noc(C)c1-c1ccc2nc(N3CCN(CC(=O)N(C)C)CC3)nc(NCc3cncc(Cl)c3)c2c1] | 2-(4-(4-(((5-chloropyridin-3-yl)methyl)amino)-6-(3,5-dimethylisoxazol-4-yl)quinazolin-2-yl)piperazin-1-yl)-N,N-dimethylacetamide, 2TFA |
| 120 | 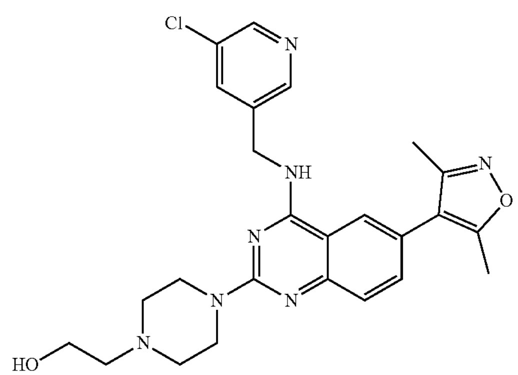 | 2-(4-(4-(((5-chloropyridin-3-yl)methyl)amino)-6-(3,5-dimethylisoxazol-4-yl)quinazolin-2-yl)piperazin-1-yl)ethanol, 2TFA |
| 121 | 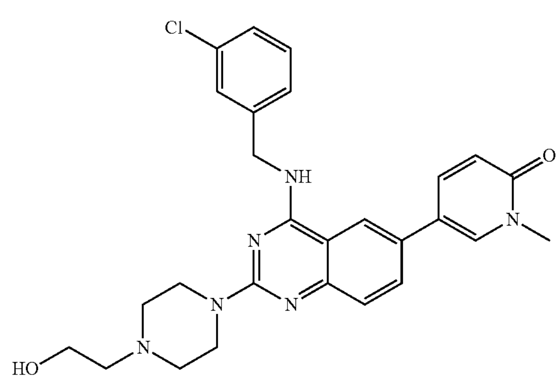 [SMILES: Cn1cc(-c2ccc3nc(N4CCN(CCO)CC4)nc(NCc4cccc(Cl)c4)c3c2)ccc1=O] | 5-(4-((3-chlorobenzyl)amino)-2-(4-(2-hydroxyethyl)piperazin-1-yl)quinazolin-6-yl)-1-methylpyridin-2(1H)-one, 2TFA |

TABLE 1-continued

| Example # | Structure | Compound Name |
|---|---|---|
| 122 | 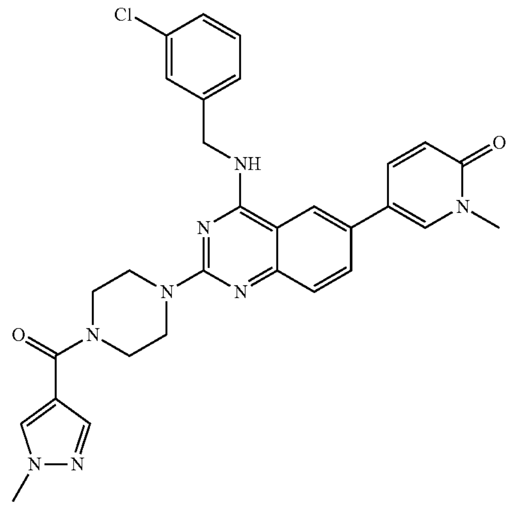 | 5-(4-((3-chlorobenzyl)amino)-2-(4-(1-methyl-1H-pyrazole-4-carbonyl)piperazin-1-yl)quinazolin-6-yl)-1-methylpyridin-2(1H)-one, 2TFA |
| 123 | 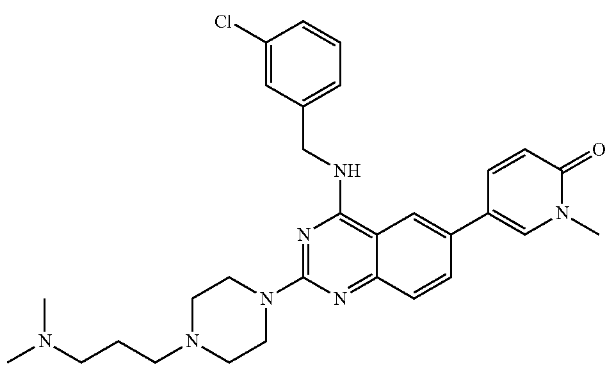 | 5-(4-((3-chlorobenzyl)amino)-2-(4-(3-(dimethylamino)propyl)piperazin-1-yl)quinazolin-6-yl)-1-methylpyridin-2(1H)-one, 2TFA |
| 124 | 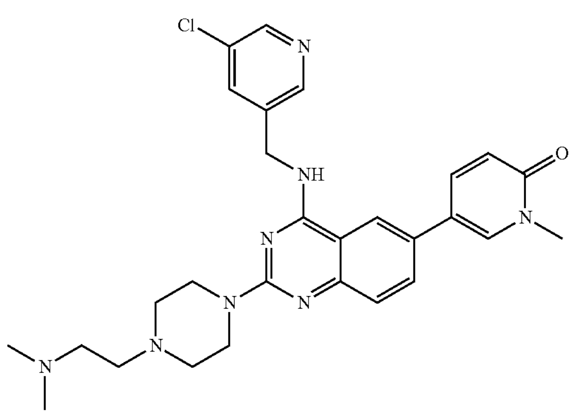 | 5-(4-(((5-chloropyridin-3-yl)methyl)amino)-2-(4-(2-(dimethylamino)ethyl)piperazin-1-yl)quinazolin-6-yl)-1-methylpyridin-2(1H)-one, 2TFA |

TABLE 1-continued

| Example # | Structure | Compound Name |
|---|---|---|
| 125 | 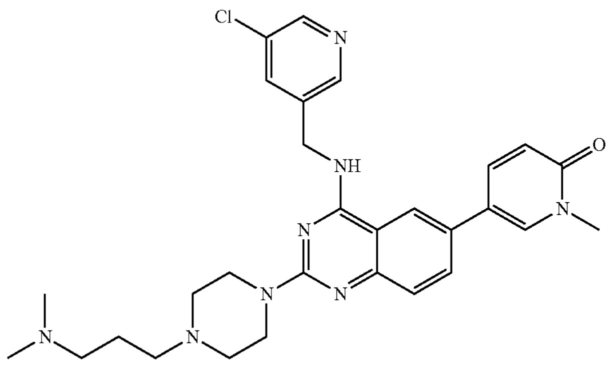 | 5-(4-(((5-chloropyridin-3-yl)methyl)amino)-2-(4-(3-(dimethylamino)propyl)piperazin-1-yl)quinazolin-6-yl)-1-methylpyridin-2(1H)-one, 2TFA |
| 126 | 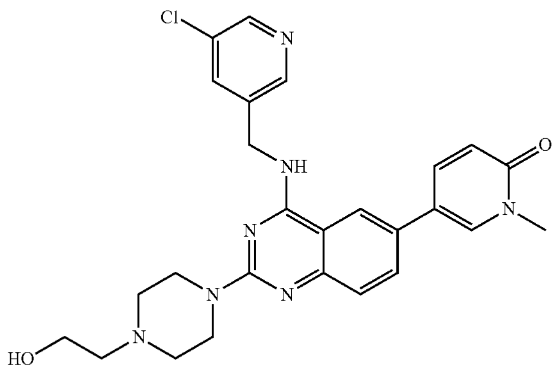 | 5-(4-(((5-chloropyridin-3-yl)methyl)amino)-2-(4-(2-hydroxyethyl)piperazin-1-yl)quinazolin-6-yl)-1-methylpyridin-2(1H)-one, 2TFA |
| 127 | 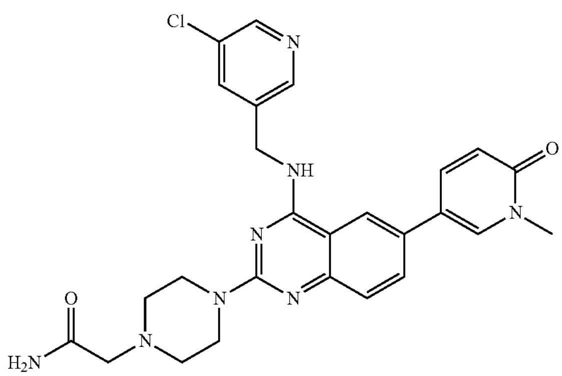 [SMILES: Cn1cc(-c2ccc3nc(N4CCN(CC(N)=O)CC4)nc(NCc4cncc(Cl)c4)c3c2)ccc1=O] | 2-(4-(4-(((5-chloropyridin-3-yl)methyl)amino)-6-(1-methyl-6-oxo-1,6-dihydropyridin-3-yl)quinazolin-2-yl)piperazin-1-yl)acetamide, 2TFA |
| 128 | 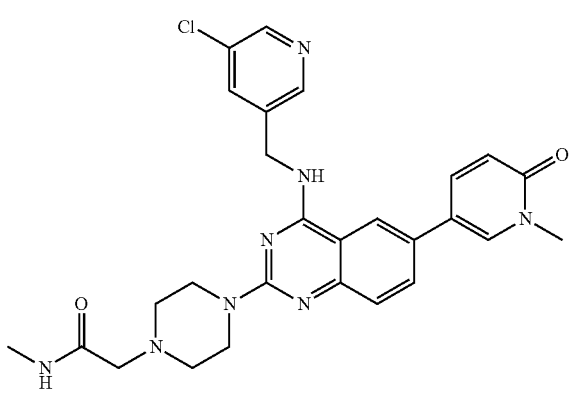 | 2-(4-(4-(((5-chloropyridin-3-yl)methyl)amino)-6-(1-methyl-6-oxo-1,6-dihydropyridin-3-yl)quinazolin-2-piperazin-1-yl)-N-methylacetamide, 2TFA |

TABLE 1-continued

| Example # | Structure | Compound Name |
|---|---|---|
| 129 | 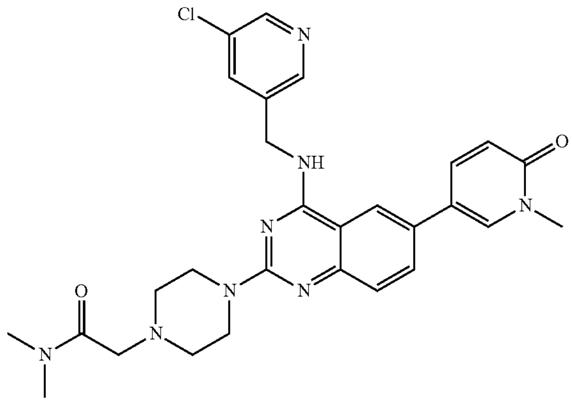 | 2-(4-(4-(((5-chloropyridin-3-yl)methyl)amino)-6-(1-methyl-6-oxo-1,6-dihydropyridin-3-yl)quinazolin-2-yl)piperazin-1-yl)-N,N-dimethylacetamide, 2TFA |
| 130 | 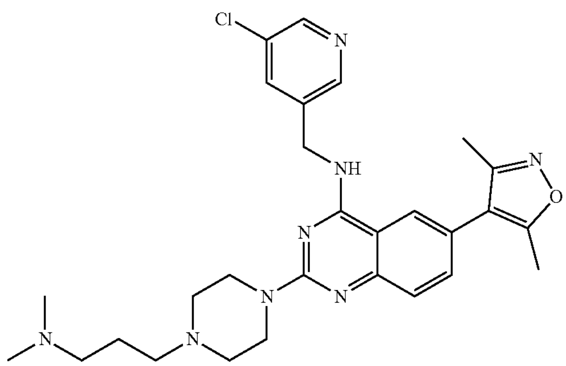 [SMILES: Cc1noc(C)c1-c1ccc2nc(N3CCN(CCCN(C)C)CC3)nc(NCc3cncc(Cl)c3)c2c1] | N-((5-chloropyridin-3-yl)methyl)-2-(4-(3-(dimethylamino)propyl)piperazin-1-yl)-6-(3,5-dimethylisoxazol-4-yl)quinazolin-4-amine, 2TFA |
| 131 | 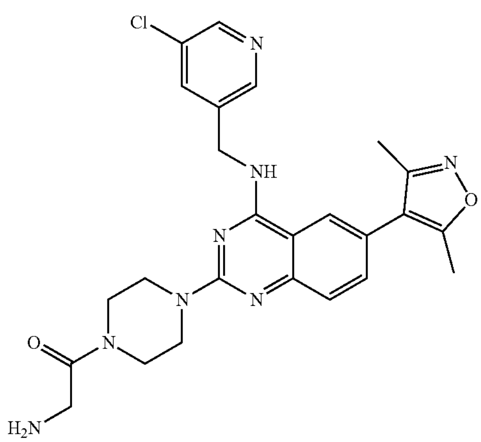 [SMILES: Cc1noc(C)c1-c1ccc2nc(N3CCN(C(=O)CN)CC3)nc(NCc3cncc(Cl)c3)c2c1] | 2-amino-1-(4-(4-(((5-chloropyridin-3-yl)methyl)amino)-6-(3,5-dimethylisoxazol-4-yl)quinazolin-2-yl)piperazin-1-yl)ethanone |

TABLE 1-continued

| Example # | Structure | Compound Name |
|---|---|---|
| 132 | 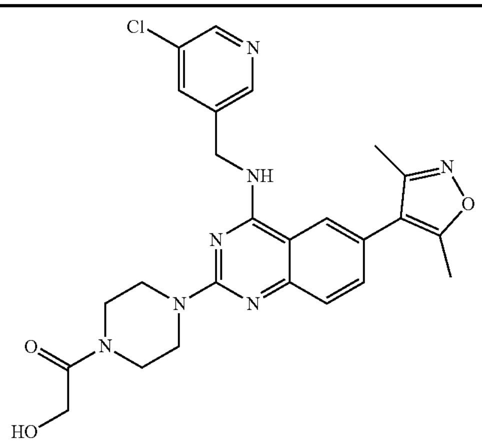 | 1-(4-(4-(((5-chloropyridin-3-yl)methyl)amino)-6-(3,5-dimethylisoxazol-4-yl)quinazolin-2-yl)piperazin-1-yl)-2-hydroxyethanone, 2TFA |
| 133 | 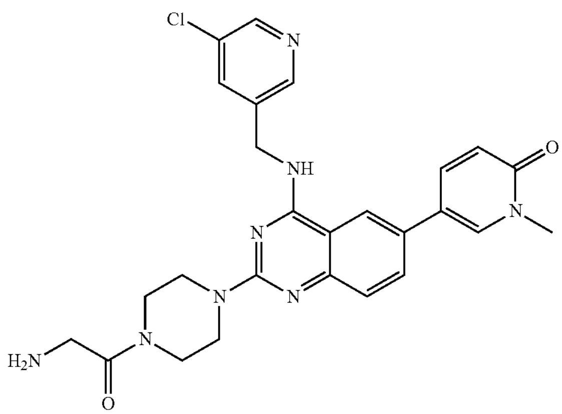 [SMILES: Cn1cc(-c2ccc3nc(N4CCN(C(=O)CN)CC4)nc(NCc4cncc(Cl)c4)c3c2)ccc1=O] | 5-(2-(4-(2-aminoacetyl)piperazin-1-yl)-4-(((5-chloropyridin-3-yl)methyl)amino)quinazolin-6-yl)-1-methylpyridin-2(1H)-one |
| 134 | 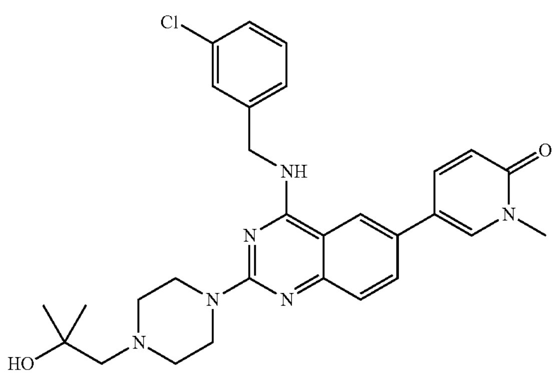 [SMILES: Cn1cc(-c2ccc3nc(N4CCN(CC(C)(C)O)CC4)nc(NCc4cccc(Cl)c4)c3c2)ccc1=O] | 5-(4-((3-chlorobenzyl)amino)-2-(4-(2-hydroxy-2-methylpropyl)piperazin-1-yl)quinazolin-6-yl)-1-methylpyridin-2(1H)-one, 2TFA |
| 135 | 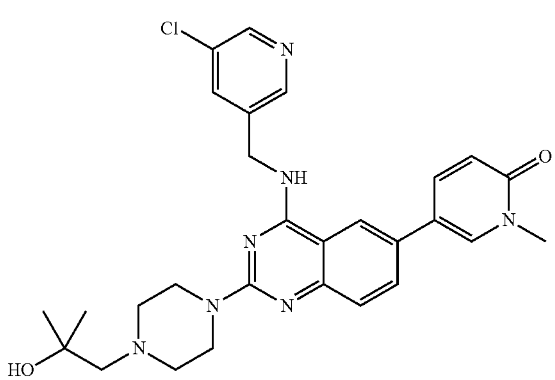 [SMILES: Cn1cc(-c2ccc3nc(N4CCN(CC(C)(C)O)CC4)nc(NCc4cncc(Cl)c4)c3c2)ccc1=O] | 5-(4-(((5-chloropyridin-3-yl)methyl)amino)-2-(4-(2-hydroxy-2-methylpropyl)piperazin-1-yl)quinazolin-6-yl)-1-methylpyridin-2(1H)-one, 2TFA |

TABLE 1-continued

| Example # | Structure | Compound Name |
|---|---|---|
| 136 | 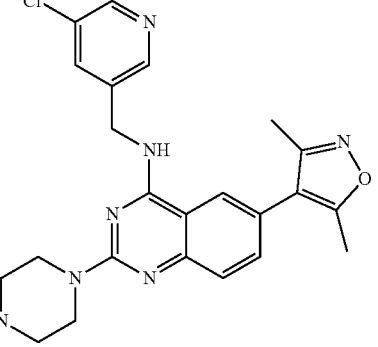 | 1-(4-(4-(((5-chloropyridin-3-yl)methyl)amino)-6-(3,5-dimethylisoxazol-4-yl)quinazolin-2-yl)piperazin-1-yl)-2-methylpropan-2-ol, 2TFA |
| 137 | 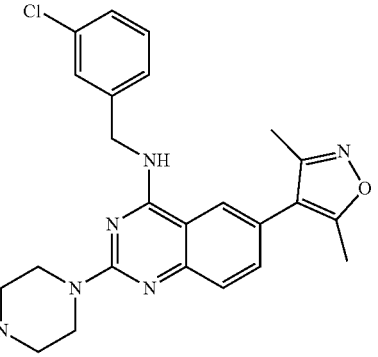 | 1-(4-(4-((3-chlorobenzyl)amino)-6-(3,5-dimethylisoxazol-4-yl)quinazolin-2-yl)piperazin-1-yl)-2-methylpropan-2-ol, 2TFA |
| 138 | 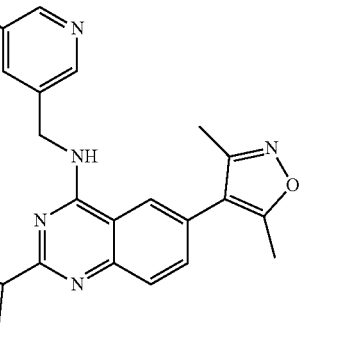 | 2-(4-(4-(((5-chloropyridin-3-yl)methyl)amino)-6-(3,5-dimethylisoxazol-4-yl)quinazolin-2-yl)-1H-pyrazol-1-yl)-2-methylpropan-1-ol, 2TFA |
| 139 | 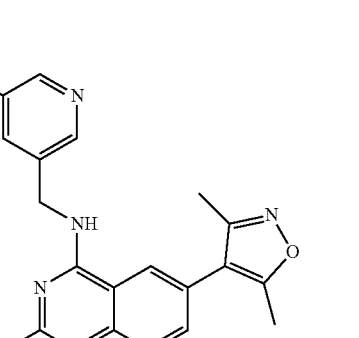 | 1-(4-(4-(((5-chloropyridin-3-yl)methyl)amino)-6-(3,5-dimethylisoxazol-4-yl)quinazolin-2-yl)-1H-pyrazol-1-yl)-2-methylpropan-2-ol, 2TFA |

TABLE 1-continued

| Example # | Structure | Compound Name |
|---|---|---|
| 140 | 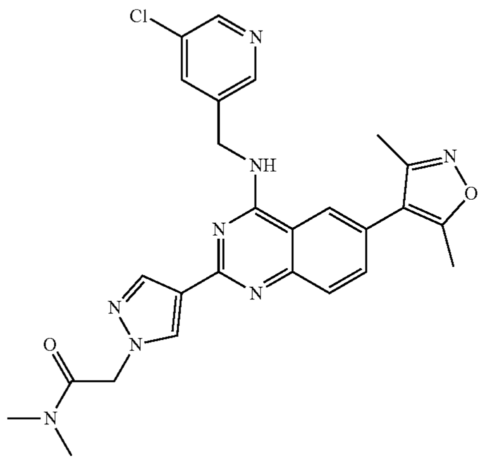 [SMILES: Cc1noc(C)c1-c1ccc2nc(-c3cnn(CC(=O)N(C)C)c3)nc(NCc3cncc(Cl)c3)c2c1] | 2-(4-(4-(((5-chloropyridin-3-yl)methyl)amino)-6-(3,5-dimethylisoxazol-4-yl)quinazolin-2-yl)-1H-pyrazol-1-yl)-N,N-dimethylacetamide, 2TFA |
| 141 | 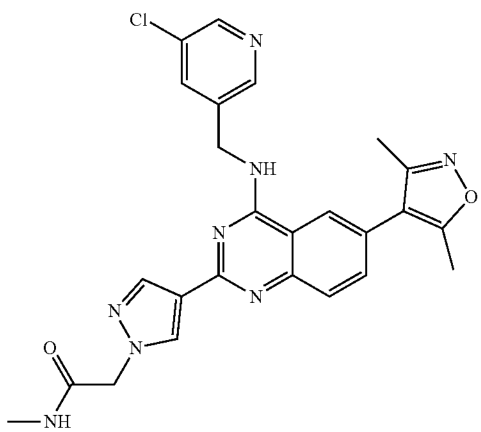 [SMILES: CNC(=O)Cn1cc(-c2nc(NCc3cncc(Cl)c3)c3cc(-c4c(C)noc4C)ccc3n2)cn1] | 2-(4-(4-(((5-chloropyridin-3-yl)methyl)amino)-6-(3,5-dimethylisoxazol-4-yl)quinazolin-2-yl)-1H-pyrazol-1-yl)-N-methylacetamide, 2TFA |
| 142 | 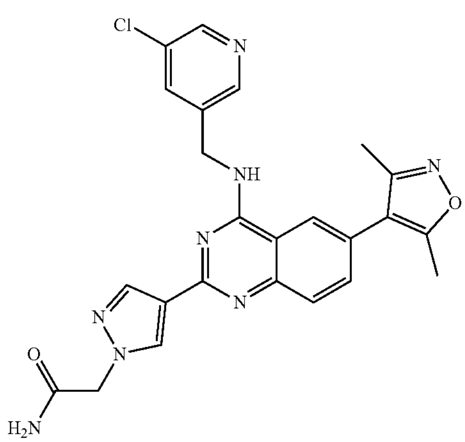 [SMILES: Cc1noc(C)c1-c1ccc2nc(-c3cnn(CC(N)=O)c3)nc(NCc3cncc(Cl)c3)c2c1] | 2-(4-(4-(((5-chloropyridin-3-yl)methyl)amino)-6-(3,5-dimethylisoxazol-4-yl)quinazolin-2-yl)-1H-pyrazol-1-yl)acetamide, 2TFA |

TABLE 1-continued

| Example # | Structure | Compound Name |
|---|---|---|
| 143 | 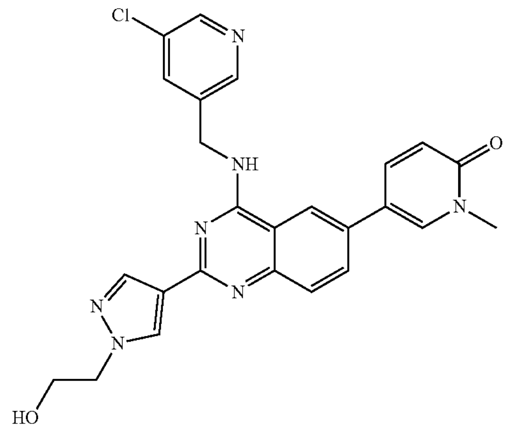 | 5-(4-(((5-chloropyridin-3-yl)methyl)amino)-2-(1-(2-hydroxyethyl)-1H-pyrazol-4-yl)quinazolin-6-yl)-1-methylpyridin-2(1H)-one, 2TFA |
| 144 | 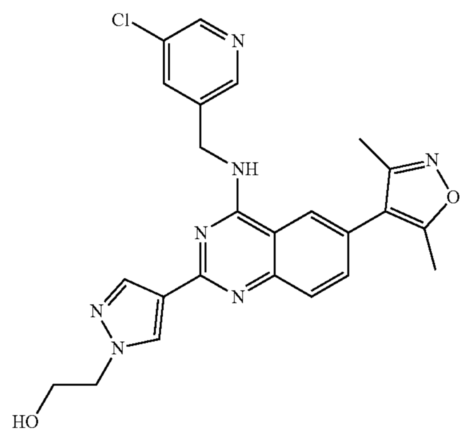 | 2-(4-(4-(((5-chloropyridin-3-yl)methyl)amino)-6-(3,5-dimethylisoxazol-4-yl)quinazolin-2-yl)-1H-pyrazol-1-yl)ethanol, 2TFA |
| 145 | 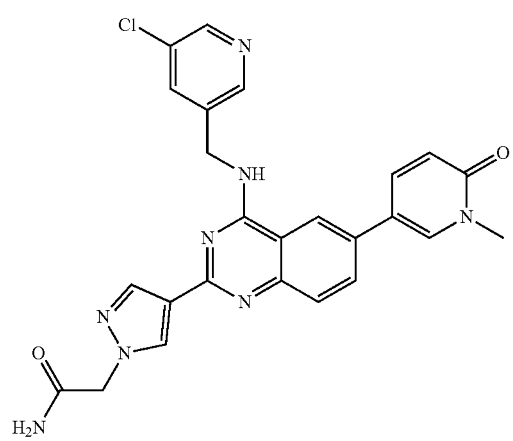 [SMILES: Cn1cc(-c2ccc3nc(-c4cnn(CC(N)=O)c4)nc(NCc4cncc(Cl)c4)c3c2)ccc1=O] | 2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)acetamide, 2TFA |

TABLE 1-continued

| Example # | Structure | Compound Name |
|---|---|---|
| 146 | 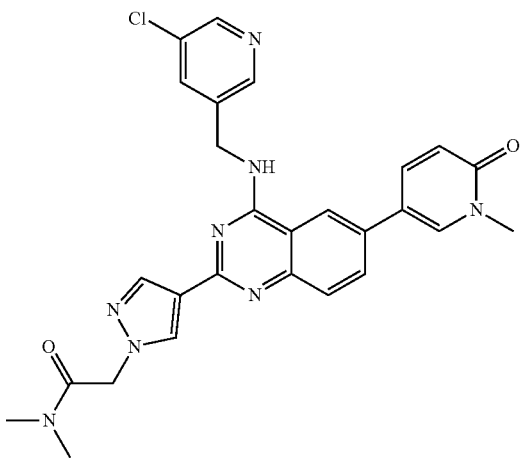 | 2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)-N,N-dimethylacetamide, 2TFA |
| 147 | 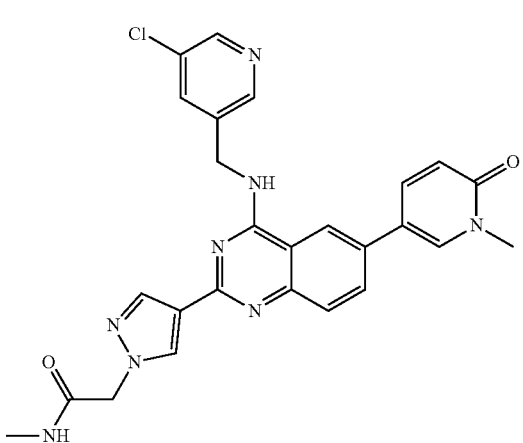 | 2-(4-(4-(((5-chloropyridin-3-yl)methyl)amino)-6-(1-methyl-6-oxo-1,6-dihydropyridin-3-yl)quinazolin-2-yl)-1H-pyrazol-1-yl)-N-methylacetamide, 2TFA |
| 148 | 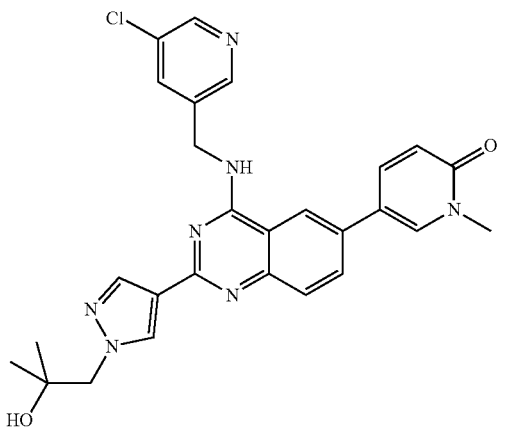 [SMILES: Cn1cc(-c2ccc3nc(-c4cnn(CC(C)(C)O)c4)nc(NCc4cncc(Cl)c4)c3c2)ccc1=O] | 5-(4-(((5-chloropyridin-3-yl)methyl)amino)-2-(1-(2-hydroxy-2-methylpropyl)-1H-pyrazol-4-yl)quinazolin-6-yl)-1-methylpyridin-2(1H)-one, 2TFA |

TABLE 1-continued

| Example # | Structure | Compound Name |
|---|---|---|
| 149 | 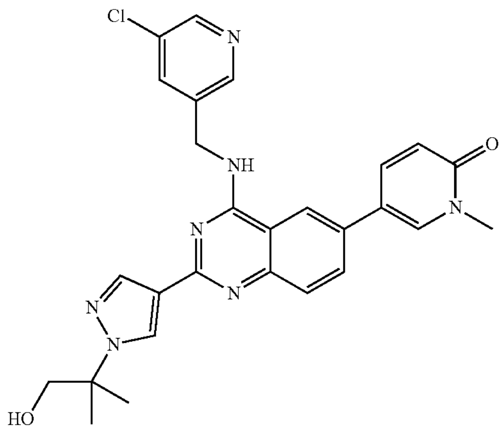 [SMILES: Cn1cc(-c2ccc3nc(-c4cnn(C(C)(C)CO)c4)nc(NCc4cncc(Cl)c4)c3c2)ccc1=O] | 5-(4-(((5-chloropyridin-3-yl)methyl)amino)-2-(1-(1-hydroxy-2-methylpropan-2-yl)-1H-pyrazol-4-yl)quinazolin-6-yl)-1-methylpyridin-2(1H)-one, 2TFA |
| 150 | 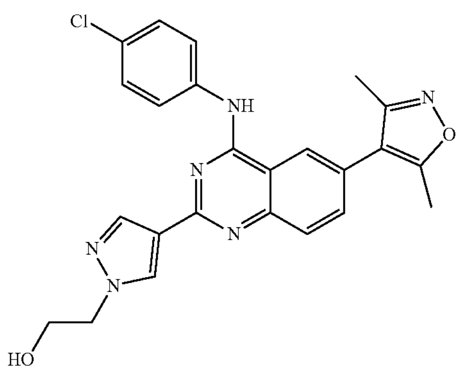 [SMILES: Cc1noc(C)c1-c1ccc2nc(-c3cnn(CCO)c3)nc(Nc3ccc(Cl)cc3)c2c1] | 2-(4-(4-((4-chlorophenyl)amino)-6-(3,5-dimethylisoxazol-4-yl)quinazolin-2-yl)-1H-pyrazol-1-yl)ethanol, 2TFA |
| 151 | 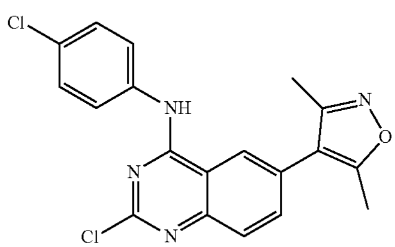 [SMILES: Cc1noc(C)c1-c1ccc2nc(Cl)nc(Nc3ccc(Cl)cc3)c2c1] | 2-chloro-N-(4-chlorophenyl)-6-(3,5-dimethylisoxazol-4-yl)quinazolin-4-amine, 2TFA |
| 152 | 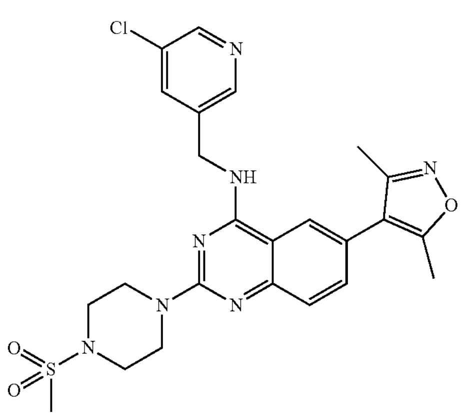 [SMILES: Cc1noc(C)c1-c1ccc2nc(N3CCN(S(C)(=O)=O)CC3)nc(NCc3cncc(Cl)c3)c2c1] | N-((5-chloropyridin-3-yl)methyl)-6-(3,5-dimethylisoxazol-4-yl)-2-(4-(methylsulfonyl)piperazin-1-yl)quinazolin-4-amine, 2TFA |

TABLE 1-continued

| Example # | Structure | Compound Name |
|---|---|---|
| 153 | 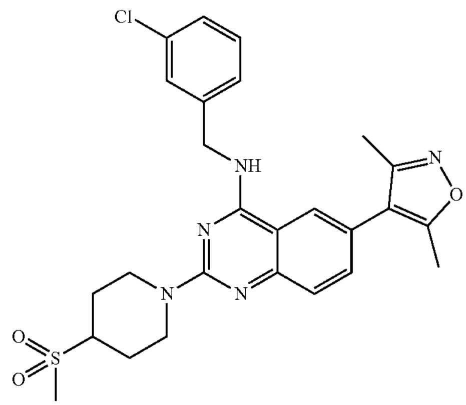 [SMILES: Cc1noc(C)c1-c1ccc2nc(N3CCC(S(C)(=O)=O)CC3)nc(NCc3cccc(Cl)c3)c2c1] | N-(3-chlorobenzyl)-6-(3,5-dimethylisoxazol-4-yl)-2-(4-(methylsulfonyl)piperidin-1-yl)quinazolin-4-amine, 2TFA |
| 154 | 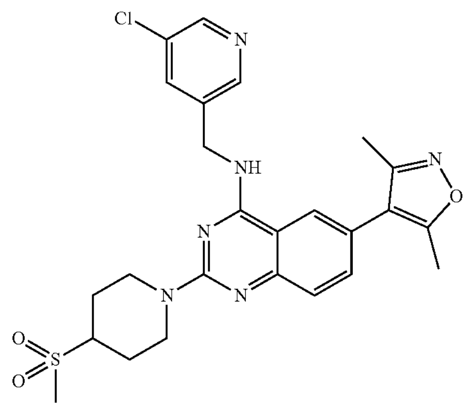 | N-((5-chloropyridin-3-yl)methyl)-6-(3,5-dimethylisoxazol-4-yl)-2-(4-(methylsulfonyl)piperidin-1-yl)quinazolin-4-amine, 2TFA |
| 155 | 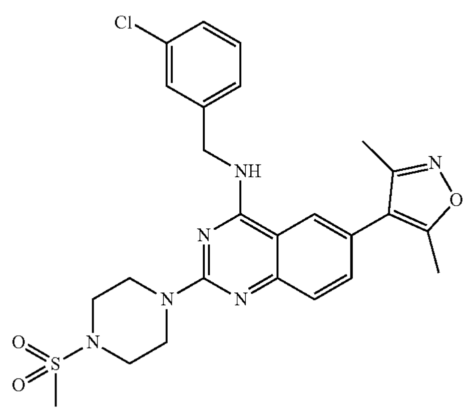 | N-(3-chlorobenzyl)-6-(3,5-dimethylisoxazol-4-yl)-2-(4-(methylsulfonyl)piperazin-1-yl)quinazolin-4-amine, 2TFA |
| 156 | 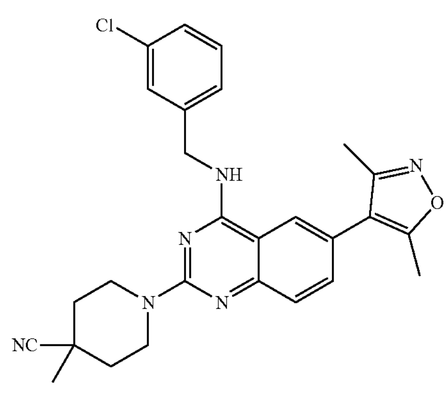 [SMILES: Cc1noc(C)c1-c1ccc2nc(N3CCC(C)(C#N)CC3)nc(NCc3cccc(Cl)c3)c2c1] | 1-(4-((3-chlorobenzyl)amino)-6-(3,5-dimethylisoxazol-4-yl)quinazolin-2-yl)-4-methylpiperidine-4-carbonitrile, 2TFA |

TABLE 1-continued

| Example # | Structure | Compound Name |
|---|---|---|
| 157 | 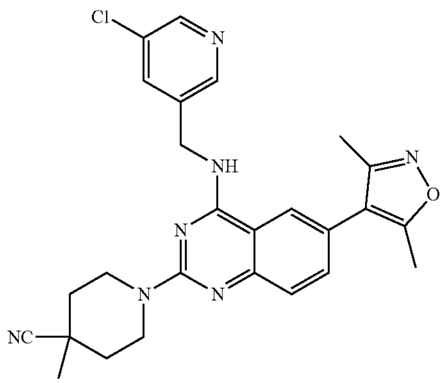 [SMILES: Cc1noc(C)c1-c1ccc2nc(N3CCC(C)(C#N)CC3)nc(NCc3cncc(Cl)c3)c2c1] | 1-(4-(((5-chloropyridin-3-yl)methyl)amino)-6-(3,5-dimethylisoxazol-4-yl)quinazolin-2-yl)-4-methylpiperidine-4-carbonitrile, 2TFA |
| 158 | 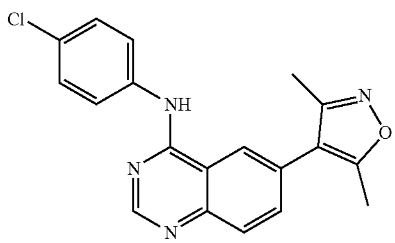 [SMILES: Cc1noc(C)c1-c1ccc2ncnc(Nc3ccc(Cl)cc3)c2c1] | N-(4-chlorophenyl)-6-(3,5-dimethylisoxazol-4-yl)quinazolin-4-amine, 2TFA |
| 159 | 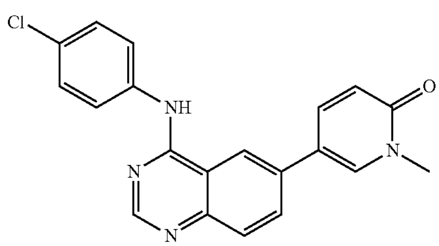 [SMILES: Cn1cc(-c2ccc3ncnc(Nc4ccc(Cl)cc4)c3c2)ccc1=O] | 5-(4-((4-chlorophenyl)amino)quinazolin-6-yl)-1-methylpyridin-2(1H)-one, TFA |
| 160 | 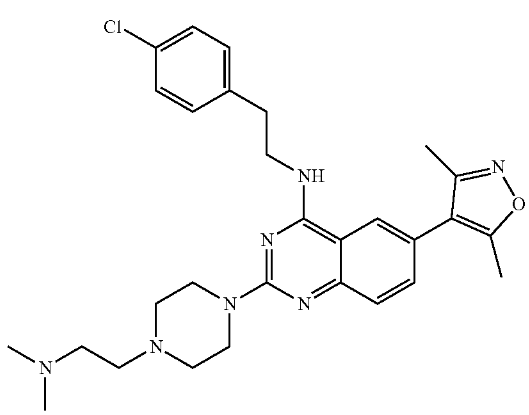 [SMILES: Cc1noc(C)c1-c1ccc2nc(N3CCN(CCN(C)C)CC3)nc(NCCc3ccc(Cl)cc3)c2c1] | N-(4-chlorophenethyl)-2-(4-(2-(dimethylamino)ethyl)piperazin-1-yl)-6-(3,5-dimethylisoxazol-4-yl)quinazolin-4-amine, 2TFA |

TABLE 1-continued

| Example # | Structure | Compound Name |
|---|---|---|
| 161 | 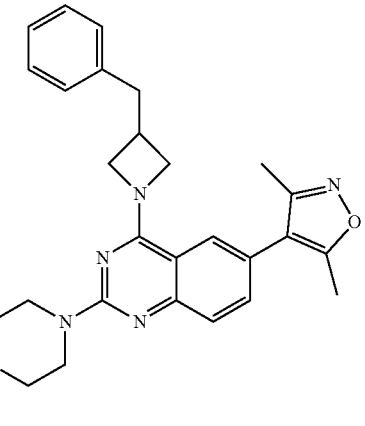 | 2-(4-(4-(3-benzylazetidin-1-yl)-6-(3,5-dimethylisoxazol-4-yl)quinazolin-2-yl)piperazin-1-yl)-N,N-dimethylethanamine, 2TFA |
| 162 | 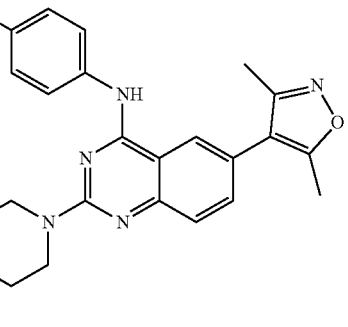 | N-(4-chlorophenyl)-2-(4-(2-(dimethylamino)ethyl)piperazin-1-yl)-6-(3,5-dimethylisoxazol-4-yl)quinazolin-4-amine, 2TFA |
| 163 | 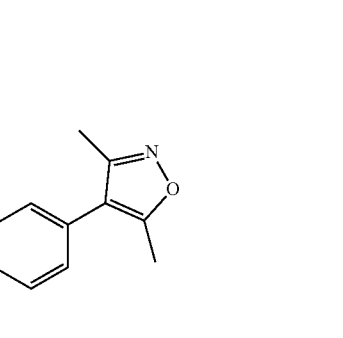 | 4-((3-chlorobenzyl)amino)-6-(3,5-dimethylisoxazol-4-yl)quinazoline-2-carboxylic acid, TFA |
| 164 | 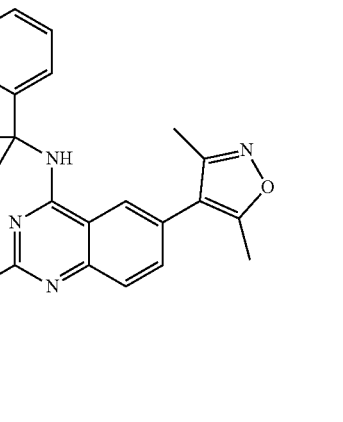 | 2-(4-(4-((1-(3-chlorophenyl)cyclopropyl)amino)-6-(3,5-dimethylisoxazol-4-yl)quinazolin-2-yl)-1H-pyrazol-1-yl)ethanol, 2TFA |

TABLE 1-continued

| Example # | Structure | Compound Name |
|---|---|---|
| 165 | 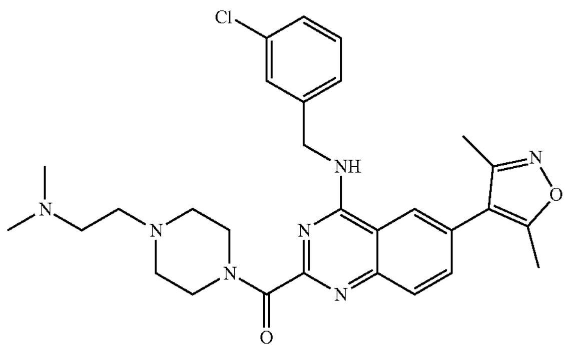 [SMILES: Cc1noc(C)c1-c1ccc2nc(C(=O)N3CCN(CCN(C)C)CC3)nc(NCc3cccc(Cl)c3)c2c1] | (4-((3-chlorobenzyl)amino)-6-(3,5-dimethylisoxazol-4-yl)quinazolin-2-yl)(4-(2-(dimethylamino)ethyl)piperazin-1-yl)methanone, 2TFA |
| 166 | 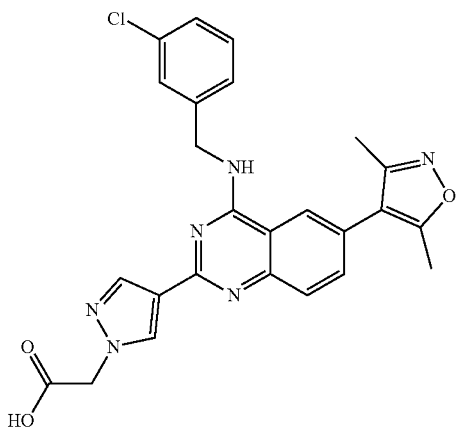 [SMILES: Cc1noc(C)c1-c1ccc2nc(-c3cnn(CC(=O)O)c3)nc(NCc3cccc(Cl)c3)c2c1] | 2-(4-(4-((3-chlorobenzyl)amino)-6-(3,5-dimethylisoxazol-4-yl)quinazolin-2-yl)-1H-pyrazol-1-yl)acetic acid, TFA |
| 167 | 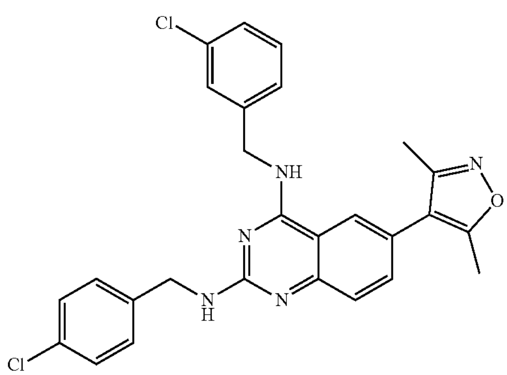 [SMILES: Cc1noc(C)c1-c1ccc2nc(NCc3ccc(Cl)cc3)nc(NCc3cccc(Cl)c3)c2c1] | N4-(3-chlorobenzyl)-N2-(4-chlorobenzyl)-6-(3,5-dimethylisoxazol-4-yl)quinazoline-2,4-diamine, 2TFA |
| 168 | 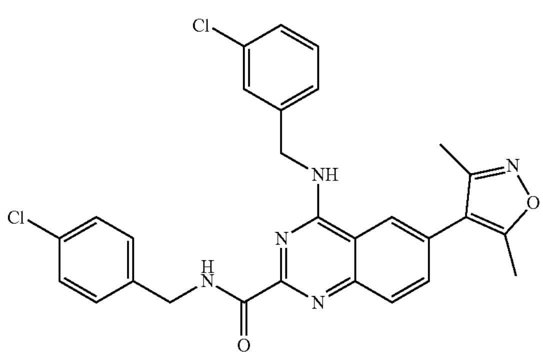 [SMILES: Cc1noc(C)c1-c1ccc2nc(C(=O)NCc3ccc(Cl)cc3)nc(NCc3cccc(Cl)c3)c2c1] | N-(4-chlorobenzyl)-4-((3-chlorobenzyl)amino)-6-(3,5-dimethylisoxazol-4-yl)quinazoline-2-carboxamide, 2TFA |

TABLE 1-continued

| Example # | Structure | Compound Name |
|---|---|---|
| 169 | 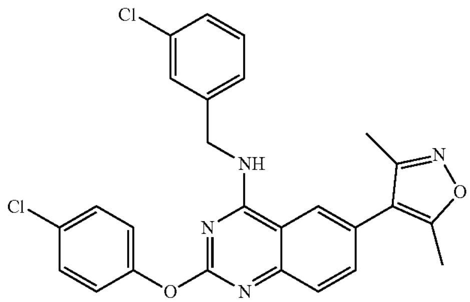 [SMILES: Cc1noc(C)c1-c1ccc2nc(Oc3ccc(Cl)cc3)nc(NCc3cccc(Cl)c3)c2c1] | N-(3-chlorobenzyl)-2-(4-chlorophenoxy)-6-(3,5-dimethylisoxazol-4-yl)quinazolin-4-amine, 2TFA |
| 170 | 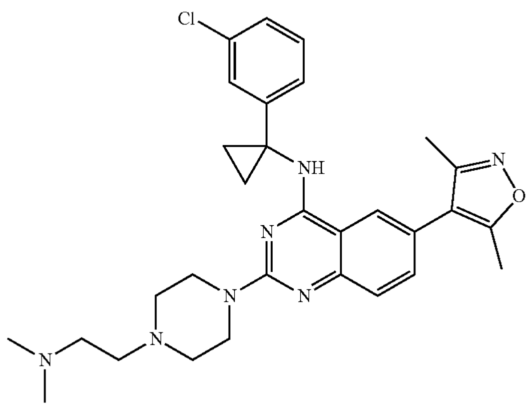 [SMILES: Cc1noc(C)c1-c1ccc2nc(N3CCN(CCN(C)C)CC3)nc(NC3(c4cccc(Cl)c4)CC3)c2c1] | N-(1-(3-chlorophenyl)cyclopropyl)-2-(4-(2-(dimethylamino)ethyl)piperazin-1-yl)-6-(3,5-dimethylisoxazol-4-yl)quinazolin-4-amine, 2TFA |
| 171 | 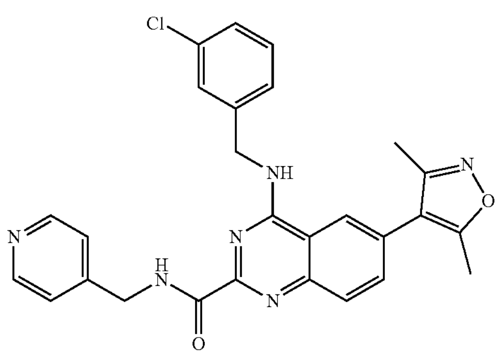 [SMILES: Cc1noc(C)c1-c1ccc2nc(C(=O)NCc3ccncc3)nc(NCc3cccc(Cl)c3)c2c1] | 4-((3-chlorobenzyl)amino)-6-(3,5-dimethylisoxazol-4-yl)-N-(pyridin-4-ylmethyl)quinazoline-2-carboxamide, 2TFA |
| 172 | 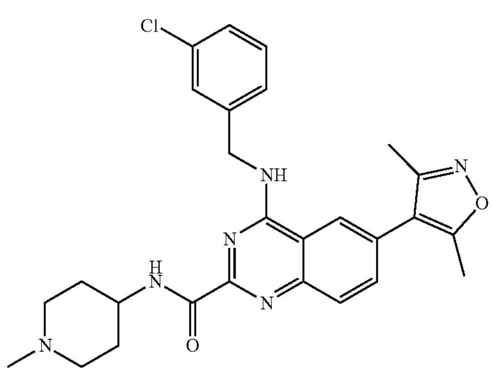 [SMILES: Cc1noc(C)c1-c1ccc2nc(C(=O)NC3CCN(C)CC3)nc(NCc3cccc(Cl)c3)c2c1] | 4-((3-chlorobenzyl)amino)-6-(3,5-dimethylisoxazol-4-yl)-N-(1-methylpiperidin-4-yl)quinazoline-2-carboxamide, 2TFA |

TABLE 1-continued

| Example # | Structure | Compound Name |
|---|---|---|
| 173 | 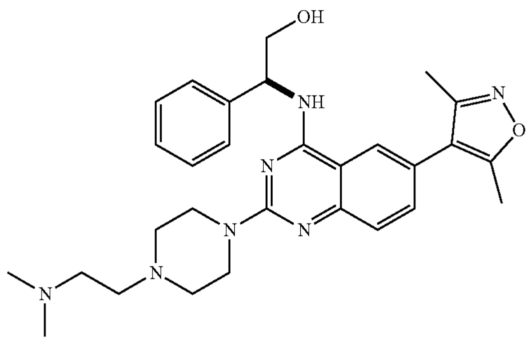 [SMILES: Cc1noc(C)c1-c1ccc2nc(N3CCN(CCN(C)C)CC3)nc(N[C@H](CO)c3ccccc3)c2c1] | (S)-2-((2-(4-(2-(dimethylamino)ethyl)piperazin-1-yl)-6-(3,5-dimethylisoxazol-4-yl)quinazolin-4-yl)amino)-2-phenylethanol, 2TFA |
| 174 | 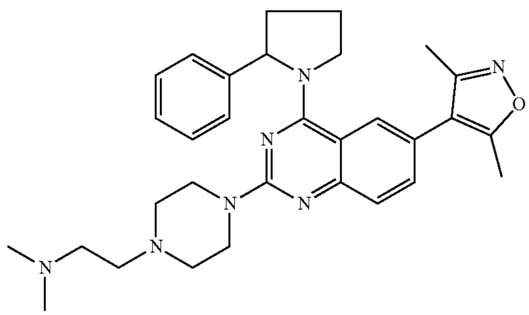 [SMILES: Cc1noc(C)c1-c1ccc2nc(N3CCN(CCN(C)C)CC3)nc(N3CCCC3c3ccccc3)c2c1] | 2-(4-(6-(3,5-dimethylisoxazol-4-yl)-4-(2-phenylpyrrolidin-1-yl)quinazolin-2-yl)piperazin-1-yl)-N,N-dimethylethanamine, 2TFA |
| 175 | 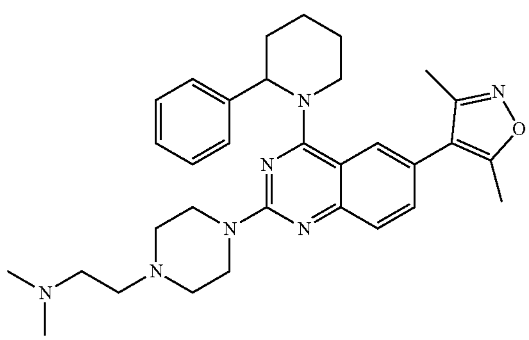 [SMILES: Cc1noc(C)c1-c1ccc2nc(N3CCN(CCN(C)C)CC3)nc(N3CCCCC3c3ccccc3)c2c1] | 2-(4-(6-(3,5-dimethylisoxazol-4-yl)-4-(2-phenylpiperidin-1-yl)quinazolin-2-yl)piperazin-1-yl)-N,N-dimethylethanamine, 2TFA |
| 176 | 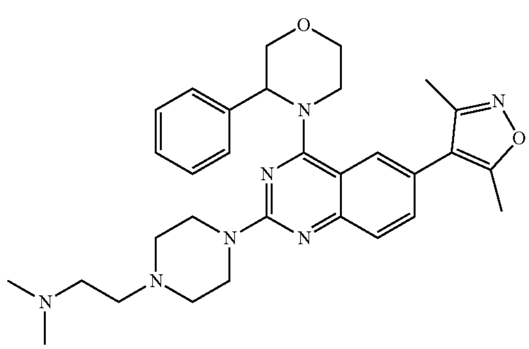 | 2-(4-(6-(3,5-dimethylisoxazol-4-yl)-4-(3-phenylmorpholino)quinazolin-2-yl)piperazin-1-yl)-N,N-dimethylethanamine, 2TFA |

TABLE 1-continued

| Example # | Structure | Compound Name |
|---|---|---|
| 177 | 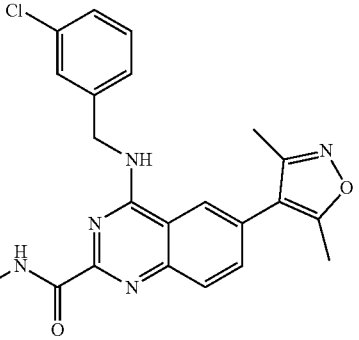 | N-((1H-imidazol-2-yl)methyl)-4-((3-chlorobenzyl)amino)-6-(3,5-dimethylisoxazol-4-yl)quinazoline-2-carboxamide, 2TFA |
| 178 | 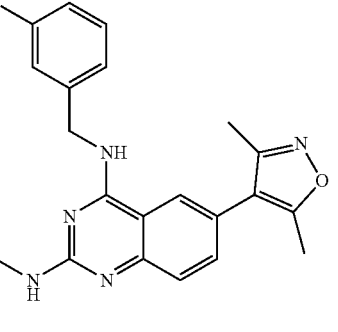 | N2-((1H-imidazol-2-yl)methyl)-N4-(3-chlorobenzyl)-6-(3,5-dimethylisoxazol-4-yl)quinazoline-2,4-diamine, 2TFA |
| 179 | 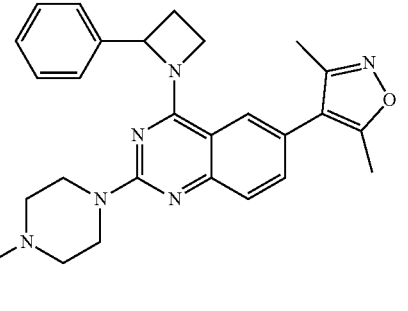 | 2-(4-(6-(3,5-dimethylisoxazol-4-yl)-4-(2-phenylazetidin-1-yl)quinazolin-2-yl)piperazin-1-yl)-N,N-dimethylethanamine, 2TFA |
| 180 | 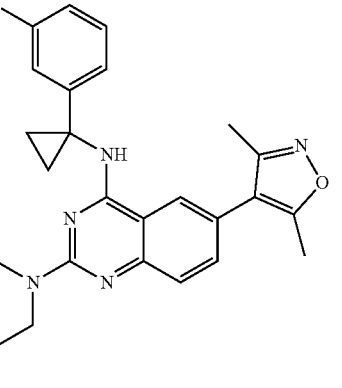 | N-(1-(3-chlorophenyl)cyclopropyl)-6-(3,5-dimethylisoxazol-4-yl)-2-(4-(methylsulfonyl)piperazin-1-yl)quinazolin-4-amine, 2TFA |

TABLE 1-continued

| Example # | Structure | Compound Name |
|---|---|---|
| 181 | 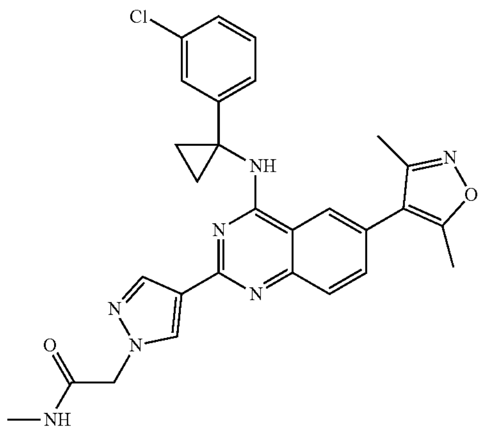 [SMILES: CNC(=O)Cn1cc(-c2nc(NC3(c4cccc(Cl)c4)CC3)c3cc(-c4c(C)noc4C)ccc3n2)cn1] | 2-(4-(4-((1-(3-chlorophenyl)cyclopropyl)amino)-6-(3,5-dimethylisoxazol-4-yl)quinazolin-2-yl)-1H-pyrazol-1-yl)-N-methylacetamide, 2TFA |
| 182 | 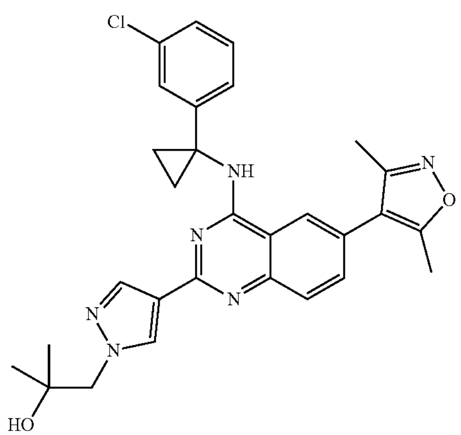 [SMILES: Cc1noc(C)c1-c1ccc2nc(-c3cnn(CC(C)(C)O)c3)nc(NC3(c4cccc(Cl)c4)CC3)c2c1] | 1-(4-(4-((1-(3-chlorophenyl)cyclopropyl)amino)-6-(3,5-dimethylisoxazol-4-yl)quinazolin-2-yl)-1H-pyrazol-1-yl)-2-methylpropan-2-ol, 2TFA |
| 183 | 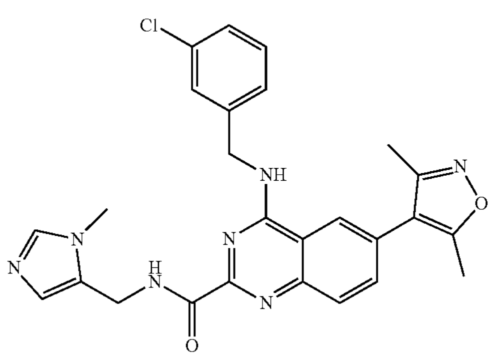 [SMILES: Cc1noc(C)c1-c1ccc2nc(C(=O)NCc3cncn3C)nc(NCc3cccc(Cl)c3)c2c1] | 4-((3-chlorobenzyl)amino)-6-(3,5-dimethylisoxazol-4-yl)-N-((1-methyl-1H-imidazol-5-yl)methyl)quinazoline-2-carboxamide, 2TFA |

TABLE 1-continued

| Example # | Structure | Compound Name |
|---|---|---|
| 184 | 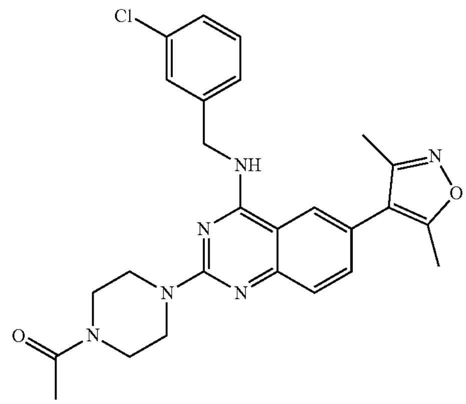 [SMILES: CC(=O)N1CCN(c2nc(NCc3cccc(Cl)c3)c3cc(-c4c(C)noc4C)ccc3n2)CC1] | 1-(4-(4-((3-chlorobenzyl)amino)-6-(3,5-dimethylisoxazol-4-yl)quinazolin-2-yl)piperazin-1-yl)ethanone, 2TFA |
| 185 | 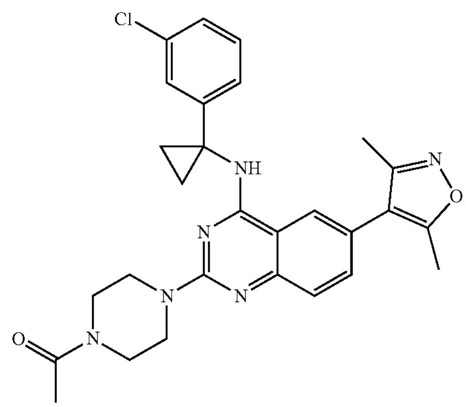 [SMILES: CC(=O)N1CCN(c2nc(NC3(c4cccc(Cl)c4)CC3)c3cc(-c4c(C)noc4C)ccc3n2)CC1] | 1-(4-(4-((1-(3-chlorophenyl)cyclopropyl)amino)-6-(3,5-dimethylisoxazol-4-yl)quinazolin-2-yl)piperazin-1-yl)ethanone, 2TFA |
| 186 | 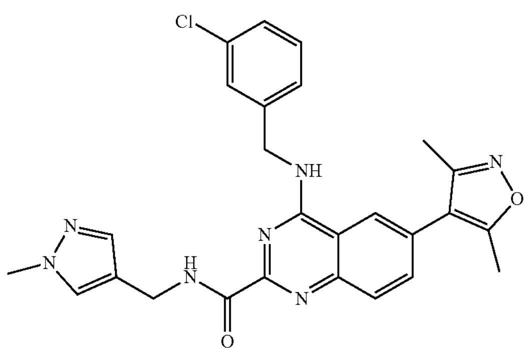 [SMILES: Cc1noc(C)c1-c1ccc2nc(C(=O)NCc3cnn(C)c3)nc(NCc3cccc(Cl)c3)c2c1] | 4-((3-chlorobenzyl)amino)-6-(3,5-dimethylisoxazol-4-yl)-N-((1-methyl-1H-pyrazol-4-yl)methyl)quinazoline-2-carboxamide, 2TFA |
| 187 | 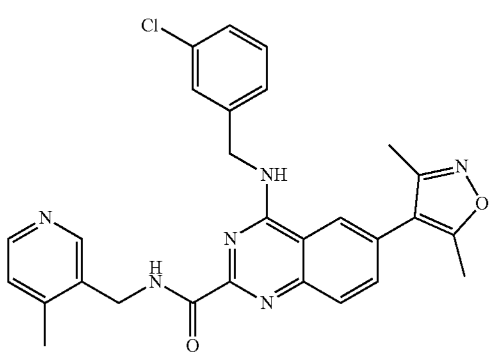 [SMILES: Cc1ccncc1CNC(=O)c1nc(NCc2cccc(Cl)c2)c2cc(-c3c(C)noc3C)ccc2n1] | 4-((3-chlorobenzyl)amino)-6-(3,5-dimethylisoxazol-4-yl)-N-((4-methylpyridin-3-yl)methyl)quinazoline-2-carboxamide, 2TFA |

TABLE 1-continued

| Example # | Structure | Compound Name |
|---|---|---|
| 188 | 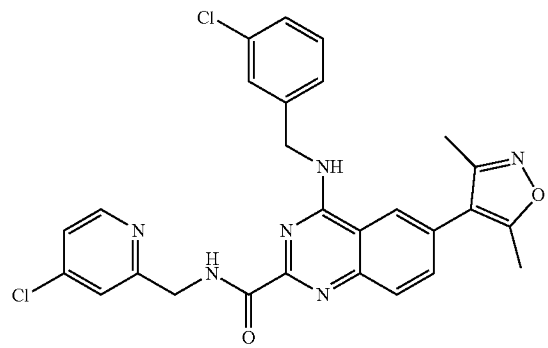 [SMILES: Cc1noc(C)c1-c1ccc2nc(C(=O)NCc3cc(Cl)ccn3)nc(NCc3cccc(Cl)c3)c2c1] | 4-((3-chlorobenzyl)amino)-N-((4-chloropyridin-2-yl)methyl)-6-(3,5-dimethylisoxazol-4-yl)quinazoline-2-carboxamide, 2TFA |
| 189 | 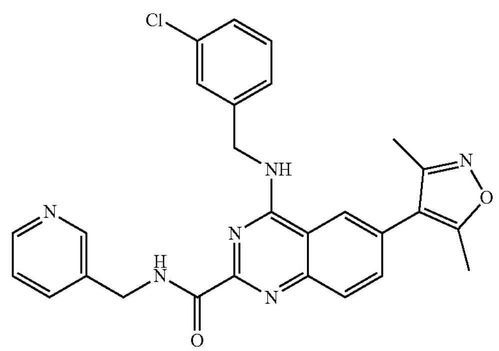 [SMILES: Cc1noc(C)c1-c1ccc2nc(C(=O)NCc3cccnc3)nc(NCc3cccc(Cl)c3)c2c1] | 4-((3-chlorobenzyl)amino)-6-(3,5-dimethylisoxazol-4-yl)-N-(pyridin-3-ylmethyl)quinazoline-2-carboxamide, 2TFA |
| 190 | 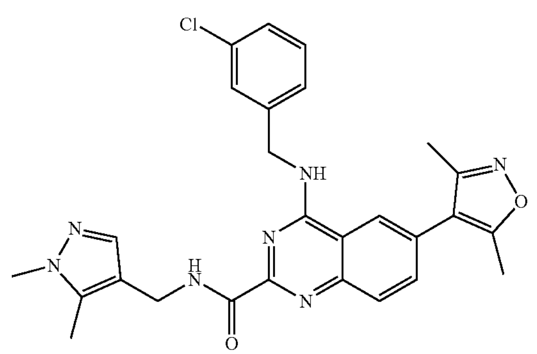 [SMILES: Cc1noc(C)c1-c1ccc2nc(C(=O)NCc3cnn(C)c3C)nc(NCc3cccc(Cl)c3)c2c1] | 4-((3-chlorobenzyl)amino)-N-((1,5-dimethyl-1H-pyrazol-4-yl)methyl)-6-(3,5-dimethylisoxazol-4-yl)quinazoline-2-carboxamide, 2TFA |
| 191 | 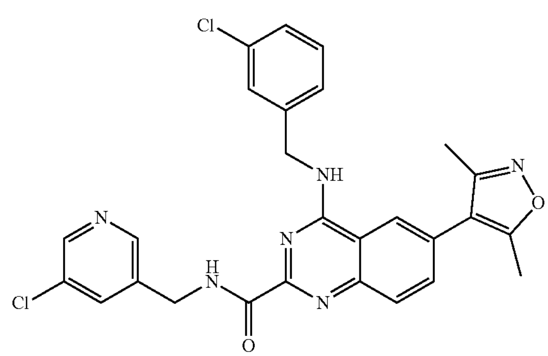 [SMILES: Cc1noc(C)c1-c1ccc2nc(C(=O)NCc3cncc(Cl)c3)nc(NCc3cccc(Cl)c3)c2c1] | 4-((3-chlorobenzyl)amino)-N-((5-chloropyridin-3-yl)methyl)-6-(3,5-dimethylisoxazol-4-yl)quinazoline-2-carboxamide, 2TFA |

TABLE 1-continued

| Example # | Structure | Compound Name |
|---|---|---|
| 192 | 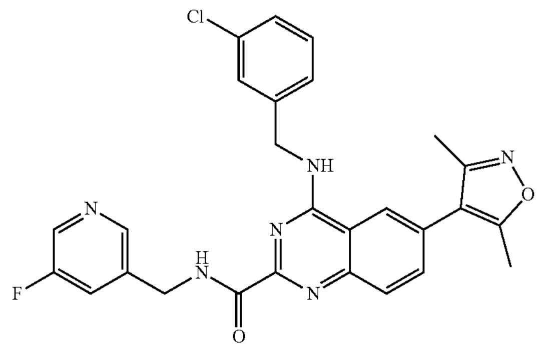 [SMILES: Cc1noc(C)c1-c1ccc2nc(C(=O)NCc3cncc(F)c3)nc(NCc3cccc(Cl)c3)c2c1] | 4-((3-chlorobenzyl)amino)-6-(3,5-dimethylisoxazol-4-yl)-N-((5-fluoropyridin-3-yl)methyl)quinazoline-2-carboxamide, 2TFA |
| 193 | 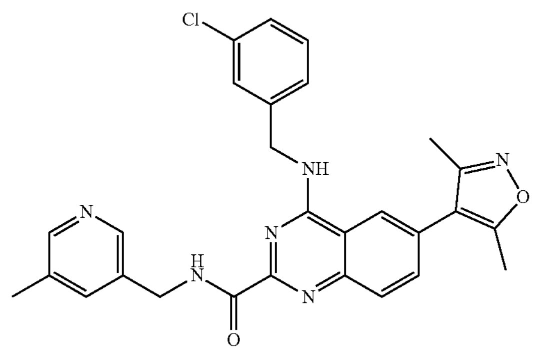 [SMILES: Cc1cncc(CNC(=O)c2nc(NCc3cccc(Cl)c3)c3cc(-c4c(C)noc4C)ccc3n2)c1] | 4-((3-chlorobenzyl)amino)-6-(3,5-dimethylisoxazol-4-yl)-N-((5-methylpyridin-3-yl)methyl)quinazoline-2-carboxamide, 2TFA |
| 194 | 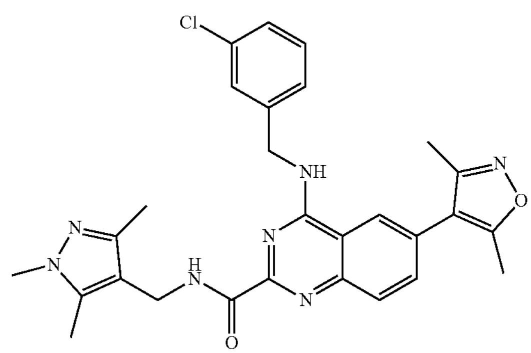 [SMILES: Cc1nn(C)c(C)c1CNC(=O)c1nc(NCc2cccc(Cl)c2)c2cc(-c3c(C)noc3C)ccc2n1] | 4-((3-chlorobenzyl)amino)-6-(3,5-dimethylisoxazol-4-yl)-N-((1,3,5-trimethyl-1H-pyrazol-4-yl)methyl)quinazoline-2-carboxamide, 2TFA |
| 195 | 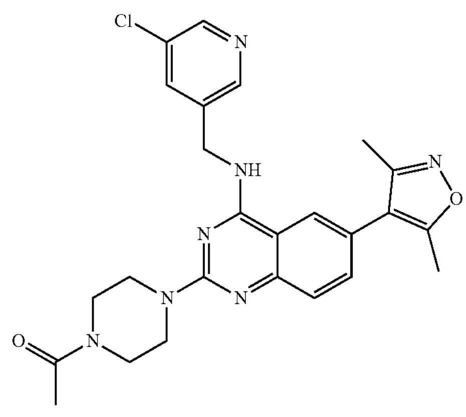 [SMILES: CC(=O)N1CCN(c2nc(NCc3cncc(Cl)c3)c3cc(-c4c(C)noc4C)ccc3n2)CC1] | 1-(4-(4-(((5-chloropyridin-3-yl)methyl)amino)-6-(3,5-dimethylisoxazol-4-yl)quinazolin-2-yl)piperazin-1-yl)ethanone, 2TFA |

TABLE 1-continued

| Example # | Structure | Compound Name |
|---|---|---|
| 196 | 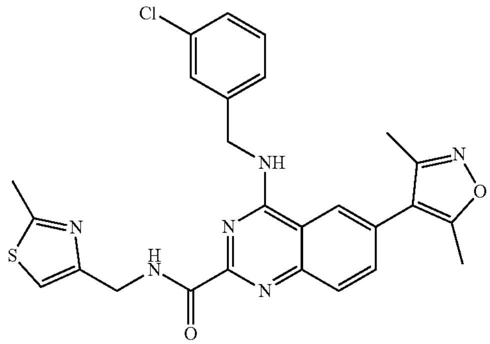 [SMILES: Cc1nc(CNC(=O)c2nc(NCc3cccc(Cl)c3)c3cc(-c4c(C)noc4C)ccc3n2)cs1] | 4-((3-chlorobenzyl)amino)-6-(3,5-dimethylisoxazol-4-yl)-N-((2-methylthiazol-4-yl)methyl)quinazoline-2-carboxamide, 2TFA |
| 197 | 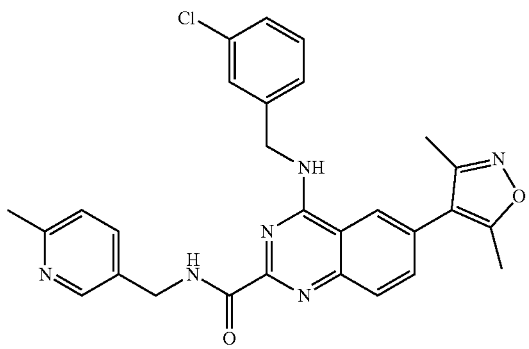 [SMILES: Cc1ccc(CNC(=O)c2nc(NCc3cccc(Cl)c3)c3cc(-c4c(C)noc4C)ccc3n2)cn1] | 4-((3-chlorobenzyl)amino)-6-(3,5-dimethylisoxazol-4-yl)-N-((6-methylpyridin-3-yl)methyl)quinazoline-2-carboxamide, 2TFA |
| 198 | 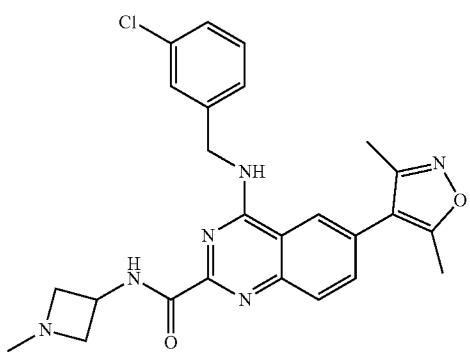 [SMILES: Cc1noc(C)c1-c1ccc2nc(C(=O)NC3CN(C)C3)nc(NCc3cccc(Cl)c3)c2c1] | 4-((3-chlorobenzyl)amino)-6-(3,5-dimethylisoxazol-4-yl)-N-(1-methylazetidin-3-yl)quinazoline-2-carboxamide, 2TFA |
| 199 | 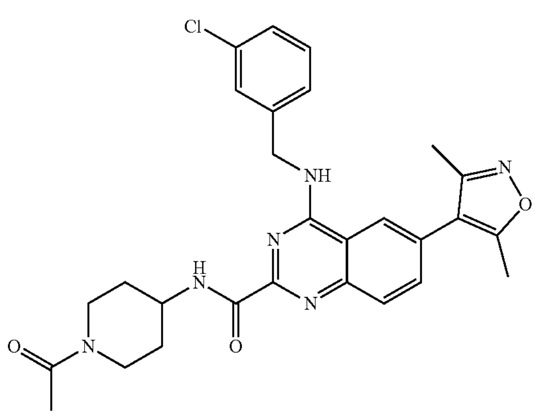 [SMILES: CC(=O)N1CCC(NC(=O)c2nc(NCc3cccc(Cl)c3)c3cc(-c4c(C)noc4C)ccc3n2)CC1] | N-(1-acetylpiperidin-4-yl)-4-((3-chlorobenzyl)amino)-6-(3,5-dimethylisoxazol-4-yl)quinazoline-2-carboxamide, 2TFA |

TABLE 1-continued

| Example # | Structure | Compound Name |
|---|---|---|
| 200 | 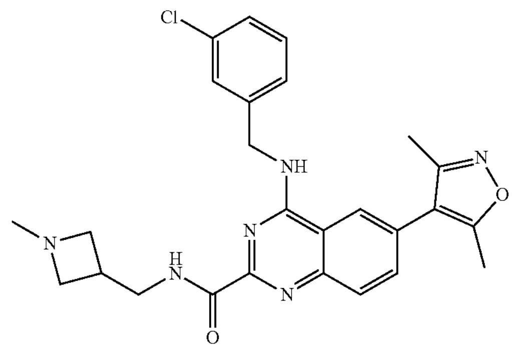 | 4-((3-chlorobenzyl)amino)-6-(3,5-dimethylisoxazol-4-yl)-N-((1-methylazetidin-3-yl)methyl)quinazoline-2-carboxamide, 2TFA |
| 201 | 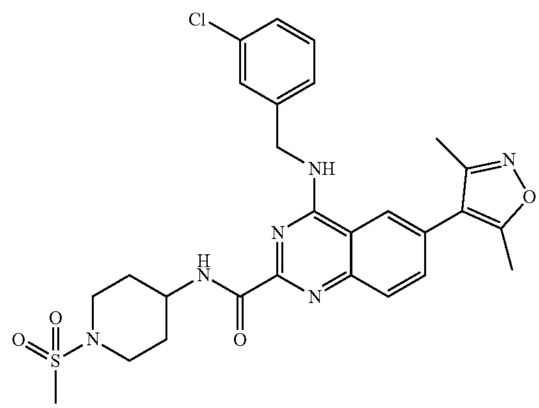 [SMILES: Cc1noc(C)c1-c1ccc2nc(C(=O)NC3CCN(S(C)(=O)=O)CC3)nc(NCc3cccc(Cl)c3)c2c1] | 4-((3-chlorobenzyl)amino)-6-(3,5-dimethylisoxazol-4-yl)-N-(1-(methylsulfonyl)piperidin-4-yl)quinazoline-2-carboxamide, 2TFA |
| 202 | 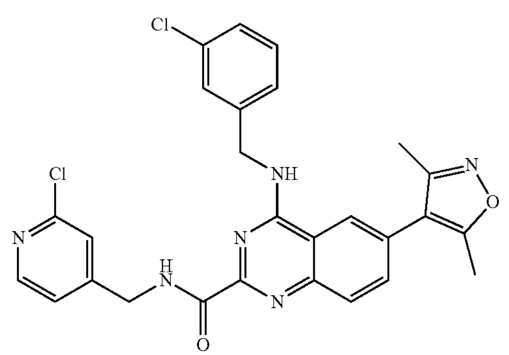 [SMILES: Cc1noc(C)c1-c1ccc2nc(C(=O)NCc3ccnc(Cl)c3)nc(NCc3cccc(Cl)c3)c2c1] | 4-((3-chlorobenzyl)amino)-N-((2-chloropyridin-4-yl)methyl)-6-(3,5-dimethylisoxazol-4-yl)quinazoline-2-carboxamide, 2TFA |
| 203 | 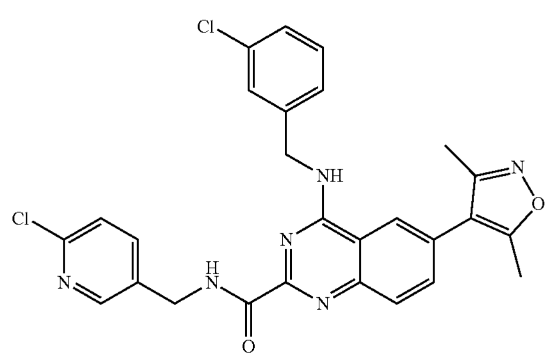 [SMILES: Cc1noc(C)c1-c1ccc2nc(C(=O)NCc3ccc(Cl)nc3)nc(NCc3cccc(Cl)c3)c2c1] | 4-((3-chlorobenzyl)amino)-N-((6-chloropyridin-3-yl)methyl)-6-(3,5-dimethylisoxazol-4-yl)quinazoline-2-carboxamide, 2TFA |

TABLE 1-continued

| Example # | Structure | Compound Name |
|---|---|---|
| 204 | 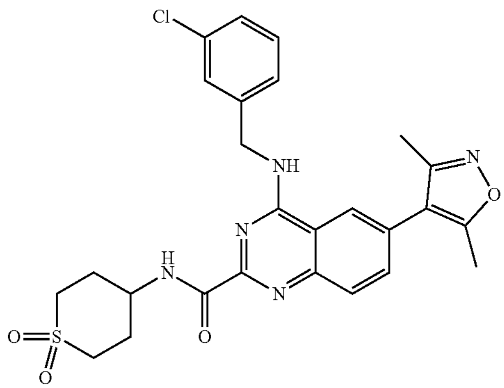 [SMILES: Cc1noc(C)c1-c1ccc2nc(C(=O)NC3CCS(=O)(=O)CC3)nc(NCc3cccc(Cl)c3)c2c1] | 4-((3-chlorobenzyl)amino)-6-(3,5-dimethylisoxazol-4-yl)-N-(1,1-dioxidotetrahydro-2H-thiopyran-4-yl)quinazoline-2-carboxamide, 2TFA |
| 205 | 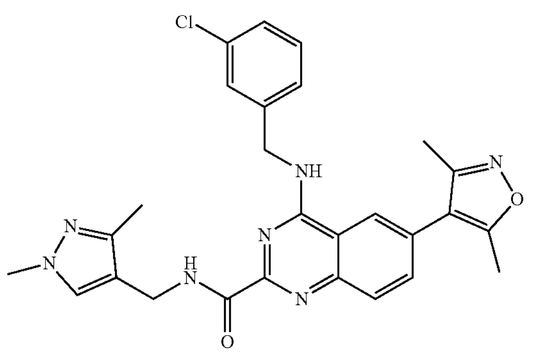 [SMILES: Cc1nn(C)cc1CNC(=O)c1nc(NCc2cccc(Cl)c2)c2cc(-c3c(C)noc3C)ccc2n1] | 4-((3-chlorobenzyl)amino)-N-((1,3-dimethyl-1H-pyrazol-4-yl)methyl)-6-(3,5-dimethylisoxazol-4-yl)quinazoline-2-carboxamide, 2TFA |
| 206 | 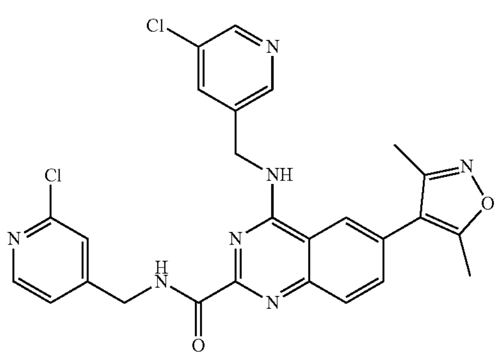 [SMILES: Cc1noc(C)c1-c1ccc2nc(C(=O)NCc3ccnc(Cl)c3)nc(NCc3cncc(Cl)c3)c2c1] | 4-(((5-chloropyridin-3-yl)methyl)amino)-N-((2-chloropyridin-4-yl)methyl)-6-(3,5-dimethylisoxazol-4-yl)quinazoline-2-carboxamide, 2TFA |
| 207 | 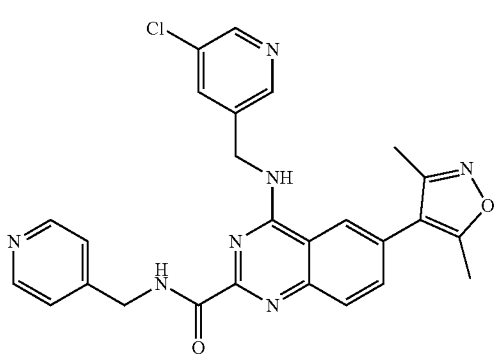 [SMILES: Cc1noc(C)c1-c1ccc2nc(C(=O)NCc3ccncc3)nc(NCc3cncc(Cl)c3)c2c1] | 4-(((5-chloropyridin-3-yl)methyl)amino)-6-(3,5-dimethylisoxazol-4-yl)-N-(pyridin-4-ylmethyl)quinazoline-2-carboxamide, 2TFA |

TABLE 1-continued

| Example # | Structure | Compound Name |
|---|---|---|
| 208 | 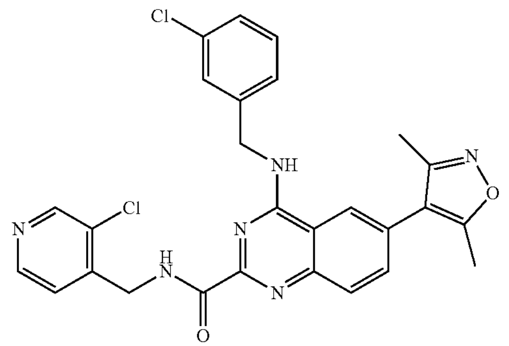 | 4-((3-chlorobenzyl)amino)-N-((3-chloropyridin-4-yl)methyl)-6-(3,5-dimethylisoxazol-4-yl)quinazoline-2-carboxamide, 2TFA |
| 209 | 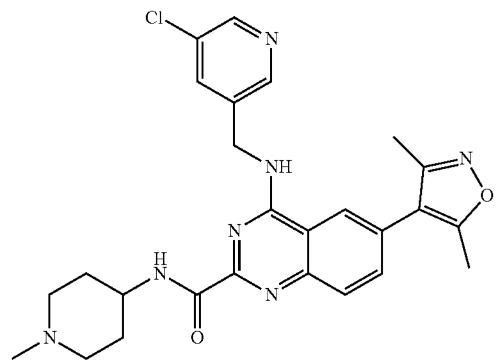 [SMILES: Cc1noc(C)c1-c1ccc2nc(C(=O)NC3CCN(C)CC3)nc(NCc3cncc(Cl)c3)c2c1] | 4-(((5-chloropyridin-3-yl)methyl)amino)-6-(3,5-dimethylisoxazol-4-yl)-N-(1-methylpiperidin-4-yl)quinazoline-2-carboxamide, 2TFA |
| 210 | 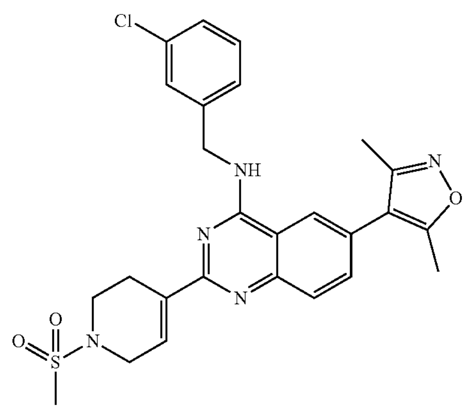 [SMILES: Cc1noc(C)c1-c1ccc2nc(C3=CCN(S(C)(=O)=O)CC3)nc(NCc3cccc(Cl)c3)c2c1] | N-(3-chlorobenzyl)-6-(3,5-dimethylisoxazol-4-yl)-2-(1-(methylsulfonyl)-1,2,3,6-tetrahydropyridin-4-yl)quinazolin-4-amine, 2TFA |
| 211 | 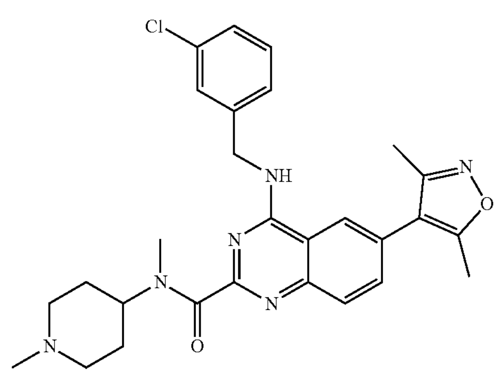 [SMILES: Cc1noc(C)c1-c1ccc2nc(C(=O)N(C)C3CCN(C)CC3)nc(NCc3cccc(Cl)c3)c2c1] | 4-((3-chlorobenzyl)amino)-6-(3,5-dimethylisoxazol-4-yl)-N-methyl-N-(1-methylpiperidin-4-yl)quinazoline-2-carboxamide, 2TFA |

TABLE 1-continued

| Example # | Structure | Compound Name |
|---|---|---|
| 212 | 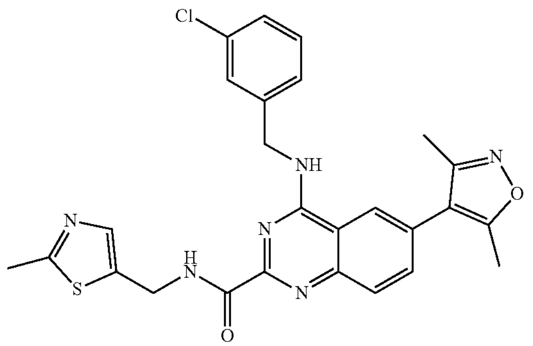 [SMILES: Cc1ncc(CNC(=O)c2nc(NCc3cccc(Cl)c3)c3cc(-c4c(C)noc4C)ccc3n2)s1] | 4-((3-chlorobenzyl)amino)-6-(3,5-dimethylisoxazol-4-yl)-N-((2-methylthiazol-5-yl)methyl)quinazoline-2-carboxamide, 2TFA |
| 213 | 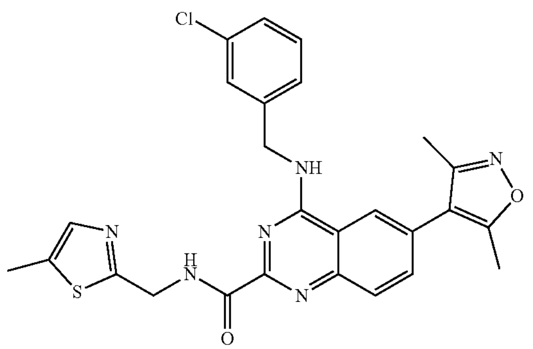 | 4-((3-chlorobenzyl)amino)-6-(3,5-dimethylisoxazol-4-yl)-N-((5-methylthiazol-2-yl)methyl)quinazoline-2-carboxamide, 2TFA |
| 214 | 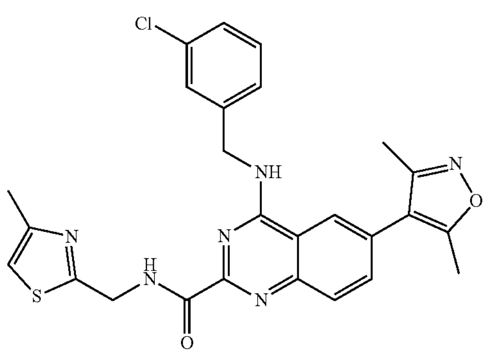 [SMILES: Cc1csc(CNC(=O)c2nc(NCc3cccc(Cl)c3)c3cc(-c4c(C)noc4C)ccc3n2)n1] | 4-((3-chlorobenzyl)amino)-6-(3,5-dimethylisoxazol-4-yl)-N-((4-methylthiazol-2-yl)methyl)quinazoline-2-carboxamide, 2TFA |
| 215 | 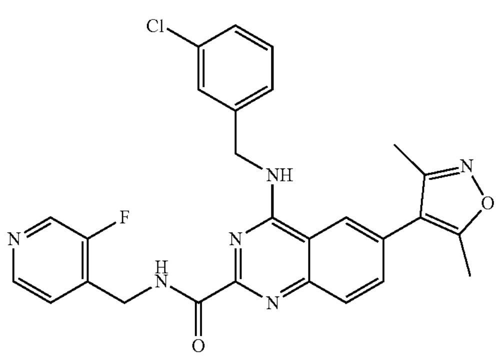 | 4-((3-chlorobenzyl)amino)-6-(3,5-dimethylisoxazol-4-yl)-N-((3-fluoropyridin-4-yl)methyl)quinazoline-2-carboxamide, 2TFA |

TABLE 1-continued

| Example # | Structure | Compound Name |
|---|---|---|
| 216 | 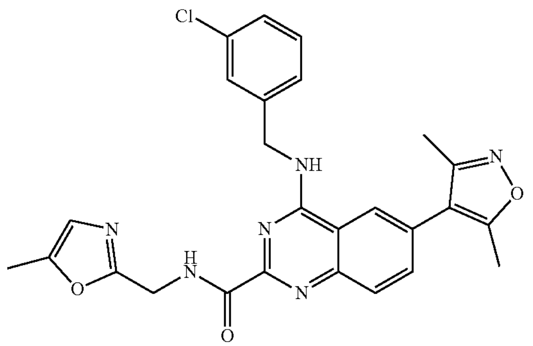 [SMILES: Cc1cnc(CNC(=O)c2nc(NCc3cccc(Cl)c3)c3cc(-c4c(C)noc4C)ccc3n2)o1] | 4-((3-chlorobenzyl)amino)-6-(3,5-dimethylisoxazol-4-yl)-N-((5-methyloxazol-2-yl)methyl)quinazoline-2-carboxamide, 2TFA |
| 217 | 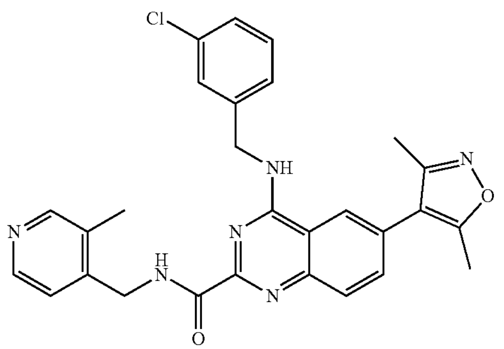 [SMILES: Cc1cnccc1CNC(=O)c1nc(NCc2cccc(Cl)c2)c2cc(-c3c(C)noc3C)ccc2n1] | 4-((3-chlorobenzyl)amino)-6-(3,5-dimethylisoxazol-4-yl)-N-((3-methylpyridin-4-yl)methyl)quinazoline-2-carboxamide, 2TFA |
| 218 | 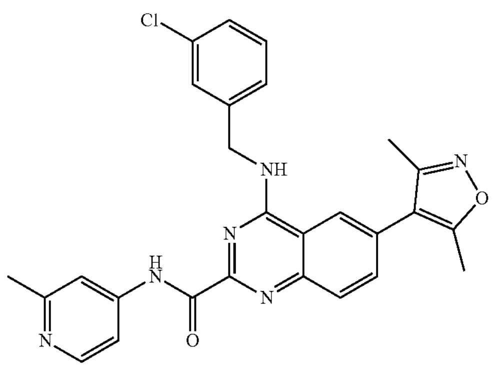 [SMILES: Cc1cc(NC(=O)c2nc(NCc3cccc(Cl)c3)c3cc(-c4c(C)noc4C)ccc3n2)ccn1] | 4-((3-chlorobenzyl)amino)-6-(3,5-dimethylisoxazol-4-yl)-N-(2-methylpyridin-4-yl)quinazoline-2-carboxamide, 2TFA |
| 219 | 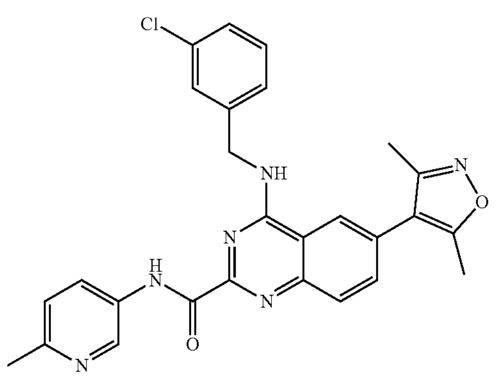 [SMILES: Cc1ccc(NC(=O)c2nc(NCc3cccc(Cl)c3)c3cc(-c4c(C)noc4C)ccc3n2)cn1] | 4-((3-chlorobenzyl)amino)-6-(3,5-dimethylisoxazol-4-yl)-N-(6-methylpyridin-3-yl)quinazoline-2-carboxamide, 2TFA |

TABLE 1-continued

| Example # | Structure | Compound Name |
|---|---|---|
| 220 | 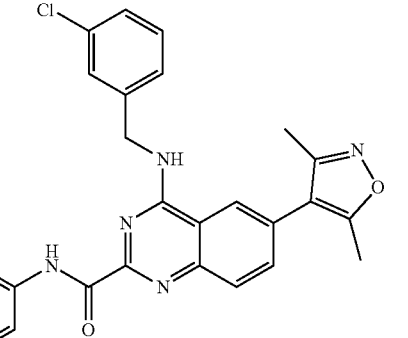 | 4-((3-chlorobenzyl)amino)-6-(3,5-dimethylisoxazol-4-yl)-N-(4-methylpyridin-3-yl)quinazoline-2-carboxamide, 2TFA |
| 221 | 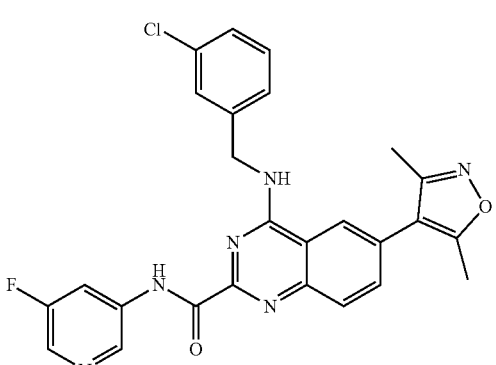 | 4-((3-chlorobenzyl)amino)-6-(3,5-dimethylisoxazol-4-yl)-N-(5-fluoropyridin-3-yl)quinazoline-2-carboxamide, 2TFA |
| 222 | 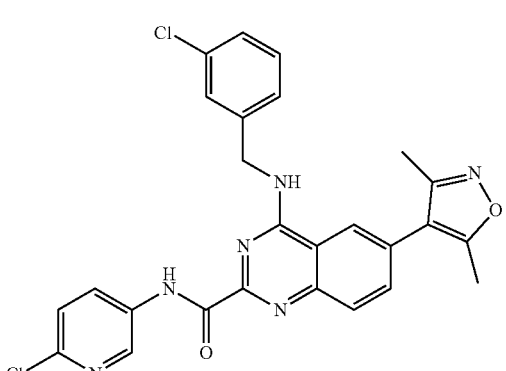 | 4-((3-chlorobenzyl)amino)-N-(6-chloropyridin-3-yl)-6-(3,5-dimethylisoxazol-4-yl)quinazoline-2-carboxamide, 2TFA |
| 223 | 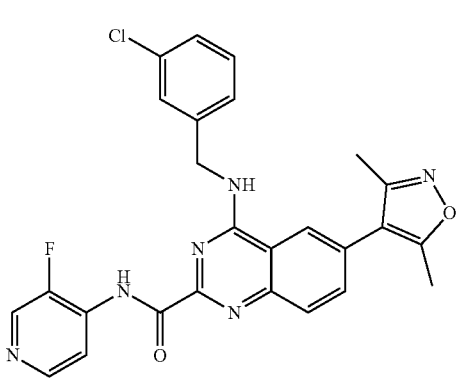 [SMILES: Cc1noc(C)c1-c1ccc2nc(C(=O)Nc3ccncc3F)nc(NCc3cccc(Cl)c3)c2c1] | 4-((3-chlorobenzyl)amino)-6-(3,5-dimethylisoxazol-4-yl)-N-(3-fluoropyridin-4-yl)quinazoline-2-carboxamide, 2TFA |

TABLE 1-continued

| Example # | Structure | Compound Name |
|---|---|---|
| 224 | 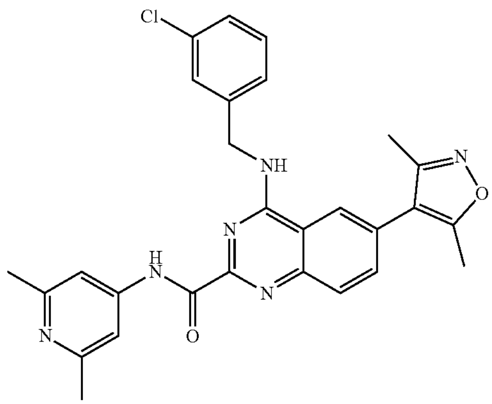 [SMILES: Cc1cc(NC(=O)c2nc(NCc3cccc(Cl)c3)c3cc(-c4c(C)noc4C)ccc3n2)cc(C)n1] | 4-((3-chlorobenzyl)amino)-6-(3,5-dimethylisoxazol-4-yl)-N-(2,6-dimethylpyridin-4-yl)quinazoline-2-carboxamide, 2TFA |
| 225 | 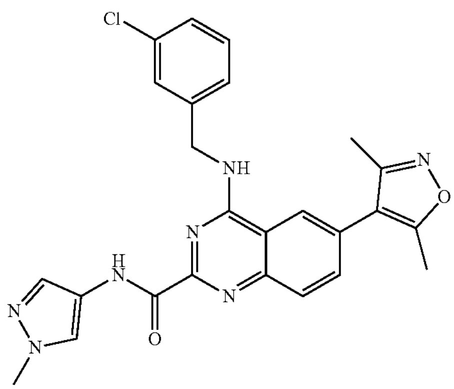 [SMILES: Cc1noc(C)c1-c1ccc2nc(C(=O)Nc3cnn(C)c3)nc(NCc3cccc(Cl)c3)c2c1] | 4-((3-chlorobenzyl)amino)-6-(3,5-dimethylisoxazol-4-yl)-N-(1-methyl-1H-pyrazol-4-yl)quinazoline-2-carboxamide, 2TFA |
| 226 | 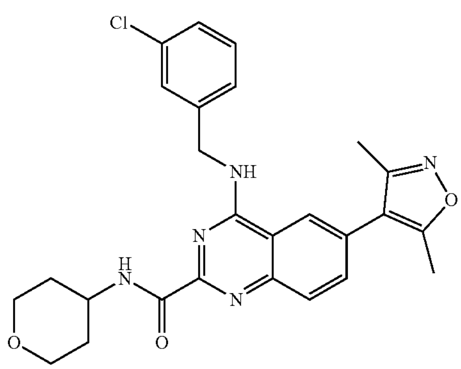 [SMILES: Cc1noc(C)c1-c1ccc2nc(C(=O)NC3CCOCC3)nc(NCc3cccc(Cl)c3)c2c1] | 4-((3-chlorobenzyl)amino)-6-(3,5-dimethylisoxazol-4-yl)-N-(tetrahydro-2H-pyran-4-yl)quinazoline-2-carboxamide, 2TFA |
| 227 | 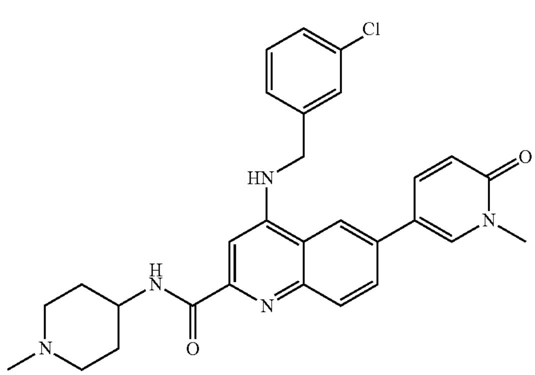 [SMILES: CN1CCC(NC(=O)c2cc(NCc3cccc(Cl)c3)c3cc(-c4ccc(=O)n(C)c4)ccc3n2)CC1] | 4-((3-chlorobenzyl)amino)-6-(1-methyl-6-oxo-1,6-dihydropyridin-3-yl)-N-(1-methylpiperidin-4-yl)quinoline-2-carboxamide, 2TFA |

TABLE 1-continued

| Example # | Structure | Compound Name |
|---|---|---|
| 228 | 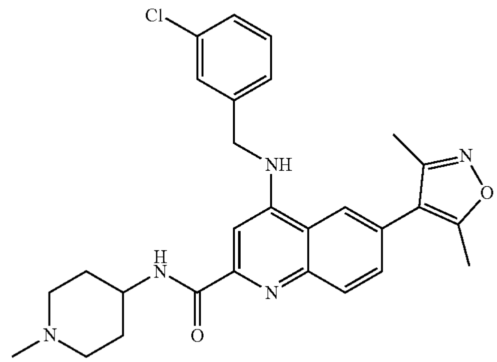 [SMILES: Cc1noc(C)c1-c1ccc2nc(C(=O)NC3CCN(C)CC3)cc(NCc3cccc(Cl)c3)c2c1] | 4-((3-chlorobenzyl)amino)-6-(3,5-dimethylisoxazol-4-yl)-N-(1-methylpiperidin-4-yl)quinoline-2-carboxamide, 2TFA |
| 229 | 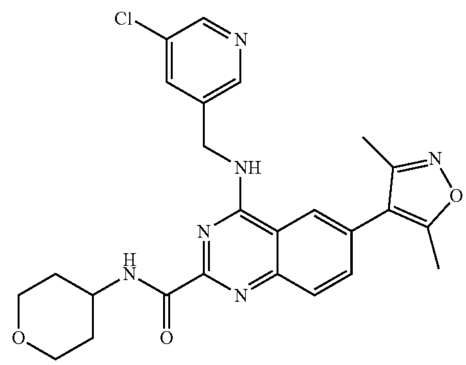 [SMILES: Cc1noc(C)c1-c1ccc2nc(C(=O)NC3CCOCC3)nc(NCc3cncc(Cl)c3)c2c1] | 4-(((5-chloropyridin-3-yl)methyl)amino)-6-(3,5-dimethylisoxazol-4-yl)-N-(tetrahydro-2H-pyran-4-yl)quinazoline-2-carboxamide, 2TFA |
| 230 | 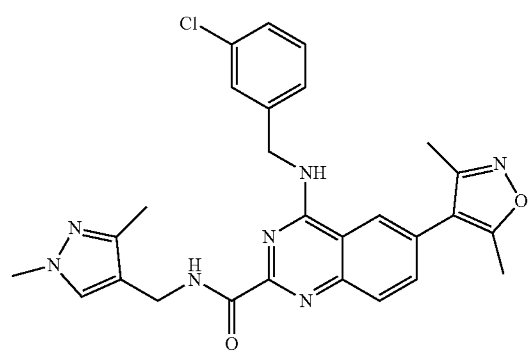 [SMILES: Cc1nn(C)cc1CNC(=O)c1nc(NCc2cccc(Cl)c2)c2cc(-c3c(C)noc3C)ccc2n1] | 4-((3-chlorobenzyl)amino)-N-((1,3-dimethyl-1H-pyrazol-4-yl)methyl)-6-(3,5-dimethylisoxazol-4-yl)quinoline-2-carboxamide, 2TFA |
| 231 | 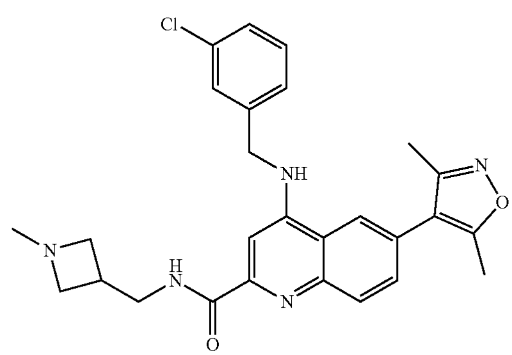 [SMILES: Cc1noc(C)c1-c1ccc2nc(C(=O)NCC3CN(C)C3)nc(NCc3cncc(Cl)c3)c2c1] | 4-((3-chlorobenzyl)amino)-6-(3,5-dimethylisoxazol-4-yl)-N-((1-methylazetidin-3-yl)methyl)quinoline-2-carboxamide, 2TFA |

TABLE 1-continued

| Example # | Structure | Compound Name |
|---|---|---|
| 232 | 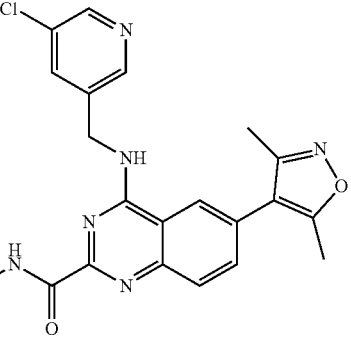 | 4-(((5-chloropyridin-3-yl)methyl)amino)-6-(3,5-dimethylisoxazol-4-yl)-N-((1-methyl-1H-imidazol-5-yl)methyl)quinazoline-2-carboxamide, 2TFA |
| 233 | 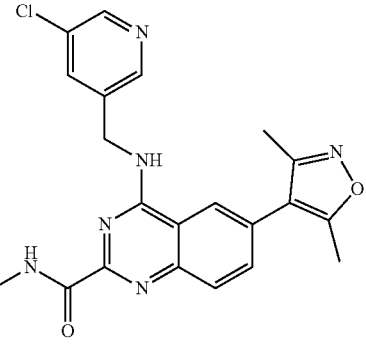 | 4-(((5-chloropyridin-3-yl)methyl)amino)-6-(3,5-dimethylisoxazol-4-yl)-N-((1-methylazetidin-3-yl)methyl)quinazoline-2-carboxamide, 2TFA |
| 234 | 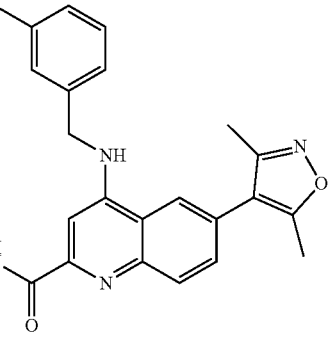 | 4-((3-chlorobenzyl)amino)-6-(3,5-dimethylisoxazol-4-yl)-N-(1-methylazetidin-3-yl)quinoline-2-carboxamide, 2TFA |
| 235 | 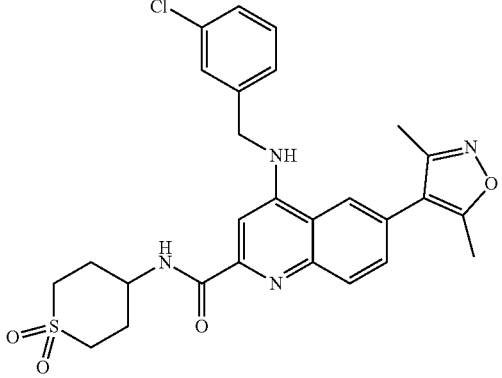 [SMILES: Cc1noc(C)c1-c1ccc2nc(C(=O)NC3CCS(=O)(=O)CC3)cc(NCc3cccc(Cl)c3)c2c1] | 4-((3-chlorobenzyl)amino)-6-(3,5-dimethylisoxazol-4-yl)-N-(1,1-dioxidotetrahydro-2H-thiopyran-4-yl)quinoline-2-carboxamide, 2TFA |

TABLE 1-continued

| Example # | Structure | Compound Name |
|---|---|---|
| 236 | 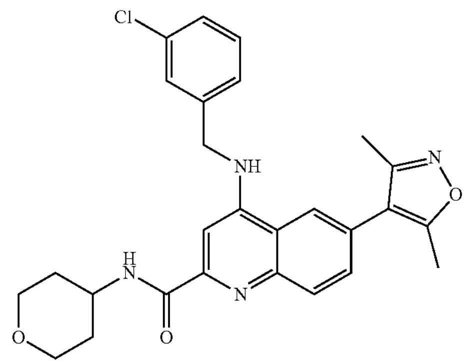 | 4-((3-chlorobenzyl)amino)-6-(3,5-dimethylisoxazol-4-yl)-N-(tetrahydro-2H-pyran-4-yl)quinoline-2-carboxamide, 2TFA |
| 237 | 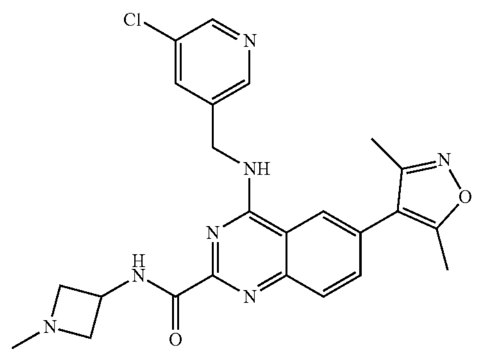 [SMILES: Cc1noc(C)c1-c1ccc2nc(C(=O)NC3CN(C)C3)nc(NCc3cncc(Cl)c3)c2c1] | 4-(((5-chloropyridin-3-yl)methyl)amino)-6-(3,5-dimethylisoxazol-4-yl)-N-(1-methylazetidin-3-yl)quinazoline-2-carboxamide, 2TFA |
| 238 | 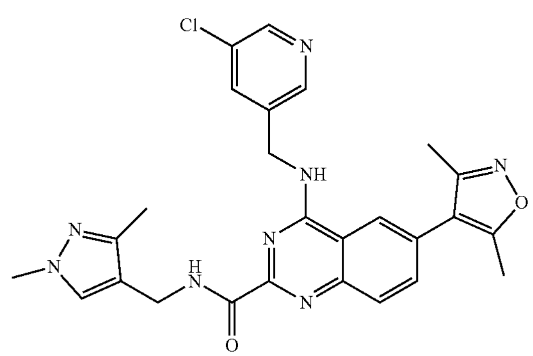 [SMILES: Cc1nn(C)cc1CNC(=O)c1nc(NCc2cncc(Cl)c2)c2cc(-c3c(C)noc3C)ccc2n1] | 4-(((5-chloropyridin-3-yl)methyl)amino)-N-((1,3-dimethyl-1H-pyrazol-4-yl)methyl)-6-(3,5-dimethylisoxazol-4-yl)quinazoline-2-carboxamide, 2TFA |
| 239 | 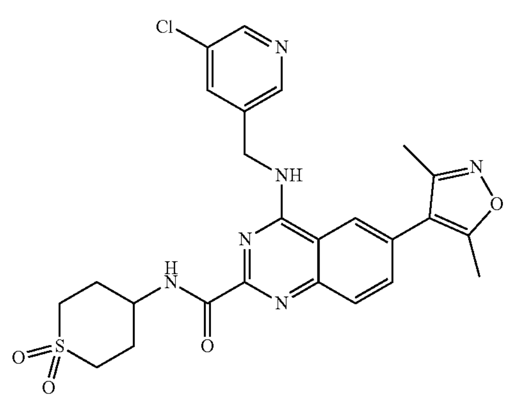 [SMILES: Cc1noc(C)c1-c1ccc2nc(C(=O)NC3CCS(=O)(=O)CC3)nc(NCc3cncc(Cl)c3)c2c1] | 4-(((5-chloropyridin-3-yl)methyl)amino)-6-(3,5-dimethylisoxazol-4-yl)-N-(1,1-dioxidotetrahydro-2H-thiopyran-4-yl)quinazoline-2-carboxamide, 2TFA |

TABLE 1-continued

| Example # | Structure | Compound Name |
|---|---|---|
| 240 | 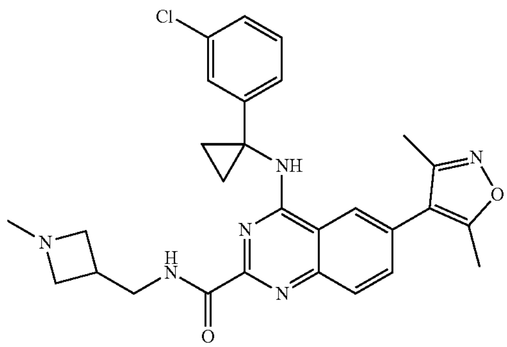 [SMILES: Cc1noc(C)c1-c1ccc2nc(C(=O)NCC3CN(C)C3)nc(NC3(c4cccc(Cl)c4)CC3)c2c1] | 4-((1-(3-chlorophenyl)cyclopropyl)amino)-6-(3,5-dimethylisoxazol-4-yl)-N-((1-methylazetidin-3-yl)methyl)quinazoline-2-carboxamide, 2TFA |
| 241 | 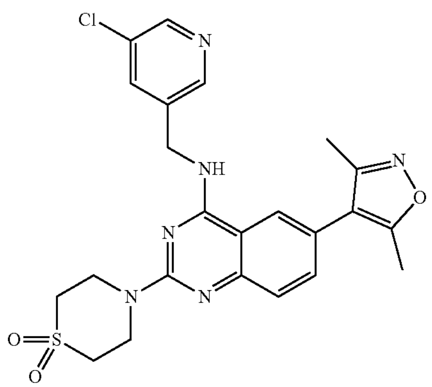 [SMILES: Cc1noc(C)c1-c1ccc2nc(N3CCS(=O)(=O)CC3)nc(NCc3cncc(Cl)c3)c2c1] | 4-(4-(((5-chloropyridin-3-yl)methyl)amino)-6-(3,5-dimethylisoxazol-4-yl)quinazolin-2-yl)thiomorpholine 1,1-dioxide, 2TFA |
| 242 | 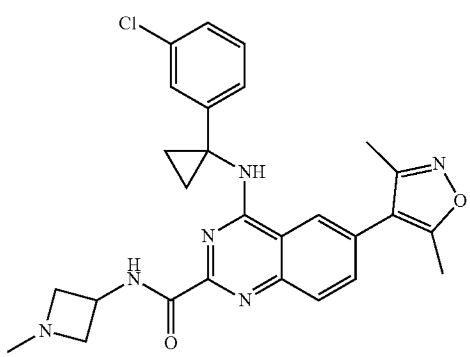 [SMILES: Cc1noc(C)c1-c1ccc2nc(C(=O)NC3CN(C)C3)nc(NC3(c4cccc(Cl)c4)CC3)c2c1] | 4-((1-(3-chlorophenyl)cyclopropyl)amino)-6-(3,5-dimethylisoxazol-4-yl)-N-(1-methylazetidin-3-yl)quinazoline-2-carboxamide, 2TFA |
| 243 | 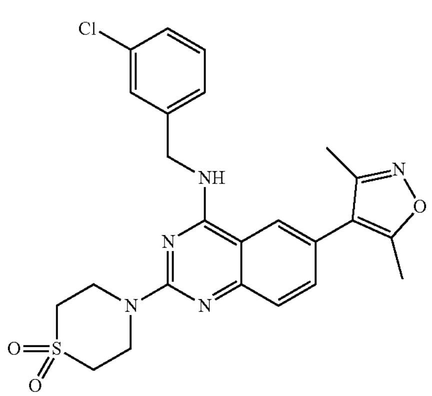 [SMILES: Cc1noc(C)c1-c1ccc2nc(N3CCS(=O)(=O)CC3)nc(NCc3cccc(Cl)c3)c2c1] | 4-(4-((3-chlorobenzyl)amino)-6-(3,5-dimethylisoxazol-4-yl)quinazolin-2-yl)thiomorpholine 1,1-dioxide, 2TFA |

TABLE 1-continued

| Example # | Structure | Compound Name |
|---|---|---|
| 244 | 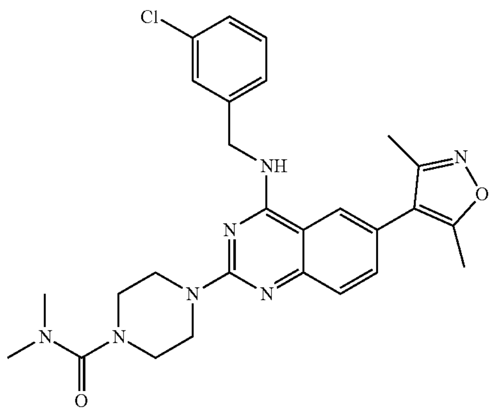 [SMILES: Cc1noc(C)c1-c1ccc2nc(N3CCN(C(=O)N(C)C)CC3)nc(NCc3cccc(Cl)c3)c2c1] | 4-(4-((3-chlorobenzyl)amino)-6-(3,5-dimethylisoxazol-4-yl)quinazolin-2-yl)-N,N-dimethylpiperazine-1-carboxamide, 2TFA |
| 245 | 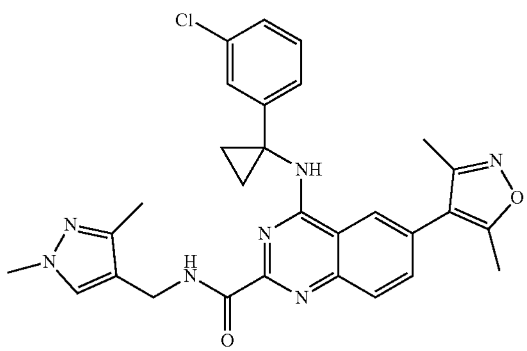 [SMILES: Cc1nn(C)cc1CNC(=O)c1nc(NC2(c3cccc(Cl)c3)CC2)c2cc(-c3c(C)noc3C)ccc2n1] | 4-((1-(3-chlorophenyl)cyclopropyl)amino)-N-((1,3-dimethyl-1H-pyrazol-4-yl)methyl)-6-(3,5-dimethylisoxazol-4-yl)quinazoline-2-carboxamide, 2TFA |
| 246 | 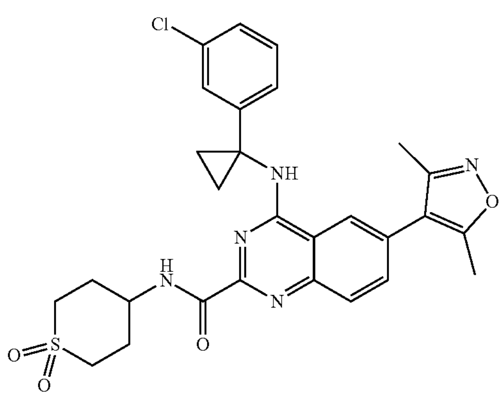 [SMILES: Cc1noc(C)c1-c1ccc2nc(C(=O)NC3CCS(=O)(=O)CC3)nc(NC3(c4cccc(Cl)c4)CC3)c2c1] | 4-((1-(3-chlorophenyl)cyclopropyl)amino)-6-(3,5-dimethylisoxazol-4-yl)-N-(1,1-dioxidotetrahydro-2H-thiopyran-4-yl)quinazoline-2-carboxamide, 2TFA |
| 247 | 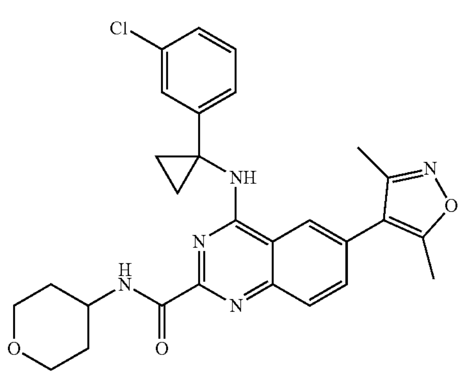 [SMILES: Cc1noc(C)c1-c1ccc2nc(C(=O)NC3CCOCC3)nc(NC3(c4cccc(Cl)c4)CC3)c2c1] | 4-((1-(3-chlorophenyl)cyclopropyl)amino)-6-(3,5-dimethylisoxazol-4-yl)-N-(tetrahydro-2H-pyran-4-yl)quinazoline-2-carboxamide, 2TFA |

TABLE 1-continued

| Example # | Structure | Compound Name |
|---|---|---|
| 248 | 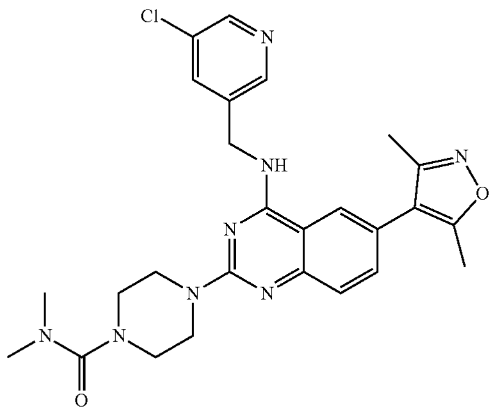 [SMILES: Cc1noc(C)c1-c1ccc2nc(N3CCN(C(=O)N(C)C)CC3)nc(NCc3cncc(Cl)c3)c2c1] | 4-(4-(((5-chloropyridin-3-yl)methyl)amino)-6-(3,5-dimethylisoxazol-4-yl)quinazolin-2-yl)-N,N-dimethylpiperazine-1-carboxamide, 2TFA |
| 249 | 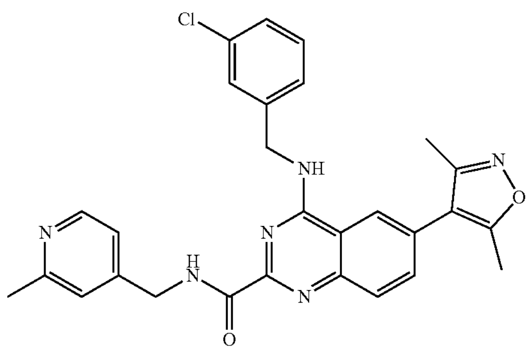 [SMILES: Cc1cc(CNC(=O)c2nc(NCc3cccc(Cl)c3)c3cc(-c4c(C)noc4C)ccc3n2)ccn1] | 4-((3-chlorobenzyl)amino)-6-(3,5-dimethylisoxazol-4-yl)-N-((2-methylpyridin-4-yl)methyl)quinazoline-2-carboxamide, 2TFA |
| 250 | 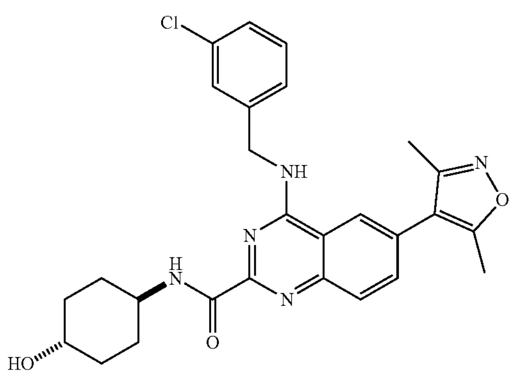 | 4-((3-chlorobenzyl)amino)-6-(3,5-dimethylisoxazol-4-yl)-N-((1r,4r)-4-hydroxycyclohexyl)quinazoline-2-carboxamide, 2TFA |
| 251 | 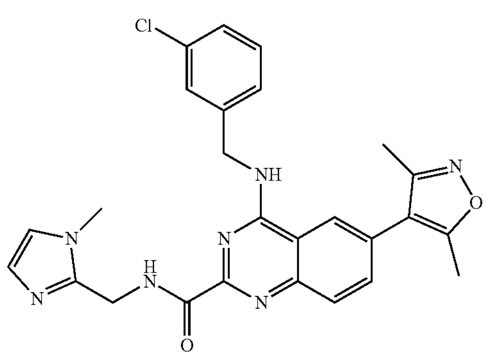 [SMILES: Cc1noc(C)c1-c1ccc2nc(C(=O)NCc3nccn3C)nc(NCc3cccc(Cl)c3)c2c1] | 4-((3-chlorobenzyl)amino)-6-(3,5-dimethylisoxazol-4-yl)-N-((1-methyl-1H-imidazol-2-yl)methyl)quinazoline-2-carboxamide, 2TFA |

TABLE 1-continued

| Example # | Structure | Compound Name |
|---|---|---|
| 252 | 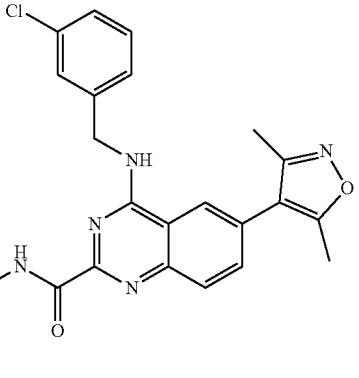 | 4-((3-chlorobenzyl)amino)-N-(4,4-difluorocyclohexyl)-6-(3,5-dimethylisoxazol-4-yl)quinazoline-2-carboxamide, 2TFA |
| 253 | 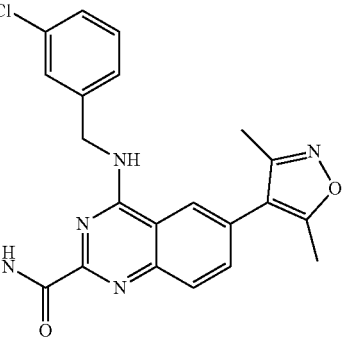 | 4-((3-chlorobenzyl)amino)-6-(3,5-dimethylisoxazol-4-yl)-N-((1r,3r)-3-hydroxycyclobutyl)quinazoline-2-carboxamide, 2TFA |
| 254 | 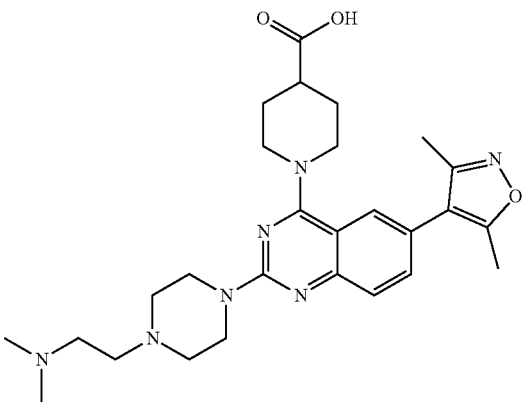 [SMILES: Cc1noc(C)c1-c1ccc2nc(N3CCN(CCN(C)C)CC3)nc(N3CCC(C(=O)O)CC3)c2c1] | 1-(2-(4-(2-(dimethylamino)ethyl)piperazin-1-yl)-6-(3,5-dimethylisoxazol-4-yl)quinazolin-4-yl)piperidine-4-carboxylic acid, 2TFA |
| 255 | 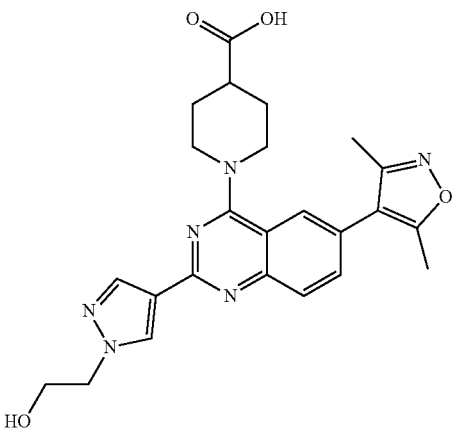 [SMILES: Cc1noc(C)c1-c1ccc2nc(-c3cnn(CCO)c3)nc(N3CCC(C(=O)O)CC3)c2c1] | 1-(6-(3,5-dimethylisoxazol-4-yl)-2-(1-(2-hydroxyethyl)-1H-pyrazol-4-yl)quinazolin-4-yl)piperidine-4-carboxylic acid, 2TFA |

TABLE 1-continued

| Example # | Structure | Compound Name |
|---|---|---|
| 256 | 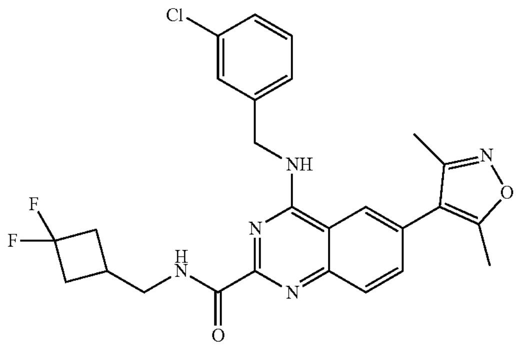 [SMILES: Cc1noc(C)c1-c1ccc2nc(C(=O)NCC3CC(F)(F)C3)nc(NCc3cccc(Cl)c3)c2c1] | 4-((3-chlorobenzyl)amino)-N-((3,3-difluorocyclobutyl)methyl)-6-(3,5-dimethylisoxazol-4-yl)quinazoline-2-carboxamide, 2TFA |
| 257 | 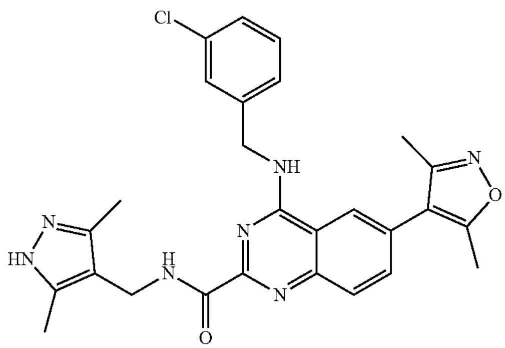 [SMILES: Cc1n[nH]c(C)c1CNC(=O)c1nc(NCc2cccc(Cl)c2)c2cc(-c3c(C)noc3C)ccc2n1] | 4-((3-chlorobenzyl)amino)-N-((3,5-dimethyl-1H-pyrazol-4-yl)methyl)-6-(3,5-dimethylisoxazol-4-yl)quinazoline-2-carboxamide, 2TFA |
| 258 | 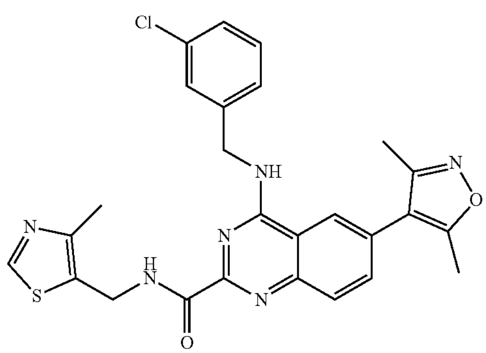 [SMILES: Cc1ncsc1CNC(=O)c1nc(NCc2cccc(Cl)c2)c2cc(-c3c(C)noc3C)ccc2n1] | 4-((3-chlorobenzyl)amino)-6-(3,5-dimethylisoxazol-4-yl)-N-((4-methylthiazol-5-yl)methyl)quinazoline-2-carboxamide, 2TFA |
| 259 | 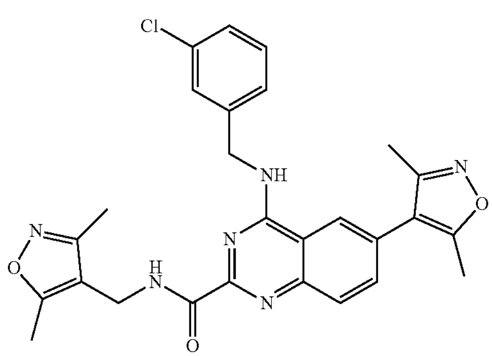 [SMILES: Cc1noc(C)c1CNC(=O)c1nc(NCc2cccc(Cl)c2)c2cc(-c3c(C)noc3C)ccc2n1] | 4-((3-chlorobenzyl)amino)-6-(3,5-dimethylisoxazol-4-yl)-N-((3,5-dimethylisoxazol-4-yl)methyl)quinazoline-2-carboxamide, 2TFA |

TABLE 1-continued

| Example # | Structure | Compound Name |
|---|---|---|
| 260 | 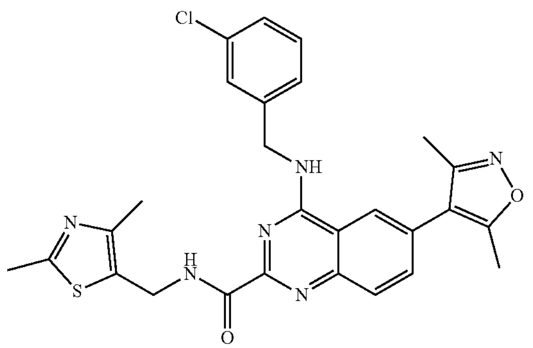 [SMILES: Cc1nc(C)c(CNC(=O)c2nc(NCc3cccc(Cl)c3)c3cc(-c4c(C)noc4C)ccc3n2)s1] | 4-((3-chlorobenzyl)amino)-6-(3,5-dimethylisoxazol-4-yl)-N-((2,4-dimethylthiazol-5-yl)methyl)quinazoline-2-carboxamide, 2TFA |
| 261 | 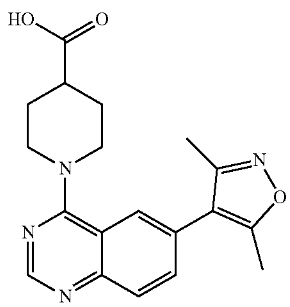 [SMILES: Cc1noc(C)c1-c1ccc2ncnc(N3CCC(C(=O)O)CC3)c2c1] | 1-(6-(3,5-dimethylisoxazol-4-yl)quinazolin-4-yl)piperidine-4-carboxylic acid |
| 262 | 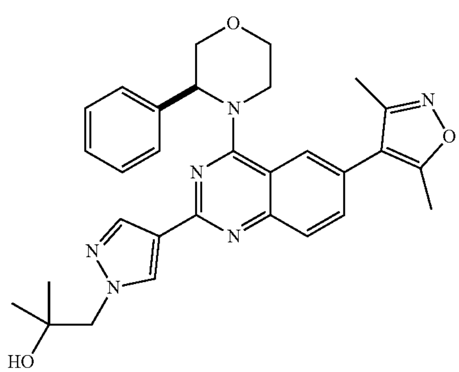 [SMILES: Cc1noc(C)c1-c1ccc2nc(-c3cnn(CC(C)(C)O)c3)nc(N3CCOC[C@@H]3c3ccccc3)c2c1] | (S)-1-(4-(6-(3,5-dimethylisoxazol-4-yl)-4-(3-phenylmorpholino)quinazolin-2-yl)-1H-pyrazol-1-yl)-2-methylpropan-2-ol, 2TFA |
| 263 | 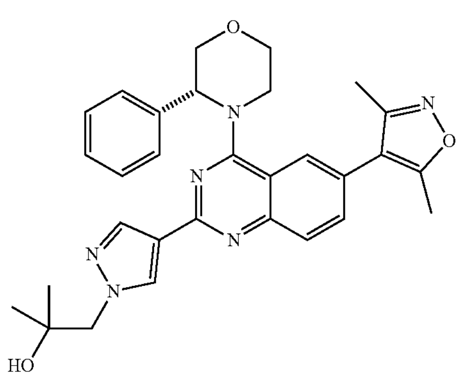 [SMILES: Cc1noc(C)c1-c1ccc2nc(-c3cnn(CC(C)(C)O)c3)nc(N3CCOC[C@H]3c3ccccc3)c2c1] | (R)-1-(4-(6-(3,5-dimethylisoxazol-4-yl)-4-(3-phenylmorpholino)quinazolin-2-yl)-1H-pyrazol-1-yl)-2-methylpropan-2-ol, 2TFA |

TABLE 1-continued

| Example # | Structure | Compound Name |
|---|---|---|
| 264 | 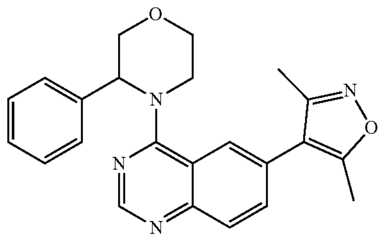 [SMILES: Cc1noc(C)c1-c1ccc2ncnc(N3CCOCC3c3ccccc3)c2c1] | 4-(6-(3,5-dimethylisoxazol-4-yl)quinazolin-4-yl)-3-phenylmorpholine, 2TFA |
| 265 | 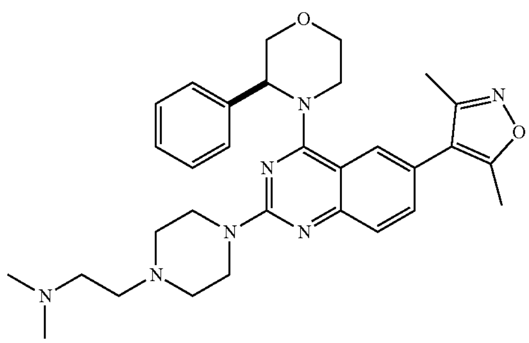 [SMILES: Cc1noc(C)c1-c1ccc2nc(N3CCN(CCN(C)C)CC3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)piperazin-1-yl)-N,N-dimethylethanamine, 2TFA |
| 266 | 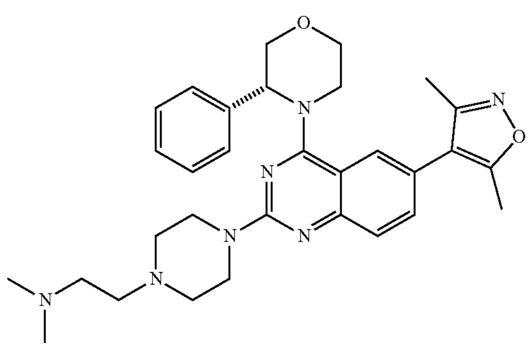 [SMILES: Cc1noc(C)c1-c1ccc2nc(N3CCN(CCN(C)C)CC3)nc(N3CCOC[C@H]3c3ccccc3)c2c1] | (R)-2-(4-(6-(3,5-dimethylisoxazol-4-yl)-4-(3-phenylmorpholino)quinazolin-2-yl)piperazin-1-yl)-N,N-dimethylethanamine, 2TFA |
| 267 | 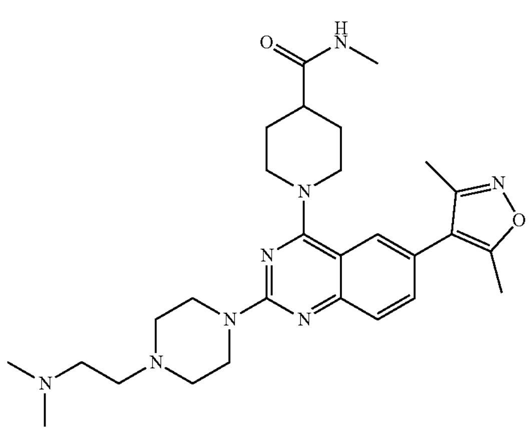 [SMILES: CNC(=O)C1CCN(c2nc(N3CCN(CCN(C)C)CC3)nc3ccc(-c4c(C)noc4C)cc23)CC1] | 1-(2-(4-(2-(dimethylamino)ethyl)piperazin-1-yl)-6-(3,5-dimethylisoxazol-4-yl)quinazolin-4-yl)-N-methylpiperidine-4-carboxamide, 2TFA |

TABLE 1-continued

| Example # | Structure | Compound Name |
|---|---|---|
| 268 | 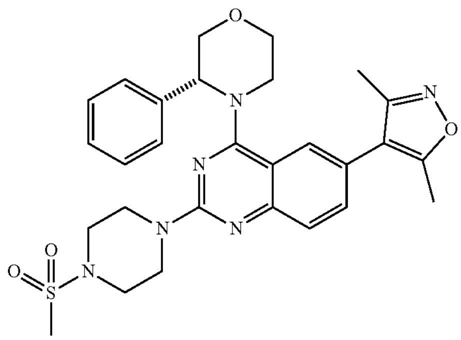 [SMILES: Cc1noc(C)c1-c1ccc2nc(N3CCN(S(C)(=O)=O)CC3)nc(N3CCOC[C@H]3c3ccccc3)c2c1] | (R)-4-(6-(3,5-dimethylisoxazol-4-yl)-2-(4-(methylsulfonyl)piperazin-1-yl)quinazolin-4-yl)-3-phenylmorpholine, 2TFA |
| 269 | 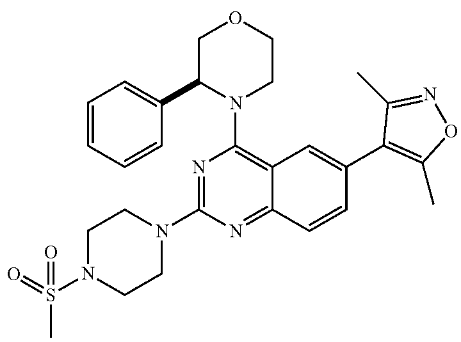 [SMILES: Cc1noc(C)c1-c1ccc2nc(N3CCN(S(C)(=O)=O)CC3)nc(N3CCOC[C@@H]3c3ccccc3)c2c1] | (S)-4-(6-(3,5-dimethylisoxazol-4-yl)-2-(4-(methylsulfonyl)piperazin-1-yl)quinazolin-4-yl)-3-phenylmorpholine, 2TFA |
| 270 | 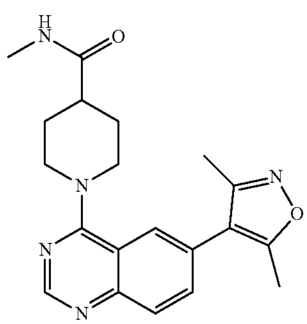 [SMILES: CNC(=O)C1CCN(c2ncnc3ccc(-c4c(C)noc4C)cc23)CC1] | 1-(6-(3,5-dimethylisoxazol-4-yl)quinazolin-4-yl)-N-methylpiperidine-4-carboxamide, 2TFA |
| 271 | 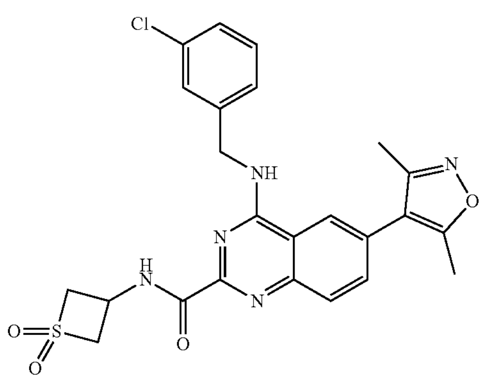 [SMILES: Cc1noc(C)c1-c1ccc2nc(C(=O)NC3CS(=O)(=O)C3)nc(NCc3cccc(Cl)c3)c2c1] | 4-((3-chlorobenzyl)amino)-6-(3,5-dimethylisoxazol-4-yl)-N-(1,1-dioxidothietan-3-yl)quinazoline-2-carboxamide, TFA |

TABLE 1-continued

| Example # | Structure | Compound Name |
|---|---|---|
| 272 | 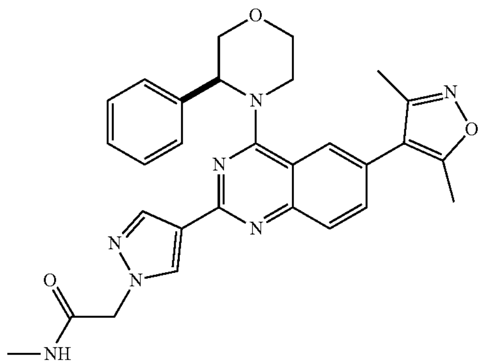 [SMILES: CNC(=O)Cn1cc(-c2nc(N3CCOC[C@@H]3c3ccccc3)c3cc(-c4c(C)noc4C)ccc3n2)cn1] | (S)-2-(4-(6-(3,5-dimethylisoxazol-4-yl)-4-(3-phenylmorpholino)quinazolin-2-yl)-1H-pyrazol-1-yl)-N-methylacetamide |
| 273 | 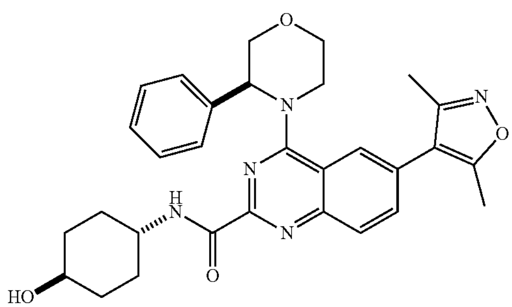 | 6-(3,5-dimethylisoxazol-4-yl)-N-((1r,4S)-4-hydroxycyclohexyl)-4-((S)-3-phenylmorpholino)quinazoline-2-carboxamide, TFA |
| 274 | 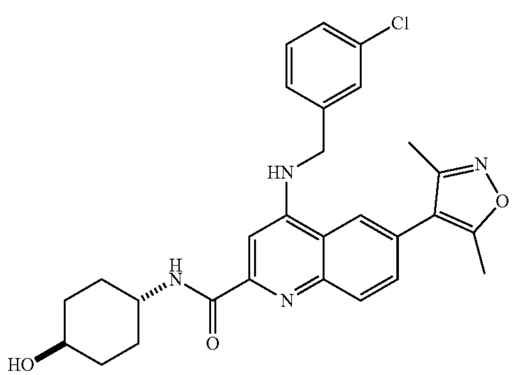 | 4-((3-chlorobenzyl)amino)-6-(3,5-dimethylisoxazol-4-yl)-N-((1r,4r)-4-hydroxycyclohexyl)quinoline-2-carboxamide, TFA |
| 275 | 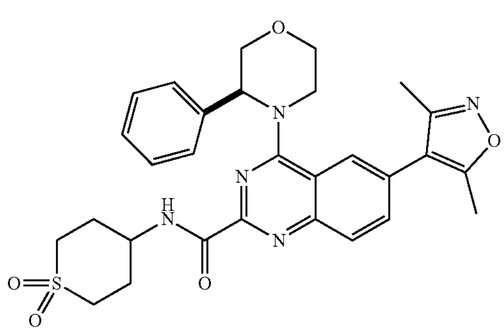 [SMILES: Cc1noc(C)c1-c1ccc2nc(C(=O)NC3CCS(=O)(=O)CC3)nc(N3CCOC[C@@H]3c3ccccc3)c2c1] | (S)-6-(3,5-dimethylisoxazol-4-yl)-N-(1,1-dioxidotetrahydro-2H-thiopyran-4-yl)-4-(3-phenylmorpholino)quinazoline-2-carboxamide, TFA |

TABLE 1-continued

| Example # | Structure | Compound Name |
|---|---|---|
| 276 | 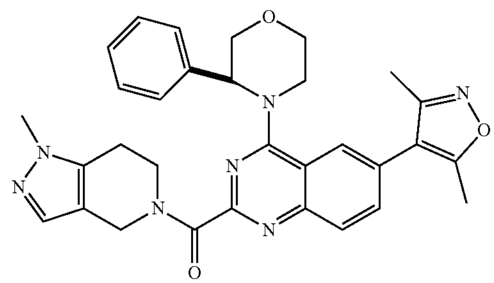 | (S)-(6-(3,5-dimethylisoxazol-4-yl)-4-(3-phenylmorpholino)quinazolin-2-yl)(1-methyl-1,4,6,7-tetrahydro-5H-pyrazolo[4,3-c]pyridin-5-yl)methanone, TFA |
| 277 | 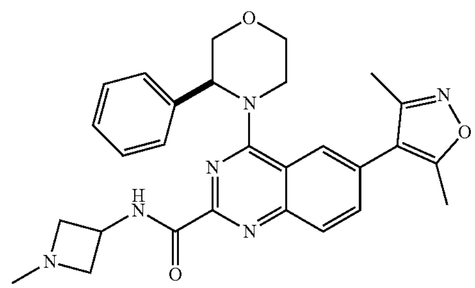 [SMILES: Cc1noc(C)c1-c1ccc2nc(C(=O)NC3CN(C)C3)nc(N3CCOC[C@@H]3c3ccccc3)c2c1] | (S)-6-(3,5-dimethylisoxazol-4-yl)-N-(1-methylazetidin-3-yl)-4-(3-phenylmorpholino)quinazoline-2-carboxamide, TFA |
| 278 | 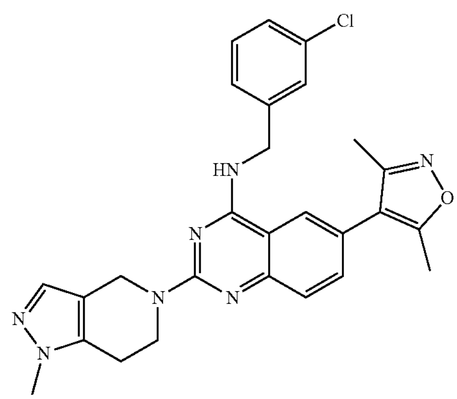 [SMILES: Cc1noc(C)c1-c1ccc2nc(N3CCc4c(cnn4C)C3)nc(NCc3cccc(Cl)c3)c2c1] | N-(3-chlorobenzyl)-6-(3,5-dimethylisoxazol-4-yl)-2-(1-methyl-1,4,6,7-tetrahydro-5H-pyrazolo[4,3-c]pyridin-5-yl)quinazolin-4-amine |
| 279 | 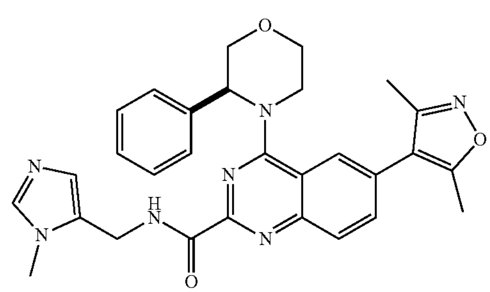 [SMILES: Cc1noc(C)c1-c1ccc2nc(C(=O)NCc3cncn3C)nc(N3CCOC[C@@H]3c3ccccc3)c2c1] | (S)-6-(3,5-dimethylisoxazol-4-yl)-N-((1-methyl-1H-imidazol-5-yl)methyl)-4-(3-phenylmorpholino)quinazoline-2-carboxamide, TFA |
| 280 | 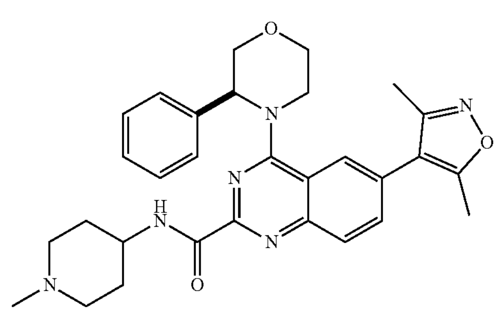 [SMILES: Cc1noc(C)c1-c1ccc2nc(C(=O)NC3CCN(C)CC3)nc(N3CCOC[C@@H]3c3ccccc3)c2c1] | (S)-6-(3,5-dimethylisoxazol-4-yl)-N-(1-methylpiperidin-4-yl)-4-(3-phenylmorpholino)quinazoline-2-carboxamide, TFA |

TABLE 1-continued

| Example # | Structure | Compound Name |
|---|---|---|
| 281 | 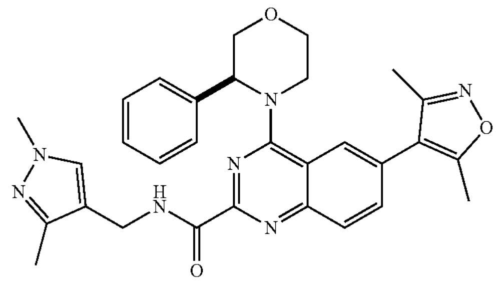 [SMILES: Cc1nn(C)cc1CNC(=O)c1nc(N2CCOC[C@@H]2c2ccccc2)c2cc(-c3c(C)noc3C)ccc2n1] | (S)-N-((1,3-dimethyl-1H-pyrazol-4-yl)methyl)-6-(3,5-dimethylisoxazol-4-yl)-4-(3-phenylmorpholino)quinazoline-2-carboxamide, TFA |
| 282 | 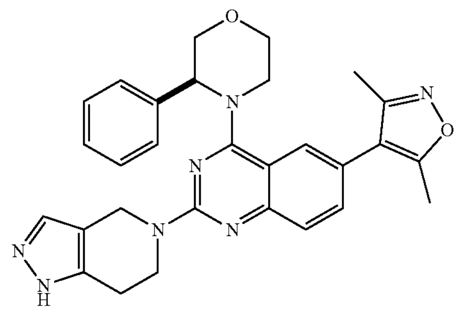 [SMILES: Cc1noc(C)c1-c1ccc2nc(N3CCc4[nH]ncc4C3)nc(N3CCOC[C@@H]3c3ccccc3)c2c1] | (S)-4-(6-(3,5-dimethylisoxazol-4-yl)-2-(1,4,6,7-tetrahydro-5H-pyrazolo[4,3-c]pyridin-5-yl)quinazolin-4-yl)-3-phenylmorpholine, TFA |
| 283 | 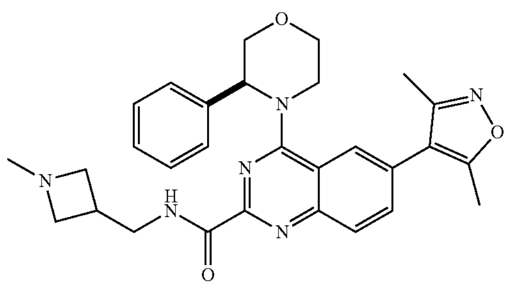 [SMILES: Cc1noc(C)c1-c1ccc2nc(C(=O)NCC3CN(C)C3)nc(N3CCOC[C@@H]3c3ccccc3)c2c1] | (S)-6-(3,5-dimethylisoxazol-4-yl)-N-((1-methylazetidin-3-yl)methyl)-4-(3-phenylmorpholino)quinazoline-2-carboxamide, TFA |
| 284 | 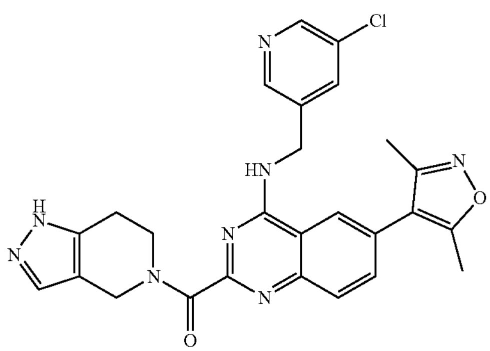 [SMILES: Cc1noc(C)c1-c1ccc2nc(C(=O)N3CCc4[nH]ncc4C3)nc(NCc3cncc(Cl)c3)c2c1] | (4-(((5-chloropyridin-3-yl)methyl)amino)-6-(3,5-dimethylisoxazol-4-yl)quinazolin-2-yl)(1,4,6,7-tetrahydro-5H-pyrazolo[4,3-c]pyridin-5-yl)methanone, TFA |
| 285 | 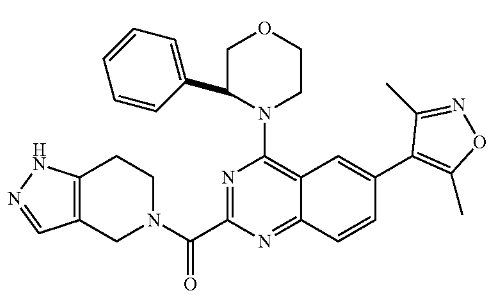 [SMILES: Cc1noc(C)c1-c1ccc2nc(C(=O)N3CCc4[nH]ncc4C3)nc(N3CCOC[C@@H]3c3ccccc3)c2c1] | (S)-(6-(3,5-dimethylisoxazol-4-yl)-4-(3-phenylmorpholino)quinazolin-2-yl)(1,4,6,7-tetrahydro-5H-pyrazolo[4,3-c]pyridin-5-yl)methanone, TFA |

TABLE 1-continued

| Example # | Structure | Compound Name |
|---|---|---|
| 286 | 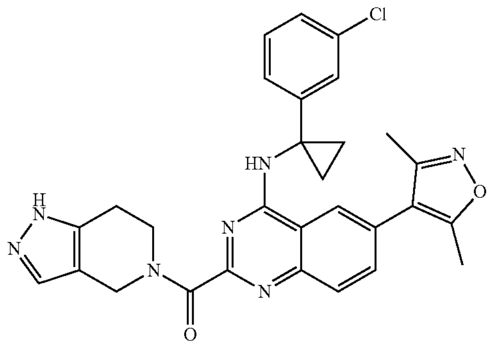 [SMILES: Cc1noc(C)c1-c1ccc2nc(C(=O)N3CCc4[nH]ncc4C3)nc(NC3(c4cccc(Cl)c4)CC3)c2c1] | (4-((1-(3-chlorophenyl)cyclopropyl)amino)-6-(3,5-dimethylisoxazol-4-yl)quinazolin-2-yl)(1,4,6,7-tetrahydro-5H-pyrazolo[4,3-c]pyridin-5-yl)methanone, TFA |
| 287 | 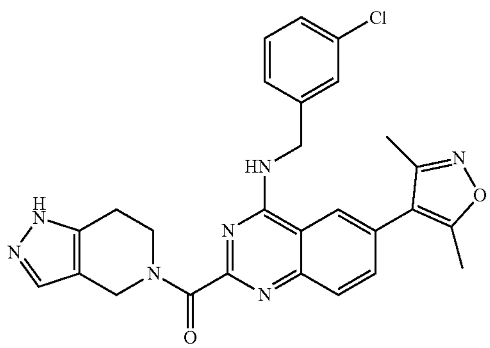 | (4-((3-chlorobenzyl)amino)-6-(3,5-dimethylisoxazol-4-yl)quinazolin-2-yl)(1,4,6,7-tetrahydro-5H-pyrazolo[4,3-c]pyridin-5-yl)methanone, TFA |
| 288 | 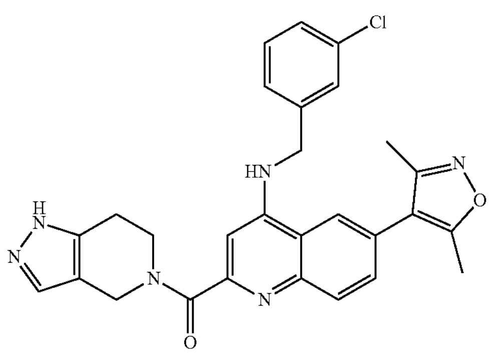 [SMILES: Cc1noc(C)c1-c1ccc2nc(C(=O)N3CCc4[nH]ncc4C3)cc(NCc3cccc(Cl)c3)c2c1] | (4-((3-chlorobenzyl)amino)-6-(3,5-dimethylisoxazol-4-yl)quinolin-2-yl)(1,4,6,7-tetrahydro-5H-pyrazolo[4,3-c]pyridin-5-yl)methanone, TFA |
| 289 | 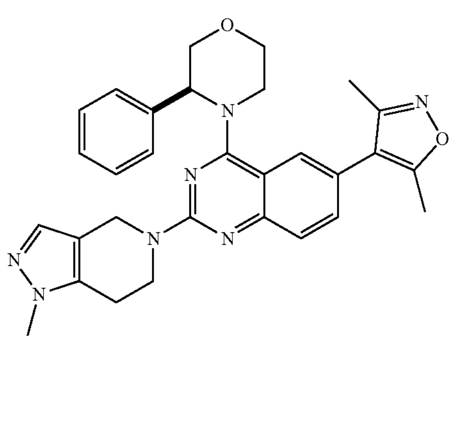 [SMILES: Cc1noc(C)c1-c1ccc2nc(N3CCc4c(cnn4C)C3)nc(N3CCOC[C@@H]3c3ccccc3)c2c1] | (S)-4-(6-(3,5-dimethylisoxazol-4-yl)-2-(1-methyl-1,4,6,7-tetrahydro-5H-pyrazolo[4,3-c]pyridin-5-yl)quinazolin-4-yl)-3-phenylmorpholine, TFA |

TABLE 1-continued

| Example # | Structure | Compound Name |
|---|---|---|
| 290 | 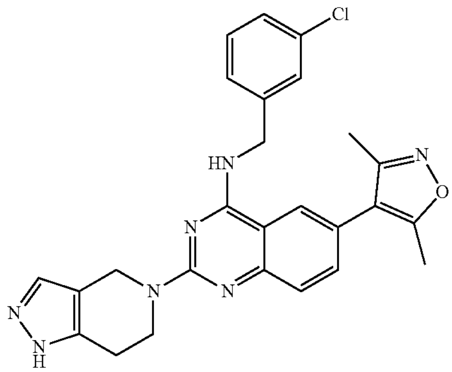 [SMILES: Cc1noc(C)c1-c1ccc2nc(N3CCc4[nH]ncc4C3)nc(NCc3cccc(Cl)c3)c2c1] | N-(3-chlorobenzyl)-6-(3,5-dimethylisoxazol-4-yl)-2-(1,4,6,7-tetrahydro-5H-pyrazolo[4,3-c]pyridin-5-yl)quinazolin-4-amine |
| 291 | 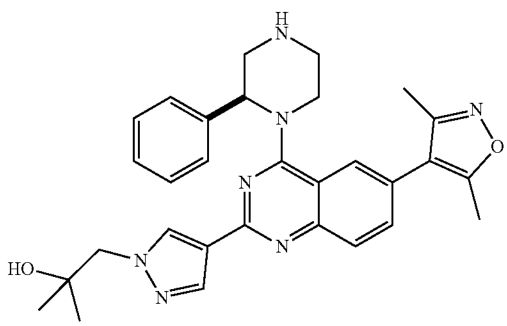 [SMILES: Cc1noc(C)c1-c1ccc2nc(-c3cnn(CC(C)(C)O)c3)nc(N3CCNC[C@@H]3c3ccccc3)c2c1] | (S)-1-(4-(6-(3,5-dimethylisoxazol-4-yl)-4-(2-phenylpiperazin-1-yl)quinazolin-2-yl)-1H-pyrazol-1-yl)-2-methylpropan-2-ol, TFA |
| 292 | 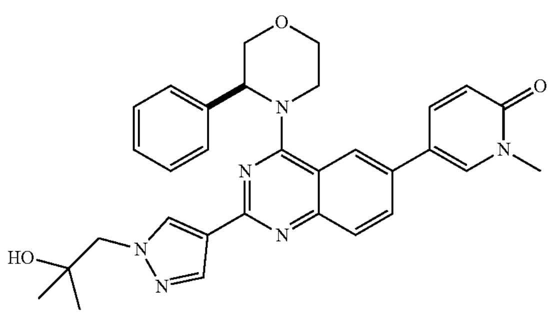 [SMILES: Cn1cc(-c2ccc3nc(-c4cnn(CC(C)(C)O)c4)nc(N4CCOC[C@@H]4c4ccccc4)c3c2)ccc1=O] | (S)-5-(2-(1-(2-hydroxy-2-methylpropyl)-1H-pyrazol-4-yl)-4-(3-phenylmorpholino)quinazolin-6-yl)-1-methylpyridin-2(1H)-one, TFA |
| 293 | 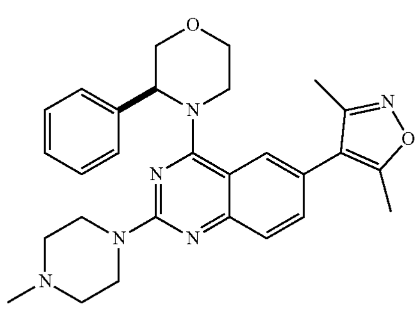 [SMILES: Cc1noc(C)c1-c1ccc2nc(N3CCN(C)CC3)nc(N3CCOC[C@@H]3c3ccccc3)c2c1] | (S)-4-(6-(3,5-dimethylisoxazol-4-yl)-2-(4-methylpiperazin-1-yl)quinazolin-4-yl)-3-phenylmorpholine, TFA |

TABLE 1-continued

| Example # | Structure | Compound Name |
|---|---|---|
| 294 | 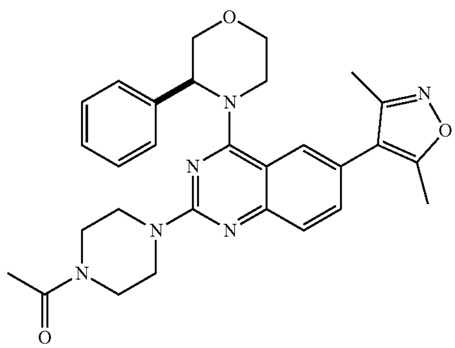 [SMILES: CC(=O)N1CCN(c2nc(N3CCOC[C@@H]3c3ccccc3)c3cc(-c4c(C)noc4C)ccc3n2)CC1] | (S)-1-(4-(6-(3,5-dimethylisoxazol-4-yl)-4-(3-phenylmorpholino)quinazolin-2-yl)piperazin-1-yl)ethan-1-one, TFA |
| 295 | 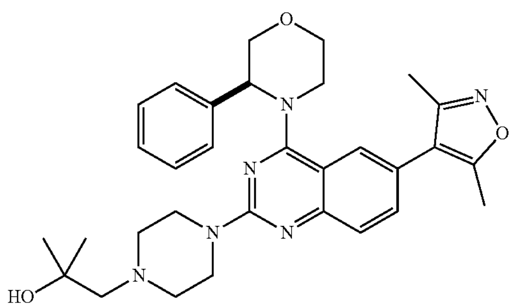 [SMILES: Cc1noc(C)c1-c1ccc2nc(N3CCN(CC(C)(C)O)CC3)nc(N3CCOC[C@@H]3c3ccccc3)c2c1] | (S)-1-(4-(6-(3,5-dimethylisoxazol-4-yl)-4-(3-phenylmorpholino)quinazolin-2-yl)piperazin-1-yl)-2-methylpropan-2-ol, TFA |
| 296 | 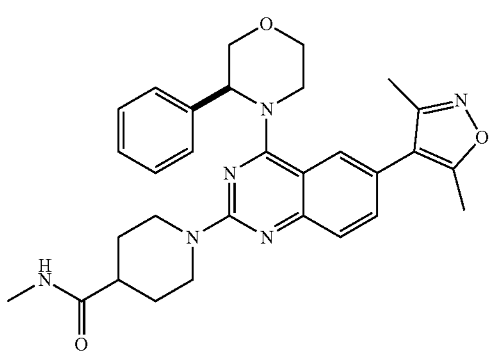 [SMILES: CNC(=O)C1CCN(c2nc(N3CCOC[C@@H]3c3ccccc3)c3cc(-c4c(C)noc4C)ccc3n2)CC1] | (S)-1-(6-(3,5-dimethylisoxazol-4-yl)-4-(3-phenylmorpholino)quinazolin-2-yl)-N-methylpiperidine-4-carboxamide, TFA |
| 297 | 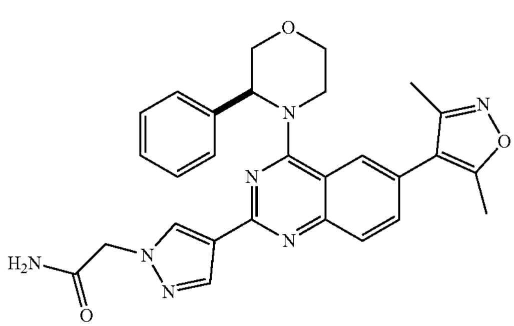 [SMILES: Cc1noc(C)c1-c1ccc2nc(-c3cnn(CC(N)=O)c3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)-1H-pyrazol-1-yl)acetamide, TFA |

TABLE 1-continued

| Example # | Structure | Compound Name |
|---|---|---|
| 298 | 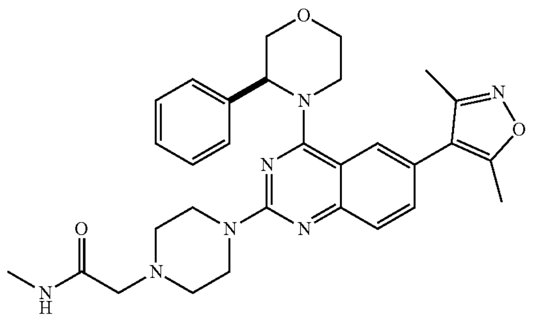 [SMILES: CNC(=O)CN1CCN(c2nc(N3CCOC[C@@H]3c3ccccc3)c3cc(-c4c(C)noc4C)ccc3n2)CC1] | (S)-2-(4-(6-(3,5-dimethylisoxazol-4-yl)-4-(3-phenylmorpholino)quinazolin-2-yl)piperazin-1-yl)-N-methylacetamide, TFA |
| 299 | 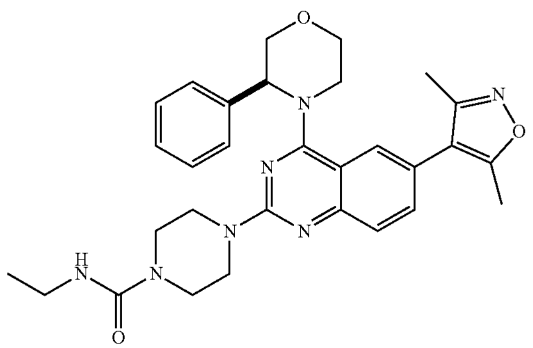 [SMILES: CCNC(=O)N1CCN(c2nc(N3CCOC[C@@H]3c3ccccc3)c3cc(-c4c(C)noc4C)ccc3n2)CC1] | (S)-4-(6-(3,5-dimethylisoxazol-4-yl)-4-(3-phenylmorpholino)quinazolin-2-yl)-N-ethylpiperazine-1-carboxamide, TFA |
| 300 | 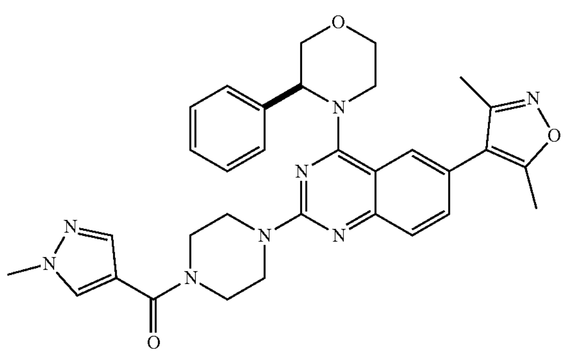 [SMILES: Cc1noc(C)c1-c1ccc2nc(N3CCN(C(=O)c4cnn(C)c4)CC3)nc(N3CCOC[C@@H]3c3ccccc3)c2c1] | (S)-(4-(6-(3,5-dimethylisoxazol-4-yl)-4-(3-phenylmorpholino)quinazolin-2-yl)piperazin-1-yl)(1-methyl-1H-pyrazol-4-yl)methanone, TFA |
| 301 | 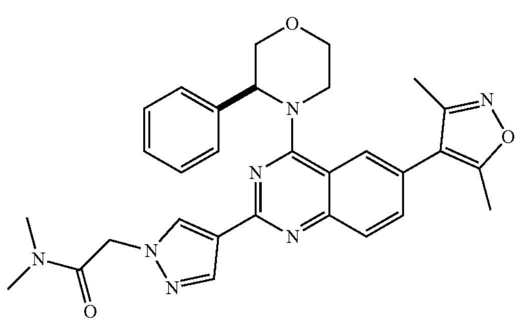 [SMILES: Cc1noc(C)c1-c1ccc2nc(-c3cnn(CC(=O)N(C)C)c3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)-1H-pyrazol-1-yl)-N,N-dimethylacetamide, TFA |

TABLE 1-continued

| Example # | Structure | Compound Name |
|---|---|---|
| 302 | 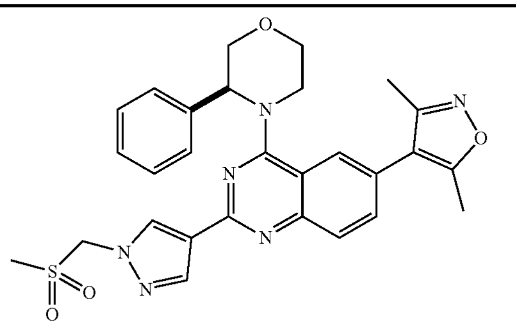 | (S)-4-(6-(3,5-dimethylisoxazol-4-yl)-2-(1-((methylsulfonyl)methyl)-1H-pyrazol-4-yl)quinazolin-4-yl)-3-phenylmorpholine, TFA |
| 303 | 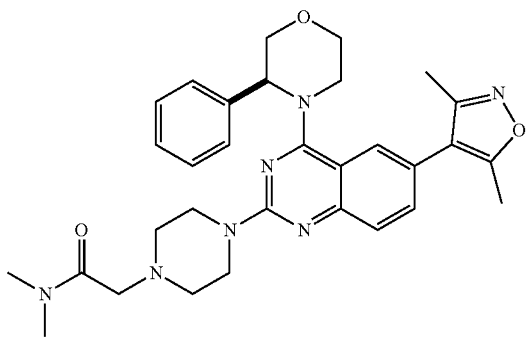 [SMILES: Cc1noc(C)c1-c1ccc2nc(N3CCN(CC(=O)N(C)C)CC3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)piperazin-1-yl)-N,N-dimethylacetamide, TFA |
| 304 | 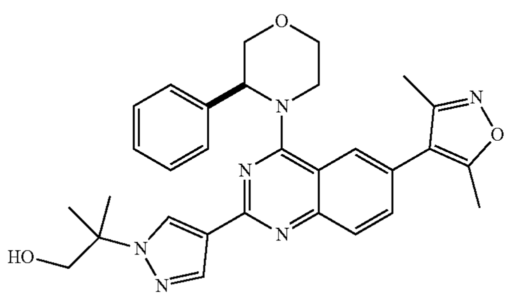 [SMILES: Cc1noc(C)c1-c1ccc2nc(-c3cnn(C(C)(C)CO)c3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)-1H-pyrazol-1-yl)-2-methylpropan-1-ol, TFA |
| 305 | 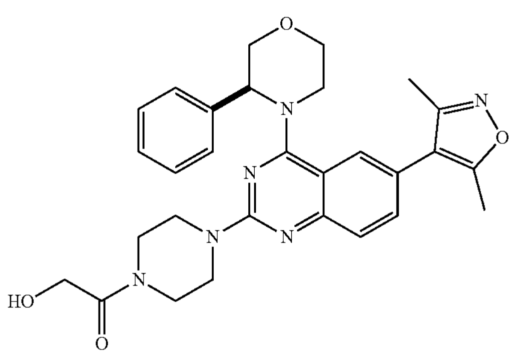 [SMILES: Cc1noc(C)c1-c1ccc2nc(N3CCN(C(=O)CO)CC3)nc(N3CCOC[C@@H]3c3ccccc3)c2c1] | (S)-1-(4-(6-(3,5-dimethylisoxazol-4-yl)-4-(3-phenylmorpholino)quinazolin-2-yl)piperazin-1-yl)-2-hydroxyethan-1-one, TFA |
| 306 | 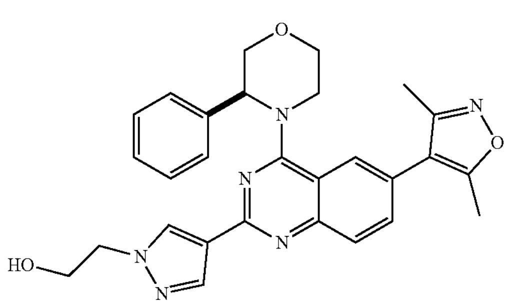 [SMILES: Cc1noc(C)c1-c1ccc2nc(-c3cnn(CCO)c3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)-1H-pyrazol-1-yl)ethan-1-ol, TFA |

TABLE 1-continued

| Example # | Structure | Compound Name |
|---|---|---|
| 307 | 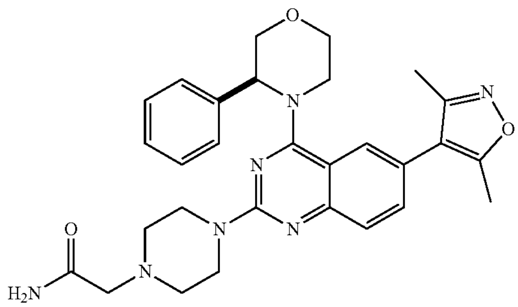 [SMILES: Cc1noc(C)c1-c1ccc2nc(N3CCN(CC(N)=O)CC3)nc(N3CCOC[C@@H]3c3ccccc3)c2c1] | (S)-2-(4-(6-(3,5-dimethylisoxazol-4-yl)-4-(3-phenylmorpholino)quinazolin-2-yl)piperazin-1-yl)acetamide, TFA |
| 308 | 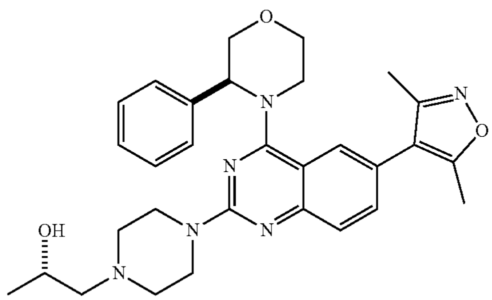 [SMILES: Cc1noc(C)c1-c1ccc2nc(N3CCN(C[C@H](C)O)CC3)nc(N3CCOC[C@@H]3c3ccccc3)c2c1] | (S)-1-(4-(6-(3,5-dimethylisoxazol-4-yl)-4-((S)-3-phenylmorpholino)quinazolin-2-yl)piperazin-1-yl)propan-2-ol, TFA |
| 309 | 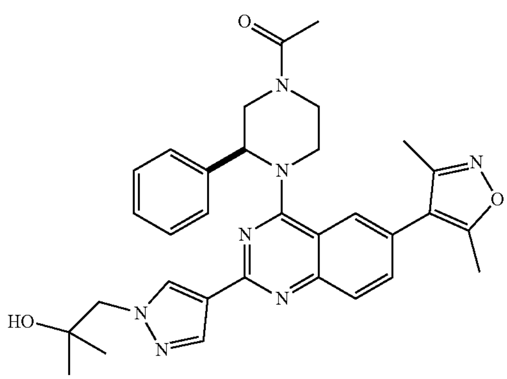 [SMILES: CC(=O)N1CCN(c2nc(-c3cnn(CC(C)(C)O)c3)nc3ccc(-c4c(C)noc4C)cc23)[C@@H](c2ccccc2)C1] | (S)-1-(4-(6-(3,5-dimethylisoxazol-4-yl)-2-(1-(2-hydroxy-2-methylpropyl)-1H-pyrazol-4-yl)quinazolin-4-yl)-3-phenylpiperazin-1-yl)ethan-1-one, TFA |
| 310 | 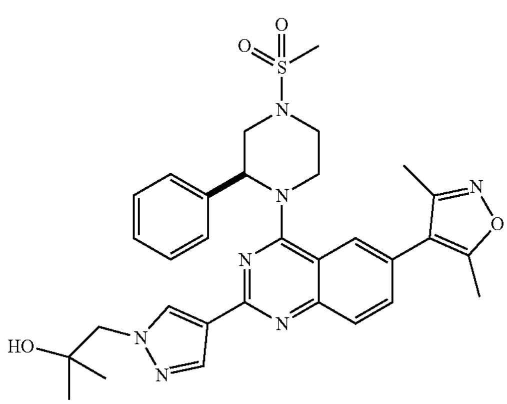 [SMILES: Cc1noc(C)c1-c1ccc2nc(-c3cnn(CC(C)(C)O)c3)nc(N3CCN(S(C)(=O)=O)C[C@@H]3c3ccccc3)c2c1] | (S)-1-(4-(6-(3,5-dimethylisoxazol-4-yl)-4-(4-(methylsulfonyl)-2-phenylpiperazin-1-yl)quinazolin-2-yl)-1H-pyrazol-1-yl)-2-methylpropan-2-ol, TFA |

TABLE 1-continued

| Example # | Structure | Compound Name |
|---|---|---|
| 311 | 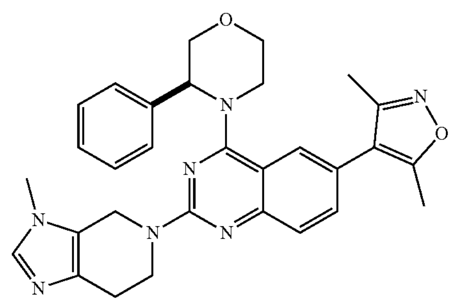 [SMILES: Cc1noc(C)c1-c1ccc2nc(N3CCc4ncn(C)c4C3)nc(N3CCOC[C@@H]3c3ccccc3)c2c1] | (S)-4-(6-(3,5-dimethylisoxazol-4-yl)-2-(3-methyl-3,4,6,7-tetrahydro-5H-imidazo[4,5-c]pyridin-5-yl)quinazolin-4-yl)-3-phenylmorpholine, TFA |
| 312 | 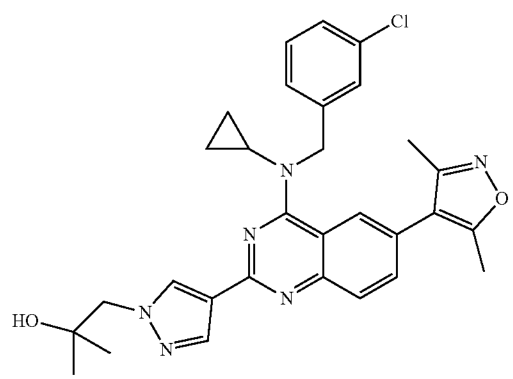 [SMILES: Cc1noc(C)c1-c1ccc2nc(-c3cnn(CC(C)(C)O)c3)nc(N(Cc3cccc(Cl)c3)C3CC3)c2c1] | 1-(4-(4-((3-chlorobenzyl)(cyclopropyl)amino)-6-(3,5-dimethylisoxazol-4-yl)quinazolin-2-yl)-1H-pyrazol-1-yl)-2-methylpropan-2-ol, TFA |
| 313 | 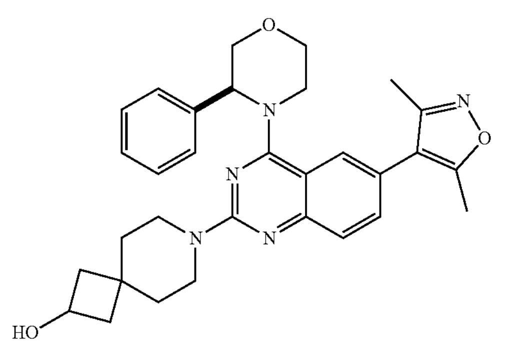 [SMILES: Cc1noc(C)c1-c1ccc2nc(N3CCC4(CC3)CC(O)C4)nc(N3CCOC[C@@H]3c3ccccc3)c2c1] | (S)-7-(6-(3,5-dimethylisoxazol-4-yl)-4-(3-phenylmorpholino)quinazolin-2-yl)-7-azaspiro[3.5]nonan-2-ol, TFA |
| 314 | 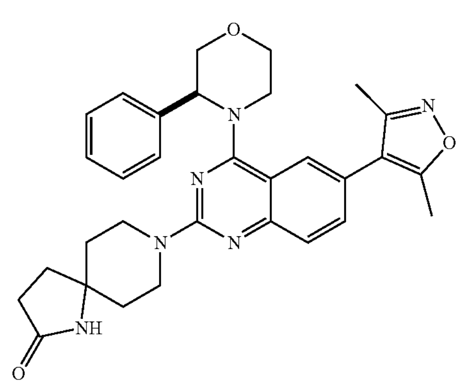 [SMILES: Cc1noc(C)c1-c1ccc2nc(N3CCC4(CCC(=O)N4)CC3)nc(N3CCOC[C@@H]3c3ccccc3)c2c1] | (S)-8-(6-(3,5-dimethylisoxazol-4-yl)-4-(3-phenylmorpholino)quinazolin-2-yl)-1,8-diazaspiro[4.5]decan-2-one, TFA |

TABLE 1-continued

| Example # | Structure | Compound Name |
|---|---|---|
| 315 | 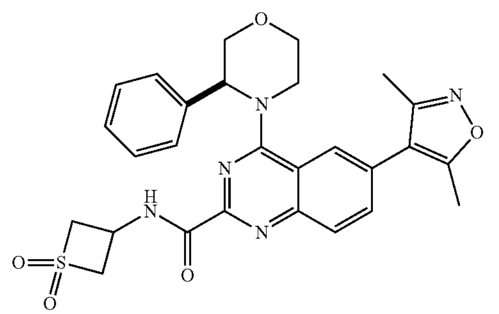 [SMILES: Cc1noc(C)c1-c1ccc2nc(C(=O)NC3CS(=O)(=O)C3)nc(N3CCOC[C@@H]3c3ccccc3)c2c1] | (S)-6-(3,5-dimethylisoxazol-4-yl)-N-(1,1-dioxidothietan-3-yl)-4-(3-phenylmorpholino)quinazoline-2-carboxamide, TFA |
| 316 | 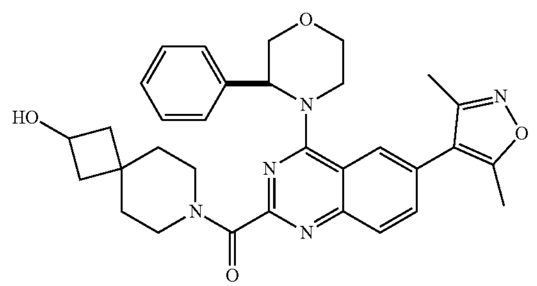 [SMILES: Cc1noc(C)c1-c1ccc2nc(C(=O)N3CCC4(CC3)CC(O)C4)nc(N3CCOC[C@@H]3c3ccccc3)c2c1] | (S)-(6-(3,5-dimethylisoxazol-4-yl)-4-(3-phenylmorpholino)quinazolin-2-yl)(2-hydroxy-7-azaspiro[3.5]nonan-7-yl)methanone, TFA |
| 317 | 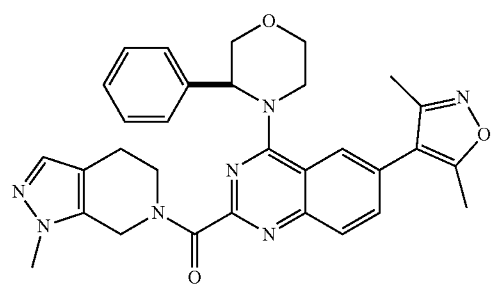 [SMILES: Cc1noc(C)c1-c1ccc2nc(C(=O)N3CCc4cnn(C)c4C3)nc(N3CCOC[C@@H]3c3ccccc3)c2c1] | (S)-(6-(3,5-dimethylisoxazol-4-yl)-4-(3-phenylmorpholino)quinazolin-2-yl)(1-methyl-1,4,5,7-tetrahydro-6H-pyrazolo[3,4-c]pyridin-6-yl)methanone, TFA |
| 318 | 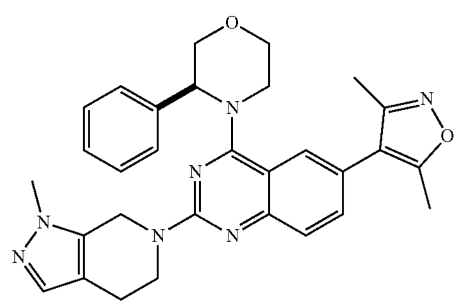 [SMILES: Cc1noc(C)c1-c1ccc2nc(N3CCc4cnn(C)c4C3)nc(N3CCOC[C@@H]3c3ccccc3)c2c1] | (S)-4-(6-(3,5-dimethylisoxazol-4-yl)-2-(1-methyl-1,4,5,7-tetrahydro-6H-pyrazolo[3,4-c]pyridin-6-yl)quinazolin-4-yl)-3-phenylmorpholine, TFA |
| 319 | 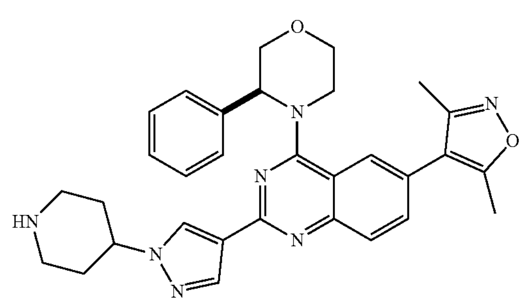 [SMILES: Cc1noc(C)c1-c1ccc2nc(-c3cnn(C4CCNCC4)c3)nc(N3CCOC[C@@H]3c3ccccc3)c2c1] | (S)-4-(6-(3,5-dimethylisoxazol-4-yl)-2-(1-(piperidin-4-yl)-1H-pyrazol-4-yl)quinazolin-4-yl)-3-phenylmorpholine, HCl |

TABLE 1-continued

| Example # | Structure | Compound Name |
|---|---|---|
| 320 | 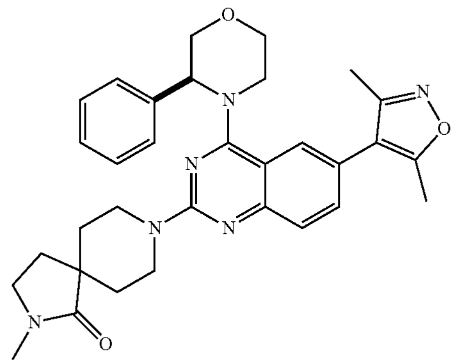 [SMILES: Cc1noc(C)c1-c1ccc2nc(N3CCC4(CCN(C)C4=O)CC3)nc(N3CCOC[C@@H]3c3ccccc3)c2c1] | (S)-8-(6-(3,5-dimethylisoxazol-4-yl)-4-(3-phenylmorpholino)quinazolin-2-yl)-2-methyl-2,8-diazaspiro[4.5]decan-1-one, TFA |
| 321 | 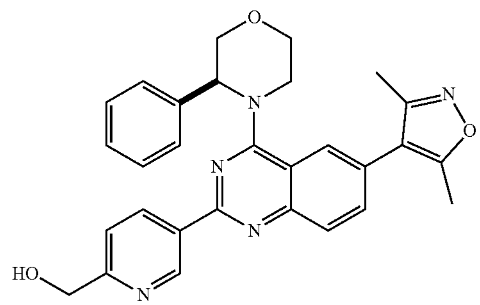 [SMILES: Cc1noc(C)c1-c1ccc2nc(-c3ccc(CO)nc3)nc(N3CCOC[C@@H]3c3ccccc3)c2c1] | (S)-(5-(6-(3,5-dimethylisoxazol-4-yl)-4-(3-phenylmorpholino)quinazolin-2-yl)pyridin-2-yl)methanol, TFA |
| 322 | 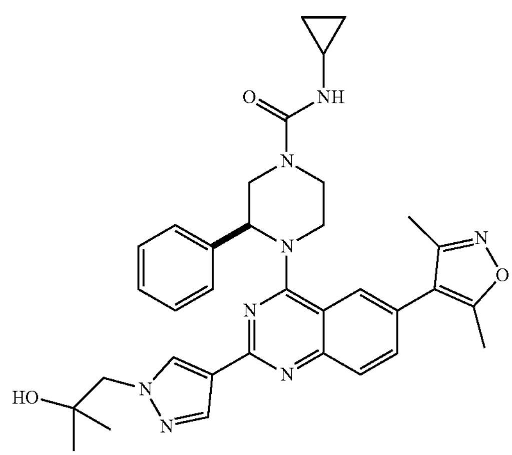 [SMILES: Cc1noc(C)c1-c1ccc2nc(-c3cnn(CC(C)(C)O)c3)nc(N3CCN(C(=O)NC4CC4)C[C@@H]3c3ccccc3)c2c1] | (S)-N-cyclopropyl-4-(6-(3,5-dimethylisoxazol-4-yl)-2-(1-(2-hydroxy-2-methylpropyl)-1H-pyrazol-4-yl)quinazolin-4-yl)-3-phenylpiperazine-1-carboxamide, TFA |
| 323 | 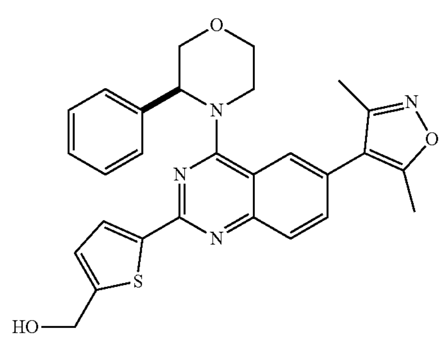 [SMILES: Cc1noc(C)c1-c1ccc2nc(-c3ccc(CO)s3)nc(N3CCOC[C@@H]3c3ccccc3)c2c1] | (S)-(5-(6-(3,5-dimethylisoxazol-4-yl)-4-(3-phenylmorpholino)quinazolin-2-yl)thiophen-2-yl)methanol, TFA |

TABLE 1-continued

| Example # | Structure | Compound Name |
|---|---|---|
| 324 | 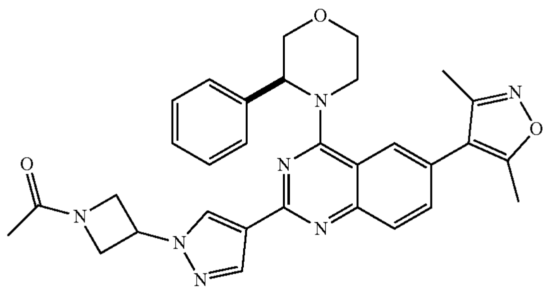 [SMILES: CC(=O)N1CC(n2cc(-c3nc(N4CCOC[C@@H]4c4ccccc4)c4cc(-c5c(C)noc5C)ccc4n3)cn2)C1] | (S)-1-(3-(4-(6-(3,5-dimethylisoxazol-4-yl)-4-(3-phenylmorpholino)quinazolin-2-yl)-1H-pyrazol-1-yl)azetidin-1-yl)ethan-1-one, TFA |
| 325 | 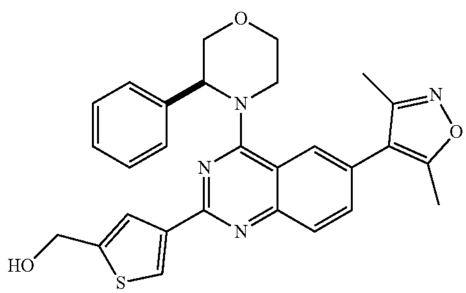 [SMILES: Cc1noc(C)c1-c1ccc2nc(-c3csc(CO)c3)nc(N3CCOC[C@@H]3c3ccccc3)c2c1] | (S)-(4-(6-(3,5-dimethylisoxazol-4-yl)-4-(3-phenylmorpholino)quinazolin-2-yl)thiophen-2-yl)methanol, TFA |
| 326 | 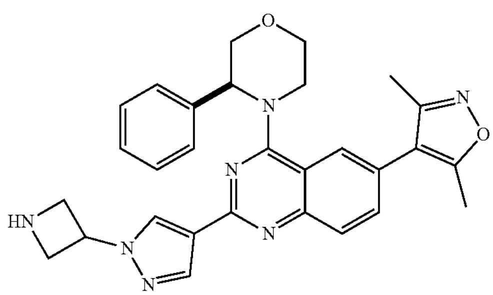 [SMILES: Cc1noc(C)c1-c1ccc2nc(-c3cnn(C4CNC4)c3)nc(N3CCOC[C@@H]3c3ccccc3)c2c1] | (S)-4-(2-(1-(azetidin-3-yl)-1H-pyrazol-4-yl)-6-(3,5-dimethylisoxazol-4-yl)quinazolin-4-yl)-3-phenylmorpholine, TFA |
| 327 | 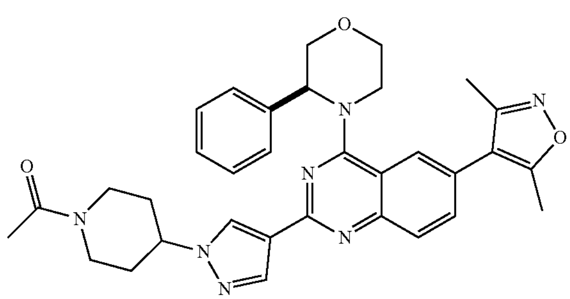 [SMILES: CC(=O)N1CCC(n2cc(-c3nc(N4CCOC[C@@H]4c4ccccc4)c4cc(-c5c(C)noc5C)ccc4n3)cn2)CC1] | (S)-1-(4-(4-(6-(3,5-dimethylisoxazol-4-yl)-4-(3-phenylmorpholino)quinazolin-2-yl)-1H-pyrazol-1-yl)piperidin-1-yl)ethan-1-one, TFA |
| 328 | 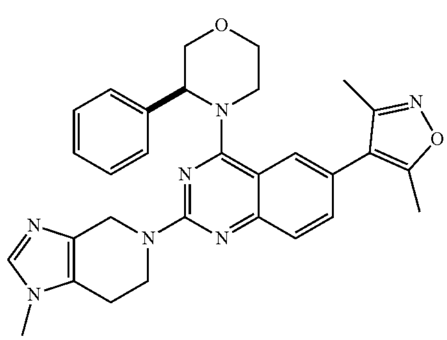 [SMILES: Cc1noc(C)c1-c1ccc2nc(N3CCc4c(ncn4C)C3)nc(N3CCOC[C@@H]3c3ccccc3)c2c1] | (S)-4-(6-(3,5-dimethylisoxazol-4-yl)-2-(1-methyl-1,4,6,7-tetrahydro-5H-imidazo[4,5-c]pyridin-5-yl)quinazolin-4-yl)-3-phenylmorpholine, TFA |

TABLE 1-continued

| Example # | Structure | Compound Name |
|---|---|---|
| 329 | 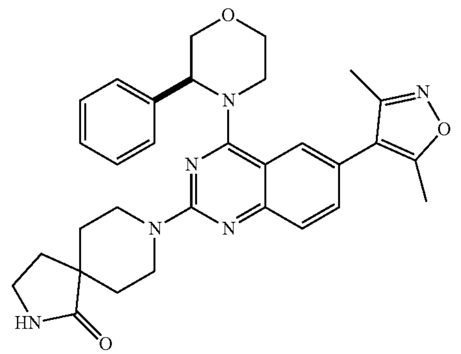 [SMILES: Cc1noc(C)c1-c1ccc2nc(N3CCC4(CCNC4=O)CC3)nc(N3CCOC[C@@H]3c3ccccc3)c2c1] | (S)-8-(6-(3,5-dimethylisoxazol-4-yl)-4-(3-phenylmorpholino)quinazolin-2-yl)-2,8-diazaspiro[4.5]decan-1-one, TFA |
| 330 | 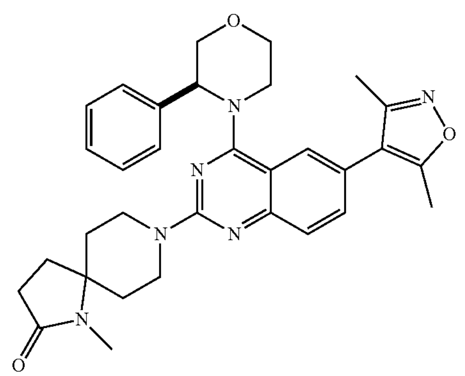 [SMILES: Cc1noc(C)c1-c1ccc2nc(N3CCC4(CCC(=O)N4C)CC3)nc(N3CCOC[C@@H]3c3ccccc3)c2c1] | (S)-8-(6-(3,5-dimethylisoxazol-4-yl)-4-(3-phenylmorpholino)quinazolin-2-yl)-1-methyl-1,8-diazaspiro[4.5]decan-2-one, TFA |
| 331 | 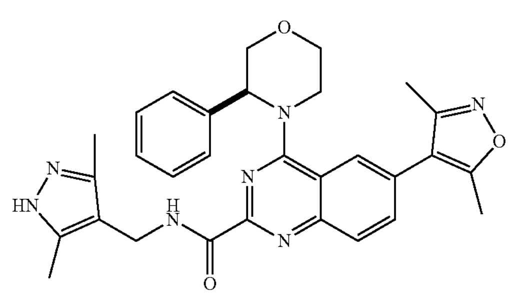 [SMILES: Cc1n[nH]c(C)c1CNC(=O)c1nc(N2CCOC[C@@H]2c2ccccc2)c2cc(-c3c(C)noc3C)ccc2n1] | (S)-N-((3,5-dimethyl-1H-pyrazol-4-yl)methyl)-6-(3,5-dimethylisoxazol-4-yl)-4-(3-phenylmorpholino)quinazoline-2-carboxamide |
| 332 | 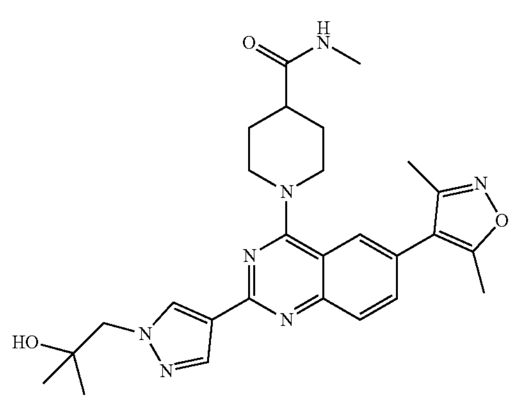 [SMILES: CNC(=O)C1CCN(c2nc(-c3cnn(CC(C)(C)O)c3)nc3ccc(-c4c(C)noc4C)cc23)CC1] | 1-(6-(3,5-dimethylisoxazol-4-yl)-2-(1-(2-hydroxy-2-methylpropyl)-1H-pyrazol-4-yl)quinazolin-4-yl)-N-methylpiperidine-4-carboxamide |

TABLE 1-continued

| Example # | Structure | Compound Name |
|---|---|---|
| 333 | 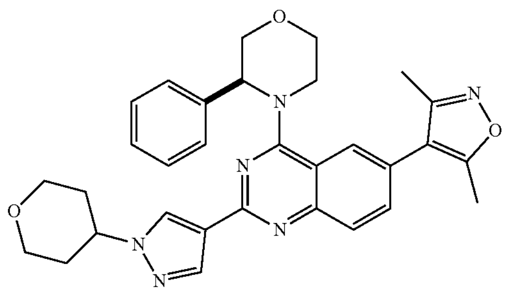 [SMILES: Cc1noc(C)c1-c1ccc2nc(-c3cnn(C4CCOCC4)c3)nc(N3CCOC[C@@H]3c3ccccc3)c2c1] | (S)-4-(6-(3,5-dimethylisoxazol-4-yl)-2-(1-(tetrahydro-2H-pyran-4-yl)-1H-pyrazol-4-yl)quinazolin-4-yl)-3-phenylmorpholine, TFA |
| 334 | 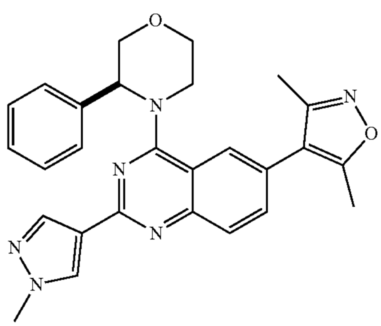 [SMILES: Cc1noc(C)c1-c1ccc2nc(-c3cnn(C)c3)nc(N3CCOC[C@@H]3c3ccccc3)c2c1] | (S)-4-(6-(3,5-dimethylisoxazol-4-yl)-2-(1-methyl-1H-pyrazol-4-yl)quinazolin-4-yl)-3-phenylmorpholine, TFA |
| 335 | 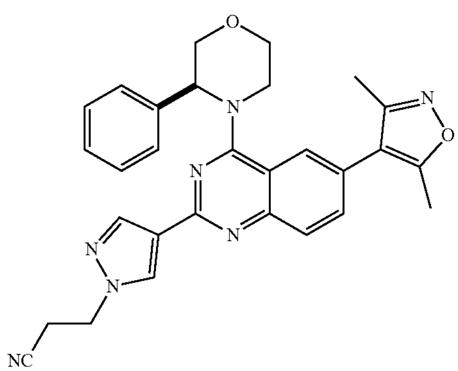 [SMILES: Cc1noc(C)c1-c1ccc2nc(-c3cnn(CCC#N)c3)nc(N3CCOC[C@@H]3c3ccccc3)c2c1] | (S)-3-(4-(6-(3,5-dimethylisoxazol-4-yl)-4-(3-phenylmorpholino)quinazolin-2-yl)-1H-pyrazol-1-yl)propanenitrile, TFA |
| 336 | 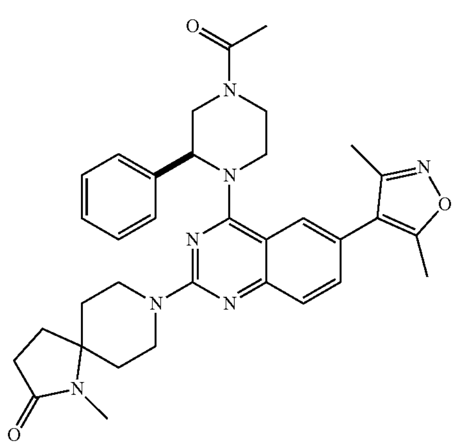 [SMILES: CC(=O)N1CCN(c2nc(N3CCC4(CCC(=O)N4C)CC3)nc3ccc(-c4c(C)noc4C)cc23)[C@@H](c2ccccc2)C1] | (S)-8-(4-(4-acetyl-2-phenylpiperazin-1-yl)-6-(3,5-dimethylisoxazol-4-yl)quinazolin-2-yl)-1-methyl-1,8-diazaspiro[4.5]decan-2-one, TFA |

TABLE 1-continued

| Example # | Structure | Compound Name |
|---|---|---|
| 337 | 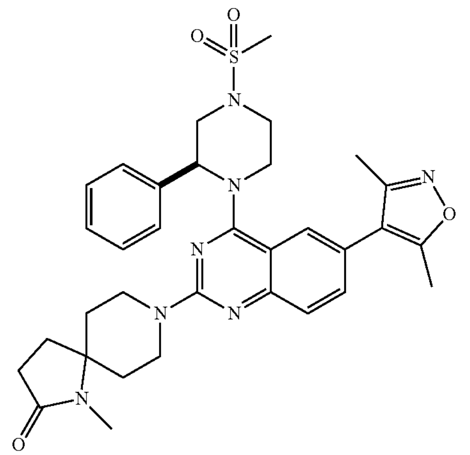 [SMILES: Cc1noc(C)c1-c1ccc2nc(N3CCC4(CCC(=O)N4C)CC3)nc(N3CCN(S(C)(=O)=O)C[C@@H]3c3ccccc3)c2c1] | (S)-8-(6-(3,5-dimethylisoxazol-4-yl)-4-(4-(methylsulfonyl)-2-phenylpiperazin-1-yl)quinazolin-2-yl)-1-methyl-1,8-diazaspiro[4.5]decan-2-one, TFA |
| 338 | 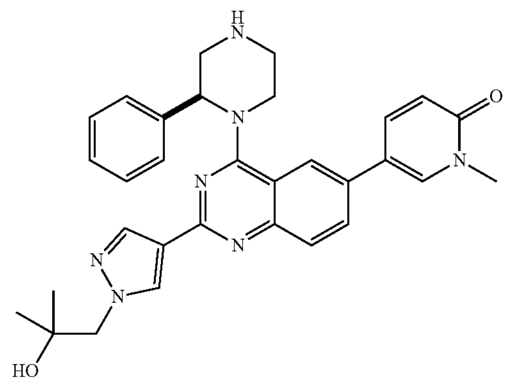 [SMILES: Cn1cc(-c2ccc3nc(-c4cnn(CC(C)(C)O)c4)nc(N4CCNC[C@@H]4c4ccccc4)c3c2)ccc1=O] | (S)-5-(2-(1-(2-hydroxy-2-methylpropyl)-1H-pyrazol-4-yl)-4-(2-phenylpiperazin-1-yl)quinazolin-6-yl)-1-methylpyridin-2(1H)-one, HCl |
| 339 | 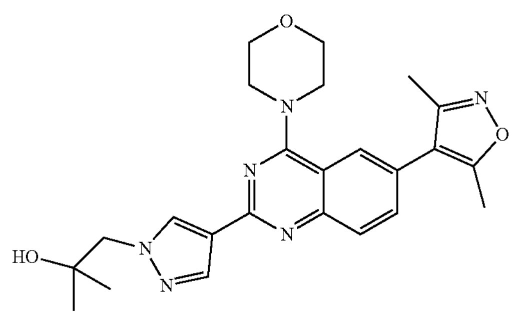 [SMILES: Cc1noc(C)c1-c1ccc2nc(-c3cnn(CC(C)(C)O)c3)nc(N3CCOCC3)c2c1] | 1-(4-(6-(3,5-dimethylisoxazol-4-yl)-4-morpholinoquinazolin-2-yl)-1H-pyrazol-1-yl)-2-methylpropan-2-ol |
| 340 | 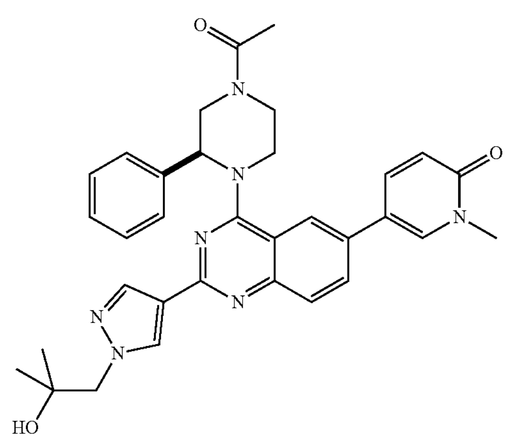 [SMILES: CC(=O)N1CCN(c2nc(-c3cnn(CC(C)(C)O)c3)nc3ccc(-c4ccc(=O)n(C)c4)cc23)[C@@H](c2ccccc2)C1] | (S)-5-(4-(4-acetyl-2-phenylpiperazin-1-yl)-2-(1-(2-hydroxy-2-methylpropyl)-1H-pyrazol-4-yl)quinazolin-6-yl)-1-methylpyridin-2(1H)-one, TFA |

Detailed Synthetic Procedures

Example 1. 2-chloro-N-(3-chlorobenzyl)-6-(3,5-dimethylisoxazol-4-yl)quinazolin-4-amine Step 1: 6-bromo-2-chloro-N-(3-chlorobenzyl)quinazolin-4-amine To a mixture of 6-bromo-2,4-dichloroquinazoline (278 mg, 1.0 mmol) and (3-chlorophenyl)methanamine (142 mg, 1.0 mmol) in THF (2 ml) was added Et$_3$N (0.209 ml, 1.5 mmol). The mixture was stirred at RT for 1 h. The mixture was poured into EtOAc/H$_2$O (5 mL/5 mL). The aqueous layer was extracted with EtOAc (3 mL×2). The combined organic layer was dried (Na$_2$SO$_4$) and filtered. After removal of solvent, the product was triturated with hexane and dried to give 6-bromo-2-chloro-N-(3-chlorobenzyl)quinazolin-4-amine (360 mg, 0.94 mmol, 94% yield) as a white solid. MS (M+H)$^+$=384.

Step 2: 2-chloro-N-(3-chlorobenzyl)-6-(3,5-dimethylisoxazol-4-yl)quinazolin-4-amine In a 2-neck flask was placed 6-bromo-2-chloro-N-(3-chlorobenzyl)quinazolin-4-amine (345 mg, 0.9 mmol), (3,5-dimethylisoxazol-4-yl)boronic acid (127 mg, 0.9 mmol), PdCl$_2$(dppf) (65.9 mg, 0.09 mmol), and K$_2$CO$_3$ (311 mg, 2.250 mmol). The air was removed and re-filled with N$_2$ (2-3 times). Then a mixture of 1,4-Dioxane (3 ml) and Water (1 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was triturated with 50% CH$_2$Cl$_2$/hexane to give 48 mg of pure solid product. The filtrate was concentrated and was purified by silica gel chromatography using 20-40% EtOAc/hexane as the eluent, then triturated the product with 5% CH$_2$Cl$_2$/hexane to give 170 mg of pure solid product. Total 218 mg of 2-chloro-N-(3-chlorobenzyl)-6-(3,5-dimethylisoxazol-4-yl)quinazolin-4-amine (218 mg, 0.546 mmol, 60.7% yield) was obtained. $^1$H NMR (400 MHz, DMSO-d$_6$) δ 9.30 (t, J=5.9 Hz, 1H), 8.26 (d, J=1.9 Hz, 1H), 7.83 (dd, J=8.5, 1.7 Hz, 1H), 7.72 (d, J=8.6 Hz, 1H), 7.44 (d, J=1.6 Hz, 1H), 7.40-7.28 (m, 3H), 4.77 (d, J=5.7 Hz, 2H), 2.44 (s, 3H), 2.27 (s, 3H); MS (M+H)$^+$=400.

Example 2. N-(3-chlorobenzyl)-6-(3,5-dimethylisoxazol-4-yl)quinazolin-4-amine

Step 1: 6-bromo-N-(3-chlorobenzyl)quinazolin-4-amine

To a mixture of 6-bromo-4-chloroquinazoline (243 mg, 1.0 mmol) and (3-chlorophenyl)methanamine (142 mg, 1.0 mmol) in THF (2 ml) was added Et$_3$N (0.21 ml, 1.5 mmol). The mixture was stirred at RT for 3 h. The mixture was poured into EtOAc/H$_2$O (5 mL/5 mL). The aqueous layer was extracted with EtOAc (3 mL×2). The combined organic layer was dried (Na$_2$SO$_4$) and filtered. After removal of solvent, the product was triturated with hexane and dried to give 6-bromo-N-(3-chlorobenzyl)quinazolin-4-amine (342 mg, 0.98 mmol, 98% yield) as a white solid. MS (M+H)$^+$=350.

Step 2: N-(3-chlorobenzyl)-6-(3,5-dimethylisoxazol-4-yl)quinazolin-4-amine

In a 2-neck flask was placed 6-bromo-N-(3-chlorobenzyl)quinazolin-4-amine (69.7 mg, 0.2 mmol), (3,5-dimethylisoxazol-4-yl)boronic acid (42.3 mg, 0.3 mmol), PdCl$_2$(dppf) (14.6 mg, 0.02 mmol), and K$_2$CO$_3$ (83 mg, 0.6 mmol). The air was removed and re-filled with N$_2$ (2-3 times). Then a mixture of 1,4-Dioxane (1.5 ml) and water (0.5 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 20-40% EtOAc/hexane as the eluent to give N-(3-chlorobenzyl)-6-(3,5-dimethylisoxazol-4-yl)quinazolin-4-amine (61.5 mg, 0.169 mmol, 84% yield). $^1$H NMR (400 MHz, Chloroform-d) δ 8.70 (s, 1H), 7.95 (d, J=8.6 Hz, 1H), 7.77-7.68 (m, 1H), 7.65-7.58 (m, 1H), 7.41 (d, J=1.3 Hz, 1H), 7.34-7.29 (m, 1H), 7.28-7.22 (m, 2H), 6.82 (s, 1H), 4.92 (d, J=5.5 Hz, 2H), 2.44-2.34 (m, 3H), 2.21 (d, J=0.6 Hz, 3H); MS (M+H)$^+$=365.

Example 3. N-(3-chlorobenzyl)-6-(3,5-dimethylisoxazol-4-yl)quinolin-4-amine

Step 1: 6-bromo-N-(3-chlorobenzyl)quinolin-4-amine

In a microwave tube was placed 6-bromo-4-chloroquinoline (242 mg, 1 mmol), (3-chlorophenyl)methanamine (283 mg, 2.0 mmol), DMSO (1 ml), and Hunig's Base (0.349 ml, 2.0 mmol). The tube was sealed and heated at 150° C. for 1 h under microwave irradiation. The mixture was poured into EtOAc/H$_2$O (30 mL/30 mL). The organic layer was washed with H$_2$O (30 mL), dried (Na$_2$SO$_4$), and filtered. After removal of solvent, the product was triturated with 2% CH$_2$Cl$_2$/hexane and then dried to give 6-bromo-N-(3-chlorobenzyl)quinolin-4-amine (238 mg, 0.685 mmol, 68.5% yield). MS (M+H)$^+$=349.

Step 2: N-(3-chlorobenzyl)-6-(3,5-dimethylisoxazol-4-yl)quinolin-4-amine

In a 2-neck flask was placed 6-bromo-N-(3-chlorobenzyl)quinolin-4-amine (87 mg, 0.25 mmol), (3,5-dimethylisoxazol-4-yl)boronic acid (70.5 mg, 0.5 mmol), PdCl$_2$(dppf) (18.29 mg, 0.025 mmol), and K$_2$CO$_3$ (138 mg, 1.0 mmol). The air was removed and re-filled with N$_2$ (2-3 times). Then a mixture of 1,4-Dioxane (1.5 ml) and water (0.5 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 0-5% MeOH/EtOAc as the eluent to give N-(3-chlorobenzyl)-6-(3,5-dimethylisoxazol-4-yl)quinolin-4-amine (88.5 mg, 0.243 mmol, 97% yield). $^1$H NMR (400 MHz, Chloroform-d) δ 8.51 (dd, J=5.5, 1.9 Hz, 1H), 8.09 (dd, J=8.6, 2.0 Hz, 1H), 7.76 (s, 1H), 7.52 (dt, J=8.7, 2.0 Hz, 1H), 7.39 (d, J=1.9 Hz, 1H), 7.33-7.23 (m, 3H), 6.44 (dd, J=5.5, 2.0 Hz, 1H), 6.01 (s, 1H), 4.60 (dd, J=5.6, 1.9 Hz, 2H), 2.42 (d, J=2.0 Hz, 3H), 2.26 (d, J=1.9 Hz, 3H); MS (M+H)$^+$=364.

Example 4. N-(3-chlorobenzyl)-6-(3,5-dimethylisoxazol-4-yl)-2-methylquinolin-4-amine Step 1: 6-bromo-N-(3-chlorobenzyl)-2-methylquinolin-4-amine In a microwave tube was placed 6-bromo-4-chloro-2-methylquinoline (257 mg, 1 mmol), (3-chlorophenyl)methanamine (283 mg, 2.0 mmol), DMSO (1 ml), and Hunig's Base (0.349 ml, 2.0 mmol). The tube was sealed and heated at 150° C. for 1 h under microwave irradiation. The mixture was poured into EtOAc/H$_2$O (30 mL/30 mL). The organic layer was washed with H$_2$O (30 mL), dried (Na$_2$SO$_4$), and filtered. After removal of solvent, the product was triturated with 2% CH$_2$Cl$_2$/hexane and then dried to give 6-bromo-N-(3-chlorobenzyl)-2-methylquinolin-4-amine (211 mg, 0.583 mmol, 58.3% yield). MS (M+H)$^+$=363.

Step 2: N-(3-chlorobenzyl)-6-(3,5-dimethylisoxazol-4-yl)-2-methylquinolin-4-amine In a 2-neck flask was placed 6-bromo-N-(3-chlorobenzyl)-2-methylquinolin-4-amine (90 mg, 0.25 mmol), (3,5-dimethylisoxazol-4-yl)boronic acid (70.5 mg, 0.5 mmol), PdCl$_2$(dppf) (18.29 mg, 0.025 mmol), and K$_2$CO$_3$ (138 mg, 1.0 mmol). The air was removed and re-filled with N$_2$ (2-3 times). Then a mixture of 1,4-Dioxane (1.5 ml) and Water (0.5 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 0-5% MeOH/EtOAc as the eluent to give N-(3-chlorobenzyl)-6-(3,5-dimethylisoxazol-4-yl)-2-methylquinolin-4-amine (88.4 mg, 0.234 mmol, 94% yield). MS (M+H)$^+$=378.

Example 5. N4-(3-chlorobenzyl)-6-(3,5-dimethylisoxazol-4-yl)-N2-methylquinazoline-2,4-diamine To a suspension of 2-chloro-N-(3-chlorobenzyl)-6-(3,5-dimethylisoxazol-4-yl)quinazolin-4-amine (Example 1, 39.9 mg, 0.1 mmol) in EtOH (1 ml) was added methanamine (1.0 ml, 2.0 mmol) (2M in THF). The tube was sealed and heated at 75° C. for 16 h. After cooling to rt, the mixture was concentrated and the residue was re-dissolved in DMSO, filtered through a filter, and submitted for purification to give N4-(3-chlorobenzyl)-6-(3,5-dimethylisoxazol-4-yl)-N2-methylquinazoline-2,4-diamine, 2TFA (15.9 mg, 0.026 mmol, 25.6% yield). MS (M+H)$^+$=394.

Example 6. N-(3-chlorobenzyl)-6-(3,5-dimethylisoxazol-4-yl)-2-(4-methylpiperazin-1yl)quinazolin-4-amine To a mixture of 2-chloro-N-(3-chlorobenzyl)-6-(3,5-dimethylisoxazol-4-yl)quinazolin-4-amine (Example 1, 33.9 mg, 0.085 mmol) and 1-methylpiperazine (102 mg, 1.02 mmol) was added EtOH (1 ml). The tube was sealed and heated at 75° C. for 6 h. After cooling to rt, the mixture was concentrated and the residue was re-dissolved in DMSO, filtered through a filter, and submitted for purification to give N-(3-chlorobenzyl)-6-(3,5-dimethylisoxazol-4-yl)-2-(4-methylpiperazin-1-yl)quinazolin-4-amine, 2TFA (23.1 mg, 0.033 mmol, 39.3% yield). $^1$H NMR (400 MHz, DMSO-d$_6$) δ 10.14 (s, 2H), 8.22 (s, 1H), 7.86-7.23 (m, 6H), 4.76 (m, 4H), 4.20-2.95 (m, 6H), 2.79 7(s, 3H), 2.43 (s, 3H), 2.26 (s, 3H) (including 1 salt NH); MS (M+H)$^+$=463.

Example 7. N4-(3-chlorobenzyl)-6-(3,5-dimethylisoxazol-4-yl)-N2-(1-methylpiperidin-4-yl)quinazoline-2,4-diamine To a mixture of 2-chloro-N-(3-chlorobenzyl)-6-(3,5-dimethylisoxazol-4-yl)quinazolin-4-amine (Example 1, 33.9 mg, 0.085 mmol) and 1-methylpiperidin-4-amine (116 mg, 1.02 mmol) was added EtOH (1 ml). The tube was sealed and heated at 85° C. for 16 h. After cooling to rt, the mixture was concentrated and the residue was re-dissolved in DMSO, filtered through a filter, and submitted for purification to give N4-(3-chlorobenzyl)-6-(3,5-dimethylisoxazol-4-yl)-N2-(1-methylpiperidin-4-yl)quinazoline-2,4-diamine, 2TFA (17 mg, 0.024 mmol, 28.4% yield). MS (M+H)$^+$=477.

Example 8. N-(3-chlorobenzyl)-6-(3,5-dimethylisoxazol-4-yl)-2-methoxyquinazolin-4-amine To 2-chloro-N-(3-chlorobenzyl)-6-(3,5-dimethylisoxazol-4-yl)quinazolin-4-amine (Example 1, 33.9 mg, 0.085 mmol) was added sodium methoxide (1405 mg, 6.5 mmol) (25 wt % in MeOH, ca. 6.5 M). The tube was sealed and heated at 75° C. for 3 h. After cooling to rt, the mixture was concentrated and then H$_2$O (6 mL) was added. The white solid was collected, triturated water (2 mL×2) and hexane (2 mL), and then dried to give N-(3-chlorobenzyl)-6-(3,5-dimethylisoxazol-4-yl)-2-methoxyquinazolin-4-amine (29 mg, 0.073 mmol, 86% yield). $^1$H NMR (400 MHz, Chloroform-d) δ 7.77 (d, J=8.8 Hz, 1H), 7.53 (dt, J=7.5, 1.6 Hz, 2H), 7.39 (s, 1H), 7.29-7.26 (m, 3H), 6.24 (br s, 1H, NH), 4.88 (d, J=5.5 Hz, 2H), 4.07 (s, 3H), 2.39 (s, 3H), 2.23 (s, 3H); MS (M+H)$^+$=395.

Example 9. N-(3-chlorobenzyl)-6-(3,5-dimethylisoxazol-4-yl)-2-methylquinazolin-4-amine)

Step 1: 6-bromo-N-(3-chlorobenzyl)-2-methylquinazolin-4-amine

To a mixture of 6-bromo-2-methylquinazolin-4-ol (120 mg, 0.5 mmol) and bromotri(pyrrolidin-1-yl)phosphonium hexafluorophosphate (583 mg, 1.25 mmol) under N$_2$ was added 1,4-dioxane (4 ml) and then triethylamine (253 mg, 2.5 mmol). The mixture was stirred at RT for 1 h and (3-chlorophenyl)methanamine (142 mg, 1.0 mmol) was added. The mixture was stirred at RT for 24 h. To the mixture was added H$_2$O (5 mL) and the aqueous layer was extracted with EtOAc (5 mL×3). The combined organic layer was dried (Na$_2$SO$_4$) and filtered. After removal of solvent, the product was purified by silica gel chromatography using 20-40% EtOAc/hexane as the eluent to give 6-bromo-N-(3-chlorobenzyl)-2-methylquinazolin-4-amine (66 mg, 0.182 mmol, 36.4% yield). MS (M+H)$^+$=364.

Step 2: N-(3-chlorobenzyl)-6-(3,5-dimethylisoxazol-4-yl)-2-methylquinazolin-4-amine In a 2-neck flask was placed 6-bromo-N-(3-chlorobenzyl)-2-methylquinazolin-4-amine (60 mg, 0.165 mmol), (3,5-dimethylisoxazol-4-yl)boronic acid (30.3 mg, 0.215 mmol), PdCl$_2$(dppf) (12.11 mg, 0.017 mmol), and K$_2$CO$_3$ (68.6 mg, 0.496 mmol). The air was removed and re-filled with N$_2$ (2-3 times). Then a mixture of 1,4-Dioxane (1 ml) and Water (0.3 ml) was added and stirred at 95° C. (pre-heated) for 2 h. The organic layer was separated and the aqueous layer was extracted with EtOAc (5 mL×2). The combined organic layer was dried (Na$_2$SO$_4$) and filtered. After removal of solvent, the product was purified by silica gel chromatography using 35-60% EtOAc/hexane as the eluent to give N-(3-chlorobenzyl)-6-(3,5-dimethylisoxazol-4-yl)-2-methylquinazolin-4-amine (52.4 mg, 0.138 mmol, 84% yield). $^1$H NMR (400 MHz, Chloroform-d) δ 7.85 (d, J=8.6 Hz, 1H), 7.57 (dd, J=8.6, 1.8 Hz, 1H), 7.50 (d, J=1.9 Hz, 1H), 7.42 (q, J=1.4 Hz, 1H), 7.29 (qd, J=4.1, 2.0 Hz, 3H), 6.00 (s, 1H), 4.90 (d, J=5.6 Hz, 2H), 2.67 (s, 3H), 2.40 (s, 3H), 2.24 (s, 3H); MS (M+H)$^+$=379.

Example 10. N4-(3-chlorobenzyl)-6-(3,5-dimethyl-isoxazol-4-yl)-N2-(2-morpholinoethyl)quinazoline-2,4-diamine To a mixture of 2-chloro-N-(3-chlorobenzyl)-6-(3,5-dimethylisoxazol-4-yl)quinazolin-4-amine (Example 1, 39.9 mg, 0.1 mmol) and 2-morpholinoethanamine (130 mg, 1.0 mmol) was added EtOH (1 ml). The tube was sealed and heated at 90° C. for 16 h. After cooling to rt, the mixture was filtered through a filter, and submitted for purification to give N4-(3-chlorobenzyl)-6-(3,5-dimethylisoxazol-4-yl)-N2-(2-morpholinoethyl)quinazoline-2,4-diamine, 2TFA (23.1 mg, 0.032 mmol, 32.0% yield). $^1$H NMR (400 MHz, DMSO-d$_6$) δ 13.00 (s, 1H), 10.10 (s, 1H), 9.77 (s, 1H), 8.38 (s, 1H), 8.26 (s, 1H), 7.84 (d, J=8.7 Hz, 1H), 7.56 (d, J=8.5 Hz, 1H), 7.46 (s, 1H), 7.42-7.29 (m, 3H), 4.87 (s, 2H), 3.46 (m, 12H), 2.42 (s, 3H), 2.24 (s, 3H). (including 2 salt NH); MS (M+H)$^+$= 493.

Example 11. N4-(3-chlorobenzyl)-6-(3,5-dimethyl-isoxazol-4-yl)-N2-(2-(4-methylpiperazin-1-yl)ethyl)quinazoline-2,4-diamine To a mixture of 2-chloro-N-(3-chlorobenzyl)-6-(3,5-dimethylisoxazol-4-yl)quinazolin-4-amine (Example 1, 39.9 mg, 0.1 mmol) and 2-(4-methylpiperazin-1-yl)ethanamine (143 mg, 1.0 mmol) was added EtOH (1 ml). The tube was sealed and heated at 90° C. for 16 h. After cooling to rt, the mixture was filtered through a filter, and submitted for purification to give N4-(3-chlorobenzyl)-6-(3,5-dimethyl-isoxazol-4-yl)-N2-(2-(4-methylpiperazin-1-yl)ethyl)quinazoline-2,4-diamine, 2TFA (28.6 mg, 0.039 mmol, 39.0% yield). $^1$H NMR (400 MHz, DMSO-d$_6$) δ 12.81 (s, 1H), 10.07 (s, 1H), 9.62 (d, J=141.1 Hz, 1H), 8.23 (d, J=1.8 Hz, 1H), 7.82 (dd, J=8.4, 1.7 Hz, 1H), 7.52 (d, J=8.5 Hz, 1H), 7.46 (t, J=1.9 Hz, 1H), 7.42-7.27 (m, 3H), 4.83 (d, J=5.7 Hz, 2H), 4.43-2.67 (m, 15H), 2.42 (s, 3H), 2.25 (d, J=1.4 Hz, 3H). (including 1 salt NH); MS (M+H)$^+$=506.

Example 12. N-(3-chlorobenzyl)-2-(4-(2-(dimethyl-amino)ethyl)piperazin-1-yl)-6-(3,5-dimethylisox-azol-4-yl)quinazolin-4-amine To a mixture of 2-chloro-N-(3-chlorobenzyl)-6-(3,5-dimethylisoxazol-4-yl)quinazolin-4-amine (Example 1, 39.9 mg, 0.1 mmol) and N,N-dimethyl-2-(piperazin-1-yl)ethanamine (157 mg, 1.0 mmol) was added EtOH (1 ml). The tube was sealed and heated at 90° C. for 16 h. After cooling to rt, the mixture was filtered through a filter, and submitted for purification to give N-(3-chlorobenzyl)-2-(4-(2-(dimethyl-amino)ethyl)piperazin-1-yl)-6-(3,5-dimethylisoxazol-4-yl)quinazolin-4-amine, 2TFA (21 mg, 0.028 mmol, 28.1% yield). $^1$H NMR (400 MHz, DMSO-d$_6$) δ 11.92 (s, 1H), 10.05 (s, 1H), 9.00 (s, 1H), 8.22 (s, 1H), 7.82 (s, 1H), 7.72 (s, 1H), 7.47 (t, J=1.7 Hz, 1H), 7.37-7.29 (m, 3H), 4.80 (d, J=5.7 Hz, 2H), 3.82 (m, 6H), 3.22 (d, J=6.1 Hz, 2H), 2.80 (s, 6H), 2.72-2.50 (m, 4H), 2.42 (s, 3H), 2.25 (s, 3H). (including 2 salt NH); MS (M+H)$^+$=520.

Example 13. 3-((4-(((3-chlorobenzyl)amino)-6-(3,5-dimethylisoxazol-4-yl)quinazolin-2-yl)amino)pro-pan-1-ol The title compound was prepared from 2-chloro-N-(3-chlorobenzyl)-6-(3,5-dimethylisoxazol-4-yl)quinazolin-4-amine (Example 1, 39.9 mg, 0.1 mmol) and 3-aminopropan-1-ol (75 mg, 1.0 mmol) according to similar procedure described in Example 12. $^1$H NMR (400 MHz, DMSO-d$_6$) δ 12.33 (s, 1H), 10.01 (s, 1H), 8.20 (s, 1H), 8.05 (s, 1H), 7.80 (d, J=8.2 Hz, 1H), 7.51 (d, J=8.5 Hz, 1H), 7.48-7.44 (m, 1H), 7.38-7.29 (m, 3H), 4.81 (d, J=5.7 Hz, 2H), 4.56 (s, 1H), 3.44 (d, J=6.5 Hz, 4H), 2.41 (s, 3H), 2.24 (s, 3H), 1.69 (d, J=58.0 Hz, 2H). (including 1 salt NH); MS (M+H)$^+$=438.

Example 14. N-(3-chlorobenzyl)-2,6-bis(3,5-dim-ethylisoxazol-4-yl)quinolin-4-amine To a mixture of 4,4'-(4-chloroquinoline-2,6-diyl)bis(3,5-dimethylisoxazole) (53.1 mg, 0.15 mmol) and (3-chlorophenyl)methanamine (212 mg, 1.5 mmol) was added DMSO (1 ml). The tube was sealed and heated at 160° C. for 1 h under microwave irradiation. The mixture was then filtered through a filter and submitted for purification to give N-(3-chlorobenzyl)-2,6-bis(3,5-dimethylisoxazol-4-yl)quinolin-4-amine, 2TFA (17.9 mg, 0.026 mmol, 17.37% yield). MS (M+H)$^+$=459.

Example 15. 6-bromo-N-(3-chlorobenzyl)-2-(3,5-dimethylisoxazol-4-yl)quinolin-4-amine To a mixture of 4-(6-bromo-4-chloroquinolin-2-yl)-3,5-dimethylisoxazole (50.6 mg, 0.15 mmol) and (3-chlorophenyl)methanamine (212 mg, 1.5 mmol) was added DMSO (Volume: 1 ml). The tube was sealed and heated at 160° C. for 1 h under microwave irradiation. The mixture was then filtered through a filter and submitted for purification to give 6-bromo-N-(3-chlorobenzyl)-2-(3,5-dimethylisoxazol-4-yl)quinolin-4-amine, 2TFA (15.9 mg, 0.024 mmol, 15.80% yield). MS (M+H)$^+$=442, 444.

Example 16. N-(3-chlorobenzyl)-2-(4-(3-(dimethyl-amino)propyl)piperazin-1-yl)-6-(3,5-dimethylisox-azol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol) and N,N-dimethyl-3-(piperazin-1-yl)propan-1-amine (42.8 mg, 0.25 mmol) according to similar procedure described in Example 12. $^1$H NMR (400 MHz, DMSO-d$_6$) δ 9.67 (s, 1H), 8.19 (s, 1H), 7.72 (m, 4H), 7.47 (s, 1H), 7.42-7.26 (m, 3H), 4.79 (s, 2H), 3.70 (m, 8H), 3.06 (m, 4H), 2.82-2.73 (m, 6H), 2.42 (s, 3H), 2.25 (s, 3H), 1.98 (bs, 2H). (including 2 salt NH); MS (M+H)$^+$=534.

Example 17. (4-(4-((3-chlorobenzyl)amino)-6-(3,5-dimethylisoxazol-4-yl)quinazolin-2-yl)piperazin-1-yl)(cyclopropyl)methanone The title compound was prepared from 2-chloro-N-(3-chlorobenzyl)-6-(3,5-dimethylisoxazol-4-yl)quinazolin-4-amine (Example 1, 19.96 mg, 0.05 mmol), cyclopropyl (piperazin-1-yl)methanone, HCl (47.7 mg, 0.25 mmol) and Hunig's Base (0.044 ml, 0.250 mmol) according to similar procedure described in Example 12. $^1$H NMR (400 MHz, DMSO-d$_6$) δ 11.95 (s, 1H), 10.10 (s, 1H), 8.23 (s, 1H), 7.79 (m, 2H), 7.50 (d, J=1.6 Hz, 1H), 7.43-7.28 (m, 3H), 4.81 (d, J=5.6 Hz, 2H), 4.01-3.34 (m, 8H), 2.43 (s, 3H), 2.26 (s, 3H), 2.05-1.93 (m, 1H), 0.80-0.66 (m, 4H). (including 1 salt NH); MS (M+H)$^+$=517.

Example 18. (4-(4-((3-chlorobenzyl)amino)-6-(3,5-dimethylisoxazol-4-yl)quinazolin-2-yl)piperazin-1-yl)(1-methyl-1H-pyrazol-4-yl)methanone The title compound was prepared from 2-chloro-N-(3-chlorobenzyl)-6-(3,5-dimethylisoxazol-4-yl)quinazolin-4-amine (Example 1, 19.96 mg, 0.05 mmol), (1-methyl-1H-pyrazol-4-yl)(piperazin-1-yl)methanone, HCl (57.7 mg, 0.25 mmol) and Hunig's Base (0.044 ml, 0.25 mmol) according to similar procedure described in Example 12. $^1$H NMR (400 MHz, DMSO-d$_6$) δ 11.99 (s, 1H), 10.10 (s, 1H), 8.23 (s, 1H), 8.10 (s, 1H), 7.84 (s, 1H), 7.75 (s, 1H), 7.70 (d, J=0.7 Hz, 1H), 7.50 (s, 1H), 7.44-7.28 (m, 3H), 4.81 (d, J=5.6 Hz, 2H), 3.89 (s, 4H), 3.85 (s, 3H), 3.73 (s, 4H), 2.43 (s, 3H), 2.26 (s, 3H). (including 1 salt NH); MS (M+H)$^+$=557.

Example 19. 6-bromo-N-(3-chlorobenzyl)-2-(4-(2-(dimethylamino)ethyl)piperazin-1-yl)quinazolin-4-amine The title compound was prepared from 6-bromo-2-chloro-N-(3-chlorobenzyl)quinazolin-4-amine (19.15 mg, 0.05 mmol) and N,N-dimethyl-2-(piperazin-1-yl)ethanamine (39.3 mg, 0.25 mmol) according to similar procedure described in Example 12. $^1$H NMR (400 MHz, DMSO-d$_6$) δ 11.96 (s, 1H), 10.07 (s, 1H), 9.08 (s, 1H), 8.52 (s, 1H), 7.93 (s, 1H), 7.54 (s, 1H), 7.47 (d, J=2.1 Hz, 1H), 7.37-7.29 (m, 3H), 4.75 (d, J=5.6 Hz, 2H), 3.80 (br s, 4H), 3.23 (s, 2H), 2.79 (s, 6H), 2.71-2.50 (m, 6H). (including 2 salt NH); MS (M+H)$^+$=505.

Example 20. 2-(4-(4-((3-chlorobenzyl)amino)-6-(3,5-dimethylisoxazol-4-yl)quinazolin-2-yl)piperazin-1-yl)ethanol The title compound was prepared from 2-chloro-N-(3-chlorobenzyl)-6-(3,5-dimethylisoxazol-4-yl)quinazolin-4-amine (Example 1, 19.96 mg, 0.05 mmol) and 2-(piperazin-1-yl)ethanol (32.5 mg, 0.25 mmol) according to similar procedure described in Example 12. MS (M+H)$^+$=493.

Example 21. N-(3-chlorobenzyl)-6-(3,5-dimethylisoxazol-4-yl)-2-(4-isopentylpiperazin-1-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol) and 1-isopentylpiperazine (39.1 mg, 0.25 mmol) according to similar procedure described in Example 12. MS (M+H)$^+$=519.

Example 22. N4-(3-chlorobenzyn-N2-(2-(dimethylamino)ethyl)-6-(3,5-dimethylisoxazol-4-yl)-N2-methylquinazoline-2,4-diamine The title compound was prepared from 2-chloro-N-(3-chlorobenzyl)-6-(3,5-dimethylisoxazol-4-yl)quinazolin-4-amine (Example 1, 19.96 mg, 0.05 mmol) and N1,N1,N2-trimethylethane-1,2-diamine (25.5 mg, 0.25 mmol) according to similar procedure described in Example 12. MS (M+H)$^+$=465.

Example 23. (1-(4-((3-chlorobenzyl)amino)-6-(3,5-dimethylisoxazol-4-yl)quinazolin-2-yl)piperidin-4-yl)methanol The title compound was prepared from 2-chloro-N-(3-chlorobenzyl)-6-(3,5-dimethylisoxazol-4-yl)quinazolin-4-amine (Example 1, 19.96 mg, 0.05 mmol) and piperidin-4-ylmethanol (28.8 mg, 0.250 mmol) according to similar procedure described in Example 12. $^1$H NMR (400 MHz, DMSO-d$_6$) δ 11.72 (s, 1H), 9.99 (s, 1H), 8.20 (s, 1H), 7.82 (d, J=8.7 Hz, 1H), 7.72 (d, J=8.7 Hz, 1H), 7.47 (d, J=2.0 Hz, 1H), 7.37-7.29 (m, 3H), 4.78 (d, J=5.6 Hz, 2H), 4.50 (br s, 3H), 3.23 (d, J=5.7 Hz, 2H), 3.11 (m, 2H), 2.42 (s, 3H), 2.25 (s, 3H), 1.76 (d, J=13.3 Hz, 3H), 1.10 (d, J=12.5 Hz, 2H). (including 1 salt NH); MS (M+H)$^+$=478.

Example 24. (1-(4-((3-chlorobenzyl)amino)-6-(3,5-dimethylisoxazol-4-yl)quinazolin-2-yl)piperidin-3-yl)methanol The title compound was prepared from 2-chloro-N-(3-chlorobenzyl)-6-(3,5-dimethylisoxazol-4-yl)quinazolin-4-amine (Example 1, 19.96 mg, 0.05 mmol) and piperidin-3-ylmethanol (28.8 mg, 0.250 mmol) according to similar procedure described in Example 12. $^1$H NMR (400 MHz, DMSO-d$_6$) δ 11.74 (s, 1H), 9.98 (s, 1H), 8.20 (s, 1H), 7.82 (d, J=8.5 Hz, 1H), 7.73 (d, J=8.7 Hz, 1H), 7.47 (s, 1H), 7.39-7.27 (m, 3H), 4.78 (d, J=5.7 Hz, 2H), 4.51 (m, 4H), 3.07 (m, 3H), 2.42 (s, 3H), 2.25 (s, 3H), 1.80-1.22 (m, 5H). (including 1 salt NH); MS (M+H)$^+$=478.

Example 25. (1-(4-((3-chlorobenzyl)amino)-6-(3,5-dimethylisoxazol-4-yl)quinazolin-2-yl)piperidin-2-yl)methanol The title compound was prepared from 2-chloro-N-(3-chlorobenzyl)-6-(3,5-dimethylisoxazol-4-yl)quinazolin-4-amine (Example 1, 19.96 mg, 0.05 mmol) and piperidin-2-ylmethanol (28.8 mg, 0.250 mmol) according to similar procedure described in Example 12. MS (M+H)$^+$=478.

Example 26. N-(3-chlorobenzyl)-2-(4-(2-(dimethylamino)ethyl)piperazin-1-yl)-6-(3,5-dimethylisoxazol-4-yl)quinolin-4-amine To a mixture of 2-chloro-N-(3-chlorobenzyl)-6-(3,5-dimethylisoxazol-4-yl)quinolin-4-amine (59.7 mg, 0.15 mmol) and N,N-dimethyl-2-(piperazin-1-yl)ethanamine (236 mg, 1.5 mmol) was added DMF (1 ml). The tube was sealed and heated at 180° C. for 1.5 h under microwave irradiation After cooling to rt, the mixture was filtered through a filter, and submitted for purification to give N-(3-chlorobenzyl)-2-(4-(2-(dimethylamino)ethyl)piperazin-1-yl)-6-(3,5-dimethylisoxazol-4-yl)quinolin-4-amine, 2TFA (21.6 mg, 0.029 mmol, 19.27% yield). $^1$H NMR (400 MHz, DMSO-d$_6$) δ 11.72 (s, 1H), 8.94 (s, 1H), 8.22 (d, J=1.8 Hz, 1H), 7.89 (d, J=8.6 Hz, 1H), 7.76 (dd, J=8.7, 1.7 Hz, 1H), 7.51 (s, 1H), 7.40-7.29 (m, 3H), 6.02 (s, 1H), 4.75 (d, J=5.9 Hz, 2H), 3.67 (t, J=4.8 Hz, 4H), 3.23 (t, J=6.0 Hz, 2H), 2.79 (s, 6H), 2.61 (m, 6H), 2.43 (s, 3H), 2.26 (s, 3H). (including 1 salt NH); MS (M+H)$^+$=519.

Example 27. N-(3-chlorobenzyl)-4-(4-(2-(dimethylamino)ethyl)piperazin-1-yl)-6-(3,5-dimethylisoxazol-4-yl)quinolin-2-amine To a mixture of 4-chloro-N-(3-chlorobenzyl)-6-(3,5-dimethylisoxazol-4-yl)quinolin-2-amine (59.7 mg, 0.15 mmol) and N,N-dimethyl-2-(piperazin-1-yl)ethanamine (236 mg, 1.500 mmol) was added DMF (1 ml). The tube was sealed and heated at 180° C. for 1.5 h under microwave irradiation After cooling to rt, the mixture was filtered through a filter, and submitted for purification to give N-(3-chlorobenzyl)-

4-(4-(2-(dimethylamino)ethyl)piperazin-1-yl)-6-(3,5-dimethylisoxazol-4-yl)quinolin-2-amine, 2TFA (22.8 mg, 0.031 mmol, 20.34% yield). $^1$H NMR (400 MHz, DMSO-d$_6$) δ 12.61 (s, 1H), 9.40 (s, 1H), 7.88 (s, 1H), 7.77 (d, J=8.6 Hz, 1H), 7.71 (d, J=1.8 Hz, 1H), 7.51 (s, 1H), 7.46-7.35 (m, 3H), 6.44 (s, 1H), 4.76 (d, J=5.7 Hz, 2H), 3.30 (d, J=37.4 Hz, 6H), 2.79 (m, 12H), 2.44 (s, 3H), 2.25 (s, 3H). (including 1 salt NH); MS (M+H)$^+$=519.

Example 28. N-(3-chlorobenzyl)-6-(3,5-dimethylisoxazol-4-yl)-2-(1-(2-morpholinoethyl)-1H-pyrazol-4-yl)quinazolin-4-amine In a 2-neck flask was placed 2-chloro-N-(3-chlorobenzyl)-6-(3,5-dimethylisoxazol-4-yl)quinazolin-4-amine (Example 1, 39.9 mg, 0.1 mmol), 4-(2-(4-(4,4,5,5-tetramethyl-1,3,2-dioxaborolan-2-yl)-1H-pyrazol-1-yl)ethyl)morpholine (61.4 mg, 0.2 mmol), PdCl$_2$(dppf)-CH$_2$Cl$_2$ adduct (8.17 mg, 10.00 μmol), and K$_2$CO$_3$ (69.1 mg, 0.5 mmol). The air was removed and re-filled with N$_2$ (2-3 times). Then a mixture of 1,4-dioxane (1.5 ml) and water (0.5 ml) was added and stirred at 95° C. (pre-heated) for 1 h. The organic layer was separated and the aqueous layer was extracted with EtOAc (5 mL×2). The combined organic was dried (Na$_2$SO$_4$) and filtered. After removal of solvent, the product was dissolved in DMF, filtered through a filter and submitted for purification to give N-(3-chlorobenzyl)-6-(3,5-dimethylisoxazol-4-yl)-2-(1-(2-morpholinoethyl)-1H-pyrazol-4-yl)quinazolin-4-amine, 2TFA (15.2 mg, 0.02 mmol, 19.69% yield). $^1$H NMR (400 MHz, DMSO-d$_6$) δ 9.98 (s, 2H), 8.73 (s, 1H), 8.33 (s, 2H), 7.90 (m, 2H), 7.55 (s, 1H), 7.47-7.26 (m, 3H), 4.99 (s, 2H), 4.62 (s, 2H), 3.62 (m, 10H), 2.45 (s, 3H), 2.28 (s, 3H). (including 1 salt NH); MS (M+H)$^+$=544.

Example 29. (4-(4-((3-chlorobenzyl)amino)-6-(3,5-dimethylisoxazol-4-yl)quinazolin-2-yl)piperazin-1-yl)(pyridin-4-yl)methanone The title compound was prepared from 2-chloro-N-(3-chlorobenzyl)-6-(3,5-dimethylisoxazol-4-yl)quinazolin-4-amine (Example 1, 19.96 mg, 0.05 mmol), piperazin-1-yl(pyridin-4-yl)methanone, 2HCl (66.0 mg, 0.25 mmol), and Hunig's base (0.175 ml, 1.0 mmol) according to similar procedure described in Example 12. $^1$H NMR (400 MHz, DMSO-d$_6$) δ 12.02 (s, 1H), 10.09 (s, 1H), 8.84-8.49 (m, 2H), 8.23 (s, 1H), 7.84 (d, J=8.7 Hz, 1H), 7.73 (d, J=8.6 Hz, 1H), 7.48 (s, 1H), 7.46-7.41 (m, 2H), 7.38-7.24 (m, 3H), 4.78 (d, J=5.6 Hz, 2H), 4.01-3.70 (m, 6H), 3.38 (s, 2H), 2.42 (s, 3H), 2.25 (s, 3H). (including 1 salt NH); MS (M+H)$^+$=554.

Example 30. 2-(1-(4-((3-chlorobenzyl)amino)-6-(3,5-dimethylisoxazol-4-yl)quinazolin-2-yl)piperidin-4-yl)ethanol The title compound was prepared from 2-chloro-N-(3-chlorobenzyl)-6-(3,5-dimethylisoxazol-4-yl)quinazolin-4-amine (Example 1, 19.96 mg, 0.05 mmol) and 2-(piperidin-4-yl)ethanol (32.3 mg, 0.25 mmol) according to similar procedure described in Example 12. $^1$H NMR (400 MHz, DMSO-d$_6$) δ 11.89-11.54 (m, 1H), 10.00 (s, 1H), 8.20 (s, 1H), 7.82 (d, J=8.7 Hz, 1H), 7.72 (d, J=8.6 Hz, 1H), 7.48 (d, J=2.1 Hz, 1H), 7.41-7.26 (m, 3H), 4.77 (d, J=5.7 Hz, 2H), 4.46 (m, 3H), 3.53-2.92 (m, 4H), 2.42 (s, 3H), 2.25 (s, 3H), 1.75 (m, 3H), 1.33 (m, 2H), 1.16-0.96 (m, 2H). (including 1 salt NH); MS (M+H)$^+$=492.

Example 31. N-(3-chlorobenzyl)-6-(3,5-dimethylisoxazol-4-yl)-2-(1,2,3,6-tetrahydropyridin-4-yl)quinazolin-4-amine Step 1: tert-butyl 4-(4-((3-chlorobenzyl)amino)-6-(3,5-dimethylisoxazol-4-yl)quinazolin-2-yl)-5,6-dihydropyridine-1(2H)-carboxylate In a 2-neck flask was placed 2-chloro-N-(3-chlorobenzyl)-6-(3,5-dimethylisoxazol-4-yl)quinazolin-4-amine (Example 1, 399 mg, 1 mmol), tert-butyl 4-(4,4,5,5-tetramethyl-1,3,2-dioxaborolan-2-yl)-5,6-dihydropyridine-1(2H)-carboxylate (464 mg, 1.5 mmol), PdCl$_2$(dppf)-CH$_2$Cl$_2$ adduct (82 mg, 0.1 mmol), and K$_2$CO$_3$ (622 mg, 4.5 mmol). The air was removed and re-filled with N$_2$ (2-3 times). Then a mixture of 1,4-Dioxane (6 ml) and Water (3 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 20-40-50% EtOAc/hexane as the eluent to give tert-butyl 4-(4-((3-chlorobenzyl)amino)-6-(3,5-dimethylisoxazol-4-yl)quinazolin-2-yl)-5,6-dihydropyridine-1(2H)-carboxylate (403 mg, 0.738 mmol, 73.8% yield). MS (M+H)$^+$=546.

Step 2: N-(3-chlorobenzyl)-6-(3,5-dimethylisoxazol-4-yl)-2-(1,2,3,6-tetrahydropyridin-4-yl)quinazolin-4-amine To a solution of tert-butyl 4-(4-((3-chlorobenzyl)amino)-6-(3,5-dimethylisoxazol-4-yl)quinazolin-2-yl)-5,6-dihydropyridine-1(2H)-carboxylate (403 mg, 0.738 mmol) in 1,4-Dioxane (2 ml) was added HCl (4M in dioxane, 2 mL). The mixture was stirred at RT for 2 h. Then, hexane (20 mL) was added and carefully removed the solvent (repeat for 3 times). Then the solid was dried in vacuo to give N-(3-chlorobenzyl)-6-(3,5-dimethylisoxazol-4-yl)-2-(1,2,3,6-tetrahydropyridin-4-yl)quinazolin-4-amine, 2HCl (390 mg, 0.752 mmol, 102% crude yield). The material was used for next step without further purification. Submitted 25 mg for purification to give N-(3-chlorobenzyl)-6-(3,5-dimethylisoxazol-4-yl)-2-(1,2,3,6-tetrahydropyridin-4-yl)quinazolin-4-amine, 2TFA (as TFA salt) for screening. $^1$H NMR (400 MHz, DMSO-d$_6$) δ 9.08 (s, 1H), 8.77 (s, 2H), 8.25 (s, 1H), 7.79 (s, 2H), 7.45 (s, 1H), 7.36-7.25 (m, 3H), 7.12 (s, 1H), 4.83 (d, J=5.7 Hz, 2H), 3.83 (br s, 2H), 3.30 (br s, 2H), 2.79 (br s, 2H), 2.45 (s, 3H), 2.28 (s, 3H). (including 1 salt NH); MS (M+H)$^+$=446.

Example 32. N-(3-chlorobenzyl)-2-(4-(2-(dimethylamino)ethyl)-1,4-diazepan-1-yl)-6-(3,5-dimethylisoxazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol) and 2-(1,4-diazepan-1-yl)-N,N-dimethylethanamine (42.8 mg, 0.25 mmol) according to similar procedure described in Example 12. $^1$H NMR (400 MHz, DMSO-d$_6$) δ 11.79 (s, 1H), 10.08 (s, 1H), 8.23 (s, 1H), 7.83 (s, 2H), 7.46 (s, 1H), 7.34 (m, 3H), 4.78 (d, J=5.6 Hz, 2H), 3.95-2.81 (m, 12H), 2.75 (s, 6H), 2.43 (s, 3H), 2.25 (s, 3H), 2.02 (br s, 1H), 1.69 (br s, 1H). (including 1 salt NH); MS (M+H)$^+$=534.

Example 33. 2-(4-(4-((3-chlorobenzyl)amino)-6-(3, 5-dimethylisoxazol-4-yl)quinazolin-2-yl)-1,4-diazepan-1-yl)ethanol The title compound was prepared from 2-chloro-N-(3-chlorobenzyl)-6-(3,5-dimethylisoxazol-4-yl)quinazolin-4-amine (Example 1, 19.96 mg, 0.05 mmol) and 2-(1,4-diazepan-1-yl)ethanol (36.1 mg, 0.25 mmol) according to similar procedure described in Example 12. $^1$H NMR (400 MHz, DMSO-d$_6$) δ 11.98 (s, 1H), 10.15 (s, 1H), 9.45 (s, 1H), 8.26 (s, 1H), 7.83 (s, 2H), 7.47 (s, 1H), 7.34 (d, J=10.8 Hz, 3H), 5.39 (s, 1H), 4.79 (d, J=19.6 Hz, 3H), 4.35 (s, 1H), 3.53 (m, 9H), 2.42 (s, 3H), 2.25 (s, 3H), 2.06 (m, 2H). (including 1 salt NH); MS (M+H)$^+$=507.

Example 34. N-(3-chlorobenzyl)-2-(4-(2-(dimethylamino)ethyl)piperidin-1-yl)-6-(3,5-dimethylisoxazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol) and N,N-dimethyl-2-(piperidin-4-yl)ethanamine (39.1 mg, 0.25 mmol) according to similar procedure described in Example 12. $^1$H NMR (400 MHz, DMSO-d$_6$) δ 11.82 (s, 1H), 10.05 (s, 1H), 9.37 (s, 1H), 8.21 (s, 1H), 7.82 (s, 1H), 7.74 (s, 1H), 7.47 (s, 1H), 7.40-7.29 (m, 3H), 4.87-4.67 (m, 2H), 4.49 (s, 2H), 3.56-2.93 (m, 4H), 2.74 (d, J=4.6 Hz, 6H), 2.42 (s, 3H), 2.25 (s, 3H), 1.82-1.42 (m, 5H), 1.16 (m, 2H). (including 2 salt NH); MS (M+H)$^+$=519.

Example 35. (4-(4-((3-chlorobenzyl)amino)-6-(3,5-dimethylisoxazol-4-yl)quinazolin-2-yl)piperazin-1-yl)(pyridin-3-yl)methanone The title compound was prepared from 2-chloro-N-(3-chlorobenzyl)-6-(3,5-dimethylisoxazol-4-yl)quinazolin-4-amine (Example 1, 19.96 mg, 0.05 mmol) and piperazin-1-yl(pyridin-3-yl)methanone (47.8 mg, 0.25 mmol) according to similar procedure described in Example 12. $^1$H NMR (400 MHz, DMSO-d$_6$) δ 11.99 (s, 1H), 10.09 (s, 1H), 8.78-8.49 (m, 2H), 8.23 (s, 1H), 7.86 (dd, J=14.7, 8.2 Hz, 2H), 7.73 (d, J=8.6 Hz, 1H), 7.55-7.44 (m, 2H), 7.41-7.26 (m, 3H), 4.79 (d, J=5.6 Hz, 2H), 3.71 (m, 8H), 2.42 (s, 3H), 2.25 (s, 3H). include 1 salt NH); MS (M+H)$^+$=554.

Example 36. (4-(4-((3-chlorobenzyl)amino)-6-(3,5-dimethylisoxazol-4-yl)quinazolin-2-yl)piperazin-1-yl)(pyridin-3-yl)methanone The title compound was prepared from 2-chloro-N-(3-chlorobenzyl)-6-(3,5-dimethylisoxazol-4-yl)quinazolin-4-amine (Example 1, 19.96 mg, 0.05 mmol) and 2-hydroxy-1-(piperazin-1-yl)ethanone (36.0 mg, 0.25 mmol) according to similar procedure described in Example 12. $^1$H NMR (400 MHz, DMSO-d$_6$) δ 11.93 (s, 1H), 10.08 (s, 1H), 8.22 (s, 1H), 7.83 (s, 1H), 7.73 (s, 1H), 7.49 (s, 1H), 7.40-7.15 (m, 3H), 4.80 (d, J=5.2 Hz, 2H), 4.12 (s, 2H), 3.84 (s, 4H), 3.52 (m, 4H), 2.96 (s, 1H), 2.42 (s, 3H), 2.25 (s, 3H). (including 1 salt NH); MS (M+H)$^+$=507.

Example 37. 1-(4-(4-((3-chlorobenzyl)amino)-6-(3, 5-dimethylisoxazol-4-yl)quinazolin-2-yl)piperazin-1-yl)-2-(dimethylamino)ethanone The title compound was prepared from 2-chloro-N-(3-chlorobenzyl)-6-(3,5-dimethylisoxazol-4-yl)quinazolin-4-amine (Example 1, 19.96 mg, 0.05 mmol), 2-(dimethylamino)-1-(piperazin-1-yl)ethanone, 2HCl (61.0 mg, 0.25 mmol), and Hunig's base (0.175 ml, 1.0 mmol) according to similar procedure described in Example 12. $^1$H NMR (400 MHz, DMSO-d$_6$) δ 12.04 (s, 1H), 10.14 (s, 1H), 9.54 (s, 1H), 8.22 (s, 1H), 7.75 (s, 2H), 7.48 (s, 1H), 7.35 (t, J=7.7 Hz, 3H), 4.79 (s, 2H), 4.28 (d, J=4.4 Hz, 2H), 3.85-3.60 (m, 8H), 2.80 (d, J=4.1 Hz, 6H), 2.42 (s, 3H), 2.25 (s, 3H). (including 2 salt NH); MS (M+H)$^+$=534.

Example 38. 2-chloro-N-(3-chlorobenzyl)-7-(3,5-dimethylisoxazol-4-yl)quinazolin-4-amine In a 2-neck flask was placed 7-bromo-2-chloro-N-(3-chlorobenzyl)quinazolin-4-amine (383 mg, 1 mmol), 3,5-dimethyl-4-(4,4,5,5-tetramethyl-1,3,2-dioxaborolan-2-yl)isoxazole (223 mg, 1.000 mmol), PdCl$_2$(dppf)-CH$_2$Cl$_2$ adduct (82 mg, 0.1 mmol), and K$_2$CO$_3$ (415 mg, 3.0 mmol). The air was removed and re-filled with N$_2$ (2-3 times). Then a mixture of 1,4-dioxane (3 ml) and water (1.5 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 25-60% EtOAc/hexane as the eluent to give 2-chloro-N-(3-chlorobenzyl)-7-(3,5-dimethylisoxazol-4-yl)quinazolin-4-amine (370 mg, 0.927 mmol, 93% yield). 25 mg of material was submitted for HPLC purification to give TFA salt for screening. MS (M+H)$^+$=399.

Example 39. N-(3-chlorobenzyl)-2-(4-(2-(dimethylamino)ethyl)piperazin-1-yl)-7-(3,5-dimethylisoxazol-4-yl)quinazolin-4-amine The title compound was prepared from 2-chloro-N-(3-chlorobenzyl)-7-(3,5-dimethylisoxazol-4-yl)quinazolin-4-amine (19.96 mg, 0.05 mmol) and N,N-dimethyl-2-(piperazin-1-yl)ethanamine (39.3 mg, 0.25 mmol) according to similar procedure described in Example 12. MS (M+H)$^+$= 520.

Example 40. 2-(4-(4-((3-chlorobenzyl)amino)-7-(3, 5-dimethylisoxazol-4-yl)quinazolin-2-yl)piperazin-1-yl)ethanol The title compound was prepared from 2-chloro-N-(3-chlorobenzyl)-7-(3,5-dimethylisoxazol-4-yl)quinazolin-4-amine (19.96 mg, 0.05 mmol) and 2-(piperazin-1-yl)ethanol (32.5 mg, 0.250 mmol) according to similar procedure described in Example 12. MS (M+H)$^+$=493.

Example 41. N-(3-chlorobenzyl)-2-(4-((dimethylamino)methyl)piperidin-1-yl)-6-(3,5-dimethylisoxazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol) and N,N-dimethyl-1-(piperidin-4-yl)methanamine (35.6 mg, 0.25 mmol) according to similar procedure described in Example 12. $^1$H NMR (400 MHz, DMSO-d$_6$) δ 11.88 (s, 1H), 10.07 (s, 1H), 9.33 (s, 1H), 8.38-8.10 (m, 1H), 7.79 (m, 2H), 7.47 (s, 1H), 7.33 (m, 3H), 4.78 (s, 2H), 4.50 (s, 2H), 3.15 (s, 2H), 2.95 (t, J=6.3 Hz, 2H), 2.79 (s, 3H), 2.77 (s, 3H), 2.42 (s, 3H), 2.25 (s, 3H), 2.12 (s, 1H), 1.79 (s, 2H), 1.18 (m, 2H). (including 2 salt NH); MS (M+H)⁺=505.

Example 42. 2-(1-(4-((3-chlorobenzyl)amino)-6-(3, 5-dimethylisoxazol-4-yl)quinazolin-2-yl)-1H-pyrazol-4-yl)ethanol To a mixture of 2-chloro-N-(3-chlorobenzyl)-6-(3,5-dimethylisoxazol-4-yl)quinazolin-4-amine (Example 1, 19.96 mg, 0.05 mmol), 2-(1H-pyrazol-4-yl)ethanol (28.0 mg, 0.250 mmol) and $K_2CO_3$ (34.6 mg, 0.25 mmol) was added DMF (Volume: 1 ml). The tube was sealed and heated at 150° C. for 1.5 h under microwave irradiation. After cooling to rt, the mixture was filtered through a filter, and submitted for purification to give 2-(1-(4-(((3-chlorobenzyl)amino)-6-(3,5-dimethylisoxazol-4-yl)quinazolin-2-yl)-1H-pyrazol-4-yl)ethanol, 2TFA (0.6 mg, 0.854 µmol, 1.707% yield). MS (M+H)⁺=475.

Example 43. N-(3-chlorobenzyl)-3-(4-(2-(dimethylamino)ethyl)piperazin-1-yl)-7-(3,5-dimethylisoxazol-4-yl)isoquinolin-1-amine To a mixture of 3-chloro-N-(3-chlorobenzyl)-7-(3,5-dimethylisoxazol-4-yl)isoquinolin-1-amine (0.02 g, 0.05 mmol) and N,N-dimethyl-2-(piperazin-1-yl)ethanamine (0.157 g, 1.0 mmol) was added DMF (1 ml). The tube was sealed and heated at 200° C. for 2 h under microwave irradiation. After cooling to rt, the mixture was filtered through a filter, and submitted for purification to give N-(3-chlorobenzyl)-3-(4-(2-(dimethylamino)ethyl)piperazin-1-yl)-7-(3,5-dimethylisoxazol-4-yl)isoquinolin-1-amine, 2TFA. MS (M+H)⁺=519.

Example 44. 2-(4-(1-((3-chlorobenzyl)amino)-7-(3, 5-dimethylisoxazol-4-yl)isoquinolin-3-yl)piperazin-1-yl)ethanol To a mixture of 3-chloro-N-(3-chlorobenzyl)-7-(3,5-dimethylisoxazol-4-yl)isoquinolin-1-amine (0.02 g, 0.05 mmol) and 2-(piperazin-1-yl)ethanol (0.13 g, 1.0 mmol) was added DMF (1 ml). The tube was sealed and heated at 200° C. for 2 h under microwave irradiation. After cooling to rt, the mixture was filtered through a filter, and submitted for purification to give 2-(4-(1-((3-chlorobenzyl)amino)-7-(3,5-dimethylisoxazol-4-yl)isoquinolin-3-yl)piperazin-1-yl)ethanol, 2TFA. MS (M+H)⁺=492.

Example 45. 1-(4-(4-((3-chlorobenzyl)amino)-6-(3, 5-dimethylisoxazol-4-yl)quinazolin-2-yl)piperazin-1-yl)propan-2-ol The title compound was prepared from 2-chloro-N-(3-chlorobenzyl)-6-(3,5-dimethylisoxazol-4-yl)quinazolin-4-amine (Example 1, 19.96 mg, 0.05 mmol) and 1-(piperazin-1-yl)propan-2-ol (36.1 mg, 0.25 mmol) according to similar procedure described in Example 12. MS (M+H)⁺=507.

Example 46. (R)-1-(4-(4-((3-chlorobenzyl)amino)-6-(3,5-dimethylisoxazol-4-yl)quinazolin-2-yl)piperazin-1-yl)propan-2-ol The title compound was prepared from 2-chloro-N-(3-chlorobenzyl)-6-(3,5-dimethylisoxazol-4-yl)quinazolin-4-amine (Example 1, 19.96 mg, 0.05 mmol) and (R)-1-(piperazin-1-yl)propan-2-ol (36.1 mg, 0.250 mmol) according to similar procedure described in Example 12. ¹H NMR (400 MHz, DMSO-$d_6$) δ 9.65 (s, 1H), 8.16 (s, 1H), 7.74 (s, 1H), 7.59 (s, 1H), 7.47 (s, 1H), 7.40-7.20 (m, 3H), 5.51 (s, 1H), 4.77 (s, 2H), 4.63 (s, 2H), 4.06 (s, 1H), 3.29 (m, 8H), 2.42 (s, 3H), 2.25 (s, 3H), 1.10 (d, J=6.1 Hz, 3H); MS (M+H)⁺=507.

Example 47. (S)-1-(4-(4-((3-chlorobenzyl)amino)-6-(3,5-dimethylisoxazol-4-yl)quinazolin-2-yl)piperazin-1-yl)propan-2-ol The title compound was prepared from 2-chloro-N-(3-chlorobenzyl)-6-(3,5-dimethylisoxazol-4-yl)quinazolin-4-amine (Example 1, 19.96 mg, 0.05 mmol) and (S)-1-(piperazin-1-yl)propan-2-ol (36.1 mg, 0.250 mmol) according to similar procedure described in Example 12. MS (M+H)⁺=507.

Example 48. 2-(4-(4-((3-chlorobenzyl)amino)-6-(3, 5-dimethylisoxazol-4-yl)quinazolin-2-yl)-1H-pyrazol-1-yl)ethanol The title compound was prepared from 2-chloro-N-(3-chlorobenzyl)-6-(3,5-dimethylisoxazol-4-yl)quinazolin-4-amine (Example 1, 19.96 mg, 0.05 mmol), 2-(4-(4,4,5,5-tetramethyl-1,3,2-dioxaborolan-2-yl)-1H-pyrazol-1-yl)ethanol (23.81 mg, 0.10 mmol), $PdCl_2(dppf)$-$CH_2Cl_2$ adduct (8.17 mg, 10.0 µmol), and $K_2CO_3$ (41.5 mg, 0.30 mmol) according to similar procedure described in Example 28. ¹H NMR (400 MHz, DMSO-$d_6$) δ 10.42 (s, 1H), 8.70 (s, 1H), 8.36 (s, 2H), 7.97 (s, 1H), 7.87 (d, J=8.5 Hz, 1H), 7.56 (d, J=2.0 Hz, 1H), 7.48-7.40 (m, 1H), 7.40-7.25 (m, 2H), 5.01 (s, 3H, including 1 OH), 4.26 (t, J=5.3 Hz, 2H), 3.77 (t, J=5.3 Hz, 2H), 2.46 (s, 3H), 2.28 (s, 3H); MS (M+H)⁺=475.

Example 49. N-(3-chlorobenzyl)-6-(3,5-dimethylisoxazol-4-yl)-2-(1-methyl-1H-pyrazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol), 1-methyl-4-(4, 4,5,5-tetramethyl-1,3,2-dioxaborolan-2-yl)-1H-pyrazole (20.81 mg, 0.10 mmol), $PdCl_2(dppf)$-$CH_2Cl_2$ adduct (8.17 mg, 10.0 µmol), and $K_2CO_3$ (41.5 mg, 0.30 mmol) according to similar procedure described in Example 28. MS (M+H)⁺=445.

Example 50. 2-(4-(4-((3-chlorobenzyl)amino)-6-(3, 5-dimethylisoxazol-4-yl)quinazolin-2-yl)-1H-pyrazol-1-yl)acetamide The title compound was prepared from 2-chloro-N-(3-chlorobenzyl)-6-(3,5-dimethylisoxazol-4-yl)quinazolin-4-amine (Example 1, 19.96 mg, 0.05 mmol), 2-(4-(4,4,5,5-tetramethyl-1,3,2-dioxaborolan-2-yl)-1H-pyrazol-1-yl)acetamide (25.1 mg, 0.10 mmol), $PdCl_2(dppf)$-$CH_2Cl_2$ adduct (8.17 mg, 10.0 µmol), and $K_2CO_3$ (41.5 mg, 0.30 mmol) according to similar procedure described in Example 28. MS (M+H)⁺=488.

Example 51. 2-(4-(4-((3-chlorobenzyl)amino)-7-(3, 5-dimethylisoxazol-4-yl)quinazolin-2-yl)-1H-pyrazol-1-yl)acetamide The title compound was prepared from 2-chloro-N-(3-chlorobenzyl)-7-(3,5-dimethylisoxazol-4-yl)quinazolin-4-amine (19.96 mg, 0.05 mmol), 2-(4-(4,4,5,5-tetramethyl-1, 3,2-dioxaborolan-2-yl)-1H-pyrazol-1-yl)acetamide (25.1 mg, 0.100 mmol), PdCl$_2$(dppf)-CH$_2$Cl$_2$ adduct (8.17 mg, 10.0 µmol), and K$_2$CO$_3$ (34.6 mg, 0.250 mmol) according to similar procedure described in Example 28. $^1$H NMR (400 MHz, DMSO-d$_6$) δ 10.48 (s, 1H), 8.70 (s, 1H), 8.46 (s, 1H), 8.31 (s, 1H), 7.70 (m, 3H), 7.55 (d, J=1.9 Hz, 1H), 7.44 (dt, J=7.5, 1.6 Hz, 1H), 7.40-7.20 (m, 3H), 5.01 (s, 2H), 4.91 (s, 2H), 2.51 (m, 3H), 2.31 (s, 3H); MS (M+H)$^+$=488.

Example 52. 2-(4-(4-((3-chlorobenzyl)amino)-6-(3, 5-dimethylisoxazol-4-yl)quinazolin-2-yl)piperazin-1-yl)-N,N-dimethylacetamide The title compound was prepared from 2-chloro-N-(3-chlorobenzyl)-6-(3,5-dimethylisoxazol-4-yl)quinazolin-4-amine (Example 1, 19.96 mg, 0.05 mmol) and N,N-dimethyl-2-(piperazin-1-yl)acetamide (42.8 mg, 0.250 mmol) according to similar procedure described in Example 12. $^1$H NMR (400 MHz, DMSO-d$_6$) δ 10.05 (s, 1H), 8.18 (s, 1H), 7.75 (s, 1H), 7.62 (s, 1H), 7.47 (s, 1H), 7.40-7.22 (m, 3H), 4.77 (s, 2H), 4.58 (s, 2H), 4.23 (s, 2H), 3.30 (m, 6H), 2.91 (s, 3H), 2.90 (s, 3H), 2.42 (s, 3H), 2.25 (s, 3H); MS (M+H)$^+$=534.

Example 53. 2-(4-(4-((3-chlorobenzyl)amino)-6-(3, 5-dimethylisoxazol-4-yl)quinazolin-2-yl)piperazin-1-yl)-N-methylacetamide The title compound was prepared from 2-chloro-N-(3-chlorobenzyl)-6-(3,5-dimethylisoxazol-4-yl)quinazolin-4-amine (Example 1, 19.96 mg, 0.05 mmol), N-methyl-2-(piperazin-1-yl)acetamide, HCl (48.4 mg, 0.25 mmol), and Hunig's base (0.175 ml, 1.0 mmol) according to similar procedure described in Example 12. $^1$H NMR (400 MHz, DMSO-d$_6$) δ 10.10 (s, 1H), 8.26 (m, 2H), 7.75 (s, 2H), 7.47 (s, 1H), 7.39-7.23 (m, 3H), 4.76 (s, 2H), 3.48 (m, 10H), 2.65 (d, J=4.6 Hz, 3H), 2.42 (s, 3H), 2.25 (s, 3H); MS (M+H)$^+$=520.

Example 54. 2-(4-(4-((3-chlorobenzyl)amino)-6-(3, 5-dimethylisoxazol-4-yl)quinazolin-2-yl)piperazin-1-yl)acetamide The title compound was prepared from 2-chloro-N-(3-chlorobenzyl)-6-(3,5-dimethylisoxazol-4-yl)quinazolin-4-amine (Example 1, 19.96 mg, 0.05 mmol), 2-(piperazin-1-yl)acetamide, HCl (44.9 mg, 0.25 mmol), and Hunig's base (0.175 ml, 1.0 mmol) according to similar procedure described in Example 12. $^1$H NMR (400 MHz, DMSO-d$_6$) δ 10.07 (s, 1H), 8.18 (s, 1H), 8.01-7.52 (m, 4H), 7.47 (s, 1H), 7.41-7.25 (m, 3H), 4.76 (s, 2H), 4.14-2.86 (m, 10H), 2.42 (s, 3H), 2.25 (s, 3H); MS (M+H)$^+$=506.

Example 55. 2-amino-1-(4-(4-((3-chlorobenzyl) amino)-6-(3,5-dimethylisoxazol-4-yl)quinazolin-2-yl)piperazin-1-yl)ethanone The title compound was prepared from 2-chloro-N-(3-chlorobenzyl)-6-(3,5-dimethylisoxazol-4-yl)quinazolin-4-amine (Example 1, 19.96 mg, 0.05 mmol), 2-amino-1-(piperazin-1-yl)ethanone, HCl (44.9 mg, 0.25 mmol), and Hunig's base (0.175 ml, 1.0 mmol) according to similar procedure described in Example 12. $^1$H NMR (400 MHz, DMSO-d$_6$) δ 12.06 (s, 1H), 10.15 (s, 1H), 8.23 (s, 1H), 8.03 (s, 3H), 7.78 (s, 2H), 7.48 (s, 1H), 7.39-7.26 (m, 3H), 4.79 (s, 2H), 3.98-3.72 (m, 6H), 3.37 (s, 4H), 2.42 (s, 3H), 2.25 (s, 3H). (including 2 salt NH); MS (M+H)$^+$=506.

Example 56. 1-(4-(4-((3-chlorobenzyl)amino)-6-(3, 5-dimethylisoxazol-4-yl)quinazolin-2-yl)-1H-pyrazol-1-yl)-2-methylpropan-2-ol The title compound was prepared from 2-chloro-N-(3-chlorobenzyl)-6-(3,5-dimethylisoxazol-4-yl)quinazolin-4-amine (Example 1, 19.96 mg, 0.05 mmol), 2-methyl-1-(4-(4,4,5,5-tetramethyl-1,3,2-dioxaborolan-2-yl)-1H-pyrazol-1-yl)propan-2-ol (26.6 mg, 0.10 mmol), PdCl$_2$(dppf)-CH$_2$Cl$_2$ adduct (8.17 mg, 10.0 µmol), and K$_2$CO$_3$ (41.5 mg, 0.30 mmol) according to similar procedure described in Example 28. MS (M+H)$^+$=503.

Example 57. 3-(4-(4-((3-chlorobenzyl)amino)-6-(3, 5-dimethylisoxazol-4-yl)quinazolin-2-yl)-1H-pyrazol-1-yl)propanenitrile The title compound was prepared from 2-chloro-N-(3-chlorobenzyl)-6-(3,5-dimethylisoxazol-4-yl)quinazolin-4-amine (Example 1, 19.96 mg, 0.05 mmol), 3-(4-(4,4,5,5-tetramethyl-1,3,2-dioxaborolan-2-yl)-1H-pyrazol-1-yl) propanenitrile (24.71 mg, 0.10 mmol), PdCl$_2$(dppf)-CH$_2$Cl$_2$ adduct (8.17 mg, 10.0 µmol), and K$_2$CO$_3$ (41.5 mg, 0.30 mmol) according to similar procedure described in Example 28. MS (M+H)$^+$=484.

Example 58. N-(3-chlorobenzyl)-6-(3,5-dimethylisoxazol-4-yl)-2-(1-(2-methoxyethyl)-1H-pyrazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol), 1-(2-methoxyethyl)-4-(4,4,5,5-tetramethyl-1,3,2-dioxaborolan-2-yl)-1H-pyrazole (25.2 mg, 0.10 mmol), PdCl$_2$(dppf)-CH$_2$Cl$_2$ adduct (8.17 mg, 10.0 µmol), and K$_2$CO$_3$ (41.5 mg, 0.30 mmol) according to similar procedure described in Example 28. $^1$H NMR (400 MHz, DMSO-d$_6$) δ 10.45 (s, 1H), 8.69 (s, 1H), 8.36 (s, 2H), 7.96 (s, 1H), 7.91-7.81 (m, 1H), 7.56 (s, 1H), 7.44 (dd, J=7.5, 1.7 Hz, 1H), 7.40-7.26 (m, 3H), 5.01 (s, 2H), 4.39 (s, 2H), 3.72 (t, J=5.1 Hz, 2H), 3.23 (s, 3H), 2.46 (s, 3H), 2.28 (s, 3H). (including 1 salt NH); MS (M+H)$^+$=489.

Example 59. 2-(4-(4-((3-chlorobenzyl)amino)-6-(3, 5-dimethylisoxazol-4-yl)quinazolin-2-yl)-1H-pyrazol-1-yl)acetonitrile The title compound was prepared from 2-chloro-N-(3-chlorobenzyl)-6-(3,5-dimethylisoxazol-4-yl)quinazolin-4-amine (Example 1, 19.96 mg, 0.05 mmol), 2-(4-(4,4,5,5-tetramethyl-1,3,2-dioxaborolan-2-yl)-1H-pyrazol-1-yl) acetonitrile (23.31 mg, 0.10 mmol), PdCl$_2$(dppf)-CH$_2$Cl$_2$ adduct (8.17 mg, 10.0 µmol), and K$_2$CO$_3$ (41.5 mg, 0.30 mmol) according to similar procedure described in Example 28. MS (M+H)$^+$=470.

Example 60. N-(3-chlorobenzyl)-2-(1-(2-(dimethylamino)ethyl)-1H-pyrazol-4-yl)-6-(3,5-dimethylisoxazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol), N,N-dimethyl-2-(4-(4,4,5,5-tetramethyl-1,3,2-dioxaborolan-2-yl)-1H- pyrazol-1-yl)ethanamine (0.027 g, 0.10 mmol), PdCl$_2$(dppf)-CH$_2$Cl$_2$ adduct (8.17 mg, 10.0 μmol), and K$_2$CO$_3$ (41.5 mg, 0.30 mmol) according to similar procedure described in Example 28. $^1$H NMR (400 MHz, DMSO-d$_6$) δ 9.47 (s, 1H), 8.71 (s, 2H), 8.32 (s, 1H), 7.88 (s, 2H), 7.54 (s, 1H), 7.46-7.39 (m, 1H), 7.38-7.31 (m, 2H), 4.98 (br s, 2H), 4.63 (br s, 2H), 3.62 (br s, 2H), 2.82 (s, 6H), 2.45 (s, 3H), 2.28 (s, 3H); MS (M+H)$^+$=502.

Example 61. N-(3-chlorobenzyl)-6-(3,5-dimethyl-isoxazol-4-yl)-2-(1-(oxetan-3-yl)-1H-pyrazol-4-yl)quinazolin-4-amine The title compound was prepared from 2-chloro-N-(3-chlorobenzyl)-6-(3,5-dimethylisoxazol-4-yl)quinazolin-4-amine (Example 1, 19.96 mg, 0.05 mmol), 1-(oxetan-3-yl)-4-(4,4,5,5-tetramethyl-1,3,2-dioxaborolan-2-yl)-1H-pyrazole (25.01 mg, 0.10 mmol), PdCl$_2$(dppf)-CH$_2$Cl$_2$ adduct (8.17 mg, 10.0 μmol), and K$_2$CO$_3$ (41.5 mg, 0.30 mmol) according to similar procedure described in Example 28. MS (M+H)$^+$=487.

Example 62. 2-(4-(4-((3-chlorobenzyl)amino)-6-(3,5-dimethylisoxazol-4-yl)quinazolin-2-yl)-1H-pyrazol-1-yl)-2-methylpropan-1-ol The title compound was prepared from 2-chloro-N-(3-chlorobenzyl)-6-(3,5-dimethylisoxazol-4-yl)quinazolin-4-amine (Example 1, 39.9 mg, 0.1 mmol), 2-methyl-2-(4-(4,4,5,5-tetramethyl-1,3,2-dioxaborolan-2-yl)-1H-pyrazol-1-yl)propan-1-ol (53.2 mg, 0.20 mmol), PdCl$_2$(dppf)-CH$_2$Cl$_2$ adduct (8.17 mg, 10.0 μmol), and K$_2$CO$_3$ (83 mg, 0.60 mmol) according to similar procedure described in Example 28. $^1$H NMR (400 MHz, DMSO-d$_6$) δ 8.85 (s, 1H), 8.19 (s, 2H), 8.01 (s, 1H), 7.72 (s, 2H), 7.52 (s, 1H), 7.41 (dt, J=7.6, 1.4 Hz, 1H), 7.34 (t, J=7.7 Hz, 1H), 7.27 (d, J=7.9 Hz, 1H), 5.03 (s, 1H), 4.83 (s, 2H), 3.60 (d, J=5.3 Hz, 2H), 2.45 (s, 3H), 2.28 (s, 3H), 1.49 (s, 6H); MS (M+H)$^+$=503.

Example 63. (5-(4-((3-chlorobenzyl)amino)-6-(3,5-dimethylisoxazol-4-yl)quinazolin-2-yl)pyridin-2-yl)methanol The title compound was prepared from 2-chloro-N-(3-chlorobenzyl)-6-(3,5-dimethylisoxazol-4-yl)quinazolin-4-amine (Example 1, 19.96 mg, 0.05 mmol), (6-(hydroxymethyl)pyridin-3-yl)boronic acid (15.29 mg, 0.10 mmol), PdCl$_2$(dppf)-CH$_2$Cl$_2$ adduct (8.17 mg, 10.0 μmol), and K$_2$CO$_3$ (41.5 mg, 0.30 mmol) according to similar procedure described in Example 28. $^1$H NMR (400 MHz, DMSO-d$_6$) δ 9.45 (br s, 1H), 9.38 (dd, J=2.2, 0.8 Hz, 1H), 8.78 (d, J=8.2 Hz, 1H), 8.33 (s, 1H), 7.96-7.81 (m, 2H), 7.69 (d, J=8.3 Hz, 1H), 7.53 (t, J=1.9 Hz, 1H), 7.42 (dt, J=7.6, 1.4 Hz, 1H), 7.35 (t, J=7.7 Hz, 1H), 7.29 (ddd, J=7.9, 2.1, 1.3 Hz, 1H), 4.95 (d, J=5.7 Hz, 2H), 4.68 (s, 2H), 2.96 (s, 1H), 2.30 (s, 3H). (One Me peak is overlapped with DMSO); MS (M+H)$^+$=472.

Example 64. N-(3-chlorobenzyl)-2-(4-(2-(dimethylamino)ethyl)piperazin-1-yl)-6-(1H-pyrazol-4-yl)quinazolin-4-amine Step 1: 6-bromo-N-(3-chlorobenzyl)-2-(4-(2-(dimethylamino)ethyl)piperazin-1-yl)quinazolin-4-amine To a suspension of 6-bromo-2-chloro-N-(3-chlorobenzyl)quinazolin-4-amine (575 mg, 1.5 mmol) in EtOH (6 ml) was added N,N-dimethyl-2-(piperazin-1-yl)ethanamine (314 mg, 1.995 mmol) and then Hunig's base (0.348 ml, 1.995 mmol). The tube was sealed and heated at 90° C. for 5 h. After cooling to rt, the mixture was poured into EtOAc/H$_2$O (50 mL/50 mL). The aqueous layer was extracted with EtOAc (50 mL). The combined organic layer was dried (Na$_2$SO$_4$) and filtered. After removal of solvent, the product was dried in vacuo to give 6-bromo-N-(3-chlorobenzyl)-2-(4-(2-(dimethylamino)ethyl)piperazin-1-yl)quinazolin-4-amine (760 mg, 1.508 mmol, 101% yield), which was used for next step without further purification. MS (M+H)$^+$=505.

Step 2: N-(3-chlorobenzyl)-2-(4-(2-(dimethylamino)ethyl)piperazin-1-yl)-6-(1H-pyrazol-4-yl)quinazolin-4-amine In a 2-neck flask was placed 6-bromo-N-(3-chlorobenzyl)-2-(4-(2-(dimethylamino)ethyl)piperazin-1-yl)quinazolin-4-amine (0.025 g, 0.05 mmol), tert-butyl 4-(4,4,5,5-tetramethyl-1,3,2-dioxaborolan-2-yl)-1H-pyrazole-1-carboxylate (0.029 g, 0.10 mmol), PdCl$_2$(dppf)-CH$_2$Cl$_2$ adduct (4.08 mg, 5.0 μmol), and K$_2$CO$_3$ (0.041 g, 0.30 mmol). The air was removed and re-filled with N$_2$ (2-3 times). Then added a mixture of 1,4-dioxane (1 ml) and water (0.5 ml) was added and stirred at 95° C. (pre-heated) for 1 h. The organic layer was separated and the aqueous layer was extracted with EtOAc (5 mL×2). The combined organic was dried (Na$_2$SO$_4$) and filtered. After removal of solvent, the product was filtered through a PL-Thio-resin, eluted with EtOAc, dried, dissolved in DMF, and submitted for purification using basic condition to give N-(3-chlorobenzyl)-2-(4-(2-(dimethylamino)ethyl)piperazin-1-yl)-6-(1H-pyrazol-4-yl)quinazolin-4-amine, 2TFA. $^1$H NMR (400 MHz, DMSO-d$_6$) δ 13.05 (br s, 1H), 11.78 (s, 1H), 9.99 (s, 1H), 8.50 (s, 1H), 8.07 (br s, 3H), 7.63 (d, J=8.8 Hz, 1H), 7.48 (s, 1H), 7.41-7.28 (m, 3H), 4.82 (s, 2H), 3.80 (s, 4H), 3.21 (s, 2H), 2.79 (s, 6H), 2.68-2.59 (m, 2H), 2.54 (br s, 4H). (including 1 salt NH); MS (M+H)$^+$=491.

Example 65. N-(3-chlorobenzyl)-6-(3,5-dimethyl-1H-pyrazol-4-yl)-2-(4-(2-(dimethylamino)ethyl)piperazin-1-yl)quinazolin-4-amine In a 2-neck flask was placed 6-bromo-N-(3-chlorobenzyl)-2-(4-(2-(dimethylamino)ethyl)piperazin-1-yl)quinazolin-4-amine (25.2 mg, 0.05 mmol), tert-butyl 3,5-dimethyl-4-(4,4,5,5-tetramethyl-1,3,2-dioxaborolan-2-yl)-1H-pyrazole-1-carboxylate (32.2 mg, 0.10 mmol), PdCl$_2$(dppf)-CH$_2$Cl$_2$ adduct (4.08 mg, 5.0 μmol), and K$_2$CO$_3$ (41.5 mg, 0.30 mmol). The air was removed and re-filled with N$_2$ (2-3 times). Then added a mixture of 1,4-dioxane (1 ml) and water (0.5 ml) was added and stirred at 95° C. (pre-heated) for overnight. The organic layer was separated and the aqueous layer was extracted with EtOAc (5 mL×2). The combined organic was dried (Na$_2$SO$_4$) and filtered. After removal of solvent, the product was filtered through a PL-Thio-resin, eluted with EtOAc, dried. Then added TFA (0.5 mL) and stirred for 10 min to help complete deprotection. Then the mixture was concentrated to remove most of TFA, dissolved in DMF, and submitted for purification using basic condition to give N-(3-chlorobenzyl)-6-(3,5-dimethyl-1H-pyrazol-4-yl)-2-(4-(2-(dimethylamino)ethyl)piperazin-1-yl)quinazolin-4-amine, 2TFA (3 mg, 4.02 μmol, 8.03% yield). $^1$H NMR (400 MHz, DMSO-d$_6$) δ 11.83 (s, 1H), 10.01 (s, 1H), 8.13 (s, 1H), 7.75 (d, J=8.7 Hz, 1H), 7.68 (d, J=8.5 Hz, 1H), 7.46 (d, J=2.0 Hz, 1H), 7.40-7.27 (m, 3H), 4.79 (d, J=5.7 Hz, 2H), 3.81 (br s, 4H), 3.22 (t, J=6.1 Hz, 2H), 2.79 (s, 6H), 2.69-2.60 (m, 2H), 2.55 (br s, 4H), 2.20 (s, 6H); MS (M+H)$^+$=519.

Example 66. 5-(4-((3-chlorobenzyl)amino)-2-(4-(2-(dimethylamino)ethyl)piperazin-1-yl)quinazolin-6-yl)-1-methylpyridin-2(1H)-one The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 1-methyl-5-(4,4,5,5-tetramethyl-1,3,2-dioxaborolan-2-yl)pyridin-2 (1H)-one (23.51 mg, 0.10 mmol), PdCl$_2$(dppf)-CH$_2$Cl$_2$ adduct (4.08 mg, 5.0 µmol), and K$_2$Cl$_3$ (41.5 mg, 0.30 mmol) according to similar procedure described in Example 65. $^1$H NMR (400 MHz, DMSO-d$_6$) δ 11.88 (s, 1H), 10.08 (s, 1H), 8.44 (s, 1H), 8.21 (d, J=2.7 Hz, 1H), 8.05 (s, 1H), 7.90 (dd, J=9.5, 2.7 Hz, 1H), 7.66 (s, 1H), 7.49 (s, 1H), 7.40-7.28 (m, 3H), 6.56 (d, J=9.5 Hz, 1H), 4.81 (d, J=5.6 Hz, 2H), 3.81 (s, 4H), 3.51 (s, 3H), 3.22 (br s, 2H), 2.79 (s, 6H), 2.64 (br s, 2H), 2.55 (s, 4H). (including 1 salt NH); MS (M+H)$^+$=532.

Example 67. 5-(4-((3-chlorobenzyl)amino)-2-(4-(2-(dimethylamino)ethyl)piperazin-1-yl)quinazolin-6-yl)pyridin-2-ol The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 5-(4,4,5,5-tetramethyl-1,3,2-dioxaborolan-2-yl)pyridin-2-ol (22.11 mg, 0.100 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. $^1$H NMR (400 MHz, DMSO-d$_6$) δ 12.03 (s, 1H), 11.83 (s, 1H), 10.06 (s, 1H), 8.44 (s, 1H), 8.06 (s, 1H), 7.92 (dd, J=9.6, 2.8 Hz, 1H), 7.82 (s, 1H), 7.64 (s, 1H), 7.48 (s, 1H), 7.41-7.28 (m, 3H), 6.50 (d, J=9.6 Hz, 1H), 4.81 (d, J=5.6 Hz, 2H), 3.81 (s, 4H), 3.22 (s, 2H), 2.79 (s, 6H), 2.68-2.60 (m, 2H), 2.55 (s, 4H). (including 1 salt NH); MS (M+H)$^+$=518.

Example 68. 2-(4-(2-(dimethylamino)ethyl)piperazin-1-yl)-6-(3,5-dimethylisoxazol-4-yl)quinazolin-4-ol Step 1: 6-bromo-4-(tert-butoxy)-2-chloroquinazoline To a partial suspension of 6-bromo-2,4-dichloroquinazoline (3.47 g, 12.5 mmol) in THF (12 ml) at 0° C. was added KOtBu (13.75 ml, 13.75 mmol) (1M solution in THF). The mixture was stirred at 0° C. for 1.5 h. The mixture was poured into H$_2$O/NH$_4$Cl$_{aq}$ (25 mL/25 mL) and extracted with EtOAc (50 mL×2). The combined organic layer was dried (Na$_2$SO$_4$) and filtered. After removal of solvent, the product was purified by silica gel chromatography using 0-5-10% EtOAc/hexane as the eluent to give 6-bromo-4-(tert-butoxy)-2-chloroquinazoline (3.91 g, 12.39 mmol, 99% crude yield). This material was used for next step without further purification.

Step 2: 4-(4-(tert-butoxy)-2-chloroquinazolin-6-yl)-3,5-dimethylisoxazole

In a 2-neck flask was placed 6-bromo-4-(tert-butoxy)-2-chloroquinazoline (1515 mg, 4.8 mmol), 3,5-dimethyl-4-(4,4,5,5-tetramethyl-1,3,2-dioxaborolan-2-yl)isoxazole (1178 mg, 5.28 mmol), PdCl$_2$(dppf)-CH$_2$Cl$_2$ adduct (392 mg, 0.48 mmol), and K$_2$CO$_3$ (2189 mg, 15.84 mmol). The air was removed and re-filled with N$_2$ (2-3 times). Then added a mixture of 1,4-dioxane (12 ml) and water (6 ml) was added and stirred at 95° C. (pre-heated) for 1.5 h. The organic layer was separated and the aqueous layer was extracted with EtOAc (5 mL×3). The combined organic was dried (Na$_2$SO$_4$) and filtered. After removal of solvent, the product was dried in vacuo to give 4-(4-(tert-butoxy)-2-chloroquinazolin-6-yl)-3,5-dimethylisoxazole (890 mg, 2.68 mmol, 55.9% yield) ($^1$H NMR (400 MHz, Chloroform-d) δ 7.92 (dd, J=2.1, 0.6 Hz, 1H), 7.87 (dd, J=8.6, 0.6 Hz, 1H), 7.67 (dd, J=8.6, 2.0 Hz, 1H), 2.44 (s, 3H), 2.29 (s, 3H), 1.75 (s, 9H). and 4,4'-(4-(tert-butoxy)quinazoline-2,6-diyl)bis(3,5-dimethylisoxazole) (158 mg, 0.403 mmol, 8.39% yield) ($^1$H NMR (400 MHz, Chloroform-d) δ 7.96 (dd, J=2.1, 0.7 Hz, 1H), 7.90 (dd, J=8.6, 0.7 Hz, 1H), 7.65 (dd, J=8.6, 2.0 Hz, 1H), 2.84 (s, 3H), 2.67 (s, 3H), 2.46 (s, 3H), 2.31 (s, 3H), 1.77 (s, 9H).

Step 3: 2-(4-(4-(tert-butoxy)-6-(3,5-dimethylisoxazol-4-yl)quinazolin-2-yl)piperazin-1-yl)-N,N-dimethylethanamine To a suspension of 4-(4-(tert-butoxy)-2-chloroquinazolin-6-yl)-3,5-dimethylisoxazole (890 mg, 2.68 mmol) in EtOH (6 ml) was added N,N-dimethyl-2-(piperazin-1-yl)ethanamine (464 mg, 2.95 mmol) and then Hunig's base (0.703 ml, 4.02 mmol). The tube was sealed and heated at 90° C. for 5 h. After cooling to rt, the mixture was concentrated to remove most of EtOH and then poured poured into EtOAc/H$_2$O/Na$_2$CO$_{3(aq)}$ (50 mL/30 mL/20 mL). The aqueous layer was extracted with EtOAc (50 mL). The combined organic layer was dried (Na$_2$SO$_4$) and filtered. After removal of solvent, the product was purified by silica gel chromatography using 0-10-20% MeOH/EtOAc as the eluent to give 2-(4-(4-(tert-butoxy)-6-(3,5-dimethylisoxazol-4-yl)quinazolin-2-yl)piperazin-1-yl)-N,N-dimethylethanamine (1030 mg, 2.276 mmol, 85% yield). $^1$H NMR (400 MHz, Chloroform-d) δ 7.72 (dd, J=2.0, 0.6 Hz, 1H), 7.50 (d, J=8.8 Hz, 1H), 7.42 (dd, J=8.6, 2.1 Hz, 1H), 3.95 (t, J=5.1 Hz, 4H), 3.03 (s, 2H), 2.89 (d, J=6.4 Hz, 2H), 2.78 (s, 6H), 2.64 (t, J=5.0 Hz, 4H), 2.40 (s, 3H), 2.26 (s, 3H), 1.68 (s, 9H). MS (M+H)$^+$=453.

Step 4: 2-(4-(2-(dimethylamino)ethyl)piperazin-1-yl)-6-(3,5-dimethylisoxazol-4-yl)quinazolin-4-ol, 2HCl To a solution of 2-(4-(4-(tert-butoxy)-6-(3,5-dimethylisoxazol-4-yl)quinazolin-2-yl)piperazin-1-yl)-N,N-dimethylethanamine (1240 mg, 2.74 mmol) in CH$_2$Cl$_2$ (6 ml) was added HCl (4M in dioxane, 12 mL). The suspension was stirred vigorously at RT for 5 h. To the mixture was added hexane (40 mL). The solid was filtered and washed with hexane (5 mL×3). Then the product was transferred to vial (hydroscopic) and dried in vacuo to give 2-(4-(2-(dimethylamino)ethyl)piperazin-1-yl)-6-(3,5-dimethylisoxazol-4-yl)quinazolin-4-ol, 2HCl as an off-white solid. The material was used for next step without further purification. MS (M+H)$^+$=397.

Example 69. 2,6-bis(3,5-dimethylisoxazol-4-yl)-N-(thiophen-2-ylmethyl)quinazolin-4-amine Step 1:
2,6-bis(3,5-dimethylisoxazol-4-yl)quinazolin-4-ol, HCl To a solution of 4,4'-(4-(tert-butoxy)quinazoline-2,6-diyl)bis(3,5-dimethylisoxazole) (500 mg, 1.274 mmol) in CH₂Cl₂ (2 ml) was added HCl (4M in dioxane, 6 mL). The suspension was stirred at RT for 3 h. To the mixture was added hexane (20 mL). The solid was filtered and washed with hexane (3 mL×3). Then the product was transferred to vial and dried in vacuo to give 2,6-bis(3,5-dimethylisoxazol-4-yl)quinazolin-4-ol, HCl (395 mg, 1.060 mmol, 83% yield) as an off-white solid. MS (M+H)⁺=337.

Step 2: 2,6-bis(3,5-dimethylisoxazol-4-yl)-N-(thiophen-2-ylmethyl)quinazolin-4-amine To a suspension of 2,6-bis(3,5-dimethylisoxazol-4-yl)quinazolin-4-ol, HCl (37.3 mg, 0.1 mmol) and bromotri(pyrrolidin-1-yl)phosphonium hexafluorophosphate (93 mg, 0.20 mmol) in 1,4-dioxane (1 ml) was added Et₃N (0.139 ml, 1.0 mmol). The mixture was stirred at RT for 2 h and then thiophen-2-ylmethanamine (22.64 mg, 0.20 mmol) was added. The mixture was stirred at 50° C. for another 5 h. The mixture was concentrated, dissolved in DMF (2 mL), filtered through a filter and submitted for purification to give 2,6-bis(3,5-dimethylisoxazol-4-yl)-N-(thiophen-2-ylmethyl)quinazolin-4-amine, 2TFA (14.1 mg, 0.021 mmol, 21.38% yield). MS (M+H)⁺=432.

Example 70. N-(3-chlorobenzyl)-2,6-bis(3,5-dimethylisoxazol-4-yl)quinazolin-4-amine To a suspension of 2,6-bis(3,5-dimethylisoxazol-4-yl)quinazolin-4-ol, HCl (37.3 mg, 0.1 mmol) and bromotri(pyrrolidin-1-yl)phosphonium hexafluorophosphate (93 mg, 0.200 mmol) in 1,4-dioxane (1 ml) was added Et₃N (0.139 ml, 1.0 mmol). The mixture was stirred at RT for 2 h and then (3-chlorophenyl)methanamine (28.3 mg, 0.20 mmol) was added. The mixture was stirred at 50° C. for another 5 h. The mixture was concentrated, dissolved in DMF (2 mL), filtered through a filter and submitted for purification to give N-(3-chlorobenzyl)-2,6-bis(3,5-dimethylisoxazol-4-yl)quinazolin-4-amine, 2TFA (15.4 mg, 0.022 mmol, 22.38% yield). MS (M+H)⁺=460.

Example 71. 2-(4-(2-(dimethylamino)ethyl)piperazin-1-yl)-6-(3,5-dimethylisoxazol-4-yl)-N-(thiophen-2-ylmethyl)quinazolin-4-amine To a suspension of 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol) and Bromotri(pyrrolidin-1-yl)phosphonium hexafluorophosphate (46.6 mg, 0.100 mmol) in 1,4-dioxane (1 ml) was added Et₃N (0.139 ml, 1.0 mmol). The mixture was stirred at RT for 2 h and then thiophen-2-ylmethanamine (11.32 mg, 0.10 mmol) was added. The mixture was stirred at 50° C. for another 5 h. The mixture was concentrated, dissolved in DMF (2 mL), filtered through a filter and submitted for purification to give 2-(4-(2-(dimethylamino)ethyl)piperazin-1-yl)-6-(3,5-dimethylisoxazol-4-yl)-N-(thiophen-2-ylmethyl)quinazolin-4-amine, 2TFA (11.6 mg, 0.016 mmol, 32.2% yield). MS (M+H)⁺=492.

Example 72. 2-(4-(2-(dimethylamino)ethyl)piperazin-1-yl)-6-(3,5-dimethylisoxazol-4-yl)-N-(2-methoxybenzyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (2-methoxyphenyl)methanamine (13.72 mg, 0.10 mmol) according to similar procedure described in Example 71. MS (M+H)⁺=516.

Example 73. 2-(4-(2-(dimethylamino)ethyl)piperazin-1-yl)-6-(3,5-dimethylisoxazol-4-yl)-N-(3-methoxybenzyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (3-methoxyphenyl)methanamine (13.72 mg, 0.10 mmol) according to similar procedure described in Example 71. ¹H NMR (400 MHz, DMSO-d6) δ 11.88 (s, 1H), 10.05 (s, 1H), 8.24 (s, 1H), 7.83 (s, 1H), 7.73 (s, 1H), 7.23 (t, J=8.0 Hz, 1H), 6.99-6.89 (m, 2H), 6.88-6.76 (m, 1H), 4.76 (d, J=5.3 Hz, 2H), 3.83 (s, 4H), 3.70 (s, 3H), 3.22 (s, 2H), 2.79 (s, 6H), 2.68-2.59 (m, 2H), 2.54 (s, 4H), 2.42 (s, 3H), 2.25 (s, 3H). (including 1 salt NH); MS (M+H)⁺=516.

Example 74. N-(2-chlorobenzyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (2-chlorophenyl)methanamine (14.16 mg, 0.10 mmol) according to similar procedure described in Example 71. MS (M+H)⁺=520.

Example 75. N-(3-bromobenzyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (3-bromophenyl)methanamine (18.60 mg, 0.100 mmol) according to similar procedure described in Example 71. MS (M+H)⁺=566.

Example 76. 2-(4-(2-(dimethylamino)ethyl)piperazin-1-yl)-6-(3,5-dimethylisoxazol-4-yl)-N-(2-fluorobenzyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (2-fluorophenyl)methanamine (12.51 mg, 0.100 mmol) according to similar procedure described in Example 71. MS (M+H)⁺=504.

Example 77. 2-(4-(2-(dimethylamino)ethyl)piperazin-1-yl)-6-(3,5-dimethylisoxazol-4-yl)-N-(3-fluorobenzyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (3-fluorophenyl)methanamine (12.51 mg, 0.100 mmol) according to similar procedure described in Example 71. MS (M+H)⁺=504.

Example 78. N-(3-chlorobenzyl)-2-(4-(2-(dimethylamino)ethyl)piperazin-1-yl)-6-(5-methylisoxazol-4-yl)quinazolin-4-amine The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 5-methyl-4-(4,4,5,5-tetramethyl-1,3,2-dioxaborolan-2-yl)isoxazole (20.9 mg, 0.10 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. $^1$H NMR (400 MHz, DMSO-d$_6$) δ 11.90 (s, 1H), 10.08 (s, 1H), 8.85 (s, 1H), 8.36 (s, 1H), 7.96 (s, 1H), 7.72 (s, 1H), 7.47 (s, 1H), 7.34 (q, J=4.8 Hz, 3H), 4.81 (s, 2H), 3.81 (br s, 4H), 3.22 (br s, 2H), 2.79 (s, 6H), 2.68-2.60 (m, 5H), 2.54 (br s, 4H). (including 1 salt NH); MS (M+H)⁺=506.

Example 79. 2-(4-(2-(dimethylamino)ethyl)piperazin-1-yl)-6-(3,5-dimethylisoxazol-4-yl)-N-(furan-2-ylmethyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and furan-2-ylmethanamine (9.71 mg, 0.10 mmol) according to similar procedure described in Example 71. $^1$H NMR (400 MHz, DMSO-d$_6$) δ 11.91 (s, 1H), 9.98 (s, 1H), 8.22 (s, 1H), 7.82 (s, 1H), 7.73 (s, 1H), 7.60 (dd, J=1.8, 0.9 Hz, 1H), 6.47-6.33 (m, 2H), 4.79 (d, J=5.4 Hz, 2H), 3.89 (br s, 4H), 3.24 (br s, 2H), 2.81 (s, 6H), 2.72-2.54 (m, 6H), 2.41 (s, 3H), 2.24 (s, 3H). (including 1 salt NH); MS (M+H)⁺=476.

Example 80. 2-(4-(2-(dimethylamino)ethyl)piperazin-1-yl)-6-(3,5-dimethylisoxazol-4-yl)-N-(Pyridin-3-ylmethyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and pyridin-3-ylmethanamine (10.81 mg, 0.10 mmol) according to similar procedure described in Example 71. $^1$H NMR (400 MHz, DMSO-d$_6$) δ 11.89 (s, 1H), 10.08 (s, 1H), 8.64 (s, 1H), 8.48 (d, J=4.9 Hz, 1H), 8.21 (s, 1H), 7.77 (d, J=37.0 Hz, 3H), 7.42-7.32 (m, 1H), 4.83 (d, J=5.5 Hz, 2H), 3.81 (br s, 4H), 3.22 (br s, 2H), 2.79 (s, 6H), 2.71-2.60 (m, 2H), 2.56 (br s, 4H), 2.42 (s, 3H), 2.25 (s, 3H). (including 1 salt NH); MS (M+H)⁺=487.

Example 81. N-((5-chloropyridin-3-yl)methyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (5-chloropyridin-3-yl)methanamine (14.26 mg, 0.10 mmol) for overnight according to similar procedure described in Example 71. MS (M+H)⁺=521.

Example 82. N-((4-chloropyridin-2-yl)methyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (4-chloropyridin-2-yl)methanamine (14.26 mg, 0.10 mmol) for overnight according to similar procedure described in Example 71. MS (M+H)⁺=521.

Example 83. 2-(4-(2-(dimethylamino)ethyl)piperazin-1-yl)-6-(3,5-dimethylisoxazol-4-yl)-N-((5-fluoropyridin-3-yl)methyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (5-fluoropyridin-3-yl)methanamine (12.61 mg, 0.10 mmol) for overnight according to similar procedure described in Example 71. MS (M+H)⁺=505.

Example 84. 2-(4-(2-(dimethylamino)ethyl)piperazin-1-yl)-6-(3,5-dimethylisoxazol-4-yl)-N-((4-methylpyridin-3-yl)methyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (4-methylpyridin-3-yl)methanamine (12.22 mg, 0.10 mmol) for overnight according to similar procedure described in Example 71. $^1$H NMR (400 MHz, DMSO-d$_6$) δ 11.95 (s, 1H), 9.86 (s, 1H), 8.56 (s, 1H), 8.45 (s, 1H), 8.25 (s, 1H), 7.82 (s, 1H), 7.73 (s, 1H), 7.40 (s, 1H), 4.87 (d, J=4.9 Hz, 2H), 3.82 (br s, 4H), 3.23 (t, J=6.0 Hz, 2H), 2.80 (s, 6H), 2.73-2.52 (m, 6H), 2.41 (br s, 6H), 2.24 (s, 3H). (including 1 salt NH); MS (M+H)⁺=501.

Example 85. N-(3-chlorobenzyl)-2-(4-(2-(dimethylamino)ethyl)piperazin-1-yl)-6-(3,5-dimethylisoxazol-4-yl)-N-methylquinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and 1-(3-chlorophenyl)-N-methylmethanamine (15.56 mg, 0.100 mmol) for overnight according to similar procedure described in Example 71. MS (M+H)⁺=534.

Example 86. 5-(4-((3-chlorobenzyl)amino)-2-(4-(2-(dimethylamino)ethyl)piperazin-1-yl)quinazolin-6-yl)-3-fluoropyridin-2-ol The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 3-fluoro-5-(4,4,5,5-tetramethyl-1,3,2-dioxaborolan-2-yl)pyridin-2-ol (0.024 g, 0.10 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. MS (M+H)$^+$=536.

Example 87. 2-(4-(2-(dimethylamino)ethyl)piperazin-1-yl)-6-(3,5-dimethylisoxazol-4-yl)-N-((4-methylthiophen-2-yl)methyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (4-methylthiophen-2-yl)methanamine (12.72 mg, 0.10 mmol) according to similar procedure described in Example 71. MS (M+H)$^+$=506.

Example 88. 2-(4-(2-(dimethylamino)ethyl)piperazin-1-yl)-6-(3,5-dimethylisoxazol-4-yl)-N-((5-methylthiophen-2-yl)methyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (5-methylthiophen-2-yl)methanamine, HCl (16.37 mg, 0.10 mmol) according to similar procedure described in Example 71. MS (M+H)$^+$=506.

Example 89. 2-(4-(2-(dimethylamino)ethyl)piperazin-1-yl)-6-(3,5-dimethylisoxazol-4-yl)-N-(1-(thiophen-2-yl)ethyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and 1-(thiophen-2-yl)ethanamine (12.72 mg, 0.10 mmol) according to similar procedure described in Example 71. MS (M+H)$^+$=506.

Example 90. N-(1-(3-chlorophenyl)ethyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and 1-(3-chlorophenyl)ethanamine (15.56 mg, 0.10 mmol) according to similar procedure described in Example 71. MS (M+H)$^+$=534.

Example 91. 5-(4-((3-chlorobenzyl)amino)-2-(4-(2-(dimethylamino)ethyl)piperazin-1-yl)quinazolin-6-yl)-3-methylpyridin-2-ol The title compound was prepared from 6-bromo-N-(3-chlorobenzyl)-2-(4-(2-(dimethylamino)ethyl)piperazin-1-yl)quinazolin-4-amine (25.2 mg, 0.05 mmol), (6-hydroxy-5-methylpyridin-3-yl)boronic acid (15.29 mg, 0.100 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. $^1$H NMR (400 MHz, DMSO-d$_6$) δ 11.93 (s, 2H), 10.07 (s, 1H), 8.43 (s, 1H), 8.05 (s, 1H), 7.82 (dd, J=2.8, 1.3 Hz, 1H), 7.73-7.60 (m, 1H), 7.48 (s, 1H), 7.39-7.29 (m, 3H), 4.81 (d, J=5.7 Hz, 2H), 3.81 (br s, 4H), 3.22 (br s, 2H), 2.79 (s, 6H), 2.70-2.51 (m, 6H), 2.06 (s, 3H). (including 1 salt NH); MS (M+H)$^+$=532.

Example 92. N-benzyl-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and phenylmethanamine (10.72 mg, 0.10 mmol) for overnight according to similar procedure described in Example 71. MS (M+H)$^+$=486.

Example 93. N-(3-chlorobenzyl)-2-(4-(2-(dimethylamino)ethyl)piperazin-1-yl)-6-(3-methylisoxazol-4-yl)quinazolin-4-amine The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 3-methyl-4-(4,4,5,5-tetramethyl-1,3,2-dioxaborolan-2-yl)isoxazole (20.90 mg, 0.10 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. $^1$H NMR (400 MHz, DMSO-d$_6$) δ 11.93 (s, 1H), 10.09 (s, 1H), 9.13 (s, 1H), 8.33 (s, 1H), 7.93 (s, 1H), 7.71 (s, 1H), 7.47 (s, 1H), 7.39-7.26 (m, 3H), 4.80 (s, 2H), 3.81 (br s, 4H), 3.22 (br s, 2H), 2.79 (s, 6H), 2.70-2.50 (m, 6H), 2.42 (s, 3H). (including 1 salt NH); MS (M+H)$^+$=506.

Example 94. N-((5-chlorothiophen-2-yl)methyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (5-chlorothiophen-2-yl)methanamine, HCl (18.41 mg, 0.10 mmol) according to similar procedure described in Example 71. MS (M+H)$^+$=526.

Example 95. N-(4-chlorobenzyl)-2-(4-(2-(dimethylamino)ethyl)piperazin-1-yl)-6-(3,5-dimethylisoxazol-4-yl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (4-chlorophenyl)methanamine (0.014 g, 0.10 mmol) according to similar procedure described in Example 71. MS (M+H)$^+$=520.

Example 96. 4-(4-((3-chlorobenzyl)amino)-2-(4-(2-(dimethylamino)ethyl)piperazin-1-yl)quinazolin-6-yl)pyridin-2-ol The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 4-(4,4,5,5-tetramethyl-1,3,2-dioxaborolan-2-yl)pyridin-2-ol (22.11 mg, 0.10 mmol), PdCl$_2$(dppf)-CH$_2$Cl$_2$ adduct (4.08 mg, 5.0 µmol), and K$_2$CO$_3$ (41.5 mg, 0.30 mmol) according to similar procedure described in Example 65. $^1$H NMR (400 MHz, DMSO-d$_6$) δ 11.95 (s, 1H), 11.67 (s, 1H), 10.18 (s, 1H), 8.66 (s, 1H), 8.16 (s, 1H), 7.71 (s, 1H), 7.49 (s, 2H), 7.41-7.26 (m, 3H), 6.77 (s, 1H), 6.61 (d, J=7.0 Hz, 1H), 4.80 br (s, 2H), 3.82 (br s, 4H), 3.22 (br s, 2H), 2.79 (s, 6H), 2.71-2.51 (m, 6H). (including 1 salt NH); MS (M+H)$^+$=518.

Example 97. 2-(4-(4-((3-chlorobenzyl)amino)-6-(3,5-dimethylisoxazol-4-yl)quinazolin-2-yl)-1H-pyrazol-1-yl)-N-methylacetamide The title compound was prepared from 2-chloro-N-(3-chlorobenzyl)-6-(3,5-dimethylisoxazol-4-yl)quinazolin-4-amine (Example 1, 19.96 mg, 0.05 mmol), N-methyl-2-(4-(4,4,5,5-tetramethyl-1,3,2-dioxaborolan-2-yl)-1H-pyrazol-1-yl)acetamide (26.5 mg, 0.10 mmol), PdCl$_2$(dppf)-CH$_2$Cl$_2$ adduct (8.17 mg, 10.0 μmol), and K$_2$CO$_3$ (41.5 mg, 0.30 mmol) according to similar procedure described in Example 28. $^1$H NMR (400 MHz, DMSO-d$_6$) δ 10.42 (s, 1H), 8.68 (s, 1H), 8.26 (d, J=71.6 Hz, 3H), 7.91 (d, J=36.9 Hz, 2H), 7.55 (s, 1H), 7.46-7.40 (m, 1H), 7.37 (t, J=7.7 Hz, 1H), 7.34-7.28 (m, 1H), 5.01 (s, 2H), 4.91 (s, 2H), 2.62 (d, J=4.6 Hz, 3H), 2.46 (s, 3H), 2.28 (s, 3H); MS (M+H)$^+$=502.

Example 98. 2-(4-(4-((3-chlorobenzyl)amino)-6-(3,5-dimethylisoxazol-4-yl)quinazolin-2-yl)-1H-pyrazol-1-yl)-N,N-dimethylacetamide The title compound was prepared from 2-chloro-N-(3-chlorobenzyl)-6-(3,5-dimethylisoxazol-4-yl)quinazolin-4-amine (Example 1, 19.96 mg, 0.05 mmol), N,N-dimethyl-2-(4-(4,4,5,5-tetramethyl-1,3,2-dioxaborolan-2-yl)-1H-pyrazol-1-yl)acetamide (27.9 mg, 0.100 mmol), PdCl$_2$(dppf)-CH$_2$Cl$_2$ adduct (8.17 mg, 10.0 μmol), and K$_2$CO$_3$ (41.5 mg, 0.30 mmol) according to similar procedure described in Example 28. $^1$H NMR (400 MHz, DMSO-d$_6$) δ 10.39 (s, 1H), 8.63 (s, 1H), 8.35 (br s, 2H), 7.91 (m, 2H), 7.55 (s, 1H), 7.46-7.40 (m, 1H), 7.37 (t, J=7.7 Hz, 1H), 7.32 (d, J=8.0 Hz, 1H), 5.26 (s, 2H), 5.01 (s, 2H), 3.04 (s, 3H), 2.85 (s, 3H), 2.46 (s, 3H), 2.28 (s, 3H); MS (M+H)$^+$=516.

Example 99. 2-(4-(2-(dimethylamino)ethyl)piperazin-1-yl)-6-(3,5-dimethylisoxazol-4-yl)-N-(4-fluorobenzyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 23.47 mg, 0.05 mmol), bromotri(pyrrolidin-1-yl)phosphonium hexafluorophosphate (46.6 mg, 0.10 mmol) and (4-fluorophenyl)methanamine (12.51 mg, 0.10 mmol) according to similar procedure described in Example 71. MS (M+H)$^+$=504.

Example 100. 5-(2-chloro-4-((3-chlorobenzyl)amino)quinazolin-6-yl)-1-methylpyridin-2(1H)-one In a 2-neck flask was placed 6-bromo-2-chloro-N-(3-chlorobenzyl)quinazolin-4-amine (766 mg, 2 mmol), 1-methyl-5-(4,4,5,5-tetramethyl-1,3,2-dioxaborolan-2-yl)pyridin-2(1H)-one (517 mg, 2.200 mmol), PdCl$_2$(dppf)-CH$_2$Cl$_2$ adduct (163 mg, 0.20 mmol), and K$_2$CO$_3$ (912 mg, 6.6 mmol). The air was removed and re-filled with N$_2$ (2-3 times). Then added a mixture of 1,4-dioxane (6 ml) and water (3 ml) was added and stirred at 95° C. (pre-heated) for 2 h. After cooling to rt, H$_2$O (20 mL) was added and the solid was filtered, washed with H$_2$O (3 mL×2), and then dried. The dried solid was put into 5% EtOAc hexane (30 mL), vigorously stirred for 30 min, and then filtered to give 5-(2-chloro-4-((3-chlorobenzyl)amino)quinazolin-6-yl)-1-methylpyridin-2(1H)-one (741 mg, 1.441 mmol, 72.1% crude yield) as yellow solid. The material ca. 80% purity was used without further purification. 20 mg of crude material was submitted for purification for screening. MS (M+H)$^+$=411.

Example 101. 2-(4-(4-((3-chlorobenzyl)amino)-6-(1-methyl-6-oxo-1,6-dihydropyridin-3-yl)quinazolin-2-yl)-1H-pyrazol-1-yl)acetamide The title compound was prepared from 5-(2-chloro-4-((3-chlorobenzyl)amino)quinazolin-6-yl)-1-methylpyridin-2(1H)-one (Example 100, 0.039 g, 0.075 mmol), 2-(4-(4,4,5,5-tetramethyl-1,3,2-dioxaborolan-2-yl)-1H-pyrazol-1-yl)acetamide (0.038 g, 0.150 mmol), PdCl$_2$(dppf)-CH$_2$Cl$_2$ adduct (12 mg, 15 μmol), and K$_2$CO$_3$ (62 mg, 0.45 mmol) according to similar procedure described in Example 28. MS (M+H)$^+$=500

Example 102. 2-(4-(4-((3-chlorobenzyl)amino)-6-(1-methyl-6-oxo-1,6-dihydropyridin-3-yl)quinazolin-2-yl)-1H-pyrazol-1-yl)-N-methylacetamide The title compound was prepared from 5-(2-chloro-4-((3-chlorobenzyl)amino)quinazolin-6-yl)-1-methylpyridin-2(1H)-one (Example 100, 0.039 g, 0.075 mmol), N-methyl-2-(4-(4,4,5,5-tetramethyl-1,3,2-dioxaborolan-2-yl)-1H-pyrazol-1-yl)acetamide (39.8 mg, 0.15 mmol), PdCl$_2$(dppf)-CH$_2$Cl$_2$ adduct (12 mg, 15 μmol), and K$_2$CO$_3$ (62 mg, 0.45 mmol) according to similar procedure described in Example 28. MS (M+H)$^+$=514.

Example 103. 5-(4-((3-chlorobenzyl)amino)-2-(1-(2-hydroxy-2-methylpropyl)-1H-pyrazol-4-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 0.039 g, 0.075 mmol), 2-methyl-1-(4-(4,4,5,5-tetramethyl-1,3,2-dioxaborolan-2-yl)-1H-pyrazol-1-yl)propan-2-ol (39.9 mg, 0.150 mmol), PdCl$_2$(dppf)-CH$_2$Cl$_2$ adduct (12 mg, 15 μmol), and K$_2$CO$_3$ (62 mg, 0.45 mmol) according to similar procedure described in Example 28. MS (M+H)$^+$=515.

Example 104. 3-(4-(4-((3-chlorobenzyl)amino)-6-(1-methyl-6-oxo-1,6-dihydropyridin-3-yl)quinazolin-2-yl)-1H-pyrazol-1-yl)propanenitrile The title compound was prepared from 5-(2-chloro-4-((3-chlorobenzyl)amino)quinazolin-6-yl)-1-methylpyridin-2(1H)-one (Example 100, 0.039 g, 0.075 mmol), 3-(4-(4,4,5,5-tetramethyl-1,3,2-dioxaborolan-2-yl)-1H-pyrazol-1-yl)propanenitrile (37.1 mg, 0.15 mmol), PdCl$_2$(dppf)-CH$_2$Cl$_2$ adduct (12 mg, 15 μmol), and K$_2$CO$_3$ (62 mg, 0.45 mmol) according to similar procedure described in Example 28. MS (M+H)$^+$=496.

Example 105. 5-(4-((3-chlorobenzyl)amino)-2-(1-(1-hydroxy-2-methylpropan-2-yl)-1H-pyrazol-4-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 0.039 g, 0.075 mmol), 2-methyl- 2-(4-(4,4,5,5-tetramethyl-1,3,2-dioxaborolan-2-yl)-1H-pyrazol-1-yl)propan-1-ol (39.9 mg, 0.150 mmol), PdCl$_2$(dppf)-CH$_2$Cl$_2$ adduct (12 mg, 15 μmol), and K$_2$CO$_3$ (62 mg, 0.45 mmol) according to similar procedure described in Example 28. MS (M+H)$^+$=515.

Example 106. 5-(4-((3-chlorobenzyl)amino)-2-(4-(2-hydroxyacetyl)piperazin-1-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol) and 2-hydroxy-1-(piperazin-1-yl)ethanone (54.1 mg, 0.375 mmol) according to similar procedure described in Example 12. MS (M+H)$^+$=519.

Example 107. 5-(2-(4-(2-aminoacetyl)piperazin-1-yl)-4-((3-chlorobenzyl)amino)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol), 2-amino-1-(piperazin-1-yl)ethanone, 2HCl (0.081 g, 0.375 mmol), and Hunig's base (0.131 ml, 0.75 mmol) according to similar procedure described in Example 12. MS (M+H)$^+$=518.

Example 108. 2-(4-(4-((3-chlorobenzyl)amino)-6-(1-methyl-6-oxo-1,6-dihydropyridin-3-yl)quinazolin-2-yl)piperazin-1-yl)acetamide The title compound was prepared from 5-(2-chloro-4-((3-chlorobenzyl)amino)quinazolin-6-yl)-1-methylpyridin-2(1H)-one (Example 100, 38.6 mg, 0.075 mmol), 2-(piperazin-1-yl)acetamide, HCl (67.4 mg, 0.375 mmol), and Hunig's base (0.131 ml, 0.75 mmol) according to similar procedure described in Example 12. MS (M+H)$^+$=518.

Example 109. 2-(4-(4-((3-chlorobenzyl)amino)-6-(1-methyl-6-oxo-1,6-dihydropyridin-3-yl)quinazolin-2-yl)piperazin-1-yl)-N-methylacetamide The title compound was prepared from 5-(2-chloro-4-((3-chlorobenzyl)amino)quinazolin-6-yl)-1-methylpyridin-2(1H)-one (Example 100, 38.6 mg, 0.075 mmol), N-methyl-2-(piperazin-1-yl)acetamide, HCl (72.6 mg, 0.375 mmol), and Hunig's base (0.131 ml, 0.75 mmol) according to similar procedure described in Example 12. MS (M+H)$^+$=532.

Example 110. 2-(4-(4-((3-chlorobenzyl)amino)-6-(1-methyl-6-oxo-1,6-dihydropyridin-3-yl)quinazolin-2-yl)piperazin-1-yl)-N,N-dimethylacetamide The title compound was prepared from 5-(2-chloro-4-((3-chlorobenzyl)amino)quinazolin-6-yl)-1-methylpyridin-2(1H)-one (Example 100, 38.6 mg, 0.075 mmol), N,N-dimethyl-2-(piperazin-1-yl)acetamide (64.2 mg, 0.375 mmol), and Hunig's base (0.131 ml, 0.75 mmol) according to similar procedure described in Example 12. MS (M+H)$^+$=546.

Example 111. (S)-5-(4-((3-chlorobenzyl)amino)-2-(4-(2-hydroxypropyl)piperazin-1-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol), (S)-1-(piperazin-1-yl)propan-2-ol, HCl (0.068 g, 0.375 mmol), and Hunig's base (0.131 ml, 0.75 mmol) according to similar procedure described in Example 12. MS (M+H)$^+$=519.

Example 112. 2-chloro-N-((5-chloropyridin-3-yl)methyl)-6-(3,5-dimethylisoxazol-4-yl)quinazolin-4-amine Step 1: 6-bromo-2-chloro-N-((5-chloropyridin-3-yl)methyl)quinazolin-4-amine To a mixture of 6-bromo-2,4-dichloroquinazoline (1.946 g, 7 mmol) in THF (Volume: 20 ml) was added (5-chloropyridin-3-yl)methanamine (0.998 g, 7.0 mmol) and then Et$_3$N (1.463 ml, 10.50 mmol) at rt. The mixture was stirred at 0° C. for 15 min and then warmed to RT for 1.5 h (complete by TLC). The mixture was poured into EtOAc/H$_2$O (50 mL/50 mL). The aqueous layer was extracted with EtOAc (50 mL×2). The combined organic layer was dried (Na$_2$SO$_4$) and filtered. After removal of solvent, the product was and some EtOAc (5-10 mL), sonicated, and then added hexane (200 mL) slowly. The solid was filtered and triturated with hexane and then dried to give 6-bromo-2-chloro-N-((5-chloropyridin-3-yl)methyl)quinazolin-4-amine (2.31 g, 6.01 mmol, 86% yield) as a solid.

Step 2: 2-chloro-N-((5-chloropyridin-3-yl)methyl)-6-(3,5-dimethylisoxazol-4-yl)quinazolin-4-amine In a 2-neck flask was placed 6-bromo-2-chloro-N-((5-chloropyridin-3-yl)methyl)quinazolin-4-amine (0.960 g, 2.5 mmol), 3,5-dimethyl-4-(4,4,5,5-tetramethyl-1,3,2-dioxaborolan-2-yl)isoxazole (0.613 g, 2.75 mmol), PdCl$_2$(dppf)-CH$_2$Cl$_2$ adduct (0.204 g, 0.25 mmol), and K$_2$CO$_3$ (1.140 g, 8.25 mmol). The air was removed and re-filled with N$_2$ (2-3 times). Then added a mixture of 1,4-dioxane (9 ml) and water (4.5 ml) was added and stirred at 95° C. (pre-heated) for 1.5 h. After cooling to rt, the organic layer was separated and the aqueous layer was extracted with EtOAc (5 mL×3). The combined organic layer was dried (Na$_2$SO$_4$) and filtered. The product was triturated with 10% EtOAc/hexane and dried to give crude 2-chloro-N-((5-chloropyridin-3-yl)methyl)-6-(3,5-dimethylisoxazol-4-yl)quinazolin-4-amine (1.5 g, 2.249 mmol, 90% crude yield). The crude material contained some impurity was used without further purification. 40 mg of material was submitted for purification for screening. MS (M+H)$^+$=400.

Example 113. 5-(2-chloro-4-(((5-chloropyridin-3-yl)methyl)amino)quinazolin-6-yl)-1-methylpyridin-2(1H)-one In a 2-neck flask was placed 6-bromo-2-chloro-N-((5-chloropyridin-3-yl)methyl)quinazolin-4-amine (1.152 g, 3 mmol), 1-methyl-5-(4,4,5,5-tetramethyl-1,3,2-dioxaborolan-2-yl)pyridin-2(1H)-one (0.776 g, 3.30 mmol), PdCl$_2$(dppf)-CH$_2$Cl$_2$ adduct (0.245 g, 0.300 mmol), and K$_2$CO$_3$ (1.368 g, 9.90 mmol). The air was removed and re-filled with N$_2$ (2-3 times). Then added a mixture of 1,4-dioxane (10 ml) and water (5 ml) was added and stirred at 95° C. (pre-heated) for 1.5 h. After cooling to rt, H$_2$O (20 mL) was added and the solid was filtered, washed with H$_2$O (5 mL×2), and then dried. Then, the product was triturated with 10% EtOAc/hexane and dried to give crude 5-(2-chloro-4-(((5-chloropyridin-3-yl)methyl)amino)quinazolin-6-yl)-1- methylpyridin-2(1H)-one (1.52 g, 2.77 mmol, 92% yield). The crude material contained some impurity was used without further purification. 40 mg of material was submitted for purification for screening. MS (M+H)⁺=412.

Example 114. 5-(4-((3-chlorobenzyl)amino)-2-(1-(2-hydroxyethyl)-1H-pyrazol-4-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 0.039 g, 0.075 mmol), 2-(4-(4,4,5,5-tetramethyl-1,3,2-dioxaborolan-2-yl)-1H-pyrazol-1-yl)ethanol (35.7 mg, 0.150 mmol), PdCl₂(dppf)-CH₂Cl₂ adduct (12 mg, 15 µmol), and K₂CO₃ (62 mg, 0.45 mmol) according to similar procedure described in Example 28. MS (M+H)⁺=487.

Example 115. 2-(4-(2-(dimethylamino)ethyl)piperazin-1-yl)-6-(3,5-dimethylisoxazol-4-yl)-N-((5-methylpyridin-3-yl)methyl)quinazolin-4-amine The title compound was prepared from 2-(4-(2-(dimethylamino)ethyl)piperazin-1-yl)-6-(3,5-dimethylisoxazol-4-yl)quinazolin-4-ol, 2HCl (Example 68, 46.9 mg, 0.1 mmol), bromotri(pyrrolidin-1-yl)phosphonium hexafluorophosphate (93 mg, 0.2 mmol) and (5-methylpyridin-3-yl)methanamine (24.43 mg, 0.20 mmol) according to similar procedure described in Example 71. MS (M+H)⁺=501.

Example 116. 4-(4-((3-chlorobenzyl)amino)-2-(4-(2-(dimethylamino)ethyl)piperazin-1-yl)quinazolin-6-yl)-1-methylpyridin-2(1H)-one The title compound was prepared from 6-bromo-N-(3-chlorobenzyl)-2-(4-(2-(dimethylamino)ethyl)piperazin-1-yl)quinazolin-4-amine (25.2 mg, 0.05 mmol), 1-methyl-4-(4,4,5,5-tetramethyl-1,3,2-dioxaborolan-2-yl)pyridin-2(1H)-one (0.024 g, 0.10 mmol), PdCl₂(dppf)-CH₂Cl₂ adduct (4.08 mg, 5.0 µmol), and K₂CO₃ (41.5 mg, 0.30 mmol) according to similar procedure described in Example 65. MS (M+H)⁺=532.

Example 117. 2-(4-(4-(((5-chloropyridin-3-yl)methyl)amino)-6-(3,5-dimethylisoxazol-4-yl)quinazolin-2-yl)piperazin-1-yl)acetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-(piperazin-1-yl)acetamide, HCl (67.4 mg, 0.375 mmol), and Hunig's base (0.131 ml, 0.75 mmol) according to similar procedure described in Example 12. MS (M+H)⁺=507.

Example 118. 2-(4-(4-(((5-chloropyridin-3-yl)methyl)amino)-6-(3,5-dimethylisoxazol-4-yl)quinazolin-2-yl)piperazin-1-yl)-N-methylacetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N-methyl-2-(piperazin-1-yl)acetamide, HCl (72.6 mg, 0.375 mmol), and Hunig's base (0.131 ml, 0.75 mmol) according to similar procedure described in Example 12. MS (M+H)⁺=521.

Example 119. 2-(4-(4-(((5-chloropyridin-3-yl)methyl)amino)-6-(3,5-dimethylisoxazol-4-yl)quinazolin-2-yl)piperazin-1-yl)-N,N-dimethylacetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-2-(piperazin-1-yl)acetamide (64.2 mg, 0.375 mmol), and Hunig's base (0.131 ml, 0.75 mmol) according to similar procedure described in Example 12. MS (M+H)⁺=535.

Example 120. 2-(4-(4-(((5-chloropyridin-3-yl)methyl)amino)-6-(3,5-dimethylisoxazol-4-yl)quinazolin-2-yl)piperazin-1-yl)ethanol The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-(piperazin-1-yl)ethanol (48.8 mg, 0.375 mmol), and Hunig's base (0.131 ml, 0.75 mmol) according to similar procedure described in Example 12. MS (M+H)⁺=494.

Example 121. 5-(4-((3-chlorobenzyl)amino)-2-(4-(2-hydroxyethyl)piperazin-1-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol), 2-(piperazin-1-yl)ethanol (48.8 mg, 0.375 mmol), and Hunig's base (0.131 ml, 0.75 mmol) according to similar procedure described in Example 12. MS (M+H)⁺=505.

Example 122. 5-(4-((3-chlorobenzyl)amino)-2-(4-(1-methyl-1H-pyrazole-4-carbonyl)piperazin-1-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol), (1-methyl-1H-pyrazol-4-yl)(piperazin-1-yl)methanone, HCl (87 mg, 0.375 mmol), and Hunig's base (0.131 ml, 0.75 mmol) according to similar procedure described in Example 12. MS (M+H)⁺=569.

Example 123. 5-(4-((3-chlorobenzyl)amino)-2-(4-(3-(dimethylamino)propyl)piperazin-1-yl)quinazolin-6-yl)-1-methylpyridin-2(1H)-one The title compound was prepared from 5-(2-chloro-4-((3-chlorobenzyl)amino)quinazolin-6-yl)-1-methylpyridin-2(1H)-one (Example 100, 38.6 mg, 0.075 mmol), N,N-dimethyl-3-(piperazin-1-yl)propan-1-amine (0.064 g, 0.375 mmol), and Hunig's base (0.131 ml, 0.75 mmol) according to similar procedure described in Example 12. MS (M+H)⁺=546.

Example 124. 5-(4-(((5-chloropyridin-3-yl)methyl)amino)-2-(4-(2-(dimethylamino)ethyl)piperazin-1-yl)quinazolin-6-yl)-1-methylpyridin-2(1H)-one The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-2-(piperazin-1-yl)ethanamine (0.059 g, 0.375

Example 125. 5-(4-(((5-chloropyridin-3-yl)methyl)amino)-2-(4-(3-(dimethylamino)propyl)piperazin-1-yl)quinazolin-6-yl)-1-methylpyridin-2(1H)-one The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-3-(piperazin-1-yl)propan-1-amine (0.064 g, 0.375 mmol), and Hunig's base (0.131 ml, 0.75 mmol) according to similar procedure described in Example 12. MS (M+H)$^+$=547.

Example 126. 5-(4-(((5-chloropyridin-3-yl)methyl)amino)-2-(4-(2-hydroxyethyl)piperazin-1-yl)quinazolin-6-yl)-1-methylpyridin-2(1H)-one The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-(piperazin-1-yl)ethanol (0.049 g, 0.375 mmol), and Hunig's base (0.131 ml, 0.75 mmol) according to similar procedure described in Example 12. MS (M+H)$^+$=506.

Example 127. 2-(4-(4-(((5-chloropyridin-3-yl)methyl)amino)-6-(1-methyl-6-oxo-1,6-dihydropyridin-3-yl)quinazolin-2-yl)piperazin-1-yl)acetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-(piperazin-1-yl)acetamide, HCl (0.067 g, 0.375 mmol), and Hunig's base (0.131 ml, 0.75 mmol) according to similar procedure described in Example 12. MS (M+H)$^+$=519.

Example 128. 2-(4-(4-(((5-chloropyridin-3-yl)methyl)amino)-6-(1-methyl-6-oxo-1,6-dihydropyridin-3-yl)quinazolin-2-yl)piperazin-1-yl)-N-methylacetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N-methyl-2-(piperazin-1-yl)acetamide, HCl (0.073 g, 0.375 mmol), and Hunig's base (0.131 ml, 0.75 mmol) according to similar procedure described in Example 12. MS (M+H)$^+$=533.

Example 129. 2-(4-(4-(((5-chloropyridin-3-yl)methyl)amino)-6-(1-methyl-6-oxo-1,6-dihydropyridin-3-yl)quinazolin-2-yl)piperazin-1-yl)-N,N-dimethylacetamide The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-2-(piperazin-1-yl)acetamide (0.064 g, 0.375 mmol), and Hunig's base (0.131 ml, 0.75 mmol) according to similar procedure described in Example 12. MS (M+H)$^+$=547.

Example 130. N-((5-chloropyridin-3-yl)methyl)-2-(4-(3-(dimethylamino)propyl)piperazin-1-yl)-6-(3,5-dimethylisoxazol-4-yl)quinazolin-4-amine The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-3-(piperazin-1-yl)propan-1-amine (64.2 mg, 0.375 mmol), and Hunig's base (0.131 ml, 0.75 mmol) according to similar procedure described in Example 12. MS (M+H)$^+$=535.

Example 131. 2-amino-1-(4-(4-(((5-chloropyridin-3-yl)methyl)amino)-6-(3,5-dimethylisoxazol-4-yl)quinazolin-2-yl)piperazin-1-yl)ethanone The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-amino-1-(piperazin-1-yl)ethanone, 2HCl (0.081 g, 0.375 mmol), and Hunig's base (0.131 ml, 0.75 mmol) according to similar procedure described in Example 12. MS (M+H)$^+$=507.

Example 132. 1-(4-(4-(((5-chloropyridin-3-yl)methyl)amino)-6-(3,5-dimethylisoxazol-4-yl)quinazolin-2-yl)piperazin-1-yl)-2-hydroxyethanone The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-hydroxy-1-(piperazin-1-yl)ethanone (54.1 mg, 0.375 mmol), and Hunig's base (0.131 ml, 0.75 mmol) according to similar procedure described in Example 12. MS (M+H)$^+$=508.

Example 133. 5-(2-(4-(2-aminoacetyl)piperazin-1-yl)-4-(((5-chloropyridin-3-yl)methyl)amino)quinazolin-6-yl)-1-methylpyridin-2(1H)-one The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-amino-1-(piperazin-1-yl)ethanone, 2HCl (81 mg, 0.375 mmol), and Hunig's base (0.131 ml, 0.75 mmol) according to similar procedure described in Example 12. MS (M+H)$^+$=519.

Example 134. 5-(4-((3-chlorobenzyl)amino)-2-(4-(2-hydroxy-2-methylpropyl)piperazin-1-yl)quinazolin-6-yl)-1-methylpyridin-2(1H)-one, 2TFA The title compound was prepared from 5-(2-chloro-4-((3-chlorobenzyl)amino)quinazolin-6-yl)-1-methylpyridin-2(1H)-one (Example 100, 30.8 mg, 0.075 mmol) and 2-methyl-1-(piperazin-1-yl)propan-2-ol, 2HCl (52.0 mg, 0.225 mmol) according to similar procedure described in Example 12. $^1$H NMR (400 MHz, DMSO-d$_6$) δ 9.30 (s, 1H), 8.40 (s, 1H), 8.20 (d, J=2.6 Hz, 1H), 8.01 (s, 1H), 7.91 (dd, J=9.5, 2.7 Hz, 1H), 7.57-7.49 (m, 3H), 7.41-7.28 (m, 2H), 6.55 (d, J=9.4 Hz, 1H), 5.28 (s, 1H), 4.81 (s, 2H), 4.68-2.78 (m, 10H), 3.51 (s, 3H), 1.24 (s, 6H); MS (M+H)$^+$=533.

Example 135. 5-(4-(((5-chloropyridin-3-yl)methyl)amino)-2-(4-(2-hydroxy-2-methylpropyl)piperazin-1-yl)quinazolin-6-yl)-1-methylpyridin-2(1H)-one, 2TFA The title compound was prepared from 5-(2-chloro-4-(((5-chloropyridin-3-yl)methyl)amino)quinazolin-6-yl)-1- methylpyridin-2(1H)-one (Example 113, 30.9 mg, 0.075 mmol) and 2-methyl-1-(piperazin-1-yl)propan-2-ol, 2HCl (52.0 mg, 0.225 mmol) according to similar procedure described in Example 12. $^1$H NMR (400 MHz, DMSO-d$_6$) δ 9.27 (s, 1H), 8.62 (d, J=1.8 Hz, 1H), 8.53 (d, J=2.3 Hz, 1H), 8.37 (s, 1H), 8.20 (d, J=2.7 Hz, 1H), 8.06-7.93 (m, 2H), 7.90 (dd, J=9.5, 2.8 Hz, 1H), 7.57 (s, 1H), 6.55 (d, J=9.5 Hz, 1H), 5.28 (s, 1H), 4.84 (s, 2H), 4.66-2.85 (m, 10H), 3.51 (s, 3H), 1.24 (s, 6H); MS (M+H)$^+$=534.

Example 136. 1-(4-(4-(((5-chloropyridin-3-yl)methyl)amino)-6-(3,5-dimethylisoxazol-4-yl)quinazolin-2-yl)piperazin-1-yl)-2-methylpropan-2-ol, 2TFA The title compound was prepared from 2-chloro-N-((5-chloropyridin-3-yl)methyl)-6-(3,5-dimethylisoxazol-4-yl)quinazolin-4-amine (Example 112, 30.0 mg, 0.075 mmol) and 2-methyl-1-(piperazin-1-yl)propan-2-ol, 2HCl (52.0 mg, 0.225 mmol) according to similar procedure described in Example 12. $^1$H NMR (400 MHz, DMSO-d$_6$) δ 9.27 (s, 1H), 8.60 (d, J=1.8 Hz, 1H), 8.52 (d, J=2.4 Hz, 1H), 8.16 (s, 1H), 7.95 (t, J=2.2 Hz, 1H), 7.76 (s, 1H), 7.62 (s, 1H), 5.27 (s, 1H), 4.82 (d, J=5.6 Hz, 2H), 4.70-2.82 (m, 10H), 2.42 (s, 3H), 2.25 (s, 3H), 1.24 (s, 6H); MS (M+H)$^+$=522.

Example 137. 1-(4-(4-((3-chlorobenzyl)amino)-6-(3,5-dimethylisoxazol-4-yl)quinazolin-2-yl)piperazin-1-yl)-2-methylpropan-2-ol, 2TFA The title compound was prepared from 2-chloro-N-(3-chlorobenzyl)-6-(3,5-dimethylisoxazol-4-yl)quinazolin-4-amine (Example 1, 0.03 g, 0.075 mmol) and 2-methyl-1-(piperazin-1-yl)propan-2-ol, 2HCl (0.052 g, 0.225 mmol) according to similar procedure described in Example 12. $^1$H NMR (400 MHz, DMSO-d$_6$) δ 9.36 (s, 1H), 8.19 (s, 1H), 7.76 (s, 1H), 7.63 (s, 1H), 7.47 (d, J=1.5 Hz, 1H), 7.41-7.22 (m, 3H), 5.26 (s, 1H), 4.79 (d, J=5.6 Hz, 2H), 4.67-2.76 (m, 10H), 2.42 (s, 3H), 2.25 (s, 3H), 1.24 (s, 6H); MS (M+H)$^+$=521.

Example 138. 2-(4-(4-(((5-chloropyridin-3-yl)methyl)amino)-6-(3,5-dimethylisoxazol-4-yl)quinazolin-2-yl)-1H-pyrazol-1-yl)-2-methylpropan-1-ol, 2TFA The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-methyl-2-(4-(4,4,5,5-tetramethyl-1,3,2-dioxaborolan-2-yl)-1H-pyrazol-1-yl)propan-1-ol (39.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.38 (s, 1H), 8.69 (d, J=1.9 Hz, 2H), 8.53 (d, J=2.4 Hz, 1H), 8.34 (s, 2H), 8.05 (t, J=2.2 Hz, 1H), 7.99 (d, J=8.9 Hz, 1H), 7.87 (d, J=8.5 Hz, 1H), 5.05 (d, J=5.5 Hz, 2H), 3.62 (s, 2H), 2.46 (s, 3H), 2.28 (s, 3H), 1.53 (s, 6H). (OH not shown); MS (M+H)$^+$=504.

Example 139. 1-(4-(4-(((5-chloropyridin-3-yl)methyl)amino)-6-(3,5-dimethylisoxazol-4-yl)quinazolin-2-yl)-1H-pyrazol-1-yl)-2-methylpropan-2-ol, 2TFA The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-methyl-1-(4-(4,4,5,5-tetramethyl-1,3,2-dioxaborolan-2-yl)-1H-pyrazol-1-yl)propan-2-ol (39.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.35 (s, 1H), 8.69-8.68 (m, 2H), 8.53 (d, J=2.4 Hz, 1H), 8.33 (s, 2H), 8.04 (t, J=2.1 Hz, 1H), 7.97 (s, 1H), 7.87 (d, J=8.5 Hz, 1H), 5.04 (s, 2H), 4.13 (s, 2H), 2.46 (s, 3H), 2.28 (s, 3H), 1.10 (s, 6H). (OH not shown); MS (M+H)$^+$=504.

Example 140. 2-(4-(4-(((5-chloropyridin-3-yl)methyl)amino)-6-(3,5-dimethylisoxazol-4-yl)quinazolin-2-yl)-1H-pyrazol-1-yl)-N,N-dimethylacetamide, 2TFA The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N,N-dimethyl-2-(4-(4,4,5,5-tetramethyl-1,3,2-dioxaborolan-2-yl)-1H-pyrazol-1-yl)acetamide (41.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.42 (s, 1H), 8.68 (d, J=1.9 Hz, 1H), 8.65 (s, 1H), 8.53 (d, J=2.4 Hz, 1H), 8.33 (s, 2H), 8.04 (t, J=2.1 Hz, 1H), 7.97 (s, 1H), 7.87 (d, J=8.6 Hz, 1H), 5.27 (s, 2H), 5.06 (s, 2H), 3.04 (s, 3H), 2.85 (s, 3H), 2.46 (s, 3H), 2.28 (s, 3H); MS (M+H)$^+$=517.

Example 141. 2-(4-(4-(((5-chloropyridin-3-yl)methyl)amino)-6-(3,5-dimethylisoxazol-4-yl)quinazolin-2-yl)-1H-pyrazol-1-yl)-N-methylacetamide, 2TFA The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), N-methyl-2-(4-(4,4,5,5-tetramethyl-1,3,2-dioxaborolan-2-yl)-1H-pyrazol-1-yl)acetamide (39.8 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.39 (s, 1H), 8.72 (s, 1H), 8.68 (d, J=1.9 Hz, 1H), 8.53 (d, J=2.3 Hz, 1H), 8.33 (s, 2H), 8.19 (s, 1H), 8.04 (t, J=2.1 Hz, 1H), 7.98 (s, 1H), 7.87 (d, J=8.3 Hz, 1H), 5.05 (s, 2H), 4.92 (s, 2H), 2.63 (d, J=4.6 Hz, 3H), 2.46 (s, 3H), 2.28 (s, 3H); MS (M+H)$^+$=503.

Example 142. 2-(4-(4-(((5-chloropyridin-3-yl)methyl)amino)-6-(3,5-dimethylisoxazol-4-yl)quinazolin-2-yl)-1H-pyrazol-1-yl)acetamide, 2TFA The title compound was prepared from 2-chloro-N-((5-chloropyridin-3-yl)methyl)-6-(3,5-dimethylisoxazol-4-yl)quinazolin-4-amine (Example 112, 46.2 mg, 0.075 mmol), 2-(4-(4,4,5,5-tetramethyl-1,3,2-dioxaborolan-2-yl)-1H-pyrazol-1-yl)acetamide (37.7 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.35 (s, 1H), 8.72 (s, 1H), 8.68 (d, J=1.8 Hz, 1H), 8.53 (d, J=2.4 Hz, 1H), 8.33 (s, 2H), 8.04 (t, J=2.1 Hz, 1H), 7.98 (s, 1H), 7.88 (d, J=8.5 Hz, 1H), 7.68 (s, 1H), 7.35 (s, 1H), 5.06 (d, J=5.6 Hz, 2H), 4.92 (s, 2H), 2.46 (s, 3H), 2.28 (s, 3H); MS (M+H)$^+$=489.

Example 143. 5-(4-(((5-chloropyridin-3-yl)methyl) amino)-2-(1-(2-hydroxyethyl)-1H-pyrazol-4-yl)quinazolin-6-yl)-1-methylpyridin-2(1H)-one, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), 2-(4-(4,4,5,5-tetramethyl-1,3,2-dioxaborolan-2-yl)-1H-pyrazol-1-yl)ethanol (35.7 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.34 (s, 1H), 8.70 (d, J=1.8 Hz, 2H), 8.54 (d, J=2.4 Hz, 1H), 8.51 (s, 1H), 8.34 (s, 1H), 8.29 (d, J=2.7 Hz, 1H), 8.18 (s, 1H), 8.06 (t, J=2.1 Hz, 1H), 7.95 (dd, J=9.5, 2.8 Hz, 1H), 7.80 (d, J=9.0 Hz, 1H), 6.58 (d, J=9.5 Hz, 1H), 5.05 (br s, 3H), 4.26 (t, J=5.3 Hz, 2H), 3.77 (t, J=5.4 Hz, 2H), 3.53 (s, 3H); MS (M+H)$^+$=488.

Example 144. 2-(4-(4-(((5-chloropyridin-3-yl) methyl)amino)-6-(3,5-dimethylisoxazol-4-yl)quinazolin-2-yl)-1H-pyrazol-1-yl)ethanol, 2TFA The title compound was prepared from 2-chloro-N-((5-chloropyridin-3-yl)methyl)-6-(3,5-dimethylisoxazol-4-yl) quinazolin-4-amine (Example 112, 46.2 mg, 0.075 mmol), 2-(4-(4,4,5,5-tetramethyl-1,3,2-dioxaborolan-2-yl)-1H-pyrazol-1-yl)ethanol (35.7 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.34 (s, 1H), 8.72 (s, 1H), 8.69 (d, J=1.8 Hz, 1H), 8.53 (d, J=2.3 Hz, 1H), 8.36 (s, 1H), 8.34-8.27 (m, 1H), 8.05 (t, J=2.1 Hz, 1H), 7.99 (d, J=9.0 Hz, 1H), 7.87 (d, J=8.6 Hz, 1H), 5.06 (d, J=5.3 Hz, 2H), 4.27 (t, J=5.3 Hz, 2H), 3.78 (t, J=5.3 Hz, 2H), 2.45 (s, 3H), 2.28 (s, 3H). (OH not shown); MS (M+H)$^+$=476.

Example 145. 2-(4-(4-(((5-chloropyridin-3-yl) methyl)amino)-6-(1-methyl-6-oxo-1,6-dihydropyridin-3-yl)quinazolin-2-yl)-1H-pyrazol-1-yl)acetamide, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), 2-(4-(4,4,5,5-tetramethyl-1,3,2-dioxaborolan-2-yl)-1H-pyrazol-1-yl)acetamide (37.7 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.39 (s, 1H), 8.70 (d, J=1.8 Hz, 2H), 8.53 (d, J=2.4 Hz, 1H), 8.51 (s, 1H), 8.29 (d, J=2.7 Hz, 2H), 8.18 (s, 1H), 8.06 (d, J=2.2 Hz, 1H), 7.95 (dd, J=9.5, 2.8 Hz, 1H), 7.80 (d, J=8.5 Hz, 1H), 7.65 (s, 1H), 7.34 (d, J=10.5 Hz, 1H), 6.58 (d, J=9.4 Hz, 1H), 5.04 (s, 2H), 4.91 (s, 2H), 3.53 (s, 3H); MS (M+H)$^+$=501.

Example 146. 2-(4-(4-(((5-chloropyridin-3-yl) methyl)amino)-6-(1-methyl-6-oxo-1,6-dihydropyridin-3-yl)quinazolin-2-yl)-1H-pyrazol-1-yl)-N,N-dimethylacetamide, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), N,N-dimethyl-2-(4-(4,4,5,5-tetramethyl-1,3,2-dioxaborolan-2-yl)-1H-pyrazol-1-yl)acetamide (41.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.38 (s, 1H), 8.70 (d, J=1.9 Hz, 1H), 8.65 (s, 1H), 8.57-8.50 (m, 2H), 8.33 (d, J=9.7 Hz, 1H), 8.30 (d, J=2.7 Hz, 1H), 8.20 (d, J=8.8 Hz, 1H), 8.06 (t, J=2.2 Hz, 1H), 7.95 (dd, J=9.5, 2.8 Hz, 1H), 7.82 (d, J=8.8 Hz, 1H), 6.59 (d, J=9.5 Hz, 1H), 5.28 (s, 2H), 5.07 (d, J=5.8 Hz, 2H), 3.53 (s, 3H), 3.04 (s, 3H), 2.85 (s, 3H); MS (M+H)$^+$=529.

Example 147. 2-(4-(4-(((5-chloropyridin-3-yl) methyl)amino)-6-(1-methyl-6-oxo-1,6-dihydropyridin-3-yl)quinazolin-2-yl)-1H-pyrazol-1-yl)-N-methylacetamide, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), N-methyl-2-(4-(4,4,5,5-tetramethyl-1,3,2-dioxaborolan-2-yl)-1H-pyrazol-1-yl)acetamide (39.8 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.36 (s, 1H), 8.70 (d, J=1.8 Hz, 2H), 8.54 (d, J=2.4 Hz, 1H), 8.51 (s, 1H), 8.29 (d, J=2.7 Hz, 2H), 8.14 (d, J=30.2 Hz, 2H), 8.08-8.02 (m, 1H), 7.95 (dd, J=9.5, 2.8 Hz, 1H), 7.80 (d, J=8.7 Hz, 1H), 6.58 (d, J=9.5 Hz, 1H), 5.06 (s, 2H), 4.91 (s, 2H), 3.53 (s, 3H), 2.62 (dd, J=4.5, 2.8 Hz, 3H); MS (M+H)$^+$=515.

Example 148. 5-(4-(((5-chloropyridin-3-yl)methyl) amino)-2-(1-(2-hydroxy-2-methylpropyl)-1H-pyrazol-4-yl)quinazolin-6-yl)-1-methylpyridin-2(1H)-one, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), 2-methyl-1-(4-(4,4,5,5-tetramethyl-1,3,2-dioxaborolan-2-yl)-1H-pyrazol-1-yl)propan-2-ol (39.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.37 (s, 1H), 8.70 (d, J=1.9 Hz, 1H), 8.65 (s, 1H), 8.54 (d, J=2.4 Hz, 1H), 8.32 (s, 1H), 8.29 (d, J=2.7 Hz, 1H), 8.18 (s, 1H), 8.06 (t, J=2.1 Hz, 1H), 7.95 (dd, J=9.5, 2.8 Hz, 1H), 7.80 (d, J=8.7 Hz, 1H), 6.58 (d, J=9.5 Hz, 1H), 5.05 (s, 2H), 4.83 (s, 1H), 4.13 (s, 2H), 3.53 (s, 3H), 1.09 (s, 6H); MS (M+H)$^+$=516.

Example 149. 5-(4-(((5-chloropyridin-3-yl)methyl) amino)-2-(1-(1-hydroxy-2-methylpropan-2-yl)-1H-pyrazol-4-yl)quinazolin-6-yl)-1-methylpyridin-2 (1H)-one, 2TFA The title compound was prepared from 5-(2-chloro-4-(((5-chloropyridin-3-yl)methyl)amino)quinazolin-6-yl)-1-methylpyridin-2(1H)-one (Example 113, 30.9 mg, 0.075 mmol), 2-methyl-2-(4-(4,4,5,5-tetramethyl-1,3,2-dioxaborolan-2-yl)-1H-pyrazol-1-yl)propan-1-ol (39.9 mg, 0.15 mmol), PdCl$_2$(dppf)-CH$_2$Cl$_2$ adduct (12.25 mg, 0.015 mmol), and K$_2$CO$_3$ (62.2 mg, 0.45 mmol) according to similar procedure described in Example 28. $^1$H NMR (400 MHz, DMSO-d$_6$) δ 10.35 (s, 1H), 8.71 (d, J=1.8 Hz, 1H), 8.67 (s, 1H), 8.53 (d, J=2.4 Hz, 2H), 8.34 (s, 1H), 8.29 (d, J=2.7 Hz, 1H), 8.19 (s, 1H), 8.07 (t, J=2.2 Hz, 1H), 7.95 (dd, J=9.5, 2.8 Hz, 1H), 7.80 (d, J=8.7 Hz, 1H), 6.59 (d, J=9.5 Hz, 1H), 5.05 (s, 3H), 3.62 (s, 2H), 3.53 (s, 3H), 1.53 (s, 6H); MS (M+H)⁺=516.

Examples 150-151

2-(4-(4-((4-chlorophenyl)amino)-6-(3,5-dimethylisoxazol-4-yl)quinazolin-2-yl)-1H-pyrazol-1-yl)ethanol, 2TFA (Example 150) and 6-bromo-2-chloro-N-(4-chlorophenyl)quinazolin-4-amine (Example 151)

Step 1: 6-bromo-2-chloro-N-(4-chlorophenyl)quinazolin-4-amine

To a mixture of 6-bromo-2,4-dichloroquinazoline (1.112 g, 4 mmol) and 4-chloroaniline (0.765 g, 6.0 mmol) in THF (10 ml) at 0° C. was added potassium t-butoxide (5.0 mL, 5.0 mmol) slowly. The mixture was stirred at 0° C. for 1 h. The mixture was poured into EtOAc/H₂O (50 mL/50 mL). The organic layer was dried over Na₂SO₄ and filtered. After removal of the solvent, the product was triturated with 10% CH₂Cl₂/hexane and then dried to give 1.25 g of crude product which was used without further purification. The filtrate was concentrated and purified by silica gel chromatography using 0-20% EtOAc/hexane as the eluent to give an additional 100 mg of crude product. Total, ~1.35 g of crude 6-bromo-2-chloro-N-(4-chlorophenyl)quinazolin-4-amine (1.35 g, 2.93 mmol, 73.2% yield) was obtained. ¹H NMR (400 MHz, DMSO-d₆) δ 10.28 (s, 1H), 8.84 (d, J=2.1 Hz, 1H), 8.00 (dd, J=8.9, 2.1 Hz, 1H), 7.85-7.76 (m, 2H), 7.65 (d, J=8.9 Hz, 1H), 7.55-7.44 (m, 2H); MS (M+H)⁺=369.

Step 2: 6-bromo-2-chloro-N-(4-chlorophenyl)quinazolin-4-amine (Example 151)

In a 2-neck flask was placed 6-bromo-2-chloro-N-(4-chlorophenyl)quinazolin-4-amine (738 mg, 2 mmol), 3,5-dimethyl-4-(4,4,5,5-tetramethyl-1,3,2-dioxaborolan-2-yl)isoxazole (491 mg, 2.2 mmol), PdCl₂(dppf)-CH₂Cl₂ adduct (163 mg, 0.2 mmol), and K₂CO₃ (912 mg, 6.6 mmol). The air was removed and re-filled with N₂ (2-3 times). Then a mixture of 1,4-dioxane (7 ml) and water (3.5 ml) was added and stirred at 95° C. (pre-heated) for 1.5 h. After cooling to rt, the organic layer was separated and the aqueous layer was extracted with EtOAc (5 mL×3). The combined organic layer was dried over Na₂SO₄ and filtered. The product was triturated with 70% EtOAc/hexane and dried to give 280 mg of crude product which was used without further purification. The filtrate was concentrated and purified by silica gel chromatography using 10-20% EtOAc/CH₂Cl₂ as the elution to give an additional 165 mg of crude product. Total 445 mg of 2-chloro-N-(4-chlorophenyl)-6-(3,5-dimethylisoxazol-4-yl)quinazolin-4-amine (1.16 mmol, 57.8% yield) was obtained. 20 mg was purified to give TFA salt for screening. MS (M+H)⁺=386.

Step 3: 2-(4-(4-((4-chlorophenyl)amino)-6-(3,5-dimethylisoxazol-4-yl)quinazolin-2-yl)-1H-pyrazol-1-yl)ethanol, 2TFA The title compound was prepared from 2-chloro-N-(4-chlorophenyl)-6-(3,5-dimethylisoxazol-4-yl)quinazolin-4-amine (48.2 mg, 0.1 mmol), 2-(4-(4,4,5,5-tetramethyl-1,3,2-dioxaborolan-2-yl)-1H-pyrazol-1-yl)ethanol (47.6 mg, 0.20 mmol), PdCl₂(dppf)-CH₂Cl₂ adduct (16.33 mg, 0.02 mmol), and K₂CO₃ (83 mg, 0.60 mmol) according to similar procedure described in Example 28. ¹H NMR (400 MHz, DMSO-d₆) δ 10.67 (s, 1H), 8.56 (s, 1H), 8.46 (s, 1H), 8.18 (s, 1H), 7.96 (d, J=8.6 Hz, 1H), 7.90 (d, J=8.6 Hz, 3H), 7.60-7.52 (m, 2H), 4.26 (t, J=5.4 Hz, 2H), 3.77 (t, J=5.4 Hz, 2H), 2.47 (s, 3H), 2.29 (s, 3H). (OH not shown); MS (M+H)⁺=461.

Example 152. N-((5-chloropyridin-3-yl)methyl)-6-(3,5-dimethylisoxazol-4-yl)-2-(4-(methylsulfonyl)piperazin-1-yl)quinazolin-4-amine, 2TFA The title compound was prepared from 2-chloro-N-((5-chloropyridin-3-yl)methyl)-6-(3,5-dimethylisoxazol-4-yl)quinazolin-4-amine (Example 112, 61.6 mg, 0.1 mmol) and 1-(methylsulfonyl)piperazine (49.3 mg, 0.30 mmol) according to similar procedure described in Example 12. ¹H NMR (400 MHz, DMSO-d₆) δ 12.05 (s, 1H), 10.09 (s, 1H), 8.60 (d, J=1.8 Hz, 1H), 8.53 (d, J=2.3 Hz, 1H), 8.19 (s, 1H), 7.97 (s, 1H), 7.82-7.71 (m, 2H), 4.83 (s, 2H), 3.92 (s, 4H), 3.19 (s, 4H), 2.87 (s, 3H), 2.42 (s, 3H), 2.25 (s, 3H). (including 1 salt NH); MS (M+H)⁺=529.

Example 153. N-(3-chlorobenzyl)-6-(3,5-dimethylisoxazol-4-yl)-2-(4-(methylsulfonyl)piperidin-1-yl)quinazolin-4-amine, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and 4-(methylsulfonyl)piperidine (49.0 mg, 0.30 mmol) according to similar procedure described in Example 12. ¹H NMR (400 MHz, DMSO-d₆) δ 11.90 (s, 1H), 10.08 (s, 1H), 8.22 (s, 1H), 7.82 (s, 1H), 7.73 (s, 1H), 7.48 (s, 1H), 7.40-7.28 (m, 3H), 4.79 (s, 2H), 4.65 (br s, 1H), 3.46 (br s, 2H), 3.19 (br s, 2H), 2.92 (s, 3H), 2.42 (s, 3H), 2.25 (s, 3H), 2.11 (d, J=12.7 Hz, 2H), 1.59 (br s, 2H). (including one salt NH); MS (M+H)⁺=527.

Example 154. N-((5-chloropyridin-3-yl)methyl)-6-(3,5-dimethylisoxazol-4-yl)-2-(4-(methylsulfonyl)piperidin-1-yl)quinazolin-4-amine, 2TFA The title compound was prepared from 2-chloro-N-((5-chloropyridin-3-yl)methyl)-6-(3,5-dimethylisoxazol-4-yl)quinazolin-4-amine (Example 112, 61.6 mg, 0.1 mmol) and 4-(methylsulfonyl)piperidine (49.0 mg, 0.30 mmol) according to similar procedure described in Example 12. ¹H NMR (400 MHz, DMSO-d₆) δ 11.92 (s, 1H), 10.06 (s, 1H), 8.60 (d, J=1.8 Hz, 1H), 8.52 (d, J=2.4 Hz, 1H), 8.19 (s, 1H), 7.98 (d, J=2.2 Hz, 1H), 7.82 (s, 1H), 7.72 (s, 1H), 4.83 (d, J=5.4 Hz, 2H), 4.63 (s, 1H), 3.44 (m, 2H), 3.16 (m, 2H), 2.91 (s, 3H), 2.42 (s, 3H), 2.25 (s, 3H), 2.10 (m, 2H), 1.58 (s, 2H). (including one salt NH); MS (M+H)⁺=528.

Example 155. N-(3-chlorobenzyl)-6-(3,5-dimethylisoxazol-4-yl)-2-(4-(methylsulfonyl)piperazin-1-yl)quinazolin-4-amine, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and 1-(methylsulfonyl)piperazine (49.3 mg, 0.30 mmol) according to similar procedure described in Example 12. ¹H NMR (400 MHz, DMSO-d₆) δ 12.02 (s, 1H), 10.11 (s, 1H), 8.22 (s, 1H), 7.82-7.72 (m, 2H), 7.48 (s, 1H), 7.41-7.27 (m, 3H), 4.79 (s, 2H), 3.92 (s, 4H), 3.19 (s, 4H), 2.87 (s, 3H), 2.42 (s, 3H), 2.25 (s, 3H). (including one salt NH); MS (M+H)⁺=528.

Example 156. 1-(4-((3-chlorobenzyl)amino)-6-(3,5-dimethylisoxazol-4-yl)quinazolin-2-yl)-4-methylpiperidine-4-carbonitrile, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and 4-methylpiperidine-4-carbonitrile, HCl (48.2 mg, 0.30 mmol) according to similar procedure described in Example 12. $^1$H NMR (400 MHz, DMSO-$d_6$) δ 11.92 (s, 1H), 10.08 (s, 1H), 8.22 (s, 1H), 7.91-7.77 (m, 1H), 7.72 (s, 1H), 7.48 (s, 1H), 7.39-7.28 (m, 3H), 4.78 (d, J=5.6 Hz, 2H), 4.50 (s, 2H), 3.27 (s, 2H), 2.42 (s, 3H), 2.25 (s, 3H), 1.98 (d, J=13.6 Hz, 2H), 1.56 (s, 2H), 1.34 (s, 3H). (including one salt NH); MS (M+H)$^+$=487.

Example 157. 1-(4-(((5-chloropyridin-3-yl)methyl)amino)-6-(3,5-dimethylisoxazol-4-yl)quinazolin-2-yl)-4-methylpiperidine-4-carbonitrile, 2TFA The title compound was prepared from 2-chloro-N-((5-chloropyridin-3-yl)methyl)-6-(3,5-dimethylisoxazol-4-yl)quinazolin-4-amine (Example 112, 61.6 mg, 0.1 mmol) and 4-methylpiperidine-4-carbonitrile, HCl (48.2 mg, 0.30 mmol) according to similar procedure described in Example 12. $^1$H NMR (400 MHz, DMSO-$d_6$) δ 11.94 (s, 1H), 10.08 (s, 1H), 8.60 (d, J=1.9 Hz, 1H), 8.53 (d, J=2.3 Hz, 1H), 8.20 (s, 1H), 7.97 (t, J=2.2 Hz, 1H), 7.82 (s, 1H), 7.73 (s, 1H), 4.84 (d, J=5.6 Hz, 2H), 4.48 (s, 2H), 3.28 (s, 2H), 2.42 (s, 3H), 2.24 (s, 3H), 1.97 (d, J=13.7 Hz, 2H), 1.56 (s, 2H), 1.34 (s, 3H). (including one salt NH); MS (M+H)$^+$=488.

Example 158. N-(4-chlorophenyl)-6-(3,5-dimethylisoxazol-4-yl)quinazolin-4-amine, 2TFA

Step 1. 6-bromo-N-(4-chlorophenyl)quinazolin-4-amine

6-Bromo-N-(4-chlorophenyl)quinazolin-4-amine was prepared from 6-bromo-2,4-dichloroquinazoline and (3-chlorophenyl)methanamine according to similar procedure described in Example 1, STEP 1.

Step 2. N-(4-chlorophenyl)-6-(3,5-dimethylisoxazol-4-yl)quinazolin-4-amine, 2TFA The title compound was prepared from 6-bromo-N-(4-chlorophenyl)quinazolin-4-amine (50.2 mg, 0.15 mmol), 3,5-dimethyl-4-(4,4,5,5-tetramethyl-1,3,2-dioxaborolan-2-yl)isoxazole (66.9 mg, 0.30 mmol), PdCl$_2$(dppf)-CH$_2$Cl$_2$ adduct (12.25 mg, 0.015 mmol), and K$_2$CO$_3$ (124 mg, 0.90 mmol) according to similar procedure described in Example 151. $^1$H NMR (400 MHz, DMSO-$d_6$) δ 10.71 (s, 1H), 8.81 (s, 1H), 8.58 (d, J=1.8 Hz, 1H), 8.01 (dd, J=8.6, 1.7 Hz, 1H), 7.91 (d, J=8.6 Hz, 1H), 7.83-7.74 (m, 2H), 7.56-7.47 (m, 2H), 2.46 (s, 3H), 2.29 (s, 3H); MS (M+H)$^+$=351.

Example 159. 5-(4-((4-chlorophenyl)amino)quinazolin-6-yl)-1-methylpyridin-2(1H)-one, TFA The title compound was prepared from 6-bromo-N-(4-chlorophenyl)quinazolin-4-amine (Example 158, STEP 1, 50.2 mg, 0.15 mmol), 1-methyl-5-(4,4,5,5-tetramethyl-1,3,2-dioxaborolan-2-yl)pyridin-2(1H)-one (35.3 mg, 0.15 mmol), PdCl$_2$(dppf)-CH$_2$Cl$_2$ adduct (12.25 mg, 0.015 mmol), and K$_2$CO$_3$ (124 mg, 0.90 mmol) according to similar procedure described in Example 151. $^1$H NMR (400 MHz, DMSO-$d_6$) δ 10.74 (s, 1H), 8.80-8.71 (m, 2H), 8.35 (d, J=2.7 Hz, 1H), 8.24 (dd, J=8.8, 1.9 Hz, 1H), 8.04 (dd, J=9.5, 2.8 Hz, 1H), 7.89-7.76 (m, 3H), 7.57-7.48 (m, 2H), 6.60 (dd, J=9.4, 0.5 Hz, 1H), 3.54 (s, 3H); MS (M+H)$^+$=363.

Example 160. N-(4-chlorophenethyl)-2-(4-(2-(dimethylamino)ethyl)piperazin-1-yl)-6-(3,5-dimethylisoxazol-4-yl)quinazolin-4-amine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 2-(4-chlorophenyl)ethanamine (62.2 mg, 0.40 mmol) for overnight according to similar procedure described in Example 71. $^1$H NMR (400 MHz, DMSO-$d_6$) δ 11.75 (s, 1H), 9.54 (s, 1H), 8.88 (s, 1H), 8.13 (s, 1H), 7.83 (d, J=8.6 Hz, 1H), 7.71 (d, J=8.7 Hz, 1H), 7.32 (d, J=7.9 Hz, 2H), 7.25 (d, J=8.2 Hz, 2H), 3.94-2.88 (m, 10H), 2.81 (s, 6H), 2.72-2.53 (m, 6H), 2.41 (s, 3H), 2.23 (s, 3H). (including two salt NH); MS (M+H)$^+$=535.

Example 161. 2-(4-(4-(3-benzylazetidin-1-yl)-6-(3,5-dimethylisoxazol-4-yl)quinazolin-2-yl)piperazin-1-yl)-N,N-dimethylethanamine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 3-benzylazetidine, HCl (73.5 mg, 0.40 mmol) for overnight according to similar procedure described in Example 71. $^1$H NMR (400 MHz, DMSO-$d_6$) δ 11.89-11.51 (m, 1H), 8.94 (s, 1H), 7.85 (d, J=8.7 Hz, 1H), 7.72 (d, J=6.2 Hz, 2H), 7.32-7.17 (m, 5H), 5.01 (s, 1H), 4.69 (s, 1H), 4.41 (d, J=10.1 Hz, 1H), 4.06 (s, 1H), 3.82 (s, 4H), 3.23 (d, J=6.0 Hz, 2H), 3.13 (q, J=6.8 Hz, 1H), 3.05-2.52 (m, 4H), 2.80 (s, 6H), 2.41 (s, 3H), 2.23 (s, 3H), 1.71 (q, J=4.0 Hz, 4H). (including two salt NH); MS (M+H)$^+$=526.

Example 162. N-(4-chlorophenyl)-2-(4-(2-(dimethylamino)ethyl)piperazin-1-yl)-6-(3,5-dimethylisoxazol-4-yl)quinazolin-4-amine, 2TFA The title compound was prepared from 2-chloro-N-(4-chlorophenyl)-6-(3,5-dimethylisoxazol-4-yl)quinazolin-4-amine (Example 151, 72.2 mg, 0.15 mmol) and N,N-dimethyl-2-(piperazin-1-yl)ethanamine, 2HCl (173 mg, 0.75 mmol) according to similar procedure described in Example 71. $^1$H NMR (400 MHz, DMSO-$d_6$) δ 9.05 (s, 1H), 8.37 (s, 1H), 7.97-7.55 (m, 4H), 7.49 (d, J=8.4 Hz, 2H), 3.93-2.51 (m, 12H), 2.79 (s, 6H), 2.43 (s, 3H), 2.26 (s, 3H); MS (M+H)$^+$=507.

Example 163. 4-((3-chlorobenzyl)amino)-6-(3,5-dimethylisoxazol-4-yl)quinazoline-2-carboxylic acid, TFA

Step 1: ethyl 6-bromo-4-((3-chlorobenzyl)amino)quinazoline-2-carboxylate

To a suspension of ethyl 6-bromo-4-hydroxyquinazoline-2-carboxylate (0.891 g, 3 mmol) and bromotri(pyrrolidin-1-yl)phosphonium hexafluorophosphate (2.10 g, 4.50 mmol) in 1,4-dioxane (12 ml) was added Et$_3$N (1.254 ml, 9.0 mmol). The mixture was stirred at rt for 3 h and then (3-chlorophenyl)methanamine (0.85 g, 6.0 mmol) was added. The mixture was stirred at rt for another 5 h. The mixture was poured into hexane/H$_2$O (10 mL/10 mL). The solid was filtered and triturated with 3% EtOAc/hexane and then dried to give ethyl 6-bromo-4-((3-chlorobenzyl)amino) quinazoline-2-carboxylate (1.2 g, 2.85 mmol, 95% yield). The material was used without further purification. MS (M+H)$^+$=421.

Step 2: ethyl 4-((3-chlorobenzyl)amino)-6-(3,5-dimethylisoxazol-4-yl)quinazoline-2-carboxylate In a 2-neck flask was placed ethyl 6-bromo-4-((3-chlorobenzyl)amino)quinazoline-2-carboxylate (1.69 g, 4 mmol), 3,5-dimethyl-4-(4,4,5,5-tetramethyl-1,3,2-dioxaborolan-2-yl)isoxazole (1.34 g, 6.0 mmol), PdCl$_2$(dppf)-CH$_2$Cl$_2$ adduct (0.33 g, 0.40 mmol), and K$_2$CO$_3$ (2.49 g, 18.0 mmol). The air was removed and re-filled with N$_2$ (2-3 times). Then a mixture of 1,4-dioxane (16 mL) and water (8 mL) was added and stirred at 85° C. (pre-heated) for 1.5 h. After cooling to rt, the organic layer was separated and extracted with EtOAc (10 mL×3). The combined organic layer was dried over Na$_2$SO$_4$ and filtered. After removal of the solvent, the product was purified by silica gel chromatography using 50-75-90% EtOAc/hexane as the eluent to give ethyl 4-((3-chlorobenzyl)amino)-6-(3,5-dimethylisoxazol-4-yl)quinazoline-2-carboxylate (1.7 g, 3.89 mmol, 97% yield). MS (M+H)$^+$=437.

Step 3: 4-((3-chlorobenzyl)amino)-6-(3,5-dimethylisoxazol-4-yl)quinazoline-2-carboxylic acid To a solution of ethyl 4-((3-chlorobenzyl)amino)-6-(3,5-dimethylisoxazol-4-yl)quinazoline-2-carboxylate (1.7 g, 3.89 mmol) in THF (11 mL) and MeOH (1 mL) was added 1N NaOH (aq) (11.7 mL, 11.7 mmol, 3 equiv). The mixture was then stirred at 50° C. for 2 h. After cooling to rt, 1N HCl (aq) was added until the pH of aqueous layer was ~4. The product became sticky gum on the surface of flask and the product was carefully separated from the solvent. The aqueous layer was extracted with EtOAc (30 mL×3). The combined organic layer was dried over Na$_2$SO$_4$, filtered, and concentrated. The residue together with the sticky gum was dried in vacuo for 1 h. To the crude product was add CH$_2$Cl$_2$ (20 mL), the mixture was sonicated, and then hexane (40 mL) was added. The solid was filtered and triturated with 2% CH$_2$Cl$_2$/hexane (3 mL×3), and then dried to give 4-((3-chlorobenzyl)amino)-6-(3,5-dimethylisoxazol-4-yl)quinazoline-2-carboxylic acid (1.11 g, 2.72 mmol, 69.8% yield). Material was purified to give TFA salt for screening. $^1$H NMR (400 MHz, DMSO-d$_6$) δ 9.47 (s, 1H), 8.32 (s, 1H), 7.94 (q, J=8.6 Hz, 2H), 7.50 (s, 1H), 7.41-7.27 (m, 3H), 4.90 (d, J=5.7 Hz, 2H), 2.45 (s, 3H), 2.28 (s, 3H). (acid OH not shown); MS (M+H)$^+$=409.

Example 164. 2-(4-(4-((1-(3-chlorophenyl)cyclopropyl)amino)-6-(3,5-dimethylisoxazol-4-yl)quinazolin-2-yl1-1H-pyrazol-1-yl)ethanol, 2TFA Step 1. 2-chloro-N-(1-(3-chlorophenyl)cyclopropyl)-6-(3,5-dimethylisoxazol-4-yl)quinazolin-4-amine 2-Chloro-N-(1-(3-chlorophenyl)cyclopropyl)-6-(3,5-dimethylisoxazol-4-yl)quinazolin-4-amine was prepared from 6-bromo-2,4-dichloroquinazoline and 1-(3-chlorophenyl) cyclopropan-1-amine according to a similar procedure described in Example 1.

Step 2. 2-(4-(4-((1-(3-chlorophenyl)cyclopropyl) amino)-6-(3,5-dimethylisoxazol-4-yl)quinazolin-2-yl)-1H-pyrazol-1-yl)ethanol, 2TFA The title compound was prepared from 2-chloro-N-(1-(3-chlorophenyl)cyclopropyl)-6-(3,5-dimethylisoxazol-4-yl) quinazolin-4-amine (63.8 mg, 0.15 mmol), 2-(4-(4,4,5,5-tetramethyl-1,3,2-dioxaborolan-2-yl)-1H-pyrazol-1-yl) ethanol (71.4 mg, 0.30 mmol), PdCl$_2$(dppf)-CH$_2$Cl$_2$ adduct (12.25 mg, 0.015 mmol), and K$_2$CO$_3$ (124 mg, 0.90 mmol) according to similar procedure described in Example 28. $^1$H NMR (400 MHz, DMSO-d$_6$) δ 10.53 (s, 1H), 8.51 (s, 1H), 8.40 (s, 1H), 8.12 (s, 1H), 7.97 (s, 1H), 7.86 (d, J=8.6 Hz, 1H), 7.46 (d, J=2.0 Hz, 1H), 7.38 (d, J=7.9 Hz, 1H), 7.30 (t, J=7.8 Hz, 1H), 7.22 (d, J=8.0 Hz, 1H), 4.99 (s, 1H), 4.26 (d, J=5.3 Hz, 2H), 3.75 (t, J=5.3 Hz, 2H), 2.50 (s, 3H), 2.30 (s, 3H), 1.59 (s, 2H), 1.44 (s, 2H); MS (M+H)$^+$=501.

Example 165. (4-((3-chlorobenzyl)amino)-6-(3,5-dimethylisoxazol-4-yl)quinazolin-2-yl)(4-(2-(dimethylamino)ethyl)piperazin-1-yl)methanone, 2TFA To a mixture of 4-((3-chlorobenzyl)amino)-6-(3,5-dimethylisoxazol-4-yl)quinazoline-2-carboxylic acid (Example 163, 136 mg, 0.15 mmol, ca. 45% purity), HATU (114 mg, 0.30 mmol) was added a solution of N,N-dimethyl-2-(piperazin-1-yl)ethanamine (47.2 mg, 0.30 mmol) in DMF (1 ml) and then added Hunig's base (0.105 ml, 0.60 mmol). The mixture was stirred at rt for 2 h. The mixture was filtered through a filter and purified to give (4-((3-chlorobenzyl) amino)-6-(3,5-dimethylisoxazol-4-yl)quinazolin-2-yl)(4-(2-(dimethylamino)ethyl)piperazin-1-yl)methanone, 2TFA (15.8 mg, 0.02 mmol, 13.57% yield). $^1$H NMR (400 MHz, DMSO-d$_6$) δ 9.25 (s, 1H), 8.97 (s, 1H), 8.29 (s, 1H), 7.85 (d, J=8.5 Hz, 1H), 7.79 (d, J=8.6 Hz, 1H), 7.41 (s, 1H), 7.37-7.26 (m, 3H), 4.78 (d, J=5.8 Hz, 2H), 3.62 (s, 2H), 3.19 (s, 4H), 2.77 (s, 6H), 2.70-2.50 (m, 6H), 2.45 (s, 3H), 2.28 (s, 3H). (including one salt NH); MS (M+H)$^+$=548.

Example 166. 2-(4-(4-((3-chlorobenzyl)amino)-6-(3, 5-dimethylisoxazol-4-yl)quinazolin-2-yl)-1H-pyrazol-1-yl)acetic acid, TFA In a 2-neck flask was placed 2-chloro-N-(3-chlorobenzyl)-6-(3,5-dimethylisoxazol-4-yl)quinazolin-4-amine (Example 1, 80 mg, 0.2 mmol), ethyl 2-(4-(4,4,5,5-tetramethyl-1,3,2-dioxaborolan-2-yl)-1H-pyrazol-1-yl)acetate (112 mg, 0.40 mmol), PdCl$_2$(dppf)-CH$_2$Cl$_2$ adduct (32.7 mg, 0.04 mmol), and K$_2$CO$_3$ (166 mg, 1.20 mmol). The air was removed and re-filled with N$_2$ (2-3 times). Then added a mixture of 1,4-dioxane (1 mL) and water (0.5 ml) was added and stirred at 95° C. (pre-heated) for 1 h. The organic layer was separated and the aqueous layer was extracted with EtOAc (5 mL×2). The combined organic layer was dried over Na$_2$SO$_4$ and filtered. After removal of the solvent, the product was dissolved in THF/MeOH (1 mL/0.3 mL) and then 1N NaOH (aq) (1 mL, 1 mmol) was added. The mixture was stirred at rt for 2 h. The mixture was neutralized to pH~4-5 and then the solvent was removed by blowing air to give the crude product. The product was dissolved in MeOH and filtered through PL-Thiol MP resin and eluted with MeOH. The filtrated was concentrated and the residue was dissolved in DMF, filtered and purified to give 2-(4-(4-((3-chlorobenzyl)amino)-6-(3,5-dimethylisoxazol-4-yl)quinazolin-2-yl)-1H-pyrazol-1-yl)acetic acid, TFA (27.2 mg, 0.045 mmol, 22.6% yield). $^1$H NMR (400 MHz, DMSO-d$_6$) δ 13.32-13.25 (m, 1H), 10.36 (s, 1H), 8.69 (s, 1H), 8.34 (br s, 2H), 7.94 (s, 1H), 7.85 (d, J=8.5 Hz, 1H), 7.55 (s, 1H), 7.44 (d, J=7.6 Hz, 1H), 7.37 (t, J=7.7 Hz, 1H), 7.32 (d, J=8.0 Hz, 1H), 5.11 (s, 2H), 5.03-4.96 (m, 2H), 2.46 (d, J=2.0 Hz, 3H), 2.28 (s, 3H); MS (M+H)$^+$=489.

Example 167. N4-(3-chlorobenzyl)-N2-(4-chlorobenzyl)-6-(3,5-dimethylisoxazol-4-yl)quinazoline-2,4-diamine, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and (4-chlorophenyl)methanamine (42.5 mg, 0.30 mmol) according to similar procedure described in Example 12. $^1$H NMR (400 MHz, DMSO-d$_6$) δ 12.59 (s, 1H), 10.00 (s, 1H), 8.59 (s, 1H), 8.20 (s, 1H), 7.81 (d, J=8.5 Hz, 1H), 7.56 (d, J=8.2 Hz, 1H), 7.38-7.03 (m, 8H), 4.89-4.70 (m, 2H), 4.59 (d, J=5.8 Hz, 2H), 2.40 (s, 3H), 2.23 (s, 3H). (including one salt NH); MS (M+H)$^+$=505.

Example 168. N-(4-chlorobenzyl)-4-((3-chlorobenzyl)amino)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 136 mg, 0.15 mmol), (4-chlorophenyl)methanamine (42.5 mg, 0.300 mmol), HATU (114 mg, 0.30 mmol), and Hunig's base (0.105 ml, 0.60 mmol) according to similar procedure described in Example 165. $^1$H NMR (400 MHz, DMSO-d$_6$) δ 9.88 (br s, 1H), 9.62 (s, 1H), 8.36 (s, 1H), 8.06 (d, J=8.5 Hz, 1H), 7.98 (d, J=8.8 Hz, 1H), 7.52 (s, 1H), 7.35-7.32 (m, 7H), 5.09 (d, J=5.6 Hz, 2H), 4.52 (d, J=6.6 Hz, 2H), 2.45 (s, 3H), 2.28 (s, 3H); MS (M+H)$^+$=533.

Example 169. N-(3-chlorobenzyl)-2-(4-chlorophenoxy)-6-(3,5-dimethylisoxazol-4-yl)quinazolin-4-amine, 2TFA To a microwave tube was placed 2-chloro-N-(3-chlorobenzyl)-6-(3,5-dimethylisoxazol-4-yl)quinazolin-4-amine (Example 1, 0.04 g, 0.1 mmol), 4-chlorophenol (0.026 g, 0.20 mmol), and K$_2$CO$_3$ (0.028 g, 0.20 mmol). Then, DMF (1 ml) was added and the tube was sealed and heated at 160° C. for 1 h under microwave irradiation. The mixture was filtered through a filter and purified to give N-(3-chlorobenzyl)-2-(4-chlorophenoxy)-6-(3,5-dimethylisoxazol-4-yl)quinazolin-4-amine, 2TFA. $^1$H NMR (400 MHz, DMSO-d$_6$) δ 9.38 (s, 1H), 8.21 (d, J=2.3 Hz, 1H), 7.74 (d, J=8.6 Hz, 1H), 7.55 (d, J=8.6 Hz, 1H), 7.48-7.37 (m, 2H), 7.32-7.26 (m, 2H), 7.26-7.18 (m, 3H), 7.13 (d, J=6.2 Hz, 1H), 4.60 (d, J=5.6 Hz, 2H), 2.42 (d, J=1.9 Hz, 3H), 2.25 (d, J=1.8 Hz, 3H); MS (M+H)$^+$=492.

Example 170. N-(1-(3-chlorophenyl)cyclopropyl)-2-(4-(2-(dimethylamino)ethyl)piperazin-1-yl)-6-(3,5-dimethylisoxazol-4-yl)quinazolin-4-amine, 2TFA The title compound was prepared from 2-chloro-N-(1-(3-chlorophenyl)cyclopropyl)-6-(3,5-dimethylisoxazol-4-yl)quinazolin-4-amine (Example 164, STEP 1, 0.064 g, 0.15 mmol) and N,N-dimethyl-2-(piperazin-1-yl)ethanamine, 2HCl (0.173 g, 0.75 mmol) according to similar procedure described in Example 12. $^1$H NMR (400 MHz, DMSO-d$_6$) δ 12.00 (s, 1H), 10.14 (s, 1H), 8.94 (s, 1H), 8.26 (s, 1H), 7.83 (s, 1H), 7.71 (s, 1H), 7.30-7.22 (m, 4H), 3.64 (d, J=73.6 Hz, 8H), 3.19 (d, J=6.2 Hz, 2H), 2.78 (s, 6H), 2.67-2.54 (m, 2H), 2.43 (s, 3H), 2.26 (s, 3H), 1.47 (s, 2H), 1.40 (s, 2H). (including two salt NH); MS (M+H)$^+$=546.

Example 171. 4-((3-chlorobenzyl)amino)-6-(3,5-dimethylisoxazol-4-yl)-N-(pyridin-4-ylmethyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 136 mg, 0.15 mmol), HATU (114 mg, 0.30 mmol), pyridin-4-ylmethanamine (16.22 mg, 0.15 mmol), and Hunig's base (0.105 ml, 0.60 mmol) according to similar procedure described in Example 165. $^1$H NMR (400 MHz, DMSO-d$_6$) δ 9.93 (s, 1H), 9.76 (s, 1H), 8.65 (d, J=5.3 Hz, 2H), 8.38 (s, 1H), 8.07 (d, J=8.8 Hz, 1H), 7.99 (d, J=8.7 Hz, 1H), 7.60 (d, J=5.3 Hz, 2H), 7.54 (s, 1H), 7.41 (d, J=7.3 Hz, 1H), 7.38-7.29 (m, 2H), 5.11 (d, J=5.6 Hz, 2H), 4.68 (d, J=6.3 Hz, 2H), 2.45 (s, 3H), 2.28 (s, 3H); MS (M+H)$^+$=499.

Example 172. 4-((3-chlorobenzyl)amino)-6-(3,5-dimethylisoxazol-4-yl)-N-(1-methylpiperidin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 136 mg, 0.15 mmol), HATU (114 mg, 0.30 mmol), 1-methylpiperidin-4-amine (17.13 mg, 0.15 mmol), and Hunig's base (0.105 ml, 0.60 mmol) according to similar procedure described in Example 165. $^1$H NMR (400 MHz, DMSO-d$_6$) δ 9.57 (s, 1H), 9.29 (s, 1H), 8.75 (d, J=8.6 Hz, 1H), 8.33 (s, 1H), 8.05-7.88 (m, 2H), 7.51 (s, 1H), 7.44-7.26 (m, 3H), 4.98 (s, 2H), 4.06-3.93 (m, 1H), 3.47 (d, J=12.3 Hz, 2H), 3.15-3.06 (m, 2H), 2.76 (d, J=4.4 Hz, 3H), 2.50 (s, 3H), 2.28 (s, 3H), 2.08-2.00 (m, 2H), 1.92-1.82 (m, 2H). (including one salt NH); MS (M+H)$^+$=505.

Example 173. (S)-2-((2-(4-(2-(dimethylamino)ethyl)piperazin-1-yl)-6-(3,5-dimethylisoxazol-4-yl)quinazolin-4-yl)amino)-2-phenylethanol, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and (S)-2-amino-2-phenylethanol (54.9 mg, 0.40 mmol) for overnight according to similar procedure described in Example 71. $^1$H NMR (400 MHz, DMSO-d$_6$) δ 11.92 (s, 1H), 9.63 (s, 1H), 8.47 (s, 1H), 7.81 (d, J=8.1 Hz, 1H), 7.70 (d, J=8.6 Hz, 1H), 7.46-7.37 (m, 2H), 7.35-7.28 (m, 2H), 7.28-7.21 (m, 1H), 5.37 (q, J=7.3 Hz, 1H), 3.94-3.67 (m, 6H), 3.22 (t, J=6.0 Hz, 2H), 3.11 (s, 1H), 2.80 (s, 6H), 2.71-2.49 (m, 6H), 2.42 (s, 3H), 2.25 (s, 3H). (including one salt NH); MS (M+H)$^+$=516.

Example 174. 2-(4-(6-(3,5-dimethylisoxazol-4-yl)-4-(2-phenylpyrrolidin-1-yl)quinazolin-2-yl)piperazin-1-yl)-N,N-dimethylethanamine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 2-phenylpyrrolidine (58.9 mg, 0.40 mmol) for overnight according to similar procedure described in Example 71. $^1$H NMR (400 MHz, DMSO-$d_6$) δ 11.92 (s, 1H), 9.10 (s, 1H), 8.22 (s, 1H), 7.83 (s, 1H), 7.71 (d, J=8.4 Hz, 1H), 7.45-7.07 (m, 5H), 5.41 (s, 1H), 4.63 (s, 1H), 4.30 (s, 1H), 3.57 (s, 3H), 3.20 (s, 2H), 2.78 (s, 6H), 2.68-1.50 (m, 17H). (including two salt NH); MS (M+H)$^+$=526.

Example 175. 2-(4-(6-(3,5-dimethylisoxazol-4-yl)-4-(2-phenylpiperidin-1-yl)quinazolin-2-yl)piperazin-1-yl)-N,N-dimethylethanamine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 2-phenylpiperidine (64.5 mg, 0.40 mmol) for overnight according to similar procedure described in Example 71. MS (M+H)$^+$=540.

Example 176. 2-(4-(6-(3,5-dimethylisoxazol-4-yl)-4-(3-phenylmorpholino)quinazolin-2-yl)piperazin-1-yl)-N,N-dimethylethanamine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 3-phenylmorpholine (65.3 mg, 0.40 mmol) for overnight according to similar procedure described in Example 71. MS (M+H)$^+$=542.

Example 177. N-((1H-imidazol-2-yl)methyl)-4-((3-chlorobenzyl)amino)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 136 mg, 0.15 mmol), HATU (114 mg, 0.30 mmol), and (1H-imidazol-2-yl)methanamine, 2HCl (25.5 mg, 0.15 mmol) according to similar procedure described in Example 165. $^1$H NMR (400 MHz, DMSO-$d_6$) δ 9.51 (s, 1H), 9.32 (s, 1H), 8.33 (s, 1H), 7.95 (d, J=8.6 Hz, 1H), 7.91 (d, J=8.7 Hz, 1H), 7.58 (s, 2H), 7.52-7.46 (m, 1H), 7.38 (dt, J=7.4, 1.7 Hz, 1H), 7.36-7.32 (m, 1H), 7.30 (dt, J=7.8, 1.8 Hz, 1H), 4.99 (d, J=5.7 Hz, 2H), 4.78 (d, J=5.8 Hz, 2H), 2.45 (s, 3H), 2.28 (s, 3H). (one NH not shown); MS (M+H)$^+$=488.

Example 178. N2-((1H-imidazol-2-yl)methyl)-N4-(3-chlorobenzyl)-6-(3,5-dimethylisoxazol-4-yl)quinazoline-2,4-diamine, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and (1H-imidazol-2-yl)methanamine, 2HCl (51.0 mg, 0.30 mmol) according to similar procedure described in Example 12. $^1$H NMR (400 MHz, DMSO-$d_6$) δ 10.09 (s, 1H), 8.72 (s, 1H), 8.23 (s, 1H), 7.85 (s, 1H), 7.61 (s, 1H), 7.44 (s, 2H), 7.36-7.21 (m, 3H), 7.17 (s, 1H), 4.92 (s, 2H), 4.71 (d, J=5.7 Hz, 2H), 2.41 (s, 3H), 2.23 (s, 3H). (one NH not shown); MS (M+H)$^+$=460.

Example 179. 2-(4-(6-(3,5-dimethylisoxazol-4-yl)-4-(2-phenylazetidin-1-yl)quinazolin-2-yl)piperazin-1-yl)-N,N-dimethylethanamine, 2TFA The title compound was prepared from 2-(4-(2-(dimethylamino)ethyl)piperazin-1-yl)-6-(3,5-dimethylisoxazol-4-yl)quinazolin-4-ol, 2HCl (Example 68, 94 mg, 0.2 mmol), bromotri(pyrrolidin-1-yl)phosphonium hexafluorophosphate (186 mg, 0.40 mmol), and 2-phenylazetidine (0.053 g, 0.40 mmol) for overnight according to similar procedure described in Example 71. MS (M+H)$^+$=512.

Example 180. N-(1-(3-chlorophenyl)cyclopropyl)-6-(3,5-dimethylisoxazol-4-yl)-2-(4-(methylsulfonyl)piperazin-1-yl)quinazolin-4-amine, 2TFA The title compound was prepared from 2-chloro-N-(1-(3-chlorophenyl)cyclopropyl)-6-(3,5-dimethylisoxazol-4-yl)quinazolin-4-amine (Example 164, STEP 1, 63.8 mg, 0.15 mmol) and 1-(methylsulfonyl)piperazine, 2HCl (178 mg, 0.75 mmol) according to similar procedure described in Example 12. $^1$H NMR (400 MHz, DMSO-$d_6$) δ 12.13 (s, 1H), 10.20 (s, 1H), 8.27 (s, 1H), 7.83 (s, 1H), 7.70 (s, 1H), 7.36 (t, J=1.9 Hz, 1H), 7.34-7.20 (m, 3H), 3.86 (t, J=4.8 Hz, 4H), 3.13 (d, J=6.0 Hz, 4H), 2.84 (s, 3H), 2.43 (s, 3H), 2.26 (s, 3H), 1.51 (s, 2H), 1.38 (s, 2H). (including one salt NH); MS (M+H)$^+$=553.

Example 181. 2-(4-(4-((1-(3-chlorophenyl)cyclopropyl)amino)-6-(3,5-dimethylisoxazol-4-yl)quinazolin-2-yl)-1H-pyrazol-1-yl)-N-methylacetamide, 2TFA The title compound was prepared from 2-chloro-N-(1-(3-chlorophenyl)cyclopropyl)-6-(3,5-dimethylisoxazol-4-yl)quinazolin-4-amine (Example 164, STEP 1, 42.5 mg, 0.1 mmol), N-methyl-2-(4-(4,4,5,5-tetramethyl-1,3,2-dioxaborolan-2-yl)-1H-pyrazol-1-yl)acetamide (53.0 mg, 0.20 mmol), PdCl$_2$(dppf)-CH$_2$Cl$_2$ adduct (8.17 mg, 10.0 μmol), and K$_2$CO$_3$ (83 mg, 0.60 mmol) according to similar procedure described in Example 28. $^1$H NMR (400 MHz, DMSO-$d_6$) δ 10.47 (s, 1H), 8.53 (s, 1H), 8.41 (s, 1H), 8.17 (s, 1H), 8.11 (s, 1H), 7.97 (s, 1H), 7.86 (d, J=8.6 Hz, 1H), 7.45 (t, J=1.9 Hz, 1H), 7.38 (dt, J=7.8, 1.5 Hz, 1H), 7.31 (t, J=7.8 Hz, 1H), 7.23 (dt, J=8.0, 1.4 Hz, 1H), 4.92 (s, 2H), 2.62 (d, J=4.6 Hz, 3H), 2.47 (s, 3H), 2.30 (s, 3H), 1.59 (s, 2H), 1.45 (s, 2H); MS (M+H)$^+$=528.

Example 182. 1-(4-(4-((1-(3-chlorophenyl)cyclopropyl)amino)-6-(3,5-dimethylisoxazol-4-yl)quinazolin-2-yl)-1H-pyrazol-1-yl)-2-methylpropan-2-ol, 2TFA The title compound was prepared from 2-chloro-N-(1-(3-chlorophenyl)cyclopropyl)-6-(3,5-dimethylisoxazol-4-yl)quinazolin-4-amine (Example 164, STEP 1, 42.5 mg, 0.1 mmol), 2-methyl-1-(4-(4,4,5,5-tetramethyl-1,3,2-dioxaborolan-2-yl)-1H-pyrazol-1-yl)propan-2-ol (53.2 mg, 0.20 mmol), PdCl$_2$(dppf)-CH$_2$Cl$_2$ adduct (8.17 mg, 10.0 μmol), and K$_2$CO$_3$ (83 mg, 0.60 mmol) according to similar procedure described in Example 28. $^1$H NMR (400 MHz, DMSO-$d_6$) δ 10.51 (s, 1H), 8.51 (s, 1H), 8.41 (s, 1H), 8.11 (s, 1H), 7.98 (d, J=8.6 Hz, 1H), 7.86 (d, J=8.6 Hz, 1H), 7.47 (t, J=1.9 Hz, 1H), 7.39 (dt, J=7.8, 1.4 Hz, 1H), 7.31 (t, J=7.8 Hz, 1H), 7.23 (dt, J=8.0, 1.4 Hz, 1H), 4.84 (s, 1H), 4.12 (s, 2H), 2.47 (s, 3H), 2.30 (s, 3H), 1.58 (d, J=5.7 Hz, 2H), 1.45 (d, J=5.4 Hz, 2H), 1.09 (s, 6H); MS (M+H)$^+$=529.

Example 183. 4-((3-chlorobenzyl)amino)-6-(3,5-dimethylisoxazol-4-yl)-N-((1-methyl-1H-imidazol-5-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol, ca. 45% purity), HATU (114 mg, 0.30 mmol), and (1-methyl-1H-imidazol-5-yl)methanamine (22.23 mg, 0.20 mmol) according to similar procedure described in Example 165. $^1$H NMR (400 MHz, DMSO-$d_6$) δ 9.59 (s, 1H), 9.43 (d, J=6.6 Hz, 1H), 9.00 (dd, J=1.6, 0.7 Hz, 1H), 8.34 (d, J=1.8 Hz, 1H), 7.98 (d, J=8.6 Hz, 1H), 7.93 (dd, J=8.6, 1.7 Hz, 1H), 7.55 (d, J=1.5 Hz, 1H), 7.52-7.49 (m, 1H), 7.38 (dt, J=7.2, 1.7 Hz, 1H), 7.36-7.26 (m, 2H), 5.01 (d, J=5.8 Hz, 2H), 4.60 (d, J=5.9 Hz, 2H), 3.85 (s, 3H), 2.45 (s, 3H), 2.28 (s, 3H); MS (M+H)$^+$=502.

Example 184. 1-(4-(4-((3-chlorobenzyl)amino)-6-(3,5-dimethylisoxazol-4-yl)quinazolin-2-yl)piperazin-1-yl)ethanone, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and 1-(piperazin-1-yl)ethanone, 2HCl (101 mg, 0.50 mmol) according to similar procedure described in Example 12. $^1$H NMR (400 MHz, DMSO-$d_6$) δ 11.97 (s, 1H), 10.07 (s, 1H), 8.23 (s, 1H), 7.84 (d, J=8.6 Hz, 1H), 7.73 (d, J=8.6 Hz, 1H), 7.54-7.44 (m, 1H), 7.43-7.26 (m, 3H), 4.81 (d, J=5.6 Hz, 2H), 3.87 (t, J=5.1 Hz, 2H), 3.80 (t, J=5.3 Hz, 2H), 3.55 (s, 4H), 2.43 (s, 3H), 2.25 (s, 3H), 2.04 (s, 3H). (including one salt NH); MS (M+H)$^+$=491.

Example 185. 1-(4-(4-((1-(3-chlorophenyl)cyclopropyl)amino)-6-(3,5-dimethylisoxazol-4-yl)quinazolin-2-yl)piperazin-1-yl)ethanone, 2TFA The title compound was prepared from 2-chloro-N-(1-(3-chlorophenyl)cyclopropyl)-6-(3,5-dimethylisoxazol-4-yl)quinazolin-4-amine (Example 164, STEP 1, 42.5 mg, 0.1 mmol) and 1-(piperazin-1-yl)ethanone, 2HCl (101 mg, 0.50 mmol) according to similar procedure described in Example 12. $^1$H NMR (400 MHz, DMSO-$d_6$) δ 12.02 (s, 1H), 10.16 (s, 1H), 8.27 (s, 1H), 7.82 (s, 1H), 7.71 (s, 1H), 7.42-7.14 (m, 4H), 3.78 (d, J=5.8 Hz, 2H), 3.71 (d, J=5.8 Hz, 2H), 3.48 (s, 4H), 2.43 (s, 3H), 2.26 (s, 3H), 2.02 (s, 3H), 1.50 (d, J=5.6 Hz, 2H), 1.38 (s, 2H). (including one salt NH); MS (M+H)$^+$=517.

Example 186. 4-((3-chlorobenzyl)amino)-6-(3,5-dimethylisoxazol-4-yl)-N-((1-methyl-1H-pyrazol-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (1-methyl-1H-pyrazol-4-yl)methanamine (22.23 mg, 0.20 mmol) according to similar procedure described in Example 165. $^1$H NMR (400 MHz, DMSO-$d_6$) δ 10.10 (s, 1H), 9.49 (s, 1H), 8.38 (d, J=1.8 Hz, 1H), 8.12 (d, J=8.7 Hz, 1H), 8.02 (d, J=8.5 Hz, 1H), 7.59 (s, 1H), 7.52 (q, J=1.2 Hz, 1H), 7.43-7.27 (m, 4H), 5.19-5.08 (m, 2H), 4.35 (d, J=6.2 Hz, 2H), 3.76 (s, 3H), 2.45 (s, 3H), 2.28 (s, 3H); MS (M+H)$^+$=502.

Example 187. 4-((3-chlorobenzyl)amino)-6-(3,5-dimethylisoxazol-4-yl)-N-((4-methylpyridin-3-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (4-methylpyridin-3-yl)methanamine (24.43 mg, 0.20 mmol) according to similar procedure described in Example 165. $^1$H NMR (400 MHz, DMSO-$d_6$) δ 9.83 (s, 1H), 9.58 (s, 1H), 8.60 (s, 1H), 8.56 (d, J=5.5 Hz, 1H), 8.37 (d, J=1.8 Hz, 1H), 8.04 (d, J=8.6 Hz, 1H), 7.97 (dd, J=8.6, 1.7 Hz, 1H), 7.63 (d, J=5.5 Hz, 1H), 7.51 (d, J=2.0 Hz, 1H), 7.43-7.37 (m, 1H), 7.37-7.26 (m, 2H), 5.07 (d, J=5.8 Hz, 2H), 4.63 (d, J=6.0 Hz, 2H), 2.51 (s, 3H), 2.45 (s, 3H), 2.28 (s, 3H); MS (M+H)$^+$=513.

Example 188. 4-((3-chlorobenzyl)amino)-N-((4-chloropyridin-2-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (4-chloropyridin-2-yl)methanamine (28.5 mg, 0.20 mmol) according to similar procedure described in Example 165. $^1$H NMR (400 MHz, DMSO-$d_6$) δ 10.18 (s, 1H), 9.81 (s, 1H), 8.50 (dd, J=5.3, 0.6 Hz, 1H), 8.41 (d, J=1.8 Hz, 1H), 8.14 (d, J=8.7 Hz, 1H), 8.04 (dd, J=8.6, 1.7 Hz, 1H), 7.55 (d, J=2.0 Hz, 1H), 7.48 (d, J=2.0 Hz, 1H), 7.46-7.40 (m, 2H), 7.39-7.29 (m, 2H), 5.17 (d, J=5.8 Hz, 2H), 4.67 (d, J=6.2 Hz, 2H), 2.46 (s, 3H), 2.29 (s, 3H); MS (M+H)$^+$=534.

Example 189. 4-((3-chlorobenzyl)amino)-6-(3,5-dimethylisoxazol-4-yl)-N-(pyridin-3-ylmethyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and pyridin-3-ylmethanamine (21.63 mg, 0.20 mmol) according to similar procedure described in Example 165. $^1$H NMR (400 MHz, DMSO-$d_6$) δ 9.95 (s, 1H), 9.71 (s, 1H), 8.70-8.60 (m, 1H), 8.58-8.49 (m, 1H), 8.37 (d, J=1.8 Hz, 1H), 8.08 (d, J=8.7 Hz, 1H), 8.00 (dd, J=8.6, 1.7 Hz, 1H), 7.88 (d, J=7.9 Hz, 1H), 7.53 (d, J=2.0 Hz, 1H), 7.48 (dd, J=7.9, 4.9 Hz, 1H), 7.41 (dt, J=6.8, 2.0 Hz, 1H), 7.38-7.26 (m, 2H), 5.11 (d, J=5.8 Hz, 2H), 4.60 (d, J=6.3 Hz, 2H), 2.45 (s, 3H), 2.28 (s, 3H); MS (M+H)$^+$=499.

Example 190. 4-((3-chlorobenzyl)amino)-N-((1,5-dimethyl-1H-pyrazol-4-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (1,5-dimethyl-1H-pyrazol-4-yl)methanamine (25.03 mg, 0.20 mmol) according to similar procedure described in Example 165. $^1$H NMR (400 MHz, DMSO-$d_6$) δ 10.22 (s, 1H), 9.45 (s, 1H), 8.39 (d, J=1.8 Hz, 1H), 8.13 (d, J=8.7 Hz, 1H), 8.03 (dd, J=8.7, 1.7 Hz, 1H), 7.52 (q, J=1.4 Hz, 1H), 7.43-7.31 (m, 3H), 7.30 (s, 1H), 5.15 (d, J=5.8 Hz, 2H), 4.30 (d, J=6.1 Hz, 2H), 3.66 (s, 3H), 2.45 (s, 3H), 2.27 (s, 3H), 2.25 (s, 3H); MS (M+H)$^+$=516.

Example 191. 4-((3-chlorobenzyl)amino)-N-((5-chloropyridin-3-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (5-chloropyridin-3-yl)methanamine (28.5 mg, 0.20 mmol) according to similar procedure described in Example 165. ¹H NMR (400 MHz, DMSO-d$_6$) δ 10.12 (s, 1H), 9.76 (s, 1H), 8.55 (d, J=1.8 Hz, 1H), 8.53 (d, J=2.4 Hz, 1H), 8.39 (d, J=1.8 Hz, 1H), 8.11 (d, J=8.7 Hz, 1H), 8.02 (dd, J=8.6, 1.7 Hz, 1H), 7.87 (t, J=2.1 Hz, 1H), 7.54 (d, J=2.1 Hz, 1H), 7.42 (dt, J=6.8, 2.0 Hz, 1H), 7.38-7.28 (m, 2H), 5.15 (d, J=5.7 Hz, 2H), 4.60 (d, J=6.3 Hz, 2H), 2.45 (s, 3H), 2.28 (s, 3H); MS (M+H)$^+$=534.

Example 192. 4-((3-chlorobenzyl)amino)-6-(3,5-dimethylisoxazol-4-yl)-N-((5-fluoropyridin-3-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (5-fluoropyridin-3-yl)methanamine (25.2 mg, 0.20 mmol) according to similar procedure described in Example 165. ¹H NMR (400 MHz, DMSO-d$_6$) δ 10.19 (s, 1H), 9.80 (s, 1H), 8.48 (d, J=2.6 Hz, 2H), 8.40 (d, J=1.8 Hz, 1H), 8.13 (d, J=8.7 Hz, 1H), 8.04 (dd, J=8.7, 1.7 Hz, 1H), 7.72-7.61 (m, 1H), 7.55 (d, J=2.1 Hz, 1H), 7.42 (dt, J=6.6, 2.3 Hz, 1H), 7.38-7.29 (m, 2H), 5.16 (d, J=5.7 Hz, 2H), 4.63 (d, J=6.3 Hz, 2H), 2.45 (s, 3H), 2.28 (s, 3H); MS (M+H)$^+$=517.

Example 193. 4-((3-chlorobenzyl)amino)-6-(3,5-dimethylisoxazol-4-yl)-N-((5-methylpyridin-3-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (5-methylpyridin-3-yl)methanamine (24.43 mg, 0.20 mmol) according to similar procedure described in Example 165. ¹H NMR (400 MHz, DMSO-d$_6$) δ 9.96 (s, 1H), 9.71 (s, 1H), 8.51 (d, J=2.0 Hz, 1H), 8.45 (s, 1H), 8.38 (d, J=1.8 Hz, 1H), 8.08 (d, J=8.7 Hz, 1H), 8.00 (dd, J=8.7, 1.7 Hz, 1H), 7.85 (s, 1H), 7.53 (d, J=2.1 Hz, 1H), 7.41 (dt, J=6.8, 2.2 Hz, 1H), 7.38-7.28 (m, 2H), 5.12 (d, J=5.8 Hz, 2H), 4.60 (d, J=6.2 Hz, 2H), 2.45 (s, 3H), 2.33 (s, 3H), 2.28 (s, 3H); MS (M+H)$^+$=513.

Example 194. 4-((3-chlorobenzyl)amino)-6-(3,5-dimethylisoxazol-4-yl)-N-((1,3,5-trimethyl-1H-pyrazol-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 91 mg, 0.1 mmol), HATU (114 mg, 0.30 mmol), and (1,3,5-trimethyl-1H-pyrazol-4-yl)methanamine (27.8 mg, 0.20 mmol) according to similar procedure described in Example 165. ¹H NMR (400 MHz, DMSO-d$_6$) δ 9.07 (t, J=6.0 Hz, 1H), 8.55 (t, J=5.8 Hz, 1H), 8.27 (d, J=1.7 Hz, 1H), 7.88 (d, J=8.6 Hz, 1H), 7.84 (dd, J=8.6, 1.7 Hz, 1H), 7.43 (q, J=1.3 Hz, 1H), 7.34-7.24 (m, 3H), 4.87 (d, J=5.8 Hz, 2H), 4.20 (d, J=5.8 Hz, 2H), 3.58 (s, 3H), 2.45 (s, 3H), 2.28 (s, 3H), 2.18 (s, 3H), 2.07 (s, 3H); MS (M+H)$^+$=530.

Example 195. 1-(4-(4-(((5-chloropyridin-3-yl)methyl)amino)-6-(3,5-dimethylisoxazol-4-yl)quinazolin-2-yl)piperazin-1-yl)ethanone, 2TFA The title compound was prepared from 2-chloro-N-((5-chloropyridin-3-yl)methyl)-6-(3,5-dimethylisoxazol-4-yl)quinazolin-4-amine (Example 112, 66.7 mg, 0.1 mmol) and 1-(piperazin-1-yl)ethanone, 2HCl (101 mg, 0.50 mmol) according to similar procedure described in Example 12. ¹H NMR (400 MHz, DMSO-d$_6$) δ 11.93 (s, 1H), 10.05 (s, 1H), 8.61 (d, J=1.9 Hz, 1H), 8.54 (d, J=2.3 Hz, 1H), 8.20 (s, 1H), 7.98 (t, J=2.2 Hz, 1H), 7.84 (d, J=8.7 Hz, 1H), 7.73 (d, J=8.6 Hz, 1H), 4.86 (d, J=5.5 Hz, 2H), 3.86 (s, 2H), 3.79 (d, J=6.0 Hz, 2H), 3.55 (s, 4H), 2.43 (s, 3H), 2.25 (s, 3H), 2.04 (s, 3H). (including one salt NH); MS (M+H)$^+$=492.

Example 196. 4-((3-chlorobenzyl)amino)-6-(3,5-dimethylisoxazol-4-yl)-N-((2-methylthiazol-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (2-methylthiazol-4-yl)methanamine (19.23 mg, 0.15 mmol), and HATU (86 mg, 0.225 mmol) according to similar procedure described in Example 165. ¹H NMR (400 MHz, DMSO-d$_6$) δ 10.19 (s, 1H), 9.67 (s, 1H), 8.41 (d, J=1.8 Hz, 1H), 8.13 (d, J=8.7 Hz, 1H), 8.03 (dd, J=8.7, 1.7 Hz, 1H), 7.53 (q, J=1.4 Hz, 1H), 7.41 (dt, J=6.6, 2.2 Hz, 1H), 7.37-7.30 (m, 2H), 7.21 (d, J=1.0 Hz, 1H), 5.16 (d, J=5.8 Hz, 2H), 4.63-4.53 (m, 2H), 2.61 (s, 3H), 2.46 (s, 3H), 2.28 (s, 3H); MS (M+H)$^+$=519.

Example 197. 4-((3-chlorobenzyl)amino)-6-(3,5-dimethylisoxazol-4-yl)-N-((6-methylpyridin-3-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (6-methylpyridin-3-yl)methanamine (18.33 mg, 0.15 mmol), and HATU (86 mg, 0.225 mmol) according to similar procedure described in Example 165. ¹H NMR (400 MHz, DMSO-d$_6$) δ 9.95 (s, 1H), 9.71 (s, 1H), 8.63 (s, 1H), 8.38 (d, J=1.9 Hz, 1H), 8.07 (d, J=8.6 Hz, 2H), 7.99 (d, J=8.3 Hz, 1H), 7.60 (d, J=8.1 Hz, 1H), 7.53 (d, J=2.0 Hz, 1H), 7.43-7.27 (m, 3H), 5.10 (d, J=5.7 Hz, 2H), 4.61 (d, J=6.2 Hz, 2H), 2.57 (s, 3H), 2.45 (s, 3H), 2.28 (s, 3H); MS (M+H)$^+$=513.

Example 198. 4-((3-chlorobenzyl)amino)-6-(3,5-dimethylisoxazol-4-yl)-N-(1-methylazetidin-3-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 1-methylazetidin-3-amine (12.92 mg, 0.15 mmol), and HATU (86 mg, 0.225 mmol) according to similar procedure described in Example 165. ¹H NMR (400 MHz, DMSO-d$_6$) δ 9.62 (s, 1H), 9.37 (d, J=7.2 Hz, 1H), 9.31 (s, 1H), 8.33 (d, J=1.9 Hz, 1H), 7.95 (d, J=8.6 Hz, 1H), 7.90 (dd, J=8.6, 1.7 Hz, 1H), 7.51 (d, J=1.7 Hz, 1H), 7.43-7.27 (m, 3H), 4.96 (t, J=6.8 Hz, 2H), 4.91-4.68 (m, 1H), 4.50-4.41 (m, 2H), 4.24-4.12 (m, 2H), 2.90 (d, J=5.0 Hz, 3H), 2.46 (s, 3H), 2.29 (s, 3H). (including one salt NH); MS (M+H)$^+$=477.

Example 199. N-(1-acetylpiperidin-4-yl)-4-((3-chlorobenzyl)amino)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 1-(4-aminopiperidin-1-yl)ethanone (21.33 mg, 0.15 mmol), and HATU (86 mg, 0.225 mmol) according to similar procedure described in Example 165. $^1$H NMR (400 MHz, DMSO-d$_6$) δ 10.16 (s, 1H), 8.75 (d, J=8.3 Hz, 1H), 8.39 (d, J=1.8 Hz, 1H), 8.11 (d, J=8.7 Hz, 1H), 8.02 (dd, J=8.7, 1.7 Hz, 1H), 7.56 (d, J=1.9 Hz, 1H), 7.46-7.29 (m, 3H), 5.10 (d, J=5.7 Hz, 2H), 4.37 (d, J=13.3 Hz, 1H), 4.15-4.02 (m, 1H), 3.83 (d, J=14.0 Hz, 1H), 3.22-3.08 (m, 1H), 2.67 (td, J=11.9, 10.4, 3.0 Hz, 1H), 2.46 (s, 3H), 2.28 (s, 3H), 2.00 (s, 3H), 1.87-1.45 (m, 4H); MS (M+H)$^+$=533.

Example 200. 4-((3-chlorobenzyl)amino)-6-(3,5-dimethylisoxazol-4-yl)-N-((1-methylazetidin-3-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (1-methylazetidin-3-yl)methanamine (15.02 mg, 0.15 mmol), and HATU (86 mg, 0.225 mmol) according to similar procedure described in Example 165. $^1$H NMR (400 MHz, DMSO-d$_6$) δ 9.64 (br s, 2H), 9.14 (s, 1H), 8.34 (t, J=2.3 Hz, 1H), 7.99 (d, J=8.3 Hz, 1H), 7.93 (d, J=8.6 Hz, 1H), 7.52 (t, J=1.7 Hz, 1H), 7.45-7.25 (m, 3H), 5.03 (d, J=6.0 Hz, 2H), 4.18 (ddd, J=11.2, 8.7, 6.3 Hz, 1H), 4.09 (dt, J=12.2, 6.4 Hz, 1H), 3.92 (td, J=11.2, 10.1, 5.0 Hz, 1H), 3.78 (ddd, J=11.0, 8.8, 6.6 Hz, 1H), 3.57 (t, J=6.5 Hz, 1H), 3.51 (t, J=6.1 Hz, 1H), 3.12-2.92 (m, 1H), 2.81 (d, J=5.2 Hz, 1.5H), 2.72 (d, J=5.1 Hz, 1.5H), 2.45 (s, 3H), 2.28 (s, 3H). (including one salt NH); MS (M+H)$^+$=491.

Example 201. 4-((3-chlorobenzyl)amino)-6-(3,5-dimethylisoxazol-4-yl)-N-(1-(methylsulfonyl)piperidin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 1-(methylsulfonyl)piperidin-4-amine (26.7 mg, 0.15 mmol), and HATU (86 mg, 0.225 mmol) according to similar procedure described in Example 165. $^1$H NMR (400 MHz, DMSO-d$_6$) δ 9.87 (s, 1H), 8.72 (s, 1H), 8.37 (d, J=1.8 Hz, 1H), 8.05 (d, J=8.4 Hz, 1H), 7.97 (d, J=8.7 Hz, 1H), 7.55 (d, J=1.8 Hz, 1H), 7.41 (dt, J=7.5, 1.6 Hz, 1H), 7.36 (t, J=7.6 Hz, 1H), 7.32 (dt, J=7.8, 1.9 Hz, 1H), 5.05 (s, 2H), 4.01-3.87 (m, 1H), 3.59 (d, J=11.7 Hz, 2H), 2.90-2.83 (m, 5H), 2.46 (s, 3H), 2.29 (s, 3H), 1.93-1.67 (m, 4H); MS (M+H)$^+$=569.

Example 202. 4-((3-chlorobenzyl)amino)-N-((2-chloropyridin-4-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (2-chloropyridin-4-yl)methanamine (21.39 mg, 0.15 mmol), and HATU (86 mg, 0.225 mmol) according to similar procedure described in Example 165. $^1$H NMR (400 MHz, DMSO-d$_6$) δ 10.01 (d, J=16.4 Hz, 1H), 9.71 (s, 1H), 8.39 (d, J=1.8 Hz, 1H), 8.34 (dd, J=5.1, 0.6 Hz, 1H), 8.09 (d, J=8.7 Hz, 1H), 8.00 (dd, J=8.6, 1.7 Hz, 1H), 7.54 (d, J=2.0 Hz, 1H), 7.45-7.28 (m, 5H), 5.12 (d, J=5.8 Hz, 2H), 4.59 (d, J=6.3 Hz, 2H), 2.46 (s, 3H), 2.28 (s, 3H); MS (M+H)$^+$=534.

Example 203. 4-((3-chlorobenzyl)amino)-N-((6-chloropyridin-3-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (6-chloropyridin-3-yl)methanamine (21.39 mg, 0.15 mmol), and HATU (86 mg, 0.225 mmol) according to similar procedure described in Example 165. $^1$H NMR (400 MHz, DMSO-d$_6$) δ 9.85 (s, 1H), 9.64 (s, 1H), 8.40 (dd, J=2.5, 0.7 Hz, 1H), 8.37 (d, J=1.8 Hz, 1H), 8.05 (d, J=8.7 Hz, 1H), 8.01-7.92 (m, 1H), 7.80 (dd, J=8.2, 2.5 Hz, 1H), 7.53 (d, J=2.0 Hz, 1H), 7.48 (dd, J=8.2, 0.7 Hz, 1H), 7.43-7.27 (m, 3H), 5.08 (d, J=5.7 Hz, 2H), 4.55 (d, J=6.3 Hz, 2H), 2.45 (s, 3H), 2.28 (s, 3H); MS (M+H)$^+$=534.

Example 204. 4-((3-chlorobenzyl)amino)-6-(3,5-dimethylisoxazol-4-yl)-N-(1,1-dioxidotetrahydro-2H-thiopyran-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 4-aminotetrahydro-2H-thiopyran 1,1-dioxide (22.38 mg, 0.15 mmol), and HATU (86 mg, 0.225 mmol) according to similar procedure described in Example 165. $^1$H NMR (400 MHz, DMSO-d$_6$) δ 10.05 (s, 1H), 8.93 (d, J=8.5 Hz, 1H), 8.38 (d, J=1.8 Hz, 1H), 8.09 (d, J=8.7 Hz, 1H), 8.00 (dd, J=8.7, 1.8 Hz, 1H), 7.56 (t, J=1.8 Hz, 1H), 7.42 (dt, J=7.4, 1.6 Hz, 1H), 7.37 (t, J=7.6 Hz, 1H), 7.33 (dt, J=7.9, 1.8 Hz, 1H), 5.18-4.96 (m, 2H), 4.32-4.18 (m, 1H), 3.39 (td, J=13.6, 3.5 Hz, 2H), 3.14-3.03 (m, 2H), 2.46 (s, 3H), 2.32-2.23 (m, 5H), 2.08 (d, J=12.5 Hz, 2H); MS (M+H)$^+$=540.

Example 205. 4-((3-chlorobenzyl)amino)-N-((1,3-dimethyl-1H-pyrazol-4-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), HATU (86 mg, 0.225 mmol), and (1,3-dimethyl-1H-pyrazol-4-yl)methanamine (18.78 mg, 0.15 mmol) according to similar procedure described in Example 165. $^1$H NMR (400 MHz, DMSO-d$_6$) δ 10.20 (s, 1H), 9.40 (s, 1H), 8.39 (d, J=1.8 Hz, 1H), 8.13 (d, J=8.7 Hz, 1H), 8.03 (dd, J=8.6, 1.8 Hz, 1H), 7.52 (q, J=1.4 Hz, 1H), 7.47 (s, 1H), 7.42-7.30 (m, 3H), 5.14 (d, J=5.8 Hz, 2H), 4.31 (d, J=6.0 Hz, 2H), 3.68 (s, 3H), 2.45 (s, 3H), 2.28 (s, 3H), 2.13 (s, 3H); MS (M+H)$^+$=516.

Example 206. 4-(((5-chloropyridin-3-yl)methyl)amino)-N-((2-chloropyridin-4-yl)methyl)-6-(3,5-dimethylisoxazol-4-yl)quinazoline-2-carboxamide, 2TFA Step 1. 4-(((5-chloropyridin-3-yl)methyl)amino)-6-(3,5-dimethylisoxazol-4-yl)quinazoline-2-carboxylic acid 4-(((5-Chloropyridin-3-yl)methyl)amino)-6-(3,5-dimethylisoxazol-4-yl)quinazoline-2-carboxylic acid was prepared from ethyl 6-bromo-4-hydroxyquinazoline-2-carboxylate and (5-chloropyridin-3-yl)methylamine according to a similar procedure described in Example 163.

Step 2. 4-(((5-chloropyridin-3-yl)methyl)amino)-N-((2-chloropyridin-4-yl)methyl)-6-(3,5-dimethylisoxazol-4-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (30.7 mg, 0.075 mmol), (2-chloropyridin-4-yl)methanamine (21.39 mg, 0.15 mmol), and HATU (86 mg, 0.225 mmol) according to similar procedure described in Example 165. $^1$H NMR (400 MHz, DMSO-d$_6$) δ 10.03 (d, J=8.5 Hz, 1H), 9.74 (s, 1H), 8.66 (d, J=1.9 Hz, 1H), 8.53 (d, J=2.4 Hz, 1H), 8.38-8.33 (m, 2H), 8.10 (d, J=8.6 Hz, 1H), 8.06-7.97 (m, 2H), 7.47-7.40 (m, 1H), 7.34 (dt, J=5.1, 1.2 Hz, 1H), 5.15 (d, J=5.7 Hz, 2H), 4.60 (d, J=6.3 Hz, 2H), 2.45 (s, 3H), 2.28 (s, 3H); MS (M+H)$^+$=535.

Example 207. 4-(((5-chloropyridin-3-yl)methyl)amino)-6-(3,5-dimethylisoxazol-4-yl)-N-(Pyridin-4-ylmethyl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), pyridin-4-ylmethanamine (16.22 mg, 0.15 mmol), and HATU (86 mg, 0.225 mmol) according to similar procedure described in Example 165. $^1$H NMR (400 MHz, DMSO-d$_6$) δ 9.97 (s, 1H), 9.79 (s, 1H), 8.72-8.67 (m, 2H), 8.66 (d, J=1.9 Hz, 1H), 8.54 (d, J=2.4 Hz, 1H), 8.36 (d, J=1.9 Hz, 1H), 8.08 (d, J=8.7 Hz, 1H), 8.04 (t, J=2.1 Hz, 1H), 8.00 (dd, J=8.6, 1.7 Hz, 1H), 7.67 (d, J=5.6 Hz, 2H), 5.13 (d, J=5.8 Hz, 2H), 4.71 (d, J=6.3 Hz, 2H), 2.46 (s, 3H), 2.28 (s, 3H); MS (M+H)$^+$=500.

Example 208. 4-((3-chlorobenzyl)amino)-N-((3-chloropyridin-4-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3-chloropyridin-4-yl)methanamine, 2HCl (32.3 mg, 0.15 mmol), and HATU (86 mg, 0.225 mmol) according to similar procedure described in Example 165. $^1$H NMR (400 MHz, DMSO-d$_6$) δ 10.09 (s, 1H), 9.73 (s, 1H), 8.62 (s, 1H), 8.46 (d, J=5.0 Hz, 1H), 8.41 (d, J=1.8 Hz, 1H), 8.11 (d, J=8.6 Hz, 1H), 8.02 (dd, J=8.6, 1.7 Hz, 1H), 7.55 (d, J=2.0 Hz, 1H), 7.42 (dt, J=7.0, 1.8 Hz, 1H), 7.39-7.30 (m, 3H), 5.14 (d, J=5.8 Hz, 2H), 4.63 (d, J=6.2 Hz, 2H), 2.46 (s, 3H), 2.29 (s, 3H); MS (M+H)$^+$=534.

Example 209. 4-(((5-chloropyridin-3-yl)methyl)amino)-6-(3,5-dimethylisoxazol-4-yl)-N-(1-methylpiperidin-4-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), 1-methylpiperidin-4-amine (17.13 mg, 0.15 mmol), and HATU (86 mg, 0.225 mmol) according to similar procedure described in Example 165. $^1$H NMR (400 MHz, DMSO-d$_6$) δ 9.55 (s, 1H), 9.28 (s, 1H), 8.75 (d, J=8.0 Hz, 1H), 8.65 (d, J=1.8 Hz, 1H), 8.51 (d, J=2.4 Hz, 1H), 8.30 (d, J=1.8 Hz, 1H), 8.02 (t, J=2.1 Hz, 1H), 7.98 (d, J=8.6 Hz, 1H), 7.92 (dd, J=8.7, 1.7 Hz, 1H), 4.98 and 4.94 (two set of d, J=5.6 Hz, 2H), 4.07-3.53 (m, 1H), 3.49-3.30 (m, 2H), 3.22-3.02 (m, 2H), 2.83 and 2.77 (two set of d, J=4.8 Hz, 3H), 2.45 (s, 3H), 2.28 (s, 3H), 2.15-1.77 (m, 4H). (2 rotamers and including 1 salt NH); MS (M+H)$^+$=506.

Example 210. N-(3-chlorobenzyl)-6-(3,5-dimethylisoxazol-4-yl)-2-(1-(methylsulfonyl)-1,2,3,6-tetrahydropyridin-4-yl)quinazolin-4-amine, 2TFA To a suspension of N-(3-chlorobenzyl)-6-(3,5-dimethylisoxazol-4-yl)-2-(1,2,3,6-tetrahydropyridin-4-yl)quinazolin-4-amine, HCl (Example 31, 48.2 mg, 0.1 mmol) in CH$_2$Cl$_2$ (3 mL) was added Et$_3$N (0.139 mL, 1.0 mmol) and then methanesulfonyl chloride (34.4 mg, 0.30 mmol). The mixture was stirred at rt for 2 h. The mixture was poured into EtOAc/H$_2$O/Na$_2$CO$_3$ (aq) (10 mL/5 mL/5 mL). The organic layer was dried over Na$_2$SO$_4$, filtered and concentrated. The residue was dissolved in DMF, filtered, and purified to give N-(3-chlorobenzyl)-6-(3,5-dimethylisoxazol-4-yl)-2-(1-(methylsulfonyl)-1,2,3,6-tetrahydropyridin-4-yl)quinazolin-4-amine, 2TFA (9.3 mg, 0.012 mmol, 12.4% yield). $^1$H NMR (400 MHz, DMSO-d$_6$) δ 8.32 (s, 1H), 7.91 (s, 2H), 7.52-7.48 (m, 1H), 7.40-7.27 (m, 3H), 7.23 (s, 1H), 4.90 (d, J=4.4 Hz, 2H), 4.05-3.96 (m, 2H), 3.37 (t, J=5.7 Hz, 2H), 2.94 (s, 3H), 2.72 (d, J=6.9 Hz, 2H), 2.45 (s, 3H), 2.28 (s, 3H). (NH is very broad at ca. 9.80 ppm); MS (M+H)$^+$=524.

Example 211. 4-((3-chlorobenzyl)amino)-6-(3,5-dimethylisoxazol-4-yl)-N-methyl-N-(1-methylpiperidin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), N,1-dimethylpiperidin-4-amine (19.23 mg, 0.15 mmol), and HATU (86 mg, 0.225 mmol) according to similar procedure described in Example 165. MS (M+H)$^+$=519.

Example 212. 4-((3-chlorobenzyl)amino)-6-(3,5-dimethylisoxazol-4-yl)-N-((2-methylthiazol-5-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (2-methylthiazol-5-yl)methanamine (19.23 mg, 0.15 mmol), and HATU (86 mg, 0.225 mmol) according to similar procedure described in Example 165. $^1$H NMR (400 MHz, DMSO-d$_6$) δ 10.21 (s, 1H), 9.79 (s, 1H), 8.40 (d, J=1.8 Hz, 1H), 8.13 (d, J=8.7 Hz, 1H), 8.03 (dd, J=8.6, 1.7 Hz, 1H), 7.57-7.49 (m, 2H), 7.45-7.28 (m, 3H), 5.15 (d, J=5.8 Hz, 2H), 4.66 (d, J=6.2 Hz, 2H), 2.58 (s, 3H), 2.45 (s, 3H), 2.27 (s, 3H); MS (M+H)$^+$=519.

Example 213. 4-((3-chlorobenzyl)amino)-6-(3,5-dimethylisoxazol-4-yl)-N-((5-methylthiazol-2-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (5-methylthiazol-2-yl)methanamine (19.23 mg, 0.15 mmol), and HATU (86 mg, 0.225 mmol) according to similar procedure described in Example 165. $^1$H NMR (400 MHz, DMSO-d$_6$) δ 10.02 (s, 1H), 9.89 (s, 1H), 8.39 (d, J=1.8 Hz, 1H), 8.10 (d, J=8.7 Hz, 1H), 8.01 (dd, J=8.6, 1.7 Hz, 1H), 7.53 (d, J=2.0 Hz, 1H), 7.45-7.27 (m, 4H), 5.14 (d, J=5.8 Hz, 2H), 4.73 (d, J=6.3 Hz, 2H), 2.46 (s, 3H), 2.38 (d, J=1.3 Hz, 3H), 2.28 (s, 3H); MS (M+H)$^+$=519.

Example 214. 4-((3-chlorobenzyl)amino)-6-(3,5-dimethylisoxazol-4-yl)-N-((4-methylthiazol-2-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (4-methylthiazol-2-yl)methanamine (19.23 mg, 0.15 mmol), and HATU (86 mg, 0.225 mmol) according to similar procedure described in Example 165. ¹H NMR (400 MHz, DMSO-d₆) δ 10.04 (s, 1H), 9.92 (s, 1H), 8.39 (d, J=1.8 Hz, 1H), 8.10 (d, J=8.7 Hz, 1H), 8.01 (dd, J=8.7, 1.7 Hz, 1H), 7.53 (q, J=1.4, 0.8 Hz, 1H), 7.42 (dt, J=7.1, 1.8 Hz, 1H), 7.39-7.28 (m, 2H), 7.17 (q, J=1.0 Hz, 1H), 5.15 (d, J=5.8 Hz, 2H), 4.77 (d, J=6.3 Hz, 2H), 2.45 (s, 3H), 2.32 (d, J=1.0 Hz, 3H), 2.28 (s, 3H); MS (M+H)⁺=519.

Example 215. 4-((3-chlorobenzyl)amino)-6-(3,5-dimethylisoxazol-4-yl)-N-((3-fluoropyridin-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3-fluoropyridin-4-yl)methanamine (18.92 mg, 0.15 mmol), and HATU (86 mg, 0.225 mmol) according to similar procedure described in Example 165. ¹H NMR (400 MHz, DMSO-d₆) δ 10.20 (s, 1H), 9.77 (s, 1H), 8.54 (d, J=1.7 Hz, 1H), 8.41 (d, J=1.8 Hz, 1H), 8.37 (dd, J=4.9, 1.1 Hz, 1H), 8.13 (d, J=8.7 Hz, 1H), 8.04 (dd, J=8.7, 1.7 Hz, 1H), 7.55 (d, J=2.0 Hz, 1H), 7.45-7.29 (m, 4H), 5.17 (d, J=5.8 Hz, 2H), 4.65 (d, J=6.2 Hz, 2H), 2.46 (s, 3H), 2.28 (s, 3H); MS (M+H)⁺=517.

Example 216. 4-((3-chlorobenzyl)amino)-6-(3,5-dimethylisoxazol-4-yl)-N-((5-methyloxazol-2-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (5-methyloxazol-2-yl)methanamine (16.82 mg, 0.15 mmol), and HATU (86 mg, 0.225 mmol) according to similar procedure described in Example 165. ¹H NMR (400 MHz, DMSO-d₆) δ 9.98 (s, 1H), 9.67 (s, 1H), 8.39 (d, J=1.8 Hz, 1H), 8.09 (d, J=8.6 Hz, 1H), 8.00 (dd, J=8.6, 1.7 Hz, 1H), 7.53 (d, J=2.0 Hz, 1H), 7.42 (dt, J=7.1, 1.7 Hz, 1H), 7.39-7.22 (m, 2H), 6.76 (q, J=1.2 Hz, 1H), 5.13 (d, J=5.7 Hz, 2H), 4.58 (d, J=6.1 Hz, 2H), 2.45 (s, 3H), 2.28 (s, 3H), 2.24 (d, J=1.3 Hz, 3H); MS (M+H)⁺=503.

Example 217. 4-((3-chlorobenzyl)amino)-6-(3,5-dimethylisoxazol-4-yl)-N-((3-methylpyridin-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3-methylpyridin-4-yl)methanamine (18.33 mg, 0.15 mmol), and HATU (86 mg, 0.225 mmol) according to similar procedure described in Example 165. ¹H NMR (400 MHz, DMSO-d₆) δ 9.85 (s, 1H), 9.68 (s, 1H), 8.61 (s, 1H), 8.55 (d, J=5.7 Hz, 1H), 8.39 (d, J=1.8 Hz, 1H), 8.06 (d, J=8.6 Hz, 1H), 7.99 (dd, J=8.6, 1.7 Hz, 1H), 7.59-7.47 (m, 2H), 7.41 (dt, J=7.2, 1.7 Hz, 1H), 7.39-7.28 (m, 2H), 5.10 (d, J=5.8 Hz, 2H), 4.66 (d, J=6.1 Hz, 2H), 2.46 (s, 3H), 2.43 (s, 3H), 2.29 (s, 3H); MS (M+H)⁺=513.

Example 218. 4-((3-chlorobenzyl)amino)-6-(3,5-dimethylisoxazol-4-yl)-N-(2-methylpyridin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 2-methylpyridin-4-amine (16.22 mg, 0.15 mmol), and HATU (86 mg, 0.225 mmol) according to similar procedure described in Example 165. ¹H NMR (400 MHz, DMSO-d₆) δ 11.51 (s, 1H), 9.32 (t, J=5.9 Hz, 1H), 8.66 (d, J=6.7 Hz, 1H), 8.37 (d, J=1.8 Hz, 1H), 8.27 (d, J=2.2 Hz, 1H), 8.22 (dd, J=6.8, 2.3 Hz, 1H), 8.01 (d, J=8.6 Hz, 1H), 7.94 (dd, J=8.6, 1.8 Hz, 1H), 7.53 (t, J=1.9 Hz, 1H), 7.41 (dt, J=7.5, 1.5 Hz, 1H), 7.34 (t, J=7.7 Hz, 1H), 7.29 (dt, J=7.9, 1.7 Hz, 1H), 4.96 (d, J=5.7 Hz, 2H), 2.66 (s, 3H), 2.47 (s, 3H), 2.31 (s, 3H); MS (M+H)⁺=499.

Example 219. 4-((3-chlorobenzyl)amino)-6-(3,5-dimethylisoxazol-4-yl)-N-(6-methylpyridin-3-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 6-methylpyridin-3-amine (16.22 mg, 0.15 mmol), and HATU (86 mg, 0.225 mmol) according to similar procedure described in Example 165. ¹H NMR (400 MHz, DMSO-d₆) δ 10.90 (s, 1H), 9.55 (s, 1H), 9.03 (d, J=2.5 Hz, 1H), 8.38 (d, J=1.9 Hz, 2H), 8.04 (d, J=8.6 Hz, 1H), 7.96 (dd, J=8.6, 1.8 Hz, 1H), 7.60-7.53 (m, 2H), 7.42 (dt, J=7.5, 1.5 Hz, 1H), 7.35 (t, J=7.7 Hz, 1H), 7.30 (ddd, J=7.9, 2.1, 1.4 Hz, 1H), 5.05 (d, J=5.7 Hz, 2H), 2.55 (s, 3H), 2.47 (s, 3H), 2.30 (s, 3H); MS (M+H)⁺=499.

Example 220. 4-((3-chlorobenzyl)amino)-6-(3,5-dimethylisoxazol-4-yl)-N-(4-methylpyridin-3-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 4-methylpyridin-3-amine (16.22 mg, 0.15 mmol), and HATU (86 mg, 0.225 mmol) according to similar procedure described in Example 165. ¹H NMR (400 MHz, DMSO-d₆) δ 10.62 (s, 1H), 9.77 (s, 1H), 8.95 (s, 1H), 8.47 (d, J=5.3 Hz, 1H), 8.41 (d, J=1.9 Hz, 1H), 8.08 (d, J=8.6 Hz, 1H), 7.99 (dd, J=8.6, 1.8 Hz, 1H), 7.61 (d, J=5.3 Hz, 1H), 7.54 (d, J=1.8 Hz, 1H), 7.41 (dt, J=7.4, 1.6 Hz, 1H), 7.36 (t, J=7.5 Hz, 1H), 7.32 (dt, J=7.8, 1.8 Hz, 1H), 5.10 (d, J=5.8 Hz, 2H), 2.47 (s, 3H), 2.33 (s, 3H), 2.31 (s, 3H); MS (M+H)⁺=499.

Example 221. 4-((3-chlorobenzyl)amino)-6-(3,5-dimethylisoxazol-4-yl)-N-(5-fluoropyridin-3-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 5-fluoropyridin-3-amine (16.82 mg, 0.15 mmol), and HATU (86 mg, 0.225 mmol) according to similar procedure described in Example 165. ¹H NMR (400 MHz, DMSO-d₆) δ 10.80 (s, 1H), 9.58 (s, 1H), 8.65 (dd, J=2.9, 1.3 Hz, 1H), 8.44-8.35 (m, 2H), 8.05 (d, J=8.6 Hz, 1H), 7.96 (dd, J=8.6, 1.8 Hz, 1H), 7.56 (t, J=1.9 Hz, 1H), 7.43 (dt, J=7.5, 1.5 Hz, 1H), 7.36 (t, J=7.7 Hz, 1H), 7.30 (ddd, J=7.9, 2.1, 1.4 Hz, 1H), 7.25 (dd, J=8.8, 3.2 Hz, 1H), 5.07 (d, J=5.7 Hz, 2H), 2.47 (s, 3H), 2.30 (s, 3H); MS (M+H)⁺=503.

Example 222. 4-((3-chlorobenzyl)amino)-N-(6-chloropyridin-3-yl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 6-chloropyridin-3-amine (19.28 mg, 0.15 mmol), and HATU (86 mg, 0.225 mmol) according to similar procedure described in Example 165. $^1$H NMR (400 MHz, DMSO-$d_6$) δ 10.80 (s, 1H), 9.38 (s, 1H), 8.94-8.76 (m, 1H), 8.36 (d, J=1.8 Hz, 1H), 8.34 (dd, J=8.7, 2.8 Hz, 1H), 8.01 (d, J=8.6 Hz, 1H), 7.93 (dd, J=8.6, 1.8 Hz, 1H), 7.58-7.52 (m, 2H), 7.42 (dt, J=7.6, 1.5 Hz, 1H), 7.35 (t, J=7.7 Hz, 1H), 7.29 (ddd, J=7.9, 2.1, 1.3 Hz, 1H), 5.01 (d, J=5.7 Hz, 2H), 2.47 (s, 3H), 2.30 (s, 3H); MS (M+H)$^+$=520.

Example 223. 4-((3-chlorobenzyl)amino)-6-(3,5-dimethylisoxazol-4-yl)-N-(3-fluoropyridin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 3-fluoropyridin-4-amine (16.82 mg, 0.15 mmol), and HATU (86 mg, 0.225 mmol) according to similar procedure described in Example 165. MS (M+H)$^+$=503.

Example 224. 4-((3-chlorobenzyl)amino)-6-(3,5-dimethylisoxazol-4-yl)-N-(2,6-dimethylpyridin-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 0.031 g, 0.075 mmol), 2,6-dimethylpyridin-4-amine (0.018 g, 0.15 mmol), and HATU (0.086 g, 0.225 mmol) according to similar procedure described in Example 165. $^1$H NMR (400 MHz, DMSO-$d_6$) δ 11.43 (s, 1H), 9.32 (t, J=5.9 Hz, 1H), 8.36 (d, J=1.8 Hz, 1H), 8.09 (s, 2H), 8.00 (d, J=8.6 Hz, 1H), 7.94 (dd, J=8.6, 1.8 Hz, 1H), 7.53 (t, J=1.9 Hz, 1H), 7.41 (dt, J=7.5, 1.5 Hz, 1H), 7.37-7.26 (m, 2H), 4.95 (d, J=5.7 Hz, 2H), 2.64 (s, 6H), 2.47 (s, 3H), 2.30 (s, 3H); MS (M+H)$^+$=513.

Example 225. 4-((3-chlorobenzyl)amino)-6-(3,5-dimethylisoxazol-4-yl)-N-(1-methyl-1H-pyrazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 1-methyl-1H-pyrazol-4-amine (14.57 mg, 0.15 mmol), and HATU (86 mg, 0.225 mmol) according to similar procedure described in Example 165. $^1$H NMR (400 MHz, DMSO-$d_6$) δ 10.84 (s, 1H), 9.94 (s, 1H), 8.40 (d, J=1.8 Hz, 1H), 8.12-8.10 (m, 2H), 8.00 (dd, J=8.6, 1.7 Hz, 1H), 7.72 (d, J=0.7 Hz, 1H), 7.56 (t, J=1.9 Hz, 1H), 7.43 (dt, J=7.5, 1.5 Hz, 1H), 7.37 (t, J=7.6 Hz, 1H), 7.32 (dt, J=8.0, 1.6 Hz, 1H), 5.17 (d, J=5.7 Hz, 2H), 3.84 (s, 3H), 2.46 (s, 3H), 2.29 (s, 3H); MS (M+H)$^+$=488.

Example 226. 4-((3-chlorobenzyl)amino)-6-(3,5-dimethylisoxazol-4-yl)-N-(tetrahydro-2H-pyran-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), tetrahydro-2H-pyran-4-amine (15.17 mg, 0.15 mmol), and HATU (86 mg, 0.225 mmol) according to similar procedure described in Example 165. $^1$H NMR (400 MHz, DMSO-$d_6$) δ 10.01 (s, 1H), 8.70 (s, 1H), 8.38 (d, J=1.8 Hz, 1H), 8.08 (d, J=8.7 Hz, 1H), 7.99 (dd, J=8.6, 1.7 Hz, 1H), 7.55 (t, J=1.8 Hz, 1H), 7.41 (dt, J=7.4, 1.6 Hz, 1H), 7.36 (t, J=7.5 Hz, 1H), 7.32 (dt, J=7.8, 1.8 Hz, 1H), 5.07 (d, J=5.6 Hz, 2H), 4.03 (q, J=7.5 Hz, 1H), 3.88 (dt, J=11.6, 3.4 Hz, 2H), 3.40 (ddd, J=14.1, 8.1, 4.3 Hz, 2H), 2.46 (s, 3H), 2.29 (s, 3H), 1.73 (td, J=10.5, 9.3, 3.8 Hz, 4H); MS (M+H)$^+$=492.

Example 227. 4-((3-chlorobenzyl)amino)-6-(1-methyl-6-oxo-1,6-dihydropyridin-3-yl)-N-(1-methylpiperidin-4-yl)quinoline-2-carboxamide, 2TFA Step 1: 6-bromo-4-chloro-N-(1-methylpiperidin-4-yl)quinoline-2-carboxamide To a mixture of 6-bromo-4-chloroquinoline-2-carboxylic acid (573 mg, 2 mmol) and HATU (1141 mg, 3.0 mmol) was added 1-methylpiperidin-4-amine (343 mg, 3.0 mmol) in DMF (6 mL) and then added Hunig's base (0.524 mL, 3.0 mmol). The mixture was stirred at rt for 2 h. The mixture was dropped into a stirred H$_2$O (150 mL). The resulting solid was filtered and washed with H$_2$O (2×5 mL) and then dried to give 6-bromo-4-chloro-N-(1-methylpiperidin-4-yl)quinoline-2-carboxamide (587 mg, 1.534 mmol, 77% yield). MS (M+H)$^+$=383.

Step 2: 6-bromo-4-((3-chlorobenzyl)amino)-N-(1-methylpiperidin-4-yl)quinoline-2-carboxamide To a solution of 6-bromo-4-chloro-N-(1-methylpiperidin-4-yl)quinoline-2-carboxamide (153 mg, 0.4 mmol) in DMF (1 mL) was added (3-chlorophenyl)methanamine (283 mg, 2.0 mmol). The tube was sealed and heated at 165° C. for 1 h under microwave irradiation. The mixture was poured into EtOAc/H$_2$O (50 mL/50 mL). The aqueous layer was washed with H$_2$O (50 mL), dried over Na$_2$SO$_4$, and filtered. After removal of the solvent, the product was purified by silica gel chromatography using 10-40% MeOH/EtOAc as the eluent to give 6-bromo-4-((3-chlorobenzyl)amino)-N-(1-methylpiperidin-4-yl)quinoline-2-carboxamide (~50% purity). The material was used without further purification.

Step 3: 4-((3-chlorobenzyl)amino)-6-(1-methyl-6-oxo-1,6-dihydropyridin-3-yl)-N-(1-methylpiperidin-4-yl)quinoline-2-carboxamide, 2TFA In a 2-neck flask was placed 6-bromo-4-((3-chlorobenzyl)amino)-N-(1-methylpiperidin-4-yl)quinoline-2-carboxamide (146 mg, 0.15 mmol-50% purity), 1-methyl-5-(4,4,5,5-tetramethyl-1,3,2-dioxaborolan-2-yl)pyridin-2(1H)-one (70.5 mg, 0.30 mmol), PdCl$_2$(dppf)-CH$_2$Cl$_2$ adduct (12.25 mg, 0.015 mmol), and K$_2$CO$_3$ (124 mg, 0.90 mmol). The air was removed and re-filled with N$_2$ (2-3 times). Then a mixture of 1,4-dioxane (1.5 mL) and water (0.5 mL) was added and stirred at 85° C. (pre-heated) for 1.5 h. After cooling to rt, the organic layer was separated and extracted with EtOAc (2×2 mL). The combined organic layer was dried over Na$_2$SO$_4$ and filtered. After removal of the solvent, the product was filtered through a PL-Thiol MP resin and eluted with MeOH. The filtrate was concentrated, re-dissolved in DMF, filtered, and then purified to give 4-((3-chlorobenzyl)amino)-6-(1-methyl-6-oxo-1,6-dihydropyridin-3-yl)-N-(1-methylpiperidin-4-yl)quinoline-2-carboxamide, 2TFA (26.7 mg, 0.036 mmol, 23.92% yield). $^1$H NMR (400 MHz, DMSO-$d_6$) δ 9.41 (s, 1H), 9.00 (s, 1H), 8.58 (s, 1H), 8.34 (d, J=2.7 Hz, 1H), 8.19-8.00 (m, 3H), 7.50 (s, 1H), 7.40-7.31 (m, 3H), 7.20 (s, 1H), 6.59 (d, J=9.5 Hz, 1H), 4.79 (s, 2H), 4.08-3.94 (m, 1H), 3.54 (s, 3H), 3.47 (d, J=12.2 Hz, 2H), 3.10 (q, J=11.2 Hz, 2H), 2.76 (d, J=4.6 Hz, 3H), 2.08-1.75 (m, 4H); MS (M+H)$^+$=516.

Example 228. 4-((3-chlorobenzyl)amino)-6-(3,5-dimethylisoxazol-4-yl)-N-(1-methylpiperidin-4-yl)quinoline-2-carboxamide, 2TFA Step 1: methyl 6-bromo-4-((3-chlorobenzyl)amino)quinoline-2-carboxylate To a suspension of methyl 6-bromo-4-oxo-1,4-dihydroquinoline-2-carboxylate (846 mg, 3 mmol) and bromotri(pyrrolidin-1-yl)phosphonium hexafluorophosphate (2098 mg, 4.50 mmol) in 1,4-dioxane (25 ml) was added Et$_3$N (1.254 ml, 9.0 mmol). The mixture was stirred at rt for 3 h and then (3-chlorophenyl)methanamine (850 mg, 6.0 mmol) was added. The mixture was stirred at rt for 2 h The reaction was then heated to 60-65° C. for overnight. Then the reaction then was heated to 95-100° C. for another 24 h. The mixture was poured into EtOAc/H$_2$O (50 mL/50 mL). The organic layer was washed with H$_2$O (30 mL), dried over Na$_2$SO$_4$, and filtered. After removal of the solvent, the product was purified by silica gel chromatography using 20-70% EtOAc/hexane as the eluent to give product. The product was triturated with 5% EtOAc/hexane and dried to give methyl 6-bromo-4-((3-chlorobenzyl)amino)quinoline-2-carboxylate (571 mg, 1.408 mmol, 46.9% yield). MS (M+H)$^+$=406.

Step 2: methyl 4-((3-chlorobenzyl)amino)-6-(3,5-dimethylisoxazol-4-yl)quinoline-2-carboxylate In a 2-neck flask was placed methyl 6-bromo-4-((3-chlorobenzyl)amino)quinoline-2-carboxylate (0.487 g, 1.2 mmol), 3,5-dimethyl-4-(4,4,5,5-tetramethyl-1,3,2-dioxaborolan-2-yl)isoxazole (0.402 g, 1.80 mmol), PdCl$_2$(dppf)-CH$_2$Cl$_2$ adduct (0.098 g, 0.12 mmol), and K$_2$CO$_3$ (0.746 g, 5.40 mmol). The air was removed and the flask was re-filled with N$_2$ (twice). Then a mixture of 1,4-dioxane (6 ml) and water (2 ml) was added and stirred at 80° C. (pre-heated) for 1.5 h. After cooling to rt, the layer was separated and the aqueous layer was extracted with EtOAc (3×5 mL). The combined organic layer was dried over Na$_2$SO$_4$ and filtered through PL-Thiol MP resin and eluted with EtOAc. The filtrate was concentrated to give crude methyl 4-((3-chlorobenzyl)amino)-6-(3,5-dimethylisoxazol-4-yl)quinoline-2-carboxylate. The material was used for next step without further purification. MS (M+H)$^+$=422.

Step 3: 4-((3-chlorobenzyl)amino)-6-(3,5-dimethylisoxazol-4-yl)quinoline-2-carboxylic acid To a suspension of methyl 4-((3-chlorobenzyl)amino)-6-(3,5-dimethylisoxazol-4-yl)quinoline-2-carboxylate (506 mg, 1.2 mmol) (crude from STEP 2) in THF (5 mL) and MeOH (1 mL) was added 1N NaOH (aq) (4.8 mL, 4.8 mmol, 4 equiv). The mixture was heated at 50° C. for 2 h. After cooling to rt, 1N HCl (aq) was added slowly until the pH of aqueous layer was ~3. Then hexane (30 mL) was slowly added. The solvent was removed and the product was dried in vacuo for 1 h. The solid was stirred in 5% EtOAc/hexane for 30 min and filtered. The product was dried to give 4-((3-chlorobenzyl)amino)-6-(3,5-dimethylisoxazol-4-yl)quinoline-2-carboxylic acid (470 mg, 1.152 mmol, 96% yield) as a yellow-brown solid. MS (M+H)$^+$=408.

Step 4: 4-((3-chlorobenzyl)amino)-6-(3,5-dimethylisoxazol-4-yl)-N-(1-methylpiperidin-4-yl)quinoline-2-carboxamide, 2TFA The title compound was prepared from 4-((3-chlorobenzyl)amino)-6-(3,5-dimethylisoxazol-4-yl)quinoline-2-carboxylic acid (30.6 mg, 0.075 mmol), 1-methylpiperidin-4-amine (17.13 mg, 0.15 mmol), and HATU (86 mg, 0.225 mmol) according to similar procedure described in Example 165. $^1$H NMR (400 MHz, DMSO-d$_6$) δ 9.31 (s, 1H), 8.93 (s, 1H), 8.37 (s, 1H), 8.13 (s, 1H), 7.83 (s, 1H), 7.46 (s, 1H), 7.42-7.28 (m, 3H), 7.16 (s, 1H), 4.73 (s, 2H), 4.00 (d, J=7.7 Hz, 1H), 3.46 (d, J=12.3 Hz, 2H), 3.16-3.01 (m, 2H), 2.76 (d, J=4.6 Hz, 3H), 2.47 (s, 3H), 2.30 (s, 3H), 2.07-1.76 (m, 4H); MS (M+H)$^+$=504.

Example 229. 4-(((5-chloropyridin-3-yl)methyl)amino)-6-(3,5-dimethylisoxazol-4-yl)-N-(tetrahydro-2H-pyran-4-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), tetrahydro-2H-pyran-4-amine (7.59 mg, 0.075 mmol), and HATU (86 mg, 0.225 mmol) according to similar procedure described in Example 165. $^1$H NMR (400 MHz, DMSO-d$_6$) δ 10.07 (s, 1H), 8.75 (d, J=8.3 Hz, 1H), 8.66 (d, J=1.8 Hz, 1H), 8.53 (d, J=2.4 Hz, 1H), 8.35 (d, J=1.8 Hz, 1H), 8.10 (d, J=8.7 Hz, 1H), 8.04 (t, J=2.1 Hz, 1H), 8.00 (dd, J=8.6, 1.7 Hz, 1H), 5.11 (d, J=5.7 Hz, 2H), 4.04 (quint, J=7.7 Hz, 1H), 3.89 (dt, J=11.5, 3.4 Hz, 2H), 3.41 (ddd, J=11.6, 7.6, 5.5 Hz, 2H), 2.46 (s, 3H), 2.28 (s, 3H), 1.77-1.71 (m, 4H); MS (M+H)$^+$=493.

Example 230. 4-((3-chlorobenzyl)amino)-N-((1,3-dimethyl-1H-pyrazol-4-yl)methyl)-6-(3,5-dimethylisoxazol-4-yl)quinoline-2-carboxamide, 2TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), (1,3-dimethyl-1H-pyrazol-4-yl)methanamine (18.78 mg, 0.15 mmol), and HATU (86 mg, 0.225 mmol) according to similar procedure described in Example 228. $^1$H NMR (400 MHz, DMSO-d$_6$) δ 9.90-9.20 (br s, 2H), 8.44 (s, 1H), 8.29 (s, 1H), 7.97 (s, 1H), 7.51 (d, J=14.8 Hz, 2H), 7.37 (tt, J=5.2, 3.1 Hz, 4H), 4.85 (s, 2H), 4.33 (d, J=5.4 Hz, 2H), 3.69 (s, 3H), 2.46 (s, 3H), 2.29 (s, 3H), 2.11 (s, 3H); MS (M+H)$^+$=515.

Example 231. 4-((3-chlorobenzyl)amino)-6-(3,5-dimethylisoxazol-4-yl)-N-((1-methylazetidin-3-yl)methyl)quinoline-2-carboxamide, 2TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), (1-methylazetidin-3-yl)methanamine (7.51 mg, 0.075 mmol), and HATU (86 mg, 0.225 mmol) according to similar procedure described in Example 228. $^1$H NMR (400 MHz, DMSO-d$_6$) δ 9.60 (s, 1H), 9.26 (s, 1H), 8.38 (s, 1H), 8.13 (s, 1H), 7.85 (s, 1H), 7.47 (s, 1H), 7.42-7.28 (m, 3H), 7.19 (s, 1H), 4.75 (s, 2H), 4.18 (ddd, J=10.9, 8.5, 6.2 Hz, 1H), 4.06 (dt, J=12.3, 6.4 Hz, 1H), 3.92 (td, J=10.0, 5.0 Hz, 1H), 3.78 (dt, J=11.0, 8.6 Hz, 1H), 3.56 (t, J=6.4 Hz, 1H), 3.52 (t, J=6.1 Hz, 1H), 3.10-2.91 (m, 1H), 2.80 and 2.75

(two set of d, J=5.2 Hz, 3H, due to the conformation of azetidine), 2.47 (s, 3H), 2.30 (s, 3H); MS (M+H)⁺=490.

Example 232. 4-(((5-chloropyridin-3-yl)methyl)amino)-6-(3,5-dimethylisoxazol-4-yl)-N-((1-methyl-1H-imidazol-5-yl)methyl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), (1-methyl-1H-imidazol-5-yl)methanamine (16.67 mg, 0.15 mmol), and HATU (86 mg, 0.225 mmol) according to similar procedure described in Example 165. $^1$H NMR (400 MHz, DMSO-$d_6$) δ 9.64 (s, 1H), 9.47 (s, 1H), 9.01 (d, J=1.7 Hz, 1H), 8.64 (d, J=1.8 Hz, 1H), 8.51 (d, J=2.4 Hz, 1H), 8.31 (d, J=1.8 Hz, 1H), 8.04-7.91 (m, 3H), 7.55 (d, J=1.5 Hz, 1H), 5.03 (d, J=5.7 Hz, 2H), 4.61 (d, J=5.9 Hz, 2H), 3.85 (s, 3H), 2.45 (s, 3H), 2.28 (s, 3H); MS (M+H)⁺=503.

Example 233. 4-(((5-chloropyridin-3-yl)methyl)amino)-6-(3,5-dimethylisoxazol-4-yl)-N-((1-methylazetidin-3-yl)methyl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), (1-methylazetidin-3-yl)methanamine (7.51 mg, 0.075 mmol), HATU (86 mg, 0.225 mmol) according to similar procedure described in Example 165. $^1$H NMR (400 MHz, DMSO-$d_6$) δ 9.65 (s, 1H), 9.24 (s, 1H), 8.66 (t, J=1.4 Hz, 1H), 8.56-8.52 (m, 1H), 8.33 (dd, J=3.6, 1.8 Hz, 1H), 8.09-7.85 (m, 3H), 5.07 (t, J=7.0 Hz, 2H), 4.19 (ddd, J=11.1, 8.6, 6.2 Hz, 1H), 4.10 (dt, J=12.2, 6.4 Hz, 1H), 3.94 (td, J=11.3, 10.2, 5.0 Hz, 1H), 3.84-3.73 (m, 1H), 3.59 (t, J=6.5 Hz, 1H), 3.53 (t, J=6.2 Hz, 1H), 3.13-2.95 (m, 1H), 2.82 and 2.74 (2 set of d, J=5.1 Hz, 3H, due to the conformation of azetidine), 2.45 (s, 3H), 2.28 (s, 3H) (a small set of rotamer was not reported); MS (M+H)⁺=492.

Example 234. 4-((3-chlorobenzyl)amino)-6-(3,5-dimethylisoxazol-4-yl)-N-(1-methylazetidin-3-yl)quinoline-2-carboxamide, 2TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), 1-methylazetidin-3-amine (6.46 mg, 0.075 mmol), and HATU (86 mg, 0.225 mmol) according to similar procedure described in Example 228. $^1$H NMR (400 MHz, DMSO-$d_6$) δ 9.54 (s, 2H), 8.39-8.31 (m, 1H), 8.07 (d, J=8.7 Hz, 1H), 7.80 (d, J=8.6 Hz, 1H), 7.44 (d, J=2.1 Hz, 1H), 7.40-7.26 (m, 3H), 7.09 (s, 1H), 4.81 (tt, J=16.4, 8.1 Hz, 1H), 4.69 (s, 2H), 4.42 (dq, J=16.1, 8.3, 7.5 Hz, 2H), 4.23-4.10 (m, 2H), 2.89 (d, J=4.8 Hz, 3H), 2.48 (s, 3H), 2.31 (s, 3H); MS (M+H)⁺=476.

Example 235. 4-((3-chlorobenzyl)amino)-6-(3,5-dimethylisoxazol-4-yl)-N-(1,1-dioxidotetrahydro-2H-thiopyran-4-yl)quinoline-2-carboxamide, 2TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), 4-aminotetrahydro-2H-thiopyran 1,1-dioxide (11.19 mg, 0.075 mmol), and HATU (86 mg, 0.225 mmol) according to similar procedure described in Example 228. $^1$H NMR (400 MHz, DMSO-$d_6$) δ 10.00-9.50 (br s, 1H), 9.08 (s, 1H), 8.43 (s, 1H), 8.24 (s, 1H), 7.94 (s, 1H), 7.51 (s, 1H), 7.44-7.33 (m, 3H), 7.30 (s, 1H), 4.83 (s, 2H), 4.24 (q, J=7.6 Hz, 1H), 3.37 (dt, J=14.5, 8.2 Hz, 2H), 3.18-3.03 (m, 2H), 2.47 (s, 3H), 2.29 (s, 3H), 2.15 (td, J=8.5, 3.1 Hz, 4H); MS (M+H)⁺=539.

Example 236. 4-((3-chlorobenzyl)amino)-6-(3,5-dimethylisoxazol-4-yl)-N-(tetrahydro-2H-pyran-4-yl)quinoline-2-carboxamide, 2TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), tetrahydro-2H-pyran-4-amine (7.59 mg, 0.075 mmol), and HATU (86 mg, 0.225 mmol) according to similar procedure described in Example 228. $^1$H NMR (400 MHz, DMSO-$d_6$) δ 10.00-9.46 (br s, 2H), 8.97 (s, 1H), 8.42 (s, 1H), 8.24 (s, 1H), 7.93 (s, 1H), 7.51 (s, 1H), 7.45-7.15 (m, 4H), 4.84 (s, 2H), 4.03 (d, J=6.3 Hz, 1H), 3.94-3.83 (m, 2H), 3.40 (td, J=11.8, 2.1 Hz, 2H), 2.47 (s, 3H), 2.30 (s, 3H), 1.86-1.75 (m, 2H), 1.70-1.53 (m, 2H). (including 1 salt NH); MS (M+H)⁺=491.

Example 237. 4-(((5-chloropyridin-3-yl)methyl)amino)-6-(3,5-dimethylisoxazol-4-yl)-N-(1-methylazetidin-3-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), 1-methylazetidin-3-amine (6.46 mg, 0.075 mmol), and HATU (86 mg, 0.225 mmol) according to similar procedure described in Example 165. $^1$H NMR (400 MHz, DMSO-$d_6$) δ 9.62 (s, 1H), 9.40 (d, J=7.6 Hz, 2H), 8.66 (d, J=1.8 Hz, 1H), 8.52 (d, J=2.4 Hz, 1H), 8.29 (q, J=2.4 Hz, 1H), 8.04 (q, J=2.3 Hz, 1H), 7.99-7.87 (m, 2H), 4.97 (dd, J=12.1, 5.6 Hz, 2H), 4.78 (q, J=8.1 Hz, 1H), 4.51-4.42 (m, 2H), 4.24-4.12 (m, 2H), 2.91 (d, J=5.0 Hz, 3H), 2.45 (s, 3H), 2.28 (s, 3H). (including one salt NH); MS (M+H)⁺=478.

Example 238. 4-(((5-chloropyridin-3-yl)methyl)amino)-N-((1,3-dimethyl-1H-pyrazol-4-yl)methyl)-6-(3,5-dimethylisoxazol-4-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), (1,3-dimethyl-1H-pyrazol-4-yl)methanamine (18.78 mg, 0.15 mmol), HATU (86 mg, 0.225 mmol) according to similar procedure described in Example 165. $^1$H NMR (400 MHz, DMSO-$d_6$) δ 10.32 (s, 1H), 9.51 (s, 1H), 8.65 (d, J=1.8 Hz, 1H), 8.55 (d, J=2.4 Hz, 1H), 8.37 (d, J=1.8 Hz, 1H), 8.15 (d, J=8.7 Hz, 1H), 8.05 (dd, J=8.6, 1.7 Hz, 1H), 8.01 (t, J=2.2 Hz, 1H), 7.47 (s, 1H), 5.20 (d, J=5.8 Hz, 2H), 4.32 (d, J=6.1 Hz, 2H), 3.68 (s, 3H), 2.45 (s, 3H), 2.27 (s, 3H), 2.13 (s, 3H); MS (M+H)⁺=517.

Example 239. 4-(((5-chloropyridin-3-yl)methyl)amino)-6-(3,5-dimethylisoxazol-4-yl)-N-(1,1-dioxidotetrahydro-2H-thiopyran-4-yl)quinazoline-2-carboxamide, 2TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), 4-aminotetrahydro-2H-thiopyran 1,1-dioxide (11.19 mg, 0.075 mmol), HATU (86 mg, 0.225 mmol) according to similar procedure described in Example 165. $^1$H NMR (400 MHz, DMSO-d$_6$) δ 10.11 (s, 1H), 8.96 (d, J=8.6 Hz, 1H), 8.67 (d, J=1.8 Hz, 1H), 8.53 (d, J=2.4 Hz, 1H), 8.35 (d, J=1.9 Hz, 1H), 8.11 (d, J=8.7 Hz, 1H), 8.05 (t, J=2.1 Hz, 1H), 8.01 (dd, J=8.7, 1.7 Hz, 1H), 5.14 (d, J=5.7 Hz, 2H), 4.31-4.20 (m, 1H), 3.39 (td, J=13.7, 3.6 Hz, 2H), 3.17-2.99 (m, 2H), 2.45 (s, 3H), 2.36-2.21 (m, 2H), 2.28 (s, 3H), 2.10-2.06 (m, 2H); MS (M+H)$^+$=541.

Example 240. 4-((1-(3-chlorophenyl)cyclopropyl)amino)-6-(3,5-dimethylisoxazol-4-yl)-N-((1-methylazetidin-3-yl)methyl)quinazoline-2-carboxamide, 2TFA Step 1. 4-((1-(3-chlorophenyl)cyclopropyl)amino)-6-(3,5-dimethylisoxazol-4-yl)quinazoline-2-carboxylic acid 4-((1-(3-Chlorophenyl)cyclopropyl)amino)-6-(3,5-dimethylisoxazol-4-yl)quinazoline-2-carboxylic acid was prepared from ethyl 6-bromo-4-hydroxyquinazoline-2-carboxylate and 1-(3-chlorophenyl)cyclopropan-1-amine according to a similar procedure described in Example 163.

Step 2. 4-((1-(3-chlorophenyl)cyclopropyl)amino)-6-(3,5-dimethylisoxazol-4-yl)-N-((1-methylazetidin-3-yl)methyl)quinazoline-2-carboxamide, 2TFA The title compound was prepared from 4-((1-(3-chlorophenyl)cyclopropyl)amino)-6-(3,5-dimethylisoxazol-4-yl)quinazoline-2-carboxylic acid (32.6 mg, 0.075 mmol), (1-methylazetidin-3-yl)methanamine (7.51 mg, 0.075 mmol), HATU (86 mg, 0.225 mmol) according to similar procedure described in Example 165. $^1$H NMR (400 MHz, DMSO-d$_6$) δ 9.54 (s, 1H), 9.45 (d, J=11.1 Hz, 1H), 8.56-8.44 (m, 1H), 8.36 (dd, J=3.8, 1.7 Hz, 1H), 7.90 (dtt, J=8.6, 4.3, 1.9 Hz, 2H), 7.43 (dt, J=8.4, 1.9 Hz, 1H), 7.39-7.25 (m, 2H), 7.22 (dq, J=7.6, 1.7 Hz, 1H), 4.14 (ddd, J=11.1, 8.6, 6.1 Hz, 1H), 4.01 (dt, J=12.3, 6.4 Hz, 1H), 3.89 (td, J=11.2, 10.1, 5.0 Hz, 1H), 3.75-3.40 (m, 3H), 3.05-2.88 (m, 1H), 2.81 and 2.70 (2 set of d, J=5.1 Hz, 3H), 2.47 (s, 3H), 2.30 (s, 3H), 1.58-1.33 (m, 4H). (including one salt NH); MS (M+H)$^+$=517.

Example 241. 4-(4-(((5-chloropyridin-3-yl)methyl)amino)-6-(3,5-dimethylisoxazol-4-yl)quinazolin-2-yl)thiomorpholine 1,1-dioxide, 2TFA The title compound was prepared from 2-chloro-N-((5-chloropyridin-3-yl)methyl)-6-(3,5-dimethylisoxazol-4-yl)quinazolin-4-amine (Example 112, 20.01 mg, 0.05 mmol) and thiomorpholine 1,1-dioxide, 2HCl (52.0 mg, 0.25 mmol) according to similar procedure described in Example 12. $^1$H NMR (400 MHz, DMSO-d$_6$) δ 12.16 (s, 1H), 10.15 (s, 1H), 8.59 (d, J=1.8 Hz, 1H), 8.54 (d, J=2.3 Hz, 1H), 8.19 (s, 1H), 7.96 (d, J=2.2 Hz, 1H), 7.80 (s, 1H), 7.75-7.55 (m, 1H), 4.83 (s, 2H), 4.22 (d, J=5.6 Hz, 4H), 3.18 (s, 4H), 2.42 (s, 3H), 2.25 (s, 3H). (including one salt NH); MS (M+H)$^+$=499.

Example 242. 4-((1-(3-chlorophenyl)cyclopropyl)amino)-6-(3,5-dimethylisoxazol-4-yl)-N-(1-methylazetidin-3-yl)quinazoline-2-carboxamide, 2TFA The title compound was prepared from 4-((1-(3-chlorophenyl)cyclopropyl)amino)-6-(3,5-dimethylisoxazol-4-yl)quinazoline-2-carboxylic acid (Example 240, STEP 1, 32.6 mg, 0.075 mmol), 1-methylazetidin-3-amine (6.46 mg, 0.075 mmol), and HATU (86 mg, 0.225 mmol) according to similar procedure described in Example 165. $^1$H NMR (400 MHz, DMSO-d$_6$) δ 9.58 and 9.51 (2 set of br s, 1H), 9.32 (d, J=4.4 Hz, 1H), 9.13 (dd, J=19.8, 7.2 Hz, 1H), 8.35 (t, J=2.1 Hz, 1H), 7.96-7.84 (m, 2H), 7.45 (dt, J=4.4, 1.9 Hz, 1H), 7.35 (ddt, J=6.9, 3.9, 1.4 Hz, 1H), 7.27 (td, J=7.8, 1.3 Hz, 1H), 7.20 (ddd, J=7.8, 2.1, 1.1 Hz, 1H), 4.75 (q, J=8.2 Hz, 1H), 4.42-4.40 (m, 2H), 4.21-4.08 (m, 2H), 2.89-2.86 (m, 3H), 2.47 (s, 3H), 2.30 (s, 3H), 1.48-1.32 (m, 4H). (including one salt NH); MS (M+H)$^+$=503.

Example 243. 4-(4-((3-chlorobenzyl)amino)-6-(3,5-dimethylisoxazol-4-yl)quinazolin-2-yl)thiomorpholine 1,1-dioxide, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and thiomorpholine 1,1-dioxide, 2HCl (104 mg, 0.500 mmol) under microwave irradiation according to similar procedure described in Example 12. $^1$H NMR (400 MHz, DMSO-d$_6$) δ 12.15 (br s, 1H), 10.15 (br s, 1H), 8.21 (s, 1H), 7.84 (d, J=29.6 Hz, 1H), 7.66 (s, 1H), 7.46 (s, 1H), 7.42-7.28 (m, 3H), 4.77 (s, 2H), 4.21 (br s, 4H), 3.18 (s, 4H), 2.42 (s, 3H), 2.25 (s, 3H). (including 1 salt NH); MS (M+H)$^+$=498.

Example 244. 4-(4-((3-chlorobenzyl)amino)-6-(3,5-dimethylisoxazol-4-yl)quinazolin-2-yl)-N,N-dimethylpiperazine-1-carboxamide, 2TFA The title compound was prepared from 2-chloro-N-(3-chlorobenzyl)-6-(3,5-dimethylisoxazol-4-yl)quinazolin-4-amine (Example 1, 39.9 mg, 0.1 mmol) and N,N-dimethylpiperazine-1-carboxamide, 2HCl (115 mg, 0.50 mmol) under microwave irradiation according to similar procedure described in Example 12. $^1$H NMR (400 MHz, DMSO-d$_6$) δ 11.91 (s, 1H), 10.06 (s, 1H), 8.22 (s, 1H), 7.82 (s, 1H), 7.73 (s, 1H), 7.49 (q, J=1.3 Hz, 1H), 7.38-7.28 (m, 3H), 4.80 (d, J=5.6 Hz, 2H), 3.82 (br s, 4H), 3.22 (br s, 4H), 2.76 (s, 6H), 2.43 (s, 3H), 2.25 (s, 3H). (including 1 salt NH); MS (M+H)$^+$=520.

Example 245. 4-((1-(3-chlorophenyl)cyclopropyl)amino)-N-((1,3-dimethyl-1H-pyrazol-4-yl)methyl)-6-(3,5-dimethylisoxazol-4-yl)quinazoline-2-carboxamide, 2TFA The title compound was prepared from 4-((1-(3-chlorophenyl)cyclopropyl)amino)-6-(3,5-dimethylisoxazol-4-yl)quinazoline-2-carboxylic acid (Example 240, STEP 1, 32.6 mg, 0.075 mmol), (1,3-dimethyl-1H-pyrazol-4-yl)methanamine (18.78 mg, 0.15 mmol), and HATU (86 mg, 0.225 mmol) according to similar procedure described in Example 165. $^1$H NMR (400 MHz, DMSO-d$_6$) δ 9.93 (s, 1H), 8.41 (d, J=1.8 Hz, 1H), 8.18 (t, J=5.9 Hz, 1H), 8.03 (d, J=8.7 Hz, 1H), 7.97 (dd, J=8.6, 1.7 Hz, 1H), 7.40 (s, 1H), 7.32-7.31 (m, 1H), 7.19 (d, J=1.4 Hz, 3H), 4.24 (d, J=5.8 Hz, 2H), 3.70 (s, 3H), 2.47 (s, 3H), 2.30 (s, 3H), 2.03 (s, 3H), 1.53-1.36 (m, 4H); MS (M+H)$^+$=542.

Example 246. 4-((1-(3-chlorophenyl)cyclopropyl)amino)-6-(3,5-dimethylisoxazol-4-yl)-N-(1,1-dioxidotetrahydro-2H-thiopyran-4-yl)quinazoline-2-carboxamide, 2TFA The title compound was prepared from 4-((1-(3-chlorophenyl)cyclopropyl)amino)-6-(3,5-dimethylisoxazol-4-yl)

quinazoline-2-carboxylic acid (Example 240, STEP 1, 32.6 mg, 0.075 mmol), 4-aminotetrahydro-2H-thiopyran 1,1-dioxide (11.19 mg, 0.075 mmol), and HATU (86 mg, 0.225 mmol) according to similar procedure described in Example 165. $^1$H NMR (400 MHz, DMSO-$d_6$) δ 9.67 (s, 1H), 8.38 (d, J=1.8 Hz, 1H), 8.03 (d, J=8.0 Hz, 1H), 7.98 (d, J=8.6 Hz, 1H), 7.92 (dd, J=8.6, 1.8 Hz, 1H), 7.39 (t, J=1.9 Hz, 1H), 7.36-7.26 (m, 2H), 7.22 (dt, J=6.9, 2.1 Hz, 1H), 4.13-4.00 (m, 1H), 3.39-3.24 (m, 2H), 3.09-2.92 (m, 2H), 2.47 (s, 3H), 2.30 (s, 3H), 2.12-1.88 (m, 4H), 1.58-1.47 (m, 2H), 1.40 (d, J=5.7 Hz, 2H); MS (M+H)$^+$=566.

Example 247. 4-((1-(3-chlorophenyl)cyclopropyl) amino)-6-(3,5-dimethylisoxazol-4-yl)-N-(tetrahydro-2H-pyran-4-yl)quinazoline-2-carboxamide, 2TFA The title compound was prepared from 4-((1-(3-chlorophenyl)cyclopropyl)amino)-6-(3,5-dimethylisoxazol-4-yl) quinazoline-2-carboxylic acid (Example 240, STEP 1, 32.6 mg, 0.075 mmol), tetrahydro-2H-pyran-4-amine (7.59 mg, 0.075 mmol), and HATU (86 mg, 0.225 mmol) according to similar procedure described in Example 165. $^1$H NMR (400 MHz, DMSO-$d_6$) δ 9.72 (s, 1H), 8.40 (d, J=1.8 Hz, 1H), 8.00 (d, J=8.6 Hz, 1H), 7.97-7.86 (m, 2H), 7.36 (dt, J=2.0, 0.9 Hz, 1H), 7.34-7.26 (m, 2H), 7.23 (ddd, J=5.9, 2.9, 2.0 Hz, 1H), 3.95-3.81 (m, 1H), 3.74 (dt, J=11.7, 3.9 Hz, 2H), 3.47-3.31 (m, 2H), 2.47 (s, 3H), 2.31 (s, 3H), 1.72 (dd, J=13.2, 3.8 Hz, 2H), 1.53 (q, J=5.0, 4.3 Hz, 2H), 1.45-1.15 (m, 4H); MS (M+H)$^+$=518.

Example 248. 4-(4-(((5-chloropyridin-3-yl)methyl) amino)-6-(3,5-dimethylisoxazol-4-yl)quinazolin-2-yl)-N,N-dimethylpiperazine-1-carboxamide, 2TFA The title compound was prepared from 2-chloro-N-((5-chloropyridin-3-yl)methyl)-6-(3,5-dimethylisoxazol-4-yl) quinazolin-4-amine (Example 112, 20.01 mg, 0.05 mmol) and N,N-dimethylpiperazine-1-carboxamide, 2HCl (57.5 mg, 0.25 mmol) under microwave irradiation according to similar procedure described in Example 12. $^1$H NMR (400 MHz, DMSO-$d_6$) δ 11.95 (s, 1H), 10.06 (s, 1H), 8.60 (d, J=1.9 Hz, 1H), 8.54 (d, J=2.4 Hz, 1H), 8.20 (s, 1H), 7.99 (t, J=2.1 Hz, 1H), 7.83 (d, J=8.6 Hz, 1H), 7.73 (d, J=8.5 Hz, 1H), 4.85 (d, J=5.6 Hz, 2H), 3.83 (t, J=5.1 Hz, 4H), 3.33-3.19 (m, 4H), 2.76 (s, 6H), 2.43 (s, 3H), 2.25 (s, 3H). (including 1 salt NH); MS (M+H)$^+$=521.

Example 249. 4-((3-chlorobenzyl)amino)-6-(3,5-dimethylisoxazol-4-yl)-N-((2-methylpyridin-4-yl) methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (2-methylpyridin-4-yl)methanamine (18.33 mg, 0.15 mmol), and HATU (86 mg, 0.225 mmol) according to similar procedure described in Example 165. $^1$H NMR (400 MHz, DMSO-$d_6$) δ 9.72 (s, 2H), 8.63 (d, J=5.9 Hz, 1H), 8.38 (d, J=1.8 Hz, 1H), 8.05 (d, J=8.7 Hz, 1H), 7.98 (dd, J=8.5, 1.8 Hz, 1H), 7.70-7.57 (m, 2H), 7.54 (d, J=2.0 Hz, 1H), 7.45-7.23 (m, 3H), 5.09 (d, J=5.7 Hz, 2H), 4.70 (d, J=6.2 Hz, 2H), 2.61 (s, 3H), 2.46 (s, 3H), 2.29 (s, 3H); MS (M+H)$^+$=513.

Example 250. 4-((3-chlorobenzyl)amino)-6-(3,5-dimethylisoxazol-4-yl)-N-((trans)-4-hydroxycyclohexyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (trans)-4-aminocyclohexanol (17.28 mg, 0.15 mmol), and HATU (86 mg, 0.225 mmol) according to similar procedure described in Example 165. $^1$H NMR (400 MHz, DMSO-$d_6$) δ 10.09 (s, 1H), 8.56 (s, 1H), 8.38 (d, J=1.8 Hz, 1H), 8.09 (d, J=8.7 Hz, 1H), 8.00 (dd, J=8.6, 1.7 Hz, 1H), 7.55 (d, J=1.9 Hz, 1H), 7.45-7.25 (m, 3H), 5.14-4.96 (m, 2H), 3.80-3.64 (m, 1H), 3.41 (td, J=10.5, 5.2 Hz, 1H), 2.46 (s, 3H), 2.28 (s, 3H), 1.95-1.71 (m, 4H), 1.60-1.39 (m, 2H), 1.39-1.13 (m, 2H). (OH not shown); MS (M+H)$^+$=506.

Example 251. 4-((3-chlorobenzyl)amino)-6-(3,5-dimethylisoxazol-4-yl)-N-((1-methyl-1H-imidazol-2-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (1-methyl-1H-imidazol-2-yl)methanamine (16.67 mg, 0.15 mmol), and HATU (86 mg, 0.225 mmol) according to similar procedure described in Example 165. $^1$H NMR (400 MHz, DMSO-$d_6$) δ 9.54 (s, 1H), 9.34 (s, 1H), 8.33 (d, J=1.6 Hz, 1H), 7.94 (d, J=8.6 Hz, 1H), 7.91 (dd, J=8.6, 1.7 Hz, 1H), 7.63 (d, J=2.0 Hz, 1H), 7.58 (d, J=2.0 Hz, 1H), 7.50 (d, J=2.0 Hz, 1H), 7.39 (dt, J=7.3, 1.7 Hz, 1H), 7.37-7.26 (m, 2H), 4.99 (d, J=5.7 Hz, 2H), 4.79 (d, J=5.7 Hz, 2H), 3.82 (s, 3H), 2.46 (s, 3H), 2.28 (s, 3H); MS (M+H)$^+$=502.

Example 252. 4-((3-chlorobenzyl)amino)-N-(4,4-difluorocyclohexyl)-6-(3,5-dimethylisoxazol-4-yl) quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 4,4-difluorocyclohexanamine (20.27 mg, 0.15 mmol), and HATU (86 mg, 0.225 mmol) according to similar procedure described in Example 165. $^1$H NMR (400 MHz, DMSO-$d_6$) δ 9.98 (s, 1H), 8.72 (s, 1H), 8.37 (d, J=1.8 Hz, 1H), 8.08 (d, J=8.7 Hz, 1H), 7.99 (dd, J=8.7, 1.7 Hz, 1H), 7.55 (t, J=1.8 Hz, 1H), 7.44-7.28 (m, 3H), 5.07 (d, J=5.6 Hz, 2H), 4.01 (d, J=9.5 Hz, 1H), 2.46 (s, 3H), 2.29 (s, 3H), 2.10-1.68 (m, 8H); MS (M+H)$^+$=526.

Example 253. 4-((3-chlorobenzyl)amino)-6-(3,5-dimethylisoxazol-4-yl)-N-((trans)-3-hydroxycyclobutyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (trans)-3-aminocyclobutanol (13.07 mg, 0.15 mmol), and HATU (86 mg, 0.225 mmol) according to similar procedure described in Example 165. $^1$H NMR (400 MHz, DMSO-$d_6$) δ 10.05 (s, 1H), 8.99 (s, 1H), 8.38 (d, J=1.8 Hz, 1H), 8.09 (d, J=8.7 Hz, 1H), 8.00 (d, J=8.8 Hz, 1H), 7.55 (d, J=1.7 Hz, 1H), 7.44-7.30 (m, 3H), 5.10 (s, 2H), 4.52 (p, J=7.3 Hz, 1H), 4.37-4.23 (m, 1H), 3.14 (s, 1H), 2.46 (s, 3H), 2.42-2.36 (m, 2H), 2.28 (s, 3H), 2.22-2.15 (m, 2H); MS (M+H)$^+$=478.

Example 254. 1-(2-(4-(2-(dimethylamino)ethyl) piperazin-1-yl)-6-(3,5-dimethylisoxazol-4-yl)quinazolin-4-yl)piperidine-4-carboxylic acid, 2TFA Step 1. methyl 1-(2-chloro-6-(3,5-dimethylisoxazol-4-yl)quinazolin-4-yl)piperidine-4-carboxylate Methyl 1-(2-chloro-6-(3,5-dimethylisoxazol-4-yl)quinazolin-4-yl)piperidine-4-carboxylate was prepared from 6-bromo-2,4-dichloroquinazoline and methyl piperidine-4-carboxylate according to a similar procedure described in Example 1.

Step 2. 1-(2-(4-(2-(dimethylamino)ethyl)piperazin-1-yl)-6-(3,5-dimethylisoxazol-4-yl)quinazolin-4-yl)piperidine-4-carboxylic acid, 2TFA To a mixture of methyl 1-(2-chloro-6-(3,5-dimethylisoxazol-4-yl)quinazolin-4-yl)piperidine-4-carboxylate (40.1 mg, 0.1 mmol) and N,N-dimethyl-2-(piperazin-1-yl)ethanamine, 2HCl (115 mg, 0.50 mmol) was added MeOH (2 mL) and Hunig's base (0.087 mL, 0.50 mmol). The tube was sealed and heated at 90° C. for 3 h. The solvent was removed by blowing air until ~0.5 mL remained. Then, THF (1 mL) and 1N NaOH (aq) (0.5 mL) was added and stirred at rt for 2 h. 1N HCl (aq) was added dropwise until the pH of aqueous layer was ~7. The solvent was removed by blowing air. The residue was dissolved in DMF, filtered through a filter, and then purified to give 1-(2-(4-(2-(dimethylamino)ethyl)piperazin-1-yl)-6-(3,5-dimethylisoxazol-4-yl)quinazolin-4-yl)piperidine-4-carboxylic acid, 2TFA (19.4 mg, 0.026 mmol, 26.4% yield). MS (M+H)$^+$=508

Example 255. 1-(6-(3,5-dimethylisoxazol-4-yl)-2-(1-(2-hydroxyethyl)-1H-pyrazol-4-yl)quinazolin-4-yl)piperidine-4-carboxylic acid, 2TFA In a 2-neck flask was placed methyl 1-(2-chloro-6-(3,5-dimethylisoxazol-4-yl)quinazolin-4-yl)piperidine-4-carboxylate (Example 254, STEP 1, 40.1 mg, 0.1 mmol), 2-(4-(4,4,5,5-tetramethyl-1,3,2-dioxaborolan-2-yl)-1H-pyrazol-1-yl)ethanol (47.6 mg, 0.20 mmol), PdCl$_2$(dppf)-CH$_2$Cl$_2$ adduct (8.17 mg, 10.0 μmol), and K$_2$CO$_3$ (83 mg, 0.60 mmol). The air was removed and re-filled with N$_2$ (2-3 times). Then a mixture of 1,4-dioxane (1 mL) and water (0.5 mL) was added and stirred at 95° C. (pre-heated) for 1.5 h. The organic layer was separated and filtered through PL-Thiol MP resin with Na$_2$SO$_4$, and then eluted with EtOAc and MeOH. After removal of solvent, the crude product was dissolved in THF/MeOH (1 mL/0.5 mL) and 1N NaOH (aq) (0.5 mL) was added. The mixture was stirred at rt for 2 h. 1N HCl (aq) was added dropwise until the pH of aqueous layer was ~7. The solvent was removed by blowing air. The residue was dissolved in DMF, filtered through a filter, and then purified to give 1-(6-(3,5-dimethylisoxazol-4-yl)-2-(1-(2-hydroxyethyl)-1H-pyrazol-4-yl)quinazolin-4-yl)piperidine-4-carboxylic acid, 2TFA (2.2 mg, 3.19 μmol, 3.19% yield). MS (M+H)$^+$=463

Example 256. 4-((3-chlorobenzyl)amino)-N-((3,3-difluorocyclobutyl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3,3-difluorocyclobutyl)methanamine, HCl (23.64 mg, 0.15 mmol), and HATU (86 mg, 0.225 mmol) according to similar procedure described in Example 165. $^1$H NMR (400 MHz, DMSO-d$_6$) δ 10.08 (s, 1H), 9.27 (s, 1H), 8.38 (d, J=1.8 Hz, 1H), 8.10 (d, J=8.7 Hz, 1H), 8.01 (dd, J=9.0, 1.7 Hz, 1H), 7.57-7.52 (m, 1H), 7.42 (dt, J=7.1, 1.8 Hz, 1H), 7.39-7.31 (m, 2H), 5.13 (d, J=5.8 Hz, 2H), 3.47 (t, J=6.3 Hz, 2H), 2.68-2.55 (m, 1H), 2.45 (s, 3H), 2.50-2.34 (m, 4H), 2.28 (s, 3H); MS (M+H)$^+$=512.

Example 257. 4-((3-chlorobenzyl)amino)-N-((3,5-dimethyl-1H-pyrazol-4-yl)methyl)-6-(3,5-dimethylisoxazol-4-yl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3,5-dimethyl-1H-pyrazol-4-yl)methanamine (18.78 mg, 0.15 mmol), and HATU (86 mg, 0.225 mmol) according to similar procedure described in Example 165. $^1$H NMR (400 MHz, DMSO-d$_6$) δ 10.30 (s, 1H), 9.39 (s, 1H), 8.39 (d, J=1.8 Hz, 1H), 8.20-7.90 (m, 2H), 7.50-7.49 (m, 1H), 7.41-7.26 (m, 3H), 5.15 (d, J=5.8 Hz, 2H), 4.29 (d, J=5.9 Hz, 2H), 2.75 (s, 3H), 2.45 (s, 3H), 2.27 (s, 3H), 2.19 (s, 3H). (two rotamers and major isomer was reported, NH of pyrazole is not shown); MS (M+H)$^+$=516.

Example 258. 4-((3-chlorobenzyl)amino)-6-(3,5-dimethylisoxazol-4-yl)-N-((4-methylthiazol-5-yl)methyl)quinazoline-2-carboxamide The title compound was prepared from 4-((3-chlorobenzyl)amino)-6-(3,5-dimethylisoxazol-4-yl)quinazoline-2-carboxylic acid (Example 163, 30.7 mg, 0.075 mmol), (4-methylthiazol-5-yl)methanamine (19.23 mg, 0.15 mmol), and HATU (86 mg, 0.225 mmol) according to similar procedure described in Example 165. $^1$H NMR (400 MHz, DMSO-d$_6$) δ 10.17 (s, 1H), 9.77 (s, 1H), 8.86 (s, 1H), 8.39 (d, J=1.8 Hz, 1H), 8.11 (d, J=8.7 Hz, 1H), 8.02 (dd, J=8.7, 1.7 Hz, 1H), 7.53 (q, J=1.4 Hz, 1H), 7.41 (ddd, J=6.5, 2.6, 1.6 Hz, 1H), 7.38-7.29 (m, 2H), 5.15 (d, J=5.8 Hz, 2H), 4.66 (d, J=6.2 Hz, 2H), 2.45 (s, 3H), 2.44 (s, 3H), 2.27 (s, 3H); MS (M+H)$^+$=519.

Example 259. 4-((3-chlorobenzyl)amino)-6-(3,5-dimethylisoxazol-4-yl)-N-((3,5-dimethylisoxazol-4-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (3,5-dimethylisoxazol-4-yl)methanamine (18.92 mg, 0.15 mmol), and HATU (86 mg, 0.225 mmol) according to similar procedure described in Example 165. $^1$H NMR (400 MHz, DMSO-d$_6$) δ 10.08 (s, 1H), 9.47 (s, 1H), 8.38 (d, J=1.8 Hz, 1H), 8.08 (d, J=8.7 Hz, 1H), 8.00 (dd, J=8.7, 1.7 Hz, 1H), 7.50 (q, J=1.1 Hz, 1H), 7.43-7.27 (m, 3H), 5.12 (d, J=5.8 Hz, 2H), 4.27 (d, J=5.9 Hz, 2H), 2.45 (s, 3H), 2.39 (s, 3H), 2.27 (s, 3H), 2.19 (s, 3H); MS (M+H)$^+$=517.

Example 260. 4-((3-chlorobenzyl)amino)-6-(3,5-dimethylisoxazol-4-yl)-N-((2,4-dimethylthiazol-5-yl)methyl)quinazoline-2-carboxamide, 2TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), (2,4-dimethylthiazol-5-yl)methanamine (21.33 mg, 0.15 mmol), and HATU (86 mg, 0.225 mmol) according to similar procedure described in Example 165. $^1$H NMR (400 MHz, DMSO-d$_6$) δ 10.11 (s, 1H), 9.68 (s, 1H), 8.38 (d, J=1.8 Hz, 1H), 8.09 (d, J=8.7 Hz, 1H), 8.01 (dd, J=8.6, 1.7 Hz, 1H), 7.53 (q, J=1.5 Hz, 1H), 7.41 (ddd, J=6.2, 3.0, 1.6 Hz, 1H), 7.37-7.30 (m, 2H), 5.13 (d, J=5.8 Hz, 2H), 4.57 (d, J=6.2 Hz, 2H), 2.51 (s, 3H), 2.45 (s, 3H), 2.35 (s, 3H), 2.28 (s, 3H); MS (M+H)$^+$=533.

Example 261. 1-(6-(3,5-dimethylisoxazol-4-yl)quinazolin-4-yl)piperidine-4-carboxylic acid Step 1. methyl 1-(6-(3,5-dimethylisoxazol-4-yl)quinazolin-4-yl)piperidine-4-carboxylate Methyl 1-(6-(3,5-dimethylisoxazol-4-yl)quinazolin-4-yl)piperidine-4-carboxylate was prepared from 6-bromo-4-chloroquinazoline and methyl piperidine-4-carboxylate according to similar procedure described in Example 1.

Step 2. 1-(6-(3,5-dimethylisoxazol-4-yl)quinazolin-4-yl)piperidine-4-carboxylic acid To a solution of methyl 1-(6-(3,5-dimethylisoxazol-4-yl)quinazolin-4-yl)piperidine-4-carboxylate (105 mg, 0.287 mmol) in THF (3 mL)/MeOH (1 mL) was added 1N NaOH (aq) (1.5 mL, 1.5 mmol, ca. 5 equiv). The mixture was stirred at rt for 2 h. 1N HCl (aq) was added slowly until the pH of aqueous layer was ~6-7. Hexane (20 mL) was added. The solid was filtered, washed with $H_2O$ (2×3 mL) and hexane (2×3 mL), and then dried. The solid was further dried at 60° C. under house vacuum for overnight to give 1-(6-(3,5-dimethylisoxazol-4-yl)quinazolin-4-yl)piperidine-4-carboxylic acid (87 mg, 0.247 mmol, 86% yield). $^1$H NMR (400 MHz, DMSO-$d_6$) δ 12.29 (s, 1H), 8.61 (s, 1H), 7.95-7.73 (m, 3H), 4.18 (dt, J=13.4, 3.8 Hz, 2H), 3.37-3.21 (m, 2H), 2.60 (tt, J=10.7, 4.0 Hz, 1H), 2.46 (s, 3H), 2.27 (s, 3H), 1.96 (dd, J=13.1, 3.7 Hz, 2H), 1.77 (qd, J=10.9, 5.6 Hz, 2H); MS (M+H)$^+$=353.

Example 262. (S)-1-(4-(6-(3,5-dimethylisoxazol-4-yl)-4-(3-phenylmorpholino)quinazolin-2-yl)-1H-pyrazol-1-yl)-2-methylpropan-2-ol Step 1: (S)-4-(6-bromo-2-chloroquinazolin-4-yl)-3-phenylmorpholine To a mixture of 6-bromo-2,4-dichloroquinazoline (4169 mg, 15 mmol) and (S)-3-phenylmorpholine (2571 mg, 15.75 mmol) in THF (25 ml) was added triethylamine (2277 mg, 22.50 mmol) at rt. The mixture was stirred at rt for 3 hr. The mixture was poured into EtOAc/$H_2O$ (60 mL/60 mL). The organic layer was dried over $Na_2SO_4$ and filtered. After removal of solvent the product was purified by silica gel chromatography using 30-70% EtOAc/hexane as the eluent to give (S)-4-(6-bromo-2-chloroquinazolin-4-yl)-3-phenylmorpholine (5611 mg, 13.86 mmol, 92% yield). MS (M+H)$^+$= 405.

Step 2: (S)-4-(2-chloro-6-(3,5-dimethylisoxazol-4-yl)quinazolin-4-yl)-3-phenylmorpholine In a 2-neck flask was placed (S)-4-(6-bromo-2-chloroquinazolin-4-yl)-3-phenylmorpholine (2428 mg, 6 mmol), 3,5-dimethyl-4-(4,4,5,5-tetramethyl-1,3,2-dioxaborolan-2-yl)isoxazole (1472 mg, 6.60 mmol), PdCl$_2$(dppf)-CH$_2$Cl$_2$ adduct (490 mg, 0.60 mmol), and potassium carbonate (2736 mg, 19.80 mmol). The air was removed and re-filled with N$_2$ (3 times). Then, 1,4-dioxane (20 mL)/water (10 mL) was added and heated at 75-80° C. for 1.5 h. After cooling to rt, the layer was separated and the aqueous layer was extracted with EtOAc (5 mL×2). The combined organic layer was dried over Na$_2$SO$_4$ and filtered. After removal of solvent, the product was purified by silica gel chromatography using 20-70% EtOAc/hexane as the eluent to give (S)-4-(2-chloro-6-(3,5-dimethylisoxazol-4-yl)quinazolin-4-yl)-3-phenylmorpholine (2414 mg, 4.88 mmol, 81% yield). (~85% purity with ~15% of di-coupled product (MW: 481)) The material was used without further purification. MS (M+H)$^+$=421.

Step 3: (S)-1-(4-(6-(3,5-dimethylisoxazol-4-yl)-4-(3-phenylmorpholino)quinazolin-2-yl)-1H-pyrazol-1-yl)-2-methylpropan-2-ol In a 2-neck flask was placed (S)-4-(2-chloro-6-(3,5-dimethylisoxazol-4-yl)quinazolin-4-yl)-3-phenylmorpholine (210 mg, 0.5 mmol), 2-methyl-1-(4-(4,4,5,5-tetramethyl-1,3,2-dioxaborolan-2-yl)-1H-pyrazol-1-yl)propan-2-ol (200 mg, 0.75 mmol), PdCl$_2$(dppf)-CH$_2$Cl$_2$ adduct (40.8 mg, 0.05 mmol), and potassium carbonate (311 mg, 2.25 mmol). The air was removed and re-filled with N$_2$ (3 times). Then, 1,4-dioxane (4.5 mL)/water (1.5 mL) was added and heated at 90° C. for 1.5 h. After cooling to rt, the layer was separated and the aqueous layer was extracted with EtOAc (5 mL×3). The combined organic layer was filtered through PL-Thiol MP resin and then eluted with MeOH. The filtrate was concentrated and then purified by silica gel chromatography using 40-100% EtOAc/hexane as the eluent to give (S)-1-(4-(6-(3,5-dimethylisoxazol-4-yl)-4-(3-phenylmorpholino)quinazolin-2-yl)-1H-pyrazol-1-yl)-2-methylpropan-2-ol (201 mg, 0.383 mmol, 77% yield) as a pale yellow solid. $^1$H NMR (400 MHz, DMSO-$d_6$) δ 8.25 (d, J=0.7 Hz, 1H), 7.97 (d, J=0.6 Hz, 1H), 7.87 (d, J=1.8 Hz, 1H), 7.83 (dd, J=8.6, 0.6 Hz, 1H), 7.79 (dd, J=8.6, 1.8 Hz, 1H), 7.56-7.48 (m, 2H), 7.29 (dd, J=8.4, 7.0 Hz, 2H), 7.23-7.15 (m, 1H), 5.33 (t, J=4.6 Hz, 1H), 4.74 (s, 1H), 4.06 (s, 2H), 4.14-3.64 (m, 6H), 2.35 (s, 3H), 2.17 (s, 3H), 1.08 (s, 6H); MS (M+H)$^+$=525. A portion of the crude product was purified by semi-preparative HPLC to give (S)-1-(4-(6-(3,5-dimethylisoxazol-4-yl)-4-(3-phenylmorpholino)quinazolin-2-yl)-1H-pyrazol-1-yl)-2-methylpropan-2-ol, 2TFA. $^1$H NMR (400 MHz, DMSO-$d_6$) δ 8.56 (s, 1H), 8.25 (s, 1H), 7.94-7.89 (m, 3H), 7.63-7.54 (m, 2H), 7.47-7.24 (m, 3H), 5.80 (s, 1H), 4.39 (s, 1H), 4.12 (s, 2H), 4.00-3.23 (m, 6H), 2.30 (s, 3H), 2.13 (s, 3H), 1.09 (s, 6H).

Example 263. (R)-1-(4-(6-(3,5-dimethylisoxazol-4-yl)-4-(3-phenylmorpholino)quinazolin-2-yl)-1H-pyrazol-1-yl)-2-methylpropan-2-ol, 2TFA Step 1. (R)-4-(2-chloro-6-(3,5-dimethylisoxazol-4-yl)quinazolin-4-yl)-3-phenylmorpholine (R)-4-(2-chloro-6-(3,5-dimethylisoxazol-4-yl)quinazolin-4-yl)-3-phenylmorpholine was prepared from 6-bromo-2,4-dichloroquinazoline and (R)-3-phenylmorpholine according to similar procedure described in Example 262, STEPS 1-2.

Step 2. (R)-1-(4-(6-(3,5-dimethylisoxazol-4-yl)-4-(3-phenylmorpholino)quinazolin-2-yl)-1H-pyrazol-1-yl)-2-methylpropan-2-ol, 2TFA The title compound was prepared from (R)-4-(2-chloro-6-(3,5-dimethylisoxazol-4-yl)quinazolin-4-yl)-3-phenylmorpholine (42.1 mg, 0.1 mmol), 2-methyl-1-(4-(4,4,5,5-tetramethyl-1,3,2-dioxaborolan-2-yl)-1H-pyrazol-1-yl)propan-2-ol (53.2 mg, 0.20 mmol), PdCl$_2$(dppf)-CH$_2$Cl$_2$ adduct (8.17 mg, 10.0 µmol), and K$_2$CO$_3$ (83 mg, 0.60 mmol) according to similar procedure described in Example 262. $^1$H NMR (400 MHz, DMSO-$d_6$) δ 8.57 (s, 1H), 8.25 (s, 1H), 7.96-7.90 (m, 3H), 7.65-7.54 (m, 2H), 7.45-7.24 (m, 3H), 5.88 (s, 1H), 4.39 (s, 1H), 4.12 (s, 2H), 4.05-3.26 (m, 6H), 2.28 (s, 3H), 2.12 (s, 3H), 1.09 (s, 6H); MS (M+H)$^+$=525.

Example 264. 4-(6-(3,5-dimethylisoxazol-4-yl)quinazolin-4-yl)-3-phenylmorpholine, 2TFA Step 1: 4-(6-bromoquinazolin-4-yl)-3-phenylmorpholine To a mixture of 6-bromo-4-chloroquinazoline (365 mg, 1.5 mmol) in THF (6 mL) was added 3-phenylmorpholine (318 mg, 1.95 mmol) and then Et$_3$N (0.418 ml, 3.0 mmol) at 70° C. The mixture was stirred at rt for 1 h and then heated at 70° C. overnight. The mixture was poured into EtOAc/H$_2$O (40 mL/40 mL). The organic layer was dried over Na$_2$SO$_4$ and filtered. After removal of the solvent the product was purified by silica gel chromatography using 30-70% EtOAc/hexane as the eluent to give 4-(6-bromoquinazolin-4-yl)-3-phenylmorpholine (230 mg, 0.621 mmol, 41.4% yield). MS (M+H)$^+$=525.

Step 2: 4-(6-(3,5-dimethylisoxazol-4-yl)quinazolin-4-yl)-3-phenylmorpholine, 2TFA In a 2-neck flask was placed 4-(6-bromoquinazolin-4-yl)-3-phenylmorpholine (37.0 mg, 0.1 mmol), 3,5-dimethyl-4-(4,4,5,5-tetramethyl-1,3,2-dioxaborolan-2-yl)isoxazole (44.6 mg, 0.20 mmol), PdCl$_2$(dppf)-CH$_2$Cl$_2$ adduct (8.17 mg, 10.0 µmol), and K$_2$CO$_3$ (83 mg, 0.60 mmol). The air was removed and re-filled with N$_2$ (2-3 times). Then a mixture of 1,4-dioxane (1.5 mL) and water (0.5 mL) was added and stirred at 85° C. (pre-heated) for 1.5 h. After cooling to rt, the organic layer was separated and extracted with EtOAc (10 mL×3). The combined organic layer was filtered through PL-Thiol MP resin with Na$_2$SO$_4$ and eluted with MeOH. The filtrate was concentrated, re-dissolved in DMF, filtered, and then purified by semi-preparative HPLC to give 4-(6-(3,5-dimethylisoxazol-4-yl)quinazolin-4-yl)-3-phenylmorpholine, 2TFA (14.6 mg, 0.024 mmol, 23.76% yield). $^1$H NMR (400 MHz, DMSO-d$_6$) δ 8.85 (s, 1H), 7.99 (dd, J=8.7, 1.7 Hz, 1H), 7.92 (d, J=8.7 Hz, 1H), 7.88 (s, 1H), 7.55 (dd, J=8.0, 1.5 Hz, 2H), 7.44-7.36 (m, 2H), 7.36-7.29 (m, 1H), 5.87 (s, 1H), 4.50-4.36 (m, 2H), 3.98-3.89 (m, 2H), 3.84-3.68 (m, 2H), 2.27 (s, 3H), 2.10 (s, 3H); MS (M+H)$^+$=387.

Example 265. (S)-2-(4-(6-(3,5-dimethylisoxazol-4-yl)-4-(3-phenylmorpholino)quinazolin-2-yl)piperazin-1-yl)-N,N-dimethylethanamine, 2TFA To a mixture of (S)-4-(2-chloro-6-(3,5-dimethylisoxazol-4-yl)quinazolin-4-yl)-3-phenylmorpholine (Example 262, STEP 2, 63.1 mg, 0.15 mmol) and N,N-dimethyl-2-(piperazin-1-yl)ethanamine (118 mg, 0.75 mmol) was added DMF (1 mL). The tube was sealed and heated at 90° C. for 3 h. After cooling to rt, the mixture was filtered through a filter, and purified by semi-preparative HPLC to give (S)-2-(4-(6-(3,5-dimethylisoxazol-4-yl)-4-(3-phenylmorpholino)quinazolin-2-yl)piperazin-1-yl)-N,N-dimethylethanamine, 2TFA (37.8 mg, 0.049 mmol, 32.7% yield). $^1$H NMR (400 MHz, DMSO-d$_6$) δ 7.76-7.69 (m, 3H), 7.49 (d, J=7.6 Hz, 2H), 7.42-7.19 (m, 3H), 5.55 (br s, 1H), 4.62-2.51 (m, 18H), 2.80 (s, 6H), 2.29 (s, 3H), 2.11 (s, 3H); MS (M+H)$^+$=542.

Example 266. (R)-2-(4-(6-(3,5-dimethylisoxazol-4-yl)-4-(3-phenylmorpholino)quinazolin-2-yl)piperazin-1-yl)-N,N-dimethylethanamine, 2TFA The title compound was prepared from (R)-4-(2-chloro-6-(3,5-dimethylisoxazol-4-yl)quinazolin-4-yl)-3-phenylmorpholine (Example 263, STEP 1, 63.1 mg, 0.15 mmol) and N,N-dimethyl-2-(piperazin-1-yl)ethanamine (118 mg, 0.75 mmol) according to similar procedure described in Example 265. $^1$H NMR (400 MHz, DMSO-d$_6$) δ 7.76-7.69 (m, 3H), 7.49 (d, J=7.6 Hz, 2H), 7.41-7.23 (m, 3H), 5.56 (s, 1H), 4.40-2.51 (m, 18H), 2.80 (s, 6H), 2.28 (s, 3H), 2.11 (s, 3H); MS (M+H)$^+$=542.

Example 267. 1-(2-(4-(2-(dimethylamino)ethyl)piperazin-1-yl)-6-(3,5-dimethylisoxazol-4-yl)quinazolin-4-yl)-N-methylpiperidine-4-carboxamide, 2TFA Step 1. 1-(2-chloro-6-(3,5-dimethylisoxazol-4-yl)quinazolin-4-yl)-N-methylpiperidine-4-carboxamide 1-(2-chloro-6-(3,5-dimethylisoxazol-4-yl)quinazolin-4-yl)-N-methylpiperidine-4-carboxamide was prepared from 6-bromo-2,4-dichloroquinazoline and N-methylpiperidine-4-carboxamide according to similar procedure described in Example 1.

Step 2. 1-(2-(4-(2-(dimethylamino)ethyl)piperazin-1-yl)-6-(3,5-dimethylisoxazol-4-yl)quinazolin-4-yl)-N-methylpiperidine-4-carboxamide, 2TFA The title compound was prepared from 1-(2-chloro-6-(3,5-dimethylisoxazol-4-yl)quinazolin-4-yl)-N-methylpiperidine-4-carboxamide (80 mg, 0.1 mmol, ca. 50% purity) and N,N-dimethyl-2-(piperazin-1-yl)ethanamine (79 mg, 0.50 mmol) according to similar procedure described in Example 265. $^1$H NMR (400 MHz, DMSO-d$_6$) δ 12.06 (s, 1H), 8.91 (s, 1H), 7.92-7.61 (m, 3H), 4.61-2.58 (m, 17H), 2.80 (d, J=2.2 Hz, 6H), 2.55 (d, J=4.5 Hz, 3H), 2.42 (s, 3H), 2.24 (s, 3H), 1.92-1.63 (m, 4H). (including one salt NH); MS (M+H)$^+$=521.

Example 268. (R)-4-(6-(3,5-dimethylisoxazol-4-yl)-2-(4-(methylsulfonyl)piperazin-1-yl)quinazolin-4-yl)-3-phenylmorpholine, 2TFA The title compound was prepared from (R)-4-(2-chloro-6-(3,5-dimethylisoxazol-4-yl)quinazolin-4-yl)-3-phenylmorpholine (Example 263, STEP 1, 42.1 mg, 0.1 mmol) and 1-(methylsulfonyl)piperazine (82 mg, 0.50 mmol) according to similar procedure described in Example 265. $^1$H NMR (400 MHz, DMSO-d$_6$) δ 7.77-7.69 (m, 3H), 7.50 (d, J=7.7 Hz, 2H), 7.45-7.22 (m, 3H), 5.58 (s, 1H), 4.38-2.99 (m, 14H), 2.87 (s, 3H), 2.28 (s, 3H), 2.10 (s, 3H); MS (M+H)$^+$=549.

Example 269. (S)-4-(6-(3,5-dimethylisoxazol-4-yl)-2-(4-(methylsulfonyl)piperazin-1-yl)quinazolin-4-yl)-3-phenylmorpholine, 2TFA The title compound was prepared from (S)-4-(2-chloro-6-(3,5-dimethylisoxazol-4-yl)quinazolin-4-yl)-3-phenylmorpholine (Example 262, STEP 2, 42.1 mg, 0.1 mmol) and 1-(methylsulfonyl)piperazine (82 mg, 0.50 mmol) according to similar procedure described in Example 265. $^1$H NMR (400 MHz, DMSO-d$_6$) δ 7.84-7.77 (m, 3H), 7.50 (d, J=7.7

Hz, 2H), 7.37-7.29 (m, 3H), 5.52 (s, 1H), 4.55-2.99 (m, 14H), 2.87 (s, 3H), 2.28 (s, 3H), 2.11 (s, 3H); MS (M+H)$^+$= 549.

Example 270. 1-(6-(3,5-dimethylisoxazol-4-yl)quinazolin-4-yl)-N-methylpiperidine-4-carboxamide, 2TFA Step 1. 1-(6-bromoquinazolin-4-yl)-N-methylpiperidine-4-carboxamide 1-(6-bromoquinazolin-4-yl)-N-methylpiperidine-4-carboxamide was prepared from 6-bromo-4-dichloroquinazoline and N-methylpiperidine-4-carboxamide according to similar procedure described in Example 1, STEP 1.

Step 2. 1-(6-(3,5-dimethylisoxazol-4-yl)quinazolin-4-yl)-N-methylpiperidine-4-carboxamide, 2TFA In a 2-neck flask was placed 1-(6-bromoquinazolin-4-yl)-N-methylpiperidine-4-carboxamide (69.8 mg, 0.2 mmol), 3,5-dimethyl-4-(4,4,5,5-tetramethyl-1,3,2-dioxaborolan-2-yl)isoxazole (89 mg, 0.40 mmol), PdCl$_2$(dppf)-CH$_2$Cl$_2$ adduct (16.33 mg, 0.02 mmol), and K$_2$CO$_3$ (166 mg, 1.20 mmol). The air was removed and re-filled with N$_2$ (2-3 times). Then a mixture of 1,4-dioxane (1.5 mL) and water (0.5 mL) was added and stirred at 85° C. (pre-heated) for 1.5 h. After cooling to rt, the organic layer was separated and the aqueous layer extracted with EtOAc (10 mL×3). The combined organic layer was filtered through PL-Thiol MP resin with Na$_2$SO$_4$ and eluted with MeOH. The filtrate was concentrated, re-dissolved in DMF, filtered, and then purified to give 1-(6-(3,5-dimethylisoxazol-4-yl)quinazolin-4-yl)-N-methylpiperidine-4-carboxamide, 2TFA (54.7 mg, 0.092 mmol, 46.1% yield). $^1$H NMR (400 MHz, DMSO-d$_6$) δ 8.81 (s, 1H), 8.02 (dd, J=8.6, 1.8 Hz, 1H), 7.99 (d, J=1.8 Hz, 1H), 7.87 (d, J=8.6 Hz, 1H), 7.82 (q, J=4.5 Hz, 1H), 4.64 (d, J=13.1 Hz, 2H), 3.62 (t, J=12.2 Hz, 2H), 2.62-2.52 (m, 1H), 2.56 (d, J=4.6 Hz, 3H), 2.45 (s, 3H), 2.27 (s, 3H), 1.97-1.70 (m, 4H); (M+H)$^+$=366.

Example 271. 4-((3-chlorobenzyl)amino)-6-(3,5-dimethylisoxazol-4-yl)-N-(1,1-dioxidothietan-3-yl)quinazoline-2-carboxamide, TFA The title compound was prepared from 4-((3-chlorobenzyl)amino)-6-(3,5-dimethylisoxazol-4-yl)quinazoline-2-carboxylic acid (Example 163, 30.7 mg, 0.075 mmol), 3-aminothietane 1,1-dioxide (18.17 mg, 0.15 mmol), and HATU (86 mg, 0.225 mmol) according to similar procedure described in Example 165. $^1$H NMR (400 MHz, DMSO-d$_6$) δ 9.70 (s, 1H), 9.40 (s, 1H), 8.36 (d, J=2.0 Hz, 1H), 8.03 (dd, J=9.3, 3.0 Hz, 1H), 8.00-7.92 (m, 1H), 7.53 (d, J=1.8 Hz, 1H), 7.42 (dt, J=7.5, 1.6 Hz, 1H), 7.36 (t, J=7.6 Hz, 1H), 7.32 (dt, J=7.9, 1.8 Hz, 1H), 5.05 (d, J=5.1 Hz, 2H), 4.65 (dt, J=13.8, 7.0 Hz, 1H), 4.60-4.52 (m, 2H), 4.50-4.41 (m, 2H), 2.46 (s, 3H), 2.28 (s, 3H); MS (M+H)$^+$=512.

Example 272. (S)-2-(4-(6-(3,5-dimethylisoxazol-4-yl)-4-(3-phenylmorpholino)quinazolin-2-yl)-1H-pyrazol-1-yl)-N-methylacetamide The title compound was prepared from (S)-4-(2-chloro-6-(3,5-dimethylisoxazol-4-yl)quinazolin-4-yl)-3-phenylmorpholine (Example 262, STEP 2, 63.1 mg, 0.15 mmol), N-methyl-2-(4-(4,4,5,5-tetramethyl-1,3,2-dioxaborolan-2-yl)-1H-pyrazol-1-yl)acetamide (80 mg, 0.30 mmol), PdCl$_2$(dppf)-CH$_2$Cl$_2$ adduct (12.25 mg, 0.015 mmol), and potassium carbonate (124 mg, 0.90 mmol) according to similar procedure described in Example 262. $^1$H NMR (400 MHz, DMSO-d$_6$) δ 8.33 (d, J=0.8 Hz, 1H), 8.03 (q, J=4.3 Hz, 1H), 7.99 (d, J=0.7 Hz, 1H), 7.86 (d, J=1.8 Hz, 1H), 7.83 (dd, J=8.6, 0.6 Hz, 1H), 7.80 (dd, J=8.7, 1.8 Hz, 1H), 7.53 (dd, J=8.0, 1.3 Hz, 2H), 7.34-7.26 (m, 2H), 7.24-7.17 (m, 1H), 5.38 (t, J=4.4 Hz, 1H), 4.82 (s, 2H), 4.12 (dd, J=12.0, 5.2 Hz, 1H), 4.02-3.79 (m, 4H), 3.71 (dd, J=11.3, 6.4 Hz, 1H), 2.62 (d, J=4.6 Hz, 3H), 2.34 (s, 3H), 2.17 (s, 3H); MS (M+H)$^+$=524.

Example 273. 6-(3,5-dimethylisoxazol-4-yl)-N-((trans)-4-hydroxycyclohexyl)-4-((S)-3-phenylmorpholino)quinazoline-2-carboxamide, TFA Step 1: ethyl (S)-6-bromo-4-(3-phenylmorpholino)quinazoline-2-carboxylate To a mixture of ethyl 6-bromo-4-oxo-3,4-dihydroquinazoline-2-carboxylate (891 mg, 3 mmol) and bromotri(pyrrolidin-1-yl)phosphonium hexafluorophosphate(V) (2098 mg, 4.50 mmol) was added 1,4-dioxane (12 mL) and then triethylamine (1366 mg, 13.50 mmol). The mixture was stirred at rt for 2-3 h and (S)-3-phenylmorpholine (588 mg, 3.60 mmol) was added. The mixture was then heated to 70° C. for 6 h. After cooling to rt, the mixture was poured into EtOAc/H$_2$O (15 mL/15 mL). The aqueous layer was extracted with EtOAc (15 mL). The combined organic layer was dried over Na$_2$SO$_4$ and filtered. After removal of solvent, the product was purified by silica gel chromatography using 30-70% EtOAc/hexane as the eluent to give ethyl (S)-6-bromo-4-(3-phenylmorpholino)quinazoline-2-carboxylate (1190 mg, 2.69 mmol, 90% yield). MS (M+H)$^+$= 443.

Step 2: ethyl (S)-6-(3,5-dimethylisoxazol-4-yl)-4-(3-phenylmorpholino)quinazoline-2-carboxylate In a microwave tube was placed ethyl (S)-6-bromo-4-(3-phenylmorpholino)quinazoline-2-carboxylate (1190 mg, 2.69 mmol), 3,5-dimethyl-4-(4,4,5,5-tetramethyl-1,3,2-dioxaborolan-2-yl)isoxazole (900 mg, 4.04 mmol), PdCl$_2$(dppf)-CH$_2$Cl$_2$ adduct (220 mg, 0.269 mmol), and K$_2$CO$_3$ (1673 mg, 12.11 mmol). The air was removed and re-filled with N$_2$ (3 times). Then, 1,4-dioxane (10 mL)/water (5 mL) was added and heated at 90° C. for 1.5 h. After cooling to rt, the layer was separated and the aqueous layer was extracted with EtOAc (5 mL×2). The combined organic layer was dried over Na$_2$SO$_4$ and filtered. After removal of the solvent, the product was purified by silica gel chromatography using 50-100% EtOAc/hexane as the eluent to give ethyl (S)-6-(3,5-dimethylisoxazol-4-yl)-4-(3-phenylmorpholino)quinazoline-2-carboxylate (1225 mg, 2.67 mmol, 99% yield). MS (M+H)$^+$=459.

Step 3: (S)-6-(3,5-dimethylisoxazol-4-yl)-4-(3-phenylmorpholino)quinazoline-2-carboxylic acid To a solution of ethyl (S)-6-(3,5-dimethylisoxazol-4-yl)-4-(3-phenylmorpholino)quinazoline-2-carboxylate (1225 mg, 2.67 mmol) in THF (10 mL) was added LiOH (aq) (1.5 N, 7.13 mL, 10.69 mmol, 4 equiv). The mixture was then stirred at rt for 1.5 h. HCl (aq) (1 N) was added slowly until the pH of aqueous layer was ~5. Some organic solvent was removed by blowing air and then hexane (30 mL) was added. The mixture was stirred for 15 min. The solid was filtered, washed with H₂O (3 mL×2) and hexane (5 mL×2), and then dried to give (S)-6-(3,5-dimethylisoxazol-4-yl)-4-(3-phenylmorpholino)quinazoline-2-carboxylic acid (980 mg, 2.277 mmol, 85% yield). MS (M+H)$^+$=431.

Step 4: 6-(3,5-dimethylisoxazol-4-yl)-N-((trans)-4-hydroxycyclohexyl)-4-((S)-3-phenylmorpholino)quinazoline-2-carboxamide, TFA To a mixture of (S)-6-(3,5-dimethylisoxazol-4-yl)-4-(3-phenylmorpholino)quinazoline-2-carboxylic acid (32.3 mg, 0.075 mmol), (trans)-4-aminocyclohexan-1-ol (25.9 mg, 0.225 mmol) and HATU (114 mg, 0.30 mmol) was added DMF (1 mL) and then Hunig's base (0.131 mL, 0.75 mmol). The mixture was stirred at rt for 3 h. The mixture was filtered through a micro-filter and purified by semi-preparative HPLC to give 6-(3,5-dimethylisoxazol-4-yl)-N-((trans)-4-hydroxycyclohexyl)-4-((S)-3-phenylmorpholino)quinazoline-2-carboxamide, TFA (5.9 mg, 9.20 μmol, 12.26% yield). $^1$H NMR (400 MHz, DMSO-d$_6$) δ 8.29 (s, 1H), 8.09 (d, J=8.7 Hz, 1H), 7.97 (dd, J=8.7, 1.8 Hz, 1H), 7.92 (s, 1H), 7.58-7.50 (m, 2H), 7.36 (dd, J=8.4, 6.8 Hz, 2H), 7.28 (t, J=7.3 Hz, 1H), 5.75 (s, 1H), 4.37-4.21 (m, 2H), 3.94 (td, J=12.1, 11.0, 4.1 Hz, 2H), 3.86-3.30 (m, 4H), 2.32 (s, 3H), 2.15 (s, 3H), 1.92-1.68 (m, 4H), 1.57-1.34 (m, 2H), 1.25 (dtd, J=13.1, 9.7, 3.2 Hz, 2H). (OH not shown); MS (M+H)$^+$= 528.

Example 274. 4-((3-chlorobenzyl)amino)-6-(3,5-dimethylisoxazol-4-yl)-N-((trans)-4-hydroxycyclohexyl)quinoline-2-carboxamide, TFA The title compound was prepared from 4-((3-chlorobenzyl)amino)-6-(3,5-dimethylisoxazol-4-yl)quinoline-2-carboxylic acid (Example 228, STEP 3, 30.6 mg, 0.075 mmol), (trans)-4-aminocyclohexan-1-ol (25.9 mg, 0.225 mmol) and and HATU (114 mg, 0.30 mmol) according to similar procedure described in Example 228. $^1$H NMR (400 MHz, DMSO-d$_6$) δ 9.65 (s, 1H), 8.80 (s, 1H), 8.41 (s, 1H), 8.22 (s, 1H), 7.92 (s, 1H), 7.50 (s, 1H), 7.37 (p, J=7.2 Hz, 4H), 4.82 (s, 2H), 3.84-3.18 (m, 2H), 2.47 (s, 4H), 2.29 (s, 3H), 1.85 (d, J=11.4 Hz, 4H), 1.43 (q, J=12.1 Hz, 2H), 1.25 (q, J=11.1 Hz, 2H). (OH not shown); MS (M+H)$^+$=506.

Example 275. (S)-6-(3,5-dimethylisoxazol-4-yl)-N-(1,1-dioxidotetrahydro-2H-thiopyran-4-yl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 4-aminotetrahydro-2H-thiopyran 1,1-dioxide (33.6 mg, 0.225 mmol) and HATU (114 mg, 0.30 mmol) according to similar procedure described in Example 273. $^1$H NMR (400 MHz, DMSO-d$_6$) δ 8.63 (d, J=8.4 Hz, 1H), 8.08 (d, J=8.7 Hz, 1H), 7.96 (dd, J=8.7, 1.8 Hz, 1H), 7.91 (s, 1H), 7.55 (d, J=7.4 Hz, 2H), 7.41-7.32 (m, 2H), 7.27 (t, J=7.3 Hz, 1H), 5.78 (s, 1H), 4.35-4.26 (m, 2H), 4.25-4.13 (m, 1H), 3.97-3.90 (m, 2H), 3.78 (d, J=8.9 Hz, 2H), 3.41-3.29 (m, 2H), 3.13-3.01 (m, 2H), 2.32 (s, 3H), 2.28-1.96 (m, 4H), 2.14 (s, 3H); MS (M+H)$^+$=562.

Example 276. (S)-(6-(3,5-dimethylisoxazol-4-yl)-4-(3-phenylmorpholino)quinazolin-2-yl)(1-methyl-1,4,6,7-tetrahydro-5H-pyrazolo[4,3-c]pyridin-5-yl)methanone, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 1-methyl-4,5,6,7-tetrahydro-1H-pyrazolo[4,3-c]pyridine, HCl (26.0 mg, 0.15 mmol) and HATU (114 mg, 0.30 mmol) according to similar procedure described in Example 273. $^1$H NMR (400 MHz, DMSO-d$_6$) δ 7.96-7.82 (m, 3H), 7.55-7.43 (m, 3H), 7.41-7.19 (m, 3H), 5.60 and 5.49 (two set of br s, 1H), 4.72-3.57 (m, 8H), 3.75 and 3.70 (two set of s, 3H), 3.37-3.31 (m, 1H), 2.72-2.61 (m, 1H), 2.55-2.48 (m, 2H), 2.31 and 2.29 (two set of s, 3H), 2.14 and 2.12 (two set of s, 3H). (two set of rotamers); (M+H)$^+$=550.

Example 277. (S)-6-(3,5-dimethylisoxazol-4-yl)-N-(1-methylazetidin-3-yl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 1-methylazetidin-3-amine (19.38 mg, 0.225 mmol) and HATU (114 mg, 0.30 mmol) according to similar procedure described in Example 273. $^1$H NMR (400 MHz, DMSO-d$_6$) δ 9.57 (s, 1H), 9.32 (dd, J=11.7, 7.1 Hz, 1H), 8.02 (dd, J=8.7, 1.6 Hz, 1H), 7.93 (dd, J=8.6, 1.8 Hz, 1H), 7.86 (d, J=1.9 Hz, 1H), 7.59-7.50 (m, 2H), 7.38 (td, J=7.6, 1.9 Hz, 2H), 7.29 (t, J=7.3 Hz, 1H), 5.75 (s, 1H), 4.91-4.71 (m, 1H), 4.53-4.26 (m, 4H), 4.18 (d, J=7.4 Hz, 2H), 3.96-3.85 (m, 2H), 3.73 (q, J=9.9, 9.2 Hz, 2H), 2.91 (four set of s, 3H), 2.29 (s, 3H), 2.11 (s, 3H). (including one salt NH); MS (M+H)$^+$=499.

Example 278. N-(3-chlorobenzyl)-6-(3,5-dimethylisoxazol-4-yl)-2-(1-methyl-1,4,6,7-tetrahydro-5H-pyrazolo[4,3-c]pyridin-5-yl)quinazolin-4-amine, TFA The title compound was prepared from 2-chloro-N-(3-chlorobenzyl)-6-(3,5-dimethylisoxazol-4-yl)quinazolin-4-amine (Example 1, 29.9 mg, 0.075 mmol) and 1-methyl-4,5,6,7-tetrahydro-1H-pyrazolo[4,3-c]pyridine, HCl (26.0 mg, 0.15 mmol) according to similar procedure described in Example 12. $^1$H NMR (400 MHz, DMSO-d$_6$) δ 11.94 (s, 1H), 10.06 (s, 1H), 8.23 (s, 1H), 7.84 (d, J=8.6 Hz, 1H), 7.76 (d, J=8.6 Hz, 1H), 7.55 (s, 1H), 7.52-7.49 (m, 1H), 7.42-7.27 (m, 3H), 4.93-4.71 (m, 4H), 4.07 (t, J=5.7 Hz, 2H), 3.76 (s, 3H), 2.69 (s, 2H), 2.43 (s, 3H), 2.26 (s, 3H). (including one salt NH); TFA; MS (M+H)$^+$=501.

Example 279. (S)-6-(3,5-dimethylisoxazol-4-yl)-N-((1-methyl-1H-imidazol-5-yl)methyl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), (1-methyl-1H-imidazol-5-yl)methanamine (0.025 g, 0.225 mmol) and HATU (114 mg, 0.30 mmol) according to similar procedure described in Example 273. $^1$H NMR (400 MHz, DMSO-d$_6$) δ 9.24 (t, J=6.0 Hz, 1H), 8.99 (d, J=1.6 Hz, 1H), 8.01 (d, J=8.7 Hz, 1H), 7.93 (dd, J=8.6, 1.8 Hz, 1H), 7.86 (d, J=1.9 Hz, 1H), 7.59-7.49 (m, 3H), 7.41-7.31 (m, 2H), 7.31-7.22 (m, 1H), 5.75 (s, 1H), 4.66-4.50 (m, 2H), 4.34 (dd, J=12.0, 3.2 Hz, 2H), 3.93-3.87 (m, 2H), 3.85 (s, 3H), 3.80-3.65 (m, 2H), 2.29 (s, 3H), 2.12 (s, 3H); MS (M+H)$^+$=524.

Example 280. (S)-6-(3,5-dimethylisoxazol-4-yl)-N-(1-methylpiperidin-4-yl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2- carboxylic acid (Example 273, STEP 3, 32.3 mg, 0.075 mmol), 1-methylpiperidin-4-amine (25.7 mg, 0.225 mmol) and HATU (114 mg, 0.30 mmol) according to similar procedure described in Example 273. $^1$H NMR (400 MHz, DMSO-$d_6$) δ 9.25 (s, 1H), 8.49 (t, J=6.9 Hz, 1H), 8.03 (d, J=8.7 Hz, 1H), 7.98-7.85 (m, 2H), 7.57-7.46 (m, 2H), 7.36 (dd, J=8.4, 6.9 Hz, 2H), 7.27 (dtd, J=8.7, 6.5, 5.6, 2.4 Hz, 1H), 5.63 (s, 1H), 4.37-2.99 (m, 11H), 2.77 (d, J=4.7 Hz, 3H), 2.32 (s, 3H), 2.15 (s, 3H), 2.11-1.68 (m, 4H). (including one salt NH); MS (M+H)$^+$=527.

Example 281. (S)—N-((1,3-dimethyl-1H-pyrazol-4-yl)methyl)-6-(3,5-dimethylisoxazol-4-yl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), (1,3-dimethyl-1H-pyrazol-4-yl)methanamine (28.2 mg, 0.225 mmol) and HATU (114 mg, 0.30 mmol) according to similar procedure described in Example 273. $^1$H NMR (400 MHz, DMSO-$d_6$) δ 9.10 (s, 1H), 8.11 (d, J=8.7 Hz, 1H), 7.99 (dd, J=8.7, 1.8 Hz, 1H), 7.88 (s, 1H), 7.53 (d, J=7.3 Hz, 2H), 7.47 (s, 1H), 7.36 (dd, J=8.3, 6.5 Hz, 2H), 7.29 (t, J=7.2 Hz, 1H), 5.94 (s, 1H), 4.40 (d, J=12.6 Hz, 1H), 4.34-4.22 (m, 2H), 3.97-3.87 (m, 2H), 3.81-3.70 (m, 3H), 3.69 (s, 3H), 2.29 (s, 3H), 2.13 (s, 3H), 2.11 (s, 3H); MS (M+H)$^+$=538.

Example 282. (S)-4-(6-(3,5-dimethylisoxazol-4-yl)-2-(1,4,6,7-tetrahydro-5H-pyrazolo[4,3-c]pyridin-5-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 4,5,6,7-tetrahydro-1H-pyrazolo[4,3-c]pyridine, 2HCl (73.5 mg, 0.375 mmol) according to similar procedure described in Example 265. $^1$H NMR (400 MHz, DMSO-$d_6$) δ 12.22 (s, 1H), 7.80 (br s, 3H), 7.53 (t, J=7.7 Hz, 3H), 7.39 (s, 2H), 7.31 (d, J=5.3 Hz, 1H), 5.73 (br s, 1H), 4.88 (d, J=15.1 Hz, 1H), 4.77 (s, 1H), 4.36 (s, 1H), 4.13-4.07 (m, 1H), 3.99-3.88 (m, 2H), 3.85-3.70 (m, 2H), 2.78 (s, 2H), 2.26 (s, 3H), 2.09 (s, 3H). (two protons are broad and not been assigned); MS (M+H)$^+$=508.

Example 283. (S)-6-(3,5-dimethylisoxazol-4-yl)-N-((1-methylazetidin-3-yl)methyl)-4-(3-phenylmorpholino)quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), (1-methylazetidin-3-yl)methanamine (0.023 g, 0.225 mmol) and HATU (114 mg, 0.30 mmol) according to similar procedure described in Example 273. $^1$H NMR (400 MHz, DMSO-$d_6$) δ 9.57 (s, 1H), 8.96 (t, J=6.2 Hz, 1H), 8.02 (d, J=8.6 Hz, 1H), 7.93 (dd, J=8.6, 1.8 Hz, 1H), 7.87 (s, 1H), 7.59-7.49 (m, 2H), 7.38 (dd, J=8.4, 6.9 Hz, 2H), 7.29 (t, J=7.3 Hz, 1H), 5.77 (s, 1H), 4.35 (d, J=11.5 Hz, 1H), 4.24-4.02 (m, 2H), 3.96-3.86 (m, 3H), 3.84-3.42 (m, 5H), 3.12-2.92 (m, 1H), 2.82 and 2.76 (two set of d, J=5.2 Hz, 3H), 2.29 (s, 3H), 2.12 (s, 3H). (including one salt NH); MS (M+H)$^+$=513.

Example 284. (4-(((5-chloropyridin-3-yl)methyl)amino)-6-(3,5-dimethylisoxazol-4-yl)quinazolin-2-yl)(1,4,6,7-tetrahydro-5H-pyrazolo[4,3-c]pyridin-5-yl)methanone, TFA The title compound was prepared from 4-(((5-chloropyridin-3-yl)methyl)amino)-6-(3,5-dimethylisoxazol-4-yl)quinazoline-2-carboxylic acid (Example 206, STEP 1, 30.7 mg, 0.075 mmol), 4,5,6,7-tetrahydro-1H-pyrazolo[4,3-c]pyridine, 2HCl (44.1 mg, 0.225 mmol) and HATU (114 mg, 0.30 mmol) according to similar procedure described in Example 165. MS (M+H)$^+$=515.

Example 285. (S)-(6-(3,5-dimethylisoxazol-4-yl)-4-(3-phenylmorpholino)quinazolin-2-yl)(1,4,6,7-tetrahydro-5H-pyrazolo[4,3-c]pyridin-5-yl)methanone, TFA The title compound was prepared from (S)-6-(3,5-dimethylisoxazol-4-yl)-4-(3-phenylmorpholino)quinazoline-2-carboxylic acid (Example 273, STEP 3, 0.032 g, 0.075 mmol), 4,5,6,7-tetrahydro-1H-pyrazolo[4,3-c]pyridine, 2HCl (0.044 g, 0.225 mmol) and HATU (0.114 g, 0.30 mmol) according to similar procedure described in Example 273. $^1$H NMR (400 MHz, DMSO-$d_6$) δ 7.94-7.82 (m, 3H), 7.54-7.44 (m, 3H), 7.41-7.14 (m, 3H), 5.60 and 5.50 (2 set of s, 1H), 4.74-2.51 (m, 12H), 2.31 and 2.29 (2 set of s, 3H), 2.13 and 2.12 (2 set of s, 3H). (two rotamers; NH of pyrazole not shown); MS (M+H)$^+$=536.

Example 286. (4-((1-(3-chlorophenyl)cyclopropyl)amino)-6-(3,5-dimethylisoxazol-4-yl)quinazolin-2-yl)(1,4,6,7-tetrahydro-5H-pyrazolo[4,3-c]pyridin-5-yl)methanone, TFA The title compound was prepared from 4-((1-(3-chlorophenyl)cyclopropyl)amino)-6-(3,5-dimethylisoxazol-4-yl)quinazoline-2-carboxylic acid (Example 240, STEP 1, 32.6 mg, 0.075 mmol), 4,5,6,7-tetrahydro-1H-pyrazolo[4,3-c]pyridine, 2HCl (44.1 mg, 0.225 mmol) and HATU (114 mg, 0.30 mmol) according to similar procedure described in Example 165. $^1$H NMR (400 MHz, DMSO-$d_6$) δ 9.51 and 9.59 (2 set of s, 1H), 8.40-8.38 (m, 1H), 7.94-7.78 (m, 2H), 7.52-7.02 (m, 5H), 4.58 (s, 1H), 4.01 (s, 1H), 3.82 (t, J=5.8 Hz, 1H), 3.34 (t, J=5.7 Hz, 1H), 2.69 (t, J=5.8 Hz, 1H), 2.31-2.28 (m, 4H), 1.48-1.40 (m, 4H). (NH of pyrazole not shown; one CH$_3$ is overlapped with DMSO); MS (M+H)$^+$=540.

Example 287. (4-((3-chlorobenzyl)amino)-6-(3,5-dimethylisoxazol-4-yl)quinazolin-2-yl)(1,4,6,7-tetrahydro-5H-pyrazolo[4,3-c]pyridin-5-yl)methanone, TFA The title compound was prepared from 4-((3-chlorobenzyl)amino)-6-(3,5-dimethylisoxazol-4-yl)quinazoline-2-carboxylic acid (Example 163, 0.031 g, 0.075 mmol), 4,5,6,7-tetrahydro-1H-pyrazolo[4,3-c]pyridine, 2HCl (0.044 g, 0.225 mmol) and HATU (0.114 g, 0.30 mmol) according to similar procedure described in Example 165. MS (M+H)$^+$=514.

Example 288. (4-((3-chlorobenzyl)amino)-6-(3,5-dimethylisoxazol-4-yl)quinolin-2-yl)(1,4,6,7-tetrahydro-5H-pyrazolo[4,3-c]pyridin-5-yl)methanone, TFA The title compound was prepared from 4-((3-chlorobenzyl)amino)-6-(3,5-dimethylisoxazol-4-yl)quinoline-2-carboxylic acid (Example 228, STEP 3, 0.031 g, 0.075 mmol), 4,5,6,7-tetrahydro-1H-pyrazolo[4,3-c]pyridine, 2HCl (0.044 g, 0.225 mmol) and HATU (0.114 g, 0.30 mmol) according to similar procedure described in Example 228. MS (M+H)$^+$=513.

Example 289. (S)-4-(6-(3,5-dimethylisoxazol-4-yl)-2-(1-methyl-1,4,6,7-tetrahydro-5H-pyrazolo[4,3-c]pyridin-5-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-methyl-4,5,6,7-tetrahydro-1H-pyrazolo[4,3-c]pyridine, HCl (26.0 mg, 0.15 mmol) according to similar procedure described in Example 165. $^1$H NMR (400 MHz, DMSO-$d_6$) δ 12.16 (s, 1H), 8.00-7.05 (m, 9H), 5.73 (br s, 1H), 4.95-3.17 (m, 11H), 3.75 (s, 3H), 2.86-2.60 (m, 1H), 2.26 (br s, 3H), 2.09 (br s, 3H) (including one salt NH); MS (M+H)$^+$=522.

Example 290. N-(3-chlorobenzyl)-6-(3,5-dimethylisoxazol-4-yl)-2-(1,4,6,7-tetrahydro-5H-pyrazolo[4,3-c]pyridin-5-yl)quinazolin-4-amine, TFA The title compound was prepared from 2-chloro-N-(3-chlorobenzyl)-6-(3,5-dimethylisoxazol-4-yl)quinazolin-4-amine (Example 1, 29.9 mg, 0.075 mmol) and 4,5,6,7-tetrahydro-1H-pyrazolo[4,3-c]pyridine, 2HCl (29.4 mg, 0.15 mmol) according to similar procedure described in Example 12. $^1$H NMR (400 MHz, DMSO-$d_6$) δ 11.96 (s, 1H), 10.06 (s, 1H), 8.23 (s, 1H), 7.84 (d, J=8.9 Hz, 1H), 7.76 (d, J=8.6 Hz, 1H), 7.52 (dd, J=2.5, 1.3 Hz, 2H), 7.41-7.28 (m, 3H), 4.83 (t, J=3.0 Hz, 4H), 4.09 (t, J=5.8 Hz, 2H), 2.75 (s, 2H), 2.43 (s, 3H), 2.26 (s, 3H); MS (M+H)$^+$=486.

Example 291. (S)-1-(4-(6-(3,5-dimethylisoxazol-4-yl)-4-(2-phenylpiperazin-1-yl)quinazolin-2-yl)-1H-pyrazol-1-yl)-2-methylpropan-2-ol, TFA

Step 1: tert-butyl (S)-4-(6-bromo-2-chloroquinazolin-4-yl)-3-phenylpiperazine-1-carboxylate To a mixture of 6-bromo-2,4-dichloroquinazoline (834 mg, 3 mmol) and tert-butyl (S)-3-phenylpiperazine-1-carboxylate (866 mg, 3.30 mmol) in THF (6 mL) was added triethylamine (455 mg, 4.50 mmol) at rt. The mixture was stirred at rt for overnight. The mixture was poured into EtOAc/H$_2$O (40 mL/40 mL). The organic layer was dried over Na$_2$SO$_4$ and filtered. After removal of the solvent, the product was purified by silica gel chromatography using 10-50% EtOAc/hexane as the eluent to give tert-butyl (S)-4-(6-bromo-2-chloroquinazolin-4-yl)-3-phenylpiperazine-1-carboxylate (1151 mg, 2.285 mmol, 76% yield). MS (M+H)$^+$=504.

Step 2: tert-butyl (S)-4-(2-chloro-6-(3,5-dimethylisoxazol-4-yl)quinazolin-4-yl)-3-phenylpiperazine-1-carboxylate In a microwave tube was placed tert-butyl (S)-4-(6-bromo-2-chloroquinazolin-4-yl)-3-phenylpiperazine-1-carboxylate (1151 mg, 2.285 mmol), 3,5-dimethyl-4-(4,4,5,5-tetramethyl-1,3,2-dioxaborolan-2-yl)isoxazole (561 mg, 2.51 mmol), PdCl$_2$(dppf)-CH$_2$Cl$_2$ adduct (187 mg, 0.228 mmol), and potassium carbonate (1042 mg, 7.54 mmol). The air was removed and re-filled with N$_2$ (3 times). Then, 1,4-dioxane (8 mL)/water (4 mL) was added and heated at 75-80° C. for 1.5 h. After cooling to rt, the layer was separated and the aqueous layer was extracted with EtOAc (5 mL×2). The combined organic layer was dried over Na$_2$SO$_4$ and filtered. After removal of the solvent, the product was purified by silica gel chromatography using 20-50% EtOAc/hexane as the eluent to give tert-butyl (S)-4-(2-chloro-6-(3,5-dimethylisoxazol-4-yl)quinazolin-4-yl)-3-phenylpiperazine-1-carboxylate (975 mg, 1.312 mmol, 57.4% yield, ca. 70% purity). MS (M+H)$^+$=520.

Step 3: (S)-4-(2-chloro-4-(2-phenylpiperazin-1-yl)quinazolin-6-yl)-3,5-dimethylisoxazole, 2HCl To a solution of tert-butyl (S)-4-(2-chloro-6-(3,5-dimethylisoxazol-4-yl)quinazolin-4-yl)-3-phenylpiperazine-1-carboxylate (975 mg, 1.31 mmol) in 1,4-dioxane (4 mL) was added HCl (4M in dioxane, 3 mL, 12 mmol). The mixture was stirred at rt for 2 h. Then hexane (15 mL) was added and stirred vigorously for 30 min. The solvent was removed by pipet and then hexane was added (15 mL). This process was repeated 3 times. The solid residue was dried in vacuo to give (S)-4-(2-chloro-4-(2-phenylpiperazin-1-yl)quinazolin-6-yl)-3,5-dimethylisoxazole, 2HCl (756 mg, 1.273 mmol, 97% yield, ~83% purity) which was used for next step without further purification. MS (M+H)$^+$=420.

Step 4: (S)-1-(4-(6-(3,5-dimethylisoxazol-4-yl)-4-(2-phenylpiperazin-1-yl)quinazolin-2-yl)-1H-pyrazol-1-yl)-2-methylpropan-2-ol, TFA In a microwave tube was placed (S)-4-(2-chloro-4-(2-phenylpiperazin-1-yl)quinazolin-6-yl)-3,5-dimethylisoxazole, 2HCl (59.4 mg, 0.1 mmol, ~83% purity), 2-methyl-1-(4-(4,4,5,5-tetramethyl-1,3,2-dioxaborolan-2-yl)-1H-pyrazol-1-yl)propan-2-ol (53.2 mg, 0.20 mmol), PdCl$_2$(dppf)-CH$_2$Cl$_2$ adduct (8.17 mg, 10.0 μmol), and potassium carbonate (83 mg, 0.60 mmol). The air was removed and re-filled with N$_2$ (3 times). Then, 1,4-dioxane (1.5 mL)/water (0.5 mL) was added and heated at 90° C. for 1.5 h. After cooling to rt, the layer was separated and the aqueous layer was extracted with EtOAc (3 mL×2). The combined organic layer was filtered through PL-Thiol MP resin and then eluted with MeOH. After removal of solvent, the crude product dissolved in DMF, filtered, and purified by semi-preparative HPLC to give (S)-1-(4-(6-(3,5-dimethylisoxazol-4-yl)-4-(2-phenylpiperazin-1-yl)quinazolin-2-yl)-1H-pyrazol-1-yl)-2-methylpropan-2-ol, TFA (11.1 mg, 0.017 mmol, 17.41% yield). $^1$H NMR (400 MHz, DMSO-$d_6$) δ 8.94 (s, 2H), 8.32 (s, 1H), 8.03 (s, 1H), 7.89 (s, 1H), 7.87 (s, 2H), 7.62-7.55 (m, 2H), 7.35 (t, J=7.5 Hz, 2H), 7.27 (d, J=7.4 Hz, 1H), 5.46 (s, 1H), 4.75 (s, 1H), 4.08 (s, 2H), 4.05-3.30 (m, 6H), 2.34 (s, 3H), 2.17 (s, 3H), 1.09 (d, J=1.5 Hz, 6H) (including one salt NH); MS (M+H)$^+$=524.

Example 292. (S)-5-(2-(1-(2-hydroxy-2-methylpropyl)-1H-pyrazol-4-yl)-4-(3-phenylmorpholino)quinazolin-6-yl)-1-methylpyridin-2(1H)-one, TFA

Step 1: (S)-5-(2-chloro-4-(3-phenylmorpholino)quinazolin-6-yl)-1-methylpyridin-2(1H)-one In a microwave tube was placed (S)-4-(6-bromo-2-chloroquinazolin-4-yl)-3-phenylmorpholine (809 mg, 2 mmol), 1-methyl-5-(4,4,5,5-tetramethyl-1,3,2-dioxaborolan-2-yl)pyridin-2(1H)-one (517 mg, 2.20 mmol), PdCl$_2$(dppf)-CH$_2$Cl$_2$ adduct (163 mg, 0.20 mmol), and potassium carbonate (912 mg, 6.60 mmol). The air was removed and re-filled with N$_2$ (3 times). Then, 1,4-dioxane (6 mL)/water (3 mL) was added and heated at 75-80° C. for 1.5 h. After cooling to rt, the layer was separated and the aqueous layer was extracted with EtOAc (5 mL×2). The combined organic layer was dried over Na₂SO₄ and filtered. After removal of solvent, the product was purified by silica gel chromatography using 0-10% MeOH/EtOAc as the eluent to give (S)-5-(2-chloro-4-(3-phenylmorpholino)quinazolin-6-yl)-1-methylpyridin-2(1H)-one (636 mg, 1.469 mmol, 73.5% yield). MS (M+H)⁺=433.

Step 2: (S)-5-(2-(1-(2-hydroxy-2-methylpropyl)-1H-pyrazol-4-yl)-4-(3-phenylmorpholino)quinazolin-6-yl)-1-methylpyridin-2(1H)-one, TFA In a microwave tube was placed (S)-5-(2-chloro-4-(3-phenylmorpholino)quinazolin-6-yl)-1-methylpyridin-2(1H)-one (43.3 mg, 0.1 mmol), 2-methyl-1-(4-(4,4,5,5-tetramethyl-1,3,2-dioxaborolan-2-yl)-1H-pyrazol-1-yl)propan-2-ol (53.2 mg, 0.20 mmol), PdCl₂(dppf)-CH₂Cl₂ adduct (8.17 mg, 10.0 µmol), and potassium carbonate (83 mg, 0.60 mmol). The air was removed and re-filled with N₂ (3 times). Then, 1,4-dioxane (1.5 mL)/water (0.5 mL) was added and heated at 90° C. for 1.5 h. After cooling to rt, the layer was separated and the aqueous layer was extracted with EtOAc (3 mL×2). The combined organic layer was filtered through PL-Thiol MP resin and then eluted with MeOH. After removal of solvent, the crude product dissolved in DMF, filtered, and purified by semi-preparative HPLC to give (S)-5-(2-(1-(2-hydroxy-2-methylpropyl)-1H-pyrazol-4-yl)-4-(3-phenylmorpholino)quinazolin-6-yl)-1-methylpyridin-2(1H)-one, TFA (13 mg, 0.020 mmol, 19.98% yield). $^1$H NMR (400 MHz, DMSO-d₆) δ 8.54 (s, 1H), 8.36-7.88 (m, 5H), 7.84 (d, J=8.7 Hz, 1H), 7.61 (d, J=7.6 Hz, 2H), 7.35 (d, J=38.1 Hz, 3H), 6.41 (s, 1H), 5.73 (s, 1H), 5.02-4.56 (m, 1H), 4.34 (s, 1H), 4.11 (s, 2H), 4.06-3.94 (m, 2H), 3.81 (d, J=9.9 Hz, 1H), 3.46 (s, 3H), 1.09 (s, 6H) (one CH₂ peak not shown due to overlap with water peak); MS (M+H)⁺=537.

Example 293. (S)-4-(6-(3,5-dimethylisoxazol-4-yl)-2-(4-methylpiperazin-1-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-methylpiperazine (22.54 mg, 0.225 mmol) according to similar procedure described in Example 265. $^1$H NMR (400 MHz, DMSO-d₆) δ 9.69 (s, 1H), 7.76 (s, 1H), 7.71-7.64 (m, 1H), 7.55 (d, J=8.7 Hz, 1H), 7.46 (d, J=7.4 Hz, 2H), 7.31 (t, J=7.5 Hz, 2H), 7.23 (dd, J=8.3, 6.2 Hz, 1H), 5.24 (s, 1H), 4.71-4.61 (m, 2H), 4.16-2.91 (m, 12H), 2.78 (s, 3H), 2.36-2.26 (m, 3H), 2.14 (s, 3H) (including one salt NH); MS (M+H)⁺=485.

Example 294. (S)-1-(4-(6-(3,5-dimethylisoxazol-4-yl)-4-(3-phenylmorpholino)quinazolin-2-yl)piperazin-1-yl)ethan-1-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-(piperazin-1-yl)ethan-1-one (28.8 mg, 0.225 mmol) according to similar procedure described in Example 265. $^1$H NMR (400 MHz, DMSO-d₆) δ 7.76 (br s, 3H), 7.50 (d, J=7.5 Hz, 2H), 7.37-7.30 (m, 3H), 5.73 (br s, 1H), 4.47-3.18 (m, 14H), 2.25 (s, 3H), 2.11 (s, 3H), 2.03 (s, 3H); MS (M+H)⁺=513.

Example 295. (S)-1-(4-(6-(3,5-dimethylisoxazol-4-yl)-4-(3-phenylmorpholino)quinazolin-2-yl)piperazin-1-yl)-2-methylpropan-2-ol, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 2-methyl-1-(piperazin-1-yl)propan-2-ol, 2HCl (52.0 mg, 0.225 mmol) according to similar procedure described in Example 265. $^1$H NMR (400 MHz, DMSO-d₆) δ 9.14 (s, 1H), 7.76 (s, 1H), 7.68 (d, J=8.8 Hz, 1H), 7.55 (d, J=8.6 Hz, 1H), 7.49-7.42 (m, 2H), 7.32 (t, J=7.5 Hz, 2H), 7.24 (t, J=7.3 Hz, 1H), 5.26 (s, 2H), 4.43 (d, J=18.1 Hz, 2H), 4.15-3.22 (m, 10H), 3.10 (s, 3H), 2.95 (s, 1H), 2.35-2.25 (m, 3H), 2.14 (s, 3H), 1.24 (s, 6H). (including one salt NH); MS (M+H)⁺=543.

Example 296. (S)-1-(6-(3,5-dimethylisoxazol-4-yl)-4-(3-phenylmorpholino)quinazolin-2-yl)-N-methylpiperidine-4-carboxamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and N-methylpiperidine-4-carboxamide (32.0 mg, 0.225 mmol) according to similar procedure described in Example 265. MS (M+H)⁺=527.

Example 297. (S)-2-(4-(6-(3,5-dimethylisoxazol-4-yl)-4-(3-phenylmorpholino)quinazolin-2-yl)-1H-pyrazol-1-yl)acetamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol), 2-(4-(4,4,5,5-tetramethyl-1,3,2-dioxaborolan-2-yl)-1H-pyrazol-1-yl)acetamide (37.7 mg, 0.15 mmol), PdCl₂(dppf)-CH₂Cl₂ adduct (6.12 mg, 7.50 µmol), and potassium carbonate (62.2 mg, 0.45 mmol) according to similar procedure described in Example 262. $^1$H NMR (400 MHz, DMSO-d₆) δ 8.59 (s, 1H), 8.23 (s, 1H), 7.92 (d, J=5.9 Hz, 3H), 7.63 (s, 1H), 7.58 (d, J=7.6 Hz, 2H), 7.47-7.21 (m, 4H), 5.73 (s, 1H), 4.88 (s, 2H), 4.52-3.19 (m, 6H), 2.30 (s, 3H), 2.13 (s, 3H); MS (M+H)⁺=510.

Example 298. (S)-1-(6-(3,5-dimethylisoxazol-4-yl)-4-(3-phenylmorpholino)quinazolin-2-yl)-N-methylpiperidine-4-carboxamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and N-methyl-2-(piperazin-1-yl)acetamide, HCl (43.6 mg, 0.225 mmol) according to similar procedure described in Example 265. $^1$H NMR (400 MHz, DMSO-d₆) δ 10.13 (s, 1H), 8.40 (s, 1H), 7.76 (s, 1H), 7.68 (d, J=8.8 Hz, 1H), 7.55 (d, J=8.8 Hz, 1H), 7.46 (d, J=7.6 Hz, 2H), 7.31 (t, J=7.5 Hz, 2H), 7.22 (t, J=7.4 Hz, 1H), 5.23 (s, 1H), 4.58 (s, 2H), 4.27-2.93 (m, 14H), 2.66 (d, J=4.6 Hz, 3H), 2.31 (s, 3H), 2.14 (s, 3H) (including one salt NH); MS (M+H)⁺=542.

Example 299. (S)-4-(6-(3,5-dimethylisoxazol-4-yl)-4-(3-phenylmorpholino)quinazolin-2-yl)-N-ethylpiperazine-1-carboxamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and N-ethylpiperazine-1-carboxamide, HCl (43.6 mg, 0.225 mmol) according to similar procedure described in Example 265. $^1$H NMR (400 MHz, DMSO-$d_6$) δ 11.99 (s, 1H), 7.77 (s, 3H), 7.50 (d, J=7.4 Hz, 2H), 7.38-7.30 (m, 3H), 6.56 (s, 1H), 6.08-5.40 (m, 1H), 4.54-3.13 (m, 14H), 3.11-2.97 (m, 2H), 2.30 (s, 3H), 2.10 (s, 3H), 1.00 (t, J=7.1 Hz, 3H) (including one salt NH); MS (M+H)$^+$=542.

Example 300. (S)-(4-(6-(3,5-dimethylisoxazol-4-yl)-4-(3-phenylmorpholino)quinazolin-2-yl)piperazin-1-yl)(1-methyl-1H-pyrazol-4-yl)methanone, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and (1-methyl-1H-pyrazol-4-yl)(piperazin-1-yl)methanone, 2HCl (60.1 mg, 0.225 mmol) according to similar procedure described in Example 265. $^1$H NMR (400 MHz, DMSO-$d_6$) δ 8.09 (s, 1H), 7.75 (br s, 3H), 7.69 (s, 1H), 7.51 (d, J=7.6 Hz, 2H), 7.33 (m, 3H), 5.73 (s, 1H), 3.85 (s, 3H), 4.55-3.17 (m, 14H), 2.27 (s, 3H), 2.10 (s, 3H); MS (M+H)$^+$=579.

Example 301. (S)-2-(4-(6-(3,5-dimethylisoxazol-4-yl)-4-(3-phenylmorpholino)quinazolin-2-yl)-1H-pyrazol-1-yl)-N,N-dimethylacetamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol), N,N-dimethyl-2-(4-(4,4,5,5-tetramethyl-1,3,2-dioxaborolan-2-yl)-1H-pyrazol-1-yl)acetamide (41.9 mg, 0.15 mmol), PdCl$_2$(dppf)-CH$_2$Cl$_2$ adduct (6.12 mg, 7.50 µmol), and potassium carbonate (62.2 mg, 0.45 mmol) according to similar procedure described in Example 262. $^1$H NMR (400 MHz, DMSO-$d_6$) δ 8.56 (s, 1H), 8.24 (s, 1H), 8.01-7.71 (m, 3H), 7.58 (d, J=7.6 Hz, 2H), 7.46-7.24 (m, 3H), 5.73 (s, 1H), 5.24 (s, 2H), 4.56-3.35 (m, 6H), 3.04 (s, 3H), 2.85 (s, 3H), 2.36-2.20 (m, 3H), 2.12 (s, 3H); MS (M+H)$^+$=538.

Example 302. (S)-4-(6-(3,5-dimethylisoxazol-4-yl)-2-(1-((methylsulfonyl)methyl)-1H-pyrazol-4-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol), 1-((methylsulfonyl)methyl)-4-(4,4,5,5-tetramethyl-1,3,2-dioxaborolan-2-yl)-1H-pyrazole (42.9 mg, 0.15 mmol), PdCl$_2$(dppf)-CH$_2$Cl$_2$ adduct (6.12 mg, 7.50 µmol), and potassium carbonate (62.2 mg, 0.45 mmol) according to similar procedure described in Example 262. $^1$H NMR (400 MHz, DMSO-$d_6$) δ 8.66 (s, 1H), 8.33 (s, 1H), 7.90 (br s, 3H), 7.57 (d, J=7.6 Hz, 2H), 7.36 (t, J=7.6 Hz, 2H), 7.26 (t, J=7.4 Hz, 1H), 5.87 (s, 2H), 5.72 (br s, 1H), 4.42-3.40 (m, 6H), 3.07 (s, 3H), 2.31 (s, 3H), 2.14 (s, 3H); MS (M+H)$^+$=545.

Example 303. (S)-2-(4-(6-(3,5-dimethylisoxazol-4-yl)-4-(3-phenylmorpholino)quinazolin-2-yl)piperazin-1-yl)-N,N-dimethylacetamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and N,N-dimethyl-2-(piperazin-1-yl)acetamide, 2HCl (54.9 mg, 0.225 mmol) according to similar procedure described in Example 265. $^1$H NMR (400 MHz, DMSO-$d_6$) δ 9.97 (s, 1H), 7.76 (s, 1H), 7.68 (d, J=8.7 Hz, 1H), 7.54 (d, J=8.7 Hz, 1H), 7.49-7.42 (m, 2H), 7.31 (t, J=7.5 Hz, 2H), 7.22 (t, J=7.3 Hz, 1H), 5.21 (s, 1H), 4.55 (s, 2H), 4.24 (s, 2H), 4.11-2.96 (m, 12H), 2.90 (s, 6H), 2.32 (s, 3H), 2.15 (s, 3H) (including one salt NH); MS (M+H)$^+$=556.

Example 304. (S)-2-(4-(6-(3,5-dimethylisoxazol-4-yl)-4-(3-phenylmorpholino)quinazolin-2-yl)-1H-pyrazol-1-yl)-2-methylpropan-1-ol, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol), 2-methyl-2-(4-(4,4,5,5-tetramethyl-1,3,2-dioxaborolan-2-yl)-1H-pyrazol-1-yl)propan-1-ol (39.9 mg, 0.15 mmol), PdCl$_2$(dppf)-CH$_2$Cl$_2$ adduct (6.12 mg, 7.50 µmol), and potassium carbonate (62.2 mg, 0.45 mmol) according to similar procedure described in Example 262. $^1$H NMR (400 MHz, DMSO-$d_6$) δ 8.49 (br s, 1H), 8.20 (br s, 1H), 7.95-7.88 (m, 3H), 7.56 (d, J=7.6 Hz, 2H), 7.33 (d, J=28.8 Hz, 3H), 5.09 (s, 1H), 4.47-3.02 (m, 7H), 3.61 (s, 2H), 2.34 (br s, 3H), 2.17 (br s, 3H), 1.51 (s, 6H); MS (M+H)$^+$=525.

Example 305. (S)-1-(4-(6-(3,5-dimethylisoxazol-4-yl)-4-(3-phenylmorpholino)quinazolin-2-yl)piperazin-1-yl)-2-hydroxyethan-1-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 2-hydroxy-1-(piperazin-1-yl)ethan-1-one (32.4 mg, 0.225 mmol) according to similar procedure described in Example 265. $^1$H NMR (400 MHz, DMSO-$d_6$) δ 7.75 (s, 3H), 7.50 (d, J=7.5 Hz, 2H), 7.36-7.29 (m, 3H), 6.09-5.20 (m, 1H), 4.12 (s, 2H), 4.03-3.16 (m, 15H), 2.30 (s, 3H), 2.11 (s, 3H); MS (M+H)$^+$=529.

Example 306. (S)-2-(4-(6-(3,5-dimethylisoxazol-4-yl)-4-(3-phenylmorpholino)quinazolin-2-yl)-1H-pyrazol-1-yl)ethan-1-ol, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol), 2-(4-(4,4,5,5-tetramethyl-1,3,2-dioxaborolan-2-yl)-1H-pyrazol-1-yl)ethan-1-ol (35.7 mg, 0.15 mmol), PdCl$_2$(dppf)-CH$_2$Cl$_2$ adduct (6.12 mg, 7.50 µmol), and potassium carbonate (62.2 mg, 0.45 mmol) according to similar procedure described in Example 262. $^1$H NMR (400 MHz, DMSO-$d_6$) δ 8.57 (s, 1H), 8.23 (s, 1H), 7.91 (s, 3H), 7.57 (d, J=7.6 Hz, 2H), 7.33 (d, J=35.3 Hz, 3H), 5.97-5.33 (m, 1H), 4.96 (s, 1H), 4.36 (s, 1H), 4.23 (t, J=5.4 Hz, 2H), 4.02-3.89 (m, 2H), 3.77 (t, J=5.4 Hz, 3H), 2.40-2.21 (m, 3H), 2.13 (s, 3H) (one set of CH$_2$ not shown due to overlap with water peak); MS (M+H)$^+$=497.

Example 307. (S)-2-(4-(6-(3,5-dimethylisoxazol-4-yl)-4-(3-phenylmorpholino)quinazolin-2-yl)piperazin-1-yl)acetamide, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 2-(piperazin-1-yl)acetamide, HCl (40.4 mg, 0.225 mmol) according to similar procedure described in Example 265. $^1$H NMR (400 MHz, DMSO-$d_6$) δ 10.00 (s, 1H), 7.91 (s, 1H), 7.76 (s, 1H), 7.69-7.67 (m, 2H), 7.54 (d, J=8.7 Hz, 1H), 7.46 (d, J=7.3 Hz, 2H), 7.31 (t, J=7.5 Hz, 2H), 7.22 (t, J=7.3 Hz, 1H), 5.22 (s, 1H), 4.61 (s, 2H), 4.20-2.96 (m, 14H), 2.31 (d, J=5.4 Hz, 3H), 2.14 (s, 3H) (including one salt NH); MS (M+H)$^+$=528.

Example 308. (S)-1-(4-(6-(3,5-dimethylisoxazol-4-yl)-4-((S)-3-phenylmorpholino)quinazolin-2-yl)piperazin-1-yl)propan-2-ol, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and (S)-1-(piperazin-1-yl)propan-2-ol (32.4 mg, 0.225 mmol) according to similar procedure described in Example 265. $^1$H NMR (400 MHz, DMSO-d$_6$) δ 9.54 (s, 1H), 7.75 (s, 1H), 7.72-7.63 (m, 1H), 7.55 (d, J=8.7 Hz, 1H), 7.46 (d, J=7.3 Hz, 2H), 7.32 (t, J=7.5 Hz, 2H), 7.23 (t, J=7.3 Hz, 1H), 5.49 (s, 1H), 5.26 (s, 1H), 4.59 (d, J=14.3 Hz, 2H), 4.29-2.68 (m, 15H), 2.31 (s, 3H), 2.14 (s, 3H), 1.10 (d, J=6.1 Hz, 3H) (including one salt NH); MS (M+H)$^+$=529.

Example 309. (S)-1-(4-(6-(3,5-dimethylisoxazol-4-yl)-2-(1-(2-hydroxy-2-methylpropyl)-1H-pyrazol-4-yl)quinazolin-4-yl)-3-phenylpiperazin-1-yl)ethan-1-one, TFA Step 1: (S)-1-(4-(2-chloro-6-(3,5-dimethylisoxazol-4-yl)quinazolin-4-yl)-3-phenylpiperazin-1-yl)ethan-1-one To a solution of (S)-4-(2-chloro-4-(2-phenylpiperazin-1-yl)quinazolin-6-yl)-3,5-dimethylisoxazole, 2HCl (Example 291, STEP 3, 178 mg, 0.3 mmol) in CH$_2$Cl$_2$ (3 ml) was added Et$_3$N (0.418 ml, 3.00 mmol) and then acetyl chloride (70.6 mg, 0.90 mmol) slowly. The mixture was stirred at rt for 30 min. The mixture was poured into CH$_2$Cl$_2$/H$_2$O (10 mL/10 mL). The organic layer was washed with H$_2$O (10 mL), dried over Na$_2$SO$_4$, and filtered. After removal of solvent, the product was dried in vacuo to give (S)-1-(4-(2-chloro-6-(3,5-dimethylisoxazol-4-yl)quinazolin-4-yl)-3-phenylpiperazin-1-yl)ethan-1-one (172 mg, 0.309 mmol, 103% yield), which was used for next step without further purification. MS (M+H)$^+$=462.

Step 2: (S)-1-(4-(6-(3,5-dimethylisoxazol-4-yl)-2-(1-(2-hydroxy-2-methylpropyl)-1H-pyrazol-4-yl)quinazolin-4-yl)-3-phenylpiperazin-1-yl)ethan-1-one, TFA In a microwave tube was placed (S)-1-(4-(2-chloro-6-(3,5-dimethylisoxazol-4-yl)quinazolin-4-yl)-3-phenylpiperazin-1-yl)ethan-1-one (85 mg, 0.15 mmol), 2-methyl-1-(4-(4,4,5,5-tetramethyl-1,3,2-dioxaborolan-2-yl)-1H-pyrazol-1-yl)propan-2-ol (80 mg, 0.30 mmol), PdCl$_2$(dppf)-CH$_2$Cl$_2$ adduct (12.25 mg, 0.015 mmol), and potassium carbonate (124 mg, 0.90 mmol). The air was removed and re-filled with N$_2$ (3 times). Then, 1,4-dioxane (1.5 ml)/water (0.5 ml) was added and heated at 90° C. for 1.5 h. After cooling to rt, the layer was separated and the aqueous layer was extracted with EtOAc (3 mL×2). The combined organic layer was filtered through PL-Thiol MP resin and then eluted with MeOH. After removal of solvent, the crude product dissolved in DMF, filtered, and purified by semi-preparative HPLC to give (S)-1-(4-(6-(3,5-dimethylisoxazol-4-yl)-2-(1-(2-hydroxy-2-methylpropyl)-1H-pyrazol-4-yl)quinazolin-4-yl)-3-phenylpiperazin-1-yl)ethan-1-one, TFA (23 mg, 0.034 mmol, 22.56% yield). $^1$H NMR (400 MHz, DMSO-d$_6$) δ 8.48 (s, 1H), 8.12 (s, 1H), 8.00-7.83 (m, 3H), 7.61 (d, J=7.7 Hz, 1H), 7.55 (d, J=7.6 Hz, 1H), 7.31 (dd, J=33.6, 6.5 Hz, 3H), 5.89 (d, J=35.1 Hz, 1H), 5.05-3.17 (m, 9H), 2.33 (br s, 3H), 2.16 (br s, 3H), 1.94 (d, J=12.4 Hz, 3H), 1.08 (s, 6H); MS (M+H)$^+$=566.

Example 310. (S)-1-(4-(6-(3,5-dimethylisoxazol-4-yl)-4-(4-(methylsulfonyl)-2-phenylpiperazin-1-yl)quinazolin-2-yl)-1H-pyrazol-1-yl)-2-methylpropan-2-ol, TFA Step 1: (S)-4-(2-chloro-4-(4-(methylsulfonyl)-2-phenylpiperazin-1-yl)quinazolin-6-yl)-3,5-dimethylisoxazole To a solution of (S)-4-(2-chloro-4-(2-phenylpiperazin-1-yl)quinazolin-6-yl)-3,5-dimethylisoxazole, 2HCl (Example 291, STEP 3, 178 mg, 0.3 mmol) in CH$_2$Cl$_2$ (3 mL) was added Et$_3$N (0.418 ml, 3.00 mmol) and then methanesulfonyl chloride (103 mg, 0.90 mmol) slowly. The mixture was stirred at rt for 30 min. The mixture was poured into CH$_2$Cl$_2$/H$_2$O (10 mL/10 mL). The organic layer was washed with H$_2$O (10 mL), dried over Na$_2$SO$_4$, and filtered. After removal of solvent, the product was dried in vacuo to give (S)-4-(2-chloro-4-(4-(methylsulfonyl)-2-phenylpiperazin-1-yl)quinazolin-6-yl)-3,5-dimethylisoxazole (177 mg, 0.291 mmol, 97% yield), which was used for next step without further purification. MS (M+H)$^+$=498.

Step 2: (S)-1-(4-(6-(3,5-dimethylisoxazol-4-yl)-4-(4-(methylsulfonyl)-2-phenylpiperazin-1-yl)quinazolin-2-yl)-1H-pyrazol-1-yl)-2-methylpropan-2-ol, TFA In a microwave tube was placed (S)-4-(2-chloro-4-(4-(methylsulfonyl)-2-phenylpiperazin-1-yl)quinazolin-6-yl)-3,5-dimethylisoxazole (74.7 mg, 0.15 mmol), 2-methyl-1-(4-(4,4,5,5-tetramethyl-1,3,2-dioxaborolan-2-yl)-1H-pyrazol-1-yl)propan-2-ol (80 mg, 0.30 mmol), PdCl$_2$(dppf)-CH$_2$Cl$_2$ adduct (12.25 mg, 0.015 mmol), and potassium carbonate (124 mg, 0.90 mmol). The air was removed and re-filled with N$_2$ (3 times). Then, 1,4-dioxane (1.5 mL)/water (0.5 mL) was added and heated at 90° C. for 1.5 h. After cooling to rt, the layer was separated and the aqueous layer was extracted with EtOAc (3 mL×2). The combined organic layer was filtered through PL-Thiol MP resin and then eluted with MeOH. After removal of solvent, the crude product dissolved in DMF, filtered, and purified by semi-preparative HPLC to give (S)-1-(4-(6-(3,5-dimethylisoxazol-4-yl)-4-(4-(methylsulfonyl)-2-phenylpiperazin-1-yl)quinazolin-2-yl)-1H-pyrazol-1-yl)-2-methylpropan-2-ol, TFA (18.9 mg, 0.026 mmol, 17.60% yield). $^1$H NMR (400 MHz, DMSO-d$_6$) δ 8.50 (s, 1H), 8.19 (s, 1H), 7.93 (s, 3H), 7.56 (d, J=7.7 Hz, 2H), 7.39 (t, J=7.5 Hz, 2H), 7.30 (t, J=7.4 Hz, 1H), 5.94 (s, 1H), 4.97-3.16 (m, 9H), 2.88 (s, 3H), 2.31 (s, 3H), 2.14 (s, 3H), 1.09 (s, 6H); MS (M+H)$^+$=602.

Example 311. (S)-4-(6-(3,5-dimethylisoxazol-4-yl)-2-(3-methyl-3,4,6,7-tetrahydro-5H-imidazo[4,5-c]pyridin-5-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 3-methyl-4,5,6,7-tetrahydro-3H-imidazo[4,5-c]pyridine, 2HCl (47.3 mg, 0.225 mmol) according to similar procedure described in Example 265. ¹H NMR (400 MHz, DMSO-d₆) δ 8.90 (s, 1H), 7.78 (s, 1H), 7.70 (d, J=8.8 Hz, 1H), 7.60 (s, 1H), 7.48 (d, J=7.7 Hz, 2H), 7.31 (t, J=7.5 Hz, 2H), 7.22 (t, J=7.4 Hz, 1H), 5.27 (s, 1H), 4.97 (d, J=16.3 Hz, 1H), 4.68 (s, 1H), 4.23-3.37 (m, 9H), 3.82 (s, 3H), 2.72 (d, J=14.7 Hz, 1H), 2.32 (s, 3H), 2.15 (s, 3H); MS (M+H)⁺= 522.

Example 312. 1-(4-(4-((3-chlorobenzyl)(cyclopropyl)amino)-6-(3,5-dimethylisoxazol-4-yl)quinazolin-2-yl)-1H-pyrazol-1-yl)-2-methylpropan-2-ol, TFA Step 1: 6-bromo-2-chloro-N-(3-chlorobenzyl)-N-cyclopropylquinazolin-4-amine To a mixture of 6-bromo-2,4-dichloroquinazoline (2223 mg, 8 mmol) and N-(3-chlorobenzyl)cyclopropanamine, HCl (1832 mg, 8.40 mmol) in THF (25 mL) was added triethylamine (1214 mg, 12.0 mmol) at rt. The mixture was stirred at rt for 2 h. The mixture was poured into EtOAc/H₂O (60 mL/60 mL). The organic layer was dried over Na₂SO₄ and filtered. After removal of solvent the product was purified by silica gel chromatography using 0-40% EtOAc/hexane as the eluent to give 6-bromo-2-chloro-N-(3-chlorobenzyl)-N-cyclopropylquinazolin-4-amine (2927 mg, 6.92 mmol, 86% yield). MS (M+H)⁺=424.

Step 2: 2-chloro-N-(3-chlorobenzyl)-N-cyclopropyl-6-(3,5-dimethylisoxazol-4-yl)quinazolin-4-amine In a 2-neck flask was placed 6-bromo-2-chloro-N-(3-chlorobenzyl)-N-cyclopropylquinazolin-4-amine (1058 mg, 2.5 mmol), 3,5-dimethyl-4-(4,4,5,5-tetramethyl-1,3,2-dioxaborolan-2-yl)isoxazole (613 mg, 2.75 mmol), PdCl₂(dppf)-CH₂Cl₂ adduct (204 mg, 0.25 mmol), and potassium carbonate (1140 mg, 8.25 mmol). The air was removed and re-filled with N₂ (3 times). Then, 1,4-dioxane (10 mL)/water (4 mL) was added and heated at 75-80° C. for 1.5 h. After cooling to rt, the layer was separated and the aqueous layer was extracted with EtOAc (5 mL×2). The combined organic layer was dried over Na₂SO₄ and filtered. After removal of solvent, the product was purified by silica gel chromatography using 20-70% EtOAc/hexane as the eluent to give 2-chloro-N-(3-chlorobenzyl)-N-cyclopropyl-6-(3,5-dimethylisoxazol-4-yl)quinazolin-4-amine (1013 mg, 2.306 mmol, 92% yield). MS (M+H)⁺=440.

Step 3: 1-(4-(4-((3-chlorobenzyl)(cyclopropyl)amino)-6-(3,5-dimethylisoxazol-4-yl)quinazolin-2-yl)-1H-pyrazol-1-yl)-2-methylpropan-2-ol, TFA In a microwave tube was placed 2-chloro-N-(3-chlorobenzyl)-N-cyclopropyl-6-(3,5-dimethylisoxazol-4-yl)quinazolin-4-amine (65.9 mg, 0.15 mmol), 2-methyl-1-(4-(4,4,5,5-tetramethyl-1,3,2-dioxaborolan-2-yl)-1H-pyrazol-1-yl) propan-2-ol (80 mg, 0.30 mmol), PdCl₂(dppf)-CH₂Cl₂ adduct (12.25 mg, 0.015 mmol), and potassium carbonate (124 mg, 0.90 mmol). The air was removed and re-filled with N₂ (3 times). Then, 1,4-dioxane (1.5 ml)/water (0.5 mL) was added and heated at 90° C. for 1.5 hr. After cooling to rt, the layer was separated and the aqueous layer was extracted with EtOAc (3 mL×2). The combined organic layer was filtered through PL-Thiol MP resin and then eluted with MeOH. After removal of solvent, the crude product dissolved in DMF, filtered, and purified by semi-preparative HPLC to give 1-(4-(4-((3-chlorobenzyl)(cyclopropyl) amino)-6-(3,5-dimethylisoxazol-4-yl)quinazolin-2-yl)-1H-pyrazol-1-yl)-2-methylpropan-2-ol, TFA (23.6 mg, 0.036 mmol, 23.94% yield). MS (M+H)⁺=543.

Example 313. (S)-7-(6-(3,5-dimethylisoxazol-4-yl)-4-(3-phenylmorpholino)quinazolin-2-yl)-7-azaspiro[3.5]nonan-2-ol, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 7-azaspiro[3.5]nonan-2-ol, HCl (40.0 mg, 0.225 mmol) according to similar procedure described in Example 265. ¹H NMR (400 MHz, DMSO-d₆) δ 11.98 (s, 1H), 7.85-7.60 (m, 3H), 7.51 (d, J=7.7 Hz, 2H), 7.44-7.25 (m, 3H), 5.73 (s, 1H), 5.00-2.96 (m, 12H), 2.35-1.83 (m, 8H), 1.71-1.31 (m, 6H). (including one salt NH); MS (M+H)⁺=526.

Example 314. (S)-8-(6-(3,5-dimethylisoxazol-4-yl)-4-(3-phenylmorpholino)quinazolin-2-yl)-1,8-diazaspiro[4.5]decan-2-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1,8-diazaspiro[4.5]decan-2-one, HCl (42.9 mg, 0.225 mmol) according to similar procedure described in Example 265. ¹H NMR (400 MHz, DMSO-d₆) δ 12.06 (s, 1H), 8.13 (s, 1H), 7.79 (s, 2H), 7.51 (d, J=7.3 Hz, 2H), 7.44-7.21 (m, 3H), 5.73 (s, 1H), 4.77-2.99 (m, 10H), 2.35-2.16 (m, 5H), 2.09 (s, 3H), 1.87 (t, J=7.8 Hz, 2H), 1.62 (s, 4H); MS (M+H)⁺=539.

Example 315. (S)-6-(3,5-dimethylisoxazol-4-yl)-N-(1,1-dioxidothietan-3-yl)-4-(3-phenylmorpholino) quinazoline-2-carboxamide, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 3-aminothietane 1,1-dioxide (27.3 mg, 0.225 mmol) and HATU (114 mg, 0.30 mmol) according to similar procedure described in Example 273. ¹H NMR (400 MHz, DMSO-d₆) δ 9.26 (d, J=6.1 Hz, 1H), 8.05 (d, J=8.7 Hz, 1H), 7.95 (dd, J=8.7, 1.7 Hz, 1H), 7.87 (s, 1H), 7.55 (d, J=7.6 Hz, 2H), 7.38 (t, J=7.5 Hz, 2H), 7.28 (t, J=7.4 Hz, 1H), 5.78 (s, 1H), 4.76-3.72 (m, 11H), 2.29 (s, 3H), 2.12 (s, 3H); MS (M+H)⁺=534.

Example 316. (S)-(6-(3,5-dimethylisoxazol-4-yl)-4-(3-phenylmorpholino)quinazolin-2-yl)(2-hydroxy-7-azaspiro[3.5]nonan-7-yl)methanone, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 7-azaspiro[3.5]nonan-2-ol, HCl (40.0 mg, 0.225 mmol) and HATU (114 mg, 0.30 mmol) according to similar procedure described in Example 273. ¹H NMR (400 MHz, DMSO-d₆) δ 7.93-7.86 (m, 3H), 7.48 (d, J=8.1 Hz, 2H), 7.39-7.31 (m, 2H), 7.31-7.23 (m, 1H), 5.51 (d, J=4.0 Hz, 1H), 4.26 (dt, J=12.4, 3.8 Hz, 1H), 4.16-3.32 (m, 9H), 2.91

(t, J=5.6 Hz, 1H), 2.83 (t, J=5.8 Hz, 1H), 2.30 (s, 3H), 2.17-2.08 (m, 5H), 1.64-1.14 (m, 6H); MS (M+H)$^+$=554.

Example 317. (S)-(6-(3,5-dimethylisoxazol-4-yl)-4-(3-phenylmorpholino)quinazolin-2-yl)(1-methyl-1,4,5,7-tetrahydro-6H-pyrazolo[3,4-c]pyridin-6-yl)methanone, TFA The title compound was prepared from (S)-6-(3,5-dimethylisoxazol-4-yl)-4-(3-phenylmorpholino)quinazoline-2-carboxylic acid (Example 273, STEP 3, 32.3 mg, 0.075 mmol), 1-methyl-4,5,6,7-tetrahydro-1H-pyrazolo[3,4-c]pyridine, HCl (39.1 mg, 0.225 mmol) and HATU (114 mg, 0.30 mmol) according to similar procedure described in Example 273. $^1$H NMR (400 MHz, DMSO-d$_6$) δ 7.97-7.81 (m, 3H), 7.52-7.47 (m, 2H), 7.41-7.20 (m, 3H), 7.28 and 7.02 (two set of s, 1H), 5.60 and 5.49 (two set of br s, 1H), 4.37-3.67 (m, 10H), 3.66 and 3.64 (two set of s, 3H), 3.38-3.36 (m, 1H), 2.81-2.49 (m, 1H), 2.30 and 2.29 (two set of s, 3H), 2.13 and 2.12 (two set of s, 3H) (two rotamers); MS (M+H)$^+$=550.

Example 318. (S)-4-(6-(3,5-dimethylisoxazol-4-yl)-2-(1-methyl-1,4,5,7-tetrahydro-6H-pyrazolo[3,4-c]pyridin-6-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-methyl-4,5,6,7-tetrahydro-1H-pyrazolo[3,4-c]pyridine, 2HCl (47.3 mg, 0.225 mmol) according to similar procedure described in Example 265. $^1$H NMR (400 MHz, DMSO-d$_6$) δ 7.92-7.62 (m, 3H), 7.52 (d, J=7.5 Hz, 2H), 7.45-7.23 (m, 4H), 5.80 (br s, 1H), 4.82 (d, J=14.9 Hz, 1H), 4.69 (s, 1H), 4.52-3.17 (m, 12H), 2.78 (br s, 1H), 2.26 (s, 3H), 2.09 (s, 3H); MS (M+H)$^+$=522.

Example 319. tert-butyl (S)-4-(4-(6-(3,5-dimethylisoxazol-4-yl)-4-(3-phenylmorpholino)quinazolin-2-yl)-1H-pyrazol-1-yl)piperidine-1-carboxylate Step 1: tert-butyl (S)-4-(4-(6-(3,5-dimethylisoxazol-4-yl)-4-(3-phenylmorpholino)quinazolin-2-yl)-1H-pyrazol-1-yl)piperidine-1-carboxylate In a 2-neck flask was placed (S)-4-(2-chloro-6-(3,5-dimethylisoxazol-4-yl)quinazolin-4-yl)-3-phenylmorpholine (Example 262, STEP 2, 168 mg, 0.4 mmol), tert-butyl 4-(4-(4,4,5,5-tetramethyl-1,3,2-dioxaborolan-2-yl)-1H-pyrazol-1-yl)piperidine-1-carboxylate (226 mg, 0.60 mmol), PdCl$_2$(dppf)-CH$_2$Cl$_2$ adduct (32.7 mg, 0.04 mmol), and potassium carbonate (249 mg, 1.80 mmol). The air was removed and re-filled with N$_2$ (3 times). Then, 1,4-dioxane (3 mL)/water (1 mL) was added and heated at 90° C. for 1.5 h. After cooling to rt, the layer was separated and the aqueous layer was extracted with EtOAc (5 mL×2). The combined organic layer was dried over Na$_2$SO$_4$ and filtered. After removal of solvent, the product was purified by silica gel chromatography using 40-100% EtOAc/hexane as the eluent to give tert-butyl (S)-4-(4-(6-(3,5-dimethylisoxazol-4-yl)-4-(3-phenylmorpholino)quinazolin-2-yl)-1H-pyrazol-1-yl)piperidine-1-carboxylate (221 mg, 0.348 mmol, 87% yield). MS (M+H)$^+$=636.

Step 2: (S)-4-(6-(3,5-dimethylisoxazol-4-yl)-2-(1-(piperidin-4-yl)-1H-pyrazol-4-yl)quinazolin-4-yl)-3-phenylmorpholine, HCl To a solution of tert-butyl (S)-4-(4-(6-(3,5-dimethylisoxazol-4-yl)-4-(3-phenylmorpholino)quinazolin-2-yl)-1H-pyrazol-1-yl)piperidine-1-carboxylate (221 mg, 0.348 mmol) in CH$_2$Cl$_2$ (2 mL) was add HCl (4 M in 1,4-dioxane, 2.78 mmol, 0.7 mL, 8 equiv). The mixture was stirred at rt for 2 hr. Then, hexane (15 mL) was added and stirred for 15 min. The solvent was then removed by pipet. Additional hexane (15 mL) was added and removed 3 times. The remaining solid was dried to give (S)-4-(6-(3,5-dimethylisoxazol-4-yl)-2-(1-(piperidin-4-yl)-1H-pyrazol-4-yl)quinazolin-4-yl)-3-phenylmorpholine, HCl (195 mg, 0.341 mmol, 98% yield). $^1$H NMR (400 MHz, DMSO-d$_6$) δ 9.36-8.75 (m, 4H), 8.62 (s, 1H), 8.37 (s, 1H), 8.01 (d, J=8.7 Hz, 1H), 7.60 (d, J=7.7 Hz, 2H), 7.42-7.33 (m, 3H), 5.73 (br s, 1H), 4.72-4.35 (m, 2H), 3.98-3.95 (m, 2H), 3.78-3.73 (m, 1H), 3.42-3.33 (m, 3H), 3.12-3.03 (m, 3H), 2.42-1.90 (m, 10H) (including one salt NH); MS (M+H)$^+$=536.

Example 320. (S)-8-(6-(3,5-dimethylisoxazol-4-yl)-4-(3-phenylmorpholino)quinazolin-2-yl)-2-methyl-2,8-diazaspiro[4.5]decan-1-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 2-methyl-2,8-diazaspiro[4.5]decan-1-one, HCl (46.1 mg, 0.225 mmol) according to similar procedure described in Example 265. $^1$H NMR (400 MHz, DMSO-d$_6$) δ 12.00 (s, 1H), 7.85-7.65 (m, 3H), 7.51 (d, J=7.4 Hz, 2H), 7.43-7.25 (m, 3H), 5.76 (br s, 1H), 4.58-3.11 (m, 12H), 2.71 (s, 3H), 2.25 (s, 3H), 2.08 (s, 3H), 1.98 (t, J=6.9 Hz, 2H), 1.69-1.47 (m, 4H) (including one salt NH); MS (M+H)$^+$=553.

Example 321. (S)-(5-(6-(3,5-dimethylisoxazol-4-yl)-4-(3-phenylmorpholino)quinazolin-2-yl)pyridin-2-yl)methanol, TFA The title compound was prepared from (S)-4-(2-chloro-6-(3,5-dimethylisoxazol-4-yl)quinazolin-4-yl)-3-phenylmorpholine (Example 262, STEP 2, 42.1 mg, 0.1 mmol), (6-(hydroxymethyl)pyridin-3-yl)boronic acid (30.6 mg, 0.20 mmol), PdCl$_2$(dppf)-CH$_2$Cl$_2$ adduct (8.17 mg, 10.0 μmol), and potassium carbonate (83 mg, 0.60 mmol) according to similar procedure described in Example 262. $^1$H NMR (400 MHz, DMSO-d$_6$) δ 9.36 (d, J=2.4 Hz, 1H), 8.73 (dd, J=8.2, 2.2 Hz, 1H), 7.99 (d, J=8.6 Hz, 1H), 7.93 (d, J=1.8 Hz, 1H), 7.90 (dd, J=8.6, 1.9 Hz, 1H), 7.65 (d, J=8.3 Hz, 1H), 7.59-7.52 (m, 2H), 7.33 (dd, J=8.4, 7.0 Hz, 2H), 7.26-7.19 (m, 1H), 5.54 (s, 1H), 4.66 (s, 2H), 4.19 (dd, J=12.0, 4.7 Hz, 1H), 4.11 (d, J=12.9 Hz, 1H), 4.04-3.72 (m, 5H), 2.34 (s, 3H), 2.16 (s, 3H); MS (M+H)$^+$=494.

Example 322. (S)—N-cyclopropyl-4-(6-(3,5-dimethylisoxazol-4-yl)-2-(1-(2-hydroxy-2-methylpropyl)-1H-pyrazol-4-yl)quinazolin-4-yl)-3-phenylpiperazine-1-carboxamide, TFA Step 1: (S)-4-(2-chloro-6-(3,5-dimethylisoxazol-4-yl)quinazolin-4-yl)-N-cyclopropyl-3-phenylpiperazine-1-carboxamide To a solution of (S)-4-(2-chloro-4-(2-phenylpiperazin-1-yl)quinazolin-6-yl)-3,5-dimethylisoxazole, 2HCl (Example 291, STEP 3, 0.178 g, 0.3 mmol) in CH$_2$Cl$_2$ (3 ml) was added Et$_3$N (0.418 ml, 3.0 mmol) and then isocyanatocyclopropane (0.075 g, 0.90 mmol) slowly. The mixture was stirred at rt for 30 min. The mixture was concentrated and EtOAc/H$_2$O (5 mL/5 mL) was added. The aqueous layer was extracted with EtOAc (5 mL×2). The combined organic layer was dried over Na$_2$SO$_4$, and filtered. After removal of the solvent, the product was dried in vacuo to give (S)-4-(2-chloro-6-(3,5-dimethylisoxazol-4-yl)quinazolin-4-yl)-N-cyclopropyl-3-phenylpiperazine-1-carboxamide, which was used for next step without further purification. MS (M+H)$^+$=503.

Step 2: (S)—N-cyclopropyl-4-(6-(3,5-dimethylisoxazol-4-yl)-2-(1-(2-hydroxy-2-methylpropyl)-1H-pyrazol-4-yl)quinazolin-4-yl)-3-phenylpiperazine-1-carboxamide, TFA In a microwave tube was placed (S)-4-(2-chloro-6-(3,5-dimethylisoxazol-4-yl)quinazolin-4-yl)-N-cyclopropyl-3-phenylpiperazine-1-carboxamide (92 mg, 0.15 mmol), 2-methyl-1-(4-(4,4,5,5-tetramethyl-1,3,2-dioxaborolan-2-yl)-1H-pyrazol-1-yl)propan-2-ol (80 mg, 0.30 mmol), PdCl$_2$(dppf)-CH$_2$Cl$_2$ adduct (12.25 mg, 0.015 mmol), and potassium carbonate (124 mg, 0.90 mmol). The air was removed and re-filled with N$_2$ (3 times). Then, 1,4-dioxane (1.5 mL)/water (0.5 mL) was added and heated at 90° C. for 1.5 h. After cooling to rt, the layer was separated and the aqueous layer was extracted with EtOAc (3 mL×2). The combined organic layer was filtered through PL-Thiol MP resin and then eluted with MeOH. After removal of solvent, the crude product was dissolved in DMF, filtered, and purified by semi-preparative HPLC to give (S)—N-cyclopropyl-4-(6-(3,5-dimethylisoxazol-4-yl)-2-(1-(2-hydroxy-2-methylpropyl)-1H-pyrazol-4-yl)quinazolin-4-yl)-3-phenylpiperazine-1-carboxamide, TFA (8.9 mg, 0.012 mmol, 8.23% yield). $^1$H NMR (400 MHz, DMSO-d$_6$) δ 8.48 (s, 1H), 8.09 (s, 1H), 7.92-7.87 (m, 3H), 7.57-7.48 (m, 2H), 7.33-7.24 (m, 3H), 6.58 (d, J=2.7 Hz, 1H), 5.78 (br s, 1H), 4.09 (s, 2H), 5.02-2.91 (m, 7H), 2.50-2.00 (m, 7H), 1.08 (s, 6H), 0.55-0.38 (m, 2H), 0.38-0.17 (m, 2H); MS (M+H)$^+$=607.

Example 323. (S)-(5-(6-(3,5-dimethylisoxazol-4-yl)-4-(3-phenylmorpholino)quinazolin-2-yl)thiophen-2-yl)methanol, TFA The title compound was prepared from (S)-4-(2-chloro-6-(3,5-dimethylisoxazol-4-yl)quinazolin-4-yl)-3-phenylmorpholine (Example 262, STEP 2, 42.1 mg, 0.1 mmol), (5-(hydroxymethyl)thiophen-2-yl)boronic acid (31.6 mg, 0.20 mmol), PdCl$_2$(dppf)-CH$_2$Cl$_2$ adduct (8.17 mg, 10.0 µmol), and potassium carbonate (83 mg, 0.60 mmol) according to similar procedure described in Example 262. $^1$H NMR (400 MHz, DMSO-d$_6$) δ 7.89-7.78 (m, 4H), 7.59-7.50 (m, 2H), 7.34 (t, J=7.6 Hz, 2H), 7.24 (dd, J=8.3, 6.4 Hz, 2H), 7.02 (d, J=3.7 Hz, 1H), 5.55 (s, 1H), 4.68-4.60 (m, 2H), 4.30-3.63 (m, 7H), 2.30 (s, 3H), 2.13 (s, 3H); MS (M+H)$^+$=499.

Examples 324 and 326 (S)-1-(3-(4-(6-(3,5-dimethylisoxazol-4-yl)-4-(3-phenylmorpholino)quinazolin-2-yl)-1H-pyrazol-1-yl)azetidin-1-yl)ethan-1-one, TFA (Example 324) and (S)-4-(2-(1-(azetidin-3-yl)-1H-pyrazol-4-yl)-6-(3,5-dimethylisoxazol-4-yl)quinazolin-4-yl)-3-phenylmorpholine, TFA (Example 326)

Step 1: tert-butyl (S)-3-(4-(6-(3,5-dimethylisoxazol-4-yl)-4-(3-phenylmorpholino)quinazolin-2-yl)-1H-pyrazol-1-yl)azetidine-1-carboxylate In a 2-neck flask was placed (S)-4-(2-chloro-6-(3,5-dimethylisoxazol-4-yl)quinazolin-4-yl)-3-phenylmorpholine (Example 262, STEP 2, 168 mg, 0.4 mmol), tert-butyl 3-(4-(4,4,5,5-tetramethyl-1,3,2-dioxaborolan-2-yl)-1H-pyrazol-1-yl)azetidine-1-carboxylate (210 mg, 0.60 mmol), PdCl$_2$(dppf)-CH$_2$Cl$_2$ adduct (32.7 mg, 0.04 mmol), and potassium carbonate (249 mg, 1.80 mmol). The air was removed and re-filled with N$_2$ (3 times). Then, 1,4-dioxane (3 mL)/water (1 mL) was added and heated at 90° C. for 1.5 h. After cooling to rt, the layer was separated and the aqueous layer was extracted with EtOAc (5 mL×2). The combined organic layer was dried over Na$_2$SO$_4$ and filtered. After removal of solvent, the product was purified by silica gel chromatography using 40-100% EtOAc/hexane as the eluent to give tert-butyl (S)-3-(4-(6-(3,5-dimethylisoxazol-4-yl)-4-(3-phenylmorpholino)quinazolin-2-yl)-1H-pyrazol-1-yl)azetidine-1-carboxylate (220 mg, 0.362 mmol, 91% yield). MS (M+H)$^+$=608.

Step 2: (S)-4-(2-(1-(azetidin-3-yl)-1H-pyrazol-4-yl)-6-(3,5-dimethylisoxazol-4-yl)quinazolin-4-yl)-3-phenylmorpholine, TFA (Example 326)

To a solution of tert-butyl (S)-3-(4-(6-(3,5-dimethylisoxazol-4-yl)-4-(3-phenylmorpholino)quinazolin-2-yl)-1H-pyrazol-1-yl)azetidine-1-carboxylate (220 mg, 0.362 mmol) in CH$_2$Cl$_2$ (2 mL) was add HCl (4 M in 1,4-dioxane, 2.89 mmol, 0.72 mL, 8 equiv.). The mixture was stirred at rt for 2 h. Then, hexane (15 mL) was added and stirred for 15 min. The solvent was removed by pipet. Additional hexane (15 mL) was added and removed 3 times. The remaining solid was dried to give 191 mg of HCl salt (~97%). About 40 mg of the product was dissolved in DMF and purified by semi-preparative HPLC to give (S)-4-(2-(1-(azetidin-3-yl)-1H-pyrazol-4-yl)-6-(3,5-dimethylisoxazol-4-yl)quinazolin-4-yl)-3-phenylmorpholine, TFA (2 mg, 3.22 µmol, 0.889% yield). The rest of material was used for next step without further purification. $^1$H NMR (400 MHz, DMSO-d$_6$) δ 9.05 (s, 1H), 8.83 (s, 1H), 8.58 (s, 1H), 8.27 (s, 1H), 7.85 (s, 3H), 7.59-7.48 (m, 2H), 7.33 (t, J=7.5 Hz, 2H), 7.23 (t, J=7.3 Hz, 1H), 5.66-5.35 (m, 2H), 4.49-3.43 (m, 10H), 2.32 (s, 3H), 2.14 (s, 3H). (including one salt NH); MS (M+H)$^+$=508.

Step 3: (S)-1-(3-(4-(6-(3,5-dimethylisoxazol-4-yl)-4-(3-phenylmorpholino)quinazolin-2-yl)-1H-pyrazol-1-yl)azetidin-1-yl)ethan-1-one, TFA (Cpd. 324)

To a solution of (S)-4-(2-(1-(azetidin-3-yl)-1H-pyrazol-4-yl)-6-(3,5-dimethylisoxazol-4-yl)quinazolin-4-yl)-3-phenylmorpholine, HCl (40.8 mg, 0.075 mmol) in CH$_2$Cl$_2$ (1 mL) was added Et$_3$N (0.063 mL, 0.45 mmol) and then acetyl chloride (0.016 mL, 0.225 mmol). The mixture was stirred at rt for 30 min. The mixture was concentrated and then EtOAc/H$_2$O/Na$_2$CO$_3$ (aq) (3 mL/2/mL/2 mL) was added. The aqueous layer (basic) was extracted with EtOAc (3 mL×2). The combined organic layer was dried over Na$_2$SO$_4$ and filtered. After removal of the solvent, the crude product was dissolved in DMF, filtered, and purified by semi-preparative HPLC to give (S)-1-(3-(4-(6-(3,5-dimethylisoxazol-4-yl)-4-(3-phenylmorpholino)quinazolin-2-yl)-1H-pyrazol-1-yl)azetidin-1-yl)ethan-1-one, TFA (4.7 mg, 7.08 µmol, 9.44% yield). $^1$H NMR (400 MHz, DMSO-d$_6$) δ 8.73 (s, 1H), 8.33 (s, 1H), 7.91-7.86 (m, 3H), 7.56 (d, J=7.6 Hz, 2H), 7.37 (t, J=7.6 Hz, 2H), 7.27 (t, J=7.4 Hz, 1H), 5.75 (br s, 1H), 5.35 (ddd, J=10.3, 8.1, 5.2 Hz, 1H), 4.59 (t, J=8.5 Hz, 1H), 4.42 (dt, J=9.4, 4.9 Hz, 1H), 4.37-4.25 (m, 1H), 4.13 (dt, J=10.0, 5.0 Hz, 1H), 4.04-3.58 (m, 6H), 2.30 (s, 3H), 2.12 (s, 3H), 1.81 (s, 3H); MS (M+H)$^+$=550.

Example 325. (S)-(4-(6-(3,5-dimethylisoxazol-4-yl)-4-(3-phenylmorpholino)quinazolin-2-yl)thiophen-2-yl)methanol, TFA The title compound was prepared from (S)-4-(2-chloro-6-(3,5-dimethylisoxazol-4-yl)quinazolin-4-yl)-3-phenylmorpholine (Example 262, STEP 2, 42.1 mg, 0.1 mmol), (5-(hydroxymethyl)thiophen-3-yl)boronic acid (31.6 mg, 0.20 mmol), PdCl$_2$(dppf)-CH$_2$Cl$_2$ adduct (8.17 mg, 10.0 µmol), and potassium carbonate (83 mg, 0.60 mmol) according to similar procedure described in Example 262. $^1$H NMR (400 MHz, DMSO-d$_6$) δ 8.39 (s, 1H), 8.00-7.83 (m, 3H), 7.70 (s, 1H), 7.56 (d, J=7.7 Hz, 2H), 7.35 (t, J=7.4 Hz, 2H), 7.26 (q, J=6.6 Hz, 1H), 5.69 (br s, 1H), 4.67 (d, J=1.1 Hz, 2H), 4.38-3.45 (m, 7H), 2.31 (s, 3H), 2.14 (s, 3H); MS (M+H)$^+$=499.

Example 327. (S)-1-(4-(4-(6-(3,5-dimethylisoxazol-4-yl)-4-(3-phenylmorpholino)quinazolin-2-yl)-1H-pyrazol-1-yl)piperidin-1-yl)ethan-1-one, TFA To a solution of (S)-4-(6-(3,5-dimethylisoxazol-4-yl)-2-(1-(piperidin-4-yl)-1H-pyrazol-4-yl)quinazolin-4-yl)-3-phenylmorpholine, HCl (Example 319, 42.9 mg, 0.075 mmol) in CH$_2$Cl$_2$ (1 mL) was added Et$_3$N (0.063 mL, 0.45 mmol) and then acetyl chloride (0.016 mL, 0.225 mmol). The mixture was stirred at rt for 30 min. The mixture was concentrated and then EtOAc/H$_2$O/Na$_2$CO$_{3(aq)}$ (3 mL/2/mL/2 mL) was added. The basic aqueous layer was extracted with EtOAc (3 mL×2). The combined organic layer was dried over Na$_2$SO$_4$ and filtered. After removal of solvent, the crude product was dissolved in DMF, filtered, and purified by semi-preparative HPLC to give (S)-1-(4-(4-(6-(3,5-dimethylisoxazol-4-yl)-4-(3-phenylmorpholino)quinazolin-2-yl)-1H-pyrazol-1-yl)piperidin-1-yl)ethan-1-one, TFA (6.3 mg, 9.11 µmol, 12.14% yield). $^1$H NMR (400 MHz, DMSO-d$_6$) δ 8.66 (s, 1H), 8.27 (s, 1H), 7.92-7.82 (m, 3H), 7.57 (d, J=7.6 Hz, 2H), 7.38 (t, J=6.2 Hz, 2H), 7.29 (d, J=6.0 Hz, 1H), 5.78 (br s, 1H), 4.60-4.26 (m, 3H), 4.02-3.71 (m, 6H), 3.20 (t, J=12.0 Hz, 1H), 2.78-2.65 (m, 1H), 2.30 (s, 3H), 2.11 (s, 3H), 2.06 (br s, 2H), 2.03 (s, 3H), 1.91 (qd, J=11.2, 10.5, 4.0 Hz, 1H), 1.84-1.70 (m, 1H); MS (M+H)$^+$=578.

Example 328. (S)-4-(6-(3,5-dimethylisoxazol-4-yl)-2-(1-methyl-1,4,6,7-tetrahydro-5H-imidazo[4,5-c]pyridin-5-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-methyl-4,5,6,7-tetrahydro-1H-imidazo[4,5-c]pyridine (30.9 mg, 0.225 mmol) according to similar procedure described in Example 265. $^1$H NMR (400 MHz, DMSO-d$_6$) δ 8.83 (s, 1H), 7.76 (s, 1H), 7.68 (d, J=8.7 Hz, 1H), 7.56 (s, 1H), 7.47 (d, J=7.6 Hz, 2H), 7.31 (t, J=7.6 Hz, 2H), 7.22 (t, J=7.4 Hz, 1H), 5.24 (s, 1H), 4.95 (d, J=16.5 Hz, 1H), 4.74 (d, J=16.4 Hz, 1H), 4.19-3.49 (m, 9H), 3.68 (s, 3H), 2.69 (br s, 1H), 2.30 (s, 3H), 2.13 (s, 3H); MS (M+H)$^+$=522.

Example 329. (S)-8-(6-(3,5-dimethylisoxazol-4-yl)-4-(3-phenylmorpholino)quinazolin-2-yl)-2,8-diazaspiro[4.5]decan-1-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 2,8-diazaspiro[4.5]decan-1-one, HCl (42.9 mg, 0.225 mmol) according to similar procedure described in Example 265. $^1$H NMR (400 MHz, DMSO-d$_6$) δ 12.02 (s, 1H), 7.90-7.67 (m, 3H), 7.62 (s, 1H), 7.51 (d, J=6.5 Hz, 2H), 7.42-7.22 (m, 3H), 5.78 (br s, 1H), 4.57-3.02 (m, 12H), 2.26 (s, 3H), 2.09 (s, 3H), 2.01 (dd, J=8.0, 5.2 Hz, 2H), 1.68-1.47 (m, 4H) (including one salt NH); MS (M+H)$^+$=539.

Example 330. (S)-8-(6-(3,5-dimethylisoxazol-4-yl)-4-(3-phenylmorpholino)quinazolin-2-yl)-1-methyl-1,8-diazaspiro[4.5]decan-2-one, TFA The title compound was prepared from (S)-4-(2-chloro-6-(3,5-dimethylisoxazol-4-yl)quinazolin-4-yl)-3-phenylmorpholine (Example 262, STEP 2, 31.6 mg, 0.075 mmol) and 1-methyl-1,8-diazaspiro[4.5]decan-2-one, 2HCl (54.3 mg, 0.225 mmol) according to similar procedure described in Example 265. $^1$H NMR (400 MHz, DMSO-d$_6$) δ 12.32-11.75 (m, 1H), 7.90-7.63 (m, 3H), 7.56-7.44 (m, 2H), 7.40-7.29 (m, 3H), 5.78 (br s, 1H), 4.73-2.91 (m, 13H), 2.52 (br s, 2H), 2.34-2.20 (m, 5H), 2.10 (s, 3H), 2.03-1.26 (m, 4H); (including one salt NH) MS (M+H)$^+$=553.

Example 331. (S)—N-((3,5-dimethyl-1H-pyrazol-4-yl)methyl)-6-(3,5-dimethylisoxazol-4-yl)-4-(3-phenylmorpholino)quinazoline-2-carboxamide The title compound was prepared from (S)-6-(3,5-dimethylisoxazol-4-yl)-4-(3-phenylmorpholino)quinazoline-2-carboxylic acid (Example 273, STEP 3, 0.032 g, 0.075 mmol), (3,5-dimethyl-1H-pyrazol-4-yl)methanamine, HCl (0.036 g, 0.225 mmol) and HATU (0.114 g, 0.30 mmol) according to similar procedure described in Example 273. MS (M+H)$^+$=538.

Example 332. 1-(6-(3,5-dimethylisoxazol-4-yl)-2-(1-(2-hydroxy-2-methylpropyl)-1H-pyrazol-4-yl)quinazolin-4-yl)-N-methylpiperidine-4-carboxamide The title compound was prepared from 1-(2-chloro-6-(3,5-dimethylisoxazol-4-yl)quinazolin-4-yl)-N-methylpiperidine-4-carboxamide (Example 267, STEP 1, 0.08 g, 0.1 mmol), 2-methyl-1-(4-(4,4,5,5-tetramethyl-1,3,2-dioxaborolan-2-yl)-1H-pyrazol-1-yl)propan-2-ol (0.053 g, 0.20 mmol), PdCl$_2$(dppf)-CH$_2$Cl$_2$ adduct (8.17 mg, 10.0 µmol), and potassium carbonate (0.083 g, 0.60 mmol) according to similar procedure described in Example 262. MS (M+H)$^+$=504.

Example 333. (S)-4-(6-(3,5-dimethylisoxazol-4-yl)-2-(1-(tetrahydro-2H-pyran-4-yl)-1H-pyrazol-4-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 0.032 g, 0.075 mmol), 1-(tetrahydro-2H-pyran-4-yl)-4-(4,4,5,5-tetramethyl-1,3,2-dioxaborolan-2-yl)-1H-pyrazole (0.042 g, 0.15 mmol), PdCl$_2$(dppf)-CH$_2$Cl$_2$ adduct (6.12 mg, 7.50 μmol), and potassium carbonate (0.062 g, 0.45 mmol) according to similar procedure described in Example 262. MS (M+H)$^+$=537.

Example 334. (S)-4-(6-(3,5-dimethylisoxazol-4-yl)-2-(1-methyl-1H-pyrazol-4-yl)quinazolin-4-yl)-3-phenylmorpholine, TFA The title compound was prepared from (S)-4-(2-chloro-6-(3,5-dimethylisoxazol-4-yl)quinazolin-4-yl)-3-phenylmorpholine (Example 262, STEP 2, 63.1 mg, 0.15 mmol), 1-methyl-4-(4,4,5,5-tetramethyl-1,3,2-dioxaborolan-2-yl)-1H-pyrazole (62.4 mg, 0.30 mmol), PdCl$_2$(dppf)-CH$_2$Cl$_2$ adduct (12.25 mg, 0.015 mmol), and potassium carbonate (124 mg, 0.90 mmol) according to similar procedure described in Example 262. $^1$H NMR (400 MHz, DMSO-d$_6$) δ 8.57 (s, 1H), 8.21 (s, 1H), 7.95-7.80 (m, 3H), 7.57 (d, J=7.6 Hz, 2H), 7.37 (t, J=7.5 Hz, 2H), 7.29 (d, J=7.3 Hz, 1H), 6.10-5.50 (br s, 1H), 4.35 (br s, 2H), 3.97-3.95 (m, 2H), 3.92 (s, 3H), 3.85-3.71 (m, 2H), 2.38-2.21 (s, 3H), 2.12 (s, 3H); MS (M+H)$^+$=467.

Example 335. (S)-3-(4-(6-(3,5-dimethylisoxazol-4-yl)-4-(3-phenylmorpholino)quinazolin-2-yl)-1H-pyrazol-yl)propanenitrile, TFA The title compound was prepared from (S)-4-(2-chloro-6-(3,5-dimethylisoxazol-4-yl)quinazolin-4-yl)-3-phenylmorpholine (Example 262, STEP 2, 63.1 mg, 0.15 mmol), 3-(4-(4,4,5,5-tetramethyl-1,3,2-dioxaborolan-2-yl)-1H-pyrazol-1-yl)propanenitrile (74.1 mg, 0.30 mmol), PdCl$_2$(dppf)-CH$_2$Cl$_2$ adduct (12.25 mg, 0.015 mmol), and potassium carbonate (124 mg, 0.90 mmol) according to a similar procedure described in Example 262. $^1$H NMR (400 MHz, DMSO-d$_6$) δ 8.66 (s, 1H), 8.26 (s, 1H), 7.90 (s, 3H), 7.57 (d, J=7.4 Hz, 2H), 7.36 (t, J=7.6 Hz, 2H), 7.27 (t, J=7.5 Hz, 1H), 6.00-5.50 (br s, 1H), 4.49 (t, J=6.3 Hz, 2H), 4.41-3.71 (m, 6H), 3.17-3.09 (m, 2H), 2.30 (s, 3H), 2.12 (s, 3H); MS (M+H)$^+$=506.

Example 336. (S)-8-(4-(4-acetyl-2-phenylpiperazin-1-yl)-6-(3,5-dimethylisoxazol-4-yl)quinazolin-2-yl)-1-methyl-1,8-diazaspiro[4.5]decan-2-one, TFA The title compound was prepared from (S)-1-(4-(2-chloro-6-(3,5-dimethylisoxazol-4-yl)quinazolin-4-yl)-3-phenylpiperazin-1-yl)ethan-1-one (Example 309, STEP 1, 83 mg, 0.15 mmol) and 1-methyl-1,8-diazaspiro[4.5]decan-2-one, 2HCl (109 mg, 0.450 mmol) according to a similar procedure described in Example 265. $^1$H NMR (400 MHz, DMSO-d$_6$) δ 12.01 (s, 1H), 7.90-7.60 (m, 3H), 7.52-7.45 (m, 2H), 7.33-7.26 (m, 3H), 5.69 (m, 1H), 4.81-2.83 (m, 10H), 2.60-1.04 (m, 20H). (including one salt NH, some peaks are too broad to be assigned); MS (M+H)$^+$=594.

Example 337. (S)-8-(6-(3,5-dimethylisoxazol-4-yl)-4-(4-(methylsulfonyl)-2-phenylpiperazin-1-yl)quinazolin-2-yl)-1-methyl-1,8-diazaspiro[4.5]decan-2-one, TFA The title compound was prepared from (S)-4-(2-chloro-4-(4-(methylsulfonyl)-2-phenylpiperazin-1-yl)quinazolin-6-yl)-3,5-dimethylisoxazole (Example 310, STEP 1, 49.8 mg, 0.1 mmol) and 1-methyl-1,8-diazaspiro[4.5]decan-2-one, 2HCl (72.3 mg, 0.30 mmol) according to a similar procedure described in Example 265. $^1$H NMR (400 MHz, DMSO-d$_6$) δ 12.10 (s, 1H), 7.90-7.65 (m, 3H), 7.45-7.25 (d, J=7.6 Hz, 2H), 7.33 (m, 3H), 5.76 (d, J=31.5 Hz, 1H), 3.27 (d, J=108.3 Hz, 10H), 2.87 (s, 3H), 2.57-1.26 (m, 17H). (including one salt NH, some peaks are too broad to assign); MS (M+H)$^+$=630.

Example 338. (S)-5-(2-(1-(2-hydroxy-2-methylpropyl)-1H-pyrazol-4-yl)-4-(2-phenylpiperazin-1-yl)quinazolin-6-yl)-1-methylpyridin-2(1H)-one, HCl Step 1: tert-butyl (S)-4-(2-chloro-6-(1-methyl-6-oxo-1,6-dihydropyridin-3-yl)quinazolin-4-yl)-3-phenylpiperazine-1-carboxylate In a microwave tube was placed tert-butyl (S)-4-(6-bromo-2-chloroquinazolin-4-yl)-3-phenylpiperazine-1-carboxylate (Example 291, STEP 1, 756 mg, 1.5 mmol), 1-methyl-5-(4,4,5,5-tetramethyl-1,3,2-dioxaborolan-2-yl)pyridin-2(1H)-one (388 mg, 1.65 mmol), PdCl$_2$(dppf)-CH$_2$Cl$_2$ adduct (122 mg, 0.15 mmol), and potassium carbonate (684 mg, 4.95 mmol). The air was removed and re-filled with N$_2$ (3 times). Then, 1,4-dioxane (6 mL)/water (3 mL) was added and heated at 75° C. for 1 hr. After cooling to room temperature, H$_2$O (6 mL) and hexane (6 mL) were added. The solid was filtered, washed with H$_2$O (3 mL×3) and hexane (5 mL×3), and then dried to give tert-butyl (S)-4-(2-chloro-6-(1-methyl-6-oxo-1,6-dihydropyridin-3-yl)quinazolin-4-yl)-3-phenylpiperazine-1-carboxylate (768 mg, 1.443 mmol, 96% yield). The material contained some impurity and was used for next step without further purification. MS (M+H)$^+$=532.

Step 2: tert-butyl (S)-4-(2-(1-(2-hydroxy-2-methylpropyl)-1H-pyrazol-4-yl)-6-(1-methyl-6-oxo-1,6-dihydropyridin-3-yl)quinazolin-4-yl)-3-phenylpiperazine-1-carboxylate In a 2-neck flask was placed tert-butyl (S)-4-(2-chloro-6-(1-methyl-6-oxo-1,6-dihydropyridin-3-yl)quinazolin-4-yl)-3-phenylpiperazine-1-carboxylate (399 mg, 0.75 mmol), 2-methyl-1-(4-(4,4,5,5-tetramethyl-1,3,2-dioxaborolan-2-yl)-1H-pyrazol-1-yl)propan-2-ol (299 mg, 1.125 mmol), PdCl$_2$(dppf)-CH$_2$Cl$_2$ adduct (61.2 mg, 0.075 mmol), and potassium carbonate (466 mg, 3.38 mmol). The air was removed and the flask was re-filled with N$_2$ (3 times). Then, 1,4-dioxane (3 mL)/water (1 mL) was added and heated at 90° C. for 1.5 h. After cooling to room temperature, the layers were separated and the aqueous layer was extracted with EtOAc (5 mL×2). The combined organic layer was filtered through PL-Thiol MP resin and then eluted with MeOH. After removal of solvent, the product was purified by silica gel chromatography using 0-15% MeOH/EtOAc as the eluent to give tert-butyl (S)-4-(2-(1-(2-hydroxy-2-methylpropyl)-1H-pyrazol-4-yl)-6-(1-methyl-6-oxo-1,6-dihydropyridin-3-yl)quinazolin-4-yl)-3-phenylpiperazine-1-carboxylate (460 mg, 0.724 mmol, 96% yield). MS (M+H)$^+$=636.

Step 3: (S)-5-(2-(1-(2-hydroxy-2-methylpropyl)-1H-pyrazol-4-yl)-4-(2-phenylpiperazin-1-yl)quinazolin-6-yl)-1-methylpyridin-2(1H)-one, HCl To a solution of tert-butyl (S)-4-(2-(1-(2-hydroxy-2-methylpropyl)-1H-pyrazol-4-yl)-6-(1-methyl-6-oxo-1,6-dihydropyridin-3-yl)quinazolin-4-yl)-3-phenylpiperazine-1-carboxylate (460 mg, 0.724 mmol) in CH$_2$Cl$_2$ (5 ml) was added HCl (4M in dioxane, 1.45 mL, 5.79 mmol). The mixture was stirred at room temperature for 3 h. Then hexane (15 mL) was added and the mixture was stirred vigorously for 30 min. The solvent was carefully removed by pipet and then hexane (15 mL) was added. This process was repeated 3 times. The solid residue was dried in vacuo to give (S)-5-(2-(1-(2-hydroxy-2-methylpropyl)-1H-pyrazol-4-yl)-4-(2-phenylpiperazin-1-yl)quinazolin-6-yl)-1-methylpyridin-2(1H)-one, HCl (350 mg, 0.612 mmol, 85% yield). $^1$H NMR (400 MHz, DMSO-d$_6$) δ 9.95 (s, 1H), 9.34 (s, 1H), 8.87 (s, 1H), 8.55 (s, 1H), 8.35-7.85 (m, 3H), 7.68 (d, J=7.8 Hz, 2H), 7.57-7.24 (m, 3H), 6.44-6.16 (m, 1H), 5.99 (s, 1H), 4.13 (s, 2H), 5.13-3.22 (m, 10H), 1.09 (s, 6H). (some peaks are broad, NH not shown); MS (M+H)$^+$=536.

Example 339. 1-(4-(6-(3,5-dimethylisoxazol-4-yl)-4-morpholinoquinazolin-2-yl)-1H-pyrazol-1-yl)-2-methylpropan-2-ol Step 1: 1-(4-(4-(tert-butoxy)-6-(3,5-dimethylisoxazol-4-yl)quinazolin-2-yl)-1H-pyrazol-1-yl)-2-methylpropan-2-ol In a 2-neck flask was placed 4-(4-(tert-butoxy)-2-chloroquinazolin-6-yl)-3,5-dimethylisoxazole (Example 68, STEP 2, 1.27 g, 3.83 mmol), 2-methyl-1-(4-(4,4,5,5-tetramethyl-1,3,2-dioxaborolan-2-yl)-1H-pyrazol-1-yl)propan-2-ol (1.222 g, 4.59 mmol), PdCl$_2$(dppf)-CH$_2$Cl$_2$ adduct (0.313 g, 0.383 mmol), and potassium carbonate (1.904 g, 13.78 mmol). The air was removed and the flask was re-filled with N$_2$ (3 times). Then, 1,4-dioxane (10 mL)/water (5 mL) was added and heated at 90° C. for 1.5 h. After cooling to room temperature, the layers were separated and the aqueous layer was extracted with EtOAc (5 mL×3). The combined organic layer was dried (Na$_2$SO$_4$) and filtered. After removal of solvent, the product was purified by silica gel chromatography using 30-80% EtOAc/hexane as the eluent to give 1-(4-(4-(tert-butoxy)-6-(3,5-dimethylisoxazol-4-yl)quinazolin-2-yl)-1H-pyrazol-1-yl)-2-methylpropan-2-ol (1.28 g, 2.94 mmol, 77% yield). MS (M+H)$^+$=436.

Step 2: 6-(3,5-dimethylisoxazol-4-yl)-2-(1-(2-hydroxy-2-methylpropyl)-1H-pyrazol-4-yl)quinazolin-4-ol, HCl To a solution of 1-(4-(4-(tert-butoxy)-6-(3,5-dimethylisoxazol-4-yl)quinazolin-2-yl)-1H-pyrazol-1-yl)-2-methylpropan-2-ol (1.28 g, 2.94 mmol) in CH$_2$Cl$_2$ (8 mL) was added HCl (4M in dioxane, 23.5 mmol, 5.88 mL, 8 equiv) at room temperature. The mixture was stirred at room temperature for 1 h and hexane (20 mL) was added. The mixture was stirred for 10 min and the solid was filtered, triturated with hexane (3 mL×3), and then dried to give 6-(3,5-dimethylisoxazol-4-yl)-2-(1-(2-hydroxy-2-methylpropyl)-1H-pyrazol-4-yl)quinazolin-4-ol, HCl (1.21 g, 2.91 mmol, 99% yield) as a solid. The compound was used without further purification. MS (M+H)$^+$=380.

Step 3: 1-(4-(6-(3,5-dimethylisoxazol-4-yl)-4-morpholinoquinazolin-2-yl)-1H-pyrazol-1-yl)-2-methylpropan-2-ol To a suspension of 6-(3,5-dimethylisoxazol-4-yl)-2-(1-(2-hydroxy-2-methylpropyl)-1H-pyrazol-4-yl)quinazolin-4-ol, HCl (83 mg, 0.2 mmol) and bromo-tris-pyrrolidino-phosphonium hexafluorophosphate (186 mg, 0.400 mmol) in 1,4-dioxane (2 mL) was added Et$_3$N (0.195 mL, 1.40 mmol). The mixture was stirred at room temperature for 2 h and morpholine (34.8 mg, 0.40 mmol) was added. The mixture was stirred at room temperature for another 3 h. The mixture was partitioned in EtOAc/H$_2$O (5 mL/5 mL). The aqueous layer was extracted with EtOAc (5 mL×2). The combined organic layer was dried (Na$_2$SO$_4$) and filtered. After removal of solvent, the product was purified by silica gel chromatography using 0-10% MeOH/EtOAc as the eluent to give 1-(4-(6-(3,5-dimethylisoxazol-4-yl)-4-morpholinoquinazolin-2-yl)-1H-pyrazol-1-yl)-2-methylpropan-2-ol (85 mg, 0.19 mmol, 95% yield). $^1$H NMR (400 MHz, DMSO-d$_6$) δ 8.31 (s, 1H), 8.05 (s, 1H), 7.89-7.71 (m, 3H), 4.74 (s, 1H), 4.07 (s, 2H), 3.88-3.66 (m, 6H), 3.29 (s, 2H), 2.44 (s, 3H), 2.26 (s, 3H), 1.07 (s, 6H); MS (M+H)$^+$=449.

Example 340. (S)-5-(4-(4-acetyl-2-phenylpiperazin-1-yl)-2-(1-(2-hydroxy-2-methylpropyl)-1H-pyrazol-4-yl)quinazolin-6-yl)-1-methylpyridin-2(1H)-one, TFA To a solution of (S)-5-(2-(1-(2-hydroxy-2-methylpropyl)-1H-pyrazol-4-yl)-4-(2-phenylpiperazin-1-yl)quinazolin-6-yl)-1-methylpyridin-2(1H)-one, HCl (Example 338, 0.086 g, 0.15 mmol) in CH$_2$Cl$_2$ (3 ml) was added Et$_3$N (0.209 ml, 1.50 mmol) and then acetyl chloride (0.035 g, 0.45 mmol) slowly. The mixture was stirred at rt for 30 min. The mixture was concentrated and the residue was dissolved in DMF, filtered through a filter, and submitted for purification by semi-preparative HPLC to give (S)-5-(4-(4-acetyl-2-phenylpiperazin-1-yl)-2-(1-(2-hydroxy-2-methylpropyl)-1H-pyrazol-4-yl)quinazolin-6-yl)-1-methylpyridin-2(1H)-one, TFA. MS (M+H)$^+$=578.

Biological Assay

The following in vitro assay may be used to determine the activity of compounds of the present invention to interact with bromodomains. Representative data for a bromodomain assay are summarized in Table 2, thereby providing support for the utility of compounds of the present invention.

Bromodomain assays were conducted to measure interactions between certain compounds and bromodomains. In order to measure compounds' direct activity against BRD4, dissociation constants (Ki values) of the bromodomain inhibitors of the present invention were obtained using a biophysical binding assay, BROMOscan$^{SM}$ (DiscoveRx, San Diego, Calif.), a modified phage-display system originally developed for kinases (Nat. Biotechnol. 2005 March; 23(3):329-36).

The assays were conducted according to BROMOscan protocol from Discover Rx. Briefly, BRD4 bromodomains expressed as a fusion capsid protein of T7 phage were bound to acetylated peptide ligand on a solid phase and competition bindings were performed. T7 phage strains displaying bromodomains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 μm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO and subsequently diluted 1:10 in monoethylene glycol (MEG) to create stocks at 100× the screening concentration (resulting stock solution is 10% DMSO/90% MEG). The compounds were then diluted directly into the assays such that the final concentration of DMSO and MEG were 0.1% and 0.9%, respectively. All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 2 µM non-biotinylated affinity ligand) and incubated at room temperature with shaking for 30 minutes. The bromodomain concentration in the eluates was measured by qPCR. Data was collected at 11 compound concentrations ranging from 0 to 10 µM. Kd values were then derived from a standard dose-response curve generated with Hill equation (Hill Slope was set to −1) and a non-linear least square fit with the Levenberg-Marquardt algorithm.

Response=Background+Signal Background/1+(Kd Hill Slope/Dose Hill Slope)

Data is reported in Table 2 as Relative Activity, wherein a Kd of less than 0.5 µM is denoted by (+++), a Kd of between 0.5 µM and 5 µM is denoted by (++), and a Kd of greater than 5 µM is denoted by (+).

TABLE 2

| Ex. # | BROMOscan Relative Activity |
|---|---|
| 1 | ++ |
| 2 | +++ |
| 3 | ++ |
| 4 | ++ |
| 5 | ++ |
| 6 | +++ |
| 7 | +++ |
| 8 | +++ |
| 9 | +++ |
| 10 | +++ |
| 11 | +++ |
| 12 | +++ |
| 13 | +++ |
| 14 | ++ |
| 15 | + |
| 16 | +++ |
| 17 | +++ |
| 18 | +++ |
| 19 | + |
| 20 | +++ |
| 21 | ++ |
| 22 | +++ |
| 23 | ++ |
| 24 | ++ |
| 25 | ++ |
| 26 | +++ |
| 27 | ++ |
| 28 | +++ |
| 29 | +++ |
| 30 | ++ |
| 31 | +++ |
| 32 | +++ |
| 33 | +++ |
| 34 | +++ |
| 35 | +++ |
| 36 | +++ |
| 37 | +++ |
| 38 | ++ |
| 39 | ++ |
| 40 | ++ |
| 41 | +++ |
| 42 | +++ |
| 43 | ++ |
| 44 | ++ |
| 45 | +++ |
| 46 | +++ |
| 47 | +++ |
| 48 | +++ |
| 49 | +++ |
| 50 | +++ |
| 51 | ++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | + |
| 65 | ++ |
| 66 | +++ |
| 67 | ++ |
| 68 | ++ |
| 69 | ++ |
| 70 | ++ |
| 71 | +++ |
| 72 | +++ |
| 73 | +++ |
| 74 | +++ |
| 75 | +++ |
| 76 | +++ |
| 77 | +++ |
| 78 | ++ |
| 79 | ++ |
| 80 | +++ |
| 81 | +++ |
| 82 | +++ |
| 83 | +++ |
| 84 | +++ |
| 85 | +++ |
| 86 | ++ |
| 87 | +++ |
| 88 | +++ |
| 89 | +++ |
| 90 | +++ |
| 91 | +++ |
| 92 | +++ |
| 93 | +++ |
| 94 | +++ |
| 95 | ++ |
| 96 | + |
| 97 | +++ |
| 98 | +++ |
| 99 | ++ |
| 100 | + |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | ++ |

TABLE 2-continued

| Ex. # | BROMOscan Relative Activity |
|---|---|
| 113 | + |
| 114 | ++ |
| 115 | +++ |
| 116 | + |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |
| 137 | ++ |
| 138 | +++ |
| 139 | +++ |
| 140 | +++ |
| 141 | +++ |
| 142 | +++ |
| 143 | +++ |
| 144 | +++ |
| 145 | ++ |
| 146 | +++ |
| 147 | +++ |
| 148 | ++ |
| 149 | +++ |
| 150 | ++ |
| 151 | + |
| 152 | +++ |
| 153 | +++ |
| 154 | +++ |
| 155 | +++ |
| 156 | ++ |
| 157 | +++ |
| 158 | ++ |
| 159 | + |
| 160 | ++ |
| 161 | ++ |
| 162 | ++ |
| 163 | +++ |
| 164 | +++ |
| 165 | ++ |
| 166 | +++ |
| 167 | + |
| 168 | + |
| 169 | + |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | +++ |
| 210 | ++ |
| 211 | +++ |
| 212 | +++ |
| 213 | +++ |
| 214 | +++ |
| 215 | +++ |
| 216 | +++ |
| 217 | +++ |
| 218 | ++ |
| 219 | ++ |
| 220 | +++ |
| 221 | ++ |
| 222 | + |
| 223 | + |
| 224 | ++ |
| 225 | +++ |
| 226 | +++ |
| 227 | +++ |
| 228 | +++ |
| 229 | +++ |
| 230 | +++ |
| 231 | +++ |
| 232 | +++ |
| 233 | +++ |
| 234 | +++ |
| 235 | +++ |
| 236 | +++ |
| 237 | +++ |
| 238 | +++ |
| 239 | +++ |
| 240 | +++ |
| 241 | +++ |
| 242 | +++ |
| 243 | ++ |
| 244 | +++ |
| 245 | +++ |
| 246 | +++ |
| 247 | +++ |
| 248 | +++ |
| 249 | +++ |
| 250 | +++ |
| 251 | +++ |
| 252 | ++ |
| 253 | +++ |
| 254 | ++ |
| 255 | ++ |
| 256 | ++ |
| 257 | +++ |
| 258 | +++ |
| 259 | +++ |
| 260 | +++ |
| 261 | ++ |
| 262 | +++ |
| 263 | +++ |
| 264 | +++ |
| 265 | +++ |
| 266 | +++ |

TABLE 2-continued

| Ex. # | BROMOscan Relative Activity |
|---|---|
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | ++ |
| 277 | +++ |
| 278 | ++ |
| 279 | +++ |
| 280 | +++ |
| 281 | +++ |
| 282 | +++ |
| 283 | +++ |
| 284 | ++ |
| 285 | ++ |
| 286 | +++ |
| 287 | +++ |
| 288 | ++ |
| 289 | +++ |
| 290 | ++ |
| 291 | +++ |
| 292 | +++ |
| 293 | +++ |
| 294 | +++ |
| 295 | +++ |
| 296 | +++ |
| 297 | +++ |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | +++ |
| 314 | +++ |
| 315 | +++ |
| 316 | ++ |
| 317 | ++ |
| 318 | +++ |
| 319 | +++ |
| 320 | +++ |
| 321 | +++ |
| 322 | +++ |
| 323 | ++ |
| 324 | +++ |
| 325 | ++ |
| 326 | +++ |
| 327 | +++ |
| 328 | +++ |
| 329 | +++ |
| 330 | +++ |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the invention is not limited thereto. The above detailed descriptions are provided as exemplary of the present disclosure and should not be construed as constituting any limitation of the invention. Modifications will be obvious to those skilled in the art, and all modifications that do not depart from the spirit of the invention are intended to be included within the scope of the appended claims.

What is claimed is:

1. A compound, which is (S)-1-(4-(6-(3,5-dimethylisoxazol-4-yl)-4-(3-phenylmorpholino)quinazolin-2-yl)-1H-pyrazol-1-yl)-2-methylpropan-2-ol, or a pharmaceutically acceptable salt thereof.

2. A pharmaceutical composition comprising the compound of claim 1, or a pharmaceutically acceptable salt thereof, and a pharmaceutically acceptable carrier.

* * * * *